US009102625B2

(12) United States Patent
Bauer et al.

(10) Patent No.: US 9,102,625 B2
(45) Date of Patent: Aug. 11, 2015

(54) NICOTINAMIDES AS JAK KINASE MODULATORS

(75) Inventors: Shawn M. Bauer, Pacifica, CA (US); Yonghong Song, Foster City, CA (US); Qing Xu, Foster City, CA (US); Jack W. Rose, San Mateo, CA (US); Zhaozhong J. Jia, San Mateo, CA (US); Brian Kane, Oakland, CA (US); Wolin Huang, Foster City, CA (US); Anjali Pandey, Fremont, CA (US); Mukund Mehrotra, South San Francisco, CA (US)

(73) Assignee: PORTOLA PHARMACEUTICALS, INC., South San Francisco, CA (US)

( * ) Notice: Subject to any disclaimer, the term of this patent is extended or adjusted under 35 U.S.C. 154(b) by 183 days.

(21) Appl. No.: 13/286,984

(22) Filed: Nov. 1, 2011

(65) Prior Publication Data

US 2012/0108566 A1    May 3, 2012

Related U.S. Application Data

(60) Provisional application No. 61/409,030, filed on Nov. 1, 2010.

(51) Int. Cl.
| | |
|---|---|
| C07D 213/82 | (2006.01) |
| C07D 401/12 | (2006.01) |
| C07D 401/14 | (2006.01) |
| C07D 405/12 | (2006.01) |
| A61K 31/455 | (2006.01) |
| A61P 35/00 | (2006.01) |
| C07D 405/14 | (2006.01) |
| C07D 409/12 | (2006.01) |
| C07D 409/14 | (2006.01) |
| C07D 413/12 | (2006.01) |
| C07D 417/12 | (2006.01) |
| C07D 417/14 | (2006.01) |

(52) U.S. Cl.
CPC ........... *C07D 213/82* (2013.01); *C07D 401/12* (2013.01); *C07D 401/14* (2013.01); *C07D 405/12* (2013.01); *C07D 405/14* (2013.01); *C07D 409/12* (2013.01); *C07D 409/14* (2013.01); *C07D 413/12* (2013.01); *C07D 417/12* (2013.01); *C07D 417/14* (2013.01)

(58) Field of Classification Search
CPC .. C07D 213/82; C07D 401/12; C07D 401/14; C07D 405/12; A61K 31/455
USPC ............. 514/355, 352, 336, 340, 332, 318; 546/194, 316, 307, 272.7, 272.4
See application file for complete search history.

(56) References Cited

U.S. PATENT DOCUMENTS

| | | | |
|---|---|---|---|
| 5,728,536 | A | 3/1998 | Ihle et al. |
| 6,080,747 | A | 6/2000 | Uckun et al. |
| 6,080,748 | A | 6/2000 | Uckun et al. |
| 6,133,305 | A | 10/2000 | Tang et al. |
| 6,177,433 | B1 | 1/2001 | Uckun et al. |
| 6,210,654 | B1 | 4/2001 | Ihle et al. |
| 6,313,130 | B1 | 11/2001 | Uckun et al. |
| 6,316,635 | B1 | 11/2001 | Tang et al. |
| 6,433,018 | B1 | 8/2002 | Siddiqui et al. |
| 6,486,185 | B1 | 11/2002 | McMahon et al. |
| 6,506,763 | B2 | 1/2003 | Tang et al. |
| 6,528,509 | B1 | 3/2003 | Hale et al. |
| 6,593,357 | B1 | 7/2003 | Green et al. |
| 6,608,048 | B2 | 8/2003 | Tsou et al. |
| 6,610,688 | B2 | 8/2003 | Liang et al. |
| 6,635,651 | B2 | 10/2003 | Uckun et al. |
| 6,677,368 | B2 | 1/2004 | Cui et al. |
| 6,683,082 | B2 | 1/2004 | Tang et al. |
| 6,696,448 | B2 | 2/2004 | Tang et al. |
| 6,699,865 | B2 | 3/2004 | Hale et al. |
| 6,777,417 | B2 | 8/2004 | Liang et al. |
| 6,784,195 | B2 | 8/2004 | Hale et al. |
| 6,815,439 | B2 | 11/2004 | Harris et al. |
| 6,825,190 | B2 | 11/2004 | Moon et al. |
| 6,949,580 | B2 | 9/2005 | Hale et al. |
| 6,969,760 | B2 | 11/2005 | Ihle et al. |
| 6,998,391 | B2 | 2/2006 | Lyons et al. |

(Continued)

FOREIGN PATENT DOCUMENTS

| | | |
|---|---|---|
| EP | 1 184 376 A1 | 3/2002 |
| WO | WO 95/03701 A1 | 2/1995 |

(Continued)

OTHER PUBLICATIONS

Berge, S.M. et al., "Pharmaceutical Salts," Journal of Pharmaceutical Science, 66:1-19, 1977.
Blaire et al., "Lack of Expression of Thy-1 (CD90) on Acute Myeloid Leukemia Cells With Long-Term Proliferative Ability In Vitro and In Vivo," 1997, Blood 89:3104-3112.
Catlett-Falcone et al., "Constitutive Activation of Stat3 Signaling Confers Resistance to Apoptosis in Human U266 Myeloma Cells," (1999), Immunity 10:105-115.
Changelian et al., "Prevention of Organ Allograft Rejection by a Specific Janus Kinase 3 Inhibitor," (2003) Science 302:875-878.

(Continued)

*Primary Examiner* — Sreeni Padmanabhan
*Assistant Examiner* — Irina Neagu
(74) *Attorney, Agent, or Firm* — Kilpatrick Townsend & Stockton LLP

(57) ABSTRACT

The present invention is directed to compounds of formula I and pharmaceutically acceptable salts, esters, and prodrugs thereof which are inhibitors of JAK kinase. The present invention is also directed to intermediates used in making such compounds, the preparation of such a compound, pharmaceutical compositions containing such a compound, methods of inhibition JAK kinase activity, methods of inhibition the platelet aggregation, and methods to prevent or treat a number of conditions mediated at least in part by JAK kinase activity, such as undesired thrombosis and Non Hodgkin's Lymphoma.

10 Claims, No Drawings

(56) References Cited

U.S. PATENT DOCUMENTS

| | | |
|---|---|---|
| 7,056,944 B2 | 6/2006 | Hale et al. |
| 7,074,793 B2 | 7/2006 | Hudkins et al. |
| 7,105,529 B2 | 9/2006 | Davis et al. |
| 7,517,886 B2 | 4/2009 | Singh et al. |
| 8,178,671 B2 | 5/2012 | Singh et al. |
| 2001/0007033 A1 | 7/2001 | Tang et al. |
| 2002/0115173 A1 | 8/2002 | Ben-Sasson et al. |
| 2002/0137141 A1 | 9/2002 | Ben-Sasson |
| 2003/0149064 A1 | 8/2003 | Pease |
| 2003/0236244 A1 | 12/2003 | Ledford |
| 2004/0029902 A1 | 2/2004 | Singh |
| 2004/0102455 A1 | 5/2004 | Burns |
| 2004/0142404 A1 | 7/2004 | Wilks |
| 2004/0147507 A1 | 7/2004 | Ledeboer |
| 2004/0214817 A1 | 10/2004 | Pierce |
| 2011/0230467 A1* | 9/2011 | Shirakami et al. ....... 514/212.08 |
| 2011/0237590 A1* | 9/2011 | Kitamura et al. .......... 514/237.2 |

FOREIGN PATENT DOCUMENTS

| | | |
|---|---|---|
| WO | WO 99/15500 A1 | 4/1999 |
| WO | WO 00/00202 A1 | 1/2000 |
| WO | WO 00/10981 A1 | 3/2000 |
| WO | WO 00/39101 | 7/2000 |
| WO | WO 00/47583 A1 | 8/2000 |
| WO | WO 00/51587 A2 | 9/2000 |
| WO | WO 00/55159 A2 | 9/2000 |
| WO | WO 01/42246 A2 | 6/2001 |
| WO | WO 01/45641 A2 | 6/2001 |
| WO | WO 01/52892 A2 | 7/2001 |
| WO | WO 01/56993 A2 | 8/2001 |
| WO | WO 01/57022 A2 | 8/2001 |
| WO | WO 01/72758 A1 | 10/2001 |
| WO | WO 02/00661 A1 | 1/2002 |
| WO | WO 02/43735 A1 | 6/2002 |
| WO | WO 02/48336 A2 | 6/2002 |
| WO | WO 02/059110 | 8/2002 |
| WO | WO 02/060492 A1 | 8/2002 |
| WO | WO 02/060927 A1 | 8/2002 |
| WO | WO 02/092571 | 11/2002 |
| WO | WO 02/096909 A1 | 12/2002 |
| WO | WO 02/102800 A1 | 12/2002 |
| WO | WO 03/002542 | 1/2003 |
| WO | WO 03/020698 A2 | 3/2003 |
| WO | WO 03/030909 | 4/2003 |
| WO | WO 03/048162 A1 | 6/2003 |
| WO | WO 03/063794 | 8/2003 |
| WO | WO 03/066601 | 8/2003 |
| WO | WO 03/074515 | 9/2003 |
| WO | WO 03/101989 A1 | 12/2003 |
| WO | WO 03/106416 | 12/2003 |
| WO | WO 2004/014382 | 2/2004 |
| WO | WO 2004/016597 A2 | 2/2004 |
| WO | WO 2004/041789 A1 | 5/2004 |
| WO | WO 2004/041810 A1 | 5/2004 |
| WO | WO 2004/041814 A1 | 5/2004 |
| WO | WO 2004/046112 A2 | 6/2004 |
| WO | WO 2004/046118 | 6/2004 |
| WO | WO 2004/046120 A2 | 6/2004 |
| WO | WO 2004/047843 A1 | 6/2004 |
| WO | WO 2004/058749 A1 | 7/2004 |
| WO | WO 2004/058753 A1 | 7/2004 |
| WO | WO 2004/085388 A2 | 10/2004 |
| WO | WO 2004/092154 A1 | 10/2004 |
| WO | WO 2005/009957 A1 | 2/2005 |
| WO | WO 2005/012294 | 2/2005 |
| WO | WO 2005/016344 A1 | 2/2005 |
| WO | WO 2005/016893 | 2/2005 |
| WO | WO 2005/016894 | 2/2005 |
| WO | WO 2005/028475 A2 | 3/2005 |
| WO | WO 2005/033107 A1 | 4/2005 |
| WO | WO 2005/037800 | 4/2005 |
| WO | WO 2005/066156 | 7/2005 |
| WO | WO 2005/095400 | 10/2005 |
| WO | WO 2008/024963 A1 | 2/2008 |
| WO | WO 2008/135786 | 11/2008 |
| WO | WO2010/058846 * | 5/2010 ........... C07D 213/82 |
| WO | WO 2010/058846 A1 | 5/2010 |
| WO | WO2010/061971 * | 6/2010 ........... C07D 213/82 |
| WO | WO 2010/061971 A1 | 6/2010 |

OTHER PUBLICATIONS

Demoulin et al., "A Single Tyrosine of the Interleukin-9 (IL-9) Receptor Is Required for STAT Activation, Antiapoptotic Activity, and Growth Regulation by IL-9," (1996), Mol. Cell. Biol. 16:4710-6.

Frank, "STAT Signaling in the Pathogenesis and Treatment of Cancer," (1999), Mol. Med. 5:432:456.

Garcia-Bustos et al., "PIK1, an essential phosphatidylinositol 4-kinase associated with the yeast nucleus," (1994), EMBO J. 13:2352-2361.

Hahn, Cynthia K. et al., "Syk is a new target for AML differentiation," Blood, 2007, 110, Abstract 209.

Hanks & Hunter, "The eukaryotic protein kinase superfamily: kinase (catalytic) domain structure and classification," (1995), FASEB J. 9:576-596.

Haura et al, "Mechanisms of Disease: insights into the emerging role of signal transducers and activators of transcription in cancer," Oncology, 2005, 2(6), 315-324.

Hiles et al., "Phosphatidylinositol 3-Kinase: Structure and Expression of the 110 kd Catalytic Subunit," (1992), Cell 70:419-429.

Jurlander et al., "Characterization of Interleukin-10 Receptor Expression on B-Cell Chronic Lymphocytic Leukemia Cells," (1997), Blood. 89:4146-52.

Kaneko et al., "Characterization of Interleukin-10 Receptor Expression on B-Cell Chronic Lymphocytic Leukemia Cells," (1997), Clin. Exp. Immun. 109:185-193.

Kirken, "Targeting JAK3 for Immune Suppression and Allograft Acceptance," (2001), Transpl. Proc. 33:3268-3270.

Knighton et al., "Crystal structure of the catalytic subunit of cyclic adenosine monophosphate-dependent protein kinase," (1991), Science 253:407-414.

Kudlacz et al., "The Novel JAK-3 Inhibitor CP-690550 Is a Potent Immunosuppressive Agent in Various Murine Models," (2004) Am. J. Transplant 4:51-57.

Kunz et al., "Target of Rapamycin in Yeast, TOR2, Is an Essential Phosphatidylinositol Kinase Homolog Required for G1 Progression," (1993), Cell 73:585-596.

Leonard et al., "Molecular mechanisms in allergy and clinical immunology." (2000), J. Allergy Clin. Immunol. 105:877-888.

Malaviya et al., "Genetic and Biochemical Evidence for a Critical Role of Janus Kinase (JAK)-3 in Mast Cell-Mediated Type I Hypersensitivity Reactions," (1999), Biochem. Biophys. Res. Commun. 257:807-813.

Mocsai et al., "Syk Is Required for Integrin Signaling in Neutrophils," (2002), Immunity 16:547-558.

Muller-Ladner et al., "Activation of the IL-4 STAT Pathway in Rheumatoid Synovium," (2000), J. Immunol. 164:3894-3901.

Nakamura et al., "An Epidermal Growth Factor Receptor/Jak2 Tyrosine Kinase Domain Chimera Induces Tyrosine Phosphorylation of Stat5 and Transduces a Growth Signal in Hematopoietic Cells," (1996), J. Biol. Chem. 271: 19483-8.

Nielsen et al., "Constitutive activation of a slowly migrating isoform of Stat3 in mycosis fungoides: Tyrphostin AG490 inhibits Stat3 activation and growth of mycosis fungoides tumor cell lines," (1997), Prac. Natl. Acad. Sci. USA 94:6764-6769.

Passegue et al., "Normal and leukemic hematopoiesis: Are leukemias a stem cell disorder or a reacquisition of stem cell characteristics?," Proc. Natl. Acad. Sci. USA, 2003, 100:11842-9.

Seidel et al., "Pharmaceutical intervention in the JAK/STAT signaling pathway," (2000), Oncogene 19:2645-2656.

Sudbeck et al., << Structure-based Design of Specific Inhibitors of Janus Kinase 3 as Apoptosis-inducing Antileukemic Agents, (1999), Clin. Cancer Res. 5:1569-1582.

Trieu et al., "A Specific Inhibitor of Janus Kinase-3 Increases Survival in a Transgenic Mouse Model of Amyotrophic Lateral Sclerosis," (2000), Biochem Biophys. Res. Commun. 267:22-25.

(56) References Cited

OTHER PUBLICATIONS

Turhan et al., "Highly Purified Primitive Hematopoietic Stem Cells Are PML-RARA Negative and Generate Nonclonal Progenitors in Acute Promyelocytic Leukemia," 1995, Blood 85:2154-2161.

Turner et al., "Tyrosine kinase SYK: essential functions for immunoreceptor signaling," Immunology Today, (2000) 21:148-154.

Van Gurp et al., "The Effect of the JAK Inhibitor CP-690,550 on Peripheral Immune Parameters in Stable Kidney Allograft Patients," (2009) Transplantation 87:79-86.

Yu et al., "Constitutive Activation of the Janus Kinase STAT Pathway in T Lymphoma Overexpressing the Lck Protein Tyrosine Kinase," (1997), J. Immunol. 159:5206-5210.

* cited by examiner

NICOTINAMIDES AS JAK KINASE MODULATORS

CROSS-REFERENCES TO RELATED APPLICATIONS

This application claims priority under 35 U.S.C. §119(e) from U.S. Provisional Application 61/409,030, filed Nov. 1, 2010, which is incorporated by reference in its entirety herewith.

BACKGROUND OF THE INVENTION

This invention is directed to nicotinamide-based compounds which act as inhibitors of JAK kinases. This invention is also directed to pharmaceutical compositions containing the nicotinamide compounds and methods of using the compounds or compositions to treat a condition mediated at least in part by JAK kinase activity. The invention is also directed to methods of making the compounds described herein.

Protein kinases constitute a large family of structurally related enzymes that are responsible for the control of a variety of signal transduction processes within cells (see, e.g., Hardie and Hanks, The Protein Kinase Facts Book, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), FASEB J. 9:576-596; Knighton et al., (1991), Science 253:407-414; Hiles et al., (1992), Cell 70:419-429; Kunz et al., (1993), Cell 73:585-596; Garcia-Bustos et al., (1994), EMBO J. 13:2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies, asthma, alzheimer's disease and hormone-related diseases. As a consequence, there has been substantial efforts in medicinal chemistry to find inhibitors of protein kinases for use as therapeutic agents.

JAK kinases (Janus Kinases) are a family of cytoplasmic protein tyrosine kinases including JAK1, JAK2, JAK3 and TYK2. The JAKs play a crucial role in cytokine signaling. Each of the JAK kinases is selective for the receptors of certain cytokines, though multiple JAK kinases can be affected by particular cytokine or signaling pathways. Studies suggest that JAK3 associates with the common cytokine receptor gamma chain (Fcγ or γc) of the various cytokine receptors. JAK3 in particular selectively binds to receptors and is part of the cytokine signaling pathway for and activated by IL-2, IL-4, IL-7, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

The downstream substrates of JAK family kinases include the signal transducer activator of transcription (STAT) proteins. Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), Mol. Med. 5:432:456 and Seidel et al., (2000), Oncogene 19:2645-2656.

Several mutated forms of JAK2 have been identified in a variety of disease settings, for example translocations resulting in the fusion of the JAK2 kinase domain with an oligomeriaztiondomain, TEL-JAK2, Bcr-JAK2 and PCM1-JAK2 have been implicated in the pathogenesis of various hematological malignancies (S D Turner and Alesander D R, Leukemia, 2006, 20, 572-582). Recently a unique mutation encoding a valine to phenylalanine substitution in JAK2 was detected in a significant number of myeloproliferative diseases such as polycythemia vera (PV), essential thrombocythemia (ET) and idiopathic myelofibrosis patients.

Constitutive activation of the STAT family, in particular STAT3 and STAT5 have been detected in a wide range of cancers and hyperproliferative diseases (Haura et al, Oncology, 2005, 2(6), 315-324). Further, aberrant activation of the JAK/STAT pathway provides an important proliferative and/or anti-apoptotic drive downstream of many kinases (e.g. Flt3, EGFR) whose constitutive activation have been implicated as key drivers in a variety of cancers and hyperproliferative disorders. Potent and specific inhibitors of JAK1 and JAK2 will be useful in the treatment of cancers including multiple myeloma, prostate, breast and lung cancer, B-cell Chronic Lymphocytic Leukemia, metastatic melanoma, multiple myeloma, and hepatoma.

JAK3 in particular has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad. Sci. USA 94:6764-6769); and abnormal cell growth (Yu et al., (1997), J. Immunol. 159:5206-5210; Catlett-Falcone et al., (1999), Immunity 10:105-115). Therefore, compounds that inhibit JAK-3 can be therapeutically useful in treatment of chronic and/or acute organ transplant and autoimmune diseases such as Type 1 diabetes, systemic lupus, multiple sclerosis, Crohn's disease and inflammatory diseases such as, asthma, psoriasis, chronic obstructive pulmonary disease.

JAK1, JAK2, and TYK2 are expressed ubiquitously, whereas JAK3 is expressed predominantly in hematopoietic cells. The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important for lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes, rheumatoid arthritis, lupus, psoriasis), and inflammation (e.g., asthma, allergic reactions). Conditions which can benefit from JAK3 inhibition are discussed in greater detail below. Recent data on JAK inhibition has been reported in kidney allograft patients treated with CP-690,550 (Tasocitinib) and showed that markers of allogeneic response (interferon gamma) can be reduced (Van Gurp E A et al (2009) Transplantation 87:79-86).

In view of the numerous conditions that are contemplated to benefit by treatment involving modulation of the JAK pathway it is immediately apparent that new compounds that modulate JAK pathways and methods of using these compounds should provide substantial therapeutic benefits to a wide variety of patients. Provided herein are novel 2,4-nicotinamide-based compounds for use in the treatment of conditions in which targeting of the JAK pathway or inhibition of JAK kinases, particularly JAK3, are therapeutically useful.

Patents and patent applications related to modulation of the JAK pathway include: U.S. Pat. Nos. 5,728,536; 6,080,747; 6,080,748; 6,133,305; 6,177,433; 6,210,654; 6,313,130; 6,316,635; 6,433,018; 6,486,185; 6,506,763; 6,528,509; 6,593,357; 6,608,048; 6,610,688; 6,635,651; 6,677,368; 6,683,082; 6,696,448; 6,699,865; 6,777,417; 6,784,195; 6,825,190; 6,506,763; 6,784,195; 6,528,509; 6,608,048; 7,105,529; 6,699,865; 6,825,190; 6,815,439; 6,949,580; 7,056,944; 6,998,391; 7,074,793; 6,969,760; U.S. Pat. App. Pub. No. 2001/0007033 A1; 2002/0115173 A1; 2002/0137141 A1; 2003/0236244 A1; 2004/0102455 A1; 2004/0142404 A1; 2004/0147507 A1; and 2004/0214817 A1; and International patent applications WO 95/03701A1; WO 99/15500A1; WO 00/00202A1; WO 00/10981A1; WO 00/47583A1; WO 00/51587A2; WO 00/55159A2; WO 01/42246A2; WO 01/45641A2; WO 01/52892A2; WO 01/56993A2; WO 01/57022A2; WO 01/72758A1; WO 02/00661A1; WO 02/43735A1; WO 02/48336A2; WO 02/060492A1; WO 02/060927A1; WO 02/096909A1; WO 02/102800A1; WO 03/020698A2; WO 03/048162A1; WO 03/101989A1; WO 2004/016597A2; WO 2004/041789A1; WO 2004/041810A1; WO 2004/041814A1; WO 2004/046112A2; WO 2004/046120A2; WO 2004/047843A1; WO 2004/058749A1; WO 2004/058753A1; WO 2004/085388A2; WO 2004/092154A1; WO 2005/009957A1; WO 2005/016344A1; WO 2005/028475A2; and WO 2005/033107A1. Vertex has described aza indoles as JAK inhibitors (WO2005/95400). AstraZeneca has published quinoline 3-carboxamides as JAK 3 inhibitors (WO2002/92571) and other compounds for inhibition of all JAKs for the treatment of cancer (WO2008/135786).

While progress has been made in this field, there remains a need in the art for compounds that inhibit JAK kinases, as well as for methods for treating conditions in a patient, such as autoimmune diseases, inflammatory diseases, bone diseases, metabolic diseases, neurological and neurodegenerative diseases, cancer, cardiovascular diseases, allergies, asthma, alzheimer's disease and hormone-related diseases that can benefit from such inhibition. Moreover, the availability of compounds that selectively inhibit one of these kinases as compared to other kinases would also be desirable. The present invention satisfies this and other needs.

BRIEF SUMMARY OF THE INVENTION

The present invention provides novel compounds having activity as inhibitors of JAK kinase activity (also referred to herein as "JAK inhibitors"), as well as to methods for their preparation and use, and to pharmaceutical compositions containing the same. Such compounds have the following structure (I):

The present invention provides in one embodiment, a compound of having the formula (I):

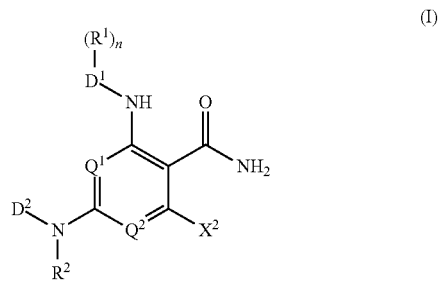

or a tautomer thereof or a pharmaceutically acceptable salt or hydrate thereof, wherein $D^1$, $R^1$, $D^2$, $R^2$, $Q^1$, $Q^2$, $X^2$ and n are as defined below.

The present invention also provides a pharmaceutical composition comprising a therapeutically effective amount of a compound of formula I, or a pharmaceutical acceptable salt thereof, and a pharmaceutically acceptable carrier and/or diluent.

The compounds of the present invention have utility over a wide range of therapeutic applications, and may be used to treat a variety of conditions, mediated at least in part by JAK activity, in both men and women, as well as a mammal in general (also referred to herein as a "subject"). For example, such conditions include, but are not limited to, those associated with cardiovascular disease, inflammatory disease or autoimmune disease. More specifically, the compounds of the present invention have utility for treating conditions or disorders including, but not limited to: vascular inflammation, allergy, asthma, rheumatoid arthritis, T-cell mediated diseases such as irritable bowel disease, Crohn's disease, lupus, psoriasis, multiple sclerosis, and transplant rejection and other inflammatory and autoimmune diseases. Thus, in one embodiment, methods are disclosed which include the administration of an effective amount of a compound of formula (I), typically in the form of a pharmaceutical composition, to a subject in need thereof.

The present invention also provides a method for inhibiting the JAK activity of a blood sample comprising contacting said sample with a compound of the present invention.

The present invention further provides compounds in purified forms, as well as chemical intermediates.

These and other aspects, objects, features and advantages of the invention will be apparent upon reference to the following detailed description and figures. To this end, various references are set forth herein which describe in more detail certain background information, procedures, compounds and/or compositions, and are each hereby incorporated by reference in their entirety.

DETAILED DESCRIPTION OF THE INVENTION

As used herein, the below terms have the following meanings unless specified otherwise:

1. ABBREVIATIONS AND DEFINITIONS

The abbreviations used herein are conventional, unless otherwise defined. The following abbreviations are used: AcOH=acetic acid, AIBN=azobisisobutyronitrile (also azobisisobutylonitrile), aq.=aqueous, Boc=t-butylcarboxy, Bz—benzyl, BOP=benzotriazol-1-yloxytris(dimethylamino)-phosphonium hexafluorophosphate, BPO=benzoyl peroxide, nBuOH=n-butanol, $CBr_4$=tetrabromomethane, mCPBA=m-chloroperoxybenzoic acid, $CH_2Cl_2$ or DCM=dichloromethane, $Cs_2CO_3$=cesium carbonate, $CuCl_2$=copper chloride; DIBAL=diisobutylaluminum hydride, DIEA=Hunig's base or diisopropyl ethylamine, DME=dimethoxy-ethane, DMF=dimethyl formamide, DMSO=dimethyl sulfoxide, DPPA=diphenyl phosphoryl azide, $Et_3N$=triethylamine, EtOAc=ethyl acetate, g=gram, HATU=2-(1H7-Azabenzotriazol-1-yl)-1,1,3,3-tetramethyl uronium hexafluorophosphate, $H_2$=hydrogen; $H_2O$=water; HBr=hydrogen bromide; HCl=hydrogen chloride, HIV=human immunodeficiency virus, HPLC=high pressure liquid chromatography, h=hour, IgE=immunoglobulin E, $IC_{50}$=The concentration of an inhibitor that is required for 50% inhibition of an enzyme in vitro, IPA=isopropyl alcohol, kg=kilogram, KCN=potassium cyanide, KOH=potassium hydroxide, $K_2PO_4$=potassium phosphate, LDA=lithium diisopropylamide, $LiAlH_4$=lithium aluminum hydride=LiOH: lithium hydroxide; MeCN=acetonitrile; MS=Mass Spec, m/z=mass to charge ratio, MHz=Mega Hertz, MeOH=methanol, μM=micromolar, μL=microliter, mg=milligram, mm=millimeter, mM=millimolar, mmol=millimole, mL=milliliter, mOD/min=millioptical density units per minute, min=minute, M=molar, $Na_2CO_3$=sodium carbonate, ng=nanogram, $NaHCO_3$=sodium bicarbonate; $NaNO_2$=sodium nitrite; NaOH=sodium hydroxide; $Na_2S_2O_3$=sodium thiosulfate; $Na_2SO_4$=sodium sulfate; NBS=N-bromosuccinimide; $NH_4Cl$=ammonium chloride; $NH_4OAc$=ammonium acetate; NaSMe=sodium methylthiolate, NBS=N-bromosuccinamide, n-BuLi=n-butyl lithium, nm=nanometer, nM=nanomolar, N=Normal, NMP=N-methylpyrrolidone, NMR=nuclear magnetic resonance, Pd/C=palladium on carbon, $Pd(PPh_3)_4$=Tetrakis-(triphenyl-phosphine)-palladium, pM=picomolar, Pin=pinacolato, PEG=polyethylene glycol, $PPh_3$ or $Ph_3P$=triphenyl phosphine, RLV=Raucher leukemia virus, Ra—Ni=Rainey Nickel, $SOCl_2$=thionyl chloride, RT=room temperature, TEA=triethylamine, THF=tetrahydrofuran, TFA=trifluoroacetic acid, TLC=thin layer chromatography, TMS=trimethylsilyl, Tf=trifluoromethylsulfonyl and TSC=trisodium citrate.

It is noted here that as used in this specification and the appended claims, the singular forms "a," "an," and "the" include plural reference unless the context clearly dictates otherwise.

"Alkyl," by itself or as part of another substituent, means, unless otherwise stated, a straight or branched chain, fully saturated aliphatic hydrocarbon radical having the number of carbon atoms designated. For example, "$C_{1-8}$alkyl" refers to a hydrocarbon radical straight or branched, containing from 1 to 8 carbon atoms that is derived by the removal of one hydrogen atom from a single carbon atom of a parent alkane. The phrase "unsubstituted alkyl" refers to alkyl groups that do not contain groups other than fully saturated aliphatic hydrocarbon radicals. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups such as isopropyl, t-butyl, isobutyl, sec-butyl, and the like. Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Alkylene" by itself or as part of another substituent means a divalent radical derived from an alkane, as exemplified by —$CH_2CH_2CH_2CH_2$—. Typically, an alkylene group will have from 1, 2, 3, 4, 5, 6, 7 or 8 carbon atoms that is derived by the removal of one hydrogen atom from a single carbon atom of a parent alkyl.

"Cycloalkyl" or "carbocycle", by themselves or in combination with other terms, represent, unless otherwise stated, cyclic versions of "alkyl", "alkenyl" and "alkynyl" in which all ring atoms are carbon. "Cycloalkyl" or "carbocycle" refers to a mono- or polycyclic group. When used in connection with cycloalkyl substituents, the term "polycyclic" refers herein to fused and non-fused alkyl cyclic structures. "Cycloalkyl" or "carbocycle" may form a bridged ring or a spiro ring. The cycloalkyl group may have one or more double or triple bond(s). The term "cycloalkenyl" refers to a cycloalkyl group that has at least one site of alkenyl unsaturation between the ring vertices. The term "cycloalkynyl" refers to a cycloalkyl group that has at least one site of alkynyl unsaturation between the ring vertices. When "cycloalkyl" is used in combination with "alkyl", as in $C_{3-8}$cycloalkylC$_{3-8}$alkylene-, the cycloalkyl portion is meant to have the stated number of carbon atoms (e.g., from three to eight carbon atoms), while the alkylene portion has from one to eight carbon atoms. Typical cycloalkyl substituents have from 3 to 8 ring atoms. Examples of cycloalkyl include cyclopentyl, cyclohexyl, 1-cyclohexenyl, 3-cyclohexenyl, cycloheptyl, and the like.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Thus the phrase includes, but is not limited to, groups such as phenyl, biphenyl, anthracenyl, naphthyl by way of example. Non-limiting examples of unsubstituted aryl groups include phenyl, 1-naphthyl, 2-naphthyl and 4-biphenyl. "Substituted aryl group" includes, for example, —$CH_2OH$ (one carbon atom and one heteroatom replacing a carbon atom) and —$CH_2SH$. The term "heteroalkylene" by itself or as part of another substituent means a divalent radical derived from heteroalkyl, as exemplified by —CH$_2$CH$_2$S—CH$_2$CH$_2$— and —CH$_2$S—CH$_2$CH$_2$NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "heterocycle", "heterocyclyl" or "heterocyclic" refer to a saturated or unsaturated non-aromatic cyclic group containing at least one heteroatom. As used herein, the term "heteroatom" is meant to include oxygen (O), nitrogen (N), sulfur (S) and silicon (Si). Each heterocycle can be attached at any available ring carbon or heteroatom. Each heterocycle may have one or more rings. When multiple rings are present, they can be fused together or linked covalently. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, pyridine-2-one, piperidine, morpholine, piperazine, isoxazoline, pyrazoline, imidazoline, pyrazol-5-one, pyrrolidine-2,5-dione, imidazolidine-2,4-dione, pyrrolidine, tetrahydroquinolinyl, decahydroquinolinyl, tetrahydrobenzooxazepinyl dihydrodibenzooxepin and the like.

"Heteroaryl" refers to a cyclic or polycyclic aromatic radical that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom and can contain 5 to 10 carbon atoms. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. If not specifically stated, substituents for each of the above noted aryl and heteroaryl ring systems are selected from the group of acceptable substituents described herein. "Substituted heteroaryl" refers to a unsubstituted heteroaryl group as defined above in which one or more of the ring members is bonded to a non-hydrogen atom such as described above with respect to substituted alkyl groups and substituted aryl groups. Representative substituents include straight and branched chain alkyl groups —CH$_3$, —C$_2$H$_5$, —CH$_2$OH, —OH, —OCH$_3$, —OC$_2$H$_5$, —OCF$_3$, —OC(=O)CH$_3$, —OC(=O)NH$_2$, —OC(=O)N(CH$_3$)$_2$, —CN, —NO$_2$, —C(=O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC(=O)OCH$_3$, —NHSO$_2$CH$_3$, —SO$_2$CH$_3$, —SO$_2$NH$_2$ and halo.

"Bicyclic heteroaryl" refers to bicyclic aromatic radical that contain from one to five heteroatoms selected from N, O, and S, wherein the nitrogen and sulfur atoms are optionally oxidized, and the nitrogen atom(s) are optionally quaternized. A bicyclic heteroaryl group can be attached to the remainder of the molecule through a heteroatom or through a carbon atom and can contain 5 to 10 carbon atoms. Non-limiting examples of bicyclic heteroaryl groups include 5-benzothiazolyl, purinyl, 2-benzimidazolyl, benzopyrazolyl, 5-indolyl, azaindole, 1-isoquinolyl, 5-isoquinolyl, 2-quinoxalinyl, 5-quinoxalinyl, 3-quinolyl and 6-quinolyl. If not specifically stated, substituents for each of the above noted aryl and heteroaryl ring systems are selected from the group of acceptable substituents described herein.

In each of the above embodiments designating a number of atoms e.g. "C$_{1-8}$" is meant to include all possible embodiments that have one fewer atom. Non-limiting examples include C$_{1-7}$, C$_{2-8}$, C$_{2-7}$, C$_{3-8}$, C$_{3-7}$ and the like.

Each of the terms herein (e.g., "alkyl," "cycloalkyl," "heteroalkyl," "aryl" and "heteroaryl") is meant to include both "unsubstituted" and optionally "substituted" forms of the indicated radical, unless otherwise indicated. Typically each radical is substituted with 0, 1, 2 3 4 or 5 substituents, unless otherwise indicated. Examples of substituents for each type of radical are provided below.

"Substituted" refers to a group as defined herein in which one or more bonds to a carbon(s) or hydrogen(s) are replaced by a bond to non-hydrogen and non-carbon atom "substituents" such as, but not limited to, a halogen atom such as F, Cl, Br, and I; an oxygen atom in groups such as hydroxyl groups, alkoxy groups, aryloxy, and acyloxy groups; a sulfur atom in groups such as thiol groups, alkyl and aryl sulfide groups, sulfone groups, sulfonyl groups, and sulfoxide groups; a nitrogen atom in groups such as amino, alkylamines, dialkylamines, arylamines, alkylarylamines, diarylamines, alkoxyamino, hydroxyamino, acylamino, sulfonylamino, N-oxides, imides, and enamines; and other heteroatoms in various other groups. "Substituents" also include groups in which one or more bonds to a carbon(s) or hydrogen(s) atom is replaced by a higher-order bond (e.g., a double- or triple-bond) to a heteroatom such as oxygen in oxo, acyl, amido, alkoxycarbonyl, aminocarbonyl, carboxyl, and ester groups; nitrogen in groups such as imines, oximes, hydrazones, and nitriles. "Substituents" further include groups in which one or more bonds to a carbon(s) or hydrogen(s) atoms is replaced by a bond to a cycloalkyl, heterocyclyl, aryl, and heteroaryl groups. Representative "substituents" include, among others, groups in which one or more bonds to a carbon or hydrogen atom is/are replaced by one or more bonds to fluoro, chloro, or bromo group. Another representative "substituent" is the trifluoromethyl group and other groups that contain the trifluoromethyl group. Other representative "substituents" include those in which one or more bonds to a carbon or hydrogen atom is replaced by a bond to an oxygen atom such that the substituted alkyl group contains a hydroxyl, alkoxy, or aryloxy group. Other representative "substituents" include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other representative "substituents" include those in which one or more bonds to a carbon(s) or hydrogen(s) atoms is replaced by a bond to an alkyl, cycloalkyl, aryl, heteroaryl, or heterocyclyl group.

The herein-defined groups may include prefixes and/or suffixes that are commonly used in the art to create additional well-recognized substituent groups. As examples, "alkylamino" refers to a group of the formula —NR$^a$R$^b$. Unless stated otherwise, for the following groups containing R$^a$, R$^b$, R$^c$, R$^d$ and R$^e$: R$^a$, and R$^b$ are each independently selected from H, alkyl, alkoxy, thioalkoxy, cycloalkyl, aryl, heteroaryl, or heterocyclyl or are optionally joined together with the atom(s) to which they are attached to form a cyclic group. When R$^a$ and R$^b$ are attached to the same nitrogen atom, they can be combined with the nitrogen atom to form a 5-, 6- or 7-membered ring. For example, —NR$^a$R$^b$ is meant to include 1-pyrrolidinyl and 4-morpholinyl.

R$^c$, R$^d$, R$^e$ and R$^f$ are each independently selected from alkyl, alkenyl, alkynyl, cycloalkyl, cycloalkenyl, aryl, heteroaryl, heterocyclyl or alkylenearyl as defined herein.

Typically, a particular radical will have 0, 1, 2 or 3 substituents, with those groups having two or fewer substituents being preferred in the present invention. More preferably, a radical will be unsubstituted or monosubstituted. Most preferably, a radical will be unsubstituted.

"Substituents" for the alkyl and heteroalkyl radicals (as well as those groups referred to as alkylene, alkenyl, heteroalkylene, heteroalkenyl, alkynyl, cycloalkyl, heterocyclyl) can be a variety of groups selected from: —OR$^a$, =O, =NR$^a$, =N—OR$^a$, —NR$^a$R$^b$, —SR$^a$, halogen, —SiR$^a$R$^b$R$^c$, —OC(O)R$^a$, —C(O)R$^a$, —CO$_2$R$^a$, —CONR$^a$R$^b$, —OC(O)NR$^a$R$^b$, —NR$^b$C(O)R$^a$, —NR$^a$—C(O)NR$^b$R$^c$, —NR$^a$—SO$_2$NR$^b$R$^c$, —NR$^b$CO$_2$R$^a$, —NH—C(NH$_2$)=NH, —NR$^a$C(NH$_2$)=NH, —NH—C(NH$_2$)=NR$^a$, —S(O)R$^a$, —SO$_2$R$^a$, —SO$_2$NR$^a$R$^b$, —NR$^b$SO$_2$R, —CN and —NO$_2$, in a number ranging from zero to three, with those groups having zero, one or two substituents being particularly preferred.

In some embodiments, "substituents" for the alkyl and heteroalkyl radicals are selected from: —OR$^a$, =O, —NR$^a$R$^b$, —SR$^a$, halogen, —SiR$^a$R$^b$R$^c$, —OC(O)R$^a$, —C(O)R$^a$, —CO$_2$R$^a$, —CONR$^a$R$^b$, —OC(O)NR$^a$R$^b$, —NR$^b$C(O)R$^a$, —NR$^b$CO$_2$R$^a$, —NR$^a$—SO$_2$NR$^b$R$^c$, —S(O)R$^a$, —SO$_2$R$^a$, —SO$_2$NR$^a$R$^b$, —NR$^c$SO$_2$R, —CN and —NO$_2$, where R$^a$ and R$^b$ are as defined above. In some embodiments, substituents are selected from: —OR$^a$, =O, —NR$^a$R$^b$, halogen, —OC(O)R$^a$, —CO$_2$R$^a$, —CONR$^a$R$^b$, —OC(O)NR$^a$R$^b$, —NR$^b$C(O)R$^a$, —NR$^b$CO$_2$R$^a$, —NR$^a$—SO$_2$NR$^b$R$^c$, —SO$_2$R$^a$, —SO$_2$NR$^a$R$^b$, —NR"SO$_2$R, —CN and —NO$_2$.

Examples of substituted alkyl are: —(CH$_2$)$_3$NH$_2$, —(CH$_2$)$_3$NH(CH$_3$), —(CH$_2$)$_3$NH(CH$_3$)$_2$, —CH$_2$C(=CH$_2$)CH$_2$NH$_2$, —CH$_2$C(=O)CH$_2$NH$_2$, —CH$_2$S(=O)$_2$CH$_3$, —CH$_2$OCH$_2$NH$_2$, —CO$_2$H. Examples of substituents of substituted alkyl are: CH$_2$OH, —OH, —OCH$_3$, —OC$_2$H$_5$, —OCF$_3$, —OC(=O)CH$_3$, —OC(=O)NH$_2$, —OC(=O)N(CH$_3$)$_2$, —CN, —NO$_2$, —C(=O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC(=O)OCH$_3$, —NHSO$_2$CH$_3$, —SO$_2$CH$_3$, —SO$_2$NH$_2$, and halo.

Similarly, "substituents" for the aryl and heteroaryl groups are varied and are selected from: -halogen, —OR$^a$, —OC(O)R$^a$, —NR$^a$R$^b$, —SR$^a$, —R$^a$, —CN, —NO$_2$, —CO$_2$R$^a$, —CONR$^a$R$^b$, —C(O)R$^a$, —OC(O)NR$^a$R$^b$, —NR$^b$C(O)R$^a$, —NR$^b$C(O)$_2$R$^a$, —NR$^a$—C(O)NR$^b$R$^c$, —NH—C(NH$_2$)=NH, —NR$^a$C(NH$_2$)=NH, —NH—C(NH$_2$)=NR$^a$, —S(O)R$^a$, —S(O)$_2$R$^a$, —S(O)$_2$NR$^a$R$^b$, —N$_3$, —CH(Ph)$_2$, perfluoroC$_{1-8}$alkoxy, and perfluoroC$_{1-8}$alkyl, in a number ranging from zero to the total number of open valences on the aromatic ring system; and where R$^a$, R$^b$ and R$^c$ are independently selected from hydrogen, C$_{1-6}$alkyl and heteroalkyl, unsubstituted aryl and heteroaryl, (unsubstituted aryl)-C$_{1-8}$alkyl, and (unsubstituted aryl)oxy-C$_{1-8}$alkyl.

Two of the "substituents" on adjacent atoms of the aryl or heteroaryl ring may optionally be replaced with a substituent of the formula -T-C(O)—(CH$_2$)q-U—, wherein T and U are independently —NH—, —O—, —CH$_2$— or a single bond, and q is 0, 1 or 2. Alternatively, two of the substituents on adjacent atoms of the aryl or heteroaryl ring may optionally be replaced with a substituent of the formula -A-(CH$_2$)$_r$B—, wherein A and B are independently —CH$_2$—, —O—, —NH—, —S—, —S(O)—, —S(O)$_2$—, —S(O)$_2$NR$^a$— or a single bond, and r is 1, 2 or 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR$^a$—, —S—, —S(O)—, —S(O)$_2$—, or —S(O)$_2$NR$^a$—. The substituent R$^a$ in —NR$^a$— and —S(O)$_2$NR$^a$— is selected from hydrogen or unsubstituted C$_{1-6}$alkyl. Otherwise, R' is as defined above.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

The term "acyl" refers to the group —C(=O)R$^c$ where R$^c$ is alkyl, alkenyl, alkynyl, cycloalkyl, cycloalkenyl, aryl, heteroaryl or heterocyclyl. Acyl includes the "acetyl" group —C(=O)CH$_3$.

"Acylamino-" refers to the group —NR$^a$C(=O)R$^c$ where R$^c$ is alkyl, alkenyl, alkynyl, cycloalkyl, cycloalkenyl, aryl, heteroaryl or heterocyclyl.

"Acyloxy" refers to —OC(=O)—R$^c$ where R$^c$ is alkyl, alkenyl, alkynyl, cycloalkyl, cycloalkenyl, aryl, heteroaryl or heterocyclyl.

"Alkoxy" refers to —OR$^d$ wherein R$^d$ is alkyl as defined herein. Representative examples of alkoxy groups include methoxy, ethoxy, t-butoxy, trifluoromethoxy, and the like.

"Alkoxyamino" refers to the group —NHOR$^d$ where R$^d$ is alkyl.

"Alkoxyalkyleneamino" refers to the group —NR$^a$-alkylene-OR$^d$ where R$^d$ is alkyl and —NR$^a$— is defined in amino.

"Alkoxycarbonyl" refers to —C(=O)OR$^d$ wherein R$^d$ is alkyl. Representative alkoxycarbonyl groups include, for example, those shown below.

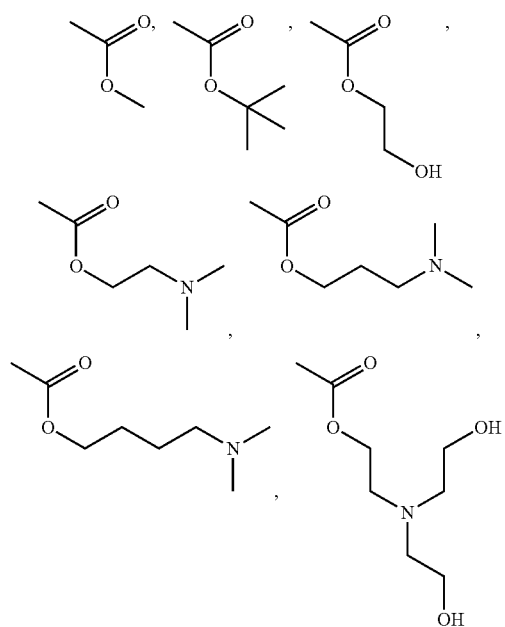

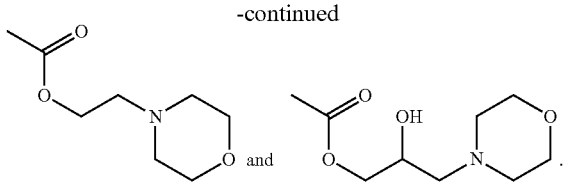

These alkoxycarbonyl groups can be further substituted as will be apparent to those having skill in the organic and medicinal chemistry arts in conjunction with the disclosure herein.

"Alkoxycarbonylalkylene" refers to the group -alkylene-C(=O)OR$^d$ wherein R$^d$ is alkyl.

"Alkoxycarbonylamino" refers to —NR$^a$C(=O)OR$^d$ wherein R$^d$ is alkyl.

"Alkoxycarbonylaminoalkylene" refers to -alkylene-NR$^a$C(=O)OR$^d$ wherein R$^d$ is alkyl.

"Alkoxycarbonylalkyleneaminosulfonyl" refers to —SO$_2$NR$^a$-alkyleneC(=O)OR$^d$ wherein R$^d$ is alkyl.

"Alkoxysulfonylamino" refers to the group —NR$^a$S(=O)$_2$—OR$^d$ where R$^d$ is alkyl.

"Alkylcarbonyl" refers to the group —C(=O)R$^c$ where R$^c$ is alkyl.

"Alkylcarbonyloxy" refers to —OC(=O)—R$^c$ where R$^c$ is alkyl.

"Alkylcarbonylamino" refers to —NR$^a$C(=O)R$^c$ wherein R$^c$ is alkyl. Representative alkylcarbonylamino groups include, for example, —NHC(=O)CH$_3$, —NHC(=O)CH$_2$CH$_3$, —NHC(=O)CH$_2$NH(CH$_3$), —NHC(=O)CH$_2$N(CH$_3$)$_2$, or —NHC(=O)(CH$_2$)$_3$OH.

"Alkylheterocyclyl" refers to the group -heterocyclyl-R$^d$. where R$^d$ is alkyl.

"Alkylheterocyclylalkylene" refers to the group -alkylene-heterocyclyl-R$^d$. where R$^d$ is alkyl.

"Alkylsulfanyl", "alkylthio", or "thioalkoxy" refers to the group S—R$^d$. where R$^d$ is alkyl.

"Alkylsulfinyl" refers to —S(=O)R$^e$ where R$^e$ is alkyl. Alkylsulfonyl groups employed in compounds of the present invention are typically C$_{1-6}$alkylsulfinyl groups.

"Alkylsulfonyl" refers to —S(=O)$_2$R$^e$ where R$^e$ is alkyl. Alkylsulfonyl groups employed in compounds of the present invention are typically C$_{1-6}$alkylsulfonyl groups.

"Alkylsulfonylalkylene" refers to -alkylene-S(=O)$_2$R$^e$ where R$^e$ is alkyl. Alkylsulfonyl groups employed in compounds of the present invention are typically C$_{1-6}$alkylsulfonyl groups.

"Alkylsulfonylamino" refers to —NR$^a$S(=O)$_2$—R$^e$ wherein R$^e$ is alkyl.

"Alkynyloxy" refers to the group —O-alkynyl, wherein alkynyl is as defined herein. Alkynyloxy includes, by way of example, ethynyloxy, propynyloxy, and the like.

"Amidino" refers to the group —C(=NR$^a$)NR$^b$R$^c$, wherein R$^b$ and R$^c$ independently are selected from the group consisting of hydrogen, alkyl, substituted alkyl, alkenyl, alkynyl, aryl, cycloalkyl, cycloalkenyl, heteroaryl, heterocyclic, and where R$^b$ and R$^c$ are optionally joined together with the nitrogen bound thereto to form a heterocyclic or substituted heterocyclic group. R$^a$ is selected from the group consisting of hydrogen, alkyl, alkenyl, alkynyl, cycloalkynyl, aryl, cycloalkyl, cycloalkenyl, heteroaryl, heterocyclic, substituted heterocyclic, nitro, nitroso, hydroxy, alkoxy, cyano, —N=N—N-alkyl, —N(alkyl)SO$_2$-alkyl, —N=N=N-alkyl, acyl and —SO$_2$-alkyl.

"Amino" refers to a monovalent radical —NR$^a$R$^b$ or divalent radical —NR$^a$—. The term includes "alkylamino" which refers to the group —NR$^a$R$^b$ where R$^a$ is alkyl and R$^b$ is H or alkyl. The term also includes "arylamino" which refers to the group —NR$^a$R$^b$ where at least one R$^a$ or R$^b$ is aryl. The term also includes "(alkyl)(aryl)amino" which refers to the group —NR$^a$R$^b$ where R$^a$ is alkyl and R$^b$ is aryl. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

"Aminoalkoxy" refers to —O-alkylene-NR$^a$R$^b$.

"Aminoalkylene" refers to -alkylene-NR$^a$R$^b$.

"Aminoalkylenecarbonyl" refers to —C(=O)-alkylene-NR$^a$R$^b$.

"Aminoalkyleneaminocarbonyl" refers to —C(=O)NR$^a$-alkylene-NR$^a$R$^b$.

"Aminoaryl" refers to -aryl-NR$^a$R$^b$.

"Aminocarbonyl" or "aminoacyl" refers to the amide —C(=O)—NR$^a$R$^b$. The term "alkylaminocarbonyl" refers herein to the group —C(=O)—NR$^a$R$^b$ where R$^a$ is alkyl and R$^b$ is H or alkyl. The term "arylaminocarbonyl" refers herein to the group —C(=O)—NR$^a$R$^b$ where R$^a$ or R$^b$ is aryl. Representative aminocarbonyl groups include, for example, those shown below. These aminocarbonyl group can be further substituted as will be apparent to those having skill in the organic and medicinal chemistry arts in conjunction with the disclosure herein.

"Aminocarbonylalkoxy" refers to —O-alkylene-C(=O)—NR$^a$R$^b$ wherein R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where R$^a$ and R$^b$ are optionally joined together with the nitrogen bound thereto to form a heterocyclic or substituted heterocyclic group.

"Aminocarbonylalkylene" refers to -alkylene-C(=O)—NR$^a$R$^b$ wherein R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where R$^a$ and R$^b$ are optionally joined together with the nitrogen bound thereto to form a heterocyclic or substituted heterocyclic group.

"Aminocarbonylalkyleneaminosulfonyl" refers to —S(O)$_2$NR$^a$-alkylene-C(=O)—NR$^a$R$^b$ wherein each R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where R$^a$ and R$^b$ of the amino group are optionally joined together with the nitrogen bound thereto to form a heterocyclic or substituted heterocyclic group.

"Aminocarbonylamino" refers to the group —NR$^a$C(O)NR$^a$R$^b$, wherein R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where R$^a$ and R$^b$ are optionally joined together with the nitrogen bound thereto to form a heterocyclic or substituted heterocyclic group.

"Aminocarbonylaminoalkylene" refers to the group -alkylene-NR$^a$C(O)NR$^a$R$^b$, wherein R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where R$^a$ and R$^b$ are optionally joined together with the nitrogen bound thereto to form a heterocyclic or substituted heterocyclic group.

"Aminocarboxyalkylene" refers to the group -alkylene-OC(O)NR$^a$R$^b$, wherein R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where $R^a$ and $R^b$ are optionally joined together with the nitrogen bound thereto to form a heterocyclic or substituted heterocyclic group.

"Aminosulfonyl" refers to $—S(O)_2NR^aR^b$ where R is independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^a$ and $R^b$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylalkylene" refers to -alkylene-$S(O)_2NR^aR^b$ where R is independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^a$ and $R^b$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

The term "alkylaminosulfonyl" refers herein to the group $—S(O)_2NR^aR^b$ where $R^a$ is alkyl and $R^b$ is H or alkyl. The term "alkylarylsulfonyl" refers herein to the group $—S(O)_2NR^aR^b$ where $R^a$ or $R^b$ is alkylaryl.

"Aminosulfonyloxy" refers to the group $—O—SO_2NR^aR^b$, wherein $R^a$ and $R^b$ independently are selected from the group consisting of hydrogen, alkyl, alkenyl, alkynyl, aryl, cycloalkyl, cycloalkenyl, heteroaryl and heterocyclic; $R^a$ and $R^b$ are optionally joined together with the nitrogen bound thereto to form a heterocyclic or substituted heterocyclic group.

"Aminosulfonylamino" refers to the group $—NR^a—SO_2NR^bR^c$, wherein $R^a$ is hydrogen or alkyl and $R^b$ and $R^c$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^b$ and $R^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group $—C(S)NR^aR^b$, wherein $R^a$ and $R^b$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^a$ and $R^b$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group $—NR^aC(S)NR^aR^b$, wherein $R^a$ is hydrogen or alkyl and $R^b$ and $R^c$ are optionally joined together with the nitrogen bound thereto to form a heterocyclic or substituted heterocyclic group.

"Arylalkoxycarbonylamino" refers to the group $—NR^aC(=O)O$-alkylene-$R^c$ where $R^c$ is aryl.

"Arylcarbonyl" refers to the group $—C(=O)R^c$ where $R^c$ is aryl.

"Arylcarbonylamino" refers to $—NR^aC(=O)R^c$ wherein $R^c$ is aryl.

"Arylcarbonyloxy" refers to $—OC(=O)—R^c$ where $R^c$ is aryl.

"Aryloxy" refers to $—OR^d$ where $R^d$ is aryl. Representative examples of aryloxy groups include phenoxy, naphthoxy, and the like.

"Aryloxycarbonyl" refers to $—C(=O)OR^d$ wherein $R^d$ is aryl.

"Aryloxycarbonylamino" refers to $—NR^aC(=O)OR^d$ wherein $R^d$ is aryl.

"Arylsulfanyl", "arylthio", or "thioaryloxy" refers to the group S—$R^d$. where $R^d$ is aryl.

"Arylsulfonyl" refers to $—S(=O)_2R^e$ where $R^e$ is aryl.

"Arylsulfonylamino" refers to $—NR^aS(=O)_2—R^e$ wherein $R^e$ is aryl.

"Arylthio" refers to the group —S-aryl, wherein aryl is as defined herein. In other embodiments, sulfur may be oxidized to —S(O)— or —$SO_2$— moieties. The sulfoxide may exist as one or more stereoisomers.

"Bond" when used a element in a Markush group means that the corresponding group does not exist, and the groups of both sides are directly linked.

"Carbonyl" refers to the divalent group —C(=O)—.

"Carboxy" or "carboxyl" refers to the group —$CO_2H$.

"Carboxyalkylene" refers to the group -alkylene-$CO_2H$.

"Carboxyalkylenesulfonylamino" refers to the group $—NR^aSO_2$-alkylene-$CO_2H$.

"Carboxyl ester", "carbonylalkoxy" or "carboxy ester" refers to the group $—C(=O)OR^c$.

"Cycloalkylalkylene" refers to a radical $—R^xR^y$ wherein $R^x$ is an alkylene group and $R^y$ is a cycloalkyl group as defined herein, e.g., cyclopropylmethyl, cyclohexenylpropyl, 3-cyclohexyl-2-methylpropyl, and the like.

"Ester" refers to $—C(=O)OR^d$ wherein $R^d$ is alkyl, cycloalkyl, aryl, heteroaryl, or heterocyclyl.

"Halo" or "halogen" by themselves or as part of another substituent, mean, unless otherwise stated, a fluorine, chlorine, bromine, or iodine atom. Additionally, terms such as "haloalkyl", are meant to include alkyl in which one or more hydrogen is substituted with halogen atoms which can be the same or different, in a number ranging from one up to the maximum number of halogens permitted e.g. for alkyl, (2 m'+1), where m' is the total number of carbon atoms in the alkyl group. For example, the term "halo$C_{1-8}$alkyl" is meant to include trifluoromethyl, 2,2,2-trifluoroethyl, 4-chlorobutyl, 3-bromopropyl, and the like. The term "perhaloalkyl" means, unless otherwise stated, alkyl substituted with (2 m'+1) halogen atoms, where m' is the total number of carbon atoms in the alkyl group. For example, the term "perhalo$C_{1-8}$alkyl", is meant to include trifluoromethyl, pentachloroethyl, 1,1,1-trifluoro-2-bromo-2-chloroethyl, and the like. Additionally, term "haloalkoxy" refers to an alkoxy radical substituted with one or more halogen atoms.

"Heterocyclylcarbonyl" refers to the —C(=O)R$^c$ where R$^c$ is heterocyclyl.

"Hydroxy" or "hydroxyl" refers to the group —OH.

"Hydroxyalkylene" refers to the group -alkylene-OH.

"Hydroxyalkyleneamino" refers to the group —NR$^a$-alkylene-OH.

"Hydroxyalkyleneaminocarbonyl" refers to the group —C(=O)NR$^a$-alkylene-OH.

"Hydroxyalkyleneaminosulfonyl" refers to the group —SO$_2$NR$^a$-alkylene-OH.

"Hydroxyamino" refers to the group —NHOH.

"Hydroxyalkylenecarbonylamino" refers to the group —NR$^a$C(=O)-alkylene-OH.

"Imino" refers to the group =NR$^a$.

"Nitro" refers to —NO$_2$.

"Nitroso" refers to the group —NO.

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group means that the alkyl may but need not be present, and the description includes situations where the heterocyclo group is mono- or disubstituted with an alkyl group and situations where the heterocyclo group is not substituted with the alkyl group.

"Optionally substituted" means a ring which is optionally substituted independently with substituents. A site of a group that is unsubstituted may be substituted with hydrogen.

"Oxo" refers to the divalent group =O.

"Sulfanyl" refers to the group —SR$^f$ where R$^f$ is as defined herein.

"Sulfinyl" refers to the group —S(=O)—R$^e$ where R$^e$ is as defined herein.

"Sulfonic acid" refers to the group —S(O)$_2$—OH.

"Sulfonyl" refers to the group —S(O)$_2$—R$^e$ where R$^e$ is as defined herein.

"Sulfonylamino" refers to —NR$^a$S(=O)$_2$—R$^e$ where R$^a$ is selected from the group consisting of hydrogen, alkyl, alkenyl, alkynyl, aryl, cycloalkyl, cycloalkenyl, heteroaryl and heterocyclyl and R$^e$ is as defined herein.

"Sulfonyloxy" refers to the group —OSO$_2$—R$^c$.

Compounds that have the same molecular formula but differ in the nature or sequence of bonding of their atoms or the arrangement of their atoms in space are termed "isomers". Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

"Thioacyl" refers to the groups R$^a$—C(S)—.

"Thiol" refers to the group —SH.

"Tautomer" refers to alternate forms of a molecule that differ in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to -substituted aryl-(substituted aryl)-substituted aryl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3$^{rd}$ Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl and trityl ethers, as well as alkyl ethers, tetrahydropyranyl ethers, trialkylsilyl ethers (e.g., TMS or TIPPS groups) and allyl ethers.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," *Journal of Pharmaceutical Science*, 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug ester form. "Prodrug"s of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

A wide variety of progroups, as well as the resultant promoieties, suitable for masking functional groups in the active JAK3 selective inhibitory compounds to yield prodrugs are well-known in the art. For example, a hydroxyl functional group may be masked as a sulfonate, ester (such as acetate or maleate) or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including methyl, ethyl, pivaloyloxymethyl, silyl esters and thioesters), amide or hydrazide promoiety, which may be hydrolyzed in vivo to provide the carboxyl group. The invention includes those esters and acyl groups known in the art for modifying the solubility or hydrolysis characteristics for use as sustained-release or prodrug formulations. Other specific examples of suitable progroups and their respective promoieties will be apparent to those of skill in the art.

Certain compounds of the present invention can exist in unsolvated forms as well as solvated forms, including hydrated forms. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chrial auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

An "agonist" or "activator" refers to an agent or molecule that binds to a receptor of the invention, stimulates, increases, opens, activates, facilitates, enhances activation or enzymatic activity, sensitizes or up regulates the activity of a receptor of the invention.

An "antagonist" or "inhibitor" refers to an agent or molecule that inhibits or binds to, partially or totally blocks stimulation or activity, decreases, closes, prevents, delays activation or enzymatic activity, inactivates, desensitizes, or down regulates the activity of a receptor of the invention. As used herein, "antagonist" also includes a reverse or inverse agonist.

As used herein, the term "condition or disorder responsive to modulation of JAK" and related terms and phrases refer to a condition or disorder associated with inappropriate, e.g., less than or greater than normal, activity of JAK and at least partially responsive to or affected by modulation of JAK (e.g., JAK antagonist or agonist results in some improvement in patient well-being in at least some patients). Inappropriate functional activity of JAK might arise as the result of expression of JAK in cells which normally do not express the receptor, greater than normal production of JAK, or slower than normal metabolic inactivation or elimination of JAK or its active metabolites, increased expression of JAK or degree of intracellular activation (leading to, e.g., inflammatory and immune-related disorders and conditions) or decreased expression of JAK. A condition or disorder associated with JAK may include a "JAK-mediated condition or disorder". Examples of immune-related disorders, include, but are not limited to T-cell mediated disease, an autoimmune disease, host versus graft rejection, graft versus host rejection, a Type IV hypersensitivity reaction and allograft rejection.

As used herein, the phrases "a condition or disorder mediated at least in part by JAK kinase activity", and related phrases and terms refer to a condition or disorder characterized by inappropriate, e.g., greater than normal JAK activity. Inappropriate JAK functional activity might arise as the result of JAK expression in cells which normally do not express JAK or increased JAK expression or degree of intracellular activation (leading to, e.g., inflammatory and immune-related disorders and conditions). A condition or disorder mediated at least in part by JAK kinase activity may be completely or partially mediated by inappropriate JAK functional activity. However, a condition or disorder mediated at least in part by JAK kinase activity is one in which modulation of JAK results in some effect on the underlying condition or disorder (e.g., an JAK antagonist results in some improvement in patient well-being in at least some patients).

The term "inflammation" as used herein refers to infiltration of white blood cells (e.g., leukocytes, monocytes, etc.) into the area being treated for restenosis.

The term "intervention" refers to an action that produces an effect or that is intended to alter the course of a disease process. For example, "vascular intervention" refers to the use of an intravascular procedure such as angioplasty or a stent to open an obstructed blood vessel.

The term "intravascular device" refers to a device useful for a vascular recanalization procedure to restore blood flow through an obstructed blood vessel. Examples of intravascular devices include, without limitation, stents, balloon catheters, autologous venous/arterial grafts, prosthetic venous/arterial grafts, vascular catheters, and vascular shunts.

As used herein, the term "JAK3" refers to a Janus kinase (RefSeq Accession No. NP_000206.2) or a variant thereof that is capable of mediating gene expression in vitro or in vivo. JAK3 variants include proteins substantially homologous to native JAK3, i.e., proteins having one or more naturally or non-naturally occurring amino acid deletions, insertions or substitutions (e.g., JAK3 derivatives, homologs and fragments). The amino acid sequence of JAK3 variant preferably is at least about 80% identical to a native JAK3, more preferably at least about 90% identical, and most preferably at least about 95% identical.

The term "leukocyte" refers to any of the various blood cells that have a nucleus and cytoplasm, separate into a thin white layer when whole blood is centrifuged, and help protect the body from infection and disease. Examples of leukocytes include, without limitation, neutrophils, eosinophils, basophils, lymphocytes, and monocytes.

The term "mammal" includes, without limitation, humans, domestic animals (e.g., dogs or cats), farm animals (cows, horses, or pigs), monkeys, rabbits, mice, and laboratory animals.

The terms "modulate", "modulation" and the like refer to the ability of a compound to increase or decrease the function and/or expression of a JAK kinase, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with a JAK kinase, either directly or indirectly, and/or the upregulation or downregulation of the expression of a JAK kinase, either directly or indirectly. In a preferred embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of a JAK kinase can be demonstrated in a biochemical assay, e.g., binding assay, or a cell-based assay, e.g., a transient transfection assay.

"Modulators" of activity are used to refer to "ligands", "antagonists" and "agonists" identified using in vitro and in vivo assays for activity and their homologs and mimetics. Modulators include naturally occurring and synthetic ligands, antagonists, agonists, molecules and the like. Assays to identify antagonists and agonists include, e.g., applying putative modulator compounds to cells, in the presence or absence of a receptor of the invention and then determining the functional effects on a receptor of the invention activity. Samples or assays comprising a receptor of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a receptor of the invention relative to the control is about 80%, optionally 50% or 25-1%. Activation is achieved when the activity value of a receptor of the invention relative to the control is 110%, optionally 150%, optionally 200-500%, or 1000-3000% higher.

"Patient" refers to human and non-human animals, especially mammals. Examples of patients include, but are not limited to, humans, cows, dogs, cats, goats, sheep, pigs and rabbits.

Turning next to the compositions of the invention, the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

The terms "prevent", "preventing", "prevention" and grammatical variations thereof as used herein, refers to a method of partially or completely delaying or precluding the onset or recurrence of a disorder or condition and/or one or more of its attendant symptoms or barring a subject from acquiring or reacquiring a disorder or condition or reducing a subject's risk of acquiring or reacquiring a disorder or condition or one or more of its attendant symptoms.

The term "recanalization" refers to the process of restoring flow to or reuniting an interrupted channel of the body, such as a blood vessel.

The term "restenosis" refers to a re-narrowing or blockage of an artery at the same site where treatment, such as an angioplasty or a stent procedure, has been performed.

The phrase "selectively" or "specifically" when referring to binding to a receptor, refers to a binding reaction that is determinative of the presence of the receptor, often in a heterogeneous population of receptors and other biologics. Thus, under designated conditions, the compounds bind to a particular receptor at least two times the background and more typically more than 10 to 100 times background. Specific binding of a compound under such conditions requires a compound that is selected for its specificity for a particular receptor. For example, small organic molecules can be screened to obtain only those compounds that specifically or selectively bind to a selected receptor and not with other receptors or proteins. A variety of assay formats may be used to select compounds that are selective for a particular receptor. For example, High-throughput screening assays are routinely used to select compounds that are selective for a particular a receptor.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "thrombosis" refers to the blockage or clotting of a blood vessel caused by a clumping of cells, resulting in the obstruction of blood flow. The term "thrombosis" refers to the clot that is formed within the blood vessel.

The terms "treat", "treating", "treatment" and grammatical variations thereof as used herein, includes partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, pallatively or remedially.

The term "vessel" refers to any channel for carrying a fluid, such as an artery or vein. For example, a "blood vessel" refers to any of the vessels through which blood circulates in the body. The lumen of a blood vessel refers to the inner open space or cavity of the blood vessel.

2. EMBODIMENTS OF THE INVENTION a. Compounds

The present invention provides in another embodiment, a compound having the formula:

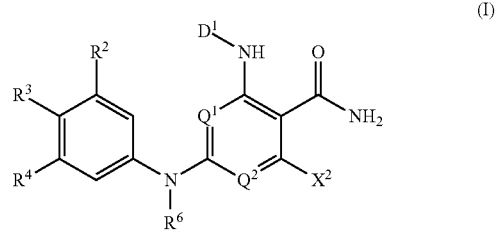

(I)

or a tautomer thereof or a pharmaceutically acceptable salt or hydrate thereof, wherein:

each $Q^1$ and $Q^2$ are selected from the group consisting of $CX^1$ or N; wherein one of $Q^1$ or $Q^2$ is N and one is $CX^1$;

each $X^1$ or $X^2$ is independently H or halogen;

$D^1$ is selected from the group consisting of:

(a) $C_{1-8}$alkyl, $C_{1-8}$alkenyl, or $C_{1-8}$alkynyl;

(b) -$L^1$-phenyl, wherein the phenyl is further optionally substituted with from 1 to 3 substituents, $R^1$, independently selected from the group consisting of $C_{1-8}$alkyl, $C_{1-8}$alkoxy, halo, hydroxy, $C_{1-8}$alkylsulfonyl, $C_{3-8}$cycloalkylsulfonyl, $C_{1-8}$dialkylaminoaminocarbonyl, $C_{1-8}$alkylcarbonyl, $C_{1-8}$alkoxy$C_{1-8}$alkylcarbonyl, $C_{1-8}$alkoxycarbonyl, heterocyclyl, heterocyclyl$C_{1-8}$alkyl, heterocyclylcarbonyl, aryl and heteroaryl, wherein the aryl is further optionally substituted with halo;

(c) -$L^1$-$C_{3-8}$cycloalkyl, wherein the $C_{3-8}$cycloalkyl is further optionally substituted with from 1 to 3 substituents, $R^1$, independently selected from the group consisting of $C_{1-8}$alkyl, $C_{1-8}$alkoxy, halo, hydroxy, $C_{1-8}$alkylsulfonyl, $C_{3-8}$cycloalkylsulfonyl, $C_{1-8}$dialkylaminoaminocarbonyl, $C_{1-8}$alkylcarbonyl, $C_{1-8}$alkoxy$C_{1-8}$alkylcarbonyl, $C_{1-8}$alkoxycarbonyl, heterocyclyl, heterocyclyl $C_{1-8}$alkyl, heterocyclylcarbonyl, aryl and heteroaryl, wherein the aryl is further optionally substituted with halo;

(d) -$L^1$-heteroaryl; wherein the heteroaryl is further optionally substituted with from 1 to 3 substituents, $R^1$, independently selected from the group consisting of $C_{1-8}$alkyl, $C_{1-8}$alkoxy, halo, hydroxy, $C_{1-8}$alkylsulfonyl, $C_{3-8}$cycloalkylsulfonyl, $C_{1-8}$dialkylaminoaminocarbonyl, $C_{1-8}$ alkylcarbonyl, $C_{1-8}$alkoxy$C_{1-8}$alkylcarbonyl, $C_{1-8}$alkoxycarbonyl, heterocyclyl, heterocyclyl $C_{1-8}$alkyl, heterocyclylcarbonyl, aryl and heteroaryl, wherein the aryl is further optionally substituted with halo; and (e) -L$^1$-heterocyclyl; wherein the heterocyclyl is further optionally substituted with from 1 to 3 substituents, R$^1$, independently selected from the group consisting of $C_{1-8}$alkyl, $C_{1-8}$ alkoxy, halo, hydroxy, $C_{1-8}$ alkylsulfonyl, $C_{3-8}$cycloalkylsulfonyl, $C_{1-8}$dialkylaminoaminocarbonyl, $C_{1-8}$alkylcarbonyl, $C_{1-8}$alkoxy$C_{1-8}$alkylcarbonyl, $C_{1-8}$alkoxycarbonyl, heterocyclyl, heterocyclyl$C_{1-8}$alkyl, heterocyclylcarbonyl, aryl and heteroaryl, wherein the aryl is further optionally substituted with halo;

L$^1$ is selected from the group consisting of a bond, —C(R)$_2$—, and CH$_2$CH$_2$;

each R is independently selected from the group consisting of hydrogen, $C_{1-8}$ alkyl, and alkoxy$C_{1-8}$ alkyl;

each R$^2$, R$^3$, and R$^4$ is independently selected from the group consisting of:

$C_{1-8}$alkyl, cyano, halo, halo$C_{1-8}$ alkyl, cyano$C_{1-8}$alkyl, $C_{1-8}$dialkylaminocarbonyl, $C_{1-8}$alkylaminocarbonyl, $C_{1-8}$alkylaminocarbonyl $C_{1-8}$alkyl, halo$C_{1-8}$alkylaminocarbonyl, halo$C_{1-8}$alkylaminocarbonyl $C_{1-8}$alkyl, halo$C_{1-8}$ alkyl($C_{1-8}$alkyl)aminocarbonyl, di$C_{1-8}$alkyl amino, $C_{1-8}$alkoxy, hydroxy$C_{1-8}$ alkyl($C_{1-8}$alkyl)aminocarbonyl, $C_{1-8}$ alkoxy$C_{1-8}$alkyl($C_{1-8}$alkyl)aminocarbonyl, $C_{1-8}$dialkylaminocarbonylamino$C_{1-8}$alkyl, $C_{1-8}$alkylcarbonylamino$C_{1-8}$alkyl, $C_{1-8}$alkylsulfonylamino$C_{1-8}$alkyl, $C_{1-8}$ dialkylaminosulfonylamino $C_{1-8}$alkyl, $C_{1-8}$dialkylaminosulfonyl$C_{1-8}$alkyl, $C_{1-8}$alkylsulfonyl$C_{1-8}$alkyl, halo$C_{1-8}$alkyl, $C_{1-8}$alkylcarbonylamino, $C_{1-8}$alkylsulfonylamino, $C_{1-8}$dialkylaminosulfonyl($C_{1-8}$alkyl)amino, $C_{1-8}$dialkylaminosulfonylamino, $C_{1-8}$alkylcarbonyl($C_{1-8}$alkyl)amino, $C_{1-8}$alkoxycarbonyl($C_{1-8}$alkyl)amino, $C_{1-8}$alkoxy $C_{1-8}$alkoxy, cyano$C_{1-8}$alkyl$C_{1-8}$alkoxy, $C_{1-8}$dialkylaminocarbonyl$C_{1-8}$alkoxy, halo$C_{1-8}$alkoxy, $C_{1-8}$dialkylaminosulfonyl, $C_{1-8}$alkylsulfonyl, heteroaryl, heterocycylcarbonyl, $C_{3-8}$cycloalkylcarbonyl($C_{1-8}$alkyl) amino, $C_{3-8}$cycloalkylcarbonylamino, heterocyclylsulfonyl, heterocyclyl$C_{1-8}$alkoxy, heterocyclylcarbonylamino, heterocyclylcarbonyl$C_{1-8}$alkoxy, heterocyclylalkyl, heterocyclyl;

or are combined to form a heteroaryl moiety is selected from the group consisting of:

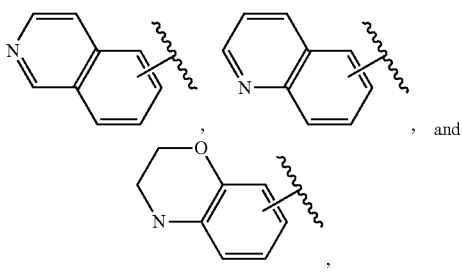

optionally substituted with from 1 to 3 R$^7$ substituents independently selected from the group consisting of: $C_{1-8}$ alkyl and oxo; and the wavy line indicates the point of attachment to the rest of the molecule;

wherein heterocyclyl is optionally substituted with 1 to 3 substituents, R$^5$, independently selected from the group consisting of $C_{1-8}$alkyl, halo, cyano$C_{1-8}$alkyl, halo $C_{1-8}$alkyl, $C_{1-8}$dialkylaminocarbonyl, $C_{1-8}$alkylsulfonyl, $C_{1-8}$ alkoxycarbonyl, $C_{1-8}$alkylcarbonyl, $C_{1-8}$alkoxy$C_{1-8}$alkylcarbonyl, formyl, heterocyclylcarbonyl, $C_{1-8}$alkylheterocyclylcarbonyl, $C_{1-8}$alkylcarbonylheterocyclylcarbonyl, $C_{1-8}$dialkylaminosulfonyl, heteraryl, oxo, cyano$C_{1-8}$alkylcarbonyl, cyano $C_{3-8}$cycloalkylcarbonyl, $C_{3-8}$cycloalkylsulfonyl, $C_{3-8}$cycloalkyl, $C_{1-8}$dialkylamino$C_{1-8}$alkylcarbonyl, $C_{1-8}$alkoxy$C_{1-8}$alkyl, hydroxy, $C_{1-8}$alkylsulfonyl, $C_{1-8}$heteroalkyl, heterocyclyl$C_{1-8}$alkoxy, or heterocyclyl; and R$^6$ is H or acyl.

The present invention provides in another group of embodiments, a compound having the formula:

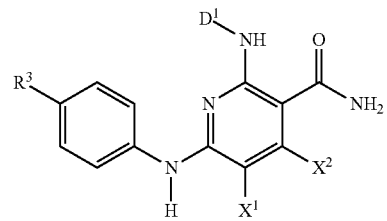

or a tautomer thereof or a pharmaceutically acceptable salt or hydrate thereof.

The present invention provides in another group of embodiments, a compound having the formula:

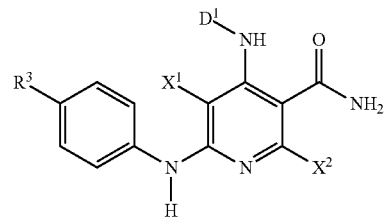

or a tautomer thereof or a pharmaceutically acceptable salt or hydrate thereof.

The present invention provides in another group of embodiments, a compound having the formula:

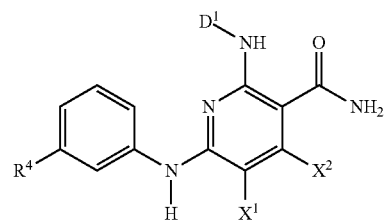

or a tautomer thereof or a pharmaceutically acceptable salt or hydrate thereof.

The present invention provides in another group of embodiments, a compound having the formula:

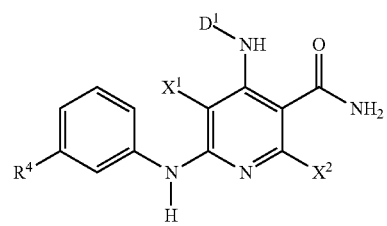

or a tautomer thereof or a pharmaceutically acceptable salt or hydrate thereof.

The present invention provides in another group of embodiments, a compound wherein $X^1$ is H. The present invention provides in another group of embodiments, a compound wherein $X^1$ is halogen. The present invention provides in another group of embodiments, a compound wherein $X^1$ is F.

The present invention provides in another group of embodiments, a compound wherein $D^1$ is $C_{1-8}$alkyl. The present invention provides in another group of embodiments, a compound wherein $D^1$ is -$L^1$-phenyl. The present invention provides in another group of embodiments, a compound wherein $D^1$ is -$L^1$-$C_{3-8}$cycloalkyl. The present invention provides in another group of embodiments, a compound wherein $D^1$ is selected from the group consisting of cyclopentyl, cyclobutyl and cyclopropyl. The present invention provides in another group of embodiments, a compound wherein D1 is -$L^1$-heteroaryl. The present invention provides in another group of embodiments, a compound wherein heteroaryl is selected from the group consisting of triazoyl, thiophenyl, thiazoyl, pyrazoyl, imidazoyl, pyridinyl, pyrimidyl, benzothiophenyl, indolyl, benzimidazoyl and benzodioxoyl. The present invention provides in another group of embodiments, a compound wherein D1 is -$L^1$-heterocyclyl. The present invention provides in another group of embodiments, a compound wherein heterocyclyl is selected from the group consisting of tetrahydropyranyl and piperidinyl.

The present invention provides in another group of embodiments, a compound wherein L is a bond. The present invention provides in another group of embodiments, a compound wherein L is —$C(R)_2$—.

The present invention provides in another group of embodiments, a compound wherein R is H.

The present invention provides in another group of embodiments, a compound wherein the moiety:

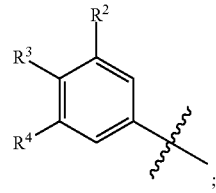

is selected from the group consisting of:

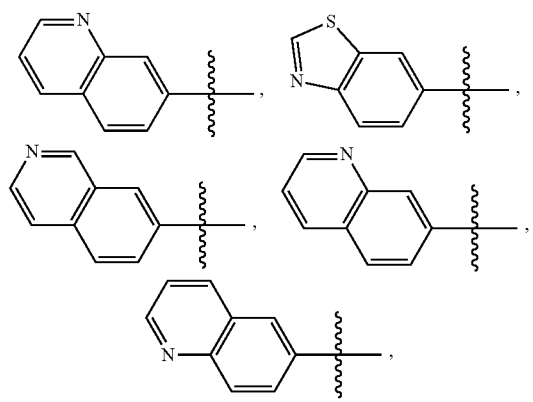

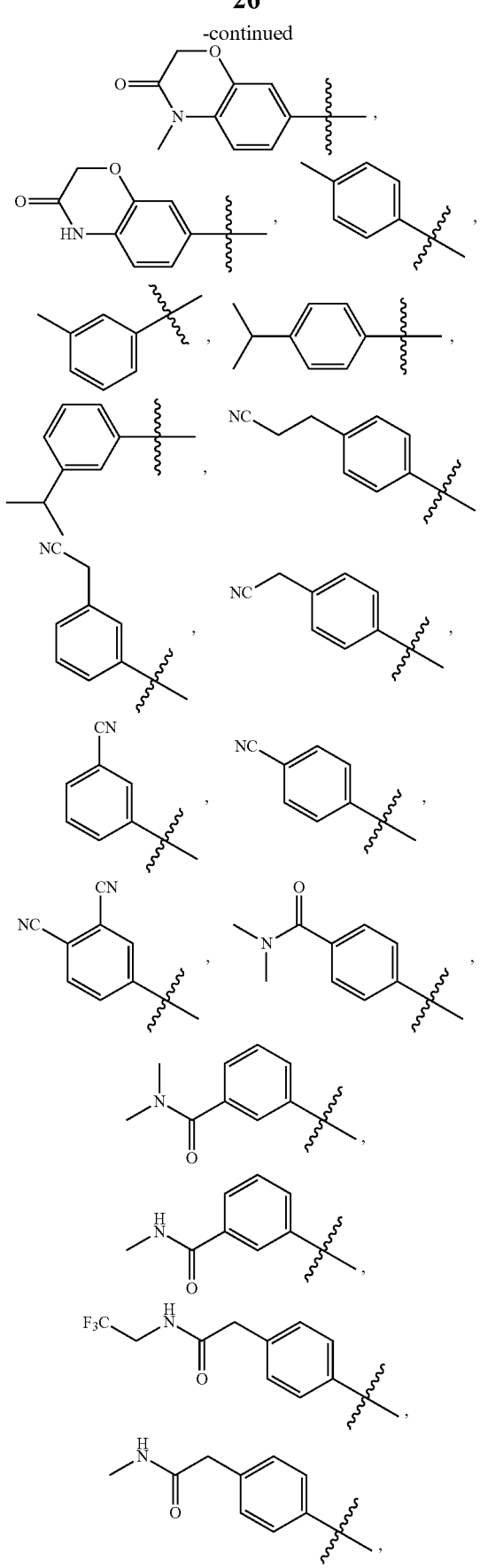

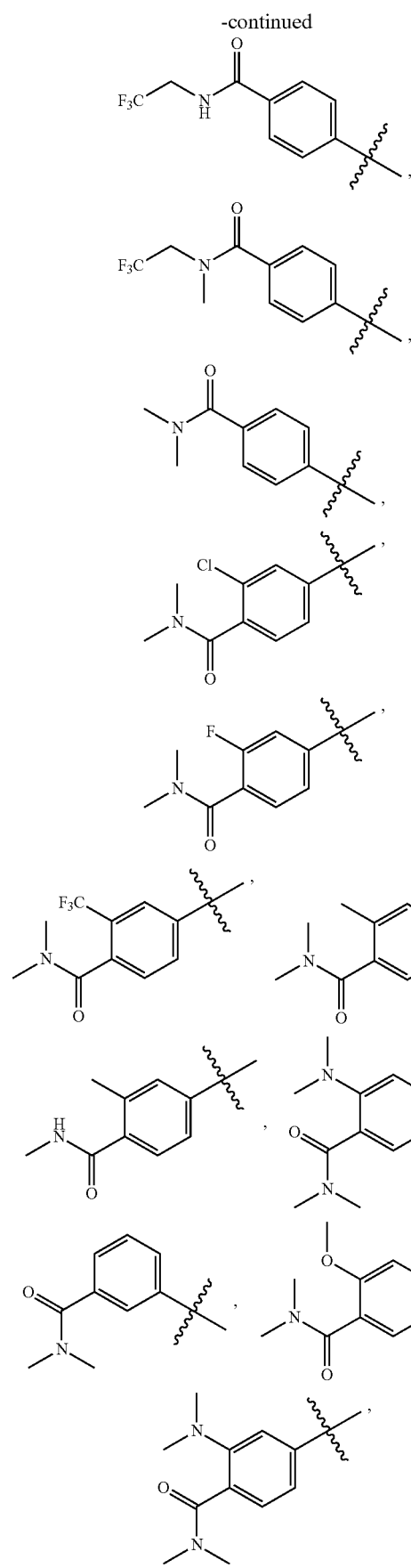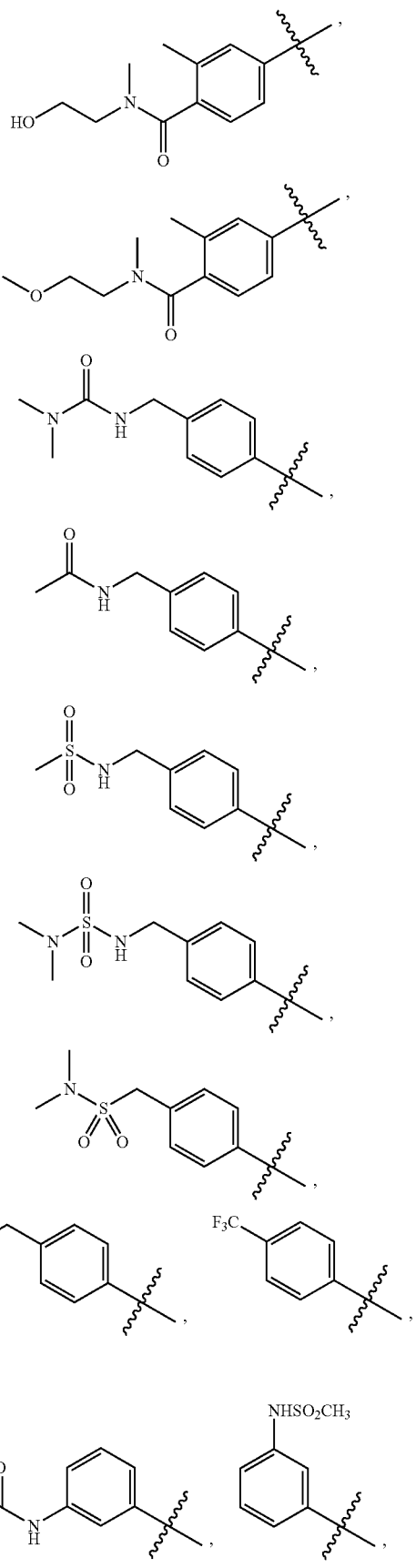

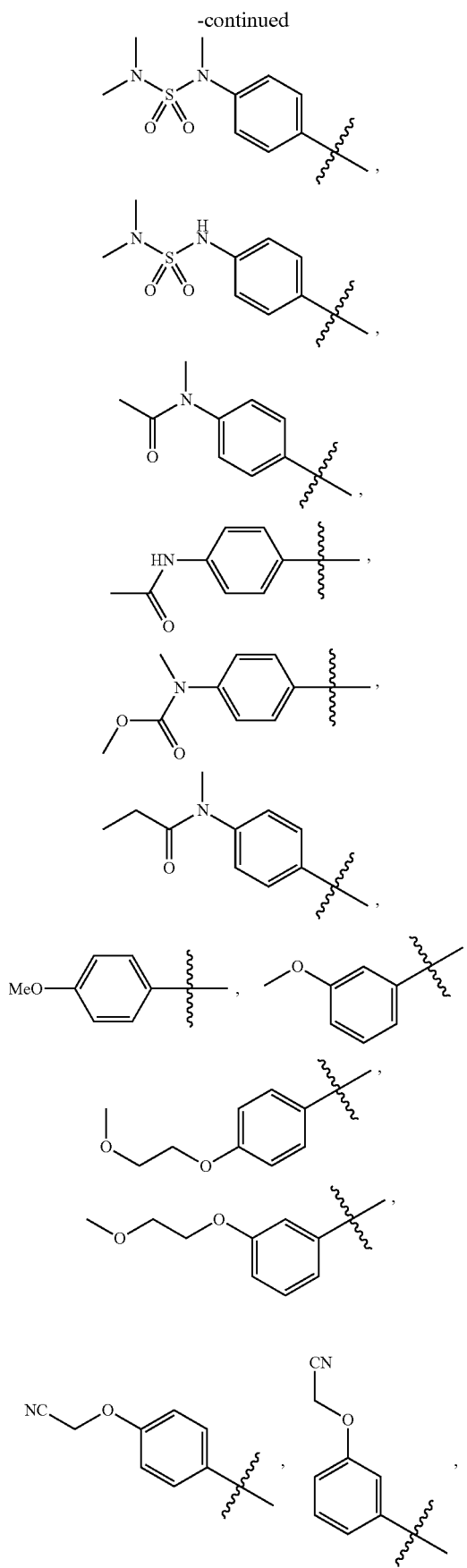
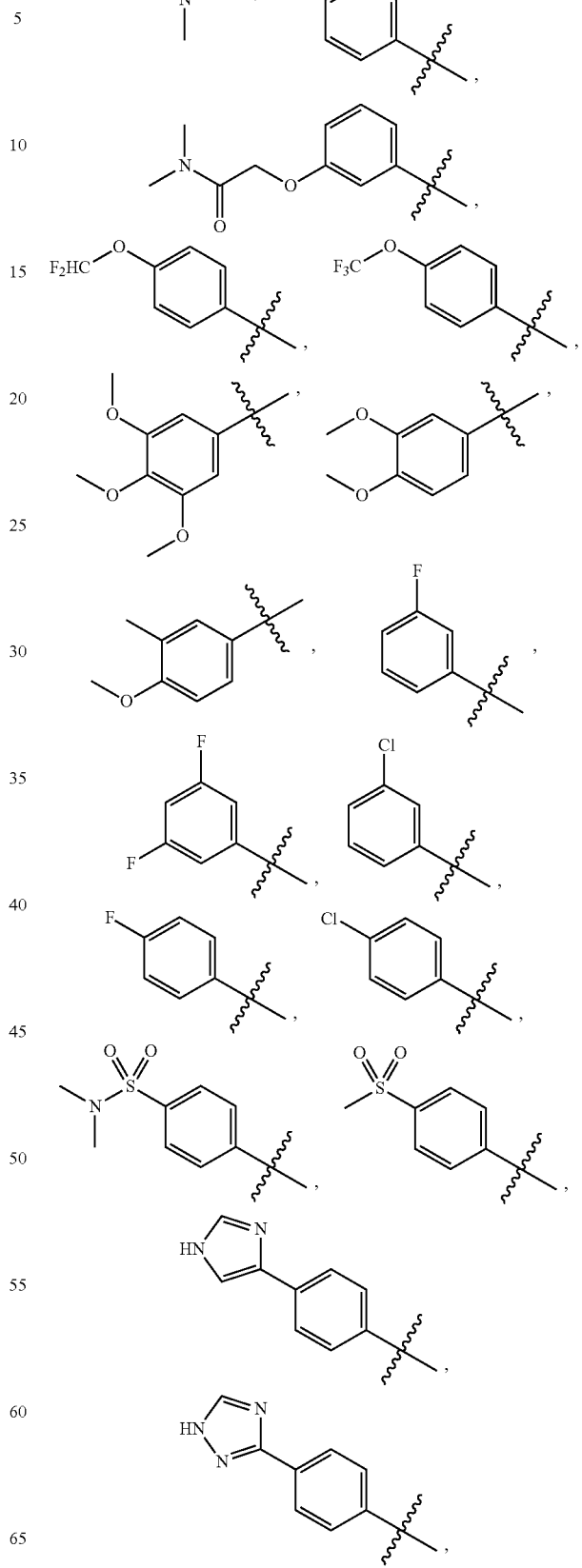

31
-continued
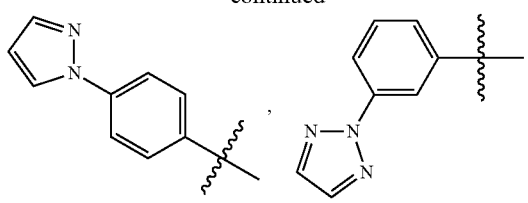
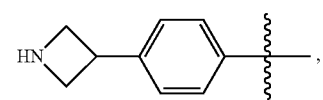
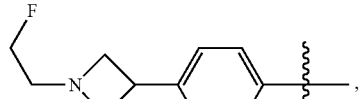
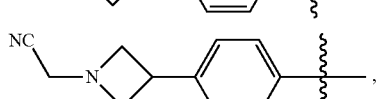
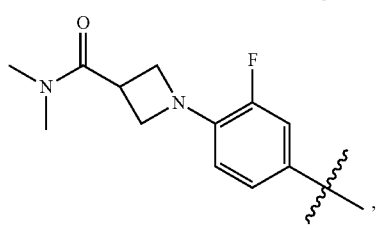
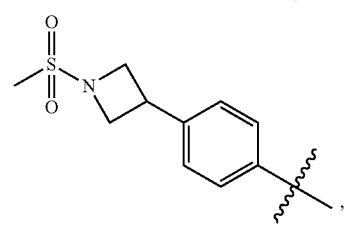
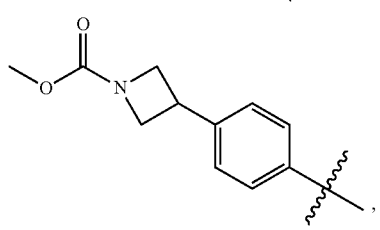
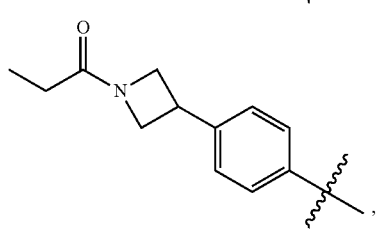
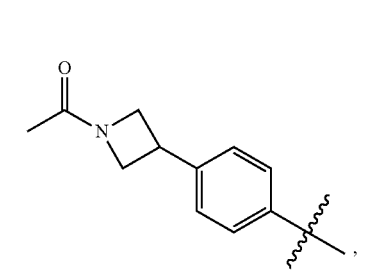
32
-continued
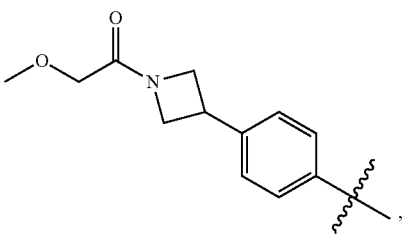
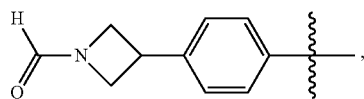
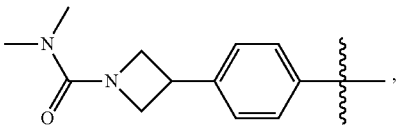
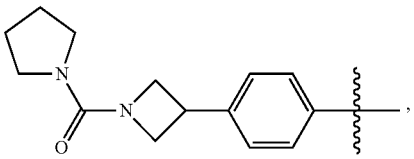
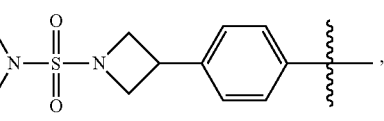
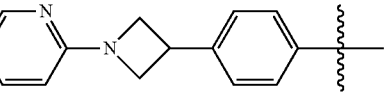
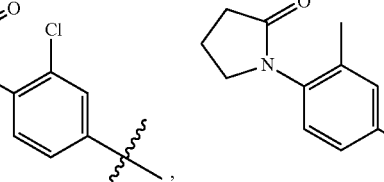
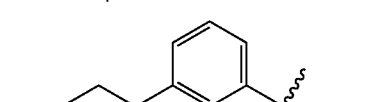
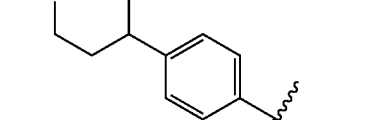
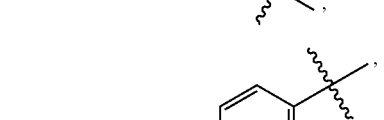
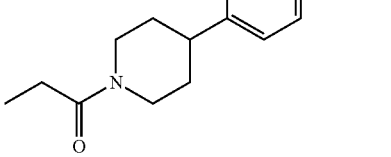

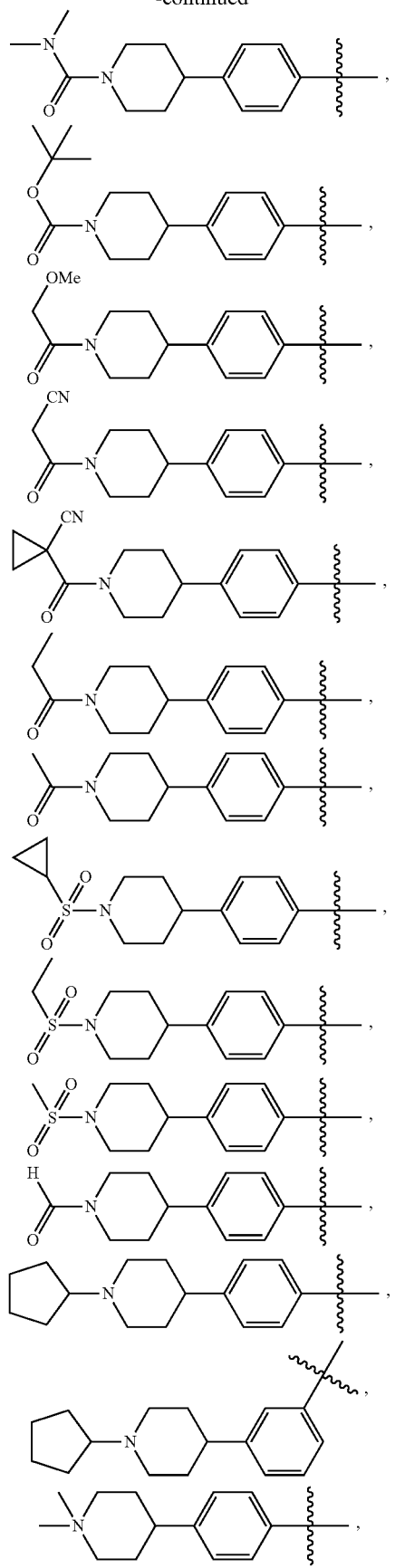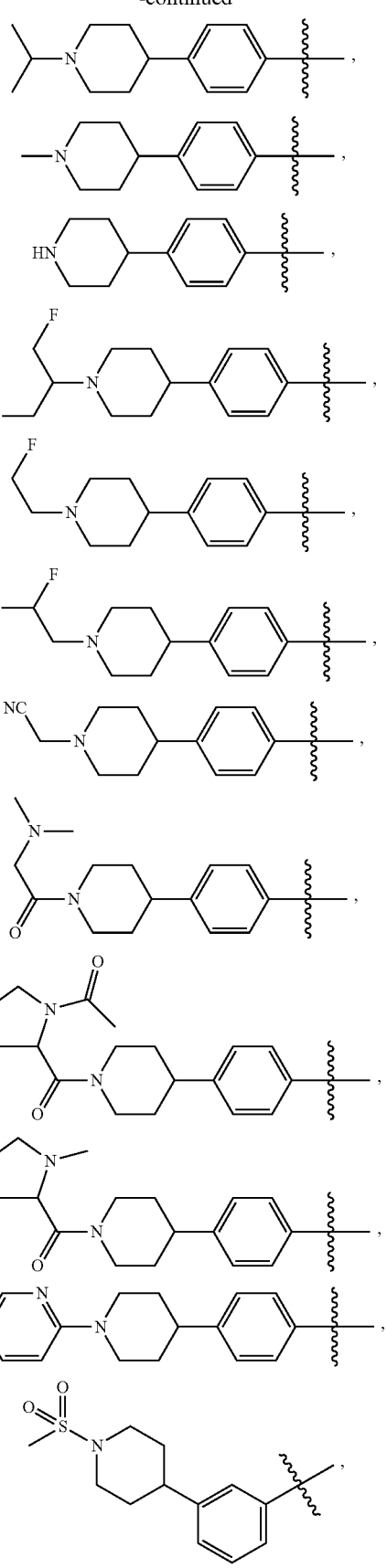

35
-continued
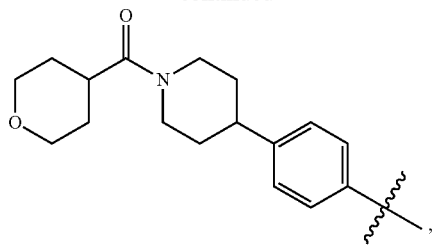
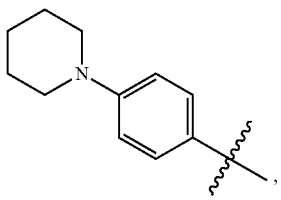
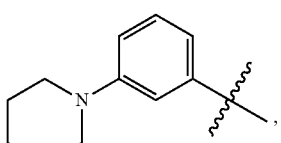
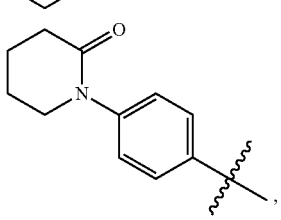
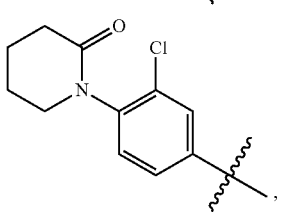
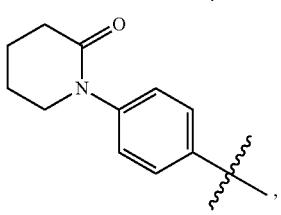
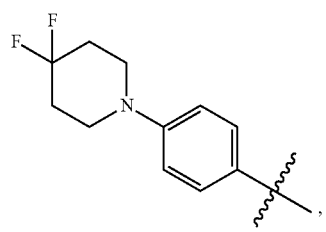
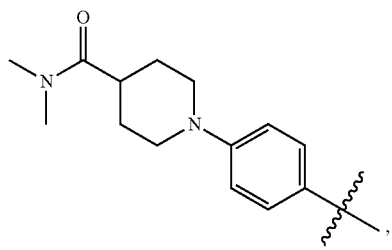
36
-continued
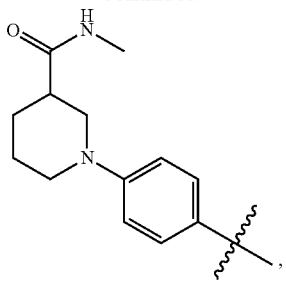
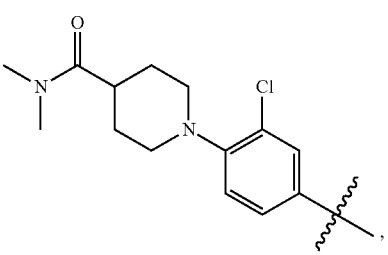
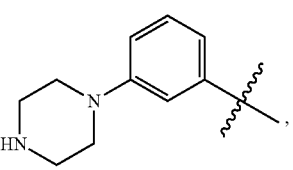
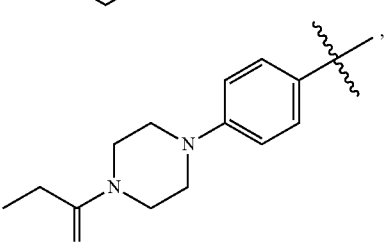
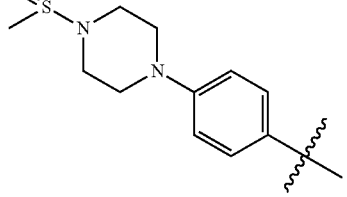
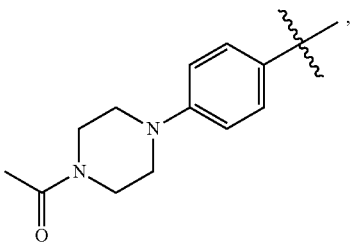
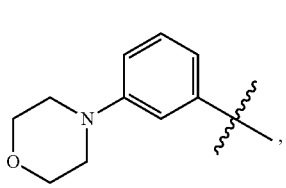

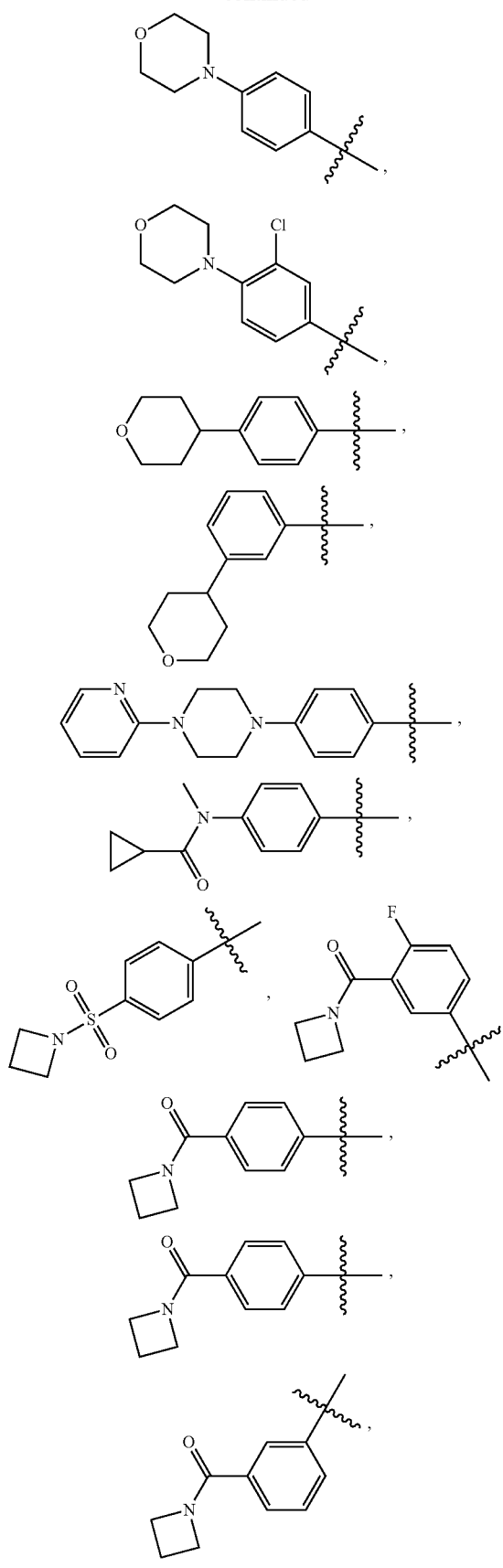
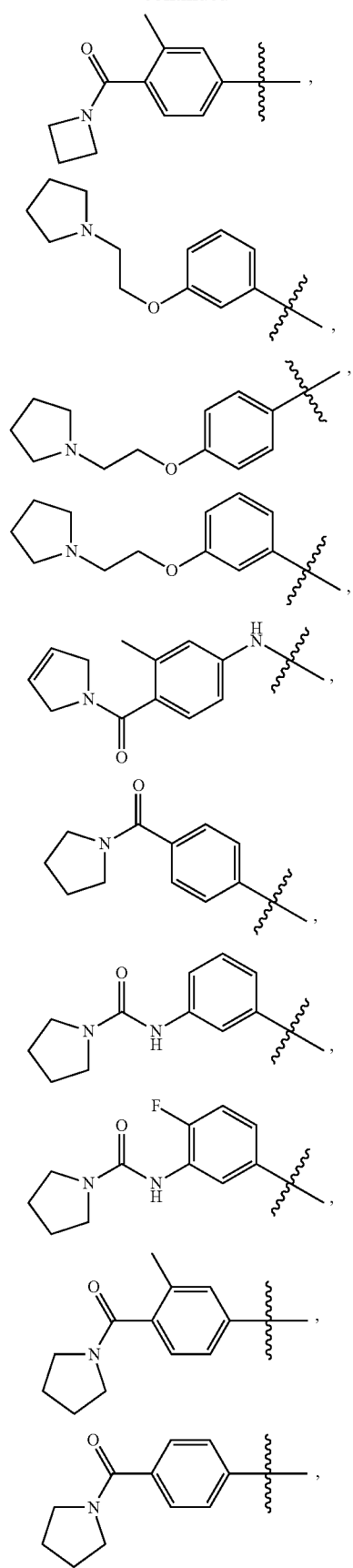

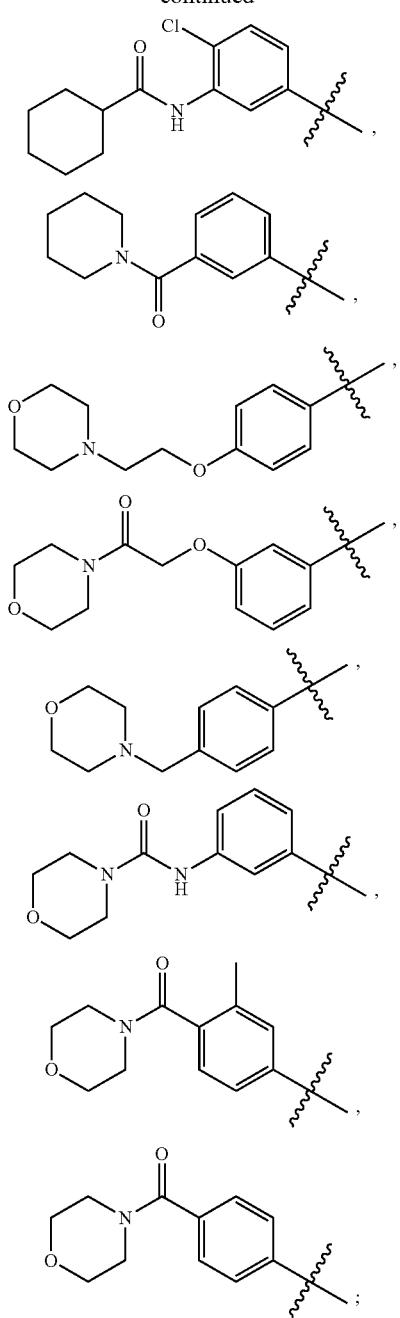

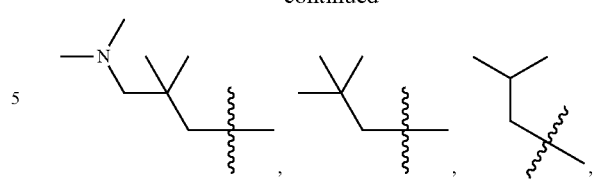

and the wavy line indicates the point of attachment to the rest of the molecule.

The present invention provides in another group of embodiments, a compound wherein $D^1$ is selected from the group consisting of:

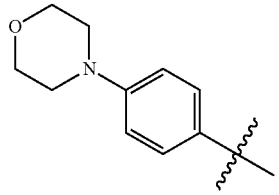

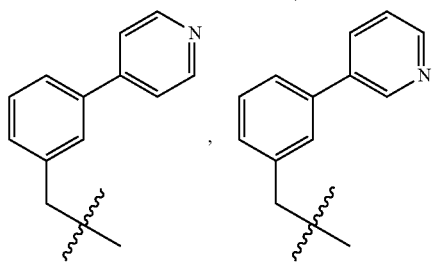

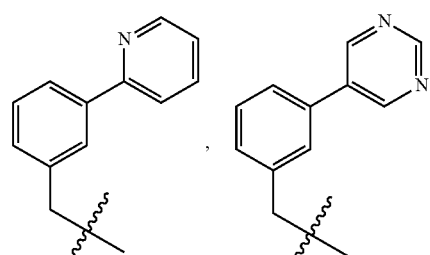

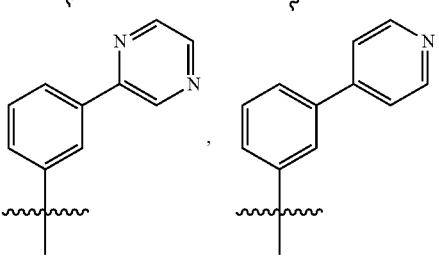

and the wavy line indicates the point of attachment to the rest of the molecule.

The present invention provides in another group of embodiments, a compound wherein $D^1$ is selected from the group consisting of:

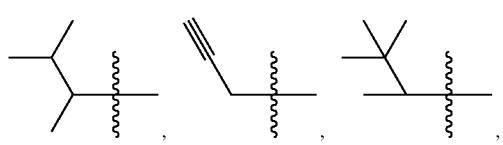

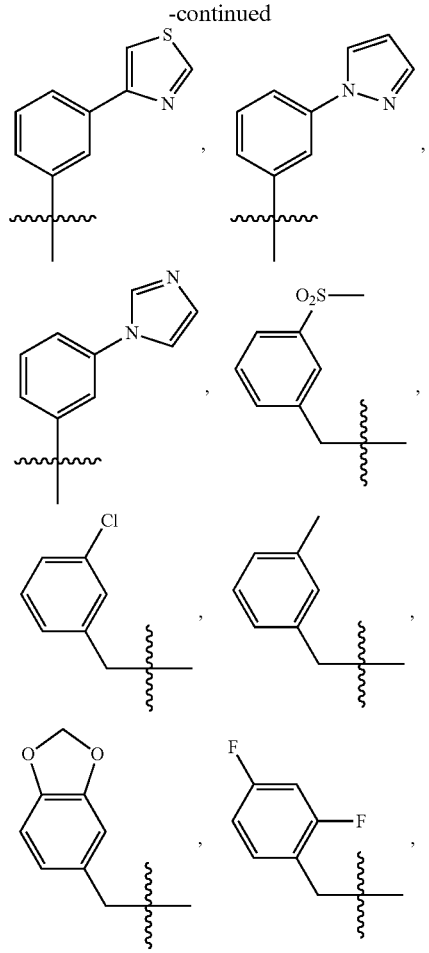
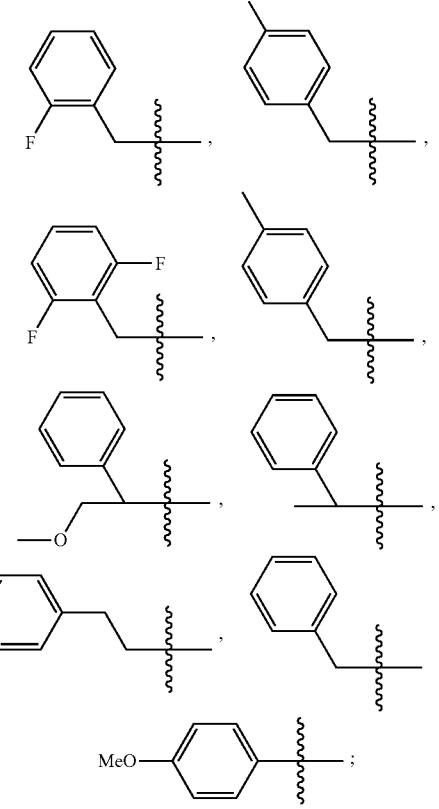
and the wavy line indicates the point of attachment to the rest of the molecule.
The present invention provides in another group of embodiments, a compound wherein $D^1$ is selected from the group consisting of:
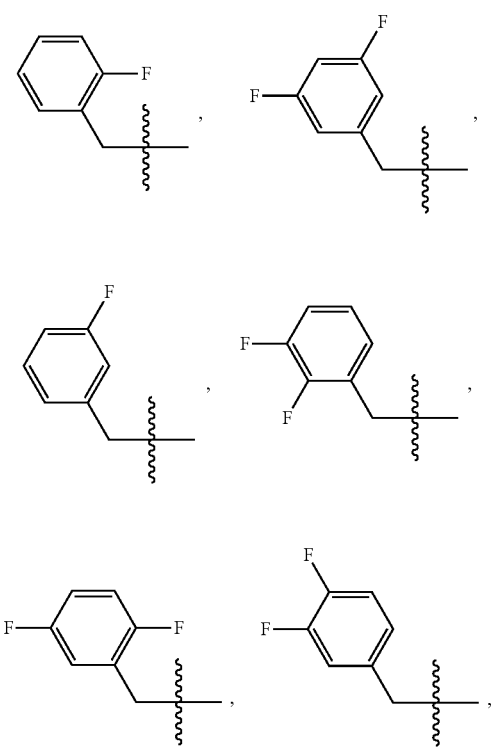
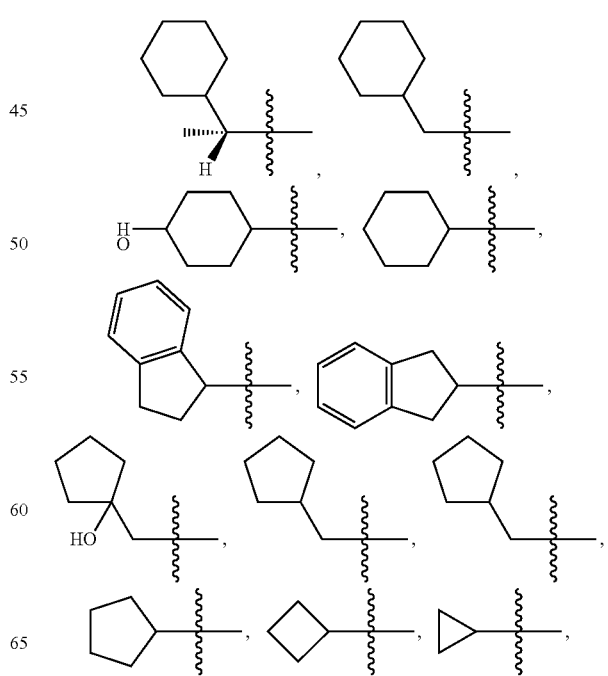

-continued

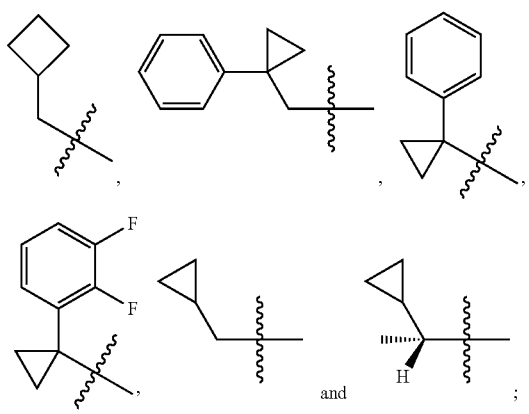

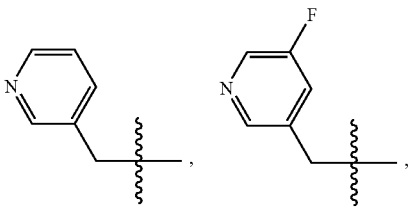

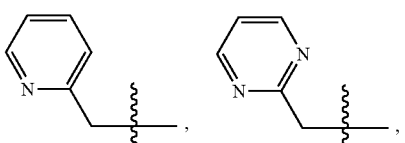

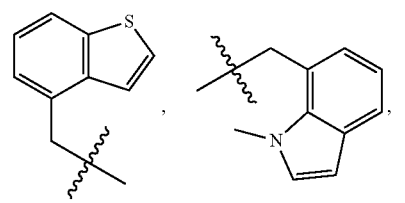

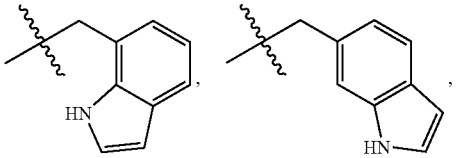

and the wavy line indicates the point of attachment to the rest of the molecule.

The present invention provides in another group of embodiments, a compound wherein $D^1$ is selected from the group consisting of:

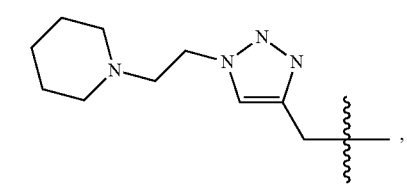

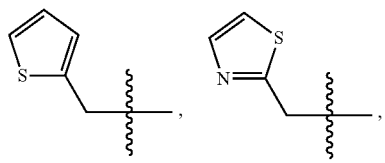

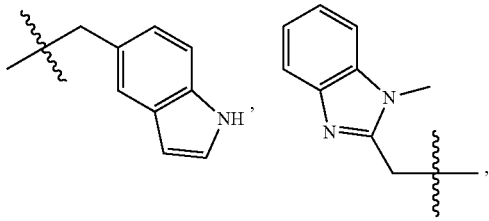

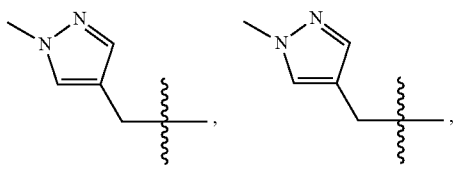

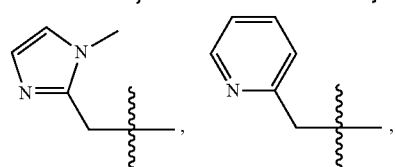

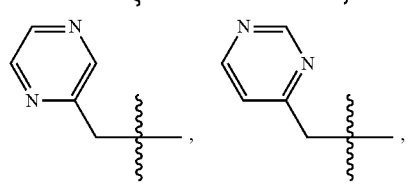

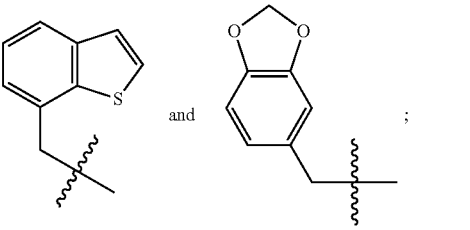

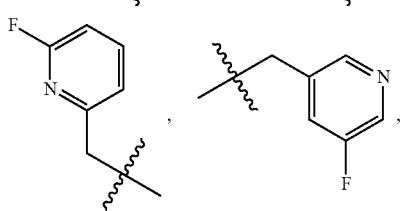

and the wavy line indicates the point of attachment to the rest of the molecule.

The present invention provides in another group of embodiments, a compound wherein $D^1$ is selected from the group consisting of:

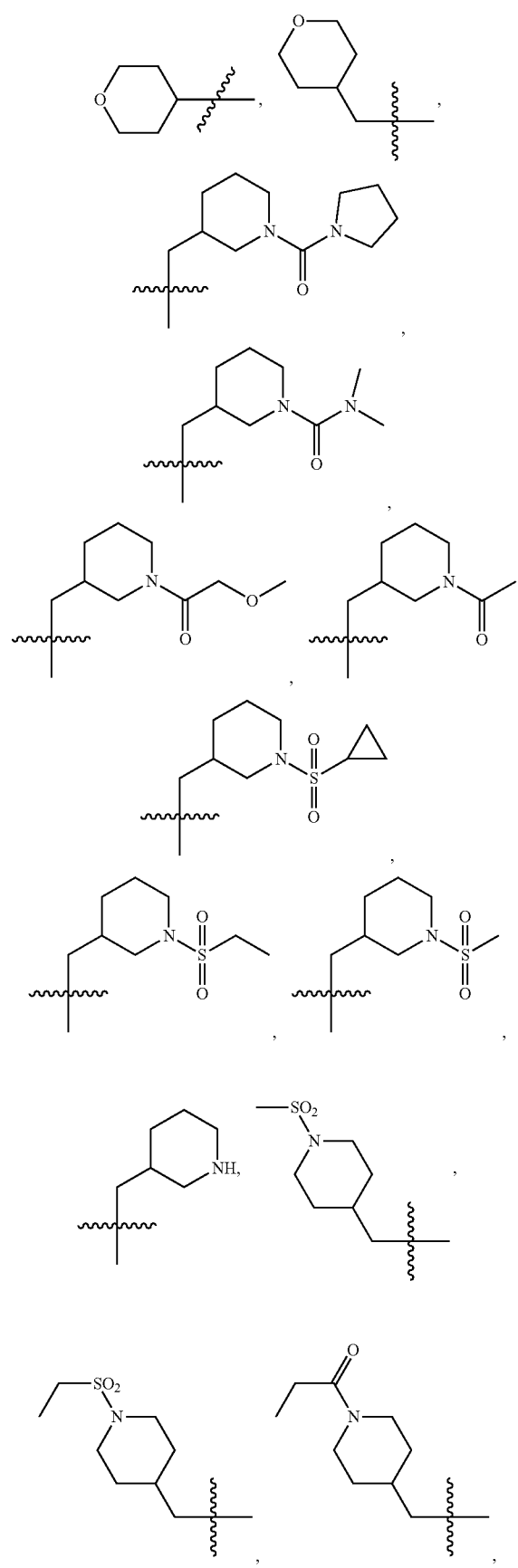

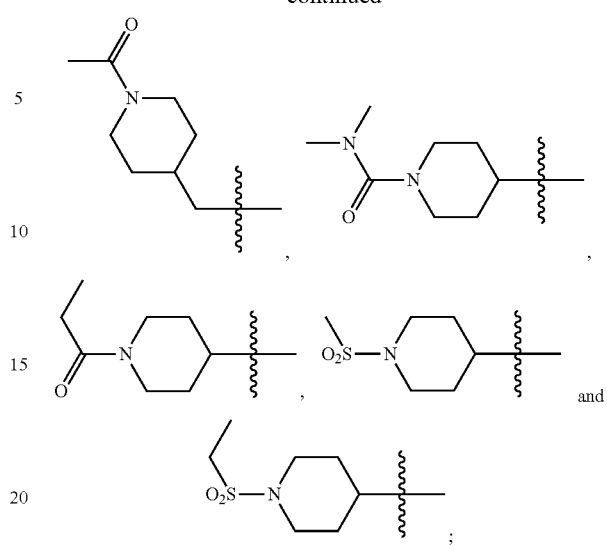

and the wavy line indicates the point of attachment to the rest of the molecule.

The present invention provides in another group of embodiments, a compound having the formula:

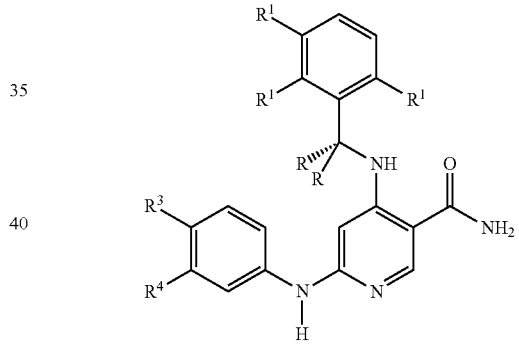

or a tautomer or pharmaceutically acceptable salt thereof.

The present invention provides in another group of embodiments, a compound having the formula:

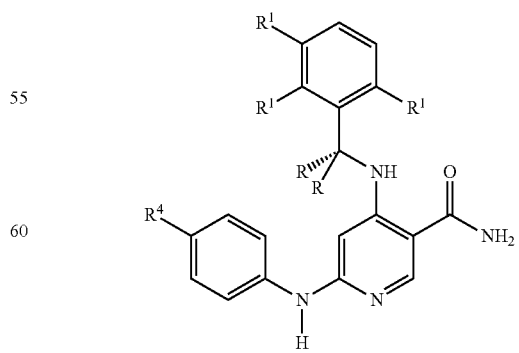

or a tautomer or pharmaceutically acceptable salt thereof.

The present invention provides in another group of embodiments, a compound having the formula:

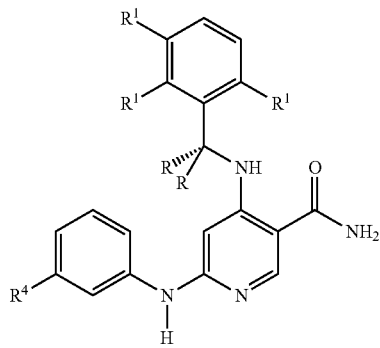

or a tautomer or pharmaceutically acceptable salt thereof.

The present invention provides in another group of embodiments, a compound selected from the group consisting of: 6-(4-(4-acetylpiperazin-1-yl)phenylamino)-2-(cyclobutylamino)nicotinamide; 6-(4-(4-acetylpiperazin-1-yl)phenylamino)-4-(benzylamino)nicotinamide; (S)-4-(benzylamino)-6-(4-(3-(methylcarbamoyl)piperidin-1-yl)phenylamino)nicotinamide; 6-(4-(4-acetylpiperazin-1-yl)-3-methylphenylamino)-4-(benzylamino)nicotinamide; (R)-4-(benzylamino)-6-(4-(3-(methylcarbamoyl)piperidin-1-yl)phenylamino)nicotinamide; (-(benzylamino)-6-(3-morpholinophenylamino)nicotinamide; 6-(4-fluoro-3-(pyrrolidine-1-carboxamido)phenylamino)-4-(pyridin-3-ylmethylamino)nicotinamide; (-(4-(4-acetylpiperazin-1-yl)phenylamino)-4-(phenethylamino)nicotinamide; 4-(benzylamino)-6-(4-(dimethylcarbamoyl)phenylamino)-N,N-dimethylnicotinamide; 4-(cyclopentylmethylamino)-6-(4-methoxyphenylamino)nicotinamide; 6-(4-methoxyphenylamino)-4-(p-tolylamino)nicotinamide; 4,6-bis(4-methoxyphenylamino)nicotinamide; 4-((1-acetylpiperidin-4-yl)methylamino)-6-(4-methoxyphenylamino)nicotinamide; (S)-4-(1-acetylpiperidin-3-ylamino)-6-(4-methoxyphenylamino)nicotinamide; (R)-4-(1-acetylpiperidin-3-ylamino)-6-(4-methoxyphenylamino)nicotinamide; (S)-4-((1-acetylpiperidin-3-yl)methylamino)-6-(4-methoxyphenylamino)nicotinamide; 4-(benzylamino)-6-(4-(pyrrolidine-1-carbonyl)phenylamino)nicotinamide; 4-(benzylamino)-6-(4-(morpholine-4-carbonyl)phenylamino)nicotinamide; 4-(cyclopentylmethylamino)-6-(4-(pyrrolidine-1-carbonyl)phenylamino)nicotinamide; 4-(cyclopentylmethylamino)-6-(4-(morpholine-4-carbonyl)phenylamino)nicotinamide; 4-((1-acetylpiperidin-4-yl)methylamino)-6-(4-(pyrrolidine-1-carbonyl)phenylamino)nicotinamide; 4-((1-acetylpiperidin-4-yl)methylamino)-6-(4-(morpholine-4-carbonyl)phenylamino)nicotinamide; 6-(3-(azetidine-1-carbonyl)phenylamino)-4-(benzylamino)nicotinamide; 6-(4-(azetidine-1-carbonyl)phenylamino)-4-(benzylamino)nicotinamide; 6-(4-(azetidin-1-ylsulfonyl)phenylamino)-4-(benzylamino)nicotinamide; 6-(4-(azetidine-1-carbonyl)phenylamino)-4-(cyclopentylmethylamino)nicotinamide; 6-(4-(azetidin-1-ylsulfonyl)phenylamino)-4-(cyclopentylmethylamino)nicotinamide; 4-((1-acetylpiperidin-4-yl)methylamino)-6-(4-(azetidine-1-carbonyl)phenylamino)nicotinamide; (S)-4-((1-(2-methoxyacetyl)piperidin-3-yl)methylamino)-6-(4-methoxyphenylamino)nicotinamide; (S)-methyl 3-((5-carbamoyl-2-(4-methoxyphenylamino)pyridin-4-ylamino)methyl)piperidine-1-carboxylate; (S)-4-((1-(dimethylcarbamoyl)piperidin-3-yl)methylamino)-6-(4-methoxyphenylamino)nicotinamide; (R)-4-((1-acetylpiperidin-3-yl)methylamino)-6-(4-methoxyphenylamino)nicotinamide; (R)-4-(1-(2-methoxyacetyl)piperidin-3-yl)methylamino)-6-(4-methoxyphenylamino)nicotinamide; (R)-methyl 3-((5-carbamoyl-2-(4-methoxyphenylamino)pyridin-4-ylamino)methyl)piperidine-1-carboxylate; (R)-6-(4-methoxyphenylamino)-4-((1-(methylsulfonyl)piperidin-3-yl)methylamino)nicotinamide; 4-(3-fluorobenzylamino)-6-(3-(2-(pyrrolidin-1-yl)ethoxy)phenylamino)nicotinamide; (S)-4-(2-hydroxy-1-phenylethylamino)-6-(3-(2-(pyrrolidin-1-yl)ethoxy)phenylamino)nicotinamide; 4-(pyridin-3-ylmethylamino)-6-(3-(2-(pyrrolidin-1-yl)ethoxy)phenylamino)nicotinamide; 4-(3-fluorobenzylamino)-6-(3-methyl-4-(2-oxopyrrolidin-1-yl)phenylamino)nicotinamide; 6-(3-chloro-4-(2-oxopyrrolidin-1-yl)phenylamino)-4-(3-fluorobenzylamino)nicotinamide; 4-(3-fluorobenzylamino)-6-(4-(2-oxopiperidin-1-yl)phenylamino)nicotinamide; 4-(3-fluorobenzylamino)-6-(3-morpholinophenylamino)nicotinamide; (6) 4-(3-fluorobenzylamino)-6-(3-morpholinophenylamino)nicotinamide; 4-(3-fluorobenzylamino)-6-(4-morpholinophenylamino)nicotinamide; 4-(3-fluorobenzylamino)-6-(3-(piperidin-1-yl)phenylamino)nicotinamide; 4-(3-fluorobenzylamino)-6-(3-(piperidin-1-yl)phenylamino)nicotinamide; 4-(3-fluorobenzylamino)-6-(4-(piperidin-4-yl)phenylamino)nicotinamide; 4-(2-fluorobenzylamino)-6-(4-(2-oxopiperidin-1-yl)phenylamino)nicotinamide; 4-(2-fluorobenzylamino)-6-(3-(2-(pyrrolidin-1-yl)ethoxy)phenylamino)nicotinamide; 4-(2-fluorobenzylamino)-6-(4-morpholinophenylamino)nicotinamide; 4-(2-fluorobenzylamino)-6-(4-(piperidin-1-yl)phenylamino)nicotinamide; (S)-4-(2-hydroxy-1-phenylethylamino)-6-(4-(piperidin-1-yl)phenylamino)nicotinamide; (S)-4-(2-hydroxy-1-phenylethylamino)-6-(3-(piperidin-1-yl)phenylamino)nicotinamide; tert-butyl 4-(4-(5-carbamoyl-4-(3-fluorobenzylamino)pyridin-2-ylamino)phenyl)piperidine-1-carboxylate; 4-(4-(5-carbamoyl-4-(3-fluorobenzylamino)pyridin-2-ylamino)phenyl)-1,1-dimethylpiperidinium formate; (-(2-fluorobenzylamino)-6-(4-(1-propionylpiperidin-4-yl)phenylamino)nicotinamide; 4-(benzylamino)-6-(4-(2-morpholino-2-oxoethoxy)phenylamino)nicotinamide; 4-(benzylamino)-6-(4-(2-(piperidin-1-yl)ethoxy)phenylamino)nicotinamide; 4-(2,6-difluorobenzylamino)-6-(4-methoxyphenylamino)nicotinamide; 4-(2,5-difluorobenzylamino)-6-(4-methoxyphenylamino)nicotinamide; 4-(benzylamino)-6-(3-oxo-3,4-dihydro-2H-benzo[b][1,4]oxazin-6-ylamino)nicotinamide; 4-(benzylamino)-6-(4-methyl-3-oxo-3,4-dihydro-2H-benzo[b][1,4]oxazin-6-ylamino)nicotinamide; 4-(benzylamino)-6-(quinolin-6-ylamino)nicotinamide; 4-(benzylamino)-6-(quinolin-7-ylamino)nicotinamide; 4-(benzylamino)-6-(isoquinolin-6-ylamino)nicotinamide; 4-(benzylamino)-6-(isoquinolin-7-ylamino)nicotinamide; 6-(benzo[d]thiazol-6-ylamino)-4-(benzylamino)nicotinamide; 4-(3-fluorobenzylamino)-6-(4-methoxyphenylamino)nicotinamide; 4-(2,5-difluorobenzylamino)-6-(4-(dimethylcarbamoyl)phenylamino)nicotinamide; 6-(4-(azetidine-1-carbonyl)phenylamino)-4-(2,5-difluorobenzylamino)nicotinamide; 4-(2,5-difluorobenzylamino)-6-(4-(2-oxopiperidin-1-yl)phenylamino)nicotinamide; 4-(cyclopentylmethylamino)-6-(3-(dimethylcarbamoyl)phenylamino)nicotinamide; 4-(cyclopentylmethylamino)-6-(4-(dimethylcarbamoyl)phenylamino)nicotinamide; 4-(cyclopentylmethylamino)-6-(4-(N,N-dimethylsulfamoyl)phenylamino)nicotinamide; 4-(2, 5-difluorobenzylamino)-6-(4-(N,N-dimethylsulfamoyl) phenylamino)nicotinamide; 6-(3-(azetidine-1-carbonyl) phenylamino)-4-(2,5-difluorobenzylamino)nicotinamide; 2-(4-(azetidin-1-ylsulfonyl)phenylamino)-4-(benzylamino) pyrimidine-5-carboxamide; 4-(2,3-difluorobenzylamino)-6-(4-methoxyphenylamino)nicotinamide; 4-(2,6-difluorobenzylamino)-6-(4-(dimethylcarbamoyl)phenylamino) nicotinamide; 4-(2,6-difluorobenzylamino)-6-(4-(2-oxopiperidin-1-yl)phenylamino)nicotinamide; 4-(2,6-difluorobenzylamino)-6-(4-(N,N-dimethylsulfamoyl) phenylamino)nicotinamide; 6-(4-(azetidine-1-carbonyl) phenylamino)-4-(2,6-difluorobenzylamino)nicotinamide; 4-(2-fluorobenzylamino)-6-(4-(piperidin-4-yl)phenylamino)nicotinamide; 4-(2-fluorobenzylamino)-6-(4-(1-methylpiperidin-4-yl)phenylamino)nicotinamide; 4-(2-fluorobenzylamino)-6-(4-(1-isopropylpiperidin-4-yl) phenylamino)nicotinamide; 6-(4-(1-cyclopentylpiperidin-4-yl)phenylamino)-4-(2-fluorobenzylamino)nicotinamide; 6-(3-(1-cyclopentylpiperidin-4-yl)phenylamino)-4-(2-fluorobenzylamino)nicotinamide; 4-(2-fluorobenzylamino)-6-(4-(1-(methylsulfonyl)piperidin-4-yl)phenylamino)nicotinamide; 6-(4-(1-(ethylsulfonyl)piperidin-4-yl) phenylamino)-4-(2-fluorobenzylamino)nicotinamide; 6-(4-(1-(cyclopropylsulfonyl)piperidin-4-yl)phenylamino)-4-(2-fluorobenzylamino)nicotinamide; 6-(4-(1-(dimethylcarbamoyl)piperidin-4-yl)phenylamino)-4-(2-fluorobenzylamino)nicotinamide; 6-(4-(1-acetylpiperidin-4-yl)phenylamino)-4-(2-fluorobenzylamino)nicotinamide; 4-(2-fluorobenzylamino)-6-(4-(1-(2-methoxyacetyl)piperidin-4-yl)phenylamino)nicotinamide; 6-(4-(1-(2-cyanoacetyl)piperidin-4-yl)phenylamino)-4-(2-fluorobenzylamino)nicotinamide; 6-(4-(1-(1-cyanocyclopropanecarbonyl)piperidin-4-yl)phenylamino)-4-(2-fluorobenzylamino)nicotinamide; 4-(2-fluorobenzylamino)-6-(4-(1-(tetrahydro-2H-pyran-4-carbonyl)piperidin-4-yl)phenylamino)nicotinamide; 4-(2-fluorobenzylamino)-6-(3-(piperidin-4-yl)phenylamino) nicotinamide; Preparation of 4-(2-fluorobenzylamino)-6-(3-(1-(methylsulfonyl)piperidin-4-yl)phenylamino) nicotinamide; 6-(4-(4-acetylpiperazin-1-yl)phenylamino)-4-(thiophen-2-ylmethylamino)nicotinamide; 6-(4-(4-acetylpiperazin-1-yl)phenylamino)-4-((1s,4s)-4-hydroxycyclohexylamino)nicotinamide; 4-(1-phenylcyclopropylamino)-6-(4-(4-propionylpiperazin-1-yl) phenylamino)nicotinamide; 6-(4-morpholinophenylamino)-4-(1-phenylcyclopropylamino)-nicotinamide; 6-(4-(4-acetylpiperazin-1-yl)phenylamino)-4-(1-phenylcyclopropylamino)nicotinamide; 6-(4-(morpholinomethyl)phenylamino)-4-(1-phenylcyclopropylamino)nicotinamide; 6-(3-morpholinophenylamino)-4-(1-phenylcyclopropylamino)-nicotinamide; 6-(3-(morpholinomethyl)phenylamino)-4-(1-phenylcyclopropylamino)nicotinamide; 6-(4-(4-acetylpiperazin-1-yl)phenylamino)-4-(1-(2-fluorophenyl) cyclopropylamino)nicotinamide; 6-(4-(4,4-difluoropiperidin-1-yl)phenylamino)-4-(1-phenylcyclopropylamino)nicotinamide; 4-(1-phenylcyclopropylamino)-6-(4-(2-(pyrrolidin-1-yl)ethoxy) phenylamino)nicotinamide; 6-(4-(2-morpholino-2-oxoethoxy)phenylamino)-4-(1-phenylcyclopropylamino) nicotinamide; 6-(3-(2-morpholino-2-oxoethoxy) phenylamino)-4-(1-phenylcyclopropylamino)nicotinamide; 6-(3-acetamidophenylamino)-4-(1-phenylcyclopropylamino)nicotinamide; and 6-(4-chloro-3-(1-methylpiperidine-4-carboxamido)phenylamino)-4-(1-phenylcyclopropylamino)nicotinamide.

The present invention provides in another embodiment, a compound selected from the group consisting of: 6-(4-chloro-3-(1-methylpiperidine-4-carboxamido)phenylamino)-4-(1-phenylcyclopropylamino)nicotinamide; 6-(4-(tetrahydro-2H-pyran-4-yl)phenylamino)-4-(tetrahydro-2H-pyran-4-ylamino)nicotinamide; 4-((tetrahydro-2H-pyran-4-yl)methylamino)-6-(4-(tetrahydro-2H-pyran-4-yl) phenylamino)nicotinamide; 4-((1-hydroxycyclopentyl) methylamino)-6-(4-(tetrahydro-2H-pyran-4-yl) phenylamino)nicotinamide; 4-(2-fluorobenzylamino)-6-(4-(tetrahydro-2H-pyran-4-yl)phenylamino)nicotinamide; 4-(3-fluorobenzylamino)-6-(4-(tetrahydro-2H-pyran-4-yl) phenylamino)nicotinamide; 6-(4-(1-propionylpiperidin-4-yl)phenylamino)-4-((tetrahydro-2H-pyran-4-yl)methylamino)nicotinamide; 4-(3-fluorobenzylamino)-6-(4-(1-propionylpiperidin-4-yl)phenylamino)nicotinamide; 6-(4-(1-propionylpiperidin-4-yl)phenylamino)-4-(tetrahydro-2H-pyran-4-ylamino)nicotinamide; 4-(cyclopentylamino)-6-(4-(1-propionylpiperidin-4-yl)phenylamino)nicotinamide; 4-(3,4-difluorobenzylamino)-6-(4-(1-propionylpiperidin-4-yl)phenylamino)nicotinamide; 4-(2,5-difluorobenzylamino)-6-(4-(1-propionylpiperidin-4-yl)phenylamino)nicotinamide; 4-(cyclopentylamino)-6-(4-(tetrahydro-2H-pyran-4-yl)phenylamino)nicotinamide; 6-(3-(tetrahydro-2H-pyran-4-yl)phenylamino)-4-(tetrahydro-2H-pyran-4-ylamino)nicotinamide; 4-(2-fluorobenzylamino)-6-(3-(tetrahydro-2H-pyran-4-yl)phenylamino)nicotinamide; 4-(cyclopropylmethylamino)-6-(4-(tetrahydro-2H-pyran-4-yl)phenylamino)nicotinamide; 4-(cyclopentylmethylamino)-6-(4-(tetrahydro-2H-pyran-4-yl)phenylamino)nicotinamide; 4-(neopentylamino)-6-(4-(tetrahydro-2H-pyran-4-yl)phenylamino)nicotinamide; 4-(isobutylamino)-6-(4-(tetrahydro-2H-pyran-4-yl)phenylamino)nicotinamide; 4-(cyclohexylamino)-6-(4-(tetrahydro-2H-pyran-4-yl)phenylamino)nicotinamide; 4-(2-fluorobenzylamino)-6-(4-isopropylphenylamino)nicotinamide; 4-((1-(methylsulfonyl)piperidin-4-yl)methylamino)-6-(4-(tetrahydro-2H-pyran-4-yl) phenylamino)nicotinamide; 4-((1-(ethylsulfonyl)piperidin-4-yl)methylamino)-6-(4-(tetrahydro-2H-pyran-4-yl) phenylamino)nicotinamide; 4-((1-(ethylsulfonyl)piperidin-4-yl)methylamino)-6-(4-(tetrahydro-2H-pyran-4-yl) phenylamino)nicotinamide; 4-(2-fluorobenzylamino)-6-(3-isopropylphenylamino)nicotinamide; 4-(1-(dimethylcarbamoyl)piperidin-4-ylamino)-6-(4-(tetrahydro-2H-pyran-4-yl)phenylamino)nicotinamide; 4-(1-propionylpiperidin-4-ylamino)-6-(4-(tetrahydro-2H-pyran-4-yl)phenylamino)nicotinamide; 4-(1-(methylsulfonyl) piperidin-4-ylamino)-6-(4-(tetrahydro-2H-pyran-4-yl) phenylamino)nicotinamide; 4-(1-(ethylsulfonyl)piperidin-4-ylamino)-6-(4-(tetrahydro-2H-pyran-4-yl)phenylamino) nicotinamide; (S)-4-(3,3-dimethylbutan-2-ylamino)-6-(4-(tetrahydro-2H-pyran-4-yl)phenylamino)nicotinamide; (R)-4-(3,3-dimethylbutan-2-ylamino)-6-(4-(tetrahydro-2H-pyran-4-yl)phenylamino)nicotinamide; 4-(pyrrolidin-1-yl)-6-(4-(tetrahydro-2H-pyran-4-yl)phenylamino)nicotinamide; 4-(3-(dimethylamino)-2,2-dimethylpropylamino)-6-(4-(tetrahydro-2H-pyran-4-yl)phenylamino)nicotinamide; 6-(4-(tetrahydro-2H-pyran-4-yl)phenylamino)-4-(thiazol-2-ylmethylamino)nicotinamide; 4-((1-methyl-1H-pyrazol-4-yl) methylamino)-6-(4-(tetrahydro-2H-pyran-4-yl) phenylamino)nicotinamide; 4-(pyridin-2-ylmethylamino)-6-(4-(tetrahydro-2H-pyran-4-yl)phenylamino)nicotinamide; 4-(pyrimidin-2-ylmethylamino)-6-(4-(tetrahydro-2H-pyran-4-yl)phenylamino)nicotinamide; 4-(cyclopentylmethylamino)-6-(4-(1-propionylpiperidin-4-yl)phenylamino)nicotinamide; 6-(4-(1-propionylpiperidin-4-yl)phenylamino)-4-(thiazol-2-ylmethylamino)nicotinamide; 4-((1-methyl-1H- pyrazol-4-yl)methylamino)-6-(4-(1-propionylpiperidin-4-yl)phenylamino)nicotinamide; 6-(4-(1-propionylpiperidin-4-yl)phenylamino)-4-(pyridin-2-ylmethylamino) nicotinamide; 6-(4-(1-propionylpiperidin-4-yl) phenylamino)-4-(pyrimidin-2-ylmethylamino) nicotinamide; 4-(pyrimidin-4-ylmethylamino)-6-(4-(tetrahydro-2H-pyran-4-yl)phenylamino)nicotinamide; 4-((1-methyl-1H-benzo[d]imidazol-2-yl)methylamino)-6-(4-(tetrahydro-2H-pyran-4-yl)phenylamino)nicotinamide; 4-((1-methyl-1H-imidazol-2-yl)methylamino)-6-(4-(tetrahydro-2H-pyran-4-yl)phenylamino)nicotinamide; 4-(prop-2-ynylamino)-6-(4-(tetrahydro-2H-pyran-4-yl)phenylamino)nicotinamide; 4-(pyridin-3-ylmethylamino)-6-(4-(tetrahydro-2H-pyran-4-yl)phenylamino)nicotinamide; (S)-4-(3-methylbutan-2-ylamino)-6-(4-(tetrahydro-2H-pyran-4-yl)phenylamino)nicotinamide; 6-(4-(1-propionylpiperidin-4-yl)phenylamino)-4-(pyridin-3-ylmethylamino) nicotinamide; 4-((5-fluoropyridin-3-yl)methylamino)-6-(4-(1-propionylpiperidin-4-yl)phenylamino)nicotinamide; (R)-4-(3-methylbutan-2-ylamino)-6-(4-(1-propionylpiperidin-4-yl)phenylamino)nicotinamide; (R)-4-(3,3-dimethylbutan-2-ylamino)-6-(4-(1-propionylpiperidin-4-yl)phenylamino) nicotinamide; (R)-4-(1-cyclohexylethylamino)-6-(4-(1-propionylpiperidin-4-yl)phenylamino)nicotinamide; 4-(cyclohexylmethylamino)-6-(4-(1-propionylpiperidin-4-yl)phenylamino)nicotinamide; 4-((1-hydroxycyclopentyl) methylamino)-6-(4-(1-propionylpiperidin-4-yl)phenylamino)nicotinamide; 4-((1-phenylcyclopropyl) methylamino)-6-(4-(1-propionylpiperidin-4-yl) phenylamino)nicotinamide; 4-(3,5-difluorobenzylamino)-6-(4-(1-propionylpiperidin-4-yl)phenylamino)nicotinamide; 4-(2,3-difluorobenzylamino)-6-(4-(1-propionylpiperidin-4-yl)phenylamino)nicotinamide; 6-(4-(1-propionylpiperidin-4-yl)phenylamino)-4-(thiophen-2-ylmethylamino)nicotinamide; 4-(benzylamino)-6-(4-(1-propionylpiperidin-4-yl) phenylamino)nicotinamide; (R)-4-(1-phenylethylamino)-6-(4-(1-propionylpiperidin-4-yl)phenylamino)nicotinamide; 4-((1H-indol-4-yl)methylamino)-6-(4-(1-propionylpiperidin-4-yl)phenylamino)nicotinamide; 4-((1-(2-(piperidin-1-yl)ethyl)-1H-1,2,3-triazol-4-yl)methylamino)-6-(4-(tetrahydro-2H-pyran-4-yl)phenylamino)nicotinamide; (R)-4-(1-cyclopropylethylamino)-6-(4-(1-propionylpiperidin-4-yl) phenylamino)nicotinamide; 4-(2,6-difluorobenzylamino)-6-(4-(1-propionylpiperidin-4-yl)phenylamino)nicotinamide; 4-(3-fluorobenzylamino)-6-(3-(tetrahydro-2H-pyran-4-yl) phenylamino)nicotinamide; 4-(2,3-difluorobenzylamino)-6-(3-(tetrahydro-2H-pyran-4-yl)phenylamino)nicotinamide; 4-(3,5-difluorobenzylamino)-6-(3-(tetrahydro-2H-pyran-4-yl)phenylamino)nicotinamide; 4-(2,5-difluorobenzylamino)-6-(3-(tetrahydro-2H-pyran-4-yl)phenylamino)nicotinamide; 4-((5-fluoropyridin-3-yl)methylamino)-6-(3-(tetrahydro-2H-pyran-4-yl)phenylamino)nicotinamide; 4-(2,3-difluorobenzylamino)-6-(4-(piperidin-4-yl)phenylamino) nicotinamide; 4-((1H-indazol-4-yl)methylamino)-6-(4-(1-propionylpiperidin-4-yl)phenylamino)nicotinamide; 4-(benzo[b]thiophen-7-ylmethylamino)-6-(4-(1-propionylpiperidin-4-yl)phenylamino)nicotinamide; 6-(4-(azetidin-3-yl)phenylamino)-4-(2,3-difluorobenzylamino)nicotinamide; 6-(4-(azetidin-3-yl)phenylamino)-4-(2,5-difluorobenzylamino)nicotinamide; 4-(2,5-difluorobenzylamino)-6-(4-(piperidin-4-yl)phenylamino) nicotinamide; 6-(4-(1-(cyanomethyl)piperidin-4-yl) phenylamino)-4-(2,3-difluorobenzylamino)nicotinamide; 4-(2,3-difluorobenzylamino)-6-(4-(1-(2,2-difluoroethyl)piperidin-4-yl)phenylamino)nicotinamide; 4-(2,3-difluorobenzylamino)-6-(4-(1-(2-fluoroethyl)piperidin-4-yl)phenylamino)nicotinamide; 6-(4-(1-(cyanomethyl)piperidin-4-yl)phenylamino)-4-(2,5-difluorobenzylamino)nicotinamide; 6-(4-(1-(cyanomethyl)azetidin-3-yl)phenylamino)-4-(2,3-difluorobenzylamino)nicotinamide; 6-(4-(1-(cyanomethyl) azetidin-3-yl)phenylamino)-4-(2,5-difluorobenzylamino) nicotinamide; 4-((1H-indol-4-yl)methylamino)-6-(4-(1-(cyanomethyl)piperidin-4-yl)phenylamino)nicotinamide; 6-(3-acetamidophenylamino)-4-(thiophen-2-ylmethylamino)nicotinamide; 4-(3-(1H-imidazol-1-yl)benzylamino)-6-(4-(dimethylcarbamoyl)phenylamino)nicotinamide; 6-(4-(4-acetylpiperazin-1-yl)phenylamino)-4-(isopropylamino)nicotinamide; 6-(4-(4-acetylpiperazin-1-yl)phenylamino)-4-(isobutylamino)nicotinamide; 6-(4-(4-acetylpiperazin-1-yl)phenylamino)-4-(cyclopropylmethylamino)nicotinamide; 6-(4-(4-acetylpiperazin-1-yl)phenylamino)-4-(cyclopentylamino) nicotinamide; 6-(6-(4-acetylpiperazin-1-yl)pyridin-3-ylamino)-4-(isobutylamino)nicotinamide; 6-(4-(4-acetylpiperazin-1-yl)phenylamino)-4-(cyclobutylmethylamino)nicotinamide; 6-(4-(4-acetylpiperazin-1-yl)phenylamino)-4-(cyclopentylmethylamino)nicotinamide; 4-(benzylamino)-6-(3-(methylcarbamoyl)phenylamino)nicotinamide; 4-(benzylamino)-6-(3-(dimethylcarbamoyl)phenylamino) nicotinamide; 4-(benzylamino)-6-(4-(dimethylcarbamoyl) phenylamino)nicotinamide; 4-(benzylamino)-6-(3-(piperidine-1-carbonyl)phenylamino)nicotinamide; 4-(benzylamino)-6-(4-morpholinophenylamino)nicotinamide; 4-(benzylamino)-6-(3-chloro-4-morpholinophenylamino)nicotinamide; 6-(4-(4-acetylpiperazin-1-yl)phenylamino)-4-(4-fluorobenzylamino)nicotinamide; 6-(4-(4-acetylpiperazin-1-yl)phenylamino)-4-(2,3-dihydro-1H-inden-2-ylamino)nicotinamide; 6-(4-(4-acetylpiperazin-1-yl)phenylamino)-4-(benzo[d][1,3]dioxol-5-ylmethylamino) nicotinamide; (S)-6-(4-(4-acetylpiperazin-1-yl) phenylamino)-4-(2,3-dihydro-1H-inden-1-ylamino) nicotinamide; 6-(4-(4-acetylpiperazin-1-yl)phenylamino)-4-(2,3-difluorobenzylamino)nicotinamide; 6-(4-(4-acetylpiperazin-1-yl)phenylamino)-4-(3-chlorobenzylamino)nicotinamide; 6-(4-(4-acetylpiperazin-1-yl)phenylamino)-4-(2-fluorobenzylamino)nicotinamide; 6-(4-(4-acetylpiperazin-1-yl)phenylamino)-4-(2,4-difluorobenzylamino)nicotinamide; (S)-4-(2-methoxy-1-phenylethylamino)-6-(4-methoxyphenylamino)nicotinamide; (S)-4-(2-methoxy-1-phenylethylamino)-6-(3-morpholinophenylamino)nicotinamide; (S)-4-(2-methoxy-1-phenylethylamino)-6-(4-morpholinophenylamino) nicotinamide; (S)-6-(4-(dimethylcarbamoyl)phenylamino)-4-(2-methoxy-1-phenylethylamino)nicotinamide; (S)-6-(4-(azetidine-1-carbonyl)phenylamino)-4-(2-methoxy-1-phenylethylamino)nicotinamide; (R)-4-((1-acetylpiperidin-3-yl)methylamino)-6-(4-(pyrrolidine-1-carbonyl) phenylamino)nicotinamide; (R)-6-(4-(dimethylcarbamoyl) phenylamino)-4-((1-(2-methoxyacetyl)piperidin-3-yl) methylamino)nicotinamide; (R)-4-((1-(2-methoxyacetyl) piperidin-3-yl)methylamino)-6-(4-(pyrrolidine-1-carbonyl) phenylamino)nicotinamide; 4-(benzylamino)-6-(4-((N,N-dimethylsulfamoyl)(methyl)amino)phenylamino) nicotinamide; (R)-4-((1-acetylpiperidin-3-yl)methylamino)-6-(4-(N,N-dimethylsulfamoylamino)phenylamino) nicotinamide; (S)-6-(4-methoxyphenylamino)-4-(piperidin-3-ylmethylamino)nicotinamide; (R)-6-(4-methoxyphenylamino)-4-((1-propionylpiperidin-3-yl) methylamino)nicotinamide; 4-(benzylamino)-6-(4-(dimethylcarbamoyl)-3-(trifluoromethyl)phenylamino) nicotinamide; 4-(benzylamino)-6-(4-(dimethylcarbamoyl)-3-fluorophenylamino)nicotinamide; (R)-4-((1-acetylpiperidin-3-yl)methylamino)-6-(4-(dimethylcarbamoyl)-3-(trifluoromethyl)phenylamino) nicotinamide; (R)-4-((1-acetylpiperidin-3-yl)methylamino)-

6-(4-(dimethylcarbamoyl)-3-fluorophenylamino) nicotinamide; 6-(4-(1H-imidazol-4-yl)phenylamino)-4-(benzylamino)nicotinamide; 6-(4-(1H-pyrazol-1-yl)phenylamino)-4-(benzylamino)nicotinamide; 6-(6-(1H-pyrazol-1-yl)pyridin-3-ylamino)-4-(benzylamino) nicotinamide; 4-(benzylamino)-6-(4-methoxy-3-methylphenylamino)nicotinamide; 4-(benzylamino)-6-(3,4,5-trimethoxyphenylamino)nicotinamide; 6-(4-(1H-1,2,4-triazol-3-yl)phenylamino)-4-(benzylamino)nicotinamide; 4-((1H-indol-7-yl)methylamino)-6-(4-methoxyphenylamino)nicotinamide; 4-((1H-indol-7-yl)methylamino)-6-(4-(dimethylcarbamoyl)-3-methylphenylamino)nicotinamide; 4-(benzo[b]thiophen-7-ylmethylamino)-6-(4-methoxyphenylamino)nicotinamide; 4-(benzo[b]thiophen-7-ylmethylamino)-6-(4-(dimethylcarbamoyl)-3-methylphenylamino)nicotinamide; 6-(4-methoxyphenylamino)-4-(pyrimidin-5-ylmethylamino) nicotinamide; 6-(4-(dimethylcarbamoyl)-3-methylphenylamino)-4-(pyrimidin-5-ylmethylamino) nicotinamide; 4-((1H-indol-7-yl)methylamino)-6-(4-(dimethylcarbamoyl)phenylamino)nicotinamide; (R)-4-((1-(ethylsulfonyl)piperidin-3-yl)methylamino)-6-(4-methoxyphenylamino)nicotinamide; (R)-6-(4-methoxyphenylamino)-4-((1-(pyrrolidine-1-carbonyl)piperidin-3-yl)methylamino)nicotinamide; (R)-4-((1-(dimethylcarbamoyl)piperidin-3-yl)methylamino)-6-(4-methoxyphenylamino)nicotinamide; (R)-4-((1-(cyclopropylsulfonyl)piperidin-3-yl)methylamino)-6-(4-methoxyphenylamino)nicotinamide; 4-(benzylamino)-6-(3,4-dimethoxyphenylamino)nicotinamide; 4-((1H-indol-4-yl)methylamino)-6-(4-methoxyphenylamino)nicotinamide; 4-((1H-indol-4-yl)methylamino)-6-(4-(dimethylcarbamoyl)-3-methylphenylamino)nicotinamide; 4-((5-fluoropyridin-3-yl)methylamino)-6-(4-methoxyphenylamino)nicotinamide; 6-(4-(dimethylcarbamoyl)-3-methylphenylamino)-4-((5-fluoropyridin-3-yl)methylamino)nicotinamide; 6-(4-methoxyphenylamino)-4-(pyrimidin-4-ylmethylamino) nicotinamide; 6-(4-(dimethylcarbamoyl)phenylamino)-4-(pyrimidin-4-ylmethylamino)nicotinamide; 6-(4-methoxyphenylamino)-4-(pyrimidin-2-ylmethylamino) nicotinamide; 6-(4-methoxyphenylamino)-4-(3-(methylsulfonyl)benzylamino)nicotinamide; 6-(4-(dimethylcarbamoyl)phenylamino)-4-(3-(methylsulfonyl)benzylamino)nicotinamide; 6-(4-methoxyphenylamino)-4-((1-methyl-1H-indol-4-yl)methylamino)nicotinamide; 6-(4-(dimethylcarbamoyl)phenylamino)-4-((1-methyl-1H-indol-4-yl)methylamino)nicotinamide; 4-((5-fluoropyridin-3-yl)methylamino)-6-(4-(trifluoromethyl)phenylamino) nicotinamide; 6-(3-fluorophenylamino)-4-((5-fluoropyridin-3-yl)methylamino)nicotinamide; 6-(3-chlorophenylamino)-4-((5-fluoropyridin-3-yl)methylamino)nicotinamide; 6-(4-cyanophenylamino)-4-(5-fluoropyridin-3-yl)methylamino) nicotinamide; 6-(4-(difluoromethoxy)phenylamino)-4-(5-fluoropyridin-3-yl)methylamino)nicotinamide; 4-((5-fluoropyridin-3-yl)methylamino)-6-(4-(trifluoromethoxy) phenylamino)nicotinamide; 4-((5-fluoropyridin-3-yl)methylamino)-6-(p-tolylamino)nicotinamide; 6-(4-(dimethylcarbamoyl)phenylamino)-4-((5-fluoropyridin-3-yl)methylamino)nicotinamide; 4-((5-fluoropyridin-3-yl)methylamino)-6-(4-(2,2,2-trifluoroethylcarbamoyl) phenylamino)nicotinamide; 4-((5-fluoropyridin-3-yl)methylamino)-6-(4-(methyl(2,2,2-trifluoroethyl)carbamoyl) phenylamino)nicotinamide; 4-((6-fluoropyridin-2-yl)methylamino)-6-(4-methoxyphenylamino)nicotinamide; 6-(4-(dimethylcarbamoyl)phenylamino)-4-((6-fluoropyridin-2-yl)methylamino)nicotinamide; 6-(4-methoxyphenylamino)-4-(1-methyl-1H-indol-7- yl)methylamino)nicotinamide; 6-(4-(dimethylcarbamoyl)phenylamino)-4-((1-methyl-1H-indol-7-yl)methylamino)nicotinamide; 4-((1H-indol-4-yl)methylamino)-6-(4-fluorophenylamino) nicotinamide; 4-((1H-indol-4-yl)methylamino)-6-(4-(methylsulfonyl)phenylamino)nicotinamide; 4-((1H-indol-4-yl)methylamino)-6-(4-(difluoromethoxy)phenylamino) nicotinamide; 4-((1H-indol-4-yl)methylamino)-6-(4-(trifluoromethoxy)phenylamino)nicotinamide; 4-((1H-indol-4-yl)methylamino)-6-(3,5-difluorophenylamino) nicotinamide; 6-(4-(1-acetylazetidin-3-yl)phenylamino)-4-(benzylamino)nicotinamide; 6-(4-(azetidin-3-yl)phenylamino)-4-(benzylamino)nicotinamide; 4-(benzylamino)-6-(4-(1-propionylazetidin-3-yl)phenylamino)nicotinamide; methyl 3-(4-(4-(benzylamino)-5-carbamoylpyridin-2-ylamino)phenyl)azetidine-1-carboxylate; 4-(benzylamino)-6-(4-(2-(dimethylamino)-2-oxoethyl)phenylamino)nicotinamide; 4-(benzylamino)-6-(4-(2-oxo-2-(pyrrolidin-1-yl)ethyl)phenylamino)nicotinamide; 4-(benzylamino)-6-(4-(2-morpholino-2-oxoethyl)phenylamino) nicotinamide; 4-(benzylamino)-6-(4-(3-(dimethylcarbamoyl)azetidin-1-yl)phenylamino) nicotinamide; 4-(benzylamino)-6-(3-chloro-4-methoxyphenylamino)nicotinamide; 6-(4-(1-acetylazetidin-3-yl)phenylamino)-4-(benzo[b]thiophen-7-ylmethylamino) nicotinamide; 6-(4-(1-acetylazetidin-3-yl)phenylamino)-4-((5-fluoropyridin-3-yl)methylamino)nicotinamide; 4-(benzylamino)-6-(4-(1-(methylsulfonyl)azetidin-3-yl) phenylamino)nicotinamide; 4-(benzylamino)-6-(4-(1-(2-methoxyacetyl)azetidin-3-yl)phenylamino)nicotinamide; 4-(benzylamino)-6-(4-(1-(dimethylcarbamoyl)azetidin-3-yl)phenylamino)nicotinamide; 4-(benzylamino)-6-(4-(1-(pyrrolidine-1-carbonyl)azetidin-3-yl)phenylamino)nicotinamide; 4-(benzylamino)-6-(4-(1-(N,N-dimethylsulfamoyl) azetidin-3-yl)phenylamino)nicotinamide; 4-(benzylamino)-6-(4-(2-(methylamino)-2-oxoethyl)phenylamino) nicotinamide; 4-(benzylamino)-6-(4-(2-oxo-2-(2,2,2-trifluoroethylamino)ethyl)phenylamino)nicotinamide; 4-(benzylamino)-6-(4-(3-(dimethylcarbamoyl)azetidin-1-yl)-3-fluorophenylamino)nicotinamide; 4-(benzylamino)-6-(4-(4-(dimethylcarbamoyl)piperidin-1-yl)phenylamino) nicotinamide; 4-(benzo[b]thiophen-4-ylmethylamino)-6-(4-(4-(dimethylcarbamoyl)piperidin-1-yl)phenylamino) nicotinamide; 4-((1H-indol-4-yl)methylamino)-6-(4-(4-(dimethylcarbamoyl)piperidin-1-yl)phenylamino) nicotinamide; 4-(benzo[b]thiophen-7-ylmethylamino)-6-(4-(methylsulfonylmethyl)phenylamino)nicotinamide; 4-(benzylamino)-6-(4-(methylsulfonylmethyl)phenylamino)nicotinamide; 4-((1H-indol-4-yl)methylamino)-6-(4-(methylsulfonylmethyl)phenylamino)nicotinamide; 4-(benzo[b]thiophen-7-ylmethylamino)-6-(4-(3-(dimethylcarbamoyl)azetidin-1-yl)-3-fluorophenylamino)nicotinamide; 4-(benzo[b]thiophen-7-ylmethylamino)-6-(4-(4-(dimethylcarbamoyl)piperidin-1-yl)phenylamino)nicotinamide; 4-(benzo[b]thiophen-7-ylmethylamino)-6-(3-chloro-4-(4-(dimethylcarbamoyl)piperidin-1-yl)phenylamino)nicotinamide; 6-(4-(acetamidomethyl)phenylamino)-4-(benzo[b]thiophen-7-ylmethylamino)nicotinamide; 4-(benzo[b]thiophen-7-ylmethylamino)-6-(4-(methylsulfonamidomethyl)phenylamino)nicotinamide; 4-(benzo[b]thiophen-7-ylmethylamino)-6-(4-((3,3-dimethylureido)methyl)phenylamino)nicotinamide; 4-(benzo[b]thiophen-7-ylmethylamino)-6-(4-((N,N-dimethylsulfamoylamino)methyl)phenylamino)nicotinamide; 4-((1H-indol-5-yl)methylamino)-6-(4-(1-propionylpiperidin-4-yl) phenylamino)nicotinamide; 4-((1H-indol-6-yl)methylamino)-6-(pyridin-3-ylamino)nicotinamide; 4-((1H-indol-6-yl)methylamino)-6- (4-(1-propionylpiperidin-4-yl)

phenylamino)nicotinamide; 6-(4-(N-methylacetamido)phenylamino)-4-(1-phenylcyclopropylamino)nicotinamide; 4-(1-phenylcyclopropylamino)-6-(4-piperidin-1-yl)phenylamino) nicotinamide; 4-(1-phenylcyclopropylamino)-6-(3-(2-(pyrrolidin-1-yl)ethoxy)phenylamino)nicotinamide; 6-(4-(4-(methylsulfonyl)piperazin-1-yl)phenylamino)-4-(1-phenylcyclopropylamino)nicotinamide; 6-(3-(2-(dimethylamino)-2-oxoethoxy)phenylamino)-4-(1-phenylcyclopropylamino)nicotinamide; 6-(4-(2-(dimethylamino)-2-oxoethoxy)phenylamino)-4-(1-phenylcyclopropylamino) nicotinamide; 4-(1-phenylcyclopropylamino)-6-(3-(piperazin-1-yl)phenylamino)nicotinamide; 6-(3-(4-acetylpiperazin-1-yl)phenylamino)-4-(1-phenylcyclopropylamino)nicotinamide; 6-(N-(3-(4-acetylpiperazin-1-yl)phenyl)acetamino)-4-(1-phenylcyclopropylamino)nicotinamide; 6-(5-(4-(methylsulfonyl)piperazin-1-yl)pyridin-2-ylamino)-4-(1-phenylcyclopropylamino)nicotinamide; 4-(1-(2,3-difluorophenyl)cyclopropylamino)-6-(4-(4-propionylpiperazin-1-yl)phenylamino)nicotinamide; 4-(1-phenylcyclopropylamino)-6-(4-(1-propionylpiperidin-4-yl)phenylamino)nicotinamide; 6-(4-(4-acetylpiperazin-1-yl)phenylamino-5-chloro-4-(3-fluorobenzylamino) nicotinamide; 5-chloro-4-(3-fluorobenzylamino)-6-(4-morpholinophenylamino)nicotinamide; 4-(3-fluorobenzylamino-6-(5-(morpholine-4-carbonyl)thiazol-2-ylamino)nicotinamide; 6-(4-(dimethylcarbamoyl)phenylamino)-4-(3-(pyridine-4-yl)benzylamino) nicotinamide; 6-(4-(methylsulfonyl)phenylamino)-4-(3-(pyridine-4-yl)benzylamino)nicotinamide; 6-(4-(dimethylcarbamoyl)phenylamino)-4-(3-(pyridine-3-yl)benzylamino)nicotinamide; 6-(4-(1-propionylpiperidin-4-yl)phenylamino)-4-(3-(pyridine-3-yl)benzylamino) nicotinamide; 6-(4-(1-propionylpiperidin-4-yl)phenylamino)-4-(3-(pyridine-3-yl)benzylamino) nicotinamide; 6-(4-((N,N-dimethylsulfamoyl)methyl)phenylamino)-4-(3-(pyridine-4-yl)benzylamino) nicotinamide 6-(4-(methylsulfonylmethyl)phenylamino)-4-(3-(pyridine-4-yl)benzylamino)nicotinamide; 6-(4-(4-(dimethylcarbamoyl)piperidin-1-yl)phenylamino)-4-(3-(pyridine-4-yl)benzylamino)nicotinamide; 6-(4-(1-propionylpiperidin-4-yl)phenylamino)-4-(3-(pyridine-4-yl) benzylamino)nicotinamide; 6-(4-(dimethylcarbamoyl) phenylamino)-4-(3-(pyridine-2-yl)benzylamino) nicotinamide; 4-(3-(1H-pyrazol-1-yl)benzylamino)-6-(4-(dimethylcarbamoyl)phenylamino)nicotinamide; 6-(4-(dimethylcarbamoyl)phenylamino)-4-(3-(pyrimidine-5-yl)benzylamino)nicotinamide; 6-(4-(1-propionylpiperazin-4-yl)phenylamino)-4-(3-(pyridine-4-yl)benzylamino) nicotinamide; 6-(4-(dimethylcarbamoyl)phenylamino)-4-(3-(thiazol-4-yl)benzylamino)nicotinamide; 6-(4-(dimethylcarbamoyl)phenylamino)-4-(3-(pyrazin-2-yl) benzylamino)nicotinamide; 6-(4-(morpholinomethyl) phenylamino)-4-(3-(pyridin-4-yl)benzylamino) nicotinamide; 4-(benzylamino)-6-(4-(2-(pyrrolidin-1-yl) ethoxy)phenylamino)nicotinamide; 4-(benzylamino)-6-(4-(2-morpholinoethoxy)phenylamino)nicotinamide; 4-(benzylamino)-6-(3-(2-morpholino-2-oxoethoxy)phenylamino)nicotinamide; 4-(benzylamino)-6-(4-(morpholinomethyl)phenylamino)nicotinamide; 4-(benzylamino)-6-(4-(2-methoxyethoxy)phenylamino)nicotinamide; 4-(benzylamino)-6-(3-(2-methoxyethoxy)phenylamino) nicotinamide; 2-(4-(azetidin-1-ylsulfonyl)phenylamino)-4-(benzylamino)pyrimidine-5-carboxamide; 4-(2,3-difluorobenzylamino)-6-(4-(4-propionylpiperazin-1-yl) phenylamino)nicotinamide; 4-(benzylamino)-6-(4-(dimethylcarbamoyl)-3-methoxyphenylamino)nicotinamide; 4-(benzylamino)-6-(3-chloro-4-(dimethylcarbamoyl) phenylamino)nicotinamide; 4-(benzylamino)-6-(4-(dimethylcarbamoyl)-3-methylphenylamino)nicotinamide; 6-(3-(azetidine-1-carbonyl)-4-fluorophenylamino)-4-(benzylamino)nicotinamide; 4-(benzylamino)-6-(4-(dimethylamino)-3-(dimethylcarbamoyl)phenylamino) nicotinamide; (R)-4-((1-acetylpiperidin-3-yl)methylamino)-6-(4-(dimethylcarbamoyl)-3-methoxyphenylamino) nicotinamide; (R)-4-((1-acetylpiperidin-3-yl)methylamino)-6-(3-chloro-4-(dimethylcarbamoyl)phenylamino) nicotinamide; (R)-4-((1-acetylpiperidin-3-yl)methylamino)-6-(4-(dimethylcarbamoyl)-3-methylphenylamino) nicotinamide; (R)-4-((1-acetylpiperidin-3-yl)methylamino)-6-(3-(azetidine-1-carbonyl)-4-fluorophenylamino) nicotinamide; (R)-4-((1-acetylpiperidin-3-yl)methylamino)-6-(3-(dimethylamino)-4-(dimethylcarbamoyl)phenylamino) nicotinamide; 4-(benzylamino)-6-(3-methyl-4-(pyrrolidine-1-carbonyl)phenylamino)nicotinamide; 4-(benzylamino)-6-(3-methyl-4-(morpholine-4-carbonyl)phenylamino) nicotinamide; 6-(4-(azetidine-1-carbonyl)-3-methylphenylamino)-4-(benzylamino)nicotinamide; 4-(benzylamino)-6-(4-(2-hydroxyethylcarbamoyl)-3-methylphenylamino)nicotinamide; 4-(benzylamino)-6-(4-(cyclopropyl(methyl)carbamoyl)-3-methylphenylamino)nicotinamide; 4-(benzylamino)-6-(4-(2,5-dihydro-1H-pyrrole-1-carbonyl)-3-methylphenylamino)nicotinamide; 4-(benzylamino)-6-(4-((2-hydroxyethyl)(methyl)carbamoyl)-3-methylphenylamino)nicotinamide; 4-(benzylamino)-6-(4-((2-methoxyethyl)(methyl)carbamoyl)-3-methylphenylamino)nicotinamide; 6-(4-(azetidine-1-carbonyl)-3-methylphenylamino)-4-(2,3-difluorobenzylamino) nicotinamide; 4-(2,3-difluorobenzylamino)-6-(3-methyl-4-(morpholine-4-carbonyl)phenylamino)nicotinamide; 4-(2,3-difluorobenzylamino)-6-(3-methyl-4-(pyrrolidine-1-carbonyl)phenylamino)nicotinamide; 6-(4-(azetidine-1-carbonyl)-3-methylphenylamino)-4-(benzo[b]thiophen-7-ylmethylamino)nicotinamide; 4-(benzo[b]thiophen-7-ylmethylamino)-6-(3-methyl-4-(pyrrolidine-1-carbonyl) phenylamino)nicotinamide; 4-(benzo[b]thiophen-7-ylmethylamino)-6-(3-methyl-4-(morpholine-4-carbonyl) phenylamino)nicotinamide; 4-((1H-indol-4-yl) methylamino)-6-(4-(azetidine-1-carbonyl)-3-methylphenylamino)nicotinamide; 4-((1H-indol-4-yl) methylamino)-6-(3-methyl-4-(pyrrolidine-1-carbonyl) phenylamino)nicotinamide; 4-((1H-indol-4-yl) methylamino)-6-(3-methyl-4-(morpholine-4-carbonyl) phenylamino)nicotinamide; 4-((1H-indol-7-yl) methylamino)-6-(4-(azetidine-1-carbonyl)-3-methylphenylamino)nicotinamide; 4-((1H-indol-7-yl) methylamino)-6-(3-methyl-4-(pyrrolidine-1-carbonyl) phenylamino)nicotinamide; methyl 4-(4-(benzo[b]thiophen-7-ylmethylamino)-5-carbamoylpyridin-2-ylamino)phenyl (methyl)carbamate; 4-benzo[b]thiophen-7-ylmethylamino)-6-(4-(N-methylpropionamido) phenylamino)nicotinamide; 4-(benzo[b]thiophen-7-ylmethylamino)-6-(4-(N-methylcyclopropanecarboxamido) phenylamino)nicotinamide; 4-(benzo[b]thiophen-7-ylmethylamino)-6-(4-(N-methylacetamido)phenylamino) nicotinamide; 4-((1H-indol-4-yl)methylamino)-6-(4-(N-methylacetamido)phenylamino)nicotinamide; 4-((1H-indol-7-yl)methylamino)-6-(4-(N-methylacetamido) phenylamino)nicotinamide; 6-(4-acetamidophenylamino)-4-(benzo[b]thiophen-7-ylmethylamino)nicotinamide; 4-((1H-indol-4-yl)methylamino)-6-(4-acetamidophenylamino) nicotinamide; 4-((1H-indol-7-yl)methylamino)-6-(4-acetamidophenylamino)nicotinamide; methyl 4-(4-((1H- indol-4-yl)methylamino)-5-carbamoylpyridin-2-ylamino) phenyl(methyl)carbamate; 4-((1H-indol-4-yl) methylamino)-6-(4-(N-methylpropionamido)phenylamino) nicotinamide; 4-((1H-indol-4-yl)methylamino)-6-(4-(N-methylcyclopropanecarboxamido)phenylamino) nicotinamide; 4-((1H-indol-7-yl)methylamino)-6-(4-(N-methylpropionamido)phenylamino)nicotinamide; 4-((1H-indol-7-yl)methylamino)-6-(4-(N-methylcyclopropanecarboxamido)phenylamino) nicotinamide; methyl 4-(5-carbamoyl-4-((5-fluoropyridin-3-yl)methylamino)pyridin-2-ylamino)phenyl(methyl) carbamate; 4-((5-fluoropyridin-3-yl)methylamino)-6-(4-(N-methylpropionamido)phenylamino)nicotinamide; 4-((5-fluoropyridin-3-yl)methylamino)-6-(4-(N-methylcyclopropanecarboxamido)phenylamino) nicotinamide; methyl 4-(4-((1H-indol-7-yl)methylamino)-5-carbamoylpyridin-2-ylamino)phenyl(methyl)carbamate; 4-((5-fluoropyridin-3-yl)methylamino)-6-(4-(N-methylacetamido)phenylamino)nicotinamide; 6-(4-acetamidophenylamino)-4-((5-fluoropyridin-3-yl)methylamino)nicotinamide; 4-((6-fluoropyridin-2-yl)methylamino)-6-(4-(N-methylacetamido)phenylamino)nicotinamide; 6-(4-acetamidophenylamino)-4-((6-fluoropyridin-2-yl)methylamino)nicotinamide; methyl 4-(5-carbamoyl-4-((6-fluoropyridin-2-yl)methylamino)pyridin-2-ylamino)phenyl (methyl)carbamate; 4-((6-fluoropyridin-2-yl)methylamino)-6-(4-(N-methylpropionamido)phenylamino)nicotinamide; 4-((6-fluoropyridin-2-yl)methylamino)-6-(4-(N-methylcyclopropanecarboxamido)phenylamino)nicotinamide; 4-((6-fluoropyridin-2-yl)methylamino)-6-(4-(1-propionylazetidin-3-yl)phenylamino)nicotinamide; 4-(benzo[b]thiophen-7-ylmethylamino)-6-(4-(1-propionylazetidin-3-yl) phenylamino)nicotinamide; 4-((1H-indol-4-yl) methylamino)-6-(4-(1-propionylazetidin-3-yl)phenylamino) nicotinamide; 4-((6-fluoropyridin-2-yl)methylamino)-6-(4-(1-(2-methoxyacetyl)azetidin-3-yl)phenylamino) nicotinamide; 4-((1H-indol-4-yl)methylamino)-6-(4-(1-(2-methoxyacetyl)azetidin-3-yl)phenylamino)nicotinamide; 4-(benzo[b]thiophen-7-ylmethylamino)-6-(4-(1-(2-methoxyacetyl)azetidin-3-yl)phenylamino)nicotinamide; 4-(2,3-difluorobenzylamino)-6-(4-(1-(1,3-difluoropropan-2-yl)piperidin-4-yl)phenylamino)nicotinamide; 4-(2,3-difluorobenzylamino)-6-(4-(1-formylpiperidin-4-yl) phenylamino)nicotinamide; 4-(2,3-difluorobenzylamino)-6-(4-(1-(2-(dimethylamino)acetyl)piperidin-4-yl) phenylamino)nicotinamide; (R)-4-(2,3-difluorobenzylamino)-6-(4-(1-(1-methylpyrrolidine-2-carbonyl)piperidin-4-yl)phenylamino)nicotinamide; (S)-4-(2,3-difluorobenzylamino)-6-(4-(1-(1-methylpyrrolidine-2-carbonyl)piperidin-4-yl)phenylamino)nicotinamide; (R)-6-(4-(1-(1-acetylpyrrolidine-2-carbonyl)piperidin-4-yl) phenylamino)-4-(2,3-difluorobenzylamino)nicotinamide; (S)-6-(4-(1-(1-acetylpyrrolidine-2-carbonyl)piperidin-4-yl) phenylamino)-4-(2,3-difluorobenzylamino)nicotinamide; 4-(2,5-difluorobenzylamino)-6-(4-(1-formylpiperidin-4-yl) phenylamino)nicotinamide; 4-(2,3-difluorobenzylamino)-6-(4-(1-formylazetidin-3-yl)phenylamino)nicotinamide; 4-(2,5-difluorobenzylamino)-6-(4-(1-formylazetidin-3-yl) phenylamino)nicotinamide; 4-((1H-indol-4-yl) methylamino)-6-(4-(1-formylpiperidin-4-yl)phenylamino) nicotinamide; 4-(2,3-difluorobenzylamino)-6-(4-(1-(2-fluoroethyl)azetidin-3-yl)phenylamino)nicotinamide; 4-(2,3-difluorobenzylamino)-6-(4-(1-(pyridin-2-yl)piperidin-4-yl)phenylamino)nicotinamide; 4-(2,3-difluorobenzylamino)-6-(4-(1-(pyridin-2-yl)azetidin-3-yl) phenylamino)nicotinamide; 4-((1H-indol-4-yl) methylamino)-6-(4-(1-(pyridin-2-yl)piperidin-4-yl) phenylamino)nicotinamide.

The present invention provides in another embodiment, a compound of the examples.

The present invention provides in another embodiment, a compound of any one of the tables.

The present invention provides in another embodiment, a compound of any one of the figures.

The present invention in another group of embodiments, does not include a compound disclosed in WO 2010/058846 or WO 2010/061971.

It is understood that in another group of embodiments, any of the above embodiments may also be combined with other embodiments listed herein, to form other embodiments of the invention. Similarly, it is understood that in other embodiments, listing of groups includes embodiments wherein one or more of the elements of those groups is not included.

b. Methods of Synthesis

The compounds of the present invention may be prepared by known organic synthesis techniques, including the methods described in more detail in the Examples.

One skilled in the art will recognize that in certain embodiments of structures (I) when D1, $R^1$, $D^2$ or $R^2$ comprises a terminal heteroatom, it may be advantageous to use a protecting group strategy. The protecting group can be removed using methods known to those skilled in the art to yield compounds of structure (I).

The compounds of the present invention may generally be utilized as the free base. Alternatively, the compounds of this invention may be used in the form of acid addition salts as described below.

c. Inhibition of JAK Kinases

The activity of a specified compound as an inhibitor of a JAK kinase kinase may be assessed in vitro or in vivo. In some embodiments, the activity of a specified compound can be tested in a cellular assay. Selectivity could also be ascertained in biochemical assays with isolated kinases.

Similar types of assays can be used to assess JAK kinase inhibitory activity and to determine the degree of selectivity of the particular compound as compared to Syk kinase or to the selectivity compared to the other JAK family kinases. One means of assaying for such inhibition is detection of the effect of the compounds of the present invention on the upregulation of downstream gene products. In the Ramos/IL4 assay, B-cells are stimulated with the cytokine Interleukin-4 (IL-4) leading to the activation of the JAK/STAT pathway through phosphorylation of the JAK family kinases, JAK1 and JAK3, which in turn phosphorylate and activate the transcription factor STAT-6. One of the genes upregulated by activated STAT-6 is the low affinity IgE receptor, CD23. To study the effect of inhibitors (e.g., the 2,4-substituted pyrimindinediamine compounds described herein) on the JAK1 and JAK3 kinases, human Ramos B-cells are stimulated with human IL-4. 10' post-stimulation, cells are subjected to intracellular flow cytometry to measure the extent of STAT-6 phosphorylation. 20 to 24 hours post-stimulation, cells are stained for upregulation of CD23 and analyzed using flow cytometry. A reduction of the amount of phosphohorylated STAT-6 and/or cell surface CD23 present compared to control conditions indicates that the test compound actively inhibits a JAK kinase pathway.

Additionally, IL-6 stimulation of Ramos B-cells induces JAKs 1, 2, and Tyk2, leading to Stat-3 and Erk phosphorylation. 10' post-stimulation, cells are subjected to intracellular flow cytometry to measure the ability of compound to inhibit these phosphorylation events. To specifically measure the activity of JAK2, the CellSensor irf1-bla HEL cell line expressing the beta-lactamase reporter gene controlled by Stat5 will be used (Invitrogen, Carlsbad, Calif.). These cells express a constitutively active JAK2 mutant (JAK2V617F), found naturally in myeloproliferative neoplasms (Constantinescu, S., et. al, *Trends Biochem Sci.*, 2008; 33:122-31). A reduction in the amount of beta-lactamase reporter gene expression is used a measure of the JAK2 inhibitory activity of compounds.

The activity of the compounds of the invention may additionally be characterized by assaying the effect of the compounds of the present invention described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1 β receptor activates the TRAF6/NFκB pathway resulting in up-regulation of ICAM-1. IFNγ induces ICAM-1 up-regulation through activation of the JAK1/JAK2 pathway. The up-regulation of ICAM-1 can be quantified by flow cytometry across a compound dose curve and $EC_{50}$ values are calculated.

The activity of the compounds of the invention may additionally be characterized by assaying the effect of the compounds of the present invention described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1 β receptor activates the TRAF6/NFκB pathway resulting in up-regulation of ICAM-1. IFN γ induces ICAM-1 up-regulation through activation of the JAK1/JAK2 pathway. The up-regulation of ICAM-1 can be quantified by flow cytometry across a compound dose curve and $EC_{50}$ values are calculated. Exemplary assays of this type are described in greater detail in the Examples.

Active compounds as described herein generally inhibit a JAK kinase pathway with an $IC_{50}$ in the range of about 1 mM or less, as measured in the assays described herein. Of course, skilled artisans will appreciate that compounds which exhibit lower $IC_{50}$s, (on the order, for example, of 100 µM, 50 µM, 40 µM, 30 µM, 20 µM, 15 µM, 10 µM, 5 µM, 1 µM, 500 nM, 100 nM, 10 nM, 1 nM, or even lower) can be particularly useful in therapeutic applications. In instances where activity specific to a particular cell type is desired, the compound can be assayed for activity with the desired cell type and counter-screened for a lack of activity against other cell types. The desired degree of "inactivity" in such counter screens, or the desired ratio of activity vs. inactivity, may vary for different situations and can be selected by the user.

The active compounds also typically inhibit IL-4 stimulated phosphorylation of STAT6 or expression of CD23 in B-cells with an $IC_{50}$ in the range of about 20 µM or less, typically in the range of about 10 µM, 1 µM, 500 nM, 100 nM, 10 nM, 1 nM, or even lower. A suitable assay that can be used is the assay described in the Examples, "IL4 stimulation of JAK1/3 signaling to STAT6 in Ramos B cells." In certain embodiments, the active compounds of the present invention have an $IC_{50}$ of less than or equal to 5 µM, greater than 5 µM but less than 20 µM, greater than 20 µM, or greater than 20 µM but less than 50 µM in the assay described in the Examples.

The active compounds also typically inhibit expression of ICAM1 (CD54) induced by IFN γ exposure in A549 cells with an $IC_{50}$ in the range of about 20 µM or less, typically in the range of about 10 µM, 1 µM, 500 nM, 100 nM, 10 nM, 1 nM, or even lower. The $IC_{50}$ against expression of ICAM (CD54) in IFN γ stimulated cells can be determined in a functional cellular assay with an isolated A549 or U937 cell line. Suitable assays that can be used are the assays described in the Examples, "A549 Epithelial Line Stimulated with IFNγ". In certain embodiments, the active compounds of the present invention have an $IC_{50}$ of less than or equal to 20 µM, greater than 20 µM, or greater than 20 µM but less than 50 µM in the assays described in the Examples.

d. Compositions and Methods of Administration

The present invention further provides compositions comprising one or more compounds of formula (I) or a pharmaceutically acceptable salt, ester or prodrug thereof, and a pharmaceutically acceptable carrier or diluent. It will be appreciated that the compounds of formula (I)) in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of formula (I), similar to metabolically labile esters or carbamates, which are capable of producing the parent compounds of formula (I) in vivo, are within the scope of this invention.

As used herein, the term "pharmaceutically acceptable salts" refers to any acid or base addition salt whose counter-ions are non-toxic to the patient in pharmaceutical doses of the salts. A host of pharmaceutically acceptable salts are well known in the pharmaceutical field. If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulphates, phosphates, nitrates, sulphamates, malonates, salicylates, methylene-bis-b-hydroxynaphthoates, gentisates, isethionates, di-p-toluoyltartrates, ethanesulphonates, cyclohexylsulphamates, quinates, and the like. Pharmaceutically acceptable base addition salts include, without limitation, those derived from alkali or alkaline earth metal bases or conventional organic bases, such as triethylamine, pyridine, piperidine, morpholine, N-methylmorpholine, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Furthermore, the basic nitrogen-containing groups may be quaternized with agents like lower alkyl halides, such as methyl, ethyl, propyl and butyl chlorides, bromides and iodides; dialkyl sulfates, such as dimethyl, diethyl, dibutyl and diamyl sulfates, long chain halides, such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system, etc.), increase oral availability, increase solubility to allow administration by injection, alter metabolism and alter rate of excretion.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

The term "unit dosage form" refers to physically discrete units suitable as unitary dosages for human subjects and other mammals, each unit containing a predetermined quantity of drug calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of one or more JAK kinase inhibitors.

Methods for preparing such dosage forms are known to those skilled in the art (see, for example, REMINGTON'S PHARMACEUTICAL SCIENCES, 18TH ED., Mack Publishing Co., Easton, Pa. (1990)). In addition, pharmaceutically acceptable salts of the JAK kinase inhibitors of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, $4^{th}$ Ed. (New York: Wiley-Interscience, 1992).

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of one or more JAK kinase inhibitors, with the remainder consisting of suitable pharmaceutical carrier and/or excipients. Appropriate excipients can be tailored to the particular composition and route of administration by methods well known in the art, e.g., REMINGTON'S PHARMACEUTICAL SCIENCES, supra.

Pharmaceutically acceptable carriers that may be used in these compositions include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols. The compositions can additionally include lubricating agents such as talc, magnesium stearate, and mineral oil; wetting agents; emulsifying agents; suspending agents; preserving agents such as methyl-, ethyl-, and propyl-hydroxy-benzoates; pH adjusting agents such as inorganic and organic acids and bases; sweetening agents; and flavoring agents.

Administration of a composition comprising one or more JAK kinase inhibitors with one or more suitable pharmaceutical excipients as advantageous can be carried out via any of the accepted modes of administration. Thus, administration can be, for example, oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, or long-acting. Still further, compounds can be administered in a local rather than systemic means, such as administration (e.g., injection) as a sustained release formulation. According to a representative embodiment, the compositions of this invention are formulated for pharmaceutical administration to a mammal, preferably a human being.

The compositions of the present invention containing one or more JAK kinase inhibitors can be administered repeatedly, e.g., at least 2, 3, 4, 5, 6, 7, 8, or more times, or the composition may be administered by continuous infusion. Suitable sites of administration include, but are not limited to, skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The pharmaceutical compositions of this invention may be in any orally acceptable dosage form, including tablets, capsules, cachets, emulsions, suspensions, solutions, syrups, elixirs, sprays, boluses, lozenges, powders, granules, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like. In the case of tablets for oral use, carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

In some embodiments, the compositions take the form of a pill, tablet, or capsule, and thus, the composition can contain, along with one or more JAK kinase inhibitors, a diluent such as lactose, sucrose, dicalcium phosphate, and the like; a disintegrant such as starch or derivatives thereof; a lubricant such as magnesium stearate and the like; and/or a binder such a starch, gum acacia, polyvinylpyrrolidone, gelatin, cellulose and derivatives thereof. A tablet can be made by any compression or molding process known to those of skill in the art. Compressed tablets may be prepared by compressing in a suitable machine the JAK kinase inhibitors in a free-flowing form, e.g., a powder or granules, optionally mixed with accessory ingredients, e.g., binders, lubricants, diluents, disintegrants, or dispersing agents. Molded tablets can be made by molding in a suitable machine a mixture of the powdered JAK kinase inhibitors with any suitable carrier.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax, polyethylene glycol (PEG), hard fat, and/or hydrogenated cocoglyceride. Compositions suitable for rectal administration may also comprise a rectal enema unit containing one or more JAK kinase inhibitors and pharmaceutically-acceptable vehicles (e.g., 50% aqueous ethanol or an aqueous salt solution) that are physiologically compatible with the rectum and/or colon. The rectal enema unit contains an applicator tip protected by an inert cover, preferably comprised of polyethylene, lubricated with a lubricant such as white petrolatum, and preferably protected by a one-way valve to prevent back-flow of the dispensed formula. The rectal enema unit is also of sufficient length, preferably two inches, to be inserted into the colon via the anus.

Liquid compositions can be prepared by dissolving or dispersing one or more JAK kinase inhibitors and optionally one or more pharmaceutically acceptable adjuvants in a carrier such as, for example, aqueous saline, aqueous dextrose, glycerol, ethanol, and the like, to form a solution or suspension, e.g., for oral, topical, or intravenous administration. Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs. For topical administration, the composition containing one or more JAK kinase inhibitors can be in the form of emulsions, lotions, gels, foams, creams, jellies, solutions, suspensions, ointments, and transdermal patches.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

The pharmaceutical compositions of this invention may also be administered by nasal aerosol or inhalation. For delivery by inhalation, the compositions can be delivered as a dry powder or in liquid form via a nebulizer. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

For ophthalmic use, the pharmaceutical compositions may be formulated as micronized suspensions in isotonic, pH adjusted sterile saline, or, preferably, as solutions in isotonic, pH adjusted sterile saline, either with our without a preservative, such as benzylalkonium chloride. Alternatively, for ophthalmic uses, the pharmaceutical compositions may be formulated in an ointment, such as petrolatum.

For parenteral administration, the compositions can be in the form of sterile injectable solutions and sterile packaged powders. Preferably, injectable solutions are formulated at a pH of about 4.5 to about 7.5.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Any of the above dosage forms containing effective amounts are within the bounds of routine experimentation and within the scope of the invention. A therapeutically effective dose may vary depending upon the route of administration and dosage form. The representative compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Besides those representative dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

e. Methods of Use

The invention provides methods of inhibiting or decreasing JAK kinase activity as well as treating or ameliorating a JAK kinase associated state, symptom, condition, disorder or disease in a patient in need thereof (e.g., human or non-human). In one embodiment, the JAK kinase associated state, symptom, condition, disorder or disease is mediated, at least in part by JAK kinase activity. In more specific embodiments, the present invention provides a method for treating a condition or disorder mediated at least in part by JAK3 kinase activity is cardiovascular disease, inflammatory disease or autoimmune disease.

In one embodiment, the invention provides methods for preventing or treating a condition in a mammal mediated at least in part by JAK kinase activity comprising the step of administering to the mammal a therapeutically effective amount of a compound of the present invention. Such conditions include, but are not limited to, restenosis, acute coronary syndrome, myocardial infarction, unstable angina, refractory angina, occlusive coronary thrombosis occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolism, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

In a further embodiment, the present invention provides a method for treating thrombosis, immune thrombocytic purpura, heparin induced thrombocytopenia, dilated cardiomyopathy, sickle cell disease, atherosclerosis, myocardial infarction, vacular inflammation, unstable angina or acute coronary syndromes. Examples of sickle cell disease, include, but are not limited to sickle cell anemia, sickle-hemoglobin C disease, sickle beta-plus thalassemia, and sickle beta-zero thalassemia In another embodiment, the present invention also provides a method for treating allergy, asthma, rheumatoid arthritis, B Cell mediated disease such as Non-Hodgkin's Lymphoma, anti phospholipids syndrome, lupus, psoriasis, multiple sclerosis, end stage renal disease or chronic lymphocytic leukemia.

In another embodiment, the present invention provides a method for treating hemolytic anemia or immune thrombocytopenic purpura.

The compounds described herein are also potent and/or selective inhibitors of JAK kinases. As a consequence of this activity, the compounds can be used in a variety of in vitro, in vivo, and ex vivo contexts to regulate or inhibit JAK kinase activity, signaling cascades in which JAK kinases play a role, and the biological responses effected by such signaling cascades. For example, in one embodiment, the compounds can be used to inhibit JAK kinase, either in vitro or in vivo, in virtually any cell type expressing the JAK kinase, such as in hematopoietic cells in which, for example, JAK3 is predominantly expressed. They may also be used to regulate signal transduction cascades in which JAK kinases, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15, and IL-21 receptor signaling cascades. The compounds may also be used in vitro or in vivo to regulate, and in particular to inhibit, cellular or biological responses affected by such JAK kinase-dependent signal transduction cascades. Such cellular or biological responses are not limited to, IL-4/Ramos STAT6 phosphorylation or CD23 upregulation and IL-2 mediated T-cell STAT5 phosphorylation or proliferation. Importantly, the compounds can be used to inhibit JAK kinases in vivo as a therapeutic approach towards the treatment or prevention of diseases mediated, either wholly or in part, by a JAK kinase activity (referred to herein as "JAK kinase mediated diseases"). Non-limiting examples of JAK kinase mediated diseases that can be treated or prevented with the compounds include, but are not limited to, the following: allergies; asthma; autoimmune diseases such as transplant rejection (e.g., kidney, heart, lung, liver, pancreas, skin, small intestine, large intestine, host versus graft reaction (HVGR), and graft versus host reaction (GVHR)), rheumatoid arthritis, and amyotrophic lateral sclerosis; T-cell mediated autoimmune diseases such as multiple sclerosis, psoriasis, and Sjogren's syndrome; Type II inflammatory diseases such as vascular inflammation (including vasculitis, arteritis, atherosclerosis, and coronary artery disease); diseases of the central nervous system such as stroke; pulmonary diseases such as bronchitis obliteraus and primary pulmonary hypertension; solid, delayed Type IV hypersensitivity reactions; and hematologic malignancies such as leukemia and lymphomas.

Examples of diseases that are mediated, at least in part, by JAK kinases that can be treated or prevented according to the methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, and amyotrophic lateral sclerosis, multiple sclerosis, psoriasis and Sjogren's syndrome, Type II inflammatory disease such as vascular inflammation (including vasculitis, arteritis, atherosclerosis and coronary artery disease) or other inflammatory diseases such as osteoarthritis, inflammatory bowel disease, ulcerative colitis, Crohn's disease, idiopathic inflammatory bowel disease, irritable bowel syndrome, spastic colon, low grade scarring (e.g., scleroderma, increased fibrosis, keloids, post-surgical scars, pulmonary fibrosis, vascular spasms, migraine, reperfusion injury and post myocardial infarction), and sicca complex or syndrome, diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lyphomas.

In another embodiment, this invention provides a method of inhibiting an activity of a JAK kinase, comprising contacting the JAK kinase with an amount of a compound effective to inhibit an activity of the JAK kinase, wherein the compound is selected from the compounds of this invention. In certain embodiments of the methods described herein, the method is carried out in vivo.

In another embodiment, this invention provides a method of inhibiting an activity of a JAK kinase, comprising contacting in vitro a JAK kinase with an amount of a compound effective to inhibit an activity of the JAK kinase, wherein the compound is selected from the compounds of this invention.

In a specific embodiment, the compounds can be used to treat and/or prevent rejection in organ and/or tissue transplant recipients (i.e., treat and/or prevent allograft rejection). Allografts can be rejected through either a cell-mediated or humoral immune reaction of the recipient against transplant (histocompatibility) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans.

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relatively uncommon today.

Acute rejection is thought to be mediated by the accumulation of antigen specific cells in the graft tissue. The T-cell-mediated immune reaction against these antigens (i.e., HVGR or GVHR) is the principle mechanism of acute rejection. Accumulation of these cells leads to damage of the graft tissue. It is believed that both CD4+ helper T-cells and CD8+ cytotoxic T-cells are involved in the process and that the antigen is presented by donor and host dendritic cells. The CD4+ helper T-cells help recruit other effector cells, such as macrophages and eosinophils, to the graft. Accessing T-cell activation signal transduction cascades (for example, CD28, CD40L, and CD2 cascades) are also involved.

The cell-mediated acute rejection can be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type IV hypersensitivity. The pathologic profile differs from that of acute rejection. The arterial endothelium is primarily involved with extensive proliferation that may gradually occlude the vessel lumen, leading to ischemia, fibrosis, a thickened intima, and atherosclerotic changes. Chronic rejection is mainly due to a progressive obliteration of graft vasculature and resembles a slow, vasculitic process.

In Type IV hypersensitivity, CD8 cytotoxic T-cells and CD4 helper T cells recognize either intracellular or extracellular synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

Since JAK kinases play a critical role in the activation of T-cells, the compounds described herein can be used to treat and/or prevent many aspects of transplant rejection, and are particularly useful in the treatment and/or prevention of rejection reactions that are mediated, at least in part, by T-cells, such as HVGR or GVHR. The compounds can also be used to treat and/or prevent chronic rejection in transplant recipients and, in particular, in renal transplant recipients. The compound can also be administered to a tissue or an organ prior to transplanting the tissue or organ in the transplant recipient.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention. In certain embodiments of the methods the autoimmune disease is multiple sclerosis (MS), psoriasis, or Sjogren's syndrome. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be beta.-cell (humoral) based or T-cell based, include Cogan's syndrome, ankylosing spondylitis, Wegener's granulomatosis, autoimmune alopecia, Type I or juvenile onset diabetes, and thyroiditis.

The types of autoimmune diseases that may be treated or prevented with such prodrugs generally include those disorders involving tissue injury that occurs as a result of a humoral and/or cell-mediated response to immunogens or antigens of endogenous and/or exogenous origin. Such diseases are frequently referred to as diseases involving the nonanaphylactic (i.e., Type II, Type III and/or Type IV) hypersensitivity reactions.

Type I hypersensitivity reactions generally result from the release of pharmacologically active substances, such as histamine, from mast and/or basophil cells following contact with a specific exogenous antigen. As mentioned above, such Type I reactions play a role in numerous diseases, including allergic asthma, allergic rhinitis, etc.

Type II hypersensitivity reactions (also referred to as cytotoxic, cytolytic complement-dependent or cell-stimulating hypersensitivity reactions) result when immunoglobulins react with antigenic components of cells or tissue, or with an antigen or hapten that has become intimately coupled to cells or tissue. Diseases that are commonly associated with Type II hypersensitivity reactions include, but are not limited, to autoimmune hemolytic anemia, erythroblastosis fetalis and Goodpasture's disease.

Type III hypersensitivity reactions, (also referred to as toxic complex, soluble complex, or immune complex hypersensitivity reactions) result from the deposition of soluble circulating antigen-immunoglobulin complexes in vessels or in tissues, with accompanying acute inflammatory reactions at the site of immune complex deposition. Non-limiting examples of prototypical Type III reaction diseases include the Arthus reaction, rheumatoid arthritis, serum sickness, systemic lupus erythematosis, certain types of glomerulonephritis, multiple sclerosis and bullous pemphigoid.

Type IV hypersensitivity reactions (frequently called cellular, cell-mediated, delayed, or tuberculin-type hypersensitivity reactions) are caused by sensitized T-lymphocytes which result from contact with a specific antigen. Non-limiting examples of diseases cited as involving Type IV reactions are contact dermatitis and allograft rejection.

Autoimmune diseases associated with any of the above nonanaphylactic hypersensitivity reactions may be treated or prevented with the prodrugs according to structural formulae (I) and (Ia). In particular, the methods may be used to treat or prevent those autoimmune diseases frequently characterized as single organ or single cell-type autoimmune disorders including, but not limited to: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, as well as those autoimmune diseases frequently characterized as involving systemic autoimmune disorder, which include but are not limited to: systemic lupus erythematosis (SLE), rheumatoid arthritis, Sjogren's syndrome, Reiter's syndrome, polymyositis-dermatomyositis, systemic sclerosis, polyarteritis nodosa, multiple sclerosis and bullous pemphigoid.

It will be appreciated by skilled artisans that many of the above-listed autoimmune diseases are associated with severe symptoms, the amelioration of which provides significant therapeutic benefit even in instances where the underlying autoimmune disease may not be ameliorated.

Therapy using the compounds described herein can be applied alone, or it can be applied in combination with or adjunctive to other common immunosuppressive therapies, such as, for example, the following: mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycophenolate, mycophenolate mofetil, and azathioprine; and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also: the prescribing information in the 2006 Edition of The Physician's Desk Reference), the disclosures of which are incorporated herein by reference. Azathioprine is currently available from Salix Pharmaceuticals, Inc., under the brand name AZASAN; mercaptopurine is currently available from Gate Pharmaceuticals, Inc., under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand dame SANDIMMUNE and from Abbott under the brand name GENGRAF; IMPDH inhibitors such as mycophenolate mofetil and mycophenolic acid are currently available from Roche under the brand name CELLCEPT and from Novartis under the brand name MYFORTIC; azathioprine is currently available from Glaxo Smith Kline under the brand name IMURAN; and antibodies are currently available from Ortho Biotech under the brand name ORTHOCLONE, from Novartis under the brand name SIMULECT (basiliximab), and from Roche under the brand name ZENAPAX (daclizumab).

In another embodiment, the compounds could be administered either in combination or adjunctively with an inhibitor of a Syk kinase. Syk kinase is a tyrosine kinase known to play a critical role in Fcγ receptor signaling, as well as in other signaling cascades, such as those involving B-cell receptor signaling (Turner et al., (2000), Immunology Today 21:148-154) and integrins beta (1), beta (2), and beta (3) in neutrophils (Mocsai et al., (2002), Immunity 16:547-558). For example, Syk kinase plays a pivotal role in high affinity IgE receptor signaling in mast cells that leads to activation and subsequent release of multiple chemical mediators that trigger allergic attacks. However, unlike the JAK kinases, which help regulate the pathways involved in delayed or cell-mediated Type IV hypersensitivity reactions, Syk kinase helps regulate the pathways involved in immediate IgE-mediated, Type I hypersensitivity reactions. Certain compounds that affect the Syk pathway may or may not also affect the JAK kinase pathways.

Suitable Syk inhibitory compounds are described, for example, in Ser. No. 10/355,543 filed Jan. 31, 2003 (publication no. 2004/0029902); WO 03/063794; Ser. No. 10/631,029 filed Jul. 29, 2003; WO 2004/014382; Ser. No. 10/903,263 filed Jul. 30, 2004; PCT/US2004/24716 filed Jul. 30, 2004 (WO005/016893); Ser. No. 10/903,870 filed Jul. 30, 2004; PCT/US2004/24920 filed Jul. 30, 2004; Ser. No. 60/630,808 filed Nov. 24, 2004; Ser. No. 60/645,424 filed Jan. 19, 2005; and Ser. No. 60/654,620, filed Feb. 18, 2005, the disclosures of which are incorporated herein by reference. The described herein and Syk inhibitory compounds could be used alone or in combination with one or more conventional transplant rejection treatments, as described above.

In a specific embodiment, the compounds can be used to treat or prevent these diseases in patients that are either initially non-responsive (resistant) to or that become non-responsive to treatment with a Syk inhibitory compound or one of the other current treatments for the particular disease. The compounds could also be used in combination with Syk inhibitory compounds in patients that are Syk-compound resistant or non-responsive. Suitable Syk-inhibitory compounds with which the compounds can be administered are provided infra.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention, as described herein, and the compound is administered in combination with or adjunctively to a compound that inhibits Syk kinase with an $IC_{50}$ in the range of at least 10 µM.

In another embodiment, this invention provides a method of treating or preventing allograft transplant rejection in a transplant recipient, comprising administering to the transplant recipient an amount of a compound effective to treat or prevent the rejection wherein the compound is selected from the compounds of the invention, as described herein. In a further embodiment, the compound is administered to a tissue or an organ prior to transplanting the tissue or organ in the transplant recipient.

In another embodiment, this invention provides a method of treating or preventing allograft transplant rejection in a transplant recipient, in which the rejection is acute rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is chronic rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is mediated by HVGR or GVHR, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection wherein the compound is selected from the compounds of the invention, as described herein, in which the compound is administered in combination with or adjunctively to another immunosuppressant.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of the invention, as described herein, in which the compound is administered in combination with or adjunctively to another immunosuppressant, in which the immunosuppressant is selected from cyclosporine, tacrolimus, sirolimus, an inhibitor of IMPDH, mycophenolate, mycophanolate mofetil, an anti-T-Cell antibody, and OKT3.

The compounds described herein are cytokine moderators of IL-4 signaling. As a consequence, the compounds could slow the response of Type I hypersensitivity reactions. Thus, in a specific embodiment, the compounds could be used to treat such reactions and, therefore, the diseases associated with, mediated by, or caused by such hypersensitivity reactions (for example, allergies), prophylactically. For example, an allergy sufferer could take one or more of the JAK3 selective compounds described herein prior to expected exposure to allergens to delay the onset or progress of, or eliminate altogether, an allergic response.

When used to treat or prevent such diseases, the compounds can be administered singly, as mixtures of one or more compounds, or in mixture or combination with other agents useful for treating such diseases and/or the symptoms associated with such diseases. The compounds may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, beta.-agonists, tryptase inhibitors, aspirin, cyclooxygenase (COX) inhibitors, methotrexate, anti-TNF drugs, anti CD20 antibody, PD4 inhibitors, p38 inhibitors, PDE4 inhibitors, and antihistamines, to name a few. The compounds can be administered per se in the form of prodrugs or as pharmaceutical compositions, comprising an active compound or prodrug.

In another embodiment, this invention provides a method of treating or preventing a Type IV hypersensitivity reaction, comprising administering to a subject an amount of a compound effective to treat or prevent the hypersensitivity reaction, wherein the compound is selected from the compounds of this invention, as described herein.

In another embodiment, this invention provides a method of treating or preventing a Type IV hypersensitivity reaction, which is practical prophylactically, comprising administering to a subject an amount of a compound effective to treat or prevent the hypersensitivity reaction, wherein the compound is selected from the compounds of this invention, as described herein, and is administered prior to exposure to an allergen.

In another embodiment, this invention provides a method of inhibiting a signal transduction cascade in which JAK kinase plays a role, comprising contacting a cell expressing a receptor involved in such a signaling cascade with a compound wherein the compound is selected from the compounds of this invention, as described herein.

In another embodiment, this invention provides a method of treating or preventing a JAK kinase-mediated disease, comprising administering to a subject an amount of compound effective to treat or prevent the JAK kinase-mediated disease, wherein the compound is selected from the compounds of this invention, as described herein.

In another embodiment, this invention provides a method of treating or preventing a JAK kinase-mediated disease, in which the JAK-mediated disease is HVGR or GVHR, comprising administering to a subject an amount of compound effective to treat or prevent the JAK kinase-mediated disease, wherein the compound is selected from the compounds of the invention, as described herein.

In another embodiment, this invention provides a method of treating or preventing a JAK kinase-mediated disease, in which the JAK-mediated disease is acute allograft rejection, comprising administering to a subject an amount of compound effective to treat or prevent the JAK kinase-mediated disease, wherein the compound is selected from the compounds of the invention, as described herein.

In another embodiment, this invention provides a method of treating or preventing a JAK kinase-mediated disease, in which the JAK-mediated disease is chronic allograft rejection, comprising administering to a subject an amount of compound effective to treat or prevent the JAK kinase-mediated disease, wherein the compound is selected from the compounds of the invention, as described herein.

Active compounds of the invention typically inhibit the JAK/STAT pathway. The activity of a specified compound as an inhibitor of a JAK kinase can be assessed in vitro or in vivo. In some embodiments, the activity of a specified compound can be tested in a cellular assay.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

Generally, cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) (Cynthia K. Hahn, Kenneth N. Ross, Rose M. Kakoza, Steven Karr, Jinyan Du, Shao-E Ong, Todd R. Golub, Kimberly Stegmaier, Syk is a new target for AML differentiation, Blood, 2007, 110, Abstract 209) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34; 22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplamacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant JAK kinase activity can be treated with the JAK kinase inhibitory compounds.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9; 22)(qq34; q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant JAK kinase activity can be treated with the JAK kinase inhibitory compounds.

In some embodiments, the compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8; 21)(q22; q22), AML1 (CBF-alpha)/ETO, Acute promyelocytic leukemia (AML with t(15; 17)(q22; q11-12) and variants, PML/RAR-alpha), AML with abnormal bone marrow eosinophils (inv(16) (p13q22) or t(16; 16)(p13; q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

"Treating" within the context of the invention means an alleviation of symptoms associated with a disorder or disease, or halt of further progression or worsening of those symptoms, or prevention or prophylaxis of the disease or disorder.

The term "mammal" includes organisms which express JAK. Examples of mammals include mice, rats, cows, sheep, pigs, goats, horses, bears, monkeys, dogs, cats and, preferably, humans. Transgenic organisms which express a JAK kinase are also included in this definition.

The inventive methods comprise administering an effective amount of a compound or composition described herein to a mammal or non-human animal. As used herein, "effective amount" of a compound or composition of the invention includes those amounts that antagonize or inhibit JAK. An amount which antagonizes or inhibits JAK kinase is detectable, for example, by any assay capable of determining JAK kinase activity, including the one described below as an illustrative testing method. Effective amounts may also include those amounts which alleviate symptoms of a JAK kinase associated disorder treatable by inhibiting JAK kinase. Accordingly, "antagonists of JAK kinase" include compounds which interact with the JAK kinase, respectively, and modulate, e.g., inhibit or decrease, the ability of a second compound, e.g., another JAK kinase ligand, to interact with the JAK kinase, respectively. The JAK kinase binding compounds are preferably antagonists of JAK kinase, respectively. The language and "JAK-binding compound" (e.g., exhibits binding affinity to the receptor) includes those compounds which interact with JAK kinase resulting in modulation of the activity of JAK kinase, respectively. JAK kinase binding compounds may be identified using an in vitro (e.g., cell and non-cell based) or in vivo method. A description of in vitro methods are provided below.

The amount of compound present in the methods and compositions described herein should be sufficient to cause a detectable decrease in the severity of the disorder, as measured by any of the assays described in the examples. The amount of JAK kinase modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt, ester or prodrug thereof according to the formula I, another therapeutic agent (e.g., methotrexate) or a pharmaceutically acceptable salt, ester or prodrug thereof, and a pharmaceutically acceptable excipient or carrier.

The invention comprises a compound having the formula I, a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases (e.g., inflammatory, autoimmune, neurological, neurodegenerative, oncology and cardiovascular), organ transplants, osteoarthritis, irritable bowel disease (IBD), asthma, allergic conjunctivitis, uveitis, chronic obstructive pulmonary disease (COPD), systemic lupus erythematosus (SLE), multiple sclerosis (MS), rheumatoid arthritis (RA), Crohn's disease, Type I diabetes and psoriasis. The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

All of the compounds of the present invention are either potent inhibitors of JAK kinases, exhibiting $IC_{50}$s in the respective assay in the range of less than 5 µM, with most being in the nanomolar, and several in the sub-nanomolar, range. In some embodiments, the compounds of the present invention may be "dual" or "pan" JAK inhibitors in that they inhibit JAK1, JAK2, Tyk2, and JAK3 to some degree. In other embodiments, the compounds of the present invention may selectively inhibit JAK3 kinase, but not appreciably inhibit one or more JAK kinases.

f. Kits

Still another aspect of this invention is to provide a kit comprising separate containers in a single package, wherein the inventive pharmaceutical compounds, compositions and/or salts thereof are used in combination with pharmaceutically acceptable carriers to treat states, disorders, symptoms and diseases where JAK plays a role.

EXAMPLES

The following examples are offered to illustrate, but not to limit, the claimed invention.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods, which are well known in the art.

The compounds and/or intermediates may be characterized by high performance liquid chromatography (HPLC) using a Waters Alliance chromatography system with a 2695 Separation Module (Milford, Mass.). The analytical columns may be C-18 SpeedROD RP-18E Columns from Merck KGaA (Darmstadt, Germany). Alternately, characterization may be performed using a Waters Unity (UPLC) system with Waters Acquity UPLC BEH C-18 2.1 mm×15 mm columns. A gradient elution may be used, typically starting with 5% acetonitrile/95% water and progressing to 95% acetonitrile over a period of 5 minutes for the Alliance system and 1 minute for the Acquity system. All solvents may contain 0.1% trifluoroacetic acid (TFA). Compounds may be detected by ultraviolet light (UV) absorption at either 220 nm or 254 nm. HPLC solvents may be from EMD Chemicals, Inc. (Gibbstown, N.J.). In some instances, purity may be assessed by thin layer chromatography (TLC) using glass backed silica gel plates, such as, for example, EMD Silica Gel 60 2.5 cm×7.5 cm plates. TLC results may be readily detected visually under ultraviolet light, or by employing well known iodine vapor and other various staining techniques.

Mass spectrometric analysis may be performed on one of two Agilent 1100 series LCMS instruments with acetonitrile/water as the mobile phase. One system may use TFA as the modifier and measure in positive ion mode [reported as MH+, (M+1) or (M+H)+] and the other may use either formic acid or ammonium acetate and measure in both positive [reported as MH$^+$, (M+1) or (M+H)$^+$] and negative [reported as M−, (M−1) or (M−H)$^-$] ion modes.

Nuclear magnetic resonance (NMR) analysis may be performed on some of the compounds with a Varian 400 MHz NMR (Palo Alto, Calif.). The spectral reference may be either TMS or the known chemical shift of the solvent.

The purity of some of the invention compounds may be assessed by elemental analysis (Robertson Microlit, Madison, N.J.).

Melting points may be determined on a Laboratory Devices Mel-Temp apparatus (Holliston, Mass.).

Preparative separations may be carried out as needed, using either an Sq16x or an Sg100c chromatography system and prepackaged silica gel columns all purchased from Teledyne Isco, (Lincoln, Nebr.). Alternately, compounds and intermediates may be purified by flash column chromatography using silica gel (230-400 mesh) packing material, or by HPLC using a C-18 reversed phase column. Typical solvents employed for the Isco systems and flash column chromatography may be dichloromethane, methanol, ethyl acetate, hexane, acetone, aqueous hydroxyamine and triethyl amine. Typical solvents employed for the reverse phase HPLC may be varying concentrations of acetonitrile and water with 0.1% trifluoroacetic acid.

General Methods

The following synthetic reaction schemes are merely illustrative of some methods by which the compounds of the General Scheme for the Synthesis of Substituents:

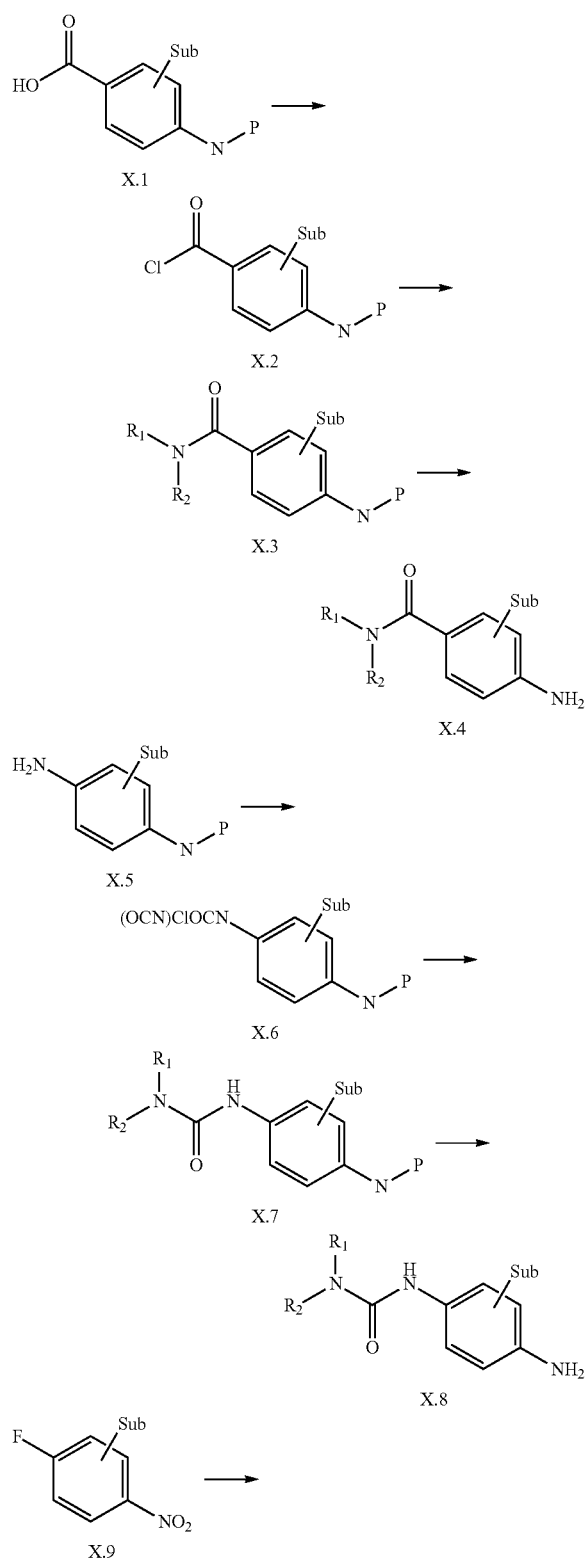

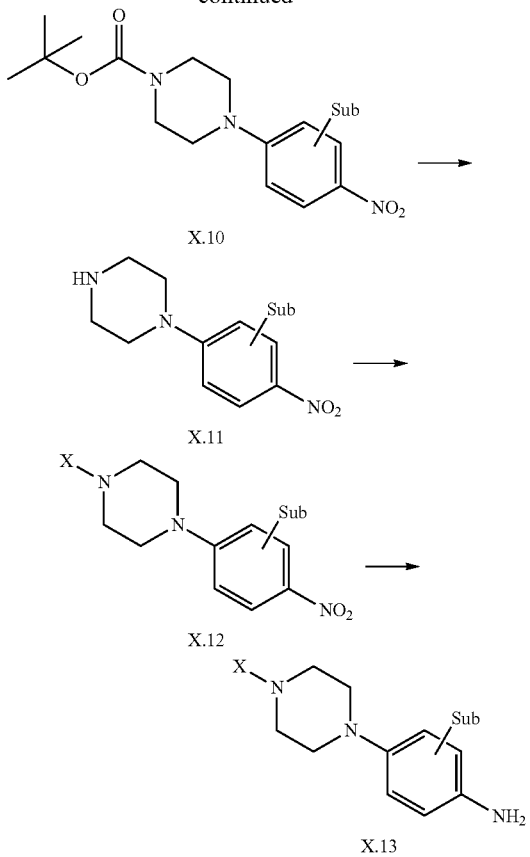

Benzamide intermediates used as the aniline component in Scheme 8 Step IV can be synthesized according to the above general scheme. A carboxylic acid (X.1) containing an amino group protected as a carbamate or more preferably as a nitro group can be converted to the acid chloride using a suitable reagent, such as oxalyl chloride containing a catalytic amount of DMF in a solvent such as dichloromethane. Once the acid chloride has been formed it can then be converted to the amide by treating it with a suitable amine in the presence of a base, such as diisopropyl ethyl amine, in a solvent such as acetonitrile. Finally, the amino group can be deprotected using catalytic palladium on carbon in the presence of hydrogen (if a nitro group or CBz group).

Urea intermediates used as the aniline component in the final coupling step can be synthesized by first forming the carbamoyl chloride by stirring a suitably protected dianiline with phosgene in a solvent such as toluene, acetonitrile, dioxane, or dichloromethane. Intermediate X.6 can then be coupled with an amine in the presence of a tertiary amine base such as diisopropylethylamine or triethylamine, in a solvent such as acetonitrile, dioxane, or dichloromethane. Alternatively, an excess of the amine used to form the urea can be used as a base. Finally, the protected amino group can be deprotected as described above.

Substituted heterocycles such as X.13 can be synthesized by starting from a suitably activated fluorobenzene intermediate such as X.9 and a monoprotected difunctional reagent such as Bocpiperazine (shown in scheme 9). Thermal displacement of the fluorine using a solvent such as acetonitrile, dioxane, NMP, or DMSO and a base such as diisopropylethylamine can be accomplished using temperatures from rt to 140° C., but most preferably in the range of 50-100° C.

Deprotection of the nitrogen can be accomplished by treatment with an acid in a suitable solvent, such as 4M HCl in dioxane, or trifluoroacetic acid in dichloromethane. The amino group can then be coupled with a variety of reagents using procedures described in the chemistry literature. Finally, the aniline to be used in the subsequent coupling can be formed by reduction of the nitro group using hydrogenolysis as described above.

Example 1

6-(4-(4-acetylpiperazin-1-yl)phenylamino)-2-(cyclobutylamino)nicotinamide

Scheme 1:

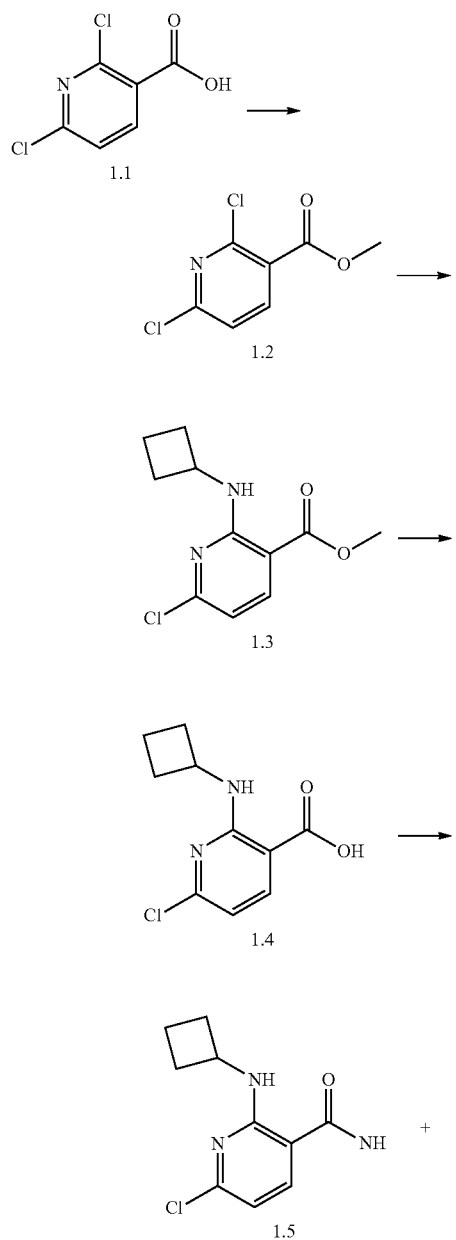

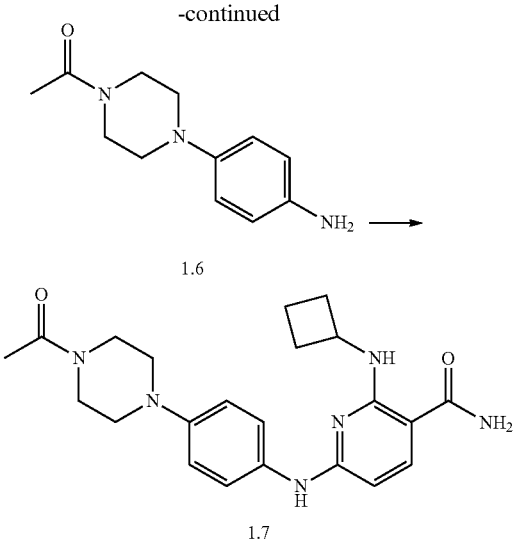

Step 1:

Dichlorocarboxylic acid 1.1 (2.0 g, 10 mmol) was diluted with 10 mL each of 1,4-dioxane and methanol, then treated with a 2.0M TMSCHN$_2$ in diethyl ether solution (7.5 mL, 15 mmol) resulting in vigorous gas evolution and a light green solution. After stirring overnight the reaction was checked by UPLC which showed complete conversion to the desired product. The reaction was concentrated to near dryness, then diluted with water and stirred vigorously. The resulting granular precipitate was then filtered and dried under vacuum affording the desired methyl ester as a light beige solid (2.01 g, 97%). MS found for $C_7H_5Cl_2NO_2$ as $(M+H)^+$ 206.0, 208.0. UV λ=276.

Step 2:

Dichloro ester 1.2 (2.0 g, 9.7 mmol) was diluted with 20 mL of acetonitrile then treated with diisopropyl ethyl amine (1.9 mL, 10.7 mmol) followed by cyclobutyl amine (0.75 mL, 9.7 mmol). The reaction as then stirred at room temperature for two days during which time a precipitate formed. When the progress was checked by UPLC the reaction was found to be only 50% complete with an 4:1 ratio of the 2-amino to 6-amino isomers. The solids were removed by filtration affording 0.40 g of the desired product. The filtrate was then diluted with water to 100 mL total volume affording an additional 0.50 g of the desired product. MS found for $C_{11}H_{13}ClN_2O_2$ as $(M+H)^+$ 241.0, 243.0. UV λ=263 (major), 288 (minor).

Step 3:

Methyl ester 1.3 (0.5 g, 2.1 mmol) was diluted with 10 mL of 1,4-dioxane and then treated with 1.0 M LiOH (2.5 mL, 2.5 mmol) and stirred at room temperature for two hours. The reaction as diluted with ca. 30 mL of water and acidified to pH=2 with 1.0 M hydrochloric acid, and extracted twice with ethyl acetate. Concentration of the combined organic layers afforded the desired carboxylic acid which was used immediately for the next step.

Step 4:

Carboxylic acid 1.4 from the previous step was dissolved in 10 mL of N,N-dimethylformamide then treated with hydroxybenzotriazole (0.54 g 4.0 mmol) and EDC (0.77 g, 4.0 mmol). The reaction was stirred until all solids dissolved (ca. 15 min), then treated with 0.5 M ammonia in dioxane (13 mL, 6.5 mmol), capped, and stirred overnight. The following morning the reaction was checked by UPLC which consumption of the starting material and the formation of two new peaks. The reaction was diluted with water and the solids isolated by filtration affording the desired product as a light beige solid (no yield calculated). UV λ=207, 265.

Step 5:

Chloropyridine 1.5 (20 mg, 0.089 mmol) was diluted with n-butanol (3 mL) then treated with aniline 1.6 (27 mg, 0.12 mmol) (prepared from Boc-piperazine and 4-fluoronitrobenzene, which was subsequently deprotected with 4 M HCl/dioxane, then acylated with acetyl chloride, and finally reduced with hydrogen and palladium on carbon) followed by trimethylsilyl chloride (23 uL, 0.18 mmol). The reaction was then capped and heated to 130° C. overnight. The reaction was checked by HPLC the following morning and found to be 15% complete. It was then diluted with water and purified by preparative HPLC, affording the desired product as a white solid after lyophilization. MS found for $C_{22}H_{28}N_6O_2$ as (M+H)+ 409.2. UV λ=258, 285. $^1$H NMR (CD$_3$OD-d$_4$, 400 MHz): δ 7.89 (d, 1H), 7.50 (d, 2H), 7.16 (d, 2H), 5.94 (d, 1H), 4.38 (m, 1H), 3.68 (m, 4H), 3.25 (m, 4H), 2.51 (m, 2H), 2.07 (m, 2H), 1.90 (m, 2H).

Example 2

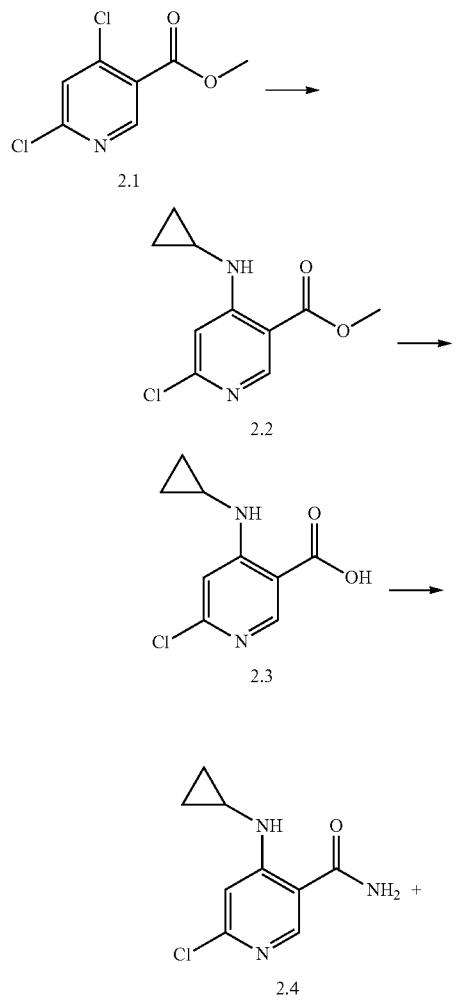

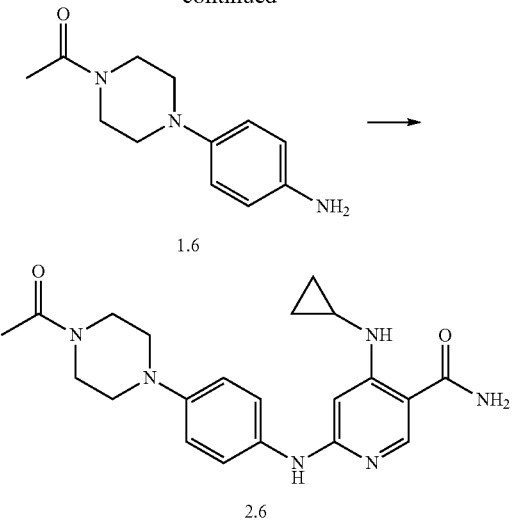

Step 1:

Dichloropyridine 1.1 (prepared using the procedure described in Brunette, S. R.; Kim, J. M.; Lemieux, R. M.; Aaron, M. US2006/0217417.) (1.0 g, 4.9 mmol) was dissolved in 10 mL of N-methylpyrrolidinone, then treated with cyclopropylamine (0.34 mL, 4.9 mmol) and diisopropylethylamine (1.7 mL, 10 mmol) and heated to 100° C. After one hour the reaction was checked by UPLC and determined to be complete. It was then cooled to room temperature and diluted with water, forming an oil. This was extracted twice with dichloromethane and the combined organic layers dried over sodium sulfate. After removal of the drying agent the solvents were removed in vacuo and the residue purified by silica gel chromatography (100% dichloromethane) affording the desired product as a colorless oil (0.97 g, 88%). $C_{10}H_{11}ClN_2O_2$ as (M+H)+ 227.0, 229.0. UV λ=235, 260.

Step 2:

Methyl ester 1.2 (0.97 g, 4.3 mmol) was diluted with 10 mL of 1,4-dioxane followed by 1.0 M LiOH (5.0 mL, 5.0 mmol), then stirred at room temperature overnight. The following morning the reaction was checked by UPLC which showed consumption of the starting material. The reaction was acidified to pH=2 with 1 M HCl then diluted with water affording only a clear solution. The aqueous phase was extracted exhaustively with ethyl acetate, the combined organic layers dried over magnesium sulfate, then concentrated to afford the desired carboxylic acid (0.28 g, 31%) as a white solid. $C_9H_9ClN_2O_2$ as (M+H)+ 213.0, 215.0. UV λ=225, 272. $^1$H NMR (CD$_3$OD-d$_4$, 400 MHz): δ 8.48 (s, 1H), 8.24 (s, 1H), 6.97 (s, 1H), 2.59 (m, 1H), 0.84 (m, 2H), 0.57 (m, 2H).

Step 3:

Carboxylic acid 1.3 (0.28 g, 1.3 mmol) was diluted with 6 mL of N,N-dimethylformamide then treated with hydroxybenzotriazole (0.27 g, 2.0 mmol) and EDC (0.38 g, 2.0 mmol). After stirring ca. 10 minutes the reaction was treated with 0.5 M ammonia in dioxane (6.0 mL, 3.0 mmol) resulting in a cloudy suspension. After stirring one hour the reaction was determined to be complete by UPLC. It was then diluted with water (50 mL) and extracted twice with ethyl acetate. The combined organic layers were dried over magnesium sulfate, then filtered, concentrated and dried under vacuum affording the desired amide which was used immediately for the next step. $C_9H_{10}ClN_3O$ as (M+H)+ 212.1, 214.0.

Step 6:

Chloropyridine 1.4 (10 mg, 0.048 mmol) was treated with aniline 1.6 (16 mg, 0.071 mmol) and diisopropylamine (17 uL, 0.096 mmol) and heated to 100° C. overnight, then 150° C. for two days. The crude reaction mixture was then diluted with a small amount of water and purified by preparative HPLC affording the desired product as an off-white solid after lyophilization (6 mg, 32%). $C_{21}H_{26}N_6O_2$ as $(M+H)^+$ 395.1. UV λ=201, 249. $^1$H NMR (CD$_3$OD-d$_4$, 400 MHz): δ 8.03 (s, 1H), 7.20 (d, 2H), 7.08 (d, 2H), 6.29 (s, 1H), 3.71 (m, 4H), 3.21 (m, 4H), 2.52 (m, 1H), 2.14 (s, 3H), 0.88 (m, 2H), 0.62 (m, 2H).

Example 3

6-(4-(4-acetylpiperazin-1-yl)phenylamino)-4-(benzylamino)nicotinamide

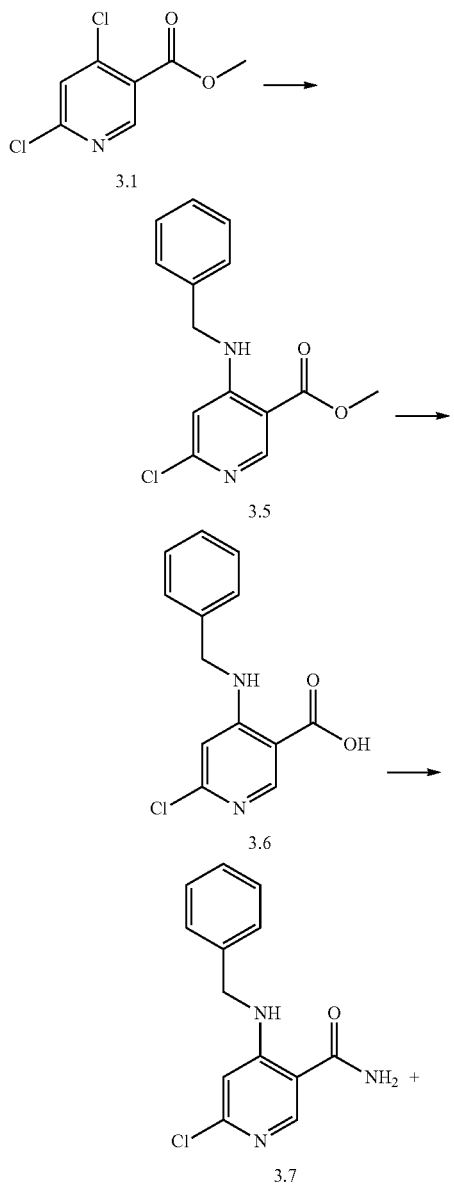

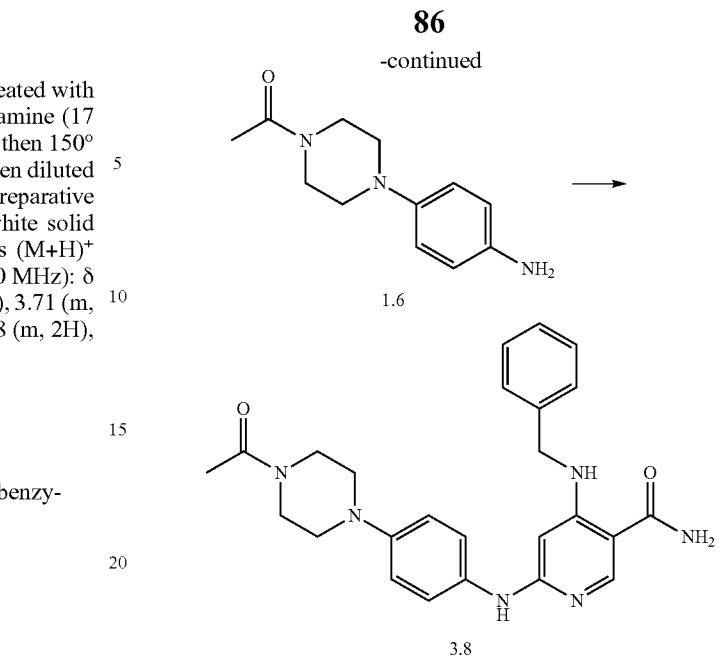

Step 1:

Dichloropyridine 3.1 (prepared using the procedure described in Brunette, S. R.; Kim, J. M.; Lemieux, R. M.; Aaron, M. US2006/0217417.) (5.0 g, 23 mmol) was diluted with 50 mL of acetonitrile, then treated with benzylamine (3.0 mL, 27 mmol) and diisopropylethylamine (6.0 mL, 35 mmol). After stirring two days at room temperature the reaction was determined to be complete by UPLC. It was then diluted with water and ethyl acetate. The organic phase was separated and the aqueous phase extracted once more with ethyl acetate. The combined organic layers were concentrate in vacuo and used immediately for the next step. $C_{15}H_{15}ClN_2O_2$ as $(M+H)^+$ 291.2. UV λ=227, 261, 310.

Step 2:

Ethyl ester 3.5 (23 mmol, theoretical) was diluted with 50 mL of 1,4-dioxane, followed by 1.0 M LiOH (35 mL, 35 mmol) and stirred at room temperature overnight after which time the saponification was complete as determined by UPLC. The reaction mixture was acidified with 1.0 M HCl to pH=7, then concentrated to remove the organic solvent. After sitting a precipitate formed which was isolate by filtration, washed with water, and aspirated to dryness, then dried under vacuum affording the desired carboxylic acid as a light brown powder (4.7 g, 78% for two steps). $C_{13}H_{11}ClN_2O_2$ as $(M+H)^+$ 263.2, 265.2. UV λ=224, 263.

Step 3:

Carboxylic acid 3.6 (4.7 g, 18 mmol) was dissolved in 40 mL of N,N-dimethylformamide, then treated with hydroxybenzotriazole (3.5 g, 23 mmol) and EDC (4.4 g, 23 mmol) affording a brown solution. After one hour, aqueous ammonia (6.0 mL) was added and the reaction stirred until conversion to the amide was complete. The mixture was then diluted with water until precipitate formation appeared complete, stirred, then the solids isolated by filtration. The solid was then aspirated to dryness affording the desired carboxamide as a light beige solid (no yield calculated). $C_{13}H_{12}ClN_3O$ as $(M+H)^+$ 262.2, 264.2. UV λ=213, 266. $^1$H NMR (DMSO-d$_6$, 400 MHz): δ 9.13 (t, 1H), 8.38 (s, 1H), 8.09 (s, 1H), 7.51 (s, 1H), 7.29 (m, 5H), 6.61 (s, 1H), 4.45 (d, 2H).

Step 4:

Combined chloropyridine 3.7 (100 mg, 0.38 mmol), aniline 1.6 (170 mg, 0.77 mmol), and diisopropylethylamine (140 uL, 0.77 mmol), in 2 mL of N-methylpyrrolidine. The reaction was then heated to 150° C. overnight. After checking by UPLC the reaction was then heated for two days at 150° C., then checked again by UPLC which showed consumption of the starting material. The reaction was then diluted to 5 mL total volume with water and purified by preparative HPLC affording 16 mg (9.4%) of the desired product. MS found for $C_{13}H_{12}ClN_3O$ as $(M+H)^+$ 445.4. $^1$H NMR ($CD_3OD$-$d_4$, 400 MHz): δ 8.18 (s, 1H), 7.39 (m, 5H), 7.08 (s, 4H), 5.82 (s, 1H), 4.53 (s, 2H), 3.78 (m, 4H), 3.25 (m, 4H), 2.19 (s, 3H).

Example 4

(S)-4-(benzylamino)-6-(4-(3-(methylcarbamoyl) piperidin-1-yl)phenylamino)nicotinamide

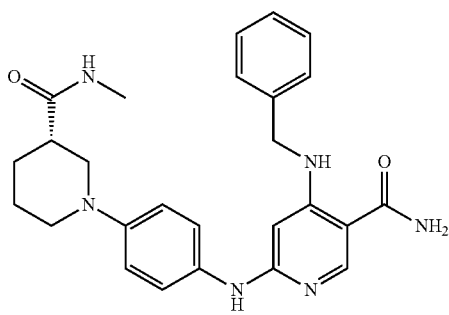 [SMILES: CNC(=O)[C@H]1CCCN(c2ccc(Nc3cc(NCc4ccccc4)c(C(N)=O)cn3)cc2)C1]

The titled compound was synthesized using a procedure similar to that in Example 3, with an aniline prepared from (S)-piperidinecarboxylic acid and 4-fluoronitrobenzene. MS found for $C_{26}H_{30}N_6O_2$ as $(M+H)^+$ 459.4. $^1$H NMR ($CD_3OD$-$d_4$, 400 MHz): δ 8.20 (s, 1H), 7.43 (m, 3H), 7.32 (d, 2H), 7.18 (d, 2H), 7.09 (d, 2H), 5.89 (s, 1H), 4.56 (s, 2H), 3.78 (m, 2H), 3.08 (m, 3H), 2.77 (s, 3H), 1.99 (m, 2H), 1.78 (m, 2H).

Example 5

6-(4-(4-acetylpiperazin-1-yl)-3-methylphenylamino)-4-(benzylamino)nicotinamide

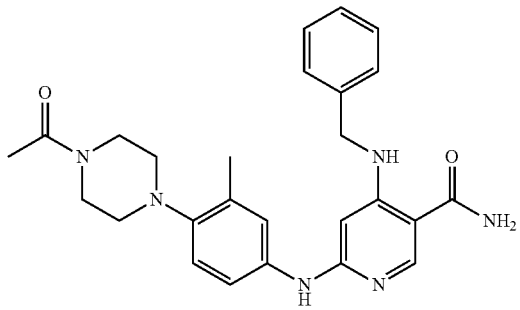 [SMILES: CC(=O)N1CCN(c2ccc(Nc3cc(NCc4ccccc4)c(C(N)=O)cn3)cc2C)CC1]

The titled compound was synthesized using a procedure similar to that in Example 3, with an aniline prepared from (S)-piperidinecarboxylic acid and 4-fluoronitrobenzene. MS found for $C_{26}H_{30}N_6O_2$ as $(M+H)^+$ 459.6. $^1$H NMR ($CD_3OD$-$d_4$, 400 MHz): δ 8.18 (s, 1H), 7.38 (m, 5H), 7.32 (d, 2H), 7.10 (d, 1H), 7.04 (d, 1H), 6.96 (dd, 1H), 5.84 (s, 2H), 4.50 (s, 2H), 4.56 (s, 2H), 3.78 (m, 4H), 2.97 (t, 2H), 2.91 (t, 2H), 2.38 (s, 3H), 2.18 (s, 3H).

Example 6

(R)-4-(benzylamino)-6-(4-(3-(methylcarbamoyl) piperidin-1-yl)phenylamino)nicotinamide

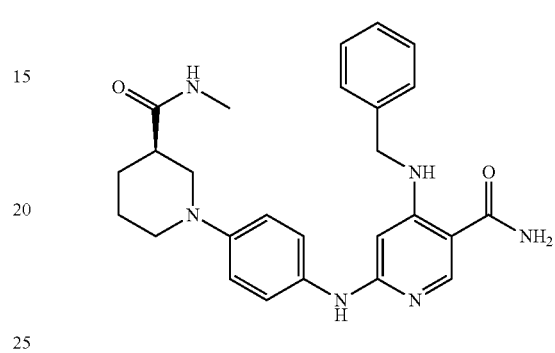

The titled compound was synthesized using a procedure similar to that in Example 3, with an aniline prepared from (R)-piperidinecarboxylic acid and 4-fluoronitrobenzene. MS found for $C_{26}H_{30}N_6O_2$ as $(M+H)^+$ 459.4. $^1$H NMR ($CD_3OD$-$d_4$, 400 MHz): δ 8.18 (s, 1H), 7.39 (m, 3H), 7.30 (d, 2H), 7.09 (d, 2H), 7.07 (d, 2H), 5.83 (s, 1H), 4.49 (s, 2H), 3.78 (m, 2H), 3.01 (m, 3H), 2.78 (s, 3H), 1.99 (m, 2H), 1.74 (m, 2H).

Example 7

(R)-6-(4-(4-acetylpiperazin-1-yl)phenylamino)-4-(1-phenylethylamino)nicotinamide

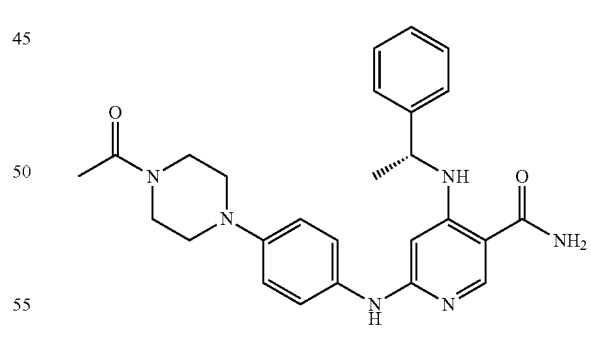

The titled compound was synthesized using a procedure similar to that in Example 3, using (R)-1-phenylethanamine in place of benzylamine. MS found for $C_{26}H_{30}N_6O_2$ as $(M+H)^+$ 459.5. $^1$H NMR ($CD_3OD$-$d_4$, 400 MHz): δ 8.28 (s, 1H), 7.37 (m, 3H), 7.25 (d, 2H), 5.64 (s, 1H), 3.76 (m, 4H), 3.26 (m, 4H), 2.18 (s, 3H), 1.58 (d, 3H). (note: benzylic proton is obscured by the water peak).

Example 8

6-(4-((R)-3-(methylcarbamoyl)piperidin-1-yl)phenylamino)-4-((R)-1-phenylethylamino)nicotinamide

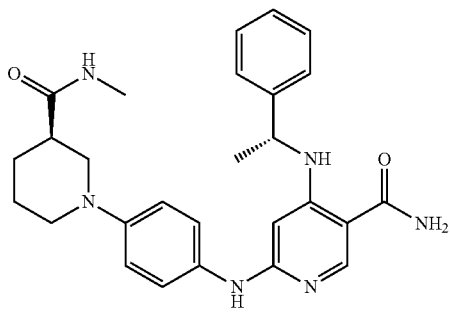 [SMILES: CNC(=O)[C@@H]1CCCN(c2ccc(Nc3cc(N[C@H](C)c4ccccc4)c(C(N)=O)cn3)cc2)C1]

The titled compound was synthesized using a procedure similar to that in Example 3, using (R)-1-phenylethanamine and an aniline described above. MS found for $C_{27}H_{32}N_6O_2$ as $(M+H)^+$ 473.5. $^1$H NMR (CD$_3$OD-d$_4$, 400 MHz): δ 8.18 (s, 1H), 7.38 (m, 3H), 7.24 (d, 2H), 7.06 (d, 2H), 6.95 (d, 2H), 5.68 (s, 1H), 3.77 (m, 3H), 3.02 (m, 1H), 2.90 (m, 1H), 2.76 (s, 3H), 1.98 (m, 2H), 1.77 (m, 2H), 1.59 (d, 3H).

Example 9

4-(benzylamino)-6-(phenylamino)nicotinamide

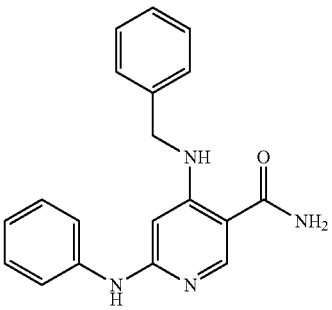 [SMILES: NC(=O)c1cnc(Nc2ccccc2)cc1NCc1ccccc1]

The titled compound was synthesized using a procedure similar to that in Example 3 using aniline in the last step. MS found for $C_{19}H_{18}N_4O$ as $(M+H)^+$ 319.4. $^1$H NMR (CD$_3$OD-d$_4$, 400 MHz): δ 8.19 (s, 1H), 7.38 (m, 8H), 7.14 (d, 2H), 5.93 (s, 1H), 4.51 (s, 2H).

Example 10

4-(benzylamino)-6-(p-tolylamino)nicotinamide

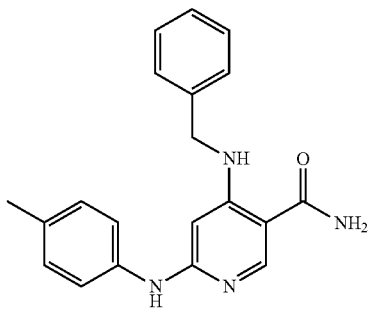 [SMILES: Cc1ccc(Nc2cc(NCc3ccccc3)c(C(N)=O)cn2)cc1]

The titled compound was synthesized using a procedure similar to that in Example 3 using p-toluidine in the last step. MS found for $C_{20}H_{20}N_4O$ as $(M+H)^+$ 333.4. $^1$H NMR (CD$_3$OD-d$_4$, 400 MHz): δ 8.17 (s, 1H), 7.32 (m, 7H), 7.02 (d, 2H), 5.87 (s, 1H), 4.49 (s, 2H), 2.42 (s, 3H).

Example 11

4-(benzylamino)-6-(3-methoxyphenylamino)nicotinamide

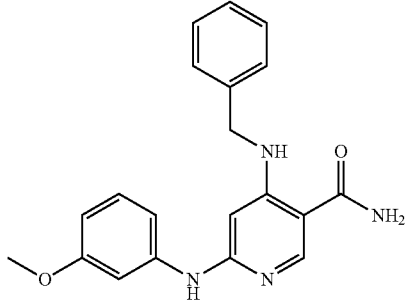 [SMILES: COc1cccc(Nc2cc(NCc3ccccc3)c(C(N)=O)cn2)c1]

The titled compound was synthesized using a procedure similar to that in Example 3 using m-anisidine in the last step. MS found for $C_{20}H_{20}N_4O_2$ as $(M+H)^+$ 349.4. $^1$H NMR (CD$_3$OD-d$_4$, 400 MHz): δ 8.18 (s, 1H), 7.37 (m, 6H), 6.88 (dd, 1H), 6.77 (d, 1H), 6.70 (dd, 1H), 4.50 (s, 2H), 3.81 (s, 3H).

Example 12

4-(benzylamino)-6-(4-methoxyphenylamino)nicotinamide

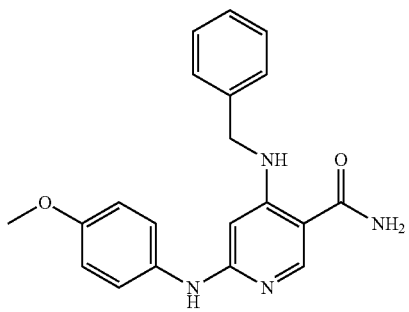 [SMILES: COc1ccc(Nc2cc(NCc3ccccc3)c(C(N)=O)cn2)cc1]

The titled compound was synthesized using a procedure similar to that in Example 3 using p-anisidine in the last step. MS found for $C_{20}H_{20}N_4O_2$ as $(M+H)^+$ 349.4. $^1$H NMR (CD$_3$OD-d$_4$, 400 MHz): δ 8.13 (s, 1H), 7.38 (m, 3H), 7.27 (d, 2H), 7.08 (d, 2H), 6.97 (d, 2H), 5.78 (s, 1H), 4.47 (s, 2H), 3.85 (s, 3H).

Example 13

4-(benzylamino)-6-(4-chlorophenylamino)nicotinamide

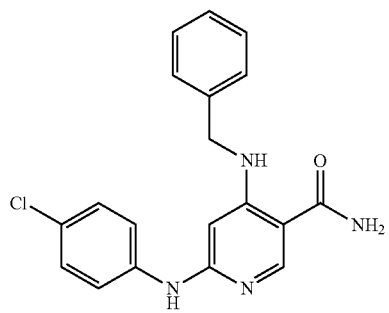 [SMILES: NC(=O)c1cnc(Nc2ccc(Cl)cc2)cc1NCc1ccccc1]

The titled compound was synthesized using a procedure similar to that in Example 3 using 4-chloroaniline in the last step. MS found for $C_{19}H_{17}ClN_4O$ as $(M+H)^+$ 353.3, 355.3. $^1H$ NMR (CD$_3$OD-d$_4$, 400 MHz): δ 8.21 (s, 1H), 7.38 (m, 5H), 7.30 (d, 2H), 7.14 (d, 2H), 5.91 (s, 1H), 4.53 (s, 2H).

Example 14

4-(3-toluidino)-6-(4-(2-(pyrrolidin-1-yl)ethoxy)phenylamino)nicotinamide

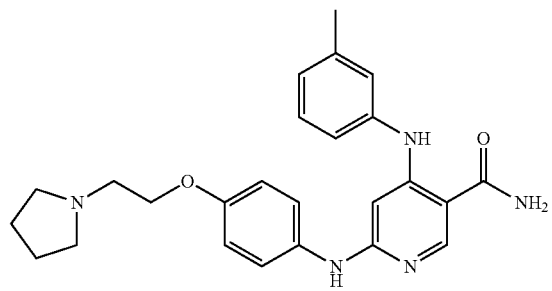 [SMILES: Cc1cccc(Nc2cc(Nc3ccc(OCCN4CCCC4)cc3)ncc2C(N)=O)c1]

The title compound was prepared with intermediate (14.2) according to the scheme below.

Scheme 2:

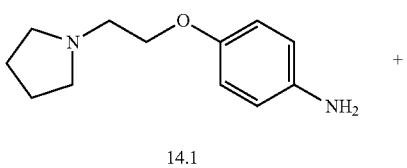

14.1

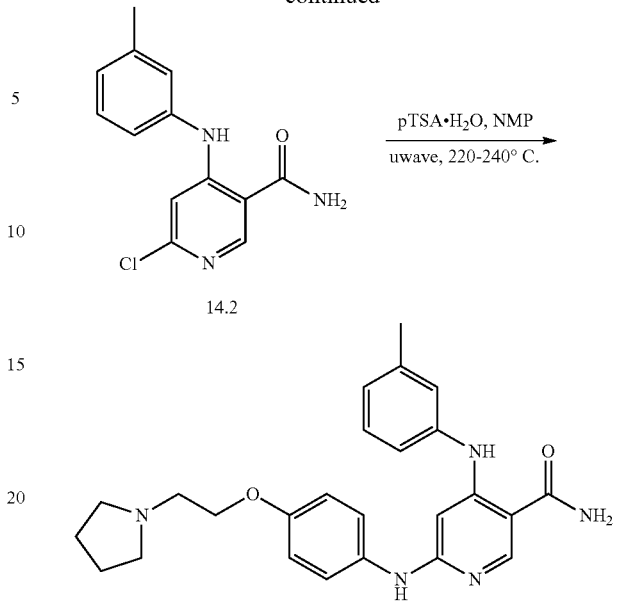

To a 5 mL microwave tube was added 8 (30 mg), 2 (30 mg), pTSA·H$_2$O (20 mg), and 3 mL NMP. Reaction mixture heated at 220° C. for 20 minutes. An additional 30 mg of 8 was added and then the reaction was heated to 240° C. for an additional 10 minutes. Water was added to the reaction mixture and the resulting solution was purified via preparative rpHPLC. Product was isolated by utilizing a mobile phase with 0.1% TFA in water as solvent A and 0.1% TFA in acetonitrile as solvent B and eluting with a 5% to 45% B mixture over 10 minutes. UV: 269 nm. M+H found for $C_{25}H_{29}N_5O_2$: 432.4. NMR (CD$_3$OD): 8.24 (1H, s), 7.30 (1H, t, J=8.0 Hz), 7.25-7.21 (2H, m), 7.10-7.03 (5H, m), 6.21 (1H, s), 4.34 (2H, dd, J=4.8 Hz, 4.8 Hz), 3.78-3.69 (2H, m), 3.67 (2H, dd, J=4.8 Hz, 4.8 Hz), 3.28-3.18 (2H, m), 2.36 (3H, s), 2.24-2.02 (4H, m) ppm.

Example 15

6-(3-toluidino)-4-(benzylamino)nicotinamide

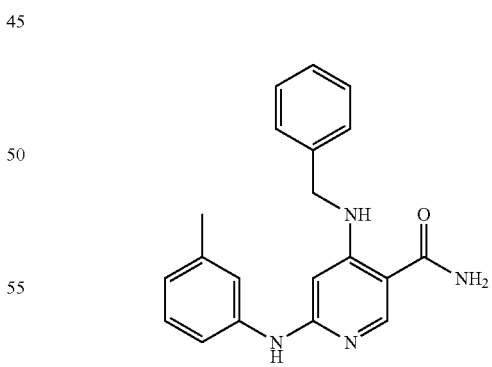

The title compound was prepared according to the procedure below.

To ~10 ml of NMP was added 15.1 (150 mg) and DIEA (~0.1 mL). To this stirring solution was added benzylamine (1.1 eq in ~5 mL NMP) dropwise. After stirring for 1 hour, H$_2$O was added to the reaction mixture, followed by EtOAc. HPLC analysis indicated substantial amounts of product in each layer. Both layers were concentrated and the resulting oil was dissolved in a H₂O/TFA/ACN mixture. This solution was purified via preparative rpHPLC utilizing a mobile phase with 0.1% TFA in water as solvent A and 0.1% TFA in acetonitrile as solvent B and eluting with a 20% to 60% B mixture over 10 minutes to give 205 mg of 4-(benzylamino)-6-chloronicotinonitrile (11). To 100 mg of 4-(benzylamino)-6-chloronicotinonitrile (11) in ~3 mL NMP was added 1 ml of 60 mg/ml m-toluidine and 45 mg pTSA.H₂O. Reaction heated at 120° C. for 72 hours. Due to inadequate conversion to product, the reaction mixture was transferred to a microwave tube and subsequently heated via microwave irradiation at 220° C. for 20 minutes. Water was added to the crude reaction mixture and a preparative rpHPLC was run in order to isolate pure 4-(benzylamino)-6-(m-tolylamino)nicotinonitrile (12). To 12 in ~3 mL DMSO was added K₂CO₃ (~100 mg) and 1.5 mL H₂O₂ (50% by wt.). The reaction was heated to 70° C. at which point the reaction mixture bubbled rigorously. Heat was removed until bubbling ceased and then the reaction mixture was again heated at 70° C. for an additional hour. The reaction mixture was cooled and a H₂O/TFA mixture was added. The resulting solution was purified via preparative rpHPLC utilizing a mobile phase with 0.1% TFA in water as solvent A and 0.1% TFA in acetonitrile as solvent B and eluting with a 15% to 55% B mixture over 10 minutes. UV: 257 nm. M+H found for $C_{20}H_{20}N_4O$: 333.3. NMR (CD₃OD): 8.12 (1H, s), 7.37-7.24 (6H, m), 7.14-7.09 (1H, m), 6.99 (1H, br), 6.92-6.87 (1H, m), 5.88 (1H, s), 4.45 (2H, s), 2.38 (3H, s) ppm.

Example 16

4,6-bis(4-morpholinophenylamino)nicotinamide

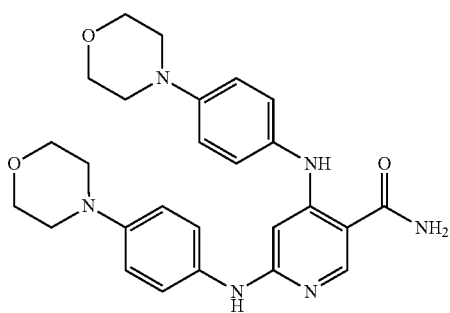 [SMILES: NC(=O)c1cnc(Nc2ccc(N3CCOCC3)cc2)cc1Nc1ccc(N2CCOCC2)cc1]

The title compound was prepared according to the scheme below.

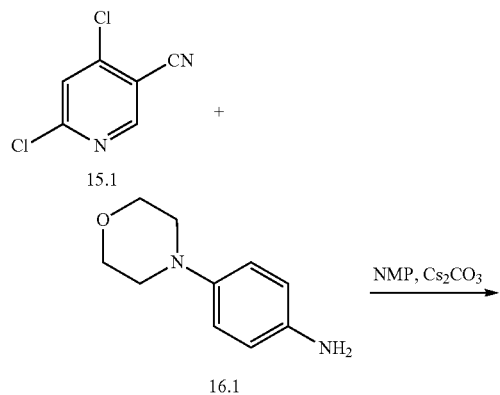

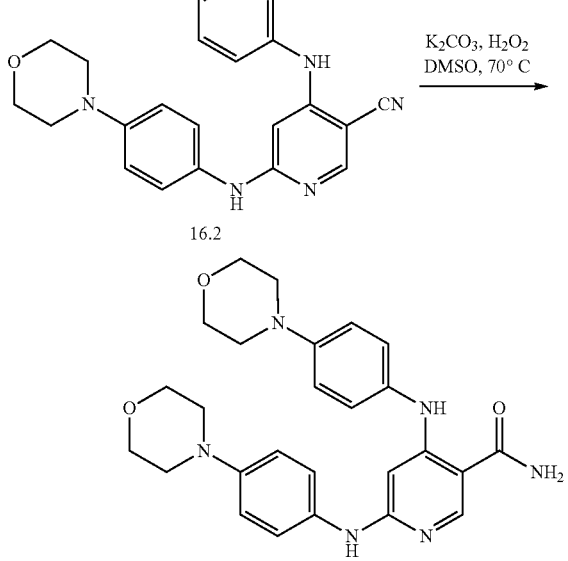

To ~10 ml of NMP was added 15.1 (375 mg), 16.1 (413 mg), and Cs₂CO₃ (780 mg). The reaction was stirred at 120° C. for 72 hours. The reaction mixture was cooled and a H₂O/TFA mixture was added. A preparative rpHPLC utilizing a mobile phase with 0.1% TFA in water as solvent A and 0.1% TFA in acetonitrile as solvent B and eluting with a 5% to 60% B mixture over 10 minutes was run. Compound 16.2 was isolated and was converted to title compound utilizing similar chemistry as described in Example 15. UV: 264 nm. M+H found for $C_{26}H_{30}N_6O_3$: 475.5. NMR (CD₃OD): 8.15 (1H, s), 7.18-7.00 (8H, m), 6.02 (1H, s), 3.84 (8H, dt, J=0.8 Hz, 8.4 Hz), 3.21-3.15 (8H, m) ppm.

Example 17

6-(4-methoxyphenylamino)-4-(4-morpholinophenylamino)nicotinamide

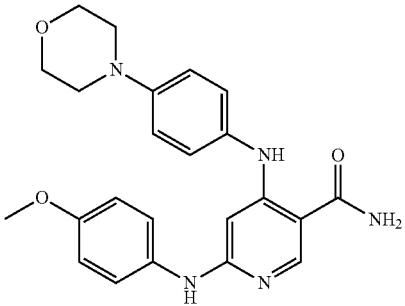 [SMILES: COc1ccc(Nc2cc(Nc3ccc(N4CCOCC4)cc3)c(C(N)=O)cn2)cc1]

The title compound was prepared utilizing similar chemistry as described for the conversion of 11 to 12 in Example 15, but with 4-methoxyaniline used in place of m-toluidine. UV: 259 nm. M+H found for $C_{23}H_{25}N_5O_3$: 420.4. NMR (CD₃OD): 8.13 (1H, s), 7.18-7.12 (4H, m), 7.05-6.95 (4H, m), 6.03 (1H, s), 3.86-3.80 (7H, m), 3.18-3.12 (4H, m) ppm.

Example 18

Preparation of 6-(3-acetamidophenylamino)-2-(cyclopentylamino)-5-fluoronicotinamide

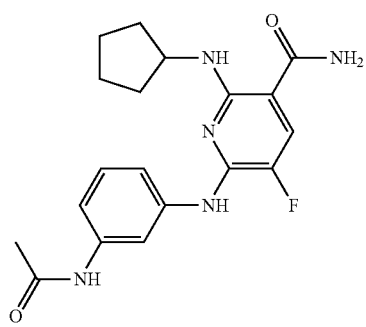 [SMILES: CC(=O)Nc1cccc(Nc2nc(NC3CCCC3)c(C(N)=O)cc2F)c1]

Scheme 5:

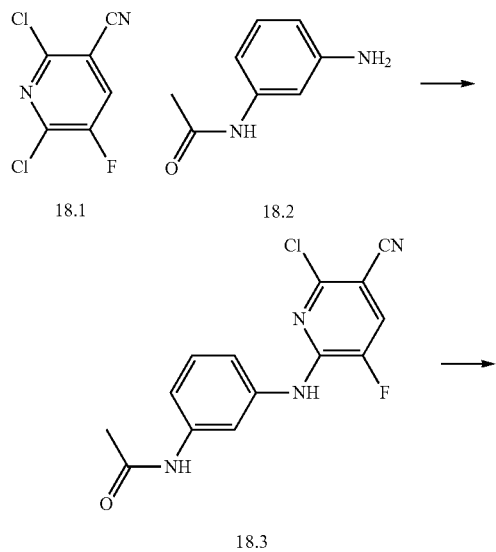

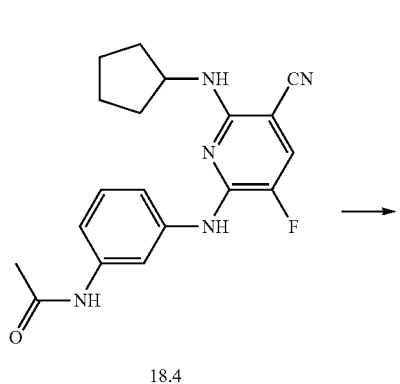

18.4

-continued

[structure]

Step 1: 2,6-Dichloro-5-fluoro-3-pyridinecarbonitrile (F1, Aldrich 422169, 2.00 g, 10.5 mmol) was dissolved in 60 mL NMP in a 500 mL flask and stirred at RT. To it was added 3'-aminoacetanilide (F2, Aldrich 485055, 1.89 g, 12.6 mmol) and DIEA (3.65 mL, 21.0 mmol). The mixture was heated to 100° C. gradually and stirred at this temperature for 3 h. The mixture was cooled to RT. To the flask then was added 400 mL cold water. A light yellow solid (compound F3) crashed out. It was isolated using Buchner funnel and washed with cold water multiple times. The solid was dried in vacuum oven at RT for two overnights (yield: 2.93 g, 91%).

Step 2: Compound F3 (100 mg, 0.33 mmol) was dissolved in 3 mL NMP in a sealed tube. To it was added cyclopentylamine (0.1 mL, 1.0 mmol). The mixture was stirred at 140° C. for overnight. The mixture was cooled to RT and diluted with 150 mL EtOAc. It was washed with brine twice, dried, concentrated in vacuo to offer crude compound 18.4.

Step 3: The above-prepared crude compound F4 was treated with 5 mL TFA and 1 mL concentrated H₂SO₄ at 80° C. for 1 h. It was diluted with water and subjected to reverse phase HPLC to isolate the title compound (45 mg). UV: 243, 281 nm. M+H found for $C_{19}H_{22}FN_5O_2$: 372.4. NMR (CD₃OD): 8.07 (1H, t, J=2.4 Hz), 7.64 (1H, d, J=12.0 Hz), 7.55 (1H, dm, J=8.0 Hz), 7.21 (1H, t, J=8.0 Hz), 7.05 (1H, dm, J=8.0 Hz), 4.35 (1H, m), 2.12 (3H, s), 2.05 (2H, m), 1.75 (2H, m), 1.63 (2H, m), 1.47 (2H, m) ppm.

Example 19

Preparation of 6-(3-acetamidophenylamino)-2-(benzylamino)-5-fluoronicotinamide

Scheme 6:

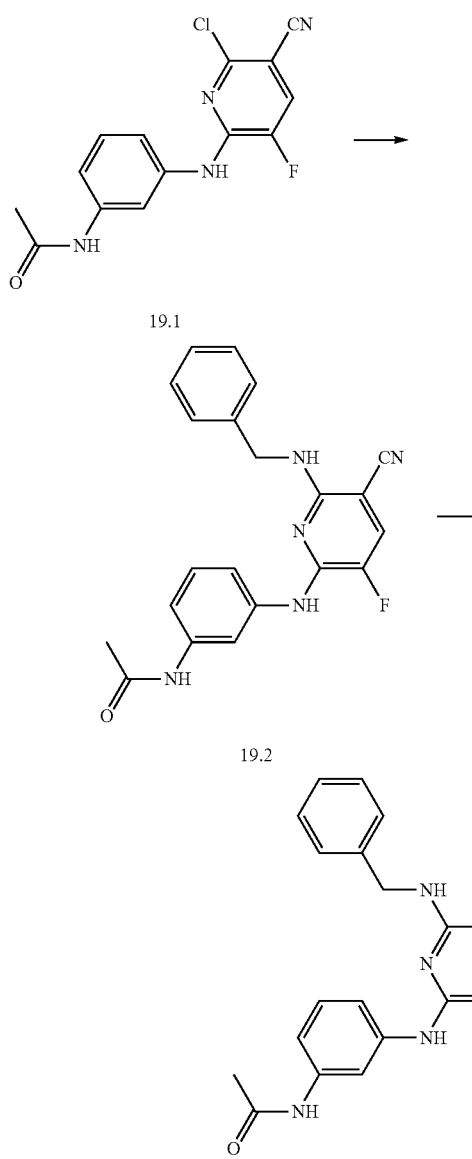

Example 20
Preparation of (R)-6-(3-acetamidophenylamino)-5-fluoro-2-(1-phenylethylamino)nicotinamide

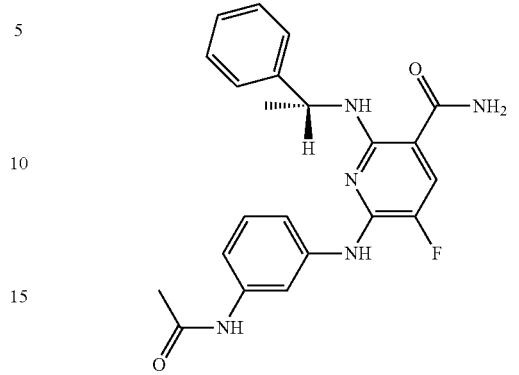

The title compound was prepared using the same chemistry shown in Example 19. UV: 249, 278 nm. M+H found for $C_{22}H_{22}FN_5O_2$: 480.4. NMR (CD$_3$OD): 7.80 (1H, t, J=2.0 Hz), 7.66 (1H, d, J=12.8 Hz), 7.32 (1H, m), 7.31-7.23 (4H, m), 7.16-7.10 (2H, m), 7.04 (1H, dm, J=8.0 Hz), 5.21 (1H, q, J=6.8 Hz), 2.13 (3H, s), 1.49 (3H, d, J=6.8 Hz) ppm.

Example 21
Preparation of 6-(3-acetamidophenylamino)-2-amino-5-fluoronicotinamide

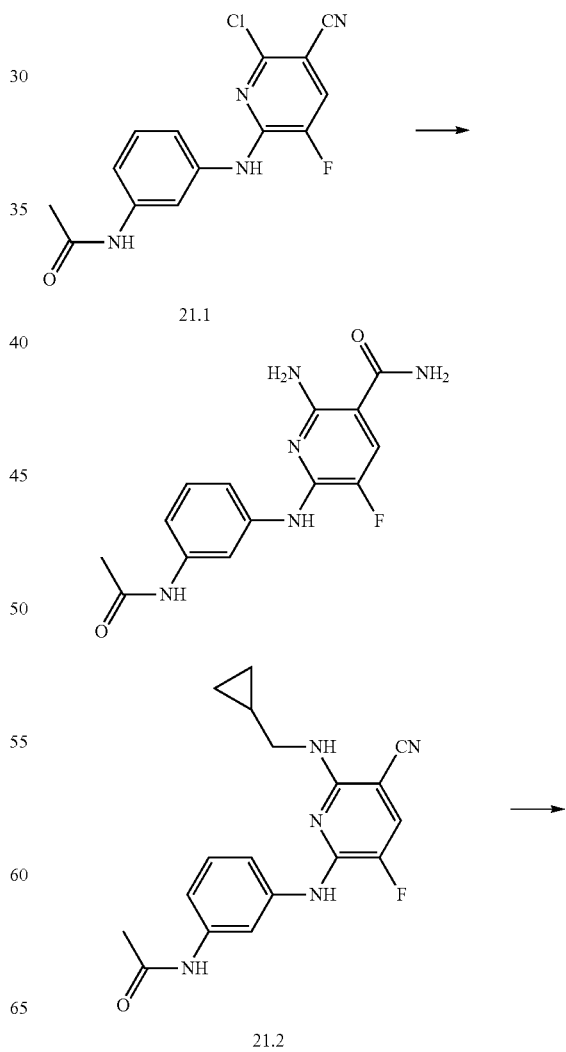

Step 1: Compound 19.1 (100 mg, 0.33 mmol) was dissolved in 3 mL NMP in a sealed tube. To it were added benzylamine (0.11 mL, 1.0 mmol) and DIEA (0.18 mL, 1.0 mmol). The mixture was stirred at 130° C. for 6 h. The mixture was cooled to RT and diluted with 150 mL EtOAc. It was washed with brine twice, dried, concentrated in vacuo to offer crude compound 19.2.

Step 2: The above-prepared crude compound 19.2 was dissolved in 4 mL DMSO. To it were added 2 mL 50% H$_2$O$_2$ and fine-powder potassium carbonate (128 mg, 1.65 mmol). The mixture was stirred at RT for 2 h. The mixture was then diluted with 150 mL EtOAc and 50 mL water. The organic phase was separated and washed with brine twice. It was dried, concentrated and subjected to reverse phase prep HPLC to isolate the title compound (91 mg). UV: 244, 278 nm. M+H found for $C_{21}H_{20}FN_5O_2$: 394.3. NMR (CD$_3$OD): 7.96 (1H, t, J=2.0 Hz), 7.68 (1H, d, J=12.0 Hz), 7.38 (1H, dm, J=8.4 Hz), 7.32-7.25 (4H, m), 7.19 (1H, m), 7.10 (1H, t, J=8.4 Hz), 7.01 (1H, dm, J=8.0 Hz), 4.66 (2H, s), 2.09 (3H, s) ppm.

-continued

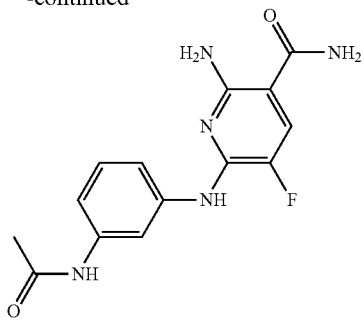

Step 1: Compound 21.1 (100 mg, 0.33 mmol) was dissolved in 3 mL NMP in a sealed tube. To it was added cyclopropylmethanamine (0.15 mL, 1.6 mmol). The mixture was stirred at 130° C. for 23 h. The mixture was cooled to RT and diluted with 150 mL EtOAc. It was washed with brine twice, dried, concentrated in vacuo to offer crude compound 21.2.

Step 2: The above-prepared crude compound 21.2 was treated with 5 mL TFA and 1 mL concentrated $H_2SO_4$ at 80° C. for 30 min. It was diluted with water and subjected to reverse phase HPLC to isolate the title compound (33 mg). UV: 240, 273 nm. M+H found for $C_{14}H_{14}FN_5O_2$: 304.3. NMR ($CD_3OD$): 8.14 (1H, m), 7.76 (1H, d, J=12.0 Hz), 7.33-7.26 (3H, m), 2.15 (3H, s) ppm.

Example 22

Preparation of 6-(3-(2H-1,2,3-triazol-2-yl)phenylamino)-2-(cyclopentylamino)-5-fluoronicotinamide

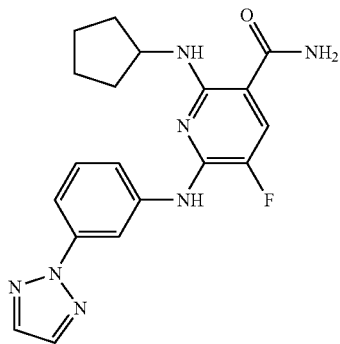 [SMILES: NC(=O)c1cc(F)c(Nc2cccc(-n3nccn3)c2)nc1NC1CCCC1]

The title compound was prepared using the same chemistry shown in Example 18. UV: 273 nm. M+H found for $C_{19}H_{20}FN_7O$: 382.3. NMR ($CD_3OD$): 9.08 (1H, t, J=2.0 Hz), 7.89 (2H, s), 7.68 (1H, d, J=12.0 Hz), 7.68 (1H, m), 7.52 (1H, dm, J=8.4 Hz), 7.40 (1H, J=8.0 Hz), 4.60 (1H, m), 2.08 (2H, m), 1.70 (2H, m), 1.57 (2H, m), 1.46 (2H, m) ppm.

Example 23

Preparation of 6-(3-(2H-1,2,3-triazol-2-yl)phenylamino)-2-(benzylamino)-5-fluoronicotinamide

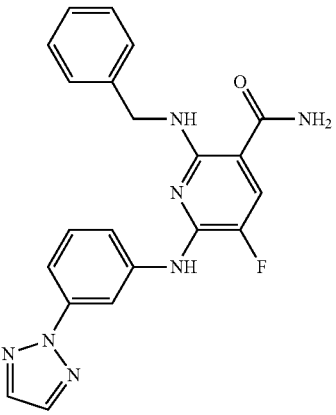 [SMILES: NC(=O)c1cc(F)c(Nc2cccc(-n3nccn3)c2)nc1NCc1ccccc1]

The title compound was prepared using the same chemistry shown in Example 19. UV: 273 nm. M+H found for $C_{21}H_{18}FN_7O$: 404.4. NMR ($CD_3OD$): 9.00 (1H, t, J=2.0 Hz), 7.81 (2H, s), 7.74 (1H, d, J=12.4 Hz), 7.65 (1H, dm, J=8.0 Hz), 7.47 (1H, dm, J=8.4 Hz), 7.34-7.25 (5H, m), 7.19 (1H, m), 4.79 (2H, s) ppm.

Example 24

Preparation of 6-(3-(2H-1,2,3-triazol-2-yl)phenylamino)-2-amino-5-fluoronicotinamide

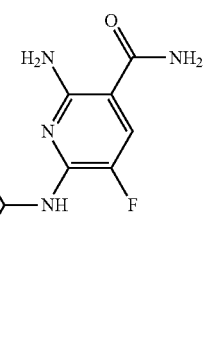

The title compound was prepared using the same chemistry shown in Example 21. UV: 273 nm. M+H found for $C_{14}H_{12}FN_7O$: 314.2. NMR ($CD_3OD$): 8.56 (1H, t, J=2.0 Hz), 7.93 (2H, s), 7.78 (1H, dm, J=8.4 Hz), 7.72 (1H, d, J=11.6 Hz), 7.71 (1H, dm, J=8.0 Hz), 7.43 (1H, t, J=8.4 Hz) ppm.

Example 25

Preparation of 2-(cyclopentylamino)-5-fluoro-6-(4-(2-(pyrrolidin-1-yl)ethoxy)phenylamino)nicotinamide

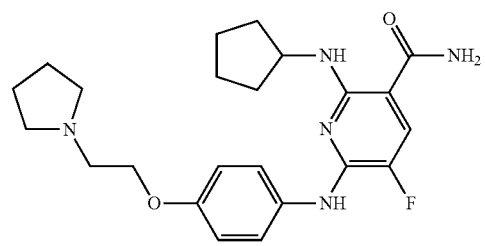 [SMILES: NC(=O)c1cc(F)c(Nc2ccc(OCCN3CCCC3)cc2)nc1NC1CCCC1]

The title compound was prepared using the same chemistry shown in Example 19. UV: 282 nm. M+H found for $C_{23}H_{30}FN_5O_2$: 428.4. NMR ($CD_3OD$): 7.75 (2H, dt, J=9.2; 2.0 Hz), 7.62 (1H, d, J=12.8 Hz), 6.97 (2H, dt, J=8.8; 2.0 Hz), 4.33-4.27 (3H, m), 3.74 (2H, m), 3.65 (2H, m), 3.24 (2H, m), 2.21-1.49 (12H, m) ppm.

Example 26

Preparation of 2-(benzylamino)-5-fluoro-6-(4-(2-(pyrrolidin-1-yl)ethoxy)phenylamino)nicotinamide

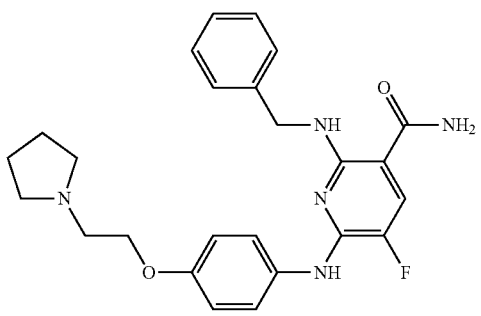 [SMILES: NC(=O)c1cc(F)c(Nc2ccc(OCCN3CCCC3)cc2)nc1NCc1ccccc1]

The title compound was prepared using the same chemistry shown in Example 19. UV: 282 nm. M+H found for $C_{25}H_{28}FN_5O_2$: 450.4. NMR ($CD_3OD$): 7.56 (1H, d, J=12.4 Hz), 7.39 (2H, dt, J=8.8; 2.4 Hz), 7.18-7.17 (4H, d, J=4.0 Hz), 7.09 (1H, m), 6.73 (2H, dt, J=8.4; 2.4 Hz), 4.50 (2H, s), 4.16 (2H, m), 3.60 (2H, m), 3.52 (2H, m), 3.10 (2H, m), 2.08 (2H, m), 1.95 (2H, m) ppm.

Example 27

Preparation of (R)-5-fluoro-2-(1-phenylethylamino)-6-(4-(2-(pyrrolidin-1-yl)ethoxy)phenylamino)nicotinamide

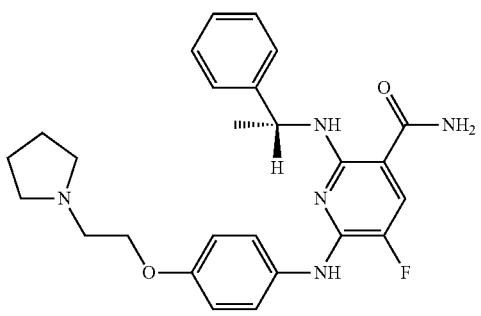 [SMILES: C[C@@H](Nc1nc(Nc2ccc(OCCN3CCCC3)cc2)c(F)cc1C(N)=O)c1ccccc1]

The title compound was prepared using the same chemistry shown in Example 19. UV: 282 nm. M+H found for $C_{26}H_{30}FN_5O_2$: 464.4. NMR ($CD_3OD$): 7.64 (1H, d, J=12.4 Hz), 7.38 (2H, dt, J=8.8; 2.4 Hz), 7.30-7.28 (4H, m), 7.17 (1H, m), 6.87 (2H, dt, J=9.6; 2.4 Hz), 5.11 (1H, q, J=6.8 Hz), 4.32 (2H, m), 3.73 (2H, m), 3.66 (2H, m), 3.25 (2H, m), 2.20 (2H, m), 2.08 (2H, m), 1.49 (3H, d, J=6.8 Hz) ppm.

Example 28

6-(4-fluoro-3-(pyrrolidine-1-carboxamido)phenylamino)-4-(pyridin-3-ylmethylamino)nicotinamide

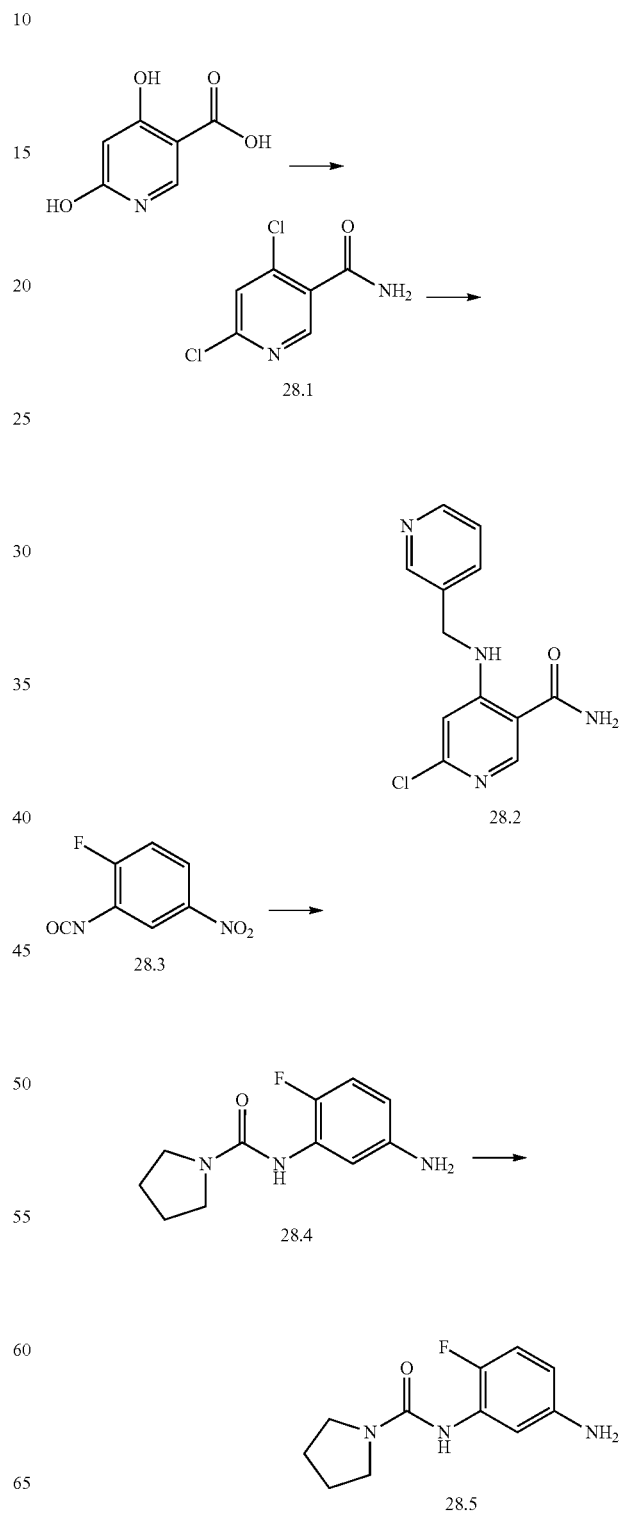

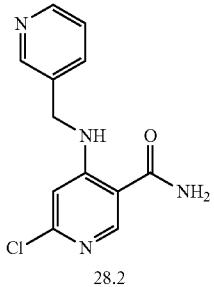
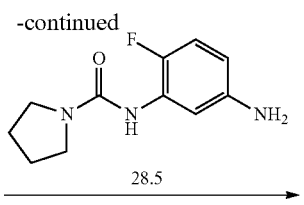

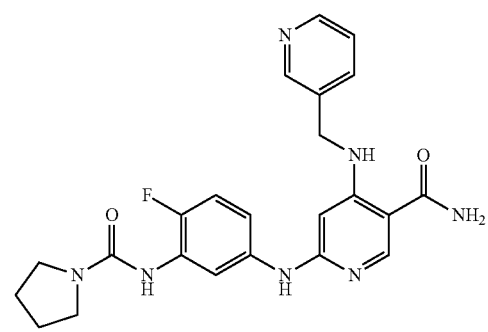

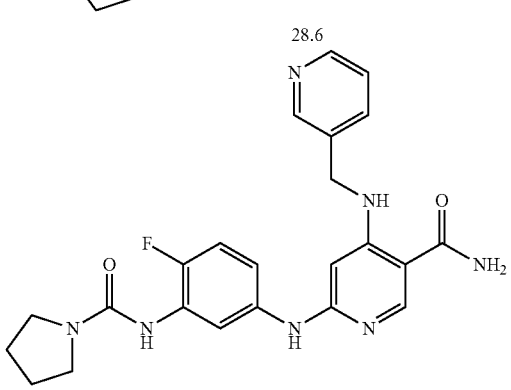

The title compound was synthesized as described in following procedures.

Step I, 4,6-Dichloronicotinamide

A suspension of 4,6-dihydroxynicotinic acid (3.10 g, 20 mmol) in phosphoryl trichloride (50 mL) was stirred at 100° C. for 4 hrs. After cooled to room temperature, the reaction solution was poured into a cold ammonium hydroxide solution (27-30%) in several portions and kept the mixture basic. The first portion of desired product as precipitate was collected by filtration. The second portion of desired product was obtained by extraction of mother aqueous liquid with DCM. The total amount of 4,6-Dichloronicotinamide (28.1) was 2.78 g. MS+: 191.0, UV: λ=201.0; 269.2 nm, $^1$H NMR: (CDCl$_3$) δ8.77 (s, 1H), δ7.45 (s, 1H), δ6.34 (b, 1H), δ6.21 (b, 1H).

Step II, 6-chloro-4-(pyridin-3-ylmethylamino)nicotinamide

A mixture of 4,6-Dichloronicotinamide (28.1, 950 mg, 5 mmol), 3-picolylamine (756 mg, 7 mmol) and DIPEA (12 mmol) in NMP (5 mL) was stirred at 60° C. for 20 hrs. The reaction mixture was concentrated under an oil pump. The residue was washed with water and dried under an oil pump. The desired 6-chloro-4-(pyridin-3-ylmethylamino)nicotinamide (28.2, 1.085 g) was obtained. MS+: 263.1, UV: λ=220.9; 260.9 nm. $^1$H NMR: (CDCl$_3$) δ8.96 (s, 1H), δ8.60 (s, 1H), δ8.57 (d, J=3.2 Hz, 1H), δ8.30 (s, 1H), δ7.64 (d, J=7.6 Hz, 1H), δ7.31 (dd, J1=7.6 Hz, J2=3.2 Hz, 1H), δ6.51 (s, 1H), δ5.80 (b, 2H), δ4.47 (s, 1H), δ4.45 (s, 1H).

Step III, N-(5-amino-2-fluorophenyl)pyrrolidine-1-carboxamide

A mixture of 1-fluoro-2-isocyanato-4-nitrobenzene (1.125 g, 6.18 mmol) and pyrrolidine (485 mg, 6.8 mmol) in DCM (20 mL) was stirred at rt for 14 hrs. After concentrated, the mixture was extracted with ethyl acetate. The organic layer was washed with aqueous citric acid solution and dried over MgSO4, followed by hydrogenation with Pd/C (wet, 10%, 0.15 g) under a hydrogen balloon overnight. After filtration and concentration, the reasonable pure N-(5-amino-2-fluorophenyl)pyrrolidine-1-carboxamide (28.5, 1.44 g) was used for the next reactions. MS+: 224.2, UV: λ=271.6 nm. $^1$H NMR: (DMSO) δ7.44 (s, 1H), δ6.78 (m, 1H), δ6.20 (m, 1H), δ3.32 (m, 4H), δ1.83 (m, 4H).

Step IV, 6-(4-fluoro-3-(pyrrolidine-1-carboxamido)phenylamino)-4-(pyridin-3-ylmethylamino)nicotinamide A mixture of 6-chloro-4-(pyridin-3-ylmethylamino)nicotinamide (28.2, 27 mg, 0.1 mmol), N-(5-amino-2-fluorophenyl)pyrrolidine-1-carboxamide (28.5, 34 mg, 0.15 mmol), Pd(OAc)2 (2 mg). BINAP (15 mg), Cs2CO3 (100 mg) in dioxane (1 mL) was heated at 120° C. under microwave for 60 min Purification with reversed phase HPLC, 6-(4-fluoro-3-(pyrrolidine-1-carboxamido)phenylamino)-4-(pyridin-3-ylmethylamino)nicotinamide (28.6, 10 mg) was obtained. MS found for C23H24FN7O2 as (M+H)$^+$ 450.5, UV: λ=249.1 nm. $^1$H NMR: (CD$_3$OD) δ8.50 (s, 1H), δ8.42 (d, 1H), δ8.26 (d, 1H), δ7.80 (dd, 1H), δ7.60 (dd, 1H), δ7.40 (dd, 1H), δ7.00 (dd, 1H), δ6.91 (m, 1H), δ5.88 (d, 1H), δ4.49 (s, 2H), δ3.48 (m, 4H), δ1.99 (b, 4H).

Alternate Synthesis of Intermediate 28.1

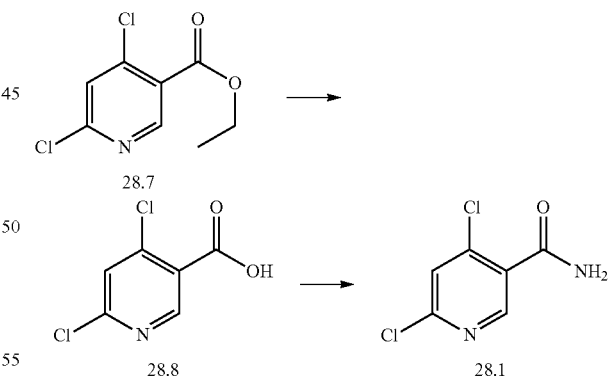

Step 1: Dichloropyridine 28.7 (prepared using the procedure described in Brunette, S. R.; Kim, J. M.; Lemieux, R. M.; Aaron, M. US2006/0217417.) (164 mmol based on the theoretical yield of the previous step) was diluted with 100 mL of 1,4-dioxane followed by 1 M LiOH (197 mL, 197 mmol). The resulting cloudy solution was then stirred at rt until all starting material was consumed. The crude mixture was then acidified to pH=2 with 6 M HCl, then diluted with water until ppt formation ceased. The solids were then isolated by filtration affording the desired product as a light beige powder (22.14 g, 70%). MS found for C6H3Cl2NO2 as (M+H)$^+$ 192.0, 194.0. UV: λ=207, 273 nm.

Step 3: Carboxylic acid 28.8 (4.37 g, 23 mmol) was dissolved in 25 mL of DMF. To this was added HOBt (4.1 g, 27 mmol) and EDC (5.2 g, 27 mmol). After stirring ca. 30 min the reaction was checked by UPLC which showed consumption of the starting carboxylic acid. Aqueous ammonia (3.3 mL, 46 mmol) was then added and the reaction stirred at rt for 1 hr. The reaction was then diluted with water and extracted twice with ethyl acetate, the combined organic layers were then washed once with saturated sodium carbonate. The organic phase was then concentrated and dried in vacuo affording the desired dichloro amide (MS found for C6H4Cl2N2O as (M+H)$^+$ 191.0, 193.0. UV: λ=202, 271 nm) as a light brown oil contaminated with a small amount of 4-(1H-benzo[d][1,2,3]triazol-1-yloxy)-6-chloronicotinamide (MS found for C12H8ClN5O2 as (M+H)$^+$ 290.0, 292.1. UV: λ=202 nm).

Example 29

(6-(4-(4-acetylpiperazin-1-yl)phenylamino)-4-(phenethylamino)nicotinamide

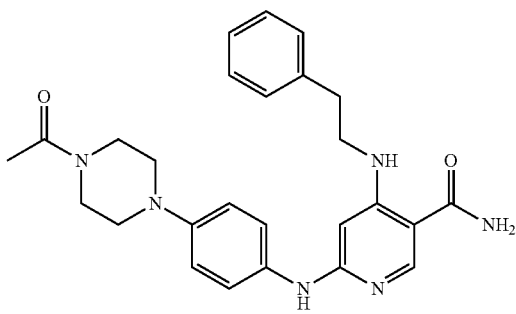 [SMILES: CC(=O)N1CCN(c2ccc(Nc3cc(NCCc4ccccc4)c(C(N)=O)cn3)cc2)CC1]

The title compound was synthesized using a procedure similar to that described in Example 3. using phenethylamine in place of benzylamine. MS found for C26H30N6O2 as (M+H)$^+$ 459.2. UV: λ=205, 258 nm. $^1$H NMR: (CD$_3$OD) δ 8.03 (s, 1H), 7.24 (m, 2H), 7.19 (m, 5H), 7.10 (d, 2H), 5.82 (s, 1H), 3.76 (m, 4H), 3.43 (t, 2H), 3.24 (m, 4H), 2.90 (t, 2H), 2.19 (s, 3H).

Example 30

4-(benzylamino)-6-(4-(dimethylcarbamoyl)phenylamino)-N,N-dimethylnicotinamide

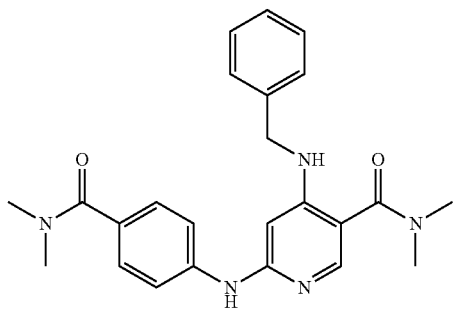

The title compound was synthesized using a procedure similar to that described in Example 3, using dimethylamine in place of ammonia. MS found for C24H27N5O2 as (M+H)$^+$ 418.3. UV: λ=207, 263, 305 nm. $^1$H NMR: (CD$_3$OD) δ 7.69 (s, 1H), 7.22 (d, 2H), 7.37 (t, 2H), 7.30 (m, 3H), 7.10 (d, 2H), 5.93 (s, 1H), 4.47 (s, 2H), 3.11 (s, 9H), 0.03 (s, 3H).

Example 31

4-(benzylamino)-6-(3-morpholinophenylamino)nicotinamide

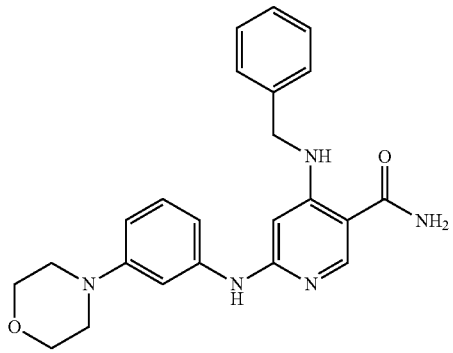 [SMILES: NC(=O)c1cnc(Nc2cccc(N3CCOCC3)c2)cc1NCc1ccccc1]

The title compound was synthesized using a procedure similar to that described in Example 3. MS found for C23H25N5O2 as (M+H)$^+$ 404.3. UV: λ=210, 258 nm. $^1$H NMR: (CD$_3$OD) δ 8.11 (s, 1H), 7.26-7.35 (m, 6H), 6.92 (d, 1H), 6.74 (s, 1H), 6.56 (d, 1H), 5.91 (s, 1H), 4.47 (s, 2H), 3.82 (m, 4H), 3.14 (m, 4H).

Example 32

4-(cyclopentylmethylamino)-6-(4-methoxyphenylamino)nicotinamide

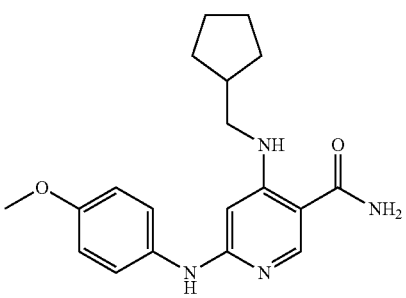 [SMILES: COc1ccc(Nc2cc(NCC3CCCC3)c(C(N)=O)cn2)cc1]

The title compound was synthesized using a procedure similar to that described in Example 3. MS found for C19H24N4O2 as (M+H)$^+$ 341.3. UV: λ=201, 222, 256 nm. $^1$H NMR: (CD$_3$OD) δ 8.056 (s, 1H), 7.24 (d, 2H0, 7.05 (d, 2H), 5.84 (s, 1H), 3.82 (s, 3H), 3.11 (2H), 2.21 (m, 1H), 1.98 (m, 1H), 1.84 (m, 2H), 1.65 (m, 4H), 1.27 (m, 2H).

Example 33

6-(4-methoxyphenylamino)-4-(p-tolylamino)nicotinamide

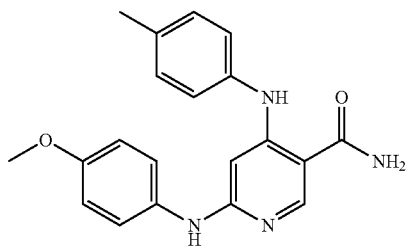 [SMILES: COc1ccc(Nc2cc(Nc3ccc(C)cc3)c(C(N)=O)cn2)cc1]

The title compound was synthesized using a procedure similar to that described in Example 3. MS found for C20H20N4O2 as (M+H)+ 349.3. UV: λ=201, 269 nm. ¹H NMR: (CD₃OD) δ 8.15 (s, 1H), 7.26 (d, 2H), 7.16 (m, 4H), 6.99 (d, 2H), 6.13 (s, 1H), 3.81 (s, 3H), 2.35 (s, 3H).

Example 34

4,6-bis(4-methoxyphenylamino)nicotinamide

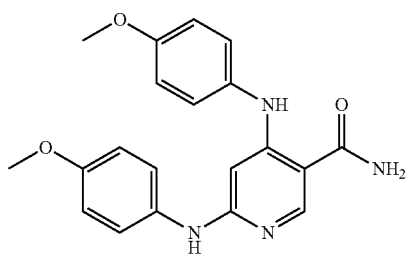 [SMILES: COc1ccc(Nc2cc(Nc3ccc(OC)cc3)c(C(N)=O)cn2)cc1]

The title compound was synthesized using a procedure similar to that described in Example 3. MS found for C20H20N4O3 as (M+H)+ 365.3. UV: λ=201, 269 nm. ¹H NMR: (CD₃OD) δ 8.14 (s, 1H), 7.19 (d, 2H), 7.16 (d, 2H), 6.99 (m, 4H), 6.01 (s, 1H), 3.81 (s, 6H).

Example 35

4-((1-acetylpiperidin-4-yl)methylamino)-6-(4-methoxyphenylamino)nicotinamide

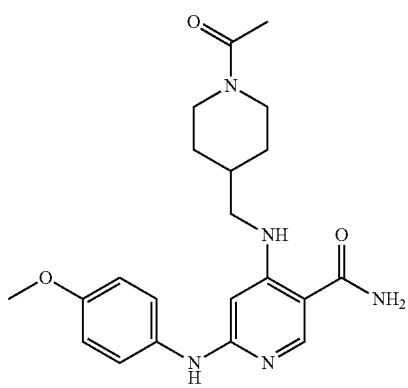 [SMILES: COc1ccc(Nc2cc(NCC3CCN(C(C)=O)CC3)c(C(N)=O)cn2)cc1]

The title compound was synthesized using a procedure similar to that described in Example 36. MS found for C21H27N5O3 as (M+H)+ 398.3. UV: λ=202, 256 nm. ¹H NMR: (CD₃OD) δ 8.06 (s, 1H), 7.24 (dd, 2H), 7.06 (dd, 2H), 5.85 (s, 1H), 4.55 (m, 1H), 3.96 (m, 1H), 3.83 (s, 3H), 3.12 (m, 4H), 2.63 (m, 1H), 2.09 (s, 3H), 1.82 (m, 1H), 1.77 (m, 2H), 1.27 (m, 1H), 1.16 (m, 1H).

Example 36

(S)-4-(1-acetylpiperidin-3-ylamino)-6-(4-methoxyphenylamino)nicotinamide

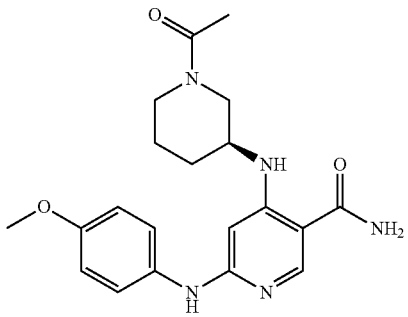 [SMILES: COc1ccc(Nc2cc(N[C@H]3CCCN(C(C)=O)C3)c(C(N)=O)cn2)cc1]

The title compound was synthesized using a procedure similar to that described in Example 3, using the following procedure in place of Step 4

(S)-4-(1-acetylpiperidin-3-ylamino)-6-chloronicotinamide (50 mg, 0.17 mmol), p-anisidine (31 mg, 0.26 mmol), Cs₂CO₃ (111 mg, 0.34 mmol), BINAP (16 mg, 0.026 mmol), and Pd(OAc)₂ (4 mg, 0.017 mmol) and degassed dioxane (4 mL) were heated to 100° C. under Argon overnight. The following morning the mixture was determined to be complete by UPLC. The reaction was diluted with water, acetonitrile, and TFA, then purified by HPLC affording 4 mg of the desired product after lyophilization. MS found for C20H25N5O3 as (M+H)+ 384.3. UV: λ=202, 257 nm. ¹H NMR: (CD₃OD) (mixture of rotamers) δ 8.12 (s, 0.4H), 8.06 (s, 0.6H), 7.24 (dd, 2H), 7.06 (dd, 2H), 5.98 (s, 0.7H), 5.89 (s, 0.3H), 3.84 (s, 3H), 3.40-3.68 (m, 5H), 2.13 (s, 2H), 2.03 (m, 1H), 1.98 (s, 1H), 1.52-1.93 (m, 3H).

Example 37

(R)-4-(1-acetylpiperidin-3-ylamino)-6-(4-methoxyphenylamino)nicotinamide

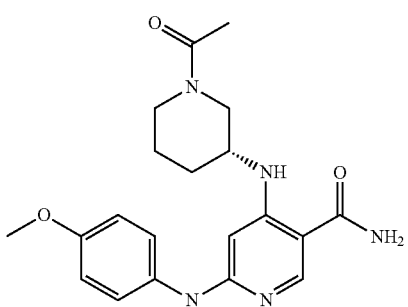

The title compound was synthesized using a procedure similar to that described in Example 36. MS found for C20H25N5O3 as (M+H)+ 384.3. UV: λ=201, 257 nm. ¹H NMR: (CD₃OD) (mixture of rotamers) δ 8.12 (s, 0.4H), 8.06 (s, 0.6H), 7.25 (dd, 2H), 7.05 (dd, 2H), 5.98 (s, 0.7H), 5.89 (s, 0.3H), 3.84 (s, 3H), 3.40-3.68 (m, 5H), 2.13 (s, 2H), 2.03 (m, 1H), 1.98 (s, 1H), 1.52-1.93 (m, 3H)

Example 38

(S)-4-((1-acetylpiperidin-3-yl)methylamino)-6-(4-methoxyphenylamino)nicotinamide

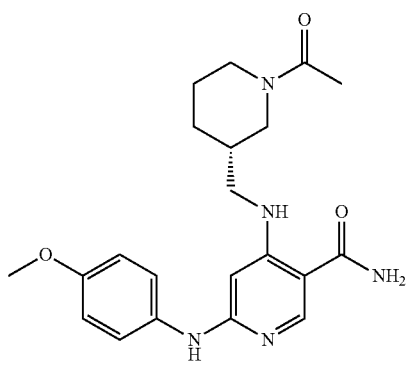 [SMILES: COc1ccc(Nc2cc(NC[C@@H]3CCCN(C(C)=O)C3)c(C(N)=O)cn2)cc1]

The title compound was synthesized using a procedure similar to that described in Example 36. MS found for C21H27N5O3 as (M+H)⁺ 398.3. UV: λ=202, 256 nm. ¹H NMR: (CD₃OD) (mixture of rotamers) δ 8.08 (s, 0.3H), 8.05 (s, 0.7H), 7.25 (dd, 2H), 7.06 (dd, 2H), 5.86 (s, 0.7H), 5.85 (s, 0.3H), 4.24 (m, 1H), 3.84 (s, 3H), 3.78 (m, 1H), 3.18 (m, 3.3H), 2.98 (dd, 0.7H), 2.81 (m, 0.7H), 2.69 (m, 0.7H), 2.10 (s, 0.7H), 2.06 (0.3H), 1.91 (m, 1H), 1.79 (m, 2H), 1.49 (m, 1H).

Example 39

4-(benzylamino)-6-(4-(pyrrolidine-1-carbonyl)phenylamino)nicotinamide

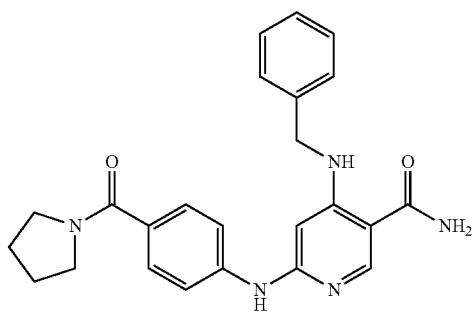 [SMILES: NC(=O)c1cnc(Nc2ccc(C(=O)N3CCCC3)cc2)cc1NCc1ccccc1]

The title compound was synthesized using a procedure similar to that described in Example 36 and an aniline derived from 4-nitrobenzoyl chloride and piperidine in two steps. MS found for C24H25N5O2 as (M+H)⁺ 416.3. UV: λ=202, 262 nm. ¹H NMR: (CD₃OD) δ 8.19 (s, 1H), 7.56 (d, 2H), 7.37 (m, 2H), 7.18 (m, 3H), 7.16 (dd, 2H), 6.02 (s, 1H), 4.52 (s, 2H), 3.61 (dd, 1H), 3.52 (dd, 1H), 2.02 (m, 2H), 1.94 (m, 2H).

Example 40

4-(benzylamino)-6-(4-(morpholine-4-carbonyl)phenylamino)nicotinamide

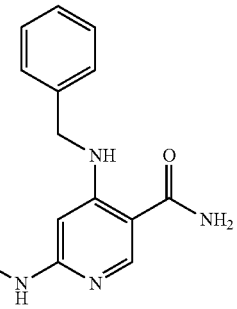

The title compound was synthesized using a procedure similar to that described in Example 36 and an aniline derived from 4-nitrobenzoyl chloride and morpholine in two steps. MS found for C24H25N5O3 as (M+H)⁺ 432.3. UV: λ=202, 267 nm. ¹H NMR: (CD₃OD) δ 8.11 (s, 1), 7.36 (d, 2H), 7.30 (m, 2H), 7.21 (m, 3H), 7.09 (d, 2H), 5.93 (s, 1H), 4.43 (s, 2H), 3.61 (m, 8H).

Example 41

4-(cyclopentylmethylamino)-6-(4-(pyrrolidine-1-carbonyl)phenylamino)nicotinamide

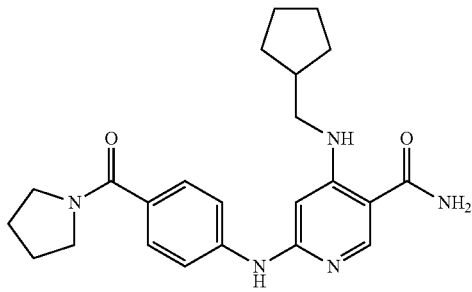 [SMILES: NC(=O)c1cnc(Nc2ccc(C(=O)N3CCCC3)cc2)cc1NCC1CCCC1]

The title compound was synthesized using a procedure similar to that described in Example 36. MS found for C23H29N5O2 as (M+H)⁺ 408.4. UV: λ=201, 261 nm. ¹H NMR: (CD₃OD) δ 8.16 (s, 1H), 7.64 (dd, 2H), 7.38 (dd, 2H), 6.10 (s, 1H), 3.61 (t, 2H), 3.52 (t, 2H), 3.17 (d, 2H), 2.23 (m, 1H), 1.80-2.09 (m, 6H), 1.58-1.73 (m, 4H), 1.29 (m, 2H).

Example 42

4-(cyclopentylmethylamino)-6-(4-(morpholine-4-carbonyl)phenylamino)nicotinamide

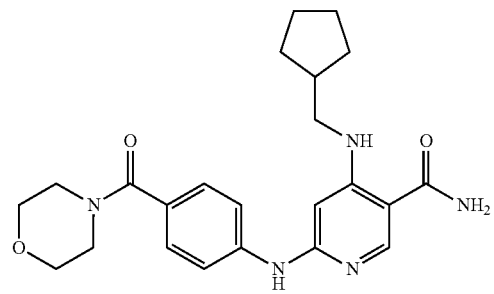 [SMILES: NC(=O)c1cnc(Nc2ccc(C(=O)N3CCOCC3)cc2)cc1NCC1CCCC1]

The title compound was synthesized using a procedure similar to that described in Example 36. MS found for C23H29N5O3 as (M+H)+ 424.4. UV: λ=203, 261 nm. ¹H NMR: (CD₃OD) δ 8.16 (s, 1H), 7.55 (dd, 2H), 7.40 (dd, 2H), 6.10 (s, 1H), 3.71 (m, 8H), 3.17 (d, 2H), 2.17 (m, 1H), 1.86 (m, 2H), 1.65 (m, 4H), 1.29 (m, 2H).

Example 43

4-((1-acetylpiperidin-4-yl)methylamino)-6-(4-(pyrrolidine-1-carbonyl)phenylamino)nicotinamide

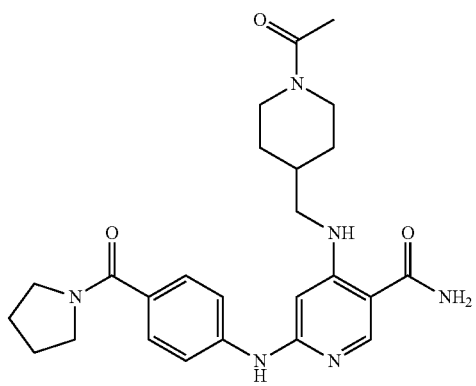 [SMILES: CC(=O)N1CCC(CNc2cc(Nc3ccc(C(=O)N4CCCC4)cc3)ncc2C(N)=O)CC1]

The title compound was synthesized using a procedure similar to that described in Example 36. MS found for C25H32N6O3 as (M+H)+ 465.4. UV: λ=202, 260 nm. ¹H NMR: (CD₃OD) δ 8.17 (s, 1H), 7.65 (d, 2H), 7.38 (d, 2H), 6.12 (s, 1H), 4.56 (d, 1H), 3.96 (d, 1H), 3.62 (t, 2H), 3.53 (t, 2H), 3.19 (d, 2H), 3.13 (t, 1H), 2.63 (t, 1H), 2.10 (s, 3H), 2.02 (m, 2H), 1.94 (m, 3H), 1.82 (m, 2H), 1.23 (m, 1H), 1.18 (m, 1H).

Example 44

4-((1-acetylpiperidin-4-yl)methylamino)-6-(4-(morpholine-4-carbonyl)phenylamino)nicotinamide

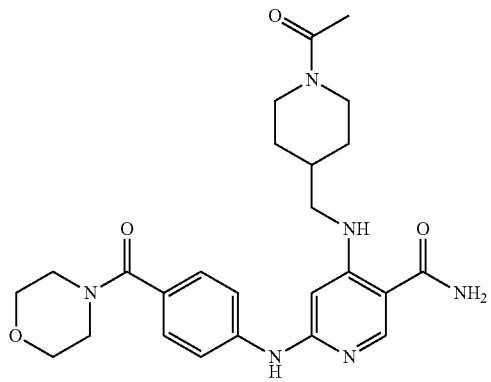 [SMILES: CC(=O)N1CCC(CNc2cc(Nc3ccc(C(=O)N4CCOCC4)cc3)ncc2C(N)=O)CC1]

The title compound was synthesized using a procedure similar to that described in Example 36. MS found for C25H32N6O4 as (M+H)+ 481.4. UV: λ=203, 260 nm. ¹H NMR: (CD₃OD) δ 8.18 (s, 1H), 7.58 (d, 2H), 7.40 (d, 2H), 6.09 (s, 1H), 4.57 (d, 1H), 3.96 (d, 1H), 3.71 (m, 8H), 3.18 (d, 2H), 11 (m, 1H), 2.62 (t, 1H), 2.08 (s, 3H), 1.97 (m, 1H), 1.82 (m, 2H), 1.24 (m, 1H), 1.18 (m, 1H).

Example 45

6-(3-(azetidine-1-carbonyl)phenylamino)-4-(benzylamino)nicotinamide

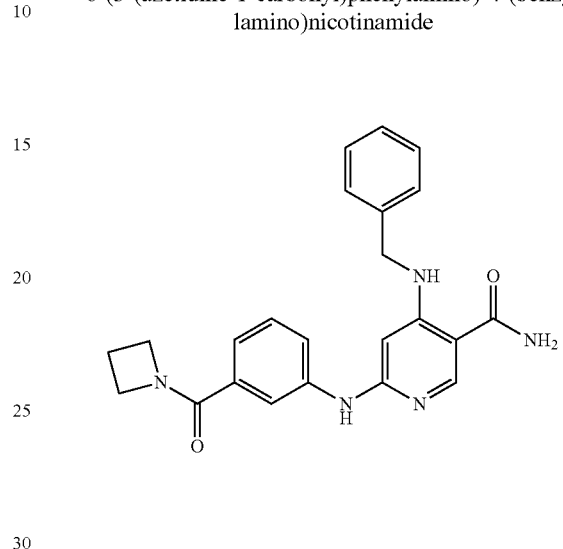

The title compound was synthesized using a procedure similar to that described in Example 36. MS found for C23H23N5O2 as (M+H)+ 402.3. UV: λ=202, 260, 272 nm. ¹H NMR: (CD₃OD) δ 8.16 (s, 1H), 7.51 (m, 3H), 7.32 (m, 6H), 5.94 (s, 1H), 4.49 (s, 2H), 4.37 (t, 2H), 4.21 (t, 2H), 2.38 (m, 2H).

Example 46

6-(4-(azetidine-1-carbonyl)phenylamino)-4-(benzylamino)nicotinamide

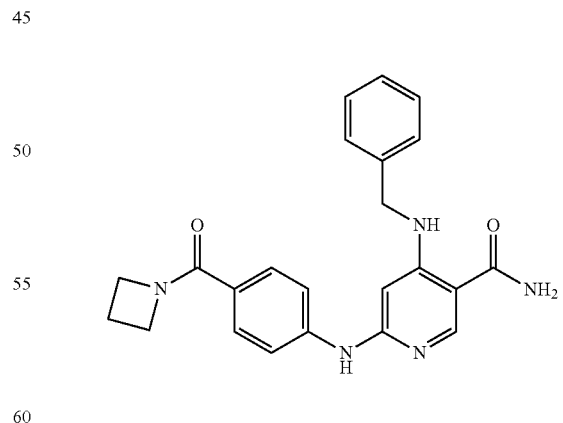

The title compound was synthesized using a procedure similar to that described in Example 36. MS found for C23H23N5O2 as (M+H)+ 402.3. UV: λ=204, 242, 282, 313 nm. ¹H NMR: (CD₃OD) δ 8.21 (s, 1H), 7.65 (dd, 2H), 7.38 (m, 2H), 7.31 (m, 3H), 6.04 (s, 1H), 4.52 (s, 2H), 4.20 (t, 2H), 4.22 (t, 2H), 2.40 (m, 2H).

Example 47

6-(4-(azetidin-1-ylsulfonyl)phenylamino)-4-(benzylamino)nicotinamide

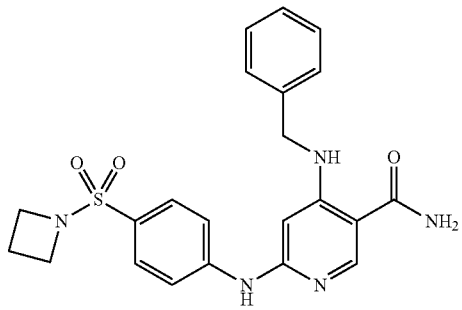 [SMILES: NC(=O)c1cnc(Nc2ccc(S(=O)(=O)N3CCC3)cc2)cc1NCc1ccccc1]

The title compound was synthesized using a procedure similar to that described in Example 36 and an aniline derived from 4-nitrobenzenesulfonyl chloride and azetidine in two steps. MS found for C22H23N5O3S as (M+H)⁺ 438.4. UV: λ=202, 257 nm. ¹H NMR: (CD₃OD) δ 8.28 (s, 1H), 7.77 (dd, 2H), 7.38 (m, 2H), 7.34 (5H), 6.14 (s, 1H), 4.56 (s, 2H), 3.78 (t, 4H), 2.10 (m, 2H).

Example 48

6-(4-(azetidine-1-carbonyl)phenylamino)-4-(cyclopentylmethylamino)nicotinamide

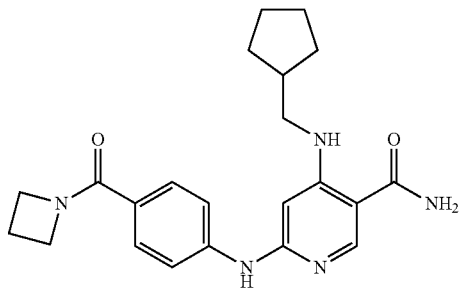 [SMILES: NC(=O)c1cnc(Nc2ccc(C(=O)N3CCC3)cc2)cc1NCC1CCCC1]

The title compound was synthesized using a procedure similar to that described in Example 36. MS found for C22H27N5O2 as (M+H)⁺ 394.4. UV: λ=203, 285 nm. ¹H NMR: (CD₃OD) δ 8.26 (s, 1H), 7.78 (dd, 2H), 7.43 (dd, 2H), 6.17 (s, 1H), 4.46 (m, 2H), 4.19 (m, 2H), 3.21 (d, 2H), 2.41 (m, 2H), 2.23 (m, 1H), 1.88 (m, 2H), 1.69 (m, 2H), 1.66 (m, 2H), 1.31 (m, 2H).

Example 49

6-(4-(azetidin-1-ylsulfonyl)phenylamino)-4-(cyclopentylmethylamino)nicotinamide

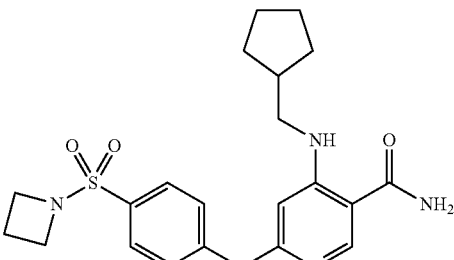

The title compound was synthesized using a procedure similar to that described in Example 36. MS found for C21H27N5O3S as (M+H)⁺ 430.3. UV: λ=203, 285 nm. ¹H NMR: (CD₃OD) δ 8.15 (s, 1H), 7.80 (d, 2H), 7.45 (d, 2H), 6.16 (s, 1H), 3.70 (t, 4H), 3.13 (d, 2H), 2.16 (m, 1H), 2.00 (m, 2H), 1.78 (m, 2H), 1.61 (m, 2H), 1.57 (m, 2H), 1.22 (m, 2H).

Example 50

4-((1-acetylpiperidin-4-yl)methylamino)-6-(4-(azetidine-1-carbonyl)phenylamino)nicotinamide

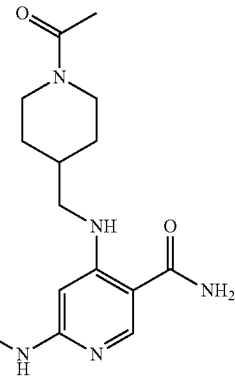

The title compound was synthesized using a procedure similar to that described in Example 36. MS found for C24H30N6O3 as (M+H)⁺ 451.4. UV: λ=202, 258, 279 nm. ¹H NMR: (CD₃OD) δ 8.17 (s, 1H), 7.75 (d, 2H), 7.37 (d, 2H), 6.14 (s, 1H), 4.56 (m, 1H), 4.43 (m, 2H), 4.21 (m, 2H), 3.97

(m, 1H), 3.24 (m, 1H), 3.20 (d, 2H), 3.09 (m, 2H), 2.42 (m, 1H), 2.37 (m, 2H), 2.08 (s, 3H), 1.97 (m, 1H), 1.82 (m, 2H), 1.29 (m, 1H), 1.17 (m, 1H).

Example 51

(S)-4-((1-(2-methoxyacetyl)piperidin-3-yl)methylamino)-6-(4-methoxyphenylamino)nicotinamide

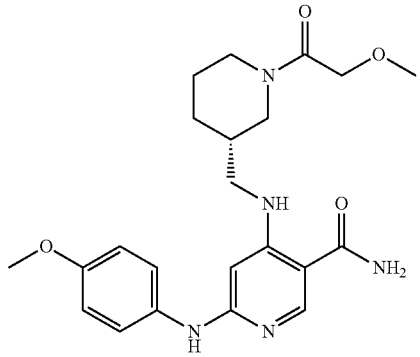

The title compound was synthesized using a procedure similar to that described in Example 36. MS found for $C_{22}H_{29}N_5O_4$ as $(M+H)^+$ 428.4. UV: λ=210, 254 nm. $^1$H NMR: (CD$_3$OD) (mixture of rotamers) δ 8.08 (s, 0.4H), 8.05 (s, 0.6H), 7.23 (dd, 2H), 7.05 (dd, 2H), 5.86 (0.6H), 5.84 (s, 0.4H), 4.22 (m, 1H), 4.14 (m, 1H), 4.08 (m, 1H), 3.84 (s, 3H), 3.71 (m, 1H), 3.38 (s, 1.2H), 3.34 (s, 0.8H), 3.17 (m, 2H), 2.84 (m, 0.6H), 2.73 (dd, 0.4H), 1.91 (m, 2H), 1.77 (m, 1H), 1.52 (m, 1H), 1.39 (m, 1H).

Example 52

(S)-methyl 3-((5-carbamoyl-2-(4-methoxyphenylamino)pyridin-4-ylamino)methyl)piperidine-1-carboxylate

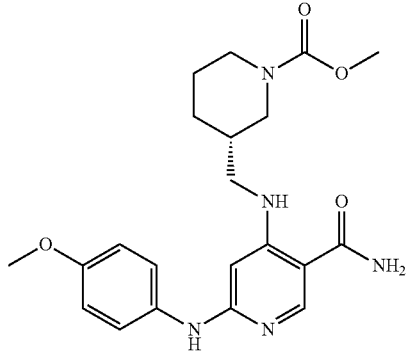

The title compound was synthesized using a procedure similar to that described in Example 36. MS found for $C_{21}H_{27}N_5O_4$ as $(M+H)^+$ 414.4. UV: λ=201, 223, 256 nm. $^1$H NMR: (CD$_3$OD) δ 8.06 (s, 1H), 7.24 (dd, 2H), 7.05 (dd, 2H), 5.85 (s, 1H), 3.84 (s, 3H), 3.67 (s, 3H), 3.13 (m, 3H), 2.99 (m, 1H), 1.84 (m, 2H), 1.73 (m, 1H), 1.47 (m, 1H), 1.31 (m, 1H).

Example 53

(S)-4-((1-(dimethylcarbamoyl)piperidin-3-yl)methylamino)-6-(4-methoxyphenylamino)nicotinamide

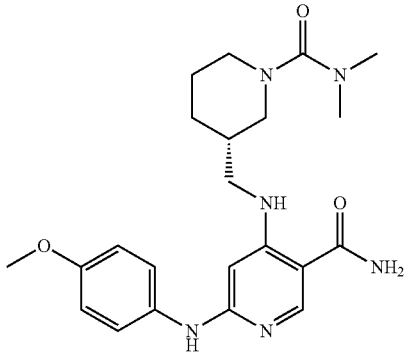

The title compound was synthesized using a procedure similar to that described in Example 36. MS found for $C_{22}H_{30}N_6O_3$ as $(M+H)^+$ 427.4. UV: λ=202, 256 nm. $^1$H NMR: (CD$_3$OD) δ 8.06 (s, 1H), 7.24 (d, 2H), 7.05 (d, 2H), 5.85 (s, 1H), 3.59 (d, 1H), 3.53 (m, 1H), 3.13 (m, 3H), 2.84 (m, 1H), 2.78 (s, 6H), 2.62 (m, 1H), 1.86 (m, 2H), 1.75 (m, 1H), 1.53 (m, 1H), 1.27 (m, 1H).

Example 54

(R)-4-(1-acetylpiperidin-3-yl)methylamino)-6-(4-methoxyphenylamino)nicotinamide

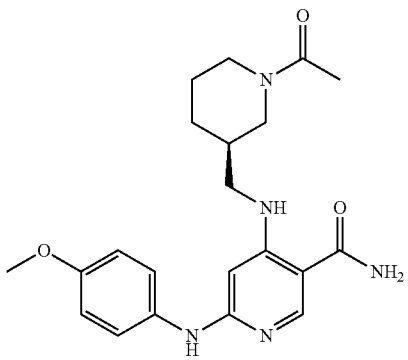 [SMILES: COc1ccc(Nc2cc(NC[C@H]3CCCN(C(C)=O)C3)c(C(N)=O)cn2)cc1]

The title compound was synthesized using a procedure similar to that described in Example 36. MS found for $C_{21}H_{27}N_5O_3$ as $(M+H)^+$ 398.4. UV: λ=201, 256 nm. $^1$H NMR: (CD$_3$OD) (mixture of rotamers) δ 8.09 (s, 0.4H), 8.05 (s, 0.6H), 7.25 (d, 2H), 7.05 (d, 2H), 5.85 (s, 1H), 4.26 (m, 1H), 3.84 (s, 3H), 3.79 (m, 1H), 3.14 (m, 4H), 2.98 (m, 0.4H), 2.82 (m, 0.6H), 2.61 (m, 1H), 2.10 (s, 1.8H), 2.06 (s, 1.2H), 1.90 (m, 1H), 1.78 (m, 1H), 1.51 (m, 1H), 1.39 (m, 1H).

Example 55

(R)-4-(1-(2-methoxyacetyl)piperidin-3-yl)methylamino)-6-(4-methoxyphenylamino)nicotinamide

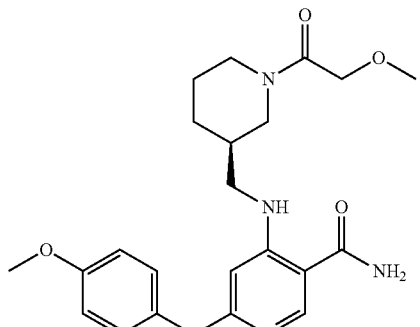

The title compound was synthesized using a procedure similar to that described in Example 36. MS found for C22H29N5O4 as (M+H)+ 428.4. UV: λ=201, 256 nm. $^1$H NMR: (CD$_3$OD) δ 8.08 (s, 0.4H), 8.06 (s, 0.6H), 7.24 (d, 2H), 7.05 (d, 2H), 5.86 (s, 0.6H), 5.84 (s, 0.4H), 4.26 (m, 1H), 4.15 (d, 1H), 4.09 (m, 1H), 3.84 (s, 3H), 3.82 (m, 0.4H), 3.71 (m, 0.6H), 3.39 (s, 1.6H), 3.34 (s, 1.4H), 3.19 (m, 3H), 2.92 (m, 1H), 2.74 (m, 0.6H), 1.89 (m, 2H), 1.77 (m, 1H), 1.52 (m, 1H), 1.39 (m, 1H).

Example 56

(R)-methyl 3-((5-carbamoyl-2-(4-methoxyphenylamino)pyridin-4-ylamino)methyl)piperidi-ne-1-carboxylate

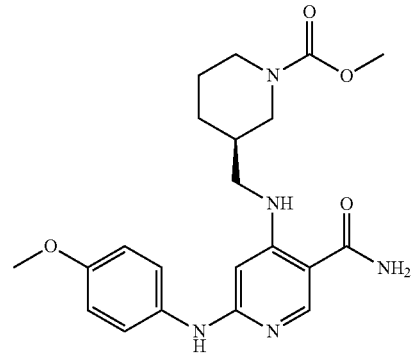

The title compound was synthesized using a procedure similar to that described in Example 36. MS found for C21H27N5O4 as (M+H)+ 414.4. UV: λ=200, 223, 256 nm. $^1$H NMR: (CD$_3$OD) δ 8.06 (s, 1H), 7.24 (d, 2H), 7.05 (d, 2H), 5.85 (s, 1H), 3.95 (m, 1H), 3.84 (s, 3H), 3.67 (s, 3H), 3.16 (m, 3H), 2.99 (m, 1H), 2.80 (m, 1H), 1.86 (m, 2H), 1.71 (m, 1H), 1.47 (m, 1H), 1.33 (m, 1H).

Example 57

(R)-6-(4-methoxyphenylamino)-4-(1-(methylsulfonyl)piperidin-3-yl)methylamino)nicotinamide

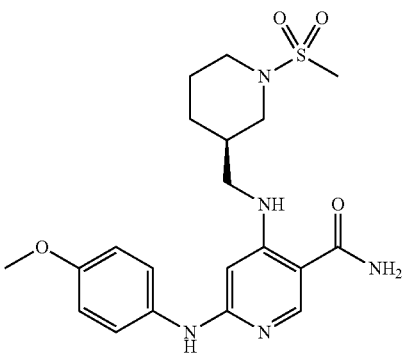 [SMILES: COc1ccc(Nc2cc(NC[C@H]3CCCN(S(C)(=O)=O)C3)c(C(N)=O)cn2)cc1]

The title compound was synthesized using a procedure similar to that described in Example 36. MS found for C20H27N5O4S as (M+H)+ 434.4. UV: λ=200, 224, 256 nm. $^1$H NMR: (CD$_3$OD) δ 8.06 (s, 1H), 7.25 (d, 2H), 7.05 (d, 2H), 5.88 (s, 1H), 3.83 (s, 3H), 3.54 (m, 1H), 3.48 (m, 1H), 3.25 (m, 1H), 3.15 (dd, 1H), 2.89 (m, 1H), 2.82 (s, 3H), 2.69 (dd, 1H), 2.35 (m, 1H), 2.00 (m, 1H), 1.83 (m, 2H), 1.62 (m, 1H), 1.30 (m, 1H).

Example 58

4-(3-fluorobenzylamino)-6-(3-(2-(pyrrolidin-1-yl)ethoxy)phenylamino)nicotinamide

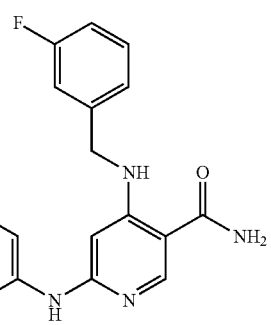

The title compound was synthesized using a procedure similar to that described in Example 36. MS found for C25H28FN5O2 as (M+H)+ 450.6. UV: λ=203, 257 nm. $^1$H NMR: (CD$_3$OD) δ 8.19 (s, 1H), 7.38 (m, 2H), 7.08 (d, 1H), 7.03 (m, 2H), 6.97 (d, 1H), 6.87 (s, 1H), 6.73 (d, 1H), 5.91 (s, 1H), 4.94 (s, 2H), 4.32 (t, 2H), 3.71 (m, 2H), 3.66 (t, 2H), 3.21 (m, 2H), 2.17 (m, 2H), 2.03 (m, 2H).

Example 59

(S)-4-(2-hydroxy-1-phenylethylamino)-6-(3-(2-(pyrrolidin-1-yl)ethoxy)phenylamino)nicotinamide

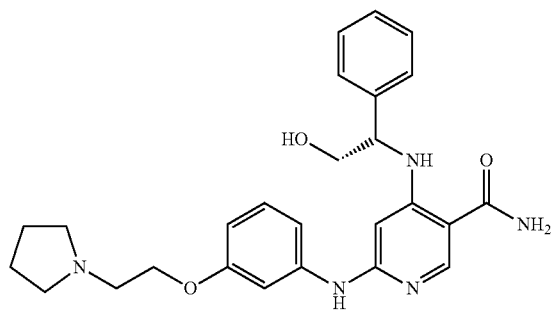

The title compound was synthesized using a procedure similar to that described in Example 36. MS found for C26H31N5O3 as (M+H)+ 462.6. UV: λ=206, 258 nm. $^1$H NMR: (CD$_3$OD) δ 8.19 (s, 1H), 7.32 (m, 3H), 7.28 (m, 3H), 6.93 (dd, 1H), 6.77 (s, 1H), 6.55 (d, 1H), 5.81 (s, 1H), 4.50 (m, 2H), 4.30 (m, 2H), 3.86 (dd, 1H), 3.73 (m, 1H), 3.71 (m, 2H), 3.70 (m, 1H), 3.23 (m, 2H), 2.19 (m, 2H), 2.06 (m, 2H).

Example 60

4-(pyridin-3-ylmethylamino)-6-(3-(2-(pyrrolidin-1-yl)ethoxy)phenylamino)nicotinamide

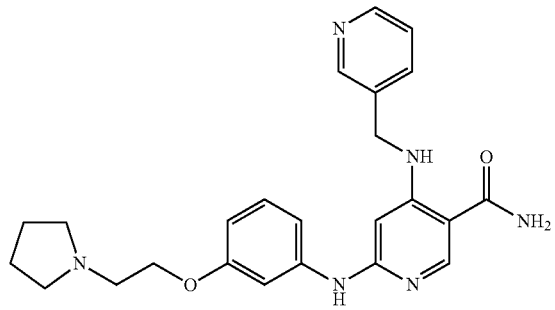 [SMILES: NC(=O)c1cnc(Nc2cccc(OCCN3CCCC3)c2)cc1NCc1cccnc1]

The title compound was synthesized using a procedure similar to that described in Example 36. MS found for C24H28N6O2 as (M+H)+ 433.6. UV: λ=205, 255 nm. $^1$H NMR: (CD$_3$OD) δ 8.46 (s, 1H), 8.45 (d, 1H), 7.80 (d, 1H), 7.42 (m, 1H), 7.13 (m, 1H), 6.98 (s, 1H), 6.73 (d, 1H), 6.58 (d, 1H), 5.89 (s, 1H), 4.47 (s, 1H), 4.11 (t, 2H), 2.97 (t, 2H), 2.74 (m, 4H), 1.85 (m, 4H).

Example 61

4-(3-fluorobenzylamino)-6-(3-methyl-4-(2-oxopyrrolidin-1-yl)phenylamino)nicotinamide

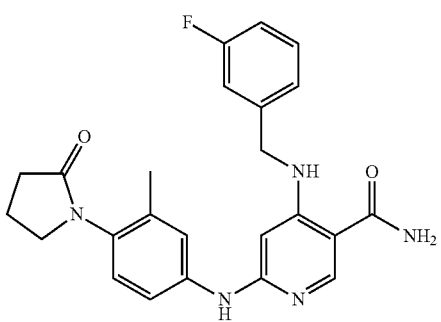 [SMILES: Cc1cc(Nc2cc(NCc3cccc(F)c3)c(C(N)=O)cn2)ccc1N1CCCC1=O]

The title compound was synthesized using a procedure similar to that described in Example 36. MS found for C24H24FN5O2 as (M+H)+ 434.5. UV: λ=207, 258 nm. $^1$H NMR: (CD$_3$OD) δ 8.16 (s, 1H0, 7.38 (m, 1H), 7.23 (d, 1H), 17.12 (s, 1H), 7.11 (d, 1H), 7.04 (d, 1H), 7.00 (m, 2H), 5.90 (s, 1H), 4.51 (s, 2H), 3.80 (t, 2H), 2.60 (t, 2H), 2.80 (m, 2H), 2.20 (s, 3H).

Example 62

6-(3-chloro-4-(2-oxopyrrolidin-1-yl)phenylamino)-4-(3-fluorobenzylamino)nicotinamide

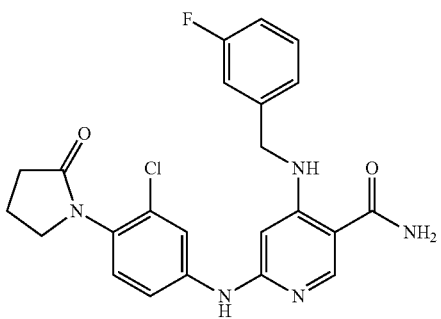 [SMILES: NC(=O)c1cnc(Nc2ccc(N3CCCC3=O)c(Cl)c2)cc1NCc1cccc(F)c1]

The title compound was synthesized using a procedure similar to that described in Example 36. MS found for C23H21ClFN5O2 as (M+H)+ 454.5. UV: λ=203, 262 nm. $^1$H NMR: (CD$_3$OD) δ 8.21 (s, 1H), 7.38 (m, 3H), 7.12 (m, 2H), 7.04 (m, 2H), 5.97 (s, 1H), 4.54 (s, 2H), 3.82 (t, 2H), 2.59 (t, 2H), 2.90 (m, 2H).

Example 63

4-(3-fluorobenzylamino)-6-(3-methoxy-4-(2-oxopyrrolidin-1-yl)phenylamino)nicotinamide

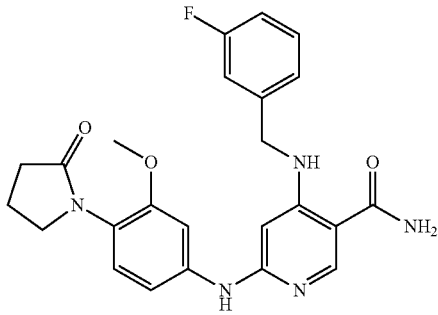 [SMILES: COc1cc(Nc2cc(NCc3cccc(F)c3)c(C(N)=O)cn2)ccc1N1CCCC1=O]

The title compound was synthesized using a procedure similar to that described in Example 36. MS found for C24H24FN5O3 as (M+H)$^+$ 450.5. $^1$H NMR: (CD$_3$OD) δ 8.16 (s, 1H), 7.37 (m, 1H), 7.24 (d, 1H), 7.11 (d, 1H), 7.03 (m, 2H), 6.92 (d, 1H), 6.74 (dd, 1H), 5.93 (s, 1H), 4.52 (s, 2H), 3.79 (t, 2H), 3.79 (s, 3H), 2.56 (t, 2H), 2.23 (m, 2H).

Example 64

4-(3-fluorobenzylamino)-6-(4-(2-oxopiperidin-1-yl)phenylamino)nicotinamide

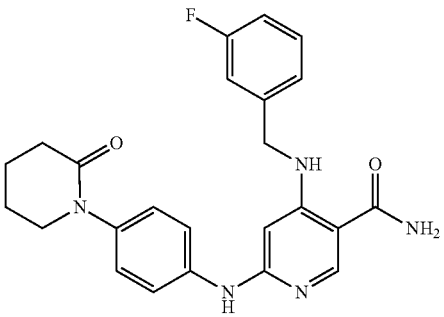 [SMILES: NC(=O)c1cnc(Nc2ccc(N3CCCCC3=O)cc2)cc1NCc1cccc(F)c1]

The title compound was synthesized using a procedure similar to that described in Example 36. MS found for C24H24FN5O2 as (M+H)$^+$ 434.5. $^1$H NMR: (CD$_3$OD) δ 8.15 (s, 1H), 7.40 (m, 1H), 7.32 (m, 2H), 7.18 (d, 2H), 7.11 (d, 1H), 7.04 (m, 2H), 5.90 (s, 1H), 4.51 (s, 2H), 3.70 (t, 2H), 2.54 (t, 2H), 1.99 (m, 4H).

Example 65

4-(3-fluorobenzylamino)-6-(3-morpholinophenylamino)nicotinamide

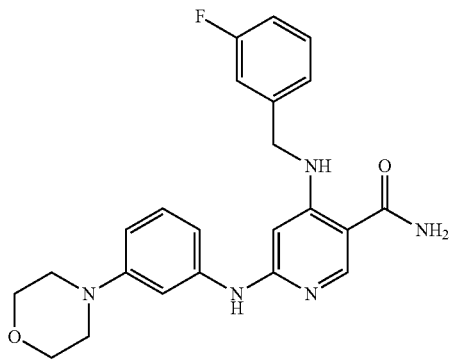 [SMILES: NC(=O)c1cnc(Nc2cccc(N3CCOCC3)c2)cc1NCc1cccc(F)c1]

The title compound was synthesized using a procedure similar to that described in Example 36. MS found for C23H24FN5O2 as (M+H)$^+$ 422.5. UV: λ=205, 258 nm. $^1$H NMR: (CD$_3$OD) δ 8.11 (s, 1H), 7.37 (m, 1H), 7.28 (t, 1H), 7.08 (d, 1H), 7.05 (s, 1H), 7.01 (d, 1H), 6.93 (dd, 1H), 6.74 (m, 1H), 6.56 (dd, 1H), 5.86 (s, 1H), 4.49 (s, 2H), 3.81 (t, 4H), 3.13 (t, 4H).

Example 66

4-((2-fluorobenzyl)amino)-6-((4-(2-morpholinoethoxy)phenyl)amino)nicotinamide

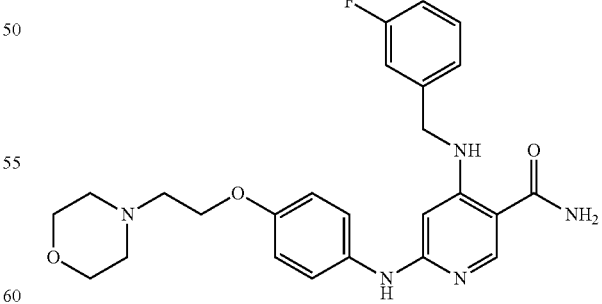

The title compound was synthesized using a procedure similar to that described in Example 36. MS found for C25H28FN5O3 as (M+H)$^+$ 466.5. UV: λ=202, 256 nm. $^1$H NMR: (CD$_3$OD) δ 8.14 (s, 1H), 7.38 (m, 1H), 7.08 (m, 6H), 6.99 (m, 1H), 5.71 (s, 1H), 4.44 (s, 2H), 4.43 (t, 2H), 3.67 (t, 2H).

Example 67

4-(3-fluorobenzylamino)-6-(4-morpholinophenylamino)nicotinamide

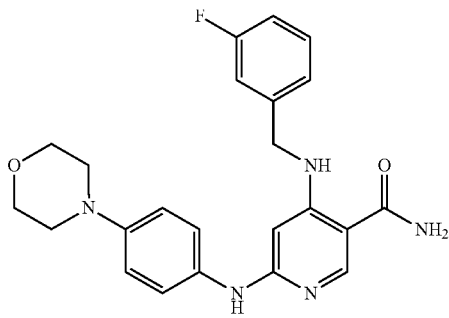 [SMILES: NC(=O)c1cnc(Nc2ccc(N3CCOCC3)cc2)cc1NCc1cccc(F)c1]

The title compound was synthesized using a procedure similar to that described in Example 36. MS found for C23H24FN5O2 as (M+H)$^+$ 422.5. UV: λ=205, 259 nm. $^1$H NMR: (CD$_3$OD) δ 8.01 (s, 1H), 7.27 (q, 1H), 6.97 (d, 1H), 6.93 (m, 6H), 5.62 (s, 1H), 4.36 (s, 1H), 3.75 (t, 4H), 3.08 (t, 4H).

Example 68

4-(3-fluorobenzylamino)-6-(3-(piperidin-1-yl)phenylamino)nicotinamide

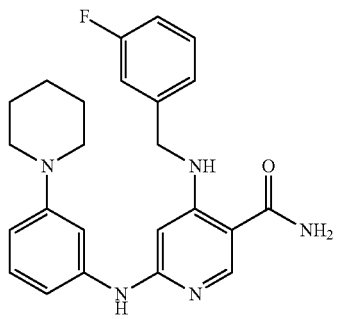 [SMILES: NC(=O)c1cnc(Nc2cccc(N3CCCCC3)c2)cc1NCc1cccc(F)c1]

The title compound was synthesized using a procedure similar to that described in Example 36. MS found for C24H26FN5O as (M+H)$^+$ 420.6. $^1$H NMR: (CD$_3$OD) δ 8.19 (s, 1H), 7.37 (m, 2H), 7.21 (dd, 1H), 7.11 (s, 1H), 7.10 (m, 1H), 7.04 (m, 2H), 6.85 (m, 1H), 5.92 (s, 1H), 4.51 (s, 2H), 3.38 (t, 4H), 1.84 (m, 4H), 1.70 (m, 2H).

Example 69

4-((2-fluorobenzyl)amino)-6-((4-(piperidin-1-yl)phenyl)amino)nicotinamide

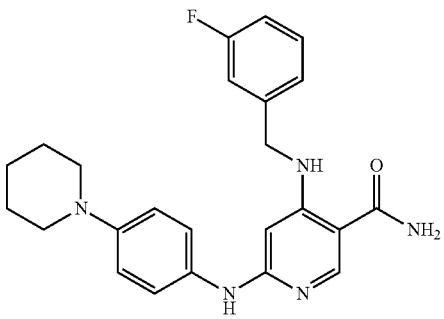 [SMILES: NC(=O)c1cnc(Nc2ccc(N3CCCCC3)cc2)cc1NCc1cccc(F)c1]

The title compound was synthesized using a procedure similar to that described in Example 36. MS found for C24H26FN5O as (M+H)$^+$ 420.5. UV: λ=257 nm. $^1$H NMR: (CD$_3$OD) δ 8.21 (s, 1H), 7.45 (d, 2H), 7.38 (m, 1H), 7.20 (d, 2H), 7.11 (d, 1H), 7.04 (m, 2H), 5.90 (s, 1H), 4.51 (s, 2H), 3.51 (t, 4H), 1.95 (m, 4H), 1.77 (m, 2H).

Example 70

4-(3-fluorobenzylamino)-6-(4-(piperidin-4-yl)phenylamino)nicotinamide

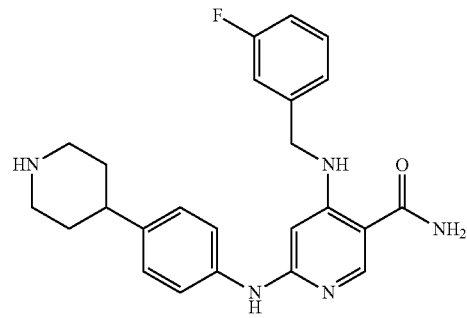 [SMILES: NC(=O)c1cnc(Nc2ccc(C3CCNCC3)cc2)cc1NCc1cccc(F)c1]

The title compound was synthesized using a procedure similar to that described in Example 36. MS found for C24H26FN5O as (M+H)$^+$ 420.5. UV: λ=202, 258 nm. $^1$H NMR: (CD$_3$OD) δ 8.08 (s, 1H), 7.27 (m, 1H), 7.21 (d, 2H), 6.99 (m, 4H), 6.89 (d, 1H), 5.72 (s, 1H), 4.38 (s, 2H), 3.43 (m, 2H), 3.06 (m, 2H), 2.87 (m, 1H), 1.99 (m, 2H), 1.84 (m, 2H).

Example 71

4-(2-fluorobenzylamino)-6-(4-(2-oxopiperidin-1-yl)phenylamino)nicotinamide

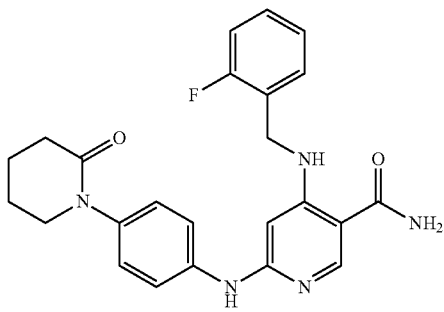 [SMILES: NC(=O)c1cnc(Nc2ccc(N3CCCCC3=O)cc2)cc1NCc1ccccc1F]

The title compound was synthesized using a procedure similar to that described in Example 36. MS found for C24H24FN5O2 as (M+H)⁺ 434.5. UV: λ=203, 257 nm. ¹H NMR: (CD₃OD) δ 8.14 (s, 1H), 7.35 (m, 4H), 7.26 (d, 2H), 7.17 (m, 2H), 6.00 (s, 1H), 4.55 (s, 2H), 3.71 (t, 2H), 2.54 (t, 2H), 1.99 (m, 2H).

Example 72

4-(2-fluorobenzylamino)-6-(3-(2-(pyrrolidin-1-yl)ethoxy)phenylamino)nicotinamide

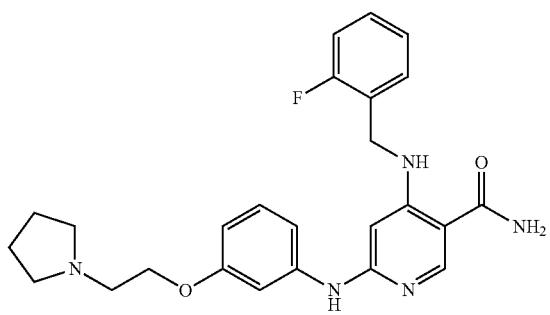 [SMILES: NC(=O)c1cnc(Nc2cccc(OCCN3CCCC3)c2)cc1NCc1ccccc1F]

The title compound was synthesized using a procedure similar to that described in Example 36. MS found for C25H28FN5O2 as (M+H)⁺ 450.6. UV: λ=203, 256 nm. ¹H NMR: (CD₃OD) δ 8.19 (s, 1H), 7.37 (t, 1H), 7.35 (m, 1H), 7.31 (m, 1H), 7.17 (ddd, 1H), 7.11 (m, 1H), 6.98 (m, 1H), 6.90 (t, 1H), 6.81 (m, 1H), 5.98 (s, 1H), 4.52 (s, 1H), 4.34 (t, 2H), 3.73 (m, 2H), 3.66 (t, 2H), 3.23 (m, 2H), 2.19 (m, 2H), 2.06 (m, 2H).

Example 73

4-(2-fluorobenzylamino)-6-(4-morpholinophenylamino)nicotinamide

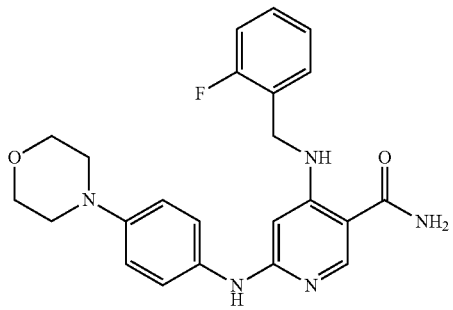

The title compound was synthesized using a procedure similar to that described in Example 36. MS found for C23H24FN5O2 as (M+H)⁺ 422.5. UV: λ=202, 258 nm. ¹H NMR: (CD₃OD) δ 8.08 (s, 1H), 7.35 (m, 1H), 7.38 (t, 1H), 7.19 (d, 1H), 7.12 (d, 1H), 7.05 (m, 4H), 5.79 (s, 1H), 4.49 (s, 2H), 3.86 (m, 4H), 3.19 (m, 4H).

Example 74

4-(2-fluorobenzylamino)-6-(4-(piperidin-1-yl)phenylamino)nicotinamide

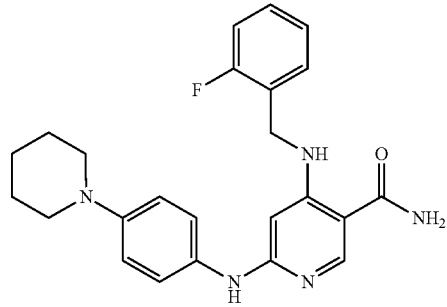 [SMILES: NC(=O)c1cnc(Nc2ccc(N3CCCCC3)cc2)cc1NCc1ccccc1F]

The title compound was synthesized using a procedure similar to that described in Scheme 7. MS found for C₂₄H₂₆FN₅O as (M+H)⁺ 420.5. UV: λ=203, 262 nm.

Example 75

(S)-4-(2-hydroxy-1-phenylethylamino)-6-(4-(piperidin-1-yl)phenylamino)nicotinamide

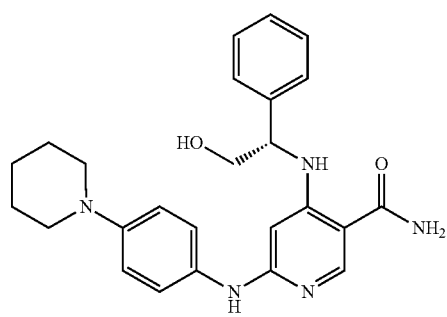 [SMILES: NC(=O)c1cnc(Nc2ccc(N3CCCCC3)cc2)cc1N[C@H](CO)c1ccccc1]

The title compound was synthesized using a procedure similar to that described in Example 36. MS found for C25H29N5O2 as (M+H)+ 432.6. UV: λ=203, 264 nm. ¹H NMR: (CD₃OD) δ 8.18 (s, 1H), 7.37 (m, 3H), 7.26 (d, 4H), 6.99 (d, 2H), 5.74 (s, 1H), 4.50 (m, 1H), 3.87 (dd, 1H), 3.74 (dd, 1H), 3.43 (m, 4H), 1.91 (m, 4H), 1.73 (m, 2H).

Example 76

(S)-4-(2-hydroxy-1-phenylethylamino)-6-(3-(piperidin-1-yl)phenylamino)nicotinamide

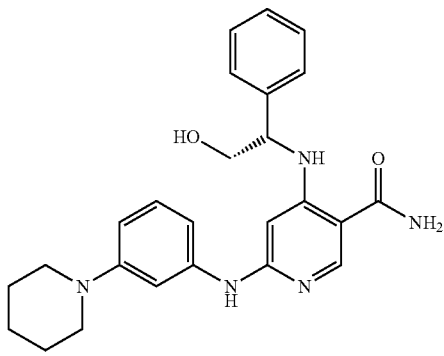

The title compound was synthesized using a procedure similar to that described in Example 36. MS found for C25H29N5O2 as (M+H)+ 432.6. UV: λ=259 nm. ¹H NMR: (CD₃OD) δ 8.19 (s, 1H), 7.30-7.38 (m, 4H), 7.26 (d, 2H), 7.15 (dd, 1H), 7.00 (s, 1H), 6.12 (dd, 1H), 5.80 (s, 1H), 4.52 (m, 1H), 3.86 (dd, 1H), 3.74 (dd, 1H), 3.46 (t, 4H), 1.83 (m, 4H), 1.70 (m, 2H).

Example 77 tert-butyl 4-(4-(5-carbamoyl-4-(3-fluorobenzylamino)pyridin-2-ylamino)phenyl)piperidine-1-carboxylate

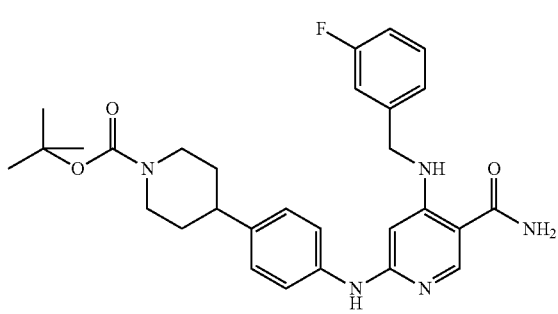 [SMILES: CC(C)(C)OC(=O)N1CCC(c2ccc(Nc3cc(NCc4cccc(F)c4)c(C(N)=O)cn3)cc2)CC1]

The title compound was synthesized using a procedure similar to that described in Example 36. MS found for C29H34FN5O3 as (M+H)+ 520.6. UV: λ=257 nm. ¹H NMR: (CD₃OD) δ 8.13 (s, 1H), 7.38 (dq, 1H), 7.28 (d, 2H), 7.07 (2H), 7.04 (d, 2H), 6.99 (m, 1H0, 5.80 (s, 1H), 4.82 (s, 2H), 4.21 (m, 2H), 2.89 (m, 2H), 2.77 (m, 1H), 1.83 (m, 2H), 1.61 (m, 2H), 1.48 (s, 9H).

Example 78

4-(4-(5-carbamoyl-4-(3-fluorobenzylamino)pyridin-2-ylamino)phenyl)-1,1-dimethylpiperidinium formate

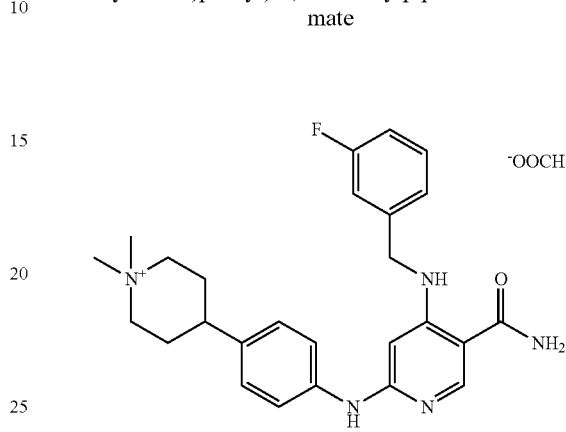

The title compound was synthesized using a procedure similar to that described in Example 36. MS found for C26H31FN5O as (M)+ 448.5. UV: λ=202, 258 nm. ¹H NMR: (CD₃OD) δ 8.54 (s, 1H), 8.28 (s, 1H), 7.36 (dq, 1H), 7.19 (d, 2H), 7.14 (d, 2H), 7.13 (m, 1H), 7.10 (m, 2H), 5.89 (s, 1H), 4.39 (s, 1H), 3.49-3.61 (m, 4H), 3.23 (s, 6H), 2.86 (m, 1H), 2.19 (m, 2H), 2.05 (m, 2H).

Example 79

(-(2-fluorobenzylamino)-6-(4-(1-propionylpiperidin-4-yl)phenylamino)nicotinamide

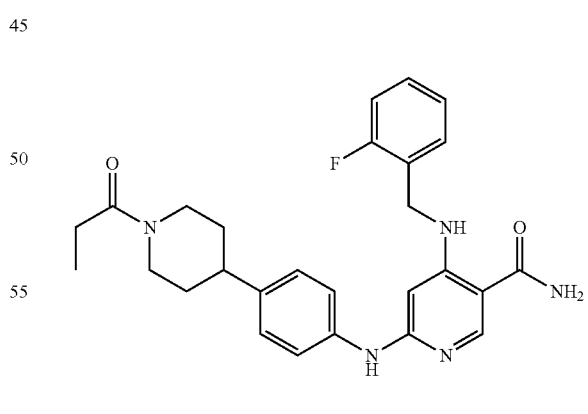

The title compound was synthesized using a procedure similar to that described in Example 36. MS found for C27H30FN5O2 as (M+H)+ 476.8. UV: λ=202, 256 nm. ¹H NMR: (CD₃OD) δ 8.12 (s, 1H), 7.27-7.38 (m, 4H), 7.10-7.19 (m, 4H), 5.87 (s, 1H), 4.70 (m, 1H), 3.23 (m, 1H), 2.90 (m, 1H), 2.73 (m, 1H), 2.46 (q, 2H), 1.92 (m, 2H), 1.58-1.69 (m, 2H), 1.50 (t, 3H).

Example 80

4-(benzylamino)-6-(4-(2-morpholino-2-oxoethoxy)phenylamino)nicotinamide

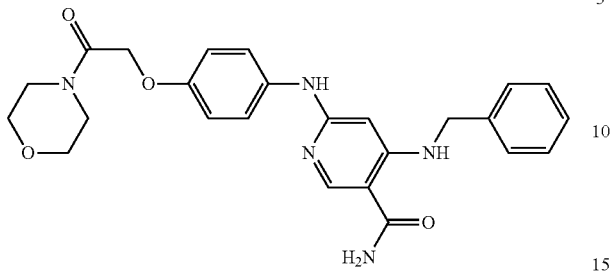

The title compound was synthesized using a procedure similar to that described in Example 36. MS found for C25H27N5O4 as (M+H)+ 462. UV: λ=206, 256 nm. ¹H NMR: (DMSO) δ9.63 (s, 1H), 8.15, (s, 1H), 7.3, (m, 5H), 7.1, (d, 1H), 6.9 (d, 1H), 5.75 (s, 1H), 4, 4.4 (d, 2H), 3.49, (dd, 4H), 3.45.

Example 81

4-(benzylamino)-6-(4-(2-(piperidin-1-yl)ethoxy)phenylamino)nicotinamide

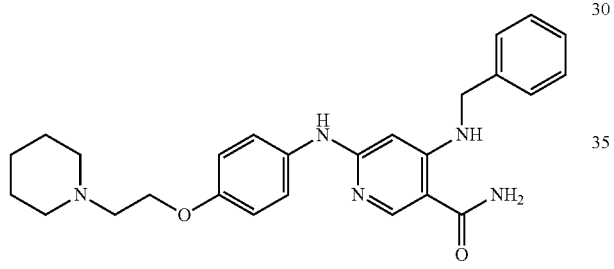

The title compound was synthesized using a procedure similar to that described in Example 36. MS found for C26H31N5O2 as (M+H)+ 446. UV: λ=256 nm. ¹H NMR: (DMSO) δ8.2, (s, 1H), 7.3, (m, 4H), 7.3, (d, 2H), 7.15, (s, 2H), 6.95, (d, 2H), 5.8, (s, 1H), 4.4, (s, 2H), 4.3, (t, 2H), 3.0, (d, 2H), 1.9, (d, 2H), 1.7, (d, 2H).

Example 82

4-(2,6-difluorobenzylamino)-6-(4-methoxyphenylamino)nicotinamide

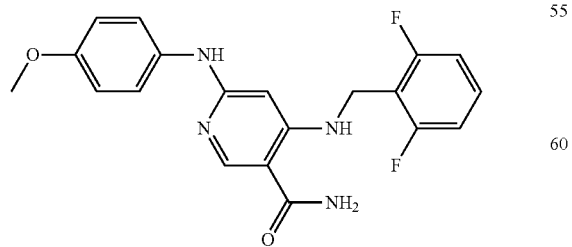

The title compound was synthesized using a procedure similar to that described in Example 36. MS found for C20H18F2N4O2 as (M+H)+ 385 UV: λ=254 nm. ¹H NMR: (CD3OD) δ8.1, (s, 1H), 7.4, (m, 1H), 7.2, (d, 2H), 7.1, (d, 2H), 7.0, (t, 2H), 5.95, (s, 1H), 4.5, (s, 2H), 3.9, (s, 3H).

Example 83

4-(2,5-difluorobenzylamino)-6-(4-methoxyphenylamino)nicotinamide

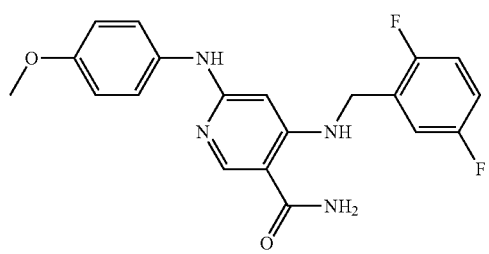 [SMILES: COc1ccc(Nc2cc(NCc3cc(F)ccc3F)c(C(N)=O)cn2)cc1]

The title compound was synthesized using a procedure similar to that described in Example 36. MS found for C20H18F2N4O2 as (M+H)+ 85 UV: λ=254 nm. ¹H NMR: (CD3OD) δ8.2, (s, 1H), 7.1, (m, 5H), 6.8, (d, 2H), 5.65, (s, 1H), 4.4, (s, 2H), 3.8, (s, 3H).

Example 84

4-(benzylamino)-6-(3-oxo-3,4-dihydro-2H-benzo[b][1,4]oxazin-6-ylamino)nicotinamide

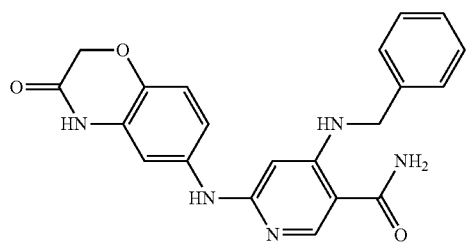 [SMILES: NC(=O)c1cnc(Nc2ccc3c(c2)NC(=O)CO3)cc1NCc1ccccc1]

The title compound was synthesized using a procedure similar to that described in Example 36. MS found for C21H19N5O3 as (M+H)+ 390 UV: λ=254 nm. ¹H NMR: (CD3OD) δ8.0, (s, 1H), 7.2, (m, 5H), 6.9, (d, 1H), 6.8, (d, 2H), 4.5, (s, 2H), 4.4, (s, 2H).

Example 85

4-(benzylamino)-6-(4-methyl-3-oxo-3,4-dihydro-2H-benzo[b][1,4]oxazin-6-ylamino)nicotinamide

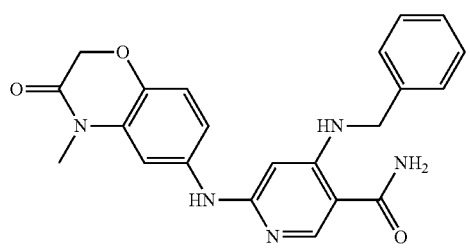 [SMILES: CN1C(=O)COc2ccc(Nc3cc(NCc4ccccc4)c(C(N)=O)cn3)cc21]

The title compound was synthesized using a procedure similar to that described in Scheme 7. MS found for C22H21N5O3 as (M+H)+ 404 UV: λ=211, 254 nm. ¹H NMR: (CD3OD) δ8.0, (s, 1H), 7.2, (m, 5H), 6.95, (d, 1H), 6.90, (d, 1H), 6.7, (dd, 1H), 5.7, (s, 1H), 4.6, (s, 2H), 4.4, (s, 2H), 3.2, (s, 3H).

Example 86

4-(benzylamino)-6-(quinolin-6-ylamino)nicotinamide

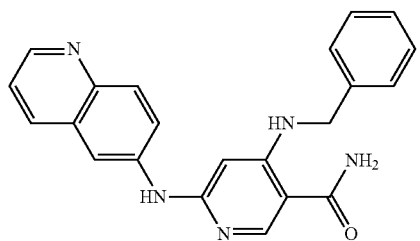 [SMILES: NC(=O)c1cnc(Nc2ccc3ncccc3c2)cc1NCc1ccccc1]

The title compound was synthesized using a procedure similar to that described in Example 36. MS found for C22H19N5O as (M+H)+ 370 UV: λ=203, 277 nm. ¹H NMR: (CD3OD) δ8.9, (d, 1H), 8.4, (d, 1H), 8.2, (s, 1H), 8.0, (d, 1H), 7.65, (s, 1H), 7.60, (m, 1H), 7.5, (d, 1H), 7.25, (d, 2H), 7.2, (d, 2H), 6.0, (1H), 4.4, (s, 2H).

Example 87

4-(benzylamino)-6-(quinolin-7-ylamino)nicotinamide

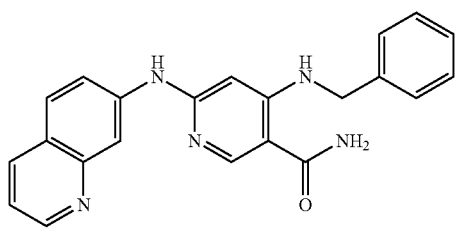 [SMILES: NC(=O)c1cnc(Nc2ccc3cccnc3c2)cc1NCc1ccccc1]

The title compound was synthesized using a procedure similar to that described in Example 36. MS found for C22H19N5O as (M+H)+ 370 UV: λ=210, 276 nm. ¹H NMR: (CD3OD) δ8.9, (d, 1H), 8.7, (d, 1H), 8.3, (s, 1H), 8.1, (s, 1H), 8.0, (d, 1H), 7.7, (d, 1H), 7.6, (d, 1H), 7.2, (m, 6H), 6.2, (s, 1H), 4.5, (s, 2H).

Example 88

4-(benzylamino)-6-(isoquinolin-6-ylamino)nicotinamide

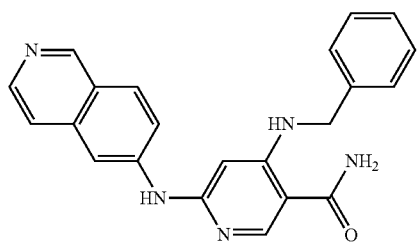 [SMILES: NC(=O)c1cnc(Nc2ccc3cnccc3c2)cc1NCc1ccccc1]

The title compound was synthesized using a procedure similar to that described in Example 36. MS found for C22H19N5O as (M+H)+ 370 UV: λ=210, 254 nm. ¹H NMR: (CD3OD) δ8.4, (s, 1H), 8.2, (d, 1H), 8.1 (s, 1H), 7.9, (bs, 1H), 7.65, (d, 1H), 7.2, (m, 6H), 6.2, (s, 1H), 4.45, (s, 2H).

Example 89

4-(benzylamino)-6-(isoquinolin-7-ylamino)nicotinamide

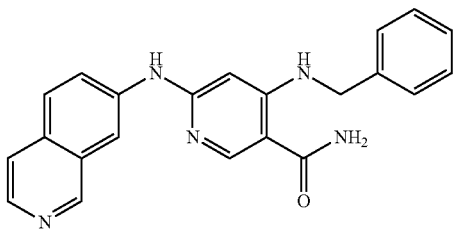 [SMILES: NC(=O)c1cnc(Nc2ccc3ccncc3c2)cc1NCc1ccccc1]

The title compound was synthesized using a procedure similar to that described in Example 36. MS found for C22H19N5O as (M+H)+ 370 UV: λ=217, 276, and 313 nm. ¹H NMR: (CD3OD) δ9.2, (s, 1H), 8.4, (d, 1H), 8.2, (s, 1H), 8.1, (m, 4H), 7.7, (d, 1H), 7.2, (m, 5H), 6.0, (s, 1H), 4.4, (s, 2H).

Example 90

6-(benzo[d]thiazol-6-ylamino)-4-(benzylamino)nicotinamide

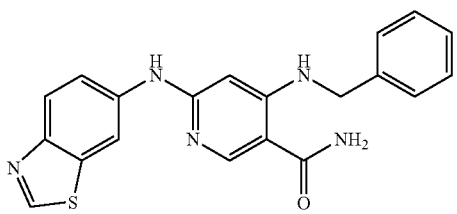 [SMILES: NC(=O)c1cnc(Nc2ccc3ncsc3c2)cc1NCc1ccccc1]

The title compound was synthesized using a procedure similar to that described in Example 36. MS found for C20H17N5OS as (M+H)+ 376 UV: λ=207, 252, and 320 nm. ¹H NMR: (CD3OD) δ9.2, (s, 1H), 8.1, (s, 1H), 8.0, (d, 1H), 7.8, (s, 1H), 7.2, (m, 5H), 7.15, (t, 1H), 5.9, (s, 1H), 4.4, (s, 2H).

Example 91

4-(3-fluorobenzylamino)-6-(4-methoxyphenylamino)nicotinamide

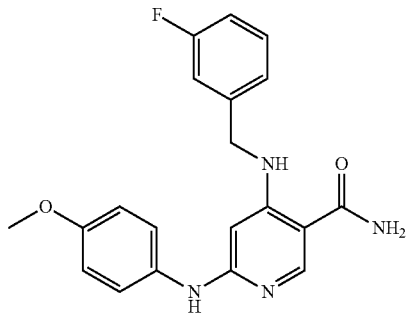 [SMILES: COc1ccc(Nc2cc(NCc3cccc(F)c3)c(C(N)=O)cn2)cc1]

The title compound was synthesized using a procedure similar to that described in Example 36. MS found for C20H19FN4O2 as (M+H)+ 367 UV: λ=202, 257 nm. ¹H NMR: (CD3OD) δ8.0, (s, 1H), 7.2, (dd, 1H), 6.9, (m, 5H), 6.85, (d, 2H), 5.6, (s, 1H), 4.4, (s, 2H), 4.75, (s, 3H).

Example 92

4-(2,5-difluorobenzylamino)-6-(4-(dimethylcarbamoyl)phenylamino)nicotinamide

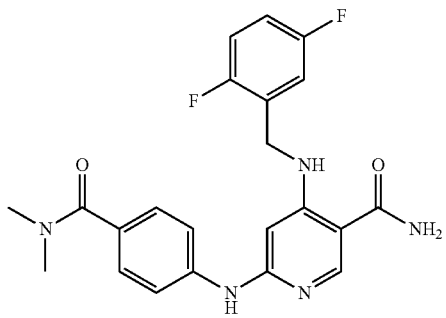 [SMILES: CN(C)C(=O)c1ccc(Nc2cc(NCc3cc(F)ccc3F)c(C(N)=O)cn2)cc1]

The title compound was synthesized using a procedure similar to that described in Example 36. MS found for C22H21F2N5O2 as (M+H)+ 426 UV: λ=204, 265 nm. ¹H NMR: (CD3OD) δ8.1, (s, 1H), 7.4, (d, 2H), 7.2, (d, 2H), 7.15, (m, 3H), 5.9, (s, 1H), 4.4, (s, 2H), 3.0, (d, 6H).

Example 93

6-(4-(azetidine-1-carbonyl)phenylamino)-4-(2,5-difluorobenzylamino)nicotinamide

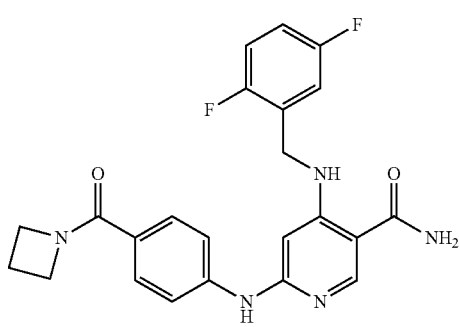 [SMILES: NC(=O)c1cnc(Nc2ccc(C(=O)N3CCC3)cc2)cc1NCc1cc(F)ccc1F]

The title compound was synthesized using a procedure similar to that described in Example 36. MS found for C23H21F2N5O2 as (M+H)+ 438 UV: λ=204, 266, and 310 nm. ¹H NMR: (CD3OD) δ8.2, (s, 1H), 7.7, (d, 2H), 7.3, (d, 2H), 7.2, (m, 1H), 7.1, (m, 2H), 6.0, (s, 1H), 4.5, (s, 2H), 4.4, (t, 2H), 4.2 (t, 2H), 2.4, (t, 2H).

Example 94

4-(2,5-difluorobenzylamino)-6-(4-(2-oxopiperidin-1-yl)phenylamino)nicotinamide

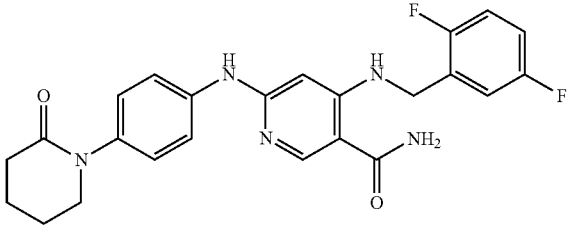 [SMILES: NC(=O)c1cnc(Nc2ccc(N3CCCCC3=O)cc2)cc1NCc1cc(F)ccc1F]

The title compound was synthesized using a procedure similar to that described in Example 36. MS found for C24H23F2N5O2 as (M+H)+ 452 UV: λ=203, 251, and 306 nm. ¹H NMR: (CD3OD) δ8.1, (s, 1H), 7.3, (d, 2H), 7.2, (d, 2H), 7.1, (m, 1H), 7.0, (m, 2H), 5.9, (s, 1H), 4.5, (s, 2H), 3.4, (t, 2H), 2.5, (t, 2H), 1.9, (m, 4H).

Example 95

4-(cyclopentylmethylamino)-6-(3-(dimethylcarbamoyl)phenylamino)nicotinamide

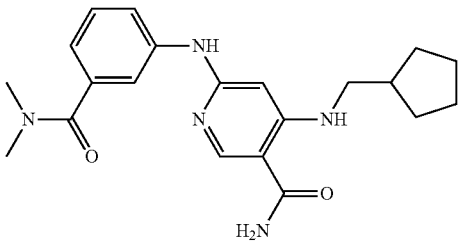 [SMILES: CN(C)C(=O)c1cccc(Nc2cc(NCC3CCCC3)c(C(N)=O)cn2)c1]

The title compound was synthesized using a procedure similar to that described in Example 36. MS found for C21H27N5O2 as (M+H)+ 382 UV: λ=246, 314 nm. ¹H NMR: (CD3OD) δ8.1, (s, 1H), 7.5, (t, 1H), 7.35, (m, 1H), 7.3, (m, 1H), 7.25, (m, 2H), 5.9, (s, 1H), 3.1 (d, 2H), 3.0, (s, 2H), 2.95, (s, 2H), 2.2, (t, 1H), 2.8, (m, 2H), 2.6 (m, 4H), 1.2, (m, 2H).

Example 96

4-(cyclopentylmethylamino)-6-(4-(dimethylcarbamoyl)phenylamino)nicotinamide

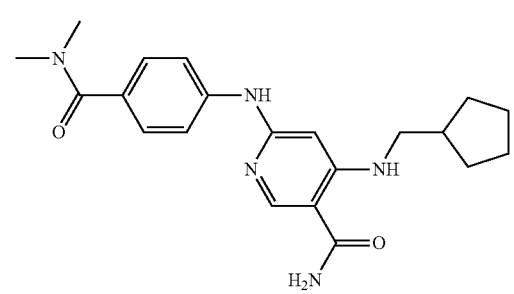 [SMILES: CN(C)C(=O)c1ccc(Nc2cc(NCC3CCCC3)c(C(N)=O)cn2)cc1]

The title compound was synthesized using a procedure similar to that described in Example 36. MS found for C21H27N5O2 as (M+H)+ 382. UV: λ=246, 314 nm. $^1$H NMR: (CD3OD) δ8.1, (s, 1H), 7.5, (d, 2H), 7.3, (d, 2H), 6.0, (s, 1H), 3.1, (d, 2H), 3.05, (s, 1H), 3.0, (d, 6H), 2.1, (m, 1H), 2.8, (m, 2H), 2.6, (m, 4H), 1.2, (m, 2H).

Example 97

4-(cyclopentylmethylamino)-6-(4-(N,N-dimethylsulfamoyl)phenylamino)nicotinamide

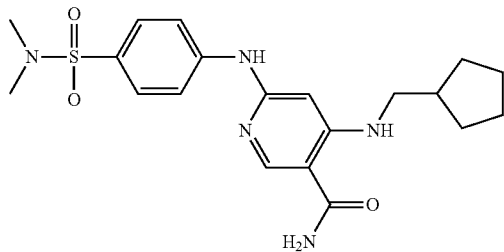

The title compound was synthesized using a procedure similar to that described in Example 36. MS found for C20H27N5O3S as (M+H)+ 418. UV: λ=207, 239, 257, 306 nm. $^1$H NMR: (CD3OD) δ8.2, (s, 1H), 7.9, (d, 2H), 7.5, (d, 2H), 6.2, (s, 1H), 3.2, (d, 2H), 2.7, (s, 6H), 2.2, (t, 1H), 1.9, (m, 2H), 1.65, (m, 4H), 1.3, (m, 2H).

Example 98

4-(2,5-difluorobenzylamino)-6-(4-(N,N-dimethylsulfamoyl)phenylamino)nicotinamide

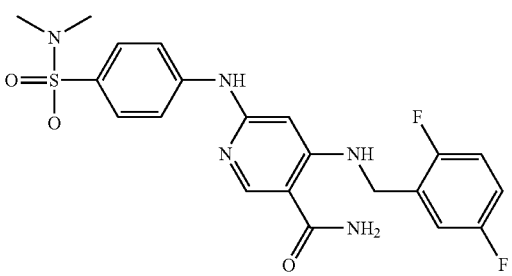

The title compound was synthesized using a procedure similar to that described in Example 36. MS found for C21H21F2N5O3S as (M+H)+ 462. UV: λ=206, 274, 311 nm. $^1$H NMR: (CD3OD) δ8.3, (s, 1H), 7.8, (d, 2H), 7.4, (d, 2H), 7.2, (m, 1H), 7.1, (m, 2H), 6.1, (s, 1H), 2.7, (s, 6H).

Example 99

6-(3-(azetidine-1-carbonyl)phenylamino)-4-(2,5-difluorobenzylamino)nicotinamide

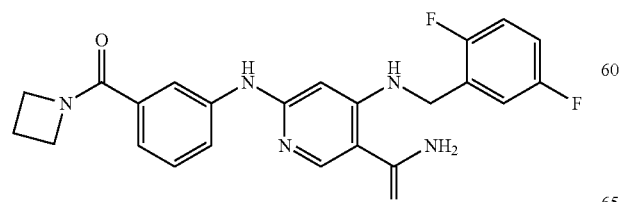

The title compound was synthesized using a procedure similar to that described in Scheme 36. MS found for C23H21F2N5O2 as (M+H)+ 438 UV: λ=203, 248, and 301 nm. $^1$H NMR: (CD3OD) δ8.1, (s, 1H), 7.4, (m, 3H), 7.2, (d, 1H), 7.0, (m, 3H), 5.9, (s, 1H), 4.5, (s, 2H), 4.3, (t, 2H), 4.1, (t, 2H), 2.3, (m, 2H).

Example 101

4-(2,3-difluorobenzylamino)-6-(4-methoxyphenylamino)nicotinamide

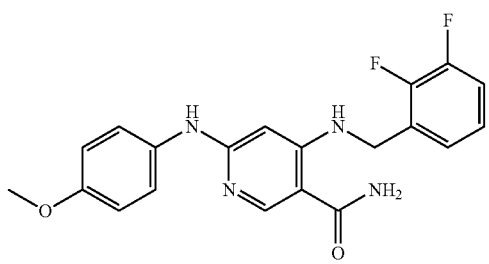 [SMILES: COc1ccc(Nc2cc(NCc3cccc(F)c3F)c(C(N)=O)cn2)cc1]

The title compound was synthesized using a procedure similar to that described in Scheme 36. MS found for C20H18F2N4O2 as (M+H)+ 385. UV: λ=204, 253 nm. $^1$H NMR: (CD3OD) δ8.1, (s, 1H), 7.25, (m, 1H), 7.15, (m, 2H), 7.1, (d, 2H), 7.0, (d, 2H), 5.75, (s, 1H), 4.5, (s, 2H), 3.8, (s, 3H).

Example 102

4-(2,6-difluorobenzylamino)-6-(4-(dimethylcarbamoyl)phenylamino)nicotinamide

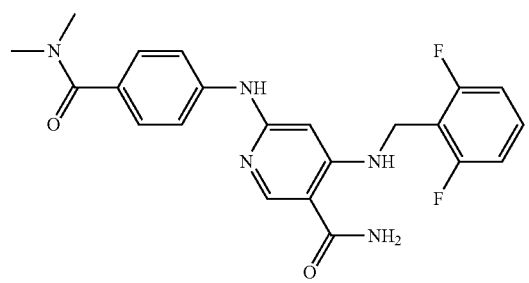 [SMILES: CN(C)C(=O)c1ccc(Nc2cc(NCc3c(F)cccc3F)c(C(N)=O)cn2)cc1]

The title compound was synthesized using a procedure similar to that described in Scheme 36. MS found for C22H21F2N5O2 as (M+H)+ 426. UV: λ=202, 258 nm. $^1$H NMR: (CD3OD) δ8.2, (s, 1H), 7.55, (d, 2H), 7.4, (d, 2H), 7.0, (m, 3H), 6.2, (s, 1H), 4.5, (s, 2H), 3.1, (d, 6H).

Example 103

4-(2,6-difluorobenzylamino)-6-(4-(2-oxopiperidin-1-yl)phenylamino)nicotinamide

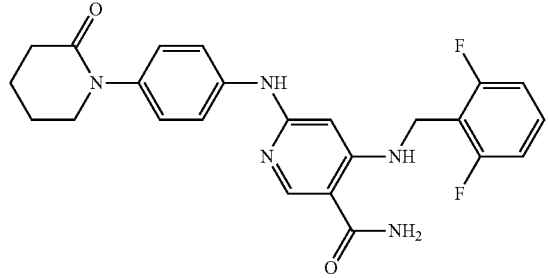 [SMILES: NC(=O)c1cnc(Nc2ccc(N3CCCCC3=O)cc2)cc1NCc1c(F)cccc1F]

The title compound was synthesized using a procedure similar to that described in Scheme 36. MS found for C24H23F2N5O2 as (M+H)+ 452. UV: λ=204, 257 nm. ¹H NMR: (CD3OD) δ8.1, (s, 1H), 7.3, (m, 5H), 6.7, (t, 2H), 6.1, (s, 1H), 4.5, (s, 2H), 3.4, (t, 2H), 2.4, (t, 2H), 1.9, (m, 4H).

Example 104

4-(2,6-difluorobenzylamino)-6-(4-(N,N-dimethylsulfamoyl)phenylamino)nicotinamide

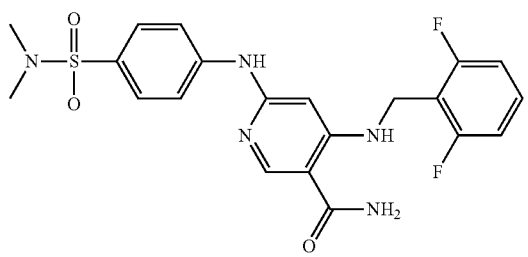

The title compound was synthesized using a procedure similar to that described in Scheme 36. MS found for C21H21F2N5O3S as (M+H)+ 462. UV: λ=204, 263 nm. ¹H NMR: (CD3OD) δ8.25, (s, 1H), 7.9, (d, 2H), 7.5, (d, 2H), 7.4, (t, 1H), 7.05, (m, 2H), 6.3, (s, 1H), 4.4, (s, 2H), 2.8, (s, 6H).

Example 105

6-(4-(azetidine-1-carbonyl)phenylamino)-4-(2,6-difluorobenzylamino)nicotinamide

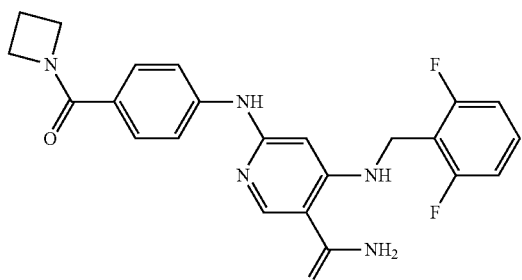

The title compound was synthesized using a procedure similar to that described in Scheme 36. MS found for C23H21F2N5O2 as (M+H)+ 438. UV: λ=202, 254 nm. ¹H NMR: (CD3OD) δ8.2, (s, 1H), 7.75, (d, 2H), 7.4, (m, 1H), 7.35, (d, 2H), 7.0, (t, 2H), 6.25, (s, 1H), 4.45, (s, 2H), 4.4, (t, 2H), 4.2, (t, 2H), 2.4, (t, 2H).

Example 106

Preparation of 4-(2-fluorobenzylamino)-6-(4-(piperidin-4-yl)phenylamino)nicotinamide

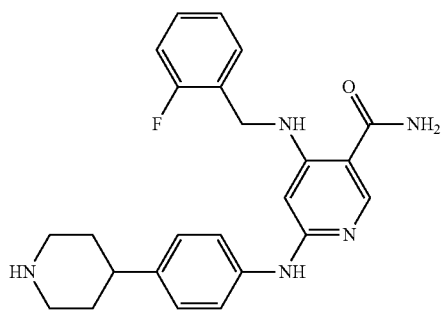 [SMILES: NC(=O)c1cnc(Nc2ccc(C3CCNCC3)cc2)cc1NCc1ccccc1F]

Scheme:

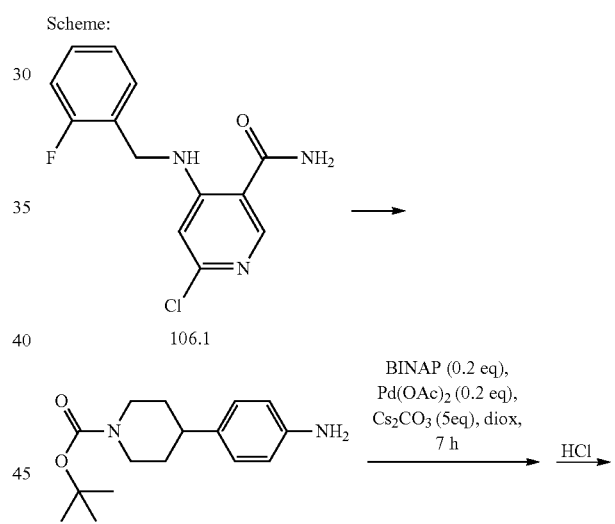

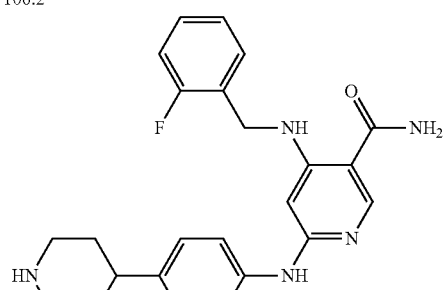

The mixture of compound 106/1 (500 mg, 1.8 mmol), aniline 106.2 (Chem-Impex #18042, 1.50 g, 5.4 mmol), powder Cs₂CO₃ (2.61 g, 8.0 mmol), BINAP (0.25 g, 0.36 mmol), Pd(OAc)₂ (0.10 g, 0.36 mmol) in 70 mL dioxane was degassed with argon stream and stirred at 105° C. bath for 7 h under argon atmosphere. It was concentrated in vacuo and taken into 300 mL EtOAc. It was washed with water twice, dried, concentrated and subjected to flash column (0-15% MeOH in DCM). The product was then treated with 4N HCl in dioxane (30 mL) at RT for overnight. The mixture was concentrated in vacuo and subjected to reverse phase prep HPLC to isolate the title compound as HCl salt. UV=259 nm. M+H found for $C_{24}H_{26}FN_5O$: 420.4. NMR (CD3OD): 8.17 (1H, s), 7.37 (1H, m), 7.33 (2H, dm, J=8.8 Hz), 7.09 (3H, m), 7.04 (1H, dd, J=8.4; 2.4 Hz), 7.00 (1H, m), 8.17 (1H, s), 4.49 (2H, s), 3.53 (2H, m), 3.17 (2H, m), 2.96 (1H, m), 2.10 (2H, m), 1.94 (2H, m) ppm.

Example 107

Preparation of 4-(2-fluorobenzylamino)-6-(4-(1-methylpiperidin-4-yl)phenylamino)nicotinamide

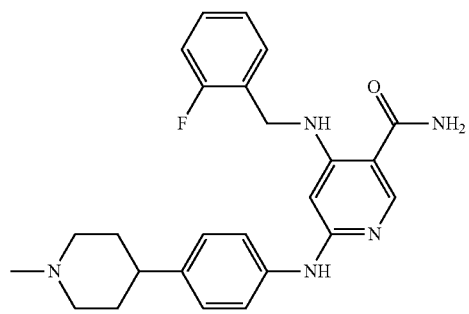 [SMILES: CN1CCC(c2ccc(Nc3cc(NCc4ccccc4F)c(C(N)=O)cn3)cc2)CC1]

The title compound was prepared using the same chemistry shown in Example 106. UV: 259 nm. M+H found for $C_{25}H_{28}FN_5O$: 434.4. NMR (CD$_3$OD): 8.16 (1H, s), 7.35 (3H, m), 7.29 (1H, td, J=7.6; 2.0 Hz), 7.20-7.10 (4H, m), 5.88 (1H, s), 4.51 (2H, s), 3.64 (2H, m), 3.18 (2H, m), 2.97 (1H, m), 2.93 (3H, s), 2.15 (2H, m), 2.01 (2H, m) ppm.

Example 108

Preparation of 4-(2-fluorobenzylamino)-6-(4-(1-isopropylpiperidin-4-yl)phenylamino)nicotinamide

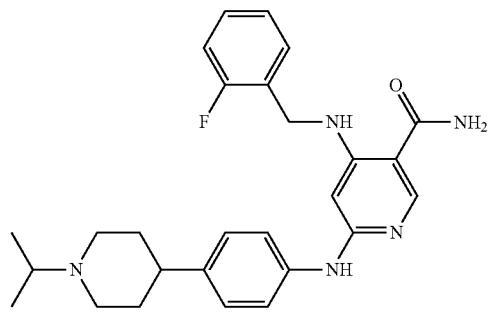 [SMILES: CC(C)N1CCC(c2ccc(Nc3cc(NCc4ccccc4F)c(C(N)=O)cn3)cc2)CC1]

Compound 4-(2-fluorobenzylamino)-6-(4-(piperidin-4-yl)phenylamino)nicotinamide (Example 106) HCl salt (110 mg, 0.24 mmol) was stirred in 5 mL 1,2-dichloroethane (DCE) and 5 mL dioxane. To the slurry were added DIEA (0.21 mL, 1.2 mmol) and acetone (0.18 mL, 2.4 mmol). The mixture was stirred at RT for 1 h. To the mixture were then added HOAc (0.25 mL) and NaBH(OAc)$_3$ (260 mg, 1.2 mmol). The mixture was stirred at RT for overnight. Water (10 mL) was added. The mixture was concentrated in vacuo. The residue was subjected to reverse phase prep HPLC to isolate the title compound as HCl salt. UV=259 nm. M+H found for $C_{27}H_{32}FN_5O$: 462.5. NMR (CD$_3$OD): 8.18 (1H, s), 7.38 (1H, m), 7.30 (2H, d, J=8.8 Hz), 7.09 (3H, m), 7.04 (1H, m), 7.00 (1H, m), 5.82 (1H, s), 4.47 (2H, s), 3.58 (2H, m), 3.22 (3H, m), 2.95 (1H, m), 2.18 (2H, m), 2.01 (2H, m), 1.42 (6H, d, J=6.8 Hz) ppm.

Example 109

Preparation of 6-(4-(1-cyclopentylpiperidin-4-yl)phenylamino)-4-(2-fluorobenzylamino)nicotinamide

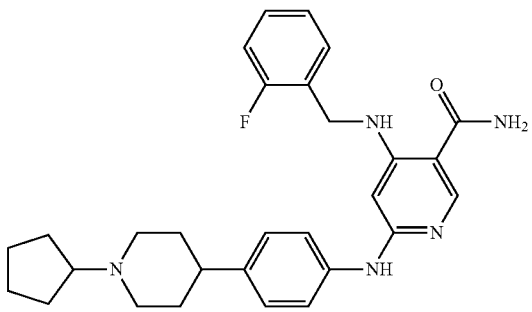 [SMILES: NC(=O)c1cnc(Nc2ccc(C3CCN(C4CCCC4)CC3)cc2)cc1NCc1ccccc1F]

The title compound was prepared using the same chemistry shown in Example 106. UV: 259 nm. M+H found for $C_{29}H_{34}FN_5O$: 488.4. NMR (CD$_3$OD): 8.16 (1H, s), 7.37-7.31 (3H, m), 7.29 (1H, td, J=7.6; 1.6 Hz), 7.19-7.10 (4H, m), 5.88 (1H, s), 4.50 (2H, s), 3.75 (2H, m), 3.57 (1H, m), 3.15 (2H, m), 2.98 (1H, m), 2.21 (4H, m), 1.99 (2H, m), 1.87 (2H, m), 1.74 (4H, m) ppm.

Example 110

Preparation of 6-(3-(1-cyclopentylpiperidin-4-yl)phenylamino)-4-(2-fluorobenzylamino)nicotinamide

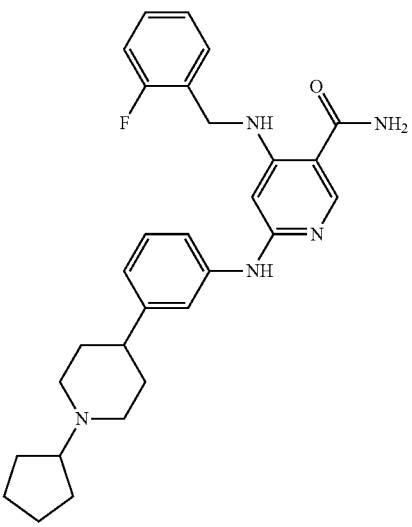 [SMILES: NC(=O)c1cnc(Nc2cccc(C3CCN(C4CCCC4)CC3)c2)cc1NCc1ccccc1F]

The title compound was prepared using the same chemistry shown in Example 106. UV: 259 nm. M+H found for C$_{29}$H$_{34}$FN$_5$O: 488.4. NMR (CD$_3$OD): 8.17 (1H, s), 7.42 (1H, t, J=8.0 Hz), 7.32 (1H, m), 7.29 (1H, m), 7.26 (1H, t, J=8.0 Hz), 7.18-7.15 (2H, m), 7.13-7.05 (2H, m), 5.94 (1H, s), 4.51 (2H, s), 3.73 (2H, m), 3.56 (1H, m), 3.12 (2H, m), 2.94 (1H, m), 2.18 (4H, m), 1.97 (2H, m), 1.87 (2H, m), 1.73 (4H, m) ppm.

Example 111

Preparation of 4-(2-fluorobenzylamino)-6-(4-(1-(methylsulfonyl)piperidin-4-yl)phenylamino)nicotinamide

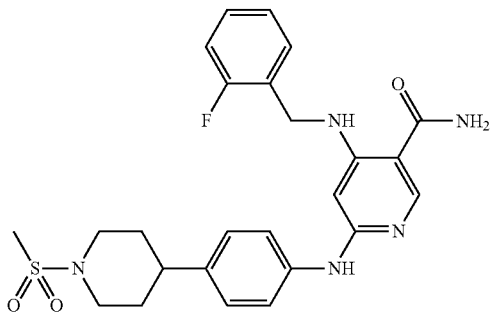 [SMILES: CS(=O)(=O)N1CCC(c2ccc(Nc3cc(NCc4ccccc4F)c(C(N)=O)cn3)cc2)CC1]

Compound 4-(2-fluorobenzylamino)-6-(4-(piperidin-4-yl)phenylamino)nicotinamide (Example 106) HCl salt (100 mg, 0.2 mmol) was stirred in 5 mL NMP. To the solution were added DIEA (0.18 mL, 1.0 mmol) and MsCl (0.047 mL, 0.6 mmol). The mixture was stirred at RT for 30 min and quenched with Me$_2$NH. The mixture was concentrated in vacuo and subjected to reverse phase prep HPLC to isolate the title compound as HCl salt. UV=259 nm. M+H found for C$_{25}$H$_{28}$FN$_5$O$_3$S: 498.5. NMR (CD$_3$OD): 8.13 (1H, s), 7.39-7.34 (3H, m), 7.29 (1H, td, J=8.0; 2.0 Hz), 7.19-7.10 (4H, m), 5.88 (1H, s), 4.51 (2H, s), 3.86 (2H, m), 2.88 (2H, m), 2.85 (3H, s), 2.75 (1H, m), 1.97 (2H, m), 1.79 (2H, m) ppm.

Example 112

Preparation of 6-(4-(1-(ethylsulfonyl)piperidin-4-yl)phenylamino)-4-(2-fluorobenzylamino)nicotinamide

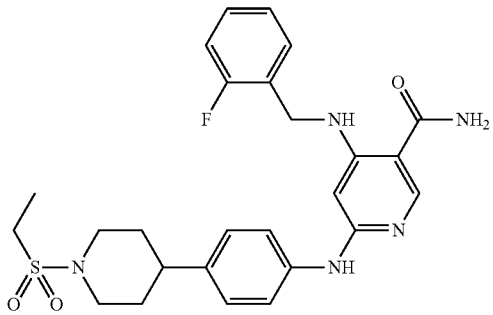 [SMILES: CCS(=O)(=O)N1CCC(c2ccc(Nc3cc(NCc4ccccc4F)c(C(N)=O)cn3)cc2)CC1]

The title compound was prepared using the same chemistry shown in Example 106. UV: 259 nm. M+H found for C$_{26}$H$_{30}$FN$_5$O$_3$S: 512.5. NMR (CD$_3$OD): 8.13 (1H, s), 7.39-7.30 (3H, m), 7.28 (1H, td, J=8.0; 2.0 Hz), 7.19-7.10 (4H, m), 5.88 (1H, s), 4.51 (2H, s), 3.89 (2H, m), 3.07 (2H, q, J=7.6 Hz), 2.98 (2H, m), 2.76 (1H, m), 1.94 (2H, m), 1.77 (2H, m), 1.35 (3H, t, J=7.2 Hz) ppm.

Example 113

Preparation of 6-(4-(1-(cyclopropylsulfonyl)piperidin-4-yl)phenylamino)-4-(2-fluorobenzylamino)nicotinamide

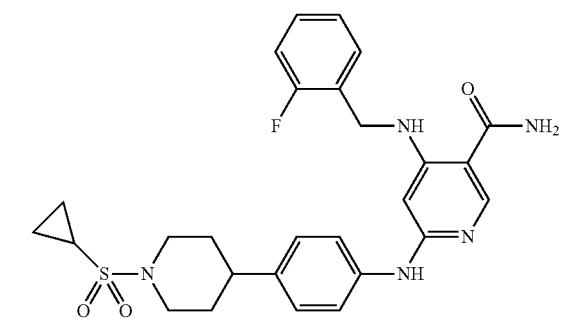 [SMILES: NC(=O)c1cnc(Nc2ccc(C3CCN(S(=O)(=O)C4CC4)CC3)cc2)cc1NCc1ccccc1F]

The title compound was prepared using the same chemistry shown in Example 111. UV: 259 nm. M+H found for C$_{27}$H$_{30}$FN$_5$O$_3$S: 524.4. NMR (CD$_3$OD): 8.14 (1H, s), 7.37 (1H, m), 7.30 (2H, d, J=8.0 Hz), 7.10-7.00 (5H, m), 5.81 (1H, s), 4.48 (2H, s), 3.88 (2H, m), 3.01 (2H, m), 2.74 (1H, m), 2.52 (1H, m), 1.95 (2H, m), 1.78 (2H, m), 1.08 (4H, m) ppm.

Example 114

Preparation of 6-(4-(1-(dimethylcarbamoyl)piperidin-4-yl)phenylamino)-4-(2-fluorobenzylamino)nicotinamide

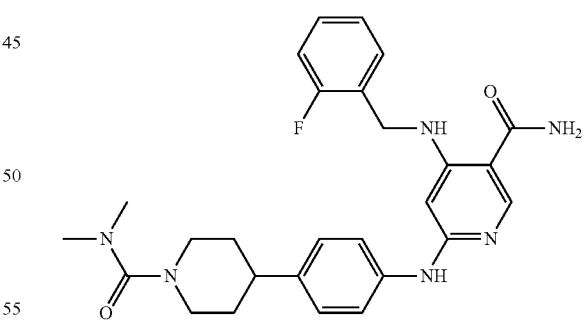

Compound 4-(2-fluorobenzylamino)-6-(4-(piperidin-4-yl)phenylamino)nicotinamide (Example 106) HCl salt (100 mg, 0.2 mmol) was stirred in 5 mL NMP. To the solution were added DIEA (0.18 mL, 1.0 mmol) and dimethylcarbamylchloride (0.055 mL, 0.6 mmol). The mixture was stirred at RT for 1 h and quenched with Me$_2$NH. The mixture was concentrated in vacuo and subjected to reverse phase prep HPLC to isolate the title compound as HCl salt. UV=259 nm. M+H found for C$_{27}$H$_{31}$FN$_6$O$_2$: 491.5. NMR (CD$_3$OD): 8.12 (1H, s), 7.37 (1H, m), 7.34 (2H, d, J=8.4 Hz), 7.28 (1H, m), 7.17

(1H, m), 7.16-7.10 (3H, m), 5.88 (1H, s), 4.51 (2H, s), 3.82 (2H, m), 2.94 (2H, m), 2.88 (6H, s), 2.80 (1H, m), 1.86 (2H, m), 1.72 (2H, m) ppm.

Example 115

Preparation of 6-(4-(1-acetylpiperidin-4-yl)phenylamino)-4-(2-fluorobenzylamino)nicotinamide

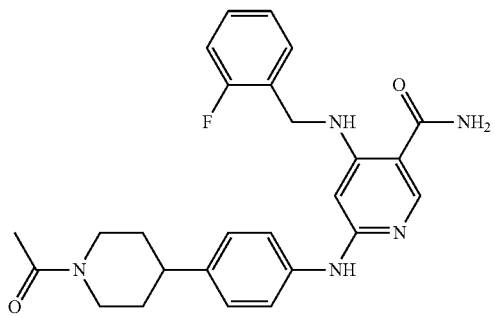 [SMILES: CC(=O)N1CCC(c2ccc(Nc3cc(NCc4ccccc4F)c(C(N)=O)cn3)cc2)CC1]

Compound 4-(2-fluorobenzylamino)-6-(4-(piperidin-4-yl)phenylamino)nicotinamide (Example 106) HCl salt (100 mg, 0.2 mmol) was stirred in 5 mL NMP. To the solution were added DIEA (0.18 mL, 1.0 mmol) and acetyl chloride (0.022 mL, 0.3 mmol). The mixture was stirred at RT for 15 min and quenched with Me$_2$NH. The mixture was concentrated in vacuo and subjected to reverse phase prep HPLC to isolate the title compound as HCl salt. UV=259 nm. M+H found for C$_{26}$H$_{28}$FN$_5$O$_2$: 462.5. NMR (CD$_3$OD): 8.12 (1H, s), 7.37 (1H, m), 7.34 (2H, d, J=8.4 Hz), 7.28 (1H, m), 7.18 (1H, m), 7.15-7.10 (3H, m), 5.88 (1H, s), 4.69 (1H, m), 4.51 (2H, s), 4.06 (1H, m), 3.24 (1H, m), 2.89 (1H, m), 2.73 (1H, m), 2.15 (3H, s), 1.92 (2H, m), 1.66 (2H, m) ppm.

Example 116

Preparation of 4-(2-fluorobenzylamino)-6-(4-(1-(2-methoxyacetyl)piperidin-4-yl)phenylamino)nicotinamide

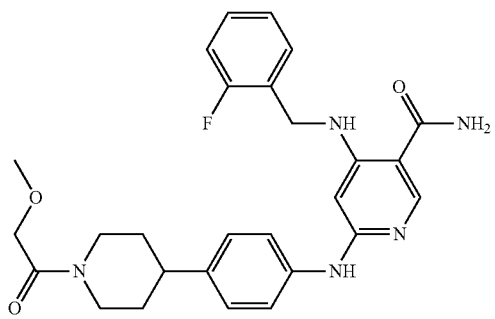 [SMILES: COCC(=O)N1CCC(c2ccc(Nc3cc(NCc4ccccc4F)c(C(N)=O)cn3)cc2)CC1]

The title compound was prepared using the same chemistry shown in Example 111. UV: 259 nm. M+H found for C$_{27}$H$_{30}$FN$_5$O$_3$: 492.4. NMR (CD$_3$OD): 8.13 (1H, s), 7.37 (1H, m), 7.28 (2H, d, J=8.4 Hz), 7.08 (1H, m), 7.06-7.02 (3H, m), 7.00 (1H, m), 5.80 (1H, s), 4.66 (1H, m), 4.48 (2H, s), 4.24 (1H, d, J=14.0 Hz), 4.16 (1H, d, J=14.0 Hz), 4.00 (1H, m), 3.43 (3H, s), 3.22 (1H, m), 2.88 (1H, m), 2.78 (1H, m), 1.92 (2H, m), 1.65 (2H, m) ppm.

Example 117

Preparation of 6-(4-(1-(2-cyanoacetyl)piperidin-4-yl)phenylamino)-4-(2-fluorobenzylamino)nicotinamide

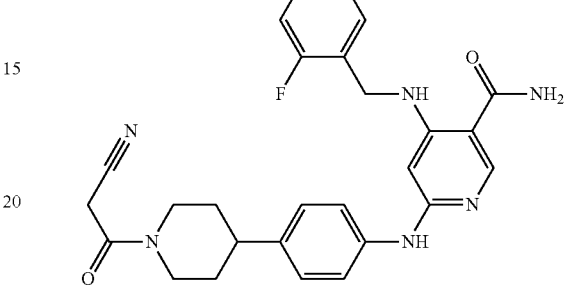

Compound 4-(2-fluorobenzylamino)-6-(4-(piperidin-4-yl)phenylamino)nicotinamide (Example 106) HCl salt (100 mg, 0.2 mmol) was stirred in 5 mL NMP. To the solution were added DIEA (0.35 mL, 2.0 mmol), cyanoacetic acid (85 mg, 1.0 mmol) and BOP (379 mg, 1.0 mmol). The mixture was stirred at RT for 3 h and quenched with TFA. The mixture was concentrated in vacuo and subjected to reverse phase prep HPLC to isolate the title compound as HCl salt. UV=259 nm. M+H found for C$_{27}$H$_{27}$FN$_6$O$_2$: 487.5. NMR (CD$_3$OD): 8.03 (1H, s), 7.27 (1H, m), 7.24 (2H, d, J=8.4 Hz), 7.19 (1H, m), 7.09 (1H, m), 7.07-7.00 (3H, m), 5.78 (1H, s), 4.56 (1H, m), 4.41 (2H, s), 3.88 (1H, d, J=18.8 Hz), 3.83 (1H, m), 3.78 (1H, d, J=18.4 Hz), 3.17 (1H, m), 2.80 (1H, m), 2.72 (1H, m), 1.83 (2H, m), 1.61 (2H, m) ppm.

Example 118

Preparation of 6-(4-(1-(1-cyanocyclopropanecarbonyl)piperidin-4-yl)phenylamino)-4-(2-fluorobenzylamino)nicotinamide

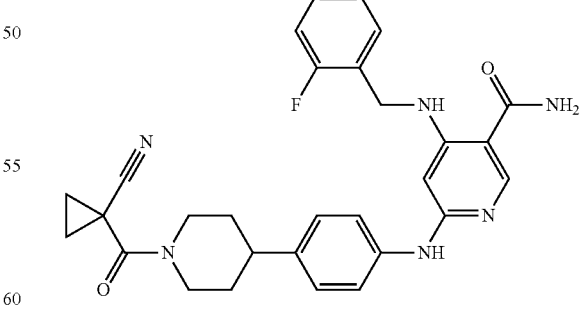

The title compound was prepared using the same chemistry shown in Example 107. UV: 259 nm. M+H found for C$_{29}$H$_{29}$FN$_6$O$_2$: 513.5. NMR (CD$_3$OD): 8.14 (1H, s), 7.38 (1H, m), 7.31 (2H, d, J=8.4 Hz), 7.09-6.99 (5H, m), 5.81 (1H, s), 4.56 (2H, m), 4.48 (2H, s), 2.94 (3H, m), 1.96-1.60 (8H, m).

Example 119

Preparation of 4-(2-fluorobenzylamino)-6-(4-(1-(tetrahydro-2H-pyran-4-carbonyl)piperidin-4-yl)phenylamino)nicotinamide

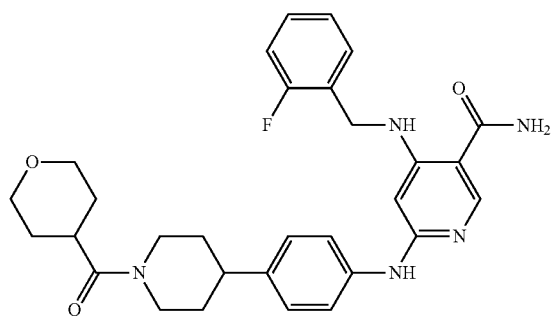 [SMILES: NC(=O)c1cnc(Nc2ccc(C3CCN(C(=O)C4CCOCC4)CC3)cc2)cc1NCc1ccccc1F]

The title compound was prepared using the same chemistry shown in Example 107. UV: 259 nm. M+H found for $C_{30}H_{34}FN_5O_3$: 532.4. NMR (CD$_3$OD): 8.14 (1H, s), 7.37 (1H, m), 7.28 (2H, d, J=8.4 Hz), 7.09-7.02 (4H, m), 6.99 (1H, m), 5.80 (1H, s), 4.70 (1H, m), 4.48 (2H, s), 4.23 (1H, m), 3.97 (2H, m), 3.50 (2H, m), 3.23 (1H, m), 3.02 (1H, m), 2.89 (1H, m), 2.73 (1H, m), 1.94 (2H, m), 1.81 (2H, m), 1.65 (2H, m), 1.59 (2H, m) ppm.

Example 120

Preparation of 4-(2-fluorobenzylamino)-6-(3-(piperidin-4-yl)phenylamino)nicotinamide

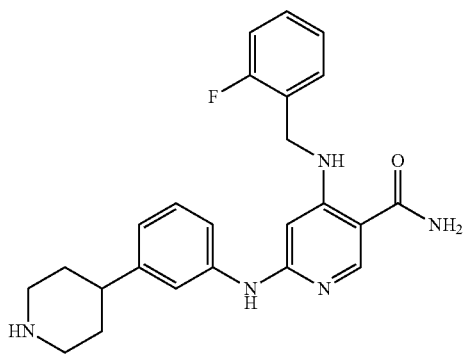 [SMILES: NC(=O)c1cnc(Nc2cccc(C3CCNCC3)c2)cc1NCc1ccccc1F]

Scheme 10:

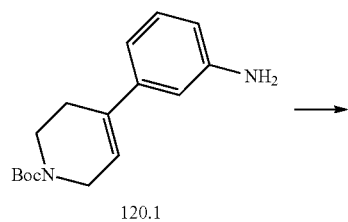

120.1

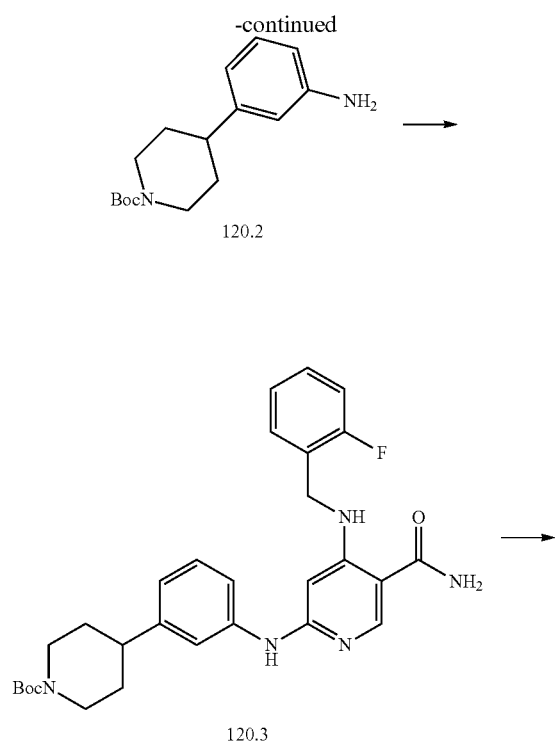

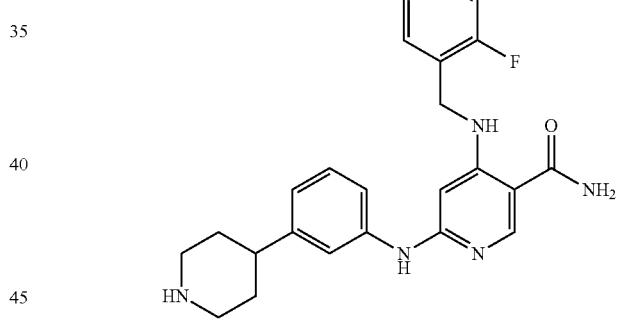

The title compound was prepared using similar chemistry as previously described. 4-(4,4,5,5-Tetramethyl[1,3,2]dioxaborolan-2-yl)-3,6-dihydro-2H-pyridine-1-carboxylic acid tert-butyl ester was used instead of 3-aminophenylboronic acid and 3-iodoaniline was used instead of 2-bromopyrimidine. 120.1 was then reduced with hydrogen in the presence of Pd/C in EtOAc as seen in scheme BS2. The resulting compound 120.2 was coupled with 4-(2-fluorobenzylamino)-6-chloronicotinamide utilizing chemistry in scheme 1 to afford 120.3. Note that 4-(2-fluorobenzylamino)-6-chloronicotinamide was synthesized analogously to 6-chloro-4-(pyridin-3-ylmethylamino)nicotinamide utilizing 2-fluorobenzylamine instead of 3-(Aminomethyl)pyridine (also see scheme 1). 120.3 was then stirred in a 50/50 mixture of CH$_2$Cl$_2$ and TFA to give the title compound which was purified by rpHPLC (described previously). UV: 257 nm. M+H found for $C_{24}H_{26}FN_5O$: 420.5. (CD$_3$OD): 8.18 (1H, s), 7.414-7.04 (8H, m), 5.94 (1H, s), 4.51 (2H, s), 3.53-3.48 (2H, m), 3.15 (2H, dt, J=2.4 Hz, 8.8 Hz), 2.93 (1H, tt, J=3.6, 8.8 Hz), 2.10-2.06 (2H, m), 1.91 (2H, dd, J=3.6, 12.4 Hz) ppm.

Example 121

Preparation of 4-(2-fluorobenzylamino)-6-(3-(1-(methylsulfonyl)piperidin-4-yl)phenylamino)nicotinamide

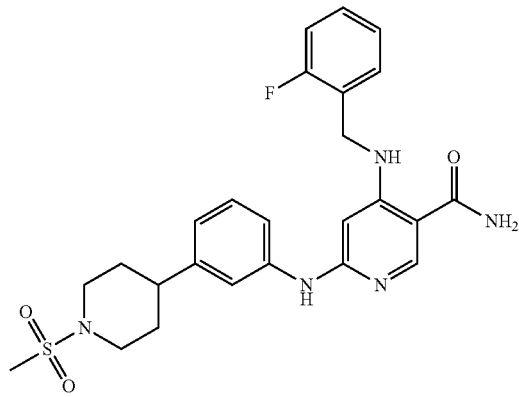 [SMILES: CS(=O)(=O)N1CCC(c2cccc(Nc3cc(NCc4ccccc4F)c(C(N)=O)cn3)c2)CC1]

The title compound was synthesized by dissolving compound 120 in NMP and DIPEA (~3 eq) and chilling to 0° C. To this chilled solution was added methanesulfonyl chloride (dropwise, 1.1 eq). The solution was allowed to warm temp and was stirred for 5 additional minutes. The reaction mixture was diluted with water and several drops of TFA were added to turn the reaction mixture acidic. Insoluble solid was filtered and the filtrate was subjected to preparative rpHPLC. This afforded the title compound. UV: 257 nm. M+H found for $C_{25}H_{28}FN_5O_3S$: 498.5. (CD$_3$OD): 8.15 (1H, s), 7.41-7.00 (8H, m), 5.93 (1H, s), 4.52 (2H, s), 3.88-3.80 (2H, m), 2.90-2.80 (5H, m), 2.69 (1H, tt), 1.97-1.91 (2H, m), 1.82-1.70 (2H, m) ppm.

Example 122

6-(4-(4-acetylpiperazin-1-yl)phenylamino)-4-(thiophen-2-ylmethylamino)nicotinamide

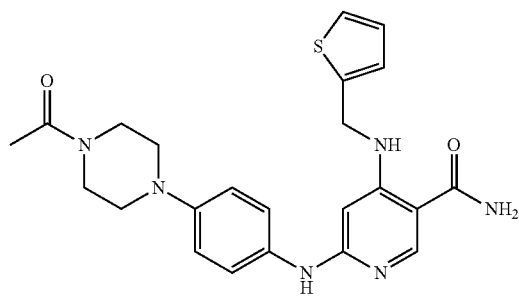

Scheme 11

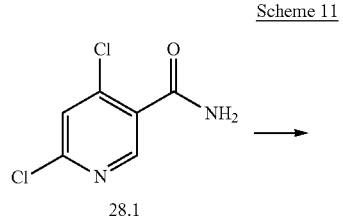

28.1

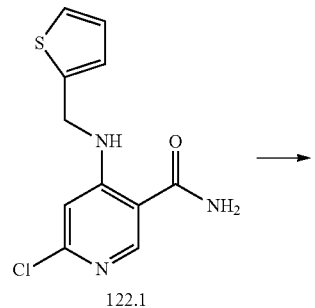

122.1

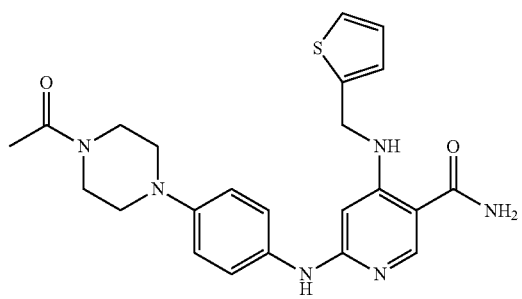 [SMILES: CC(=O)N1CCN(c2ccc(Nc3cc(NCc4cccs4)c(C(N)=O)cn3)cc2)CC1]

A solution of 4,6-dichloronicotinamide (123 mg, 0.643 mmol), thiophen-2-ylmethanamine (0.065 mL, 0.634 mmol) and DIPEA (0.230 mL, 1.32 mmol) in NMP (4 mL) was stirred at 90 C for 18 h. Water and EtOAc were added. The organic phase was separated, dried over Na$_2$SO$_4$, and concentrated in vacuo to give 6-chloro-4-(thiophen-2-ylmethylamino)nicotinamide as a solid (168 mg).

A mixture of 6-chloro-4-(thiophen-2-ylmethylamino)nicotinamide (84 mg, 0.314 mmol), 1-(4-(4-aminophenyl)piperazin-1-yl)ethanone (82 mg, 0.374 mmol), Cs2CO3 (200 mg, 0.613 mmol), BINAP (35 mg, 0.056 mmol) and Pd(OAc)$_2$ (25 mg, 0.111 mmol) in dioxane (2 mL) was degassed with Ar, then was stirred at 120 C for 3 h. The mixture was concentrated in vacuo. The residue was purified by HPLC to the titled compound (12 mg). MS 451.4 (M+H); UV 200.0, 244.3 nm; t 0.485 min.

Example 123

6-(4-(4-acetylpiperazin-1-yl)phenylamino)-4-((cis)-4-hydroxycyclohexylamino)nicotinamide

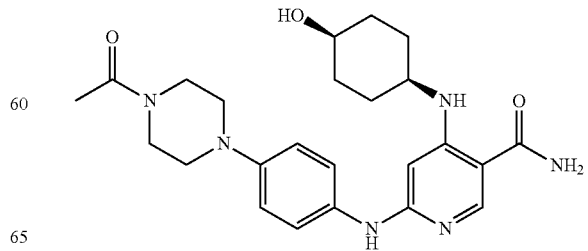

Scheme 12

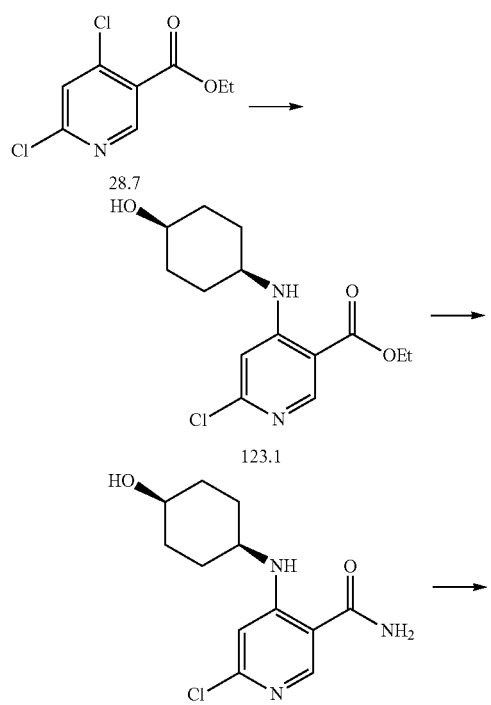

A mixture of ethyl 4,6-dichloronicotinate (160 mg, 0.727 mmol), (1s,4s)-4-aminocyclohexanol hydrochloride (110 mg, 0.726 mmol) and DIPEA (0.330 mL, 1.89 mmol) in NMP (5 mL) was stirred at 110 C for 6 h. Water and EtOAc were added. The organic phase was separated, washed with 5% NaHCO₃, dried over Na₂SO₄, concentrated in vacuo to give ethyl 6-chloro-4-((1s,4s)-4-hydroxycyclohexylamino)nicotinate as a solid (200 mg).

To a solution of ethyl 6-chloro-4-((1 s,4s)-4-hydroxycyclohexylamino)nicotinate (200 mg, 0.670 mmol) and formamide (0.600 mL, 15.0 mmol) in DMF (3 mL) at room temperature, sodium ethoxide (21% in ethanol by wt, 1.00 mL, 2.68 mmol) was added. The mixture was stirred at room temperature for 2 h. It was then concentrated in vacuo. The residue was purified by HPLC to give 6-chloro-4-((1s,4s)-4-hydroxycyclohexylamino)nicotinamide (163 mg).

A mixture of 6-chloro-4-((cis)-4-hydroxycyclohexylamino)nicotinamide (65 mg, 0.240 mmol), 1-(4-(4-aminophenyl)piperazin-1-yl)ethanone (60 mg, 0.273 mmol), sodium phenoxide trihydrate (100 mg, 0.588 mmol), xantphos (30 mg, 0.051 mmol) and Pd₂dba₃ (20 mg, 0.021 mmol) in dioxane (3 mL) was degassed with Ar, then was stirred at 120 C for 18 h. HOAc (1 mL) was added. The mixture was concentrated in vacuo. The residue was purified by HPLC to give the titled compound (14 mg). MS 453.5 (M+H); UV 202.9, 259.0 nm; t 0.380 min.

Example 124

4-(1-phenylcyclopropylamino)-6-(4-(4-propionylpiperazin-1-yl)phenylamino)nicotinamide

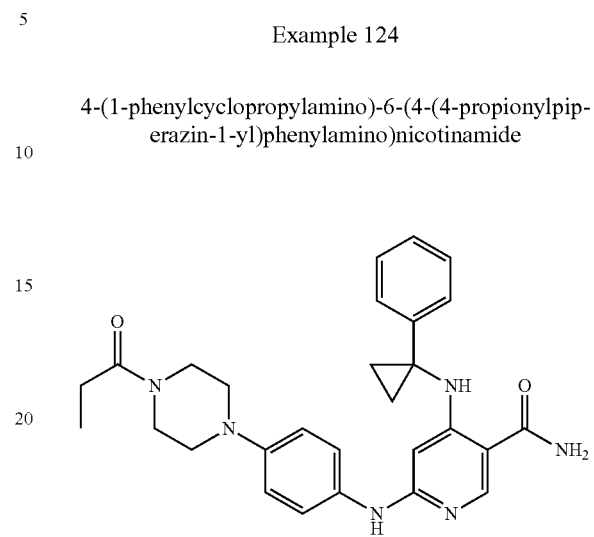

Scheme 13

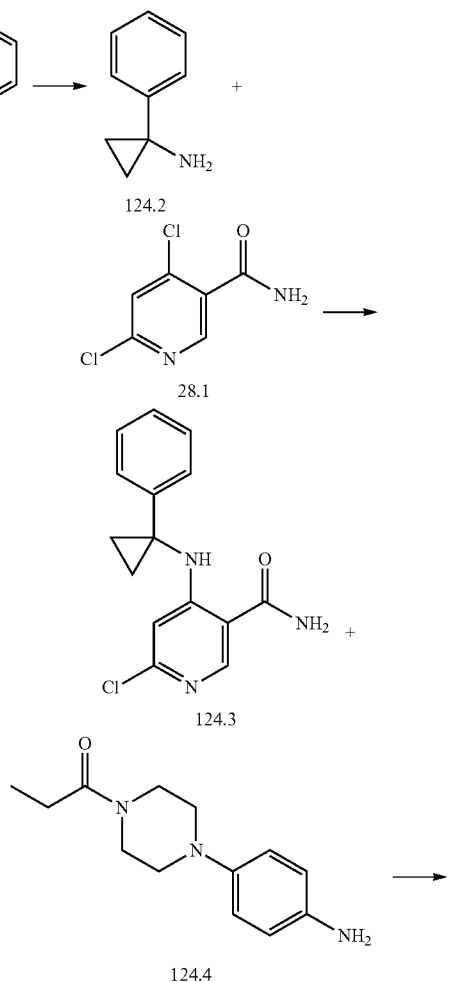

-continued

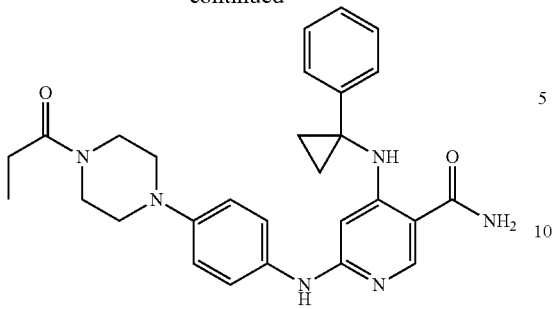

Step 1: To a solution of benzonitrile (1.03 g, 10 mmol) in DCM (50 mL) at −60° C. was added Ti(OiPr)$_4$ (3.22 mL, 11 mmol) and EtMgBr (3M in ether, 7.34 mL, 22 mmol), the resulting dark brown solution was slowly warmed up to room temperature over 1 h. BF$_3$.OEt$_2$ (2.47 mL, 20 mmol) was added, and the solution was further stirred at room temperature for 2 h. The mixture was quenched with Sat. NH4Cl and 1N HCl, aqueous layer was separated and extracted with ether, and then neutralized with 5N NaOH to pH=10. The resulting precipitate was filtered off and the filtrate was extracted with EtOAc, EtOAc layer was combined, dried and concentrated to give 1-phenylcyclopropanamine as oil (600 mg).

Step 2: To a suspension of 4,6-dichloronicotinamide (191 mg, 1 mmol) in AcCN (2 mL) was added 1-phenylcyclopropanamine (160 mg, 1.2 mmol) and DIPEA (0.213 mL, 1.2 mmol). The mixture was heated at 60° C. for 2 days. The mixture was concentrated and purified by column chromatography to give 6-chloro-4-(1-phenylcyclopropylamino) nicotinamide (105 mg).

Step 3: To a solution of 6-chloro-4-(1-phenylcyclopropylamino)nicotinamide (50 mg, 0.174 mmol) in dioxane (1 mL) was added 1-(4-(4-aminophenyl)piperazin-1-yl)propan-1-one (61 mg, 0.261 mmol), BINAP (22 mg, 0.035 mmol), Pd(OAc)$_2$ (8 mg, 0.035 mmol) and Cs$_2$CO$_3$ (170 mg, 0.52 mmol). After degassed with Argon, the mixture was heated at 80° C. for 15 h. The mixture was diluted with dioxane, precipitate was filtered off, filter cake was washed with AcCN, the filtrate was concentrated and purified by preparative HPLC to give of 4-(1-phenylcyclopropylamino)-6-(4-(4-propionylpiperazin-1-yl)phenylamino)nicotinamide (16 mg). MS found for C$_{28}$H$_{32}$N$_6$O$_2$ as (M+H)$^+$ 485.5. λ=258.2.

Example 125

6-(4-morpholinophenylamino)-4-(1-phenylcyclopropylamino)-nicotinamide

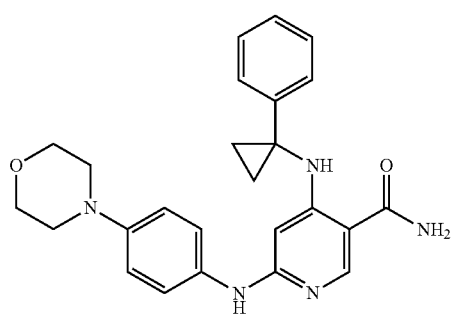 [SMILES: NC(=O)c1cnc(Nc2ccc(N3CCOCC3)cc2)cc1NC1(c2ccccc2)CC1]

The title compound was synthesized similar to Scheme 13 using 4-morpholinoaniline to replace 1-(4-(4-aminophenyl) piperazin-1-yl)propan-1-one. MS found for C$_{25}$H$_{27}$N$_5$O$_2$ as (M+H)$^+$ 430.5. λ=259.4.

Example 126

6-(4-(4-acetylpiperazin-1-yl)phenylamino)-4-(1-phenylcyclopropylamino)nicotinamide

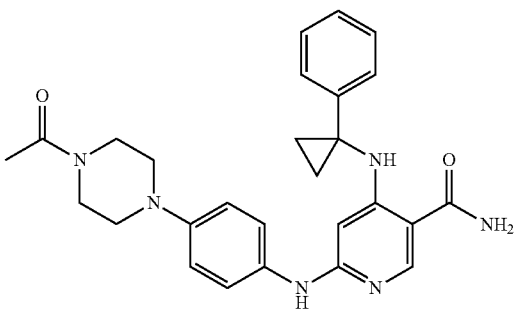 [SMILES: CC(=O)N1CCN(c2ccc(Nc3cc(NC4(c5ccccc5)CC4)c(C(N)=O)cn3)cc2)CC1]

The title compound was synthesized similar to Example 124 in Scheme 13 using 1-(4-(4-aminophenyl)piperazin-1-yl)ethanone to replace 1-(4-(4-aminophenyl)piperazin-1-yl) propan-1-one. MS found for C$_{27}$H$_{30}$N$_6$O$_2$ as (M+H)$^+$ 471.5. λ=258.2.

Example 127

6-(4-(morpholinomethyl)phenylamino)-4-(1-phenylcyclopropylamino)nicotinamide

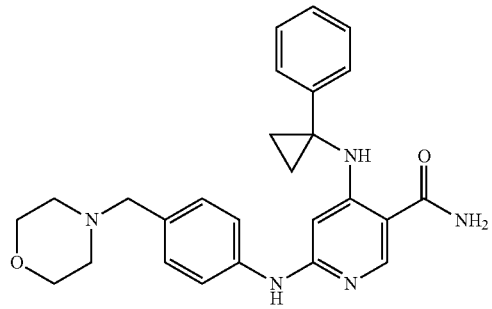 [SMILES: NC(=O)c1cnc(Nc2ccc(CN3CCOCC3)cc2)cc1NC1(c2ccccc2)CC1]

The title compound was synthesized similar to Example 124 in Scheme 13 using 4-(morpholinomethyl)aniline to replace 1-(4-(4-aminophenyl)piperazin-1-yl)propan-1-one. MS found for C$_{26}$H$_{29}$N$_5$O$_2$ as (M+H)$^+$ 444.5. λ=265.3.

Example 128

6-(3-morpholinophenylamino)-4-(1-phenylcyclopropylamino)-nicotinamide

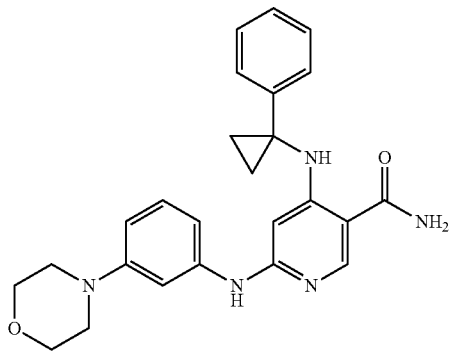 [SMILES: NC(=O)c1cnc(Nc2cccc(N3CCOCC3)c2)cc1NC1(c2ccccc2)CC1]

The title compound was synthesized similar to Example 124 in Scheme 13 using 3-morpholinoaniline to replace 1-(4-(4-aminophenyl)piperazin-1-yl)propan-1-one. MS found for $C_{25}H_{27}N_5O_2$ as $(M+H)^+$ 430.5. $\lambda=252.3$.

Example 129

6-(3-(morpholinomethyl)phenylamino)-4-(1-phenyl-cyclopropylamino)nicotinamide

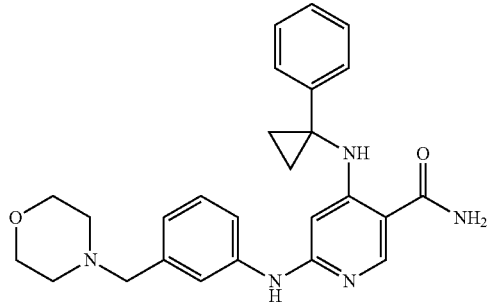 [SMILES: NC(=O)c1cnc(Nc2cccc(CN3CCOCC3)c2)cc1NC1(c2ccccc2)CC1]

The title compound was synthesized similar to Example 124 in Scheme 13 using 3-(morpholinomethyl)aniline to replace 1-(4-(4-aminophenyl)piperazin-1-yl)propan-1-one. MS found for $C_{26}H_{29}N_5O_2$ as $(M+H)^+$ 444.5. $\lambda=265.3$.

Example 130

6-(4-(4-acetylpiperazin-1-yl)phenylamino)-4-(1-(2-fluorophenyl)cyclopropylamino)nicotinamide

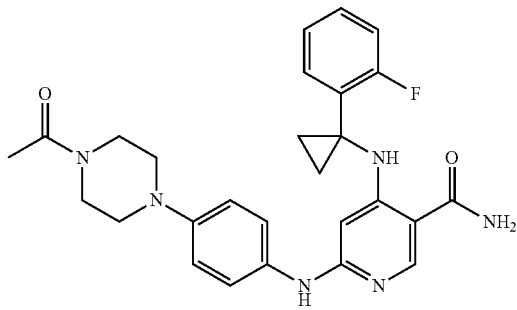 [SMILES: CC(=O)N1CCN(c2ccc(Nc3cc(NC4(c5ccccc5F)CC4)c(C(N)=O)cn3)cc2)CC1]

The title compound was synthesized similar to Example 124 in Scheme 13 using 2-fluorobenzonitrile to replace benzonitrile. MS found for $C_{27}H_{29}FN_6O_2$ as $(M+H)^+$ 489.5. $\lambda=261.7$.

Example 131

6-(4-(4,4-difluoropiperidin-1-yl)phenylamino)-4-(1-phenylcyclopropylamino)nicotinamide

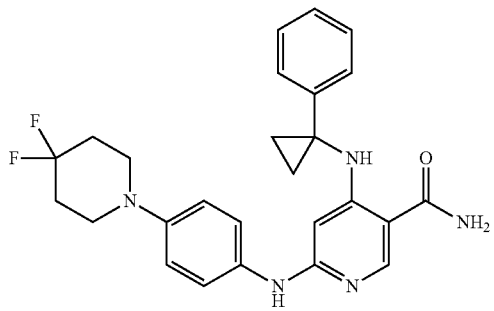 [SMILES: NC(=O)c1cnc(Nc2ccc(N3CCC(F)(F)CC3)cc2)cc1NC1(c2ccccc2)CC1]

The title compound was synthesized similar to Example 124 in Scheme 13 using 4-(4,4-difluoropiperidin-1-yl)aniline to replace 1-(4-(4-aminophen yl)piperazin-1-yl)propan-1-one. MS found for $C_{26}H_{27}F_2N_5O$ as $(M+H)^+$ 464.5. $\lambda=245.2$.

Example 132

4-(1-phenylcyclopropylamino)-6-(4-(2-(pyrrolidin-1-yl)ethoxy)phenylamino)nicotinamide

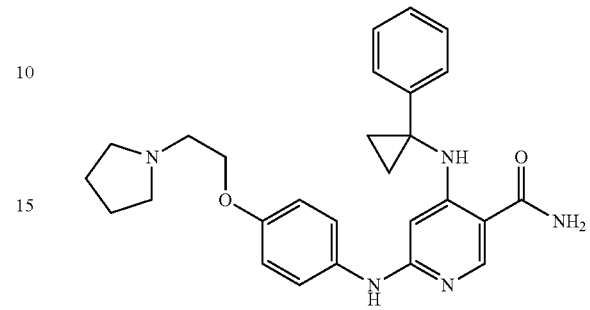

The title compound was synthesized similar to Example 124 in Scheme 13 using 4-(2-(pyrrolidin-1-yl)ethoxy)aniline to replace 1-(4-(4-aminophenyl)piperazin-1-yl)propan-1-one. MS found for $C_{27}H_{31}N_5O_2$ as $(M+H)^+$ 458.5, $\lambda=258.2$.

Example 133

6-(4-(2-morpholino-2-oxoethoxy)phenylamino)-4-(1-phenylcyclopropylamino)nicotinamide

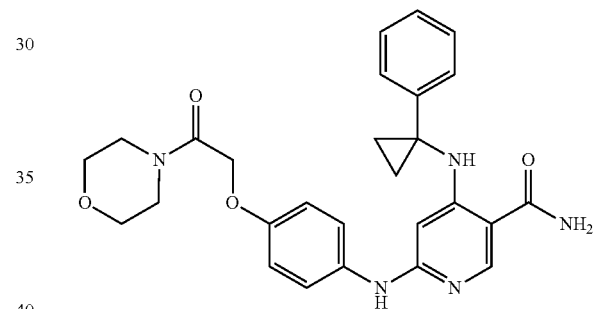

The title compound was synthesized similar to Example 124 in Scheme 13 using 4-(2-morpholino-2-oxoethoxy)aniline to replace 1-(4-(4-aminophenyl)piperazin-1-yl)propan-1-one. MS found for $C_{27}H_{29}N_5O_4$ as $(M+H)^+$ 488.6, $\lambda=258.2$.

Example 134

6-(3-(2-morpholino-2-oxoethoxy)phenylamino)-4-(1-phenylcyclopropylamino)nicotinamide

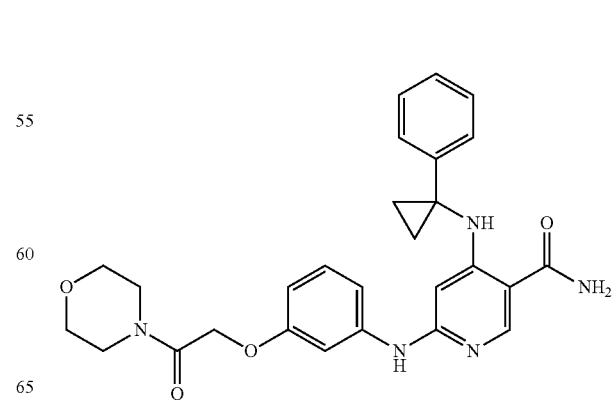

Example 135

6-(3-acetamidophenylamino)-4-(1-phenylcyclopropylamino)nicotinamide

The title compound was synthesized similar to Example 124 in Scheme 13 using 3-(2-morpholino-2-oxoethoxy) aniline to replace 1-(4-(4-aminophenyl)piperazin-1-yl)propan-1-one. MS found for $C_{27}H_{29}N_5O_4$ as $(M+H)^+$ 488.5, $\lambda=259.4$.

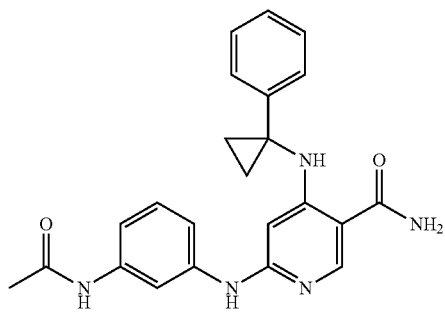 [SMILES: CC(=O)Nc1cccc(Nc2cc(NC3(c4ccccc4)CC3)c(C(N)=O)cn2)c1]

The title compound was synthesized similar to Example 124 in Scheme 13 using 3-acetaminoaniline to replace 1-(4-(4-aminophenyl)piperazin-1-yl)propan-1-one. MS found for $C_{23}H_{23}N_5O_2$ as $(M+H)^+$ 402.5, $\lambda=254.6$.

Example 136

6-(4-chloro-3-(1-methylpiperidine-4-carboxamido)phenylamino)-4-(1-phenylcyclopropylamino)nicotinamide

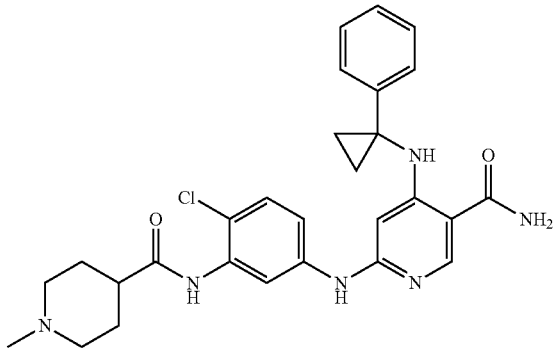 [SMILES: CN1CCC(C(=O)Nc2cc(Nc3cc(NC4(c5ccccc5)CC4)c(C(N)=O)cn3)ccc2Cl)CC1]

The title compound was synthesized similar to Example 124 in Scheme 13 using N-(5-amino-2-chlorophenyl)-1-methylpiperidine-4-carboxamide to replace 1-(4-(4-aminophenyl)piperazin-1-yl)propan-1-one. MS found for $C_{28}H_{31}ClN_6O_2$ as $(M+H)^+$ 519.5, 521.5, $\lambda=257.0$.

Example 139

Preparation of 6-(4-(tetrahydro-2H-pyran-4-yl)phenylamino)-4-(tetrahydro-2H-pyran-4-ylamino)nicotinamide

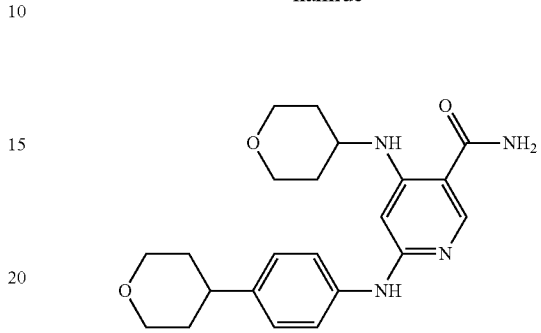

Scheme:

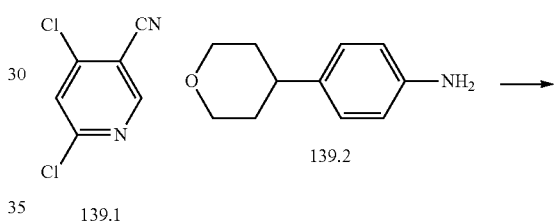

139.1    139.2

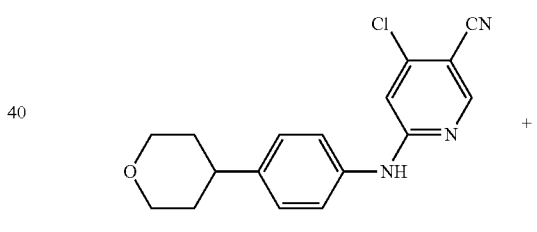

139.3

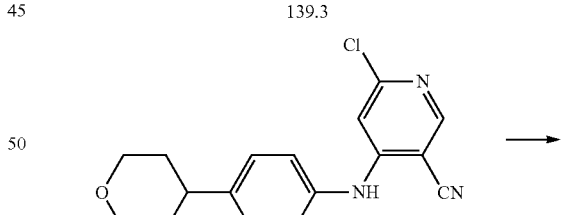

139.4

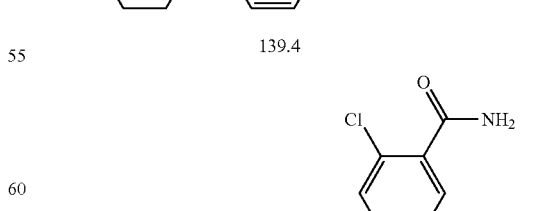

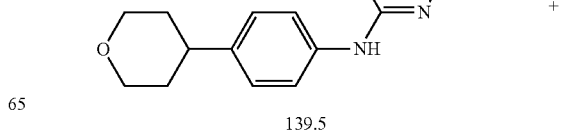

139.5

Example 140

Preparation of 4-((tetrahydro-2H-pyran-4-yl)methylamino)-6-(4-(tetrahydro-2H-pyran-4-yl)phenylamino)nicotinamide

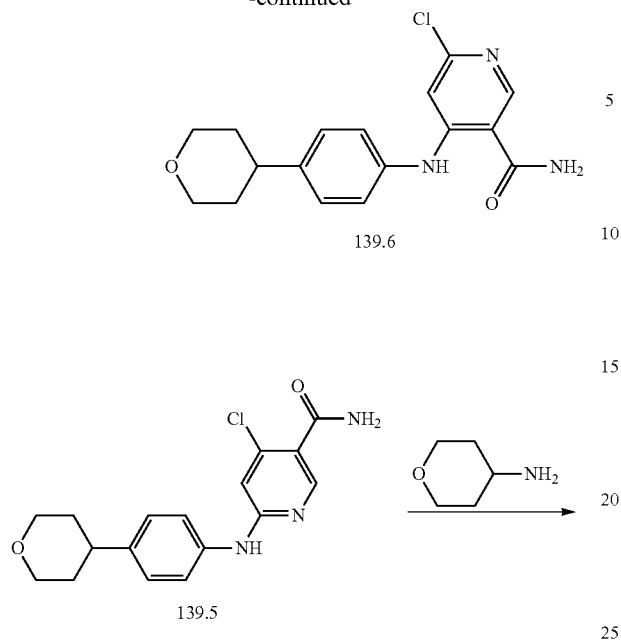
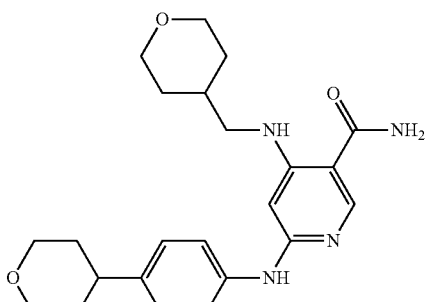

The title compound was synthesized using a procedure similar to that described in Example 139. MS found for C23H30N4O3 as (M+H)⁺ 411.3. UV: λ=259 nm. ¹H NMR: (CD3OD) δ 8.12 (1H, s), 7.39 (2H, dt, J=8.4; 2.0 Hz), 7.25 (2H, dt, 3=8.4; 2.0 Hz), 6.20 (1H, s), 4.60 (2H, s), 4.05 (2H, m), 3.73 (2H, m), 3.62-3.54 (3H, m), 3.04 (2H, m), 2.87 (1H, m), 1.95 (2H, m), 1.86-1.75 (6H, m) ppm.

Example 141

Preparation of 4-((1-hydroxycyclopentyl)methylamino)-6-(4-(tetrahydro-2H-pyran-4-yl)phenylamino)nicotinamide

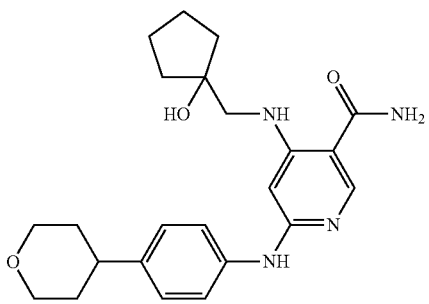 [SMILES: NC(=O)c1cnc(Nc2ccc(C3CCOCC3)cc2)cc1NCC1(O)CCCC1]

The mixture of 4,6-dichloronicotinonitrile (440 mg, 2.5 mmol), 4-(tetrahydro-2H-pyran-4-yl)aniline (530 mg, 3.0 mmol), DIEA (0.65 mL, 3.75 mmol) in 20 mL DMF was stirred at 90° C. for overnight to afford a mixture of compounds 139.3 (UV=316 nm) and 139.4 (UV=278 nm). The mixture was concentrated in vacuo and subjected to flash column (0-20% EtOAc in DCM) to isolate the 139.3/139.4 product (870 mg). This product mixture (500 mg, 1.6 mmol) was dissolved in 100 mL MeOH with 9 mL DMSO, and was stirred at RT. To it was added K₂CO₃ powder (440 mg, 3.2 mmol) and then H₂O₂ (50 wt %, 3 mL). The mixture was stirred at RT for 2 h. It was diluted with 200 mL EtOAc, filtered through celite and concentrated in vacuo. It was subjected to reverse phase prep HPLC to isolate product 139.5 (UV=278 nm) and product 139.6 (UV=287 nm). Compound 139.5 (50 mg, 0.15 mmol) was dissolved in 2 mL in a sealed tube. To it were added 4-aminotetrahydropyran (76 mg, 0.75 mmol) and DIEA (80 μL, 0.45 mmol). The mixture was stirred at 120° C. for 2 days. It was cooled to RT, treated with 0.2 ml TFA, and subjected to reverse phase prep HPLC to isolate the title compound (48 mg). MS found for C22H28N4O3 as (M+H)⁺ 397.3. UV: λ=258 nm. ¹H NMR: (CD3OD) δ 8.11 (1H, s), 7.38 (2H, dt, J=8.0; 1.6 Hz), 7.26 (2H, dt, J=8.0; 2.0 Hz), 6.03 (1H, s), 4.05 (2H, m), 3.93 (2H, m), 3.66 (1H, m), 3.61-3.51 (4H, m), 2.86 (1H, m), 1.98 (2H, m), 1.80 (4H, m), 1.61 (2H, m) ppm.

The title compound was synthesized using a procedure similar to that described in Example 139. MS found for C23H30N4O3 as (M+H)⁺ 411.3. UV: λ=258 nm. ¹H NMR: (CD3OD) δ 8.09 (1H, s), 7.39 (2H, d, J=8.0 Hz), 7.26 (2H, d, J=8.8 Hz), 6.01 (1H, s), 4.05 (2H, m), 3.57 (2H, m), 3.20 (2H, m), 2.86 (1H, m), 1.85-1.66 (12H, m) ppm.

Example 142

Preparation of 4-(2-fluorobenzylamino)-6-(4-(tetrahydro-2H-pyran-4-yl)phenylamino)nicotinamide

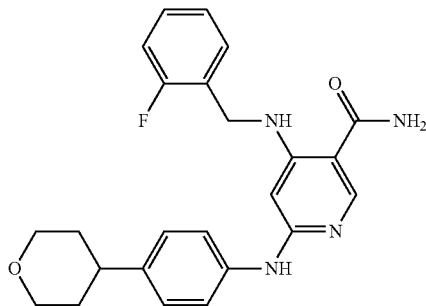 [SMILES: NC(=O)c1cnc(Nc2ccc(C3CCOCC3)cc2)cc1NCc1ccccc1F]

The title compound was synthesized using a procedure similar to that described in Example 139. MS found for C24H25FN4O2 as (M+H)$^+$ 421.3. UV: λ=259 nm. $^1$H NMR: (CD3OD) δ 8.03 (1H, s), 7.28-7.17 (4H, m), 7.09 (1H, dd, J=7.6; 1.2 Hz), 7.08-7.00 (3H, m), 5.78 (1H, s), 4.42 (2H, s), 3.96 (2H, m), 3.49 (2H, m), 2.78 (1H, m), 1.70 (4H, m) ppm.

Example 143

Preparation of 4-(3-fluorobenzylamino)-6-(4-(tetrahydro-2H-pyran-4-yl)phenylamino)nicotinamide

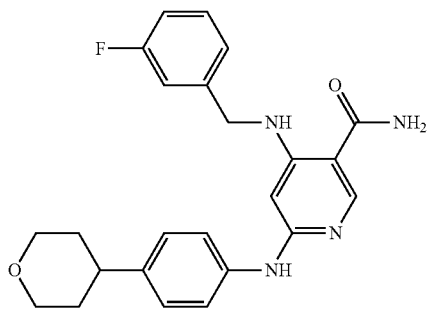 [SMILES: NC(=O)c1cnc(Nc2ccc(C3CCOCC3)cc2)cc1NCc1cccc(F)c1]

The title compound was synthesized using a procedure similar to that described in Example 139. MS found for C24H25FN4O2 as (M+H)$^+$ 421.3. UV: λ=259 nm. $^1$H NMR: (CD3OD) δ 8.14 (1H, s), 7.38 (1H, m), 7.28 (2H, dt, J=7.6; 2.0 Hz), 7.10-6.99 (5H, m), 5.81 (1H, s), 4.48 (2H, s), 4.05 (2H, m), 3.56 (2H, m), 2.84 (1H, m), 1.78 (4H, m) ppm.

Example 144

Preparation of 6-(4-(1-propionylpiperidin-4-yl)phenylamino)-4-((tetrahydro-2H-pyran-4-yl)methylamino)nicotinamide

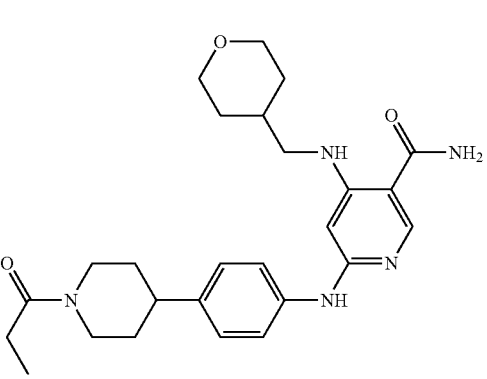 [SMILES: CCC(=O)N1CCC(c2ccc(Nc3cc(NCC4CCOCC4)c(C(N)=O)cn3)cc2)CC1]

The title compound was synthesized using a procedure similar to that described in Example 139. MS found for C26H35N5O3 as (M+H)$^+$ 466.3. UV: λ=258 nm. $^1$H NMR: (CD3OD) δ 8.12 (1H, s), 7.39 (2H, dt, J=8.4; 2.0 Hz), 7.27 (2H, dt, J=8.4; 2.0 Hz), 5.98 (1H, s), 4.70 (1H, m), 4.10 (1H, m), 3.96 (2H, m), 3.42 (2H, td, J=11.6; 2.0 Hz), 3.22 (1H, td, J=12.8; 2.4 Hz)), 3.13 (2H, d, J=7.2 Hz), 2.89 (1H, tt, J=12.0; 3.6 Hz), 2.73 (1H, td, J=12.8; 2.8 Hz), 2.46 (2H, q, J=8.0 Hz), 1.92 (3H, m), 1.69-1.57 (4H, m), 1.36 (2H, m), 1.14 (3H, t, J=7.6 Hz) ppm.

Example 145

Preparation of 4-(3-fluorobenzylamino)-6-(4-(1-propionylpiperidin-4-yl)phenylamino)nicotinamide

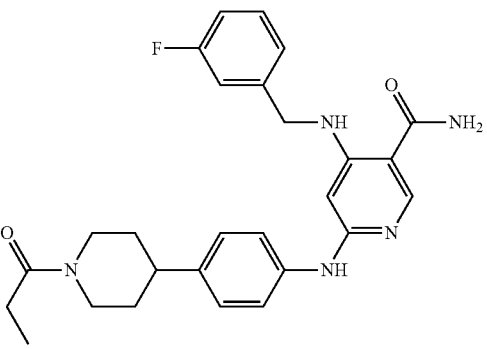 [SMILES: CCC(=O)N1CCC(c2ccc(Nc3cc(NCc4cccc(F)c4)c(C(N)=O)cn3)cc2)CC1]

The title compound was synthesized using a procedure similar to that described in Example 144. MS found for C27H30FN5O2 as (M+H)$^+$ 476.3. UV: λ=258 nm. $^1$H NMR: (CD3OD) δ 8.14 (1H, s), 7.38 (1H, m), 7.28 (2H, dt, J=6.8; 2.0 Hz), 7.09-6.98 (5H, m), 5.80 (1H, s), 4.70 (1H, m), 4.48 (2H, s), 4.10 (1H, m), 3.22 (1H, m), 2.87 (1H, tt, J=12.4; 3.6

Hz), 2.73 (1H, td, J=12.4; 2.0 Hz), 2.46 (2H, q, J=7.6 Hz), 1.92 (2H, m), 1.63 (2H, m), 1.15 (3H, t, J=7.6 Hz) ppm.

Example 146

Preparation of 6-(4-(1-propionylpiperidin-4-yl)phenylamino)-4-(tetrahydro-2H-pyran-4-ylamino)nicotinamide

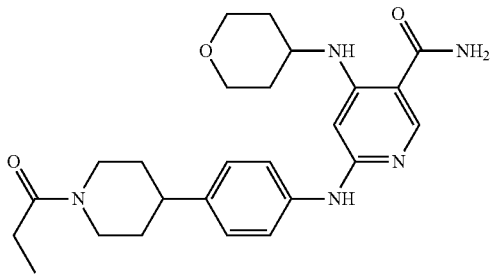 [SMILES: CCC(=O)N1CCC(c2ccc(Nc3cc(NC4CCOCC4)c(C(N)=O)cn3)cc2)CC1]

The title compound was synthesized using a procedure similar to that described in Example 144. MS found for C25H33N5O3 as (M+H)+ 452.4. UV: λ=259 nm. $^1$H NMR: (CD3OD) δ 8.12 (1H, s), 7.39 (2H, dt, J=8.4; 2.0 Hz), 7.26 (2H, dt, J=8.4; 2.0 Hz), 6.04 (1H, s), 4.70 (1H, m), 4.10 (1H, m), 3.93 (2H, m), 3.67 (1H, m), 3.54 (2H, m), 3.22 (1H, m), 2.89 (1H, m), 2.73 (1H, m), 2.46 (2H, q, J=7.6 Hz), 2.00-1.87 (4H, m), 1.70-1.56 (4H, m), 1.14 (3H, t, J=7.6 Hz) ppm.

Example 147

Preparation of 4-(cyclopentylamino)-6-(4-(1-propionylpiperidin-4-yl)phenylamino)nicotinamide

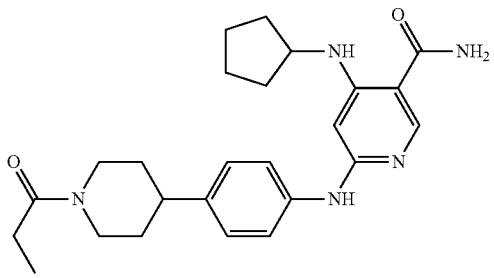 [SMILES: CCC(=O)N1CCC(c2ccc(Nc3cc(NC4CCCC4)c(C(N)=O)cn3)cc2)CC1]

The title compound was synthesized using a procedure similar to that described in Example 144. MS found for C25H33N5O2 as (M+H)+ 436.4. UV: λ=259 nm. $^1$H NMR: (CD3OD) δ 8.09 (1H, s), 7.39 (2H, dt, J=8.0; 2.0 Hz), 7.26 (2H, dt, J=8.4; 2.0 Hz), 5.98 (1H, s), 4.70 (1H, m), 4.10 (1H, m), 3.83 (1H, m), 3.22 (1H, m), 2.89 (1H, m), 2.73 (1H, m), 2.46 (2H, q, J=7.6 Hz), 2.02 (2H, m), 1.92 (2H, m), 1.79-1.57 (8H, m), 1.14 (3H, t, J=7.6 Hz) ppm.

Example 148

Preparation of 4-(3,4-difluorobenzylamino)-6-(4-(1-propionylpiperidin-4-yl)phenylamino)nicotinamide

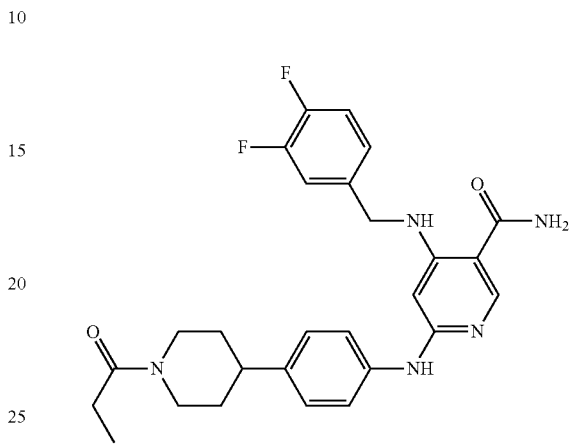

The title compound was synthesized using a procedure similar to that described in Example 114. MS found for C27H29F2N5O2 as (M+H)+ 494.3. UV: λ=259 nm. $^1$H NMR: (CD3OD) δ 8.14 (1H, s), 7.28 (2H, dt, J=8.8; 2.0 Hz), 7.26 (1H, m), 7.18 (1H, m), 7.10-7.07 (3H, m), 5.78 (1H, s), 4.70 (1H, m), 4.44 (2H, s), 4.10 (1H, m), 3.23 (1H, m), 2.87 (1H, m), 2.73 (1H, m), 2.46 (2H, q, J=8.0 Hz), 1.92 (2H, m), 1.62 (2H, m), 1.15 (3H, 7.6 Hz) ppm.

Example 149

Preparation of 4-(2,5-difluorobenzylamino)-6-(4-(1-propionylpiperidin-4-yl)phenylamino)nicotinamide

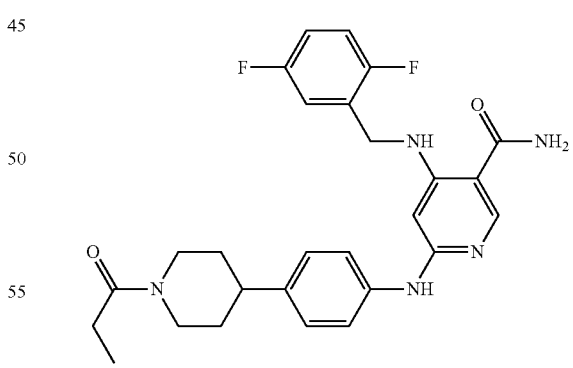

The title compound was synthesized using a procedure similar to that described in Example 114. MS found for C27H29F2N5O2 as (M+H)+ 494.3. UV: λ=259 nm. $^1$H NMR: (CD3OD) δ 8.05 (1H, s), 7.23 (2 h, td, J=8.8; 2.0 Hz), 7.08-6.97 (4H, m), 6.93 (1H, m), 5.74 (1H, s), 4.61 (1H, m), 4.41 (2H, s), 4.01 (1H, m), 3.13 (1H, m), 2.79 (1H, m), 2.64 (1H, m), 2.37 (2H, q, J=7.6 Hz), 1.83 (2H, m), 1.54 (2H, m), 1.06 (3H, t, J=7.6 Hz) ppm.

Example 150

Preparation of 4-(cyclopentylamino)-6-(4-(tetrahydro-2H-pyran-4-yl)phenylamino)nicotinamide

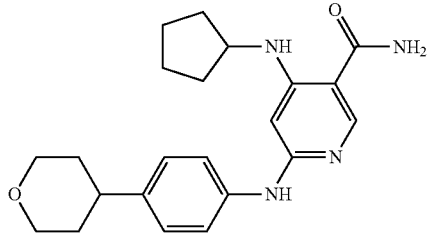 [SMILES: NC(=O)c1cnc(Nc2ccc(C3CCOCC3)cc2)cc1NC1CCCC1]

The title compound was synthesized using a procedure similar to that described in Example 139. MS found for C22H28N4O2 as (M+H)⁺ 381.3. UV: λ=259 nm. ¹H NMR: (CD3OD) δ 8.12 (1H, s), 7.34 (2H, dt, J=8.8; 2.0 Hz), 7.27 (2H, dt, J=8.4; 2.0 Hz), 5.97 (1H, s), 4.04 (2H, m), 3.80 (1H, m), 3.58 (2H, m), 2.84 (1H, m), 2.02 (2H, m), 1.82-1.57 (10H, m) ppm.

Example 151

Preparation of 6-(3-(tetrahydro-2H-pyran-4-yl)phenylamino)-4-(tetrahydro-2H-pyran-4-ylamino)nicotinamide

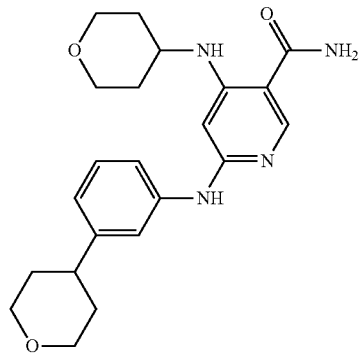 [SMILES: NC(=O)c1cnc(Nc2cccc(C3CCOCC3)c2)cc1NC1CCOCC1]

The title compound was synthesized using a procedure similar to that described in Example 139. MS found for C22H28N4O3 as (M+H)⁺ 397.3. UV: λ=259 nm. ¹H NMR: (CD3OD) δ 8.15 (1H, s), 7.42 (1H, m), 7.26-7.16 (3H, m), 6.07 (1H, s), 4.04 (2H, m), 3.94 (2H, m), 3.65-3.50 (5H, m), 2.85 (1H, m), 1.97 (2H, m), 1.79 (4H, m), 1.60 (2H, m) ppm.

Example 152

Preparation of 4-(2-fluorobenzylamino)-6-(3-(tetrahydro-2H-pyran-4-yl)phenylamino)nicotinamide

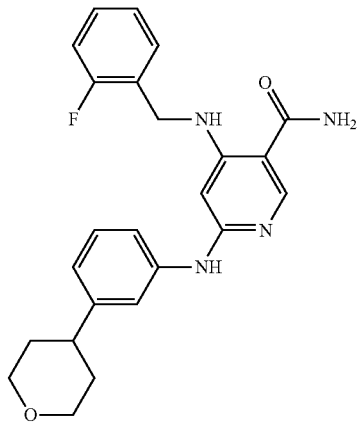 [SMILES: NC(=O)c1cnc(Nc2cccc(C3CCOCC3)c2)cc1NCc1ccccc1F]

The title compound was synthesized using a procedure similar to that described in Example 139. MS found for C24H25FN4O2 as (M+H)⁺ 421.3. UV: λ=259 nm. ¹H NMR: (CD3OD) δ 8.15 (1H, s), 7.38 (1H, t, J=8.0 Hz), 7.33 (1H, m), 7.28 (1H, dd, J=8.0; 2.0 Hz), 7.23 (1H, d, J=7.6 Hz), 7.17 (1H, dd, J=8.0; 1.2 Hz), 7.14-7.09 (2H, m), 7.02 (1H, m), 5.94 (1H, s), 4.52 (2H, s), 4.04 (2H, m), 3.55 (2H, m), 2.82 (1H, m), 1.76 (4H, m) ppm.

Example 153

Preparation of 4-(cyclopropylmethylamino)-6-(4-(tetrahydro-2H-pyran-4-yl)phenylamino)nicotinamide

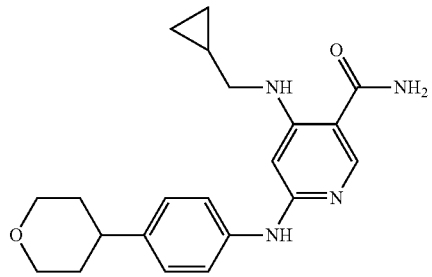 [SMILES: NC(=O)c1cnc(Nc2ccc(C3CCOCC3)cc2)cc1NCC1CC1]

The title compound was synthesized using a procedure similar to that described in Example 139. MS found for C21H26N4O2 as (M+H)⁺ 367.3. UV: λ=259 nm. ¹H NMR: (CD3OD) δ 7.82 (1H, s), 7.12 (2H, dt, J=8.4; 2.0 Hz), 6.99 (2H, dt, J=8.8; 2.0 Hz), 5.67 (1H, s), 3.77 (2H, m), 3.30 (2H, m), 2.80 (2H, d, J=7.2 Hz), 2.59 (1H, m), 1.52 (4H, m), 0.85 (1H, m), 0.34 (2H, m), 0.02 (2H, m) ppm.

Example 154

Preparation of 4-(cyclopentylmethylamino)-6-(4-(tetrahydro-2H-pyran-4-yl)phenylamino)nicotinamide

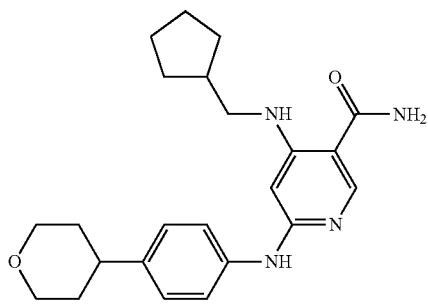 [SMILES: NC(=O)c1cnc(Nc2ccc(C3CCOCC3)cc2)cc1NCC1CCCC1]

The title compound was synthesized using a procedure similar to that described in Example 139. MS found for C23H30N4O2 as (M+H)⁺ 395.4. UV: λ=259 nm. ¹H NMR: (CD3OD) δ 8.09 (1H, s), 7.39 (2H, dt, J=8.0; 1.6 Hz), 7.26 (2H, dt, J=8.4; 2.0 Hz), 5.95 (1H, s), 4.05 (2H, m), 3.57 (2H, m), 3.13 (2H, d, J=7.2 Hz), 2.86 (1H, m), 2.22 (1H, m), 1.87-1.77 (6H, m), 1.71-1.59 (4H, m), 1.28 (2H, m) ppm.

Example 155

Preparation of 4-(neopentylamino)-6-(4-(tetrahydro-2H-pyran-4-yl)phenylamino)nicotinamide

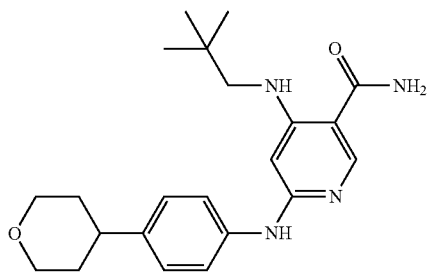 [SMILES: CC(C)(C)CNc1cc(Nc2ccc(C3CCOCC3)cc2)ncc1C(N)=O]

The title compound was synthesized using a procedure similar to that described in Example 139. MS found for C22H30N4O2 as (M+H)⁺ 383.3. UV: λ=259 nm. ¹H NMR: (CD3OD) δ 8.11 (1H, s), 7.38 (2H, dt, J=8.0; 1.6 Hz), 7.26 (2H, dt, J=8.8; 2.0 Hz), 5.97 (1H, s), 4.05 (2H, m), 3.57 (2H, m), 2.99 (2H, s), 2.86 (1H, m), 1.79 (4H, m), 1.02 (9H, s) ppm.

Example 156

Preparation of 4-(isobutylamino)-6-(4-(tetrahydro-2H-pyran-4-yl)phenylamino)nicotinamide

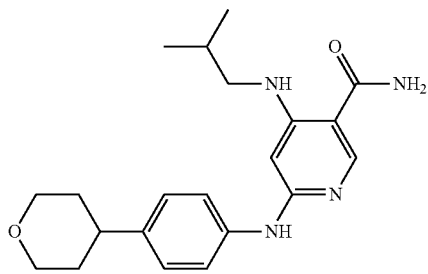 [SMILES: CC(C)CNc1cc(Nc2ccc(C3CCOCC3)cc2)ncc1C(N)=O]

The title compound was synthesized using a procedure similar to that described in Example 139. MS found for C21H28N4O2 as (M+H)⁺ 369.4. UV: λ=259 nm. ¹H NMR: (CD3OD) δ 8.10 (1H, s), 7.39 (2H, d, J=8.4 Hz), 7.26 (2H, d, J=8.0 Hz), 5.94 (1H, s), 4.05 (2H, m), 3.57 (2H, m), 3.03 (2H, d, J=6.4 Hz), 2.86 (1H, m), 1.95 (1H, m), 1.79 (4H, m), 1.00 (6H, d, J=6.8 Hz) ppm.

Example 157

Preparation of 4-(cyclohexylamino)-6-(4-(tetrahydro-2H-pyran-4-yl)phenylamino)nicotinamide

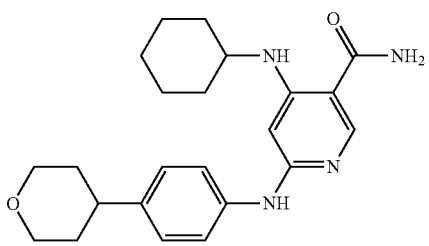 [SMILES: NC(=O)c1cnc(Nc2ccc(C3CCOCC3)cc2)cc1NC1CCCCC1]

The title compound was synthesized using a procedure similar to that described in Example 139. MS found for C23H30N4O2 as (M+H)⁺ 395.4. UV: λ=259 nm. ¹H NMR: (CD3OD) δ 8.09 (1H, s), 7.37 (2H, dt, J=8.8; 2.0 Hz), 7.26 (2H, dt, J=8.8; 2.0 Hz), 5.96 (1H, s), 4.05 (2H, m), 3.57 (2H, m), 3.36 (1H, m), 2.86 (1H, m), 1.96 (2H, m), 1.79 (6H, m), 1.62 (1H, m), 1.39 (5H, m) ppm.

Example 158

Preparation of 4-(2-fluorobenzylamino)-6-(4-isopropylphenylamino)nicotinamide

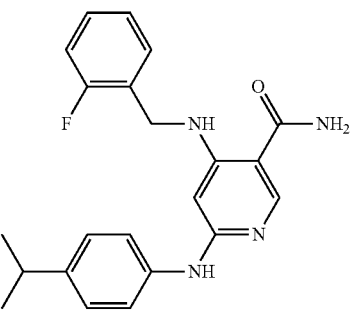 [SMILES: CC(C)c1ccc(Nc2cc(NCc3ccccc3F)c(C(N)=O)cn2)cc1]

The title compound was synthesized using a procedure similar to that described in Example 36, using 4-isopropylaniline. MS found for C22H23FN4O as (M+H)⁺ 379.3. UV: λ=259 nm. ¹H NMR: (CD3OD) δ 8.12 (1H, s), 7.35 (1H, m), 7.31 (2H, dt, J=8.0; 1.6 Hz), 7.27 (1H, m), 7.17 (1H, m), 7.13

(1H, m), 7.09 (2H, dt, J=8.8; 2.0 Hz), 5.86 (1H, s), 4.51 (2H, s), 2.96 (1H, m), 1.28 (6H, d, J=6.8 Hz) ppm.

Example 159

Preparation of 4-((1-(methylsulfonyl)piperidin-4-yl)methylamino)-6-(4-(tetrahydro-2H-pyran-4-yl)phenylamino)nicotinamide

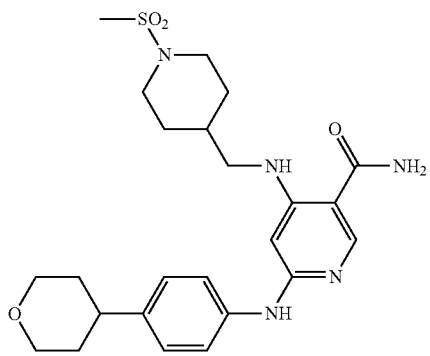

Scheme:

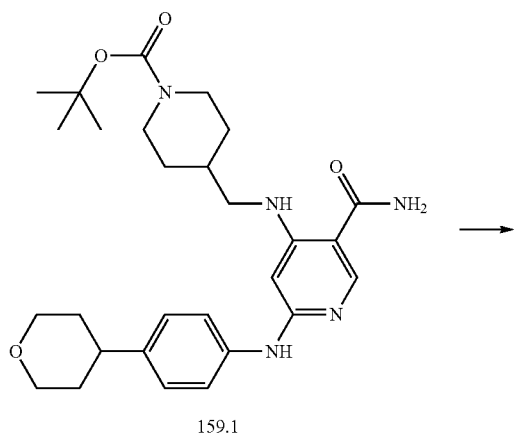

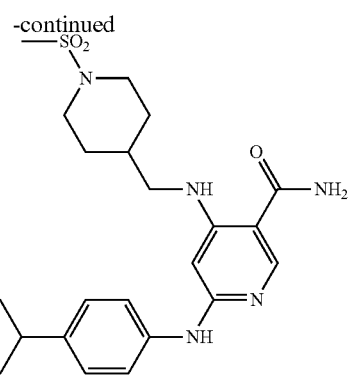

Compound 159.1 (tert-butyl 4-((5-carbamoyl-2-(4-(tetrahydro-2H-pyran-4-yl)phenylamino)pyridin-4-ylamino)methyl)piperidine-1-carboxylate) was synthesized using a procedure similar to that described in Example 139. It was treated with 1:1 DCM/TFA at RT for 90 min to afford compound 159B (4-(piperidin-4-ylmethylamino)-6-(4-(tetrahydro-2H-pyran-4-yl)phenylamino)nicotinamide). The reaction mixture was concentrated and subjected to reverse phase prep HPLC to isolate compound 159.2. Compound 159.2 (62 mg, 0.15 mmol) was dissolved in 3 mL NMP. To it were added DIEA (80 µL, 0.45 mmol) and then MeSO$_2$Cl (24 µL, 0.30 mmol). The mixture was stirred at RT for 25 m and treated with dimethylamine. The mixture was acidified with TFA and subjected to reverse phase prep HPLC to isolate the title compound (44 mg). MS found for C24H33N5O4S as (M+H)$^+$ 488.4. UV: λ=259 nm. $^1$H NMR: (CD3OD) δ 8.10 (1H, s), 7.39 (2H, dt, J=8.0; 2.0 Hz), 7.27 (2H, dt, J=8.4; 2.0 Hz), 5.97 (1H, s), 4.05 (2H, m), 3.76 (2H, m), 3.57 (2H, m), 3.17 (2H, d, J=6.4 Hz), 2.87 (1H, m), 2.82 (3H, s), 2.74 (2H, m), 1.87-1.77 (7H, m), 1.36 (2H, m) ppm.

Example 160

Preparation of 4-((1-(ethylsulfonyl)piperidin-4-yl)methylamino)-6-(4-(tetrahydro-2H-pyran-4-yl)phenylamino)nicotinamide

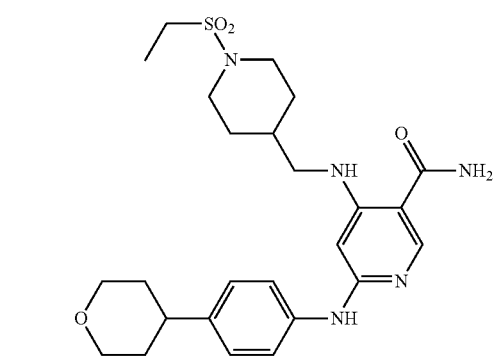

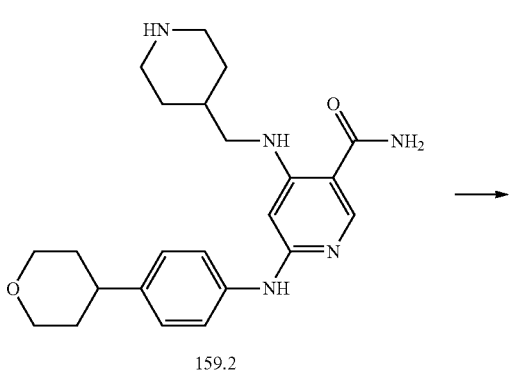

The title compound was synthesized using a procedure similar to that described in Example 159. MS found for C25H35N5O4S as (M+H)$^+$ 502.4. UV: λ=259 nm. $^1$H NMR: (CD3OD) δ 8.10 (1H, s), 7.39 (2H, dt, J=8.0; 2.0 Hz), 7.27 (2H, dt, J=8.4; 2.0 Hz), 5.96 (1H, s), 4.05 (2H, m), 3.78 (2H, m), 3.57 (2H, m), 3.15 (2H, d, J=6.0 Hz), 3.02 (2H, q, J=7.2 Hz), 2.88-2.81 (3H, m), 1.85-1.77 (7H, m), 1.35 (2H, m), 1.31 (3H, t, J=6.8 Hz) ppm.

Example 161

Preparation of 4-((1-(ethylsulfonyl)piperidin-4-yl)methylamino)-6-(4-(tetrahydro-2H-pyran-4-yl)phenylamino)nicotinamide

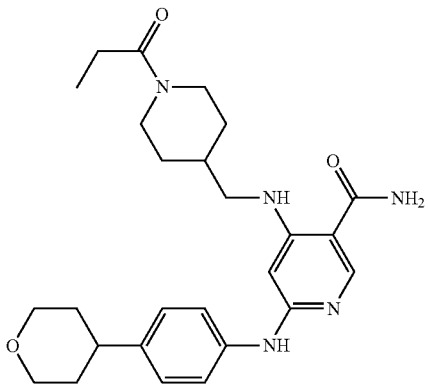 [SMILES: CCC(=O)N1CCC(CNc2cc(Nc3ccc(C4CCOCC4)cc3)ncc2C(N)=O)CC1]

The title compound was synthesized using a procedure similar to that described in Example 159. MS found for C26H35N5O3 as (M+H)⁺ 466.4. UV: λ=259 nm. ¹H NMR: (CD3OD) δ 8.10 (1H, s), 7.39 (2H, dt, J=8.0; 2.0 Hz), 7.27 (2H, dt, J=8.0; 2.0 Hz), 5.96 (1H, s), 4.57 (1H, m), 4.05 (2H, m), 4.00 (1H, m), 3.57 (2H, m), 3.14 (2H, d, J=6.8 Hz), 3.08 (1H, m), 2.86 (1H, m), 2.62 (1H, m), 2.41 (2H, q, J=7.6 Hz), 1.95 (1H, m), 1.85-1.77 (6H, m), 1.19 (2H, m), 1.11 (3H, t, J=7.6 Hz) ppm.

Example 162

Preparation of 4-(2-fluorobenzylamino)-6-(3-isopropylphenylamino)nicotinamide

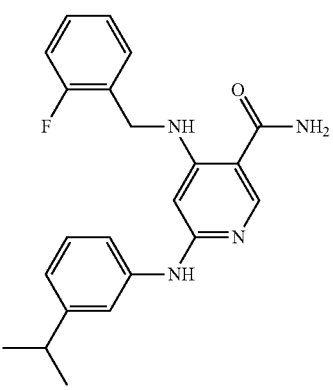 [SMILES: CC(C)c1cccc(Nc2cc(NCc3ccccc3F)c(C(N)=O)cn2)c1]

The title compound was synthesized using a procedure similar to that described in Example 3. MS found for C22H23FN4O as (M+H)⁺ 379.3. UV: λ=259 nm. ¹H NMR: (CD3OD) δ 8.15 (1H, m), 7.37-7.31 (2H, m), 7.28 (1H, m), 7.20 (1H, m), 7.17 (1H, dd, J=7.6; 1.2 Hz), 7.14-7.09 (2H, m), 6.98 (1H, m), 5.94 (1H, s), 4.51 (2H, s), 2.90 (1H, m), 1.25 (6H, d, J=7.2 Hz) ppm.

Example 163

Preparation of 4-(1-(dimethylcarbamoyl)piperidin-4-ylamino)-6-(4-(tetrahydro-2H-pyran-4-yl)phenylamino)nicotinamide

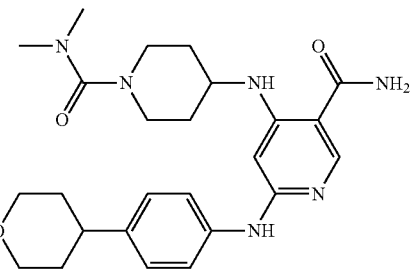

Scheme:

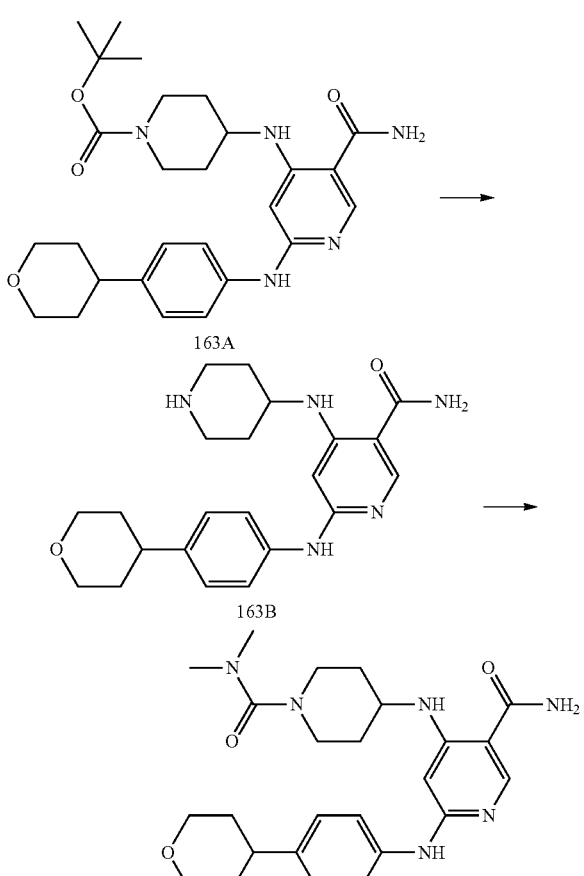

Compound 163A (tert-butyl 4-(5-carbamoyl-2-(4-(tetrahydro-2H-pyran-4-yl)phenylamino)pyridin-4-ylamino)piperidine-1-carboxylate) was synthesized using a procedure similar to that described in Example 139. It was treated with 1:1 DCM/TFA at RT for 30 m. The mixture was concentrated in vacuo and subjected to reverse phase prep HPLC to isolate compound 163B (4-(piperidin-4-ylamino)-6-(4-(tetrahydro-2H-pyran-4-yl)phenylamino)nicotinamide). Compound 163B (45 mg, 0.11 mmol) was dissolved in 3 mL NMP. To it were added DIEA (80 μL, 0.44 mmol) and then carbamyl chloride (21 μL, 0.22 mmol). The mixture was stirred at RT for 30 m and treated with dimethylamine. The mixture was acidified with TFA and subjected to reverse phase prep HPLC to isolate the title compound (31 mg). MS found for C25H34N6O3 as (M+H)+ 467.4. UV: λ=259 nm. $^1$H NMR: (CD3OD) δ 8.13 (1H, s), 7.36 (2H, dt, J=8.0; 2.0 Hz), 7.28 (2H, dt, J=8.4; 2.0 Hz), 6.02 (1H, s), 4.05 (2H, m), 3.60-3.54 (5H, m), 3.00 (2H, m), 2.85 (6H, s), 2.84 (1H, m), 2.01 (2H, m), 1.79 (4H, m), 1.57 (2H, m) ppm.

Example 164

Preparation of 4-(1-propionylpiperidin-4-ylamino)-6-(4-(tetrahydro-2H-pyran-4-yl)phenylamino)nicotinamide

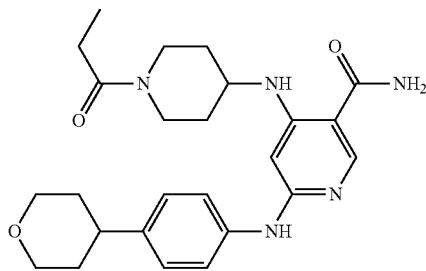 [SMILES: CCC(=O)N1CCC(Nc2cc(Nc3ccc(C4CCOCC4)cc3)ncc2C(N)=O)CC1]

The title compound was synthesized using a procedure similar to that described in Example 163. MS found for C25H33N5O3 as (M+H)+ 452.4. UV: λ=259 nm. $^1$H NMR: (CD3OD) δ 8.13 (1H, s), 7.37 (2H, dt, J=8.4; 2.0 Hz), 7.27 (2H, dt, J=8.4; 2.0 Hz), 6.04 (1H, s), 4.23 (1H, m), 4.04 (2H, m), 3.89 (1H, m), 3.69 (1H, m), 3.57 (2H, m), 3.06 (2H, m), 2.85 (1H, m), 2.43 (2H, q, J=7.2 Hz), 2.04 (2H, m), 1.82-1.76 (5H, m), 1.53 (1H, m), 1.12 (3H, q, J=7.6 Hz) ppm.

Example 165

Preparation of 4-(1-(methylsulfonyl)piperidin-4-ylamino)-6-(4-(tetrahydro-2H-pyran-4-yl)phenylamino)nicotinamide

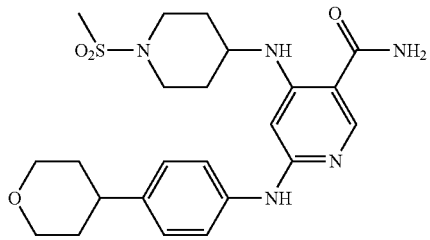 [SMILES: CS(=O)(=O)N1CCC(Nc2cc(Nc3ccc(C4CCOCC4)cc3)ncc2C(N)=O)CC1]

The title compound was synthesized using a procedure similar to that described in Example 163. MS found for C23H31N5O4S as (M+H)+ 474.3. UV: λ=259 nm. $^1$H NMR: (CD3OD) δ 8.12 (1H, s), 7.39 (2H, d, J=8.0 Hz), 7.27 (2H, d, J=8.0 Hz), 6.03 (1H, s), 4.05 (2H, m), 3.61-3.57 (5H, m), 3.06 (2H, m), 2.86 (s, 3H), 2.85 (1H, m), 2.10 (2H, m), 1.80-1.68 (6H, m) Ppm.

Example 166

Preparation of 4-(1-(ethylsulfonyl)piperidin-4-ylamino)-6-(4-(tetrahydro-2H-pyran-4-yl)phenylamino)nicotinamide

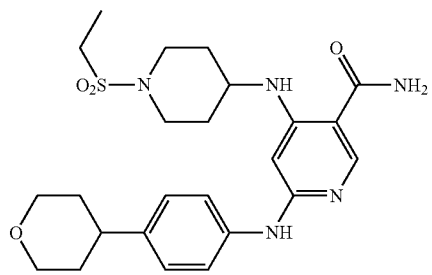 [SMILES: CCS(=O)(=O)N1CCC(Nc2cc(Nc3ccc(C4CCOCC4)cc3)ncc2C(N)=O)CC1]

The title compound was synthesized using a procedure similar to that described in Example 163. MS found for C24H33N5O4S as (M+H)+ 488.3. UV: λ=259 nm. $^1$H NMR: (CD3OD) δ 8.13 (1H, s), 7.38 (2H, dt, J=8.4; 2.0 Hz), 7.27 (2H, dt, J=8.4; 2.0 Hz), 6.02 (1H, s), 4.05 (2H, m), 3.66-3.57 (5H, m), 3.13 (2H, m), 3.06 (2H, q, J=7.2 Hz), 2.85 (1H, m), 2.08 (2H, m), 1.79 (4H, m), 1.65 (2H, m), 1.32 (3H, t, J=7.6 Hz) ppm.

Example 167

Preparation of (S)-4-(3,3-dimethylbutan-2-ylamino)-6-(4-(tetrahydro-2H-pyran-4-yl)phenylamino)nicotinamide

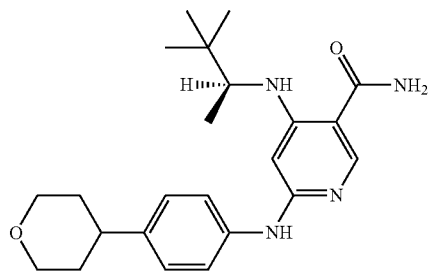 [SMILES: C[C@H](Nc1cc(Nc2ccc(C3CCOCC3)cc2)ncc1C(N)=O)C(C)(C)C]

The title compound was synthesized using a procedure similar to that described in Example 139. MS found for C23H32N4O2 as (M+H)+ 397.4. UV: λ=259 nm. $^1$H NMR: (CD3OD) δ 8.11 (1H, s), 7.39 (2H, dt, J=8.0; 1.6 Hz), 7.25 (2H, dt, J=8.8; 2.0 Hz), 6.00 (1H, s), 4.05 (2H, m), 3.57 (2H, m), 3.33 (1H, q, J=6.8 Hz), 2.86 (1H, m), 1.79 (4H, m), 1.15 (3H, d, J=6.4 Hz), 0.98 (9H, s) ppm.

Example 168

Preparation of (R)-4-(3,3-dimethylbutan-2-ylamino)-6-(4-(tetrahydro-2H-pyran-4-yl)phenylamino)nicotinamide

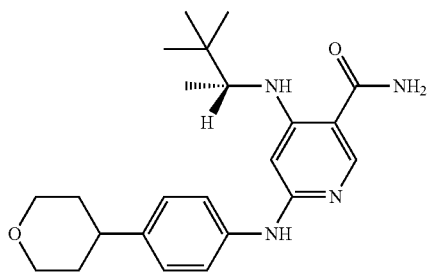 [SMILES: C[C@@H](Nc1cc(Nc2ccc(C3CCOCC3)cc2)ncc1C(N)=O)C(C)(C)C]

The title compound was synthesized using a procedure similar to that described in Example 139. MS found for C23H32N4O2 as (M+H)⁺ 397.3. UV: λ=259 nm. ¹H NMR: (CD3OD) δ 8.10 (1H, s), 7.39 (2H, dt, J=8.0; 2.0 Hz), 7.25 (2H, dt, J=8.8; 2.0 Hz), 6.01 (1H, s), 4.05 (2H, m), 3.57 (2H, m), 3.33 (1H, q, J=6.4 Hz), 2.87 (1H, m), 1.79 (4H, m), 1.16 (3H, d, J=6.8 Hz), 0.99 (9H, s) ppm.

Example 171

Preparation of 4-(3-(dimethylamino)-2,2-dimethylpropylamino)-6-(4-(tetrahydro-2H-pyran-4-yl)phenylamino)nicotinamide

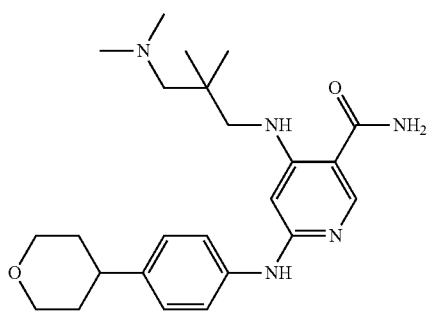 [SMILES: CN(C)CC(C)(C)CNc1cc(Nc2ccc(C3CCOCC3)cc2)ncc1C(N)=O]

The title compound was synthesized using a procedure similar to that described in Example 139. MS found for C24H35N5O2 as (M+H)⁺ 426.4. UV: λ=259 nm. ¹H NMR: (CD3OD) δ 8.17 (1H, s), 7.40 (2H, dt, J=8.0; 1.6 Hz), 7.28 (2H, dt, J=8.8; 2.0 Hz), 6.12 (1H, s), 4.05 (2H, m), 3.57 (2H, m), 3.25 (4H, m), 2.97 (6H, s), 2.87 (1H, m), 1.79 (4H, m), 1.23 (6H, s) ppm.

Example 172

Preparation of 6-(4-(tetrahydro-2H-pyran-4-yl)phenylamino)-4-(thiazol-2-ylmethylamino)nicotinamide

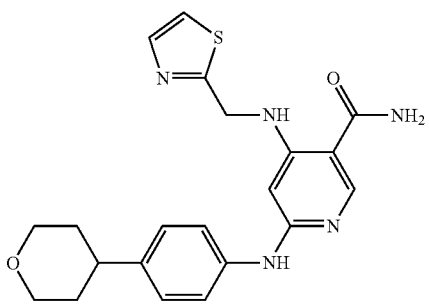 [SMILES: NC(=O)c1cnc(Nc2ccc(C3CCOCC3)cc2)cc1NCc1nccs1]

The title compound was synthesized using a procedure similar to that described in Example 139. MS found for C21H23N5O2S as (M+H)⁺ 410.2. UV: λ=259 nm. ¹H NMR: (CD3OD) δ 8.15 (1H, s), 7.78 (1H, d, J=3.6 Hz), 7.62 (1H, d, J=3.2 Hz), 7.35 (2H, dt, J=8.0; 2.0 Hz), 7.13 (2H, dt, J=8.8; 2.0 Hz), 6.00 (1H, s), 4.05 (2H, m), 3.57 (2H, m), 2.86 (1H, m), 1.79 (4H, m) ppm.

Example 173

Preparation of 4-((1-methyl-1H-pyrazol-4-yl)methylamino)-6-(4-(tetrahydro-2H-pyran-4-yl)phenylamino)nicotinamide

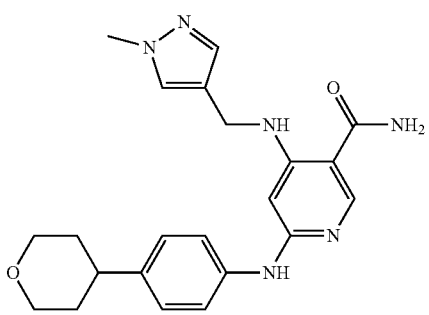 [SMILES: Cn1cc(CNc2cc(Nc3ccc(C4CCOCC4)cc3)ncc2C(N)=O)cn1]

The title compound was synthesized using a procedure similar to that described in Example 139. MS found for C22H26N6O2 as (M+H)⁺ 407.3. UV: λ=259 nm. ¹H NMR: (CD3OD) δ 8.09 (1H, s), 7.57 (1H, s), 7.39 (2H, dt, J=7.6; 1.6

Hz), 7.20 (2H, dt, J=8.8; 2.0 Hz), 5.99 (1H, s), 4.32 (2H, s), 4.05 (2H, m), 3.87 (3H, s), 3.57 (2H, m), 2.87 (1H, m), 1.80 (4H, m) ppm.

Example 174

Preparation of 4-(pyridin-2-ylmethylamino)-6-(4-(tetrahydro-2H-pyran-4-yl)phenylamino)nicotinamide

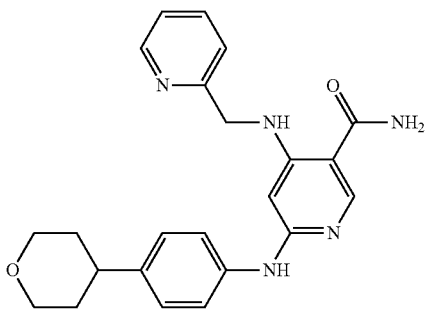

The title compound was synthesized using a procedure similar to that described in Example 139. MS found for C23H25N5O2 as (M+H)⁺ 404.3. UV: λ=259 nm. ¹H NMR: (CD3OD) δ 8.81 (1H, dd, J=4.4; 0.8 Hz), 8.53 (1H, td, J=8.0; 1.6 Hz), 8.20 (1H, s), 7.99-7.95 (2H, m), 7.34 (2H, dt, J=8.4; 2.0 Hz), 7.15 (2H, dt, J=8.4; 2.0 Hz), 5.90 (1H, s), 4.96 (2H, s), 4.05 (2H, m), 3.57 (2H, m), 2.86 (1H, m), 1.78 (4H, m) ppm.

Example 175

Preparation of 4-(pyrimidin-2-ylmethylamino)-6-(4-(tetrahydro-2H-pyran-4-yl)phenylamino)nicotinamide

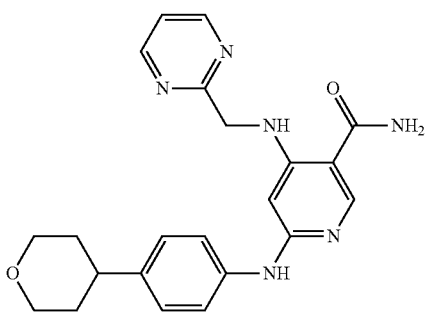 [SMILES: NC(=O)c1cnc(Nc2ccc(C3CCOCC3)cc2)cc1NCc1ncccn1]

The title compound was synthesized using a procedure similar to that described in Example 139. MS found for C22H24N6O2 as (M+H)⁺ 405.3. UV: λ=254 nm. ¹H NMR: (CD3OD) δ 8.80 (2H, d, J=4.8 Hz), 8.13 (1H, s), 7.44 (1H, t, J=5.2 Hz), 7.38 (2H, dt, J=8.4; 2.0 Hz), 7.21 (2H, dt, J=8.8; 2.0 Hz), 5.98 (1H, s), 4.67 (2H, s), 4.06 (2H, m), 3.58 (2H, m), 2.87 (1H, m), 1.79 (4H, m) ppm.

Example 176

4-(cyclopentylmethylamino)-6-(4-(1-propionylpiperidin-4-yl)phenylamino)nicotinamide

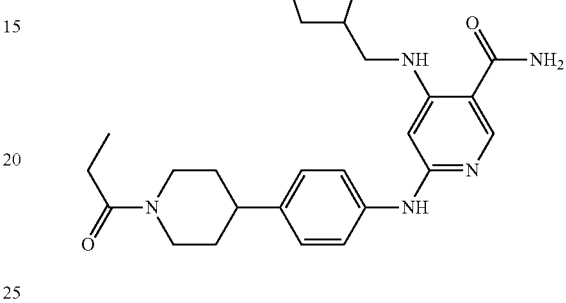

The title compound was synthesized using a procedure similar to that described in Example 144. MS found for C26H35N5O2 as (M+H)⁺ 450.4. UV: λ=259 nm. ¹H NMR: (CD3OD) δ 8.09 (1H, s), 7.39 (2H, dt, J=8.4; 2.0 Hz), 7.26 (2H, dt, J=8.8; 2.0 Hz), 5.95 (1H, s), 4.70 (1H, m), 4.10 (1H, m), 3.25 (1H, m), 3.13 (2H, d, J=7.2 Hz), 2.89 (1H, m), 2.72 (1H, m), 2.46 (2H, q, J=7.6 Hz), 2.22 (1H, m), 1.96-1.82 (4H, m), 1.73-1.57 (6H, m), 1.29 (2H, m), 1.14 (3H, t, J=7.6 Hz) ppm.

Example 177

Preparation of 6-(4-(1-propionylpiperidin-4-yl)phenylamino)-4-(thiazol-2-ylmethylamino)nicotinamide

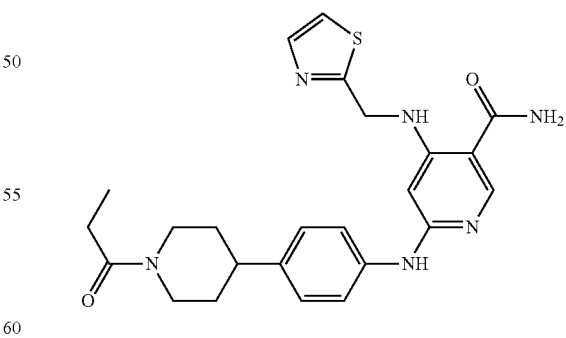

The title compound was synthesized using a procedure similar to that described in Example 144. MS found for C24H28N6O2S as (M+H)⁺ 465.4. UV: λ=259 nm. ¹H NMR: (CD3OD) δ 8.17 (1H, s), 7.86 (1H, d, J=3.2 Hz), 7.71 (1H, d, J=3.6 Hz), 7.35 (2H, dt, J=8.4; 2.0 Hz), 7.14 (2H, dt, J=8.4; 2.0 Hz), 6.00 (1H, s), 4.70 (1H, m), 4.11 (1H, m), 3.23 (1H, m), 2.89 (1H, m), 2.74 (1H, m), 2.47 (2H, q, J=7.2 Hz), 1.92 (2H, m), 1.64 (2H, m), 1.15 (3H, t, J=7.2 Hz) ppm.

Example 178

Preparation of 4-((1-methyl-1H-pyrazol-4-yl)methylamino)-6-(4-(1-propionylpiperidin-4-yl)phenylamino)nicotinamide

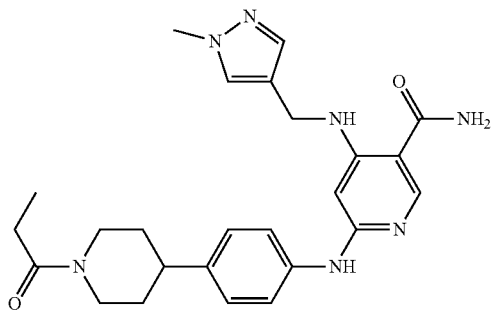 [SMILES: CCC(=O)N1CCC(c2ccc(Nc3cc(NCc4cnn(C)c4)c(C(N)=O)cn3)cc2)CC1]

The title compound was synthesized using a procedure similar to that described in Example 144. MS found for C25H31N7O2 as (M+H)+ 462.4. UV: λ=259 nm. ¹H NMR: (CD3OD) δ 8.14 (1H, s), 7.93 (1H, s), 7.83 (1H, s), 7.39 (2H, dt, J=8.4; 2.0 Hz), 7.22 (2H, dt, J=8.4; 2.0 Hz), 6.04 (1H, s), 4.70 (1H, m), 4.41 (2H, s), 4.12 (1H, m), 4.01 (3H, s), 3.25 (1H, m), 2.91 (1H, m), 2.77 (1H, m), 2.49 (2H, q, J=8.0 Hz), 1.94 (2H, m), 1.66 (2H, m), 1.16 (3H, t, J=7.6 Hz) ppm.

Example 179

Preparation of 6-(4-(1-propionylpiperidin-4-yl)phenylamino)-4-(pyridin-2-ylmethylamino)nicotinamide

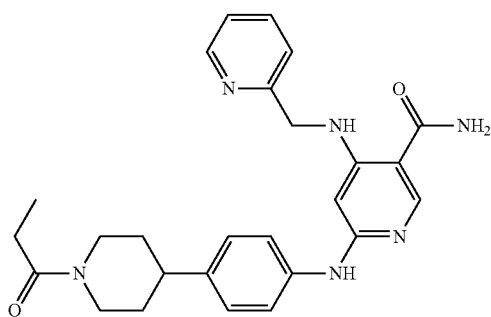 [SMILES: CCC(=O)N1CCC(c2ccc(Nc3cc(NCc4ccccn4)c(C(N)=O)cn3)cc2)CC1]

The title compound was synthesized using a procedure similar to that described in Example 144. MS found for C26H30N6O2 as (M+H)+ 459.4. UV: λ=259 nm. ¹H NMR: (CD3OD) δ 8.86 (1H, dm, J=8.4 Hz), 8.64 (1H, td, J=8.0; 1.6 Hz), 8.22 (1H, s), 8.07 (2H, m), 7.34 (2H, dt, J=8.8; 2.0 Hz), 7.15 (2H, dt, J=8.4; 2.0 Hz), 5.92 (1H, s), 5.03 (2H, s), 4.70 (1H, m), 4.11 (1H, m), 3.23 (1H, m), 2.90 (1H, m), 2.75 (1H, m), 2.48 (2H, q, J=7.2 Hz), 1.91 (2H, m), 1.61 (2H, m), 1.15 (3H, t, J=7.2 Hz) ppm.

Example 180

Preparation of 6-(4-(1-propionylpiperidin-4-yl)phenylamino)-4-(pyrimidin-2-ylmethylamino)nicotinamide

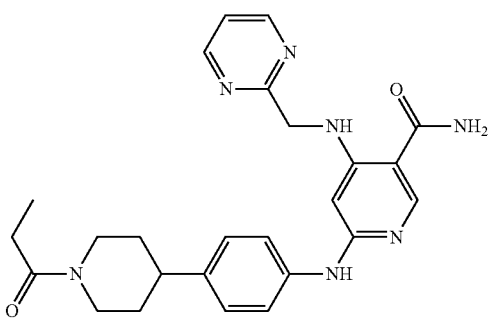 [SMILES: CCC(=O)N1CCC(c2ccc(Nc3cc(NCc4ncccn4)c(C(N)=O)cn3)cc2)CC1]

The title compound was synthesized using a procedure similar to that described in Example 144. MS found for C25H29N7O2 as (M+H)+ 460.4. UV: λ=254 nm. ¹H NMR: (CD3OD) δ 8.88 (2H, d, J=5.2 Hz), 8.18 (1H, s), 7.54 (1H, t, J=5.2 Hz), 7.36 (2H, dt, J=8.8; 2.0 Hz), 7.22 (2H, dt, J=8.4; 2.0 Hz), 6.01 (1H, s), 4.73 (2H, s), 4.69 (1H, m), 4.13 (1H, m), 3.26 (1H, m), 2.92 (1H, m), 2.79 (1H, m), 2.52 (2H, q, J=7.6 Hz), 1.94 (2H, m), 1.66 (2H, m), 1.17 (3H, t, J=7.6 Hz) ppm.

Example 181

Preparation of 4-(pyrimidin-4-ylmethylamino)-6-(4-(tetrahydro-2H-pyran-4-yl)phenylamino)nicotinamide

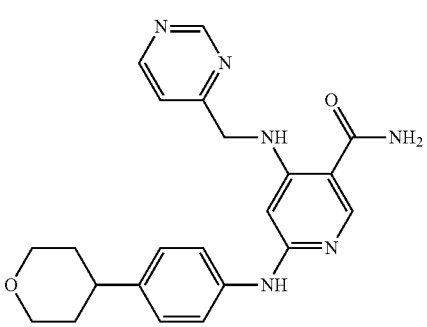 [SMILES: NC(=O)c1cnc(Nc2ccc(C3CCOCC3)cc2)cc1NCc1ccncn1]

The title compound was synthesized using a procedure similar to that described in Example 139. MS found for C22H24N6O2 as (M+H)+ 405.3. UV: λ=259 nm. ¹H NMR: (CD3OD) δ 9.14 (1H, d, J=1.2 Hz), 8.76 (1H, d, J=5.2 Hz), 8.14 (1H, s), 7.51 (1H, dd, J=5.2; 1.2 Hz), 7.34 (2H, dt, J=8.4;

1.6 Hz), 7.14 (2H, dt, J=8.4; 2.0 Hz), 5.83 (1H, s), 4.65 (2H, s), 4.06 (2H, m), 3.57 (2H, m), 2.86 (1H, m), 1.79 (4H, m) ppm.

Example 182

Preparation of 4-((1-methyl-1H-benzo[d]imidazol-2-yl)methylamino)-6-(4-(tetrahydro-2H-pyran-4-yl)phenylamino)nicotinamide

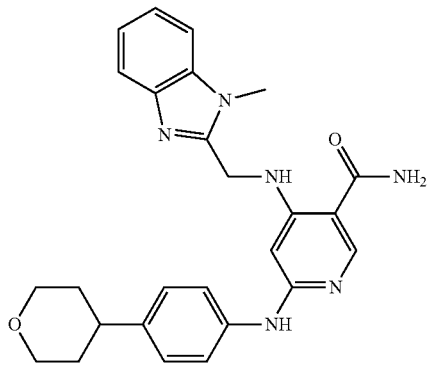 [SMILES: Cn1c(CNc2cc(Nc3ccc(C4CCOCC4)cc3)ncc2C(N)=O)nc2ccccc21]

The title compound was synthesized using a procedure similar to that described in Example 139. MS found for C26H28N6O2 as (M+H)+ 457.3. UV: λ=254 nm. ¹H NMR: (CD3OD) δ 8.14 (1H, s), 7.79 (1H, d, J=7.6 Hz), 7.66 (1H, dd, J=7.2; 1.2 Hz), 7.55 (2H, m), 7.11 (2H, dt, J=8.8; 2.0 Hz), 7.02 (2H, dt, J=8.4; 2.4 Hz), 5.90 (1H, s), 5.11 (2H, s), 3.96 (2H, m), 3.93 (3H, s), 3.46 (2H, m), 2.72 (1H, m), 1.64 (4H, m) ppm.

Example 183

Preparation of 4-((1-methyl-1H-imidazol-2-yl)methylamino)-6-(4-(tetrahydro-2H-pyran-4-yl)phenylamino)nicotinamide

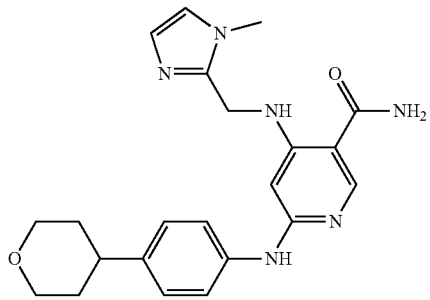 [SMILES: Cn1ccnc1CNc1cc(Nc2ccc(C3CCOCC3)cc2)ncc1C(N)=O]

The title compound was synthesized using a procedure similar to that described in Example 139. MS found for C22H26N6O2 as (M+H)+ 407.3. UV: λ=254 nm. ¹H NMR: (CD3OD) δ 8.22 (1H, s), 7.61 (1H, d, J=2.0 Hz), 7.52 (1H, d, J=2.0 Hz), 7.39 (2H, dt, J=8.0; 2.0 Hz), 7.21 (2H, dt, J=8.4; 2.0 Hz), 5.93 (1H, s), 4.99 (2H, s), 4.06 (2H, m), 3.86 (3H, s), 3.57 (2H, m), 2.88 (1H, m), 1.79 (4H, m) ppm.

Example 184

Preparation of 4-(prop-2-ynylamino)-6-(4-(tetrahydro-2H-pyran-4-yl)phenylamino)nicotinamide

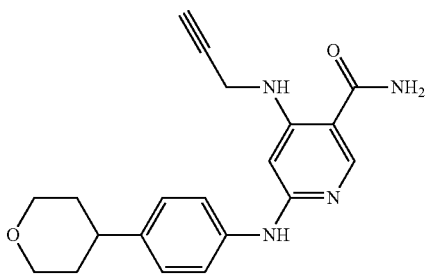 [SMILES: C#CCNc1cc(Nc2ccc(C3CCOCC3)cc2)ncc1C(N)=O]

The title compound was synthesized using a procedure similar to that described in Example 139. MS found for C20H22N4O2 as (M+H)+ 351.3. UV: λ=254 nm. ¹H NMR: (CD3OD) δ 8.03 (1H, s), 7.31 (2H, dt, J=8.0; 2.0 Hz), 7.19 (2H, dt, J=8.4; 2.0 Hz), 6.06 (1H, s), 4.01 (2H, d, J=2.8 Hz), 3.96 (2H, m), 3.48 (2H, m), 2.78 (1H, m), 2.73 (1H, t, J=2.8 Hz), 1.70 (4H, m) ppm.

Example 185

Preparation of 4-(pyridin-3-ylmethylamino)-6-(4-(tetrahydro-2H-pyran-4-yl)phenylamino)nicotinamide

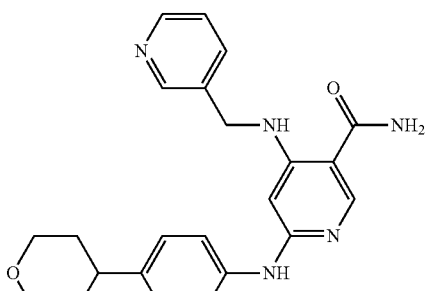

The title compound was synthesized using a procedure similar to that described in Example 139. MS found for C23H25N5O2 as (M+H)+ 404.3. UV: λ=254 nm. ¹H NMR: (CD3OD) δ 8.71 (2H, s), 8.24 (1H, d, J=6.0 Hz), 8.15 (1H, s), 7.84 (1H, m), 7.34 (2H, d, J=8.0 Hz), 7.13 (2H, d, J=8.0 Hz), 5.88 (1H, s), 4.70 (2H, s), 4.05 (2H, m), 3.57 (2H, m), 2.86 (1H, m), 1.78 (4H, m) ppm.

Example 186

Preparation of (S)-4-(3-methylbutan-2-ylamino)-6-(4-(tetrahydro-2H-pyran-4-yl)phenylamino)nicotinamide

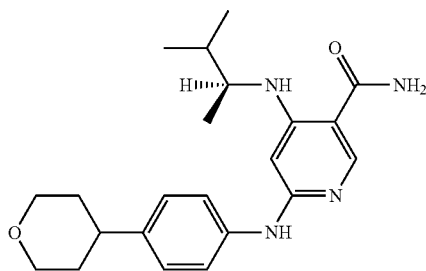

The title compound was synthesized using a procedure similar to that described in Example 139. MS found for C22H30N4O2 as (M+H)+ 383.4. UV: λ=259 nm. ¹H NMR: (CD3OD) δ 8.10 (1H, s), 7.39 (2H, dt, J=8.4; 2.0 Hz), 7.26 (2H, dt, J=8.8; 2.0 Hz), 5.96 (1H, s), 4.05 (2H, m), 3.57 (2H, m), 3.41 (1H, m), 2.86 (1H, m), 1.86 (1H, m), 1.79 (4H, m), 1.18 (3H, d, J=6.8 Hz), 0.98 (3H, d, J=6.8 Hz), 0.96 (3H, d, J=6.8 Hz) ppm.

Example 187

Preparation of 6-(4-(1-propionylpiperidin-4-yl)phenylamino)-4-(pyridin-3-ylmethylamino)nicotinamide

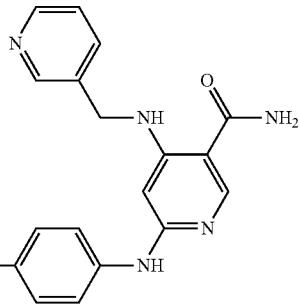

The title compound was synthesized using a procedure similar to that described in Example 144. MS found for C26H30N6O2 as (M+H)+ 459.4. UV: λ=254 nm. ¹H NMR: (CD3OD) δ 8.87 (1H, d, J=2.0 Hz), 8.84 (1H, d, J=5.2 Hz), 8.57 (1H, dm, J=8.0 Hz), 8.17 (1H, s), 8.10 (1H, m), 7.34 (2H, dt, J=8.0; 2.0 Hz), 7.16 (2H, dt, J=8.8; 2.0 Hz), 5.93 (1H, s), 4.81 (2H, s), 4.70 (1H, m), 4.10 (1H, m), 3.22 (1H, m), 2.89 (1H, m), 2.72 (1H, m), 2.46 (2H, q, J=7.6 Hz), 1.91 (2H, m), 1.62 (2H, m), 1.14 (3H, t, J=7.6 Hz) ppm.

Example 188

Preparation of 4-((5-fluoropyridin-3-yl)methylamino)-6-(4-(1-propionylpiperidin-4-yl)phenylamino)nicotinamide

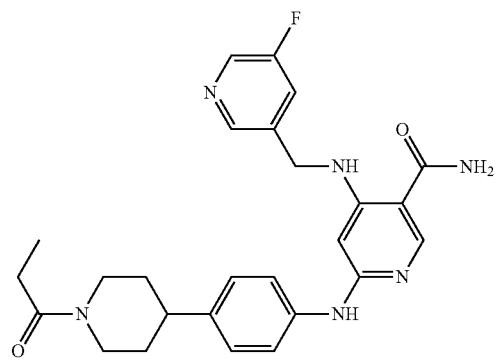 [SMILES: CCC(=O)N1CCC(c2ccc(Nc3cc(NCc4cncc(F)c4)c(C(N)=O)cn3)cc2)CC1]

The title compound was synthesized using a procedure similar to that described in Example 144. MS found for C26H29FN6O2 as (M+H)+ 477.4. UV: λ=259 nm. ¹H NMR: (CD3OD) δ 8.73 (1H, m), 8.57 (1H, m), 8.16 (1H, s), 8.02 (1H, m), 7.34 (2H, dt, J=8.4; 2.0 Hz), 7.13 (2H, dt, J=8.8; 2.0 Hz), 5.87 (1H, s), 4.71 (2H, s), 4.10 (1H, m), 3.53 (1H, m), 3.22 (1H, m), 2.89 (1H, m), 2.73 (1H, m), 2.47 (2H, q, J=8.0 Hz), 1.92 (2H, m), 1.63 (2H, m), 1.15 (3H, t, J=7.6 Hz) ppm.

Example 189

Preparation of (R)-4-(3-methylbutan-2-ylamino)-6-(4-(1-propionylpiperidin-4-yl)phenylamino)nicotinamide

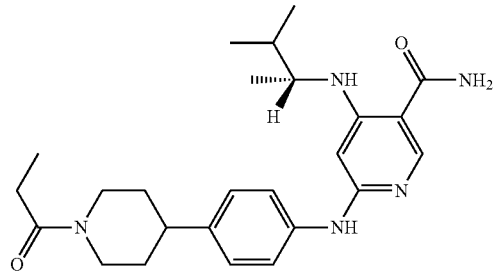 [SMILES: CCC(=O)N1CCC(c2ccc(Nc3cc(N[C@H](C)C(C)C)c(C(N)=O)cn3)cc2)CC1]

The title compound was synthesized using a procedure similar to that described in Example 144. MS found for C25H35N5O2 as (M+H)+ 438.4. UV: λ=259 nm. ¹H NMR: (CD3OD) δ 8.10 (1H, s), 7.39 (2H, dt, J=8.0; 2.0 Hz), 7.25 (2H, dt, J=8.8; 2.0 Hz), 5.96 (1H, s), 4.70 (1H, m), 4.10 (1H, m), 3.41 (1H, m), 3.22 (1H, m), 2.88 (1H, m), 2.72 (1H, m), 2.46 (2H, q, J=7.6 Hz), 1.92 (2H, m), 1.86 (1H, m), 1.63 (2H, m), 1.18 (3H, d, J=6.8 Hz), 1.14 (3H, t, J=7.6 Hz), 0.98 (3H, d, J=6.8 Hz), 0.96 (3H, d, J=6.8 Hz) ppm.

Example 190

Preparation of (R)-4-(3,3-dimethylbutan-2-ylamino)-6-(4-(1-propionylpiperidin-4-yl)phenylamino)nicotinamide

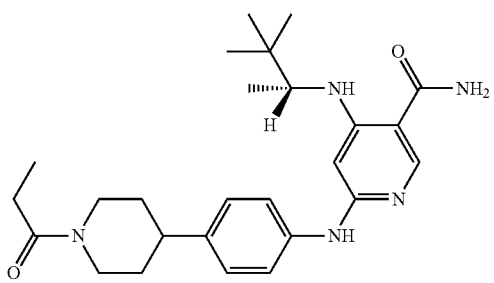 [SMILES: CCC(=O)N1CCC(c2ccc(Nc3cc(N[C@H](C)C(C)(C)C)c(C(N)=O)cn3)cc2)CC1]

The title compound was synthesized using a procedure similar to that described in Example 144. MS found for C26H37N5O2 as (M+H)+ 452.4. UV: λ=259 nm. ¹H NMR: (CD3OD) δ 8.10 (1H, s), 7.38 (2H, dt, J=8.0; 2.0 Hz), 7.25 (2H, dt, J=8.8; 2.0 Hz), 6.00 (1H, s), 4.70 (1H, m), 4.09 (1H, m), 3.35 (1H, m), 3.22 (1H, m), 2.89 (1H, m), 2.72 (1H, m), 2.46 (2H, q, J=7.6 Hz), 1.92 (2H, m), 1.63 (2H, m), 1.16 (3H, d, J=6.8 Hz), 1.14 (3H, t, J=7.6 Hz), 0.99 (9H, s) ppm.

Example 191

Preparation of (R)-4-(1-cyclohexylethylamino)-6-(4-(1-propionylpiperidin-4-yl)phenylamino)nicotinamide

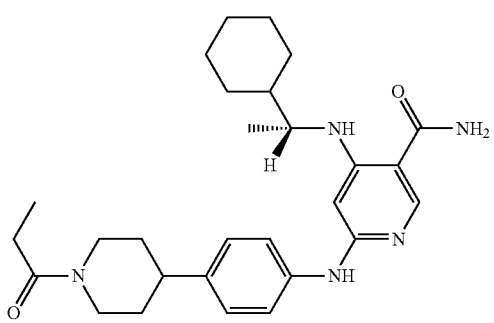 [SMILES: CCC(=O)N1CCC(c2ccc(Nc3cc(N[C@H](C)C4CCCCC4)c(C(N)=O)cn3)cc2)CC1]

The title compound was synthesized using a procedure similar to that described in Example 144. MS found for C28H39N5O2 as (M+H)+ 478.5. UV: λ=259 nm. ¹H NMR: (CD3OD) δ 8.10 (1H, s), 7.37 (2H, dt, J=8.4; 2.0 Hz), 7.25 (2H, dt, J=8.8; 2.0 Hz), 5.94 (1H, s), 4.70 (1H, m), 4.09 (1H, m), 3.35 (1H, m), 3.22 (1H, m), 2.88 (1H, m), 2.71 (1H, m), 2.46 (2H, q, J=8.0 Hz), 1.91 (2H, m), 1.78 (2H, m), 1.71-1.49 (6H, m), 1.30-1.04 (11H, m) ppm.

Example 192

Preparation of 4-(cyclohexylmethylamino)-6-(4-(1-propionylpiperidin-4-yl)phenylamino)nicotinamide

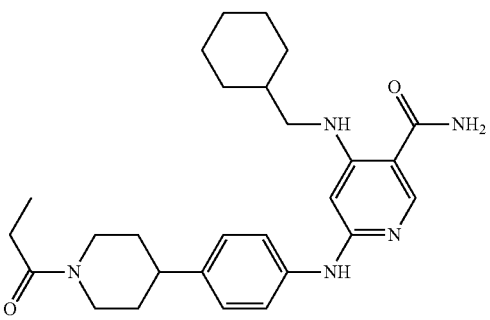 [SMILES: CCC(=O)N1CCC(c2ccc(Nc3cc(NCC4CCCCC4)c(C(N)=O)cn3)cc2)CC1]

The title compound was synthesized using a procedure similar to that described in Example 144. MS found for C27H37N5O2 as (M+H)+ 464.4. UV: λ=259 nm. ¹H NMR: (CD3OD) δ 8.09 (1H, s), 7.37 (2H, dt, J=8.8; 2.0 Hz), 7.26 (2H, dt. J=8.4; 2.0 Hz), 5.92 (1H, s), 4.70 (1H, m), 4.09 (1H, m), 3.32 (1H, m), 3.22 (1H, m), 3.03 (2H, d, J=6.8 Hz), 2.89 (1H, m), 2.72 (1H, m), 2.46 (2H, q, J=8.0 Hz), 1.92 (2H, m), 1.79-1.57 (8H, m), 1.29 (2H, m), 1.14 (3H, t, J=7.6 Hz), 1.05 (2H, m) ppm.

Example 193

Preparation of 4-((1-hydroxycyclopentyl)methylamino)-6-(4-(1-propionylpiperidin-4-yl)phenylamino)nicotinamide

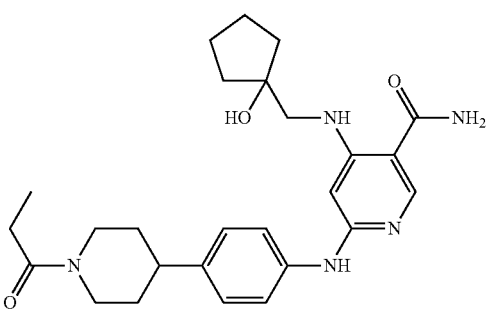 [SMILES: CCC(=O)N1CCC(c2ccc(Nc3cc(NCC4(O)CCCC4)c(C(N)=O)cn3)cc2)CC1]

The title compound was synthesized using a procedure similar to that described in Example 144. MS found for C26H35N5O3 as (M+H)+ 466.3. UV: λ=259 nm. ¹H NMR: (CD3OD) δ 7.99 (1H, s), 7.29 (2H, dt, J=8.8; 2.0 Hz), 7.16 (2H, dt, J=8.8; 2.0 Hz), 5.92 (1H, s), 4.60 (1H, m), 4.01 (1H, m), 3.16 (2H, s), 3.12 (1H, m), 2.80 (1H, m), 2.63 (1H, m), 2.37 (2H, q, J=7.6 Hz), 1.86-1.76 (5H, m), 1.66-1.48 (8H, m), 1.05 (3H, t, J=7.2 Hz) ppm.

Example 194

Preparation of 4-((1-phenylcyclopropyl)methylamino)-6-(4-(1-propionylpiperidin-4-yl)phenylamino)nicotinamide

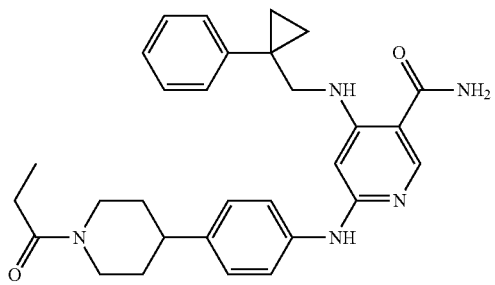 [SMILES: CCC(=O)N1CCC(c2ccc(Nc3cc(NCC4(c5ccccc5)CC4)c(C(N)=O)cn3)cc2)CC1]

The title compound was synthesized using a procedure similar to that described in Example 144. MS found for C30H35N5O2 as (M+H)⁺ 498.4. UV: λ=259 nm. ¹H NMR: (CD3OD) δ 8.05 (1H, s), 7.38 (2H, dt, J=8.8; 2.0 Hz), 7.33 (2H, dt, J=8.4; 1.6 Hz), 7.26-7.18 (5H, m), 5.78 (1H, s), 4.71 (1H, m), 4.10 (1H, m), 3.31 (2H, s), 3.22 (1H, m), 2.90 (1H, m), 2.73 (1H, m), 2.47 (2H, q, J=7.6 Hz), 1.93 (2H, m), 1.64 (2H, m), 1.15 (3H, t, J=7.2 Hz) ppm.

Example 195

Preparation of 4-(3,5-difluorobenzylamino)-6-(4-(1-propionylpiperidin-4-yl)phenylamino)nicotinamide

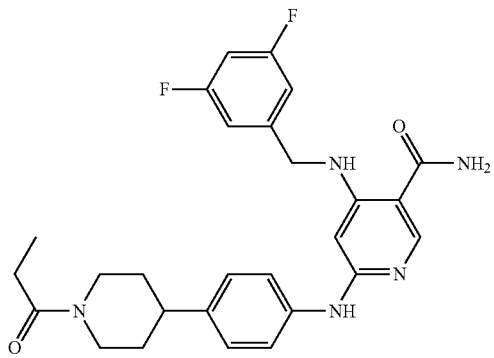 [SMILES: CCC(=O)N1CCC(c2ccc(Nc3cc(NCc4cc(F)cc(F)c4)c(C(N)=O)cn3)cc2)CC1]

The title compound was synthesized using a procedure similar to that described in Example 144. MS found for C27H29F2N5O2 as (M+H)⁺ 494.3. UV: λ=259 nm. ¹H NMR: (CD3OD) δ 8.15 (1H, s), 7.30 (2H, dt, J=8.0; 2.0 Hz), 7.06 (2H, dt, J=8.0; 2.0 Hz), 6.94-6.87 (3H, m), 5.75 (1H, s), 4.70 (1H, m), 4.50 (2H, s), 4.10 (1H, m), 3.22 (1H, m), 2.88 (1H, m), 2.73 (1H, m), 2.47 (2H, q, J=8.0 Hz), 1.92 (2H, m), 1.63 (2H, m), 1.15 (3H, t, J=7.2 Hz) ppm.

Example 196

Preparation of 4-(2,3-difluorobenzylamino)-6-(4-(1-propionylpiperidin-4-yl)phenylamino)nicotinamide

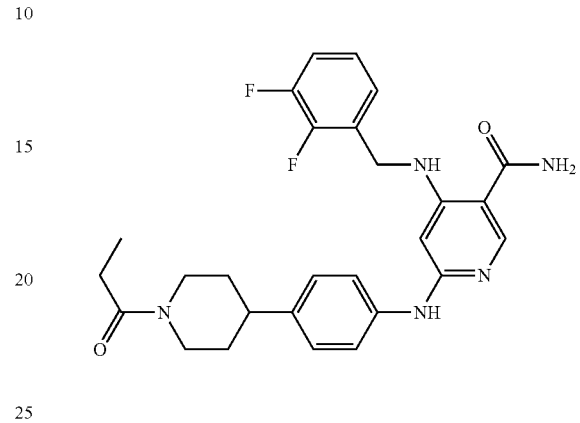

The title compound was synthesized using a procedure similar to that described in Example 144. MS found for C27H29F2N5O2 as (M+H)⁺ 494.3. UV: λ=259 nm. ¹H NMR: (CD3OD) δ 8.15 (1H, s), 7.33 (2H, dt, J=8.8; 2.0 Hz), 7.26 (1H, m), 7.17 (1H, m), 7.13-7.08 (3H, m), 5.80 (1H, s), 4.71 (1H, m), 4.55 (2H, s), 4.11 (1H, m), 3.23 (1H, m), 2.89 (1H, m), 2.73 (1H, m), 2.47 (2H, q, J=7.6 Hz), 1.93 (2H, m), 1.64 (2H, m), 1.15 (3H, t, J=7.6 Hz) ppm.

Example 197

Preparation of 6-(4-(1-propionylpiperidin-4-yl)phenylamino)-4-(thiophen-2-ylmethylamino)nicotinamide

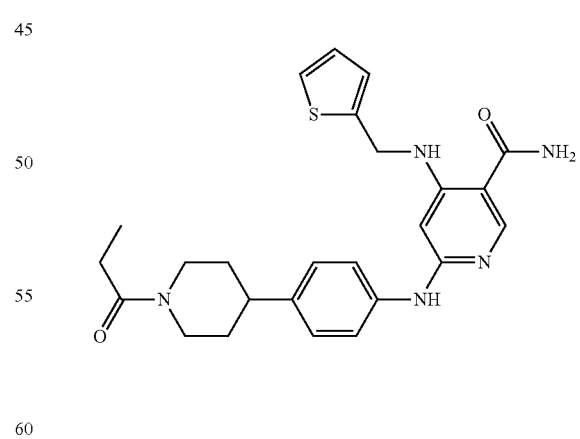

The title compound was synthesized using a procedure similar to that described in Example 144. MS found for C25H29N5O2S as (M+H)⁺ 464.3. UV: λ=259 nm. ¹H NMR: (CD3OD) δ 8.14 (1H, s), 7.38-7.34 (3H, m), 7.13 (2H, dt, J=8.4; 2.0 Hz), 7.00 (1H, m), 6.96 (1H, m), 6.02 (1H, s), 4.70 (1H, m), 4.66 (2H, s), 4.11 (1H, m), 3.22 (1H, m), 2.90 (1H, m), 2.73 (1H, m), 2.47 (2H, q, J=8.0 Hz), 1.92 (2H, m), 1.64 (2H, m), 1.15 (3H, t, J=7.6 Hz) ppm.

Example 198

Preparation of 4-(benzylamino)-6-(4-(1-propionylpiperidin-4-yl)phenylamino)nicotinamide

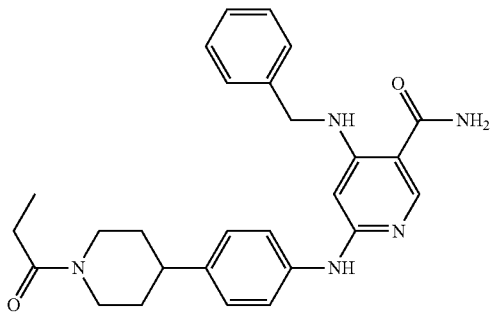 [SMILES: CCC(=O)N1CCC(c2ccc(Nc3cc(NCc4ccccc4)c(C(N)=O)cn3)cc2)CC1]

The title compound was synthesized using a procedure similar to that described in Example 144. MS found for C27H31N5O2 as (M+H)+ 458.3. UV: λ=259 nm. 1H NMR: (CD3OD) δ 8.12 (1H, s), 7.38-7.25 (7H, m), 7.07 (2H, dt, J=8.8; 2.0 Hz), 5.86 (1H, s), 4.71 (1H, m), 4.46 (2H, s). 4.11 (1H, m), 3.22 (1H, m), 2.88 (1H, m), 2.73 (1H, m), 2.47 (2H, q, J=7.6 Hz), 1.92 (2H, m), 1.63 (2H, m), 1.15 (3H, t, J=7.6 Hz) ppm.

Example 199

Preparation of (R)-4-(1-phenylethylamino)-6-(4-(1-propionylpiperidin-4-yl)phenylamino)nicotinamide

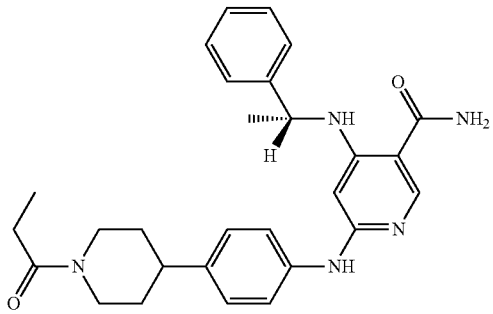 [SMILES: CCC(=O)N1CCC(c2ccc(Nc3cc(N[C@H](C)c4ccccc4)c(C(N)=O)cn3)cc2)CC1]

The title compound was synthesized using a procedure similar to that described in Example 144. MS found for C28H33N5O2 as (M+H)+ 472.4. UV: λ=259 nm. 1H NMR: (CD3OD) δ 8.14 (1H, s), 7.37-7.21 (7H, m), 6.94 (2H, d, 7.2 Hz), 5.70 (1H, s), 4.71 (1H, m), 4.52 (1H, q, J=6.4 Hz), 4.11 (1H, m), 3.23 (1H, m), 2.88 (1H, m), 2.74 (1H, m), 2.47 (2H, q, J=7.2 Hz), 1.92 (2H, m), 1.63 (2H, m), 1.56 (3H, d, J=6.8 Hz), 1.15 (3H, t, J=7.6 Hz) ppm.

Example 200

4-((1H-indol-4-yl)methylamino)-6-(4-(1-propionylpiperidin-4-yl)phenylamino)nicotinamide

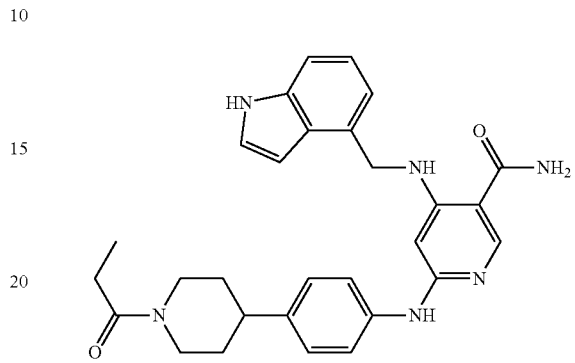

The title compound was synthesized using a procedure similar to that described in Example 144. MS found for C29H32N6O2 as (M+H)+ 497.4. UV: λ=268 nm. 1H NMR: (CD3OD) δ 8.12 (1H, m), 7.38 (1H, d, J=8.4 Hz), 7.25 (1H, d, J=3.2 Hz), 7.13 (2H, d, J=8.4 Hz), 7.09 (1H, t, J=8.4 Hz), 6.91 (2H, d, J=8.8 Hz), 6.87 (1H, d, J=8.0 Hz), 6.49 (1H, d, J=3.2 Hz), 5.92 (1H, s), 4.71 (2H, s), 4.69 (1H, m), 4.10 (1H, m), 3.22 (1H, m), 2.81 (1H, m), 2.72 (1H, m), 2.48 (2H, q, J=7.2 Hz), 1.88 (2H, m), 1.58 (2H, m), 1.16 (3H, t, J=7.6 Hz) ppm.

Example 201

Preparation of 4-((1-(2-(piperidin-1-yl)ethyl)-1H-1,2,3-triazol-4-yl)methylamino)-6-(4-(tetrahydro-2H-pyran-4-yl)phenylamino)nicotinamide

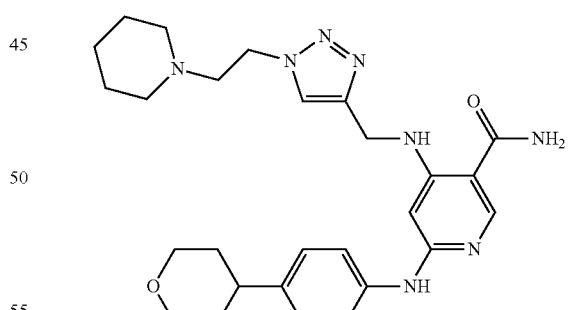

Compound 4-(prop-2-ynylamino)-6-(4-(tetrahydro-2H-pyran-4-yl)phenylamino)nicotinamide (Example 184) (20 mg, 0.057 mmol) was dissolved in 6 mL MeOH. To it were added 1-(2-azidoethyl)piperidine (18 mg, 0.11 mmol), DBU (26 μL, 0.17 mmol) and finally powder CuI (13 mg, 0.068 mmol). The mixture was stirred at RT for 5 h, filtered and subjected to reverse phase prep HPLC to isolate the title compound. MS found for C27H36N8O2 as (M+H)+ 505.4. UV: λ=259 nm. 1H NMR: (CD3OD) δ 8.14 (1H, s), 8.12 (1H, s), 7.39 (2H, dt, J=8.4; 2.0 Hz), 7.24 (2H, dt, J=8.4; 2.0 Hz), 6.20 (1H, s), 4.60 (2H, s), 4.05 (2H, m), 3.73 (2H, m), 3.59 (4H, m), 3.04 (2H, m), 2.87 (1H, m), 1.95 (2H, m), 1.86-1.75 (8H, m) ppm.

Example 202

Preparation of (R)-4-(1-cyclopropylethylamino)-6-(4-(1-propionylpiperidin-4-yl)phenylamino)nicotinamide

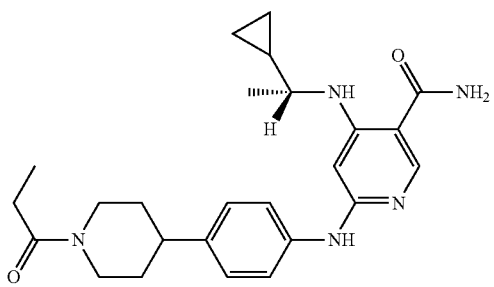 [SMILES: CCC(=O)N1CCC(c2ccc(Nc3cc(N[C@H](C)C4CC4)c(C(N)=O)cn3)cc2)CC1]

The title compound was synthesized using a procedure similar to that described in Example 144. MS found for C25H33N5O2 as (M+H)$^+$ 436.3. UV: $\lambda$=259 nm. $^1$H NMR: (CD3OD) $\delta$ 7.83 (1H, s), 7.13 (2H, dt, J=8.4; 2.0 Hz), 6.99 (2H, dt, J=8.4; 2.0 Hz), 5.68 (1H, s), 4.44 (1H, m), 3.84 (1H, m), 2.96 (1H, m), 2.82 (1H, m), 2.63 (1H, m), 2.46 (1H, m), 2.20 (2H, q, J=7.6 Hz), 1.66 (2H, m), 1.37 (2H, m), 1.03 (3H, d, J=6.0 Hz), 0.89 (3H, t, J=7.2 Hz), 0.77 (1H, m), 0.30 (2H, m), 0.02 (2H, m) ppm.

Example 203

Preparation of 4-(2,6-difluorobenzylamino)-6-(4-(1-propionylpiperidin-4-yl)phenylamino)nicotinamide

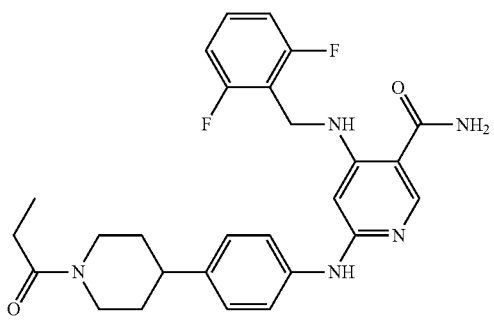 [SMILES: CCC(=O)N1CCC(c2ccc(Nc3cc(NCc4c(F)cccc4F)c(C(N)=O)cn3)cc2)CC1]

The title compound was synthesized using a procedure similar to that described in Example 144. MS found for C27H29F2N5O2 as (M+H)$^+$ 494.3. UV: $\lambda$=259 nm. $^1$H NMR: (CD3OD) $\delta$ 8.13 (1H, s), 7.42-7.38 (3H, m), 7.22 (2H, dt, J=8.0; 2.0 Hz), 7.00 (2H, t, J=8.0 Hz), 6.03 (1H, s), 4.71 (1H, m), 4.51 (2H, s), 4.11 (1H, m). 3.23 (1H, m), 2.92 (1H, m), 2.74 (1H, m), 2.47 (2H, q, J=7.6 Hz), 1.95 (2H, m), 1.66 (2H, m), 1.15 (3H, t, J=7.6 Hz) ppm.

Example 204

Preparation of 4-(3-fluorobenzylamino)-6-(3-(tetrahydro-2H-pyran-4-yl)phenylamino)nicotinamide

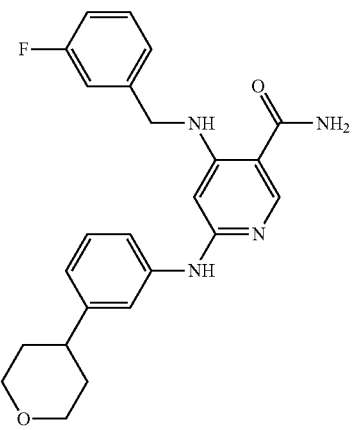 [SMILES: NC(=O)c1cnc(Nc2cccc(C3CCOCC3)c2)cc1NCc1cccc(F)c1]

The title compound was synthesized using a procedure similar to that described in Example 139. MS found for C24H25FN4O2 as (M+H)$^+$ 421.3. UV: $\lambda$=259 nm. $^1$H NMR: (CD3OD) $\delta$ 8.06 (1H, s), 7.30-7.24 (2H, m), 7.13 (1H, m), 7.00-6.91 (4H, m), 6.86 (1H, m), 5.77 (1H, s), 4.40 (2H, s), 3.93 (2H, m), 3.45 (2H, m), 2.71 (1H, m), 1.65 (4H, m) ppm.

Example 205

Preparation of 4-(2,3-difluorobenzylamino)-6-(3-(tetrahydro-2H-pyran-4-yl)phenylamino)nicotinamide

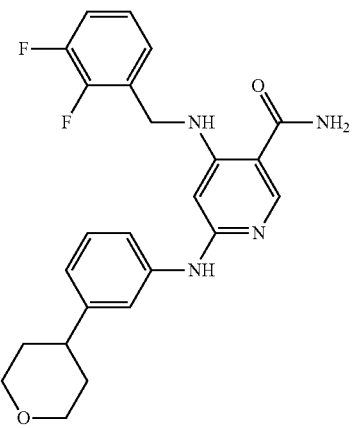 [SMILES: NC(=O)c1cnc(Nc2cccc(C3CCOCC3)c2)cc1NCc1cccc(F)c1F]

The title compound was synthesized using a procedure similar to that described in Example 139. MS found for C24H24F2N4O2 as (M+H)$^+$ 439.3. UV: $\lambda$=259 nm. $^1$H NMR: (CD3OD) $\delta$ 8.07 (1H, s), 7.26 (1H, t, J=8.0 Hz), 7.16-6.98 (5H, m), 6.92 (1H, m), 5.79 (1H, s), 4.46 (2H, s), 3.93 (2H, m), 3.46 (2H, m), 2.72 (1H, m), 1.66 (4H, m) ppm.

Example 206

Preparation of 4-(3,5-difluorobenzylamino)-6-(3-(tetrahydro-2H-pyran-4-yl)phenylamino)nicotinamide

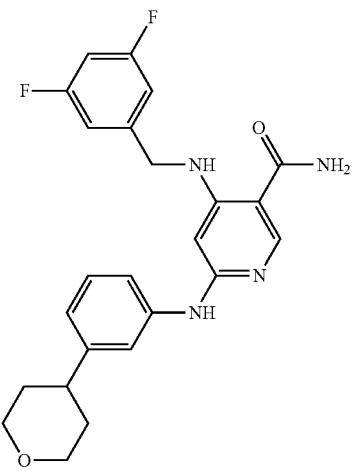 [SMILES: NC(=O)c1cnc(Nc2cccc(C3CCOCC3)c2)cc1NCc1cc(F)cc(F)c1]

The title compound was synthesized using a procedure similar to that described in Example 139. MS found for C24H24F2N4O2 as (M+H)+ 439.3. UV: λ=259 nm. $^1$H NMR: (CD3OD) δ 8.08 (1H, s), 7.23 (1H, t, J=8.0 Hz), 7.09 (1H, d, J=8.0 Hz), 7.00 (1H, t, J=2.0 Hz), 6.88 (1H, dm, J=8.0 Hz), 6.81-6.77 (3H, m), 5.71 (1H, s), 4.40 (2H, s), 3.93 (2H, m), 3.45 (2H, m), 2.71 (1H, m), 1.65 (4H, m) ppm.

Example 207

Preparation of 4-(2,5-difluorobenzylamino)-6-(3-(tetrahydro-2H-pyran-4-yl)phenylamino)nicotinamide

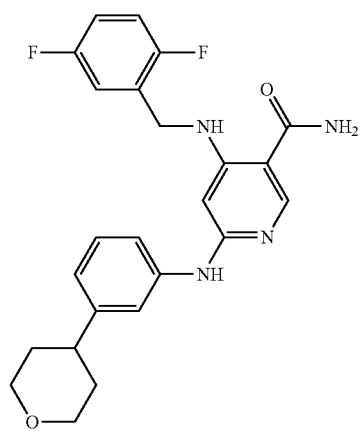 [SMILES: NC(=O)c1cnc(Nc2cccc(C3CCOCC3)c2)cc1NCc1cc(F)ccc1F]

The title compound was synthesized using a procedure similar to that described in Example 139. MS found for C24H24F2N4O2 as (M+H)+ 439.3. UV: λ=259 nm. $^1$H NMR: (CD3OD) δ 8.08 (1H, s), 7.25 (1H, t, J=8.0 Hz), 7.10-6.92 (6H, m), 5.79 (1H, s), 4.41 (2H, s), 3.94 (2H, m), 3.44 (2H, m), 2.71 (1H, m), 1.66 (4H, m) ppm.

Example 208

Preparation of 4-((5-fluoropyridin-3-yl)methylamino)-6-(3-(tetrahydro-2H-pyran-4-yl)phenylamino)nicotinamide

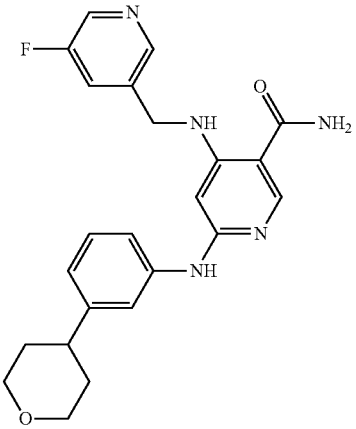 [SMILES: NC(=O)c1cnc(Nc2cccc(C3CCOCC3)c2)cc1NCc1cncc(F)c1]

The title compound was synthesized using a procedure similar to that described in Example 139. MS found for C23H24FN5O2 as (M+H)+ 422.3. UV: λ=259 nm. $^1$H NMR: (CD3OD) δ 8.54 (1H, d, J=2.8 Hz), 8.42 (1H, s), 8.15 (1H, s), 7.75 (1H, m), 7.38 (1H, t, J=8.0 Hz), 7.25 (1H, d, J=8.0 Hz), 7.10 (1H, t, J=2.0 Hz), 7.00 (1H, dm, J=8.0 Hz), 5.87 (1H, s), 4.64 (2H, s), 4.03 (2H, m), 3.56 (2H, m), 2.82 (1H, m), 1.74 (4H, m) ppm.

Example 209

Preparation of 4-(2,3-difluorobenzylamino)-6-(4-(piperidin-4-yl)phenylamino)nicotinamide

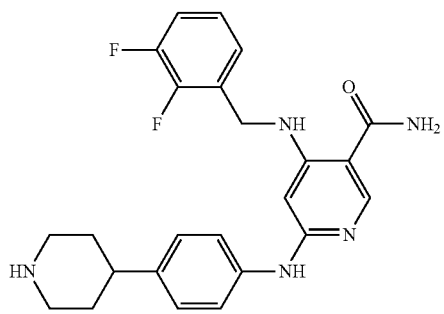 [SMILES: NC(=O)c1cnc(Nc2ccc(C3CCNCC3)cc2)cc1NCc1cccc(F)c1F]

The title compound was synthesized using a procedure similar to that described in Example 106. MS found for C24H25F2N5O as (M+H)+ 438.3. UV: λ=259 nm. $^1$H NMR: (CD3OD) δ 8.18 (1H, s), 7.35 (2H, dt, J=8.4; 2.0 Hz), 7.25 (1H, m), 7.17 (1H, m), 7.14 (2H, dt, J=8.4; 2.0 Hz), 7.11 (1H, m), 5.81 (1H, s), 4.55 (2H, s), 3.51 (2H, m), 3.17 (2H, m), 2.98 (1H, m), 2.11 (2H, m), 1.96 (2H, m) ppm.

Example 210

Preparation of 4-((1H-indazol-4-yl)methylamino)-6-(4-(1-propionylpiperidin-4-yl)phenylamino)nicotinamide

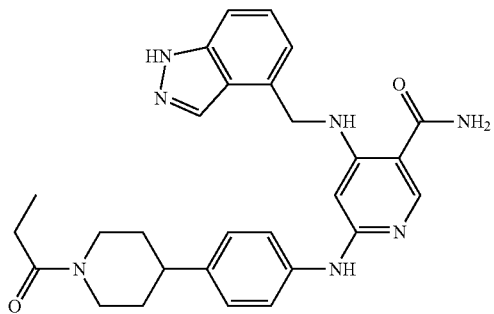 [SMILES: CCC(=O)N1CCC(c2ccc(Nc3cc(NCc4cccc5[nH]ncc45)c(C(N)=O)cn3)cc2)CC1]

The title compound was synthesized using a procedure similar to that described in Example 144. MS found for C28H31N7O2 as (M+H)+ 498.4. UV: λ=259 nm. ¹H NMR: (CD3OD) δ 8.14 (1H, d, J=1.2 Hz), 8.13 (1H, s), 7.53 (1H, d, J=8.4 Hz), 7.36 (1H, dd, J=8.4; 7.2 Hz), 7.14 (2H, dt, J=8.0; 1.6 Hz), 6.99 (1H, d, J=7.2 Hz), 6.90 (2H, dt, J=8.4; 2.0 Hz), 5.85 (1H, s), 4.70 (2H, s), 4.10 (1H, m), 2.82 (1H, m), 2.73 (1H, m), 2.47 (2H, q, J=8.0 Hz), 1.87 (2H, m), 1.58 (2H, m), 1.15 (3H, t, J=7.6 Hz) ppm.

Example 211

Preparation of 4-(benzo[b]thiophen-7-ylmethylamino)-6-(4-(1-propionylpiperidin-4-yl)phenylamino)nicotinamide

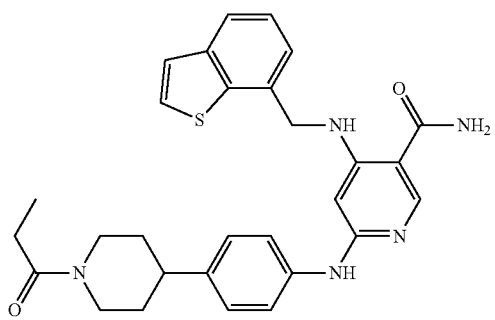 [SMILES: CCC(=O)N1CCC(c2ccc(Nc3cc(NCc4cccc5ccsc45)c(C(N)=O)cn3)cc2)CC1]

The title compound was synthesized using a procedure similar to that described in Example 144. MS found for C29H31N5O2S as (M+H)+ 514.3. UV: λ=259 nm. ¹H NMR: (CD3OD) δ 8.16 (1H, s), 7.85 (1H, m), 7.59 (1H, m), 7.47 (1H, m), 7.39 (1H, m), 7.22 (1H, m), 7.10 (2H, d, J=8.4 Hz), 6.88 (2H, d, J=8.4 Hz), 5.80 (1H, s), 4.72 (2H, s), 4.09 (1H, m), 2.76 (2H, m), 2.48 (2H, m), 1.85 (2H, m), 1.56 (2H, m), 1.16 (3H, t, J=7.2 Hz) ppm.

Example 212

Preparation of 6-(4-(azetidin-3-yl)phenylamino)-4-(2,3-difluorobenzylamino)nicotinamide

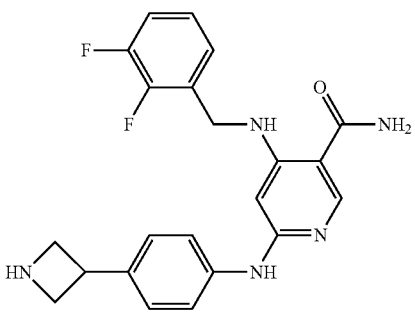 [SMILES: NC(=O)c1cnc(Nc2ccc(C3CNC3)cc2)cc1NCc1cccc(F)c1F]

The title compound was synthesized using a procedure similar to that described in Example 106. MS found for C22H21F2N5O as (M+H)+ 410.3. UV: λ=258 nm. ¹H NMR: (CD3OD) δ 8.21 (1H, s), 7.46 (2H, dt, J=8.4; 1.6 Hz), 7.25 (1H, m), 7.22 (2H, dt, J=8.4; 2.4 Hz), 7.17 (1H, m), 7.12 (1H, m), 5.82 (1H, s), 4.55 (2H, s), 4.43-4.24 (5H, m) ppm.

Example 213

Preparation of 6-(4-(azetidin-3-yl)phenylamino)-4-(2,5-difluorobenzylamino)nicotinamide

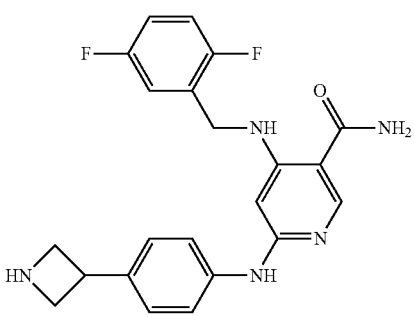 [SMILES: NC(=O)c1cnc(Nc2ccc(C3CNC3)cc2)cc1NCc1cc(F)ccc1F]

The title compound was synthesized using a procedure similar to that described in Example 106. MS found for C22H21F2N5O as (M+H)+ 410.3. UV: λ=257 nm. ¹H NMR: (CD3OD) δ 8.21 (1H, s), 7.44 (2H, d, J=8.0 Hz), 7.26 (2H, dt, J=8.4; 1.6 Hz), 7.19-7.02 (3H, m), 5.88 (1H, s), 4.50 (2H, s), 4.40 (2H, m), 4.33 (1H, m), 4.26 (2H, m) ppm.

Example 214

Preparation of 4-(2,5-difluorobenzylamino)-6-(4-(piperidin-4-yl)phenylamino)nicotinamide

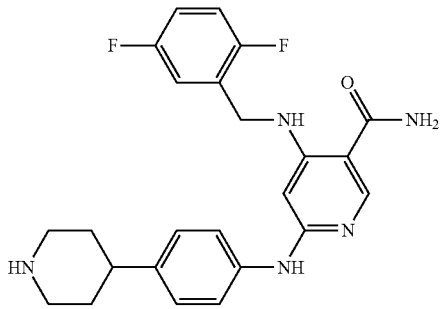 [SMILES: NC(=O)c1cnc(Nc2ccc(C3CCNCC3)cc2)cc1NCc1cc(F)ccc1F]

The title compound was synthesized using a procedure similar to that described in Example 106. MS found for C24H25F2N5O as (M+H)+ 438.3. UV: λ=257 nm. ¹H NMR: (CD3OD) δ 8.18 (1H, s), 7.37 (2H, dt, J=8.4; 2.0 Hz), 7.16 (2H, dt, J=8.4; 2.0 Hz), 7.15 (1H, m), 7.10 (1H, m), 7.04 (1H, m), 5.84 (1H, s), 4.51 (2H, s), 3.53 (2H, m), 3.17 (2H, m), 2.98 (1H, m), 2.11 (2H, m), 1.95 (2H, m) ppm.

Example 215

Preparation of 6-(4-(1-(cyanomethyl)piperidin-4-yl)phenylamino)-4-(2,3-difluorobenzylamino)nicotinamide

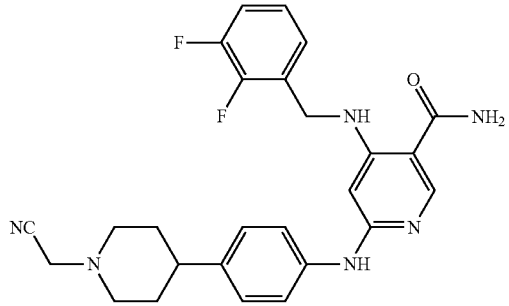 [SMILES: N#CCN1CCC(c2ccc(Nc3cc(NCc4cccc(F)c4F)c(C(N)=O)cn3)cc2)CC1]

Compound 4-(2,3-difluorobenzylamino)-6-(4-(piperidin-4-yl)phenylamino)nicotinamide (Example 209) (85 mg, 0.18 mmol) was dissolved in 3 mL NMP with DIEA (95 μL, 0.54 mmol). To it was added bromoacetonitrile (36 μL, 0.54 mmol). The mixture was stirred at RT for 40 m and quenched with TFA. The mixture was subjected to reverse phase preparative HPLC to isolate the title compound (75 mg). MS found for C26H26F2N6O as (M+H)+ 477.4. UV: λ=256 nm. ¹H NMR: (CD3OD) δ 8.17 (1H, s), 7.37 (2H, d, J=8.4 Hz), 7.25 (1H, m), 7.19-7.08 (4H, m), 5.82 (1H, s), 4.55 (2H, s), 4.43 (2H, s), 3.67 (2H, d, J=11.6 Hz), 3.23 (2H, t, J=12.0 Hz), 2.95 (1H, m), 2.19-2.03 (4H, m) ppm.

Example 216

Preparation of 4-(2,3-difluorobenzylamino)-6-(4-(1-(2,2-difluoroethyl)piperidin-4-yl)phenylamino)nicotinamide

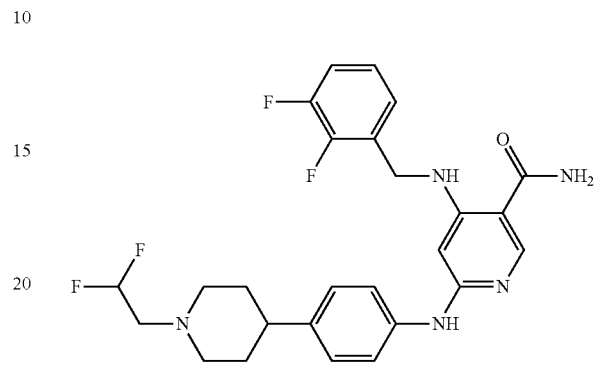

The title compound was synthesized using a procedure similar to that described in Example 215 with 2,2-difluoroethyl trifluoromethanesulfonate. MS found for C26H27F4N5O as (M+H)+ 502.4. UV: λ=256 nm. ¹H NMR: (CD3OD) δ 8.18 (1H, s), 7.37 (2H, d, J=8.8 Hz), 7.26 (1H, m), 7.19-7.14 (3H, m), 7.10 (1H, m), 6.48 (1H, tt, J=53.6; 3.6 Hz), 5.81 (1H, s), 4.55 (2H, s), 3.75 (4H, m), 3.35 (2H, m), 2.99 (1H, m), 2.15 (4H, m) ppm.

Example 217

Preparation of 4-(2,3-difluorobenzylamino)-6-(4-(1-(2-fluoroethyl)piperidin-4-yl)phenylamino)nicotinamide

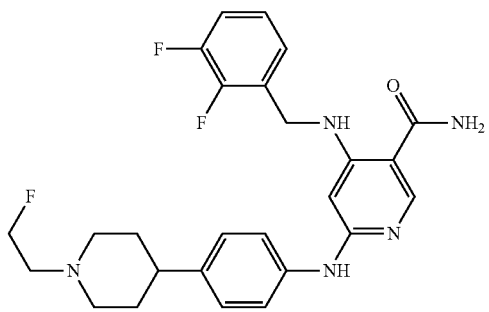 [SMILES: NC(=O)c1cnc(Nc2ccc(C3CCN(CCF)CC3)cc2)cc1NCc1cccc(F)c1F]

Compound 4-(2,3-difluorobenzylamino)-6-(4-(piperidin-4-yl)phenylamino)nicotinamide (Example 209) (85 mg, 0.18 mmol) was dissolved in 3 mL NMP with DIEA (95 μL, 0.54 mmol). To it was added 1-bromo-2-fluoroethane (230 mg, 1.8 mmol). The mixture was stirred at RT for overnight. The reaction was about 70% completion. It was quenched with TFA and concentrated in vacuo. The mixture was subjected to reverse phase preparative HPLC to isolate the title compound (53 mg). MS found for C26H28F3N5O as (M+H)+ 484.4. UV: λ=256 nm. ¹H NMR: (CD3OD) δ 8.19 (1H, s), 7.37 (2H, d, J=8.4 Hz), 7.25 (1H, m), 7.19-7.14 (3H, m), 7.10 (1H, m), 5.82 (1H, s), 4.97 (1H, m), 4.85 (1H, m), 4.55 (2H, s), 3.77

(2H, d, J=12.0 Hz), 3.62 (1H, m), 3.55 (1H, m), 3.28 (2H, m), 3.00 (1H, m), 2.15 (4H, m) ppm.

Example 218

Preparation of 6-(4-(1-(cyanomethyl)piperidin-4-yl) phenylamino)-4-(2,5-difluorobenzylamino)nicotinamide

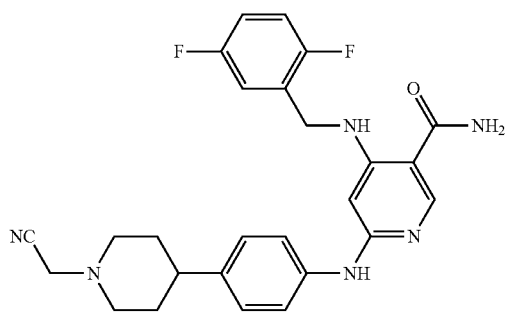 [SMILES: N#CCN1CCC(c2ccc(Nc3cc(NCc4cc(F)ccc4F)c(C(N)=O)cn3)cc2)CC1]

The title compound was synthesized using a procedure similar to that described in Example 215 with 4-(2,5-difluorobenzylamino)-6-(4-(piperidin-4-yl)phenylamino)nicotinamide (Example 214). MS found for C26H26F2N6O as (M+H)+ 477.4. UV: λ=259 nm. ¹H NMR: (CD3OD) δ 8.17 (1H, s), 7.38 (2H, dt, J=8.4; 1.6 Hz), 7.20-7.14 (3H, m), 7.11 (1H, m), 7.04 (1H, m), 5.84 (1H, s), 4.51 (2H, s), 4.47 (2H, s), 3.70 (2H, d, J=12.4 Hz), 3.27 (2H, m), 2.97 (1H, m), 2.18 (2H, m), 2.08 (2H, m) ppm.

Example 219

Preparation of 6-(4-(1-(cyanomethyl)azetidin-3-yl) phenylamino)-4-(2,3-difluorobenzylamino)nicotinamide

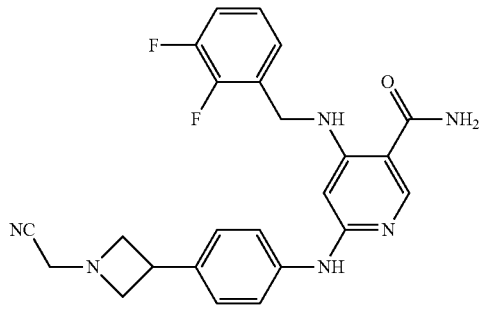 [SMILES: N#CCN1CC(c2ccc(Nc3cc(NCc4cccc(F)c4F)c(C(N)=O)cn3)cc2)C1]

The title compound was synthesized using a procedure similar to that described in Example 215 with 6-(4-(azetidin-3-yl)phenylamino)-4-(2,3-difluorobenzylamino)nicotinamide (Example 212). MS found for C24H22F2N6O as (M+H)+ 449.3. UV: λ=259 nm. ¹H NMR: (CD3OD) δ 8.18 (1H, s), 7.49 (2H, dt, J=8.8; 2.0 Hz), 7.29-7.09 (5H, m), 5.83 (1H, s), 4.59 (2H, s), 4.35 (1H, m), 4.26 (1H, m), 4.12 (4H, m), 3.86 (1H, m) ppm.

Example 220

Preparation of 6-(4-(1-(cyanomethyl)azetidin-3-yl) phenylamino)-4-(2,5-difluorobenzylamino)nicotinamide

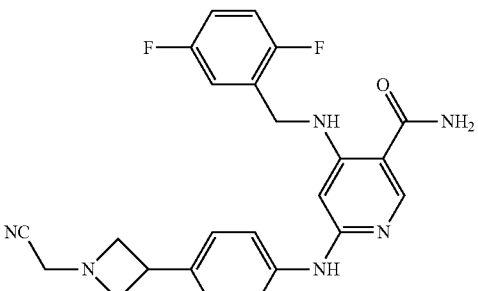

The title compound was synthesized using a procedure similar to that described in Example 215 with 6-(4-(azetidin-3-yl)phenylamino)-4-(2,5-difluorobenzylamino)nicotinamide (Example 213). MS found for C24H22F2N6O as (M+H)+ 449.4. UV: λ=259 nm. ¹H NMR: (CD3OD) δ 8.18 (1H, s), 7.50 (2H, dt, J-8.4; 2.0 Hz), 7.26-7.03 (5H, m), 5.88 (1H, s), 4.52 (2H, s), 4.39-4.16 (6H, m), 3.88 (1H, m) ppm.

Example 221

Preparation of 4-((1H-indol-4-yl)methylamino)-6-(4-(1-(cyanomethyl)piperidin-4-yl)phenylamino)nicotinamide

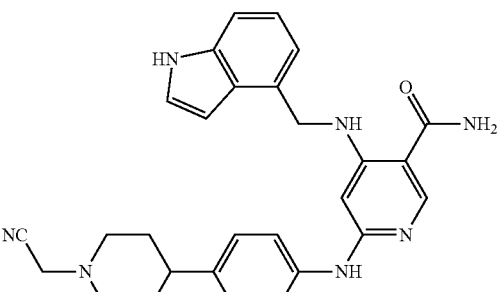

The title compound was synthesized using a procedure similar to that described in Example 215. MS found for C28H29N7O as (M+H)+ 480.4. UV: λ=268 nm. ¹H NMR: (CD3OD) δ 8.04 (1H, s), 7.30 (1H, d, J=7.6 Hz), 7.18 (1H, d, J=3.6 Hz), 7.08 (2H, d, J=8.4 Hz), 7.00 (1H, t, J=8.0 Hz), 6.84 (2H, dt, J=8.4; 2.0 Hz), 6.78 (1H, d, J=7.6 Hz), 6.41 (1H, d, J=7.2 Hz), 5.84 (1H, s), 4.63 (2H, s), 4.14 (2H, s), 3.39 (2H, m), 2.92 (2H, m), 2.70 (1H, m), 1.95 (2H, m), 1.84 (2H, m) ppm.

Example 222

6-(3-acetamidophenylamino)-4-(thiophen-2-ylmethylamino)nicotinamide

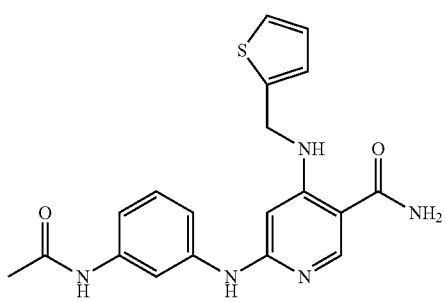 [SMILES: CC(=O)Nc1cccc(Nc2cc(NCc3cccs3)c(C(N)=O)cn2)c1]

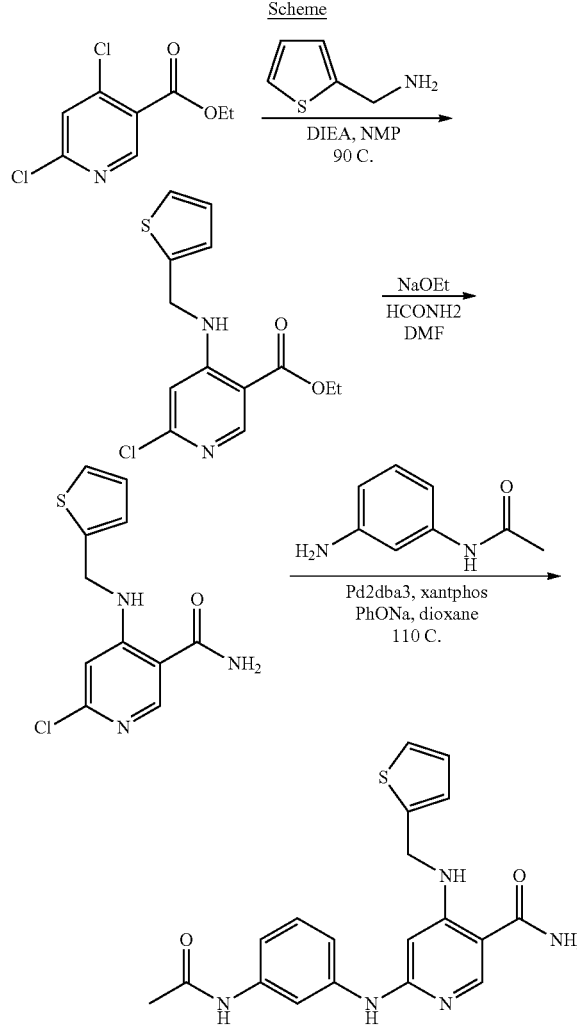

A solution of ethyl 4,6-dichloronicotinate (1.14 g, 5.18 mmol), 2-thiophenemethylamine (0.530 mL, 5.17 mmol) and DIEA (1.80 mL, 10.3 mmol) in NMP (10 mL) was stirred at 90 C for 18 h. Water and EtOAc were added. The organic phase was washed with water, then was dried over Na2SO4, concentrated in vacuo to give ethyl 6-chloro-4-(thiophen-2-ylmethylamino)nicotinate as an oil (1.54 g).

To a solution of ethyl 6-chloro-4-(thiophen-2-ylmethylamino)nicotinate (1.54 g, 5.19 mmol) in DMF (8 mL) and HCONH2 (2 mL, 50.3 mmol), NaOEt (21% by wt., 7.80 mL, 20.9 mmol) in EtOH was added. The mixture was stirred at room temperature for 20 min. HOAc (2 mL) was added to neutralize NaOEt. Water was then added to induce precipitation. The precipitate was collected, dried on vacuum to give 6-chloro-4-(thiophen-2-ylmethylamino)nicotinamide as a solid (1.10 g).

A mixture of 6-chloro-4-(thiophen-2-ylmethylamino)nicotinamide (100 mg, 0.373 mmol), 3'-aminoacetanilide (65 mg, 0.433 mmol), PhONa trihydrate (80 mg, 0.471 mmol), xantphos (30 mg, 0.051 mmol) and Pd2 dba3 (20 mg, 0.021 mmol) in dioxane (2 mL) was degassed with Ar, then was stirred at 110 C for 3 h. Water and EtOAc were added. The mixture was filtered. The organic phase was separated, washed with aq. 1N NaOH, dried over Na2SO4, concentrated in vacuo. The residue was purified by HPLC to give the titled compound (18 mg). MS 382.3 (M+H); UV 251.0 nm; t 0.465 min.

Example 224

4-(3-(1H-imidazol-1-yl)benzylamino)-6-(4-(dimethylcarbamoyl)phenylamino)nicotinamide

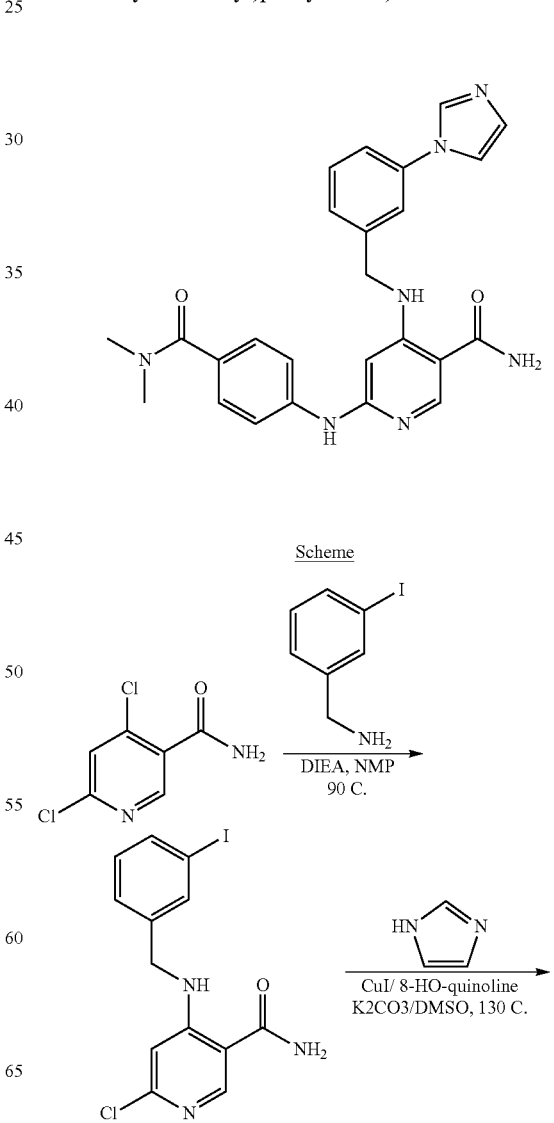

-continued

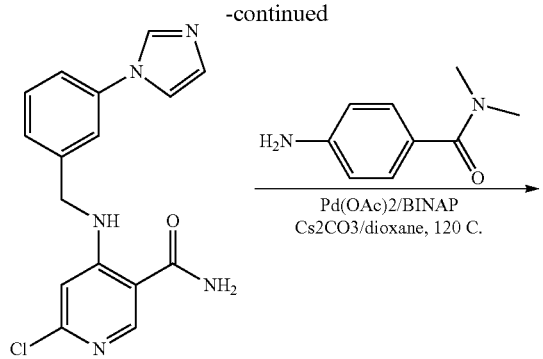

Pd(OAc)2/BINAP
Cs2CO3/dioxane, 120 C.

A solution of 4,6-dichloronicotinamide (400 mg, 2.09 mmol), 3-iodobenzylamine (0.285 mL, 2.13 mmol) and DIEA (0.500 mL, 2.87 mmol) in NMP (5 mL) was stirred at 90 C for 48 h. Water and EtOAc were added. Organic phase was separated, dried over Na2SO4, concentrated in vacuo. The residue was purified by a silica gel column, eluted with 0-100% EtOAc in hexane to give 6-chloro-4-(3-iodobenzylamino)nicotinamide as a solid (266 mg).

A mixture of 6-chloro-4-(3-iodobenzylamino)nicotinamide (130 mg, 0.335 mmol), imidazole (30 mg, 0.441 mmol), 8-hydroxyquinoline (15 mg, 0.103 mmol), K2CO3 (60 mg, 0.434 mmol) and CuI (15 mg, 0.078 mmol) in DMSO (1 mL) was degassed with Ar, then was stirred at 130 C for 2 h. The mixture was purified by HPLC to give 4-(3-(1H-imidazol-1-yl)benzylamino)-6-chloronicotinamide (56 mg).

A mixture of 4-(3-(1H-imidazol-1-yl)benzylamino)-6-chloronicotinamide (56 mg, 0.170 mmol), 4-amino-N,N-dimethylbenzamide (42 mg, 0.256 mmol), Cs2CO3 (110 mg, 0.337 mmol), BINAP (25 mg, 0.040 mmol) and Pd(OAc)2 (15 mg, 0.066 mmol) in dioxane (2 mL) was degassed with Ar, then was stirred at 120 C for 3 h. The mixture was concentrated in vacuo, the residue was purified by HPLC to give the titled compound (7 mg). MS 456.3 (M+H); UV 257.8 nm; t 0.344 min.

| Example | Structure | Formula | MS (M + H)+ | NB | Pg |
|---|---|---|---|---|---|
| 228 | 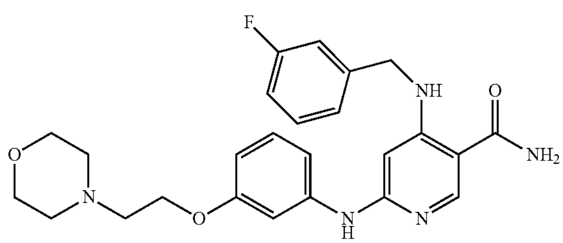 [SMILES: NC(=O)c1cnc(Nc2cccc(OCCN3CCOCC3)c2)cc1NCc1cccc(F)c1] | C25H28FN5O3 | 466.6 | PN-00747 | 66A |
| 229 | 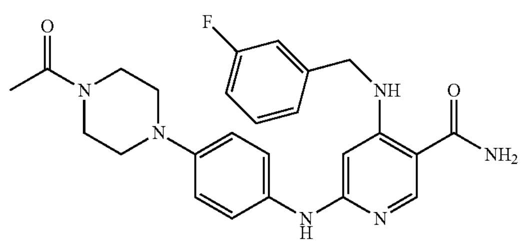 [SMILES: CC(=O)N1CCN(c2ccc(Nc3cc(NCc4cccc(F)c4)c(C(N)=O)cn3)cc2)CC1] | C25H27FN6O2 | 463.5 | PN-00747 | 67B |
| 230 | 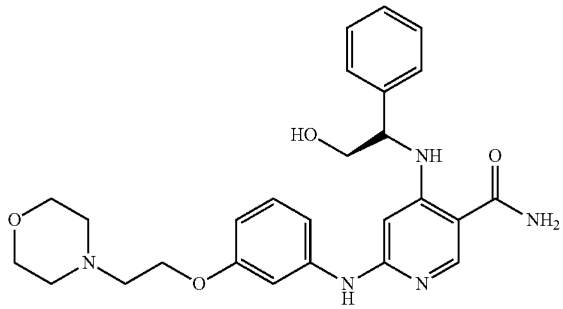 | C26H31N5O4 | 478.5 | PN-00747 | 79A |

-continued

| Example | Structure | Formula | MS (M + H)+ | NB | Pg |
|---|---|---|---|---|---|
| 231 | 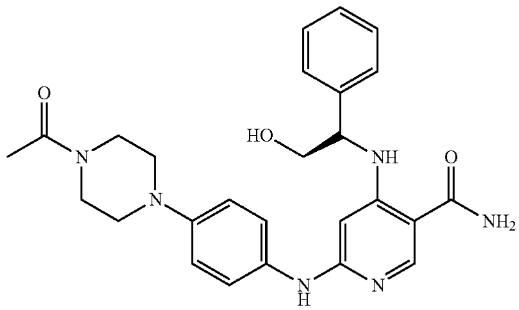 | C26H30N6O3 | 475.5 | PN-00747 | 79D |
| 232 | 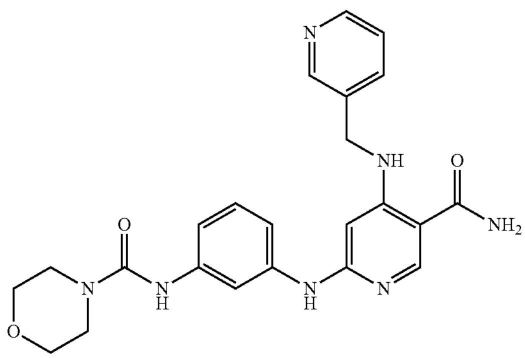 [SMILES: NC(=O)c1cnc(Nc2cccc(NC(=O)N3CCOCC3)c2)cc1NCc1cccnc1] | C23H25N7O3 | 448.2 | PN-00747 | 80D |
| 233 | 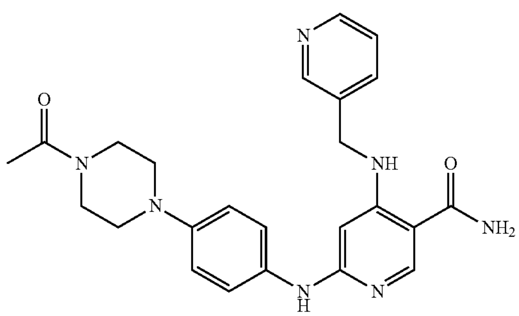 [SMILES: CC(=O)N1CCN(c2ccc(Nc3cc(NCc4cccnc4)c(C(N)=O)cn3)cc2)CC1] | C24H27N7O2 | 446.5 | PN-00747 | 81D |

Example 234

6-(4-(4-acetylpiperazin-1-yl)phenylamino)-4-(isopropylamino)nicotinamide

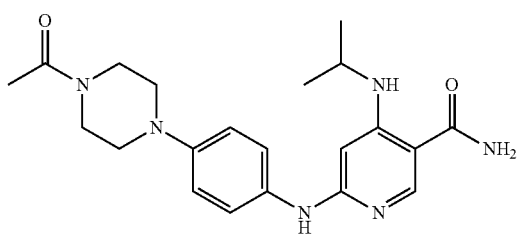 [SMILES: CC(=O)N1CCN(c2ccc(Nc3cc(NC(C)C)c(C(N)=O)cn3)cc2)CC1]

The title compound was synthesized using a procedure similar to that described in Example 36. MS found for C21H28N6O2 as (M+H)+ 397.4. UV: λ=204, 258 nm. $^1$H NMR: (CD3OD) δ 8.09 (s, 1H), 7.23 (d, 2H), 7.13 (d, 2H), 5.88 (s, 1H), 3.77 (m, 8H), 3.22 (m, 1H), 2.17 (s, 3H), 1.27 (d, 6H).

Example 235

6-(4-(4-acetylpiperazin-1-yl)phenylamino)-4-(isobutylamino)nicotinamide

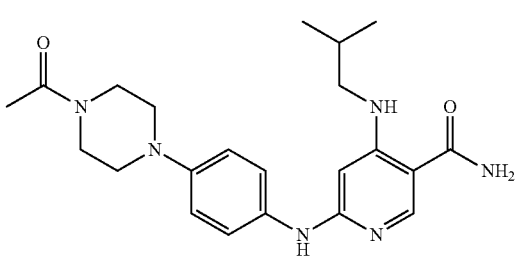 [SMILES: CC(=O)N1CCN(c2ccc(Nc3cc(NCC(C)C)c(C(N)=O)cn3)cc2)CC1]

The title compound was synthesized using a procedure similar to that described in Example 36. using the following procedure for Step 4:

(R)-6-chloro-4-(1-phenylethylamino)nicotinamide (50 mg, 0.19 mmol), 3-aminoacetanilide (57 mg, 0.38 mmol) Cs$_2$CO$_3$ (124 mg, 0.38 mmol) biphenyl-2-yldicyclohexylphosphine (20 mg, 0.057 mmol) and Pd(dba)$_3$ (22 mg, 0.038 mmol) were combined and diluted with degassed dioxane (2 mL). The resulting mixture was then stirred at 100° C. overnight. The following morning the mixture was diluted with water, acetonitrile, and TFA; and the mixture purified by preparative HPLC affording 20 mg of the desired product. MS found for C22H30N6O2 as (M+H)$^+$ 411.4. UV: λ=205, 261 nm. $^1$H NMR: (CD3OD) δ 8.04 (s, 1H), 7.20 (d, 2H), 7.09 (d, 2H), 5.83 (s, 1H), 3.72 (m, 4H), 3.24 (m, 4H), 3.05 (d, 2H), 2.18 (s, 3H), 1.97 (m, 1H), 1.03 (d, 6H).

Example 238

6-(4-(4-acetylpiperazin-1-yl)phenylamino)-4-(cyclopropylmethylamino)nicotinamide

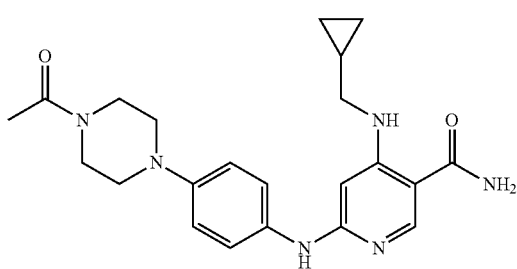 [SMILES: CC(=O)N1CCN(c2ccc(Nc3cc(NCC4CC4)c(C(N)=O)cn3)cc2)CC1]

The title compound was synthesized using a procedure similar to that described in Example 36. MS found for C22H28N6O2 as (M+H)$^+$ 409.2. UV: λ=205, 258 nm. $^1$H NMR: (CD3OD) δ 8.04 (s, 1H), 7.19 (d, 2H), 7.08 (d, 2H), 5.83 (s, 1H), 3.71 (m, 4H), 3.22 (m, 4H), 3.04 (d, 2H), 2.14 (s, 3H), 1.12 (m, 1H), 0.62 (m, 2H), 0.31 (m, 2H).

Example 239

6-(4-(4-acetylpiperazin-1-yl)phenylamino)-4-(cyclopentylamino)nicotinamide

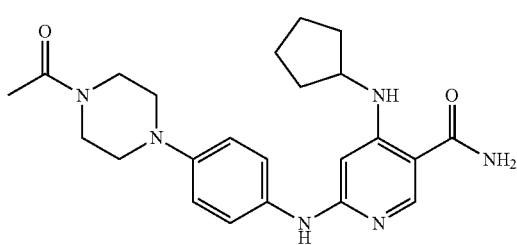 [SMILES: CC(=O)N1CCN(c2ccc(Nc3cc(NC4CCCC4)c(C(N)=O)cn3)cc2)CC1]

The title compound was synthesized using a procedure similar to that described in Example 36. MS found for C23H30N6O2 as (M+H)$^+$ 423.3. UV: λ=204, 261 nm. $^1$H NMR: (CD3OD) δ 8.02 (s, 1H), 7.21 (d, 2H), 7.08 (d, 2H), 5.82 (s, 1H), 3.82 (m, 1H), 3.73 (m, 4H), 3.22 (m, 4H), 2.13 (s, 3H), 1.99 (m, 2H), 1.85 (m, 2H), 1.71 (m, 2H), 1.66 (m, 2H).

Example 243

6-(4-(4-acetylpiperazin-1-yl)phenylamino)-4-(cyclobutylmethylamino)nicotinamide

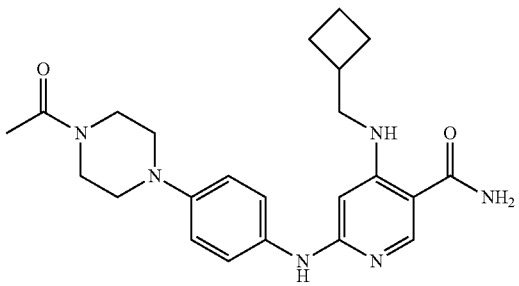 [SMILES: CC(=O)N1CCN(c2ccc(Nc3cc(NCC4CCC4)c(C(N)=O)cn3)cc2)CC1]

The title compound was synthesized using a procedure similar to that described in Example 36. MS found for C23H30N6O2 as (M+H)$^+$ 423.3. UV: λ=207, 258 nm. 1H NMR: (CD3OD) δ 8.02 (s, 1H), 7.19 (d, 2H), 7.08 (d, 2H), 5.83 (s, 1H), 3.69 (m, 4H), 3.19 (m, 4H), 2.63 (m, 1H), 2.17 (s, 3H), 2.14 (m, 2H), 1.97 (m, 2H), 1.97 (m, 2H).

Example 245

6-(4-(4-acetylpiperazin-1-yl)phenylamino)-4-(cyclopentylmethylamino)nicotinamide

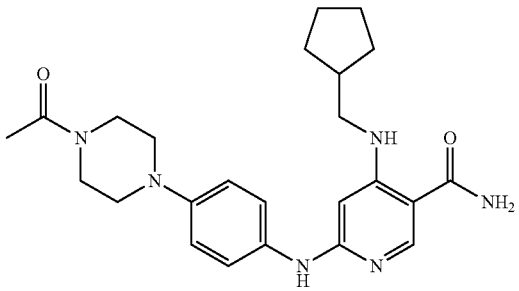 [SMILES: CC(=O)N1CCN(c2ccc(Nc3cc(NCC4CCCC4)c(C(N)=O)cn3)cc2)CC1]

The title compound was synthesized using a procedure similar to that described in Example 36. MS found for C24H32N6O2 as (M+H)$^+$ 437.3. UV: λ=205, 258 nm. 1H NMR: (CD3OD) δ 8.03 (s, 1H), 7.22 (d, 2H), 7.09 (d, 2H), 5.08 (s, 1H), 3.77 (m, 4H), 3.22 (m, 4H), 3.09 (d, 2H), 2.21 (m, 1H), 2.15 (s, 3H), 1.84 (m, 2H), 1.62 (m, 4H), 1.28 (m, 2H).

Example 246

4-(benzylamino)-6-(3-(methylcarbamoyl)phenylamino)nicotinamide

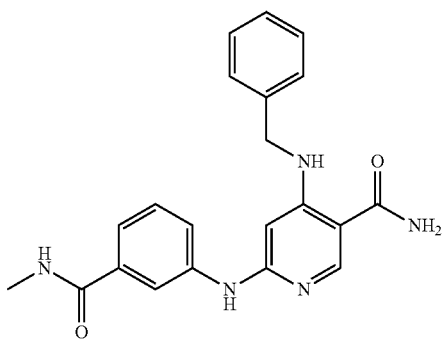 [SMILES: CNC(=O)c1cccc(Nc2cc(NCc3ccccc3)c(C(N)=O)cn2)c1]

The title compound was synthesized using a procedure similar to that described in Scheme 1. MS found for C21H21N5O2 as (M+H)+ 376.3. UV: λ=204, 256 nm. 1H NMR: (CD3OD) δ 8.16 (s, 1H), 17.67 (m, 2H), 7.48 (t, 1H), 7.27 (m, 6H), 5.92 (s, 1H), 4.80 (s, 2H), 2.93 (s, 3H).

Example 247

4-(benzylamino)-6-(3-(dimethylcarbamoyl)phenylamino)nicotinamide

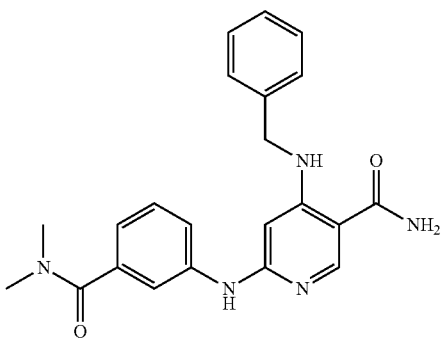 [SMILES: CN(C)C(=O)c1cccc(Nc2cc(NCc3ccccc3)c(C(N)=O)cn2)c1]

The title compound was synthesized using a procedure similar to that described in Example 36. MS found for C22H23N5O2 as (M+H)+ 390.3. UV: λ=212, 256. nm. 1H NMR: (CD3OD) δ 816 (s, 1H), 7.49 (t, 1H), 7.34 (d, 2H), 7.29 (m, 5H), 7.20 (d, 1H), 5.98 (s, 1H), 4.51 (s, 2H), 3.12 (s, 3H), 3.01 (s, 3H).

Example 248

4-(benzylamino)-6-(4-(dimethylcarbamoyl)phenylamino)nicotinamide

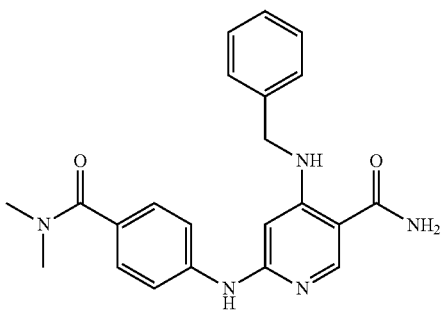 [SMILES: CN(C)C(=O)c1ccc(Nc2cc(NCc3ccccc3)c(C(N)=O)cn2)cc1]

The title compound was synthesized using a procedure similar to that described in Example 36. MS found for C22H23N5O2 as (M+H)+ 390.2. UV: λ=210, 261 nm. 1H NMR: (CD3OD) δ 8.18 (s, 1H), 7.28-7.43 (m, 7H), 7.15 (m, 2H), 6.01 (s, 1H), 4.52 (s, 2H), 3.13 (s, 3H), 3.06 (s, 3H).

Example 249

4-(benzylamino)-6-(3-(piperidine-1-carbonyl)phenylamino)nicotinamide

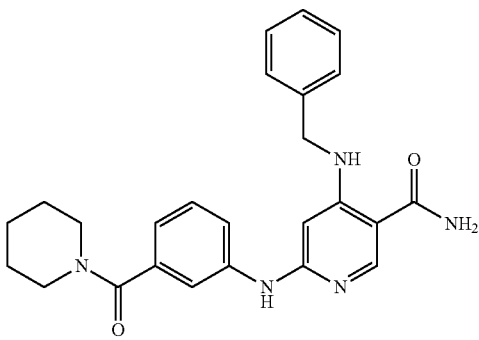 [SMILES: NC(=O)c1cnc(Nc2cccc(C(=O)N3CCCCC3)c2)cc1NCc1ccccc1]

The title compound was synthesized using a procedure similar to that described in Example 36. MS found for C25H27N5O2 as (M+H)+ 430.3. UV: λ=202, 258 nm. 1H NMR: (CD3OD) δ 8.15 (s, 1H), 7.48 (m, 1H), 7.19-7.34 (m, 8H), 5.99 (s, 1H), 4.51 (s, 2H), 3.71 (m, 2H), 3.38 (m, 2H), 1.69 (4H), 1.54 (m, 2H).

Example 250

4-(benzylamino)-6-(4-morpholinophenylamino)nicotinamide

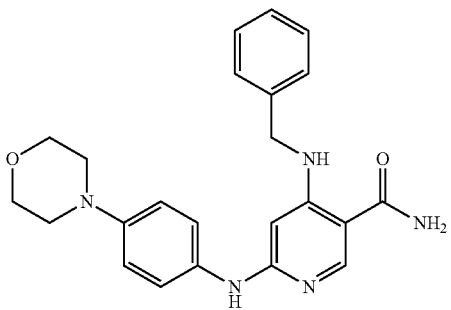 [SMILES: NC(=O)c1cnc(Nc2ccc(N3CCOCC3)cc2)cc1NCc1ccccc1]

The title compound was synthesized using a procedure similar to that described in Example 36. MS found for C23H25N5O2 as (M+H)+ 404.3. UV: λ=202, 258 nm. 1H NMR: (CD3OD) δ8.06 (s, 1H), 7.32 (m, 3H), 7.27 (d, 2H), 7.00 (s (with shoulders), 4H), 5.77 (s, 1H), 4.44 (s, 2H), 3.86 (m, 4H), 3.19 (m, 4H).

Example 251

4-(benzylamino)-6-(3-chloro-4-morpholinophenylamino)nicotinamide

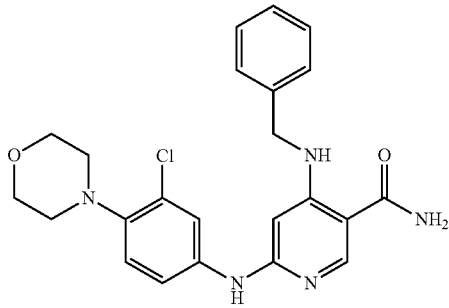 [SMILES: NC(=O)c1cnc(Nc2ccc(N3CCOCC3)c(Cl)c2)cc1NCc1ccccc1]

The title compound was synthesized using a procedure similar to that described in Example 36. MS found for C23H24ClN5O2 as (M+H)+ 438.2, 440.2. UV: λ=212, 249 nm. 1H NMR: (CD3OD) δ 8.12 (s, 1H), 7.29-7.37 (m, 4H), 7.26 (d, 2H), 7.14 (d, 1H), 7.02 (d, 1H), 5.84 (s, 1H), 4.80 (s, 2H), 3.87 (m, 4H), 3.08 (m, 4H).

Example 252

6-(4-(4-acetylpiperazin-1-yl)phenylamino)-4-(4-fluorobenzylamino)nicotinamide

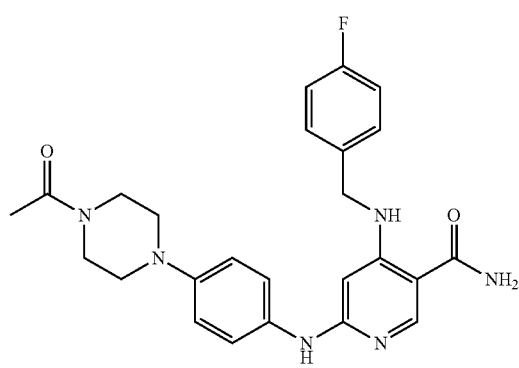 [SMILES: CC(=O)N1CCN(c2ccc(Nc3cc(NCc4ccc(F)cc4)c(C(N)=O)cn3)cc2)CC1]

The title compound was synthesized using a procedure similar to that described in Example 36. MS found for C25H27FN6O2 as (M+H)+ 463.2. UV: λ=202, 258 nm. 1H NMR: (CD3OD) δ 8.07 (s, 1H), 7.27 (m, 2H), 7.06 (m, 6H), 5.75 (s, 1H), 4.43 (s, 2H), 3.74 (m, 4H), 3.23 (m, 4H), 2.17 (s, 3H).

Example 253

6-(4-(4-acetylpiperazin-1-yl)phenylamino)-4-(2,3-dihydro-1H-inden-2-ylamino)nicotinamide

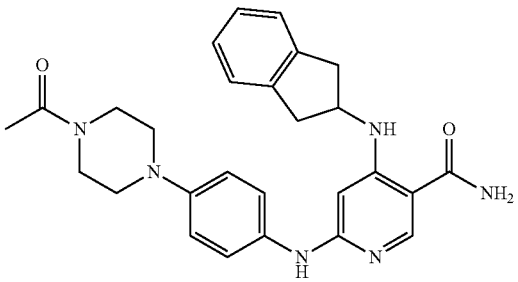 [SMILES: CC(=O)N1CCN(c2ccc(Nc3cc(NC4Cc5ccccc5C4)c(C(N)=O)cn3)cc2)CC1]

The title compound was synthesized using a procedure similar to that described in Example 36. MS found for C27H30N6O2 as (M+H)+ 471.2. UV: λ=202, 256 nm. 1H NMR: (CD3OD) δ 8.04 (sm, 1H), 7.03-7.28 (m, 8H), 5.97 (1H), 4.29 (m, 1H), 3.70 (m, 4H), 3.32 (m, 1H), 2.91 (m, 2H), 2.10 (s, 3H).

Example 254

6-(4-(4-acetylpiperazin-1-yl)phenylamino)-4-(benzo[d][1,3]dioxol-5-ylmethylamino)nicotinamide

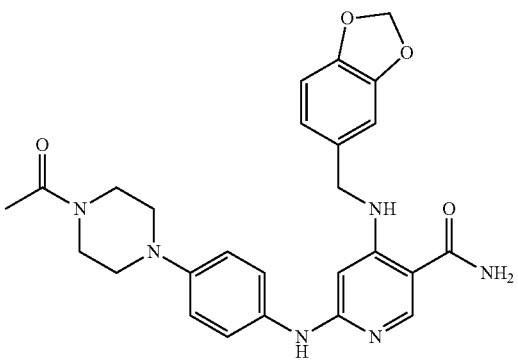 [SMILES: CC(=O)N1CCN(c2ccc(Nc3cc(NCc4ccc5c(c4)OCO5)c(C(N)=O)cn3)cc2)CC1]

The title compound was synthesized using a procedure similar to that described in Example 36. MS found for C26H28N6O4 as (M+H)+ 489.2. UV: λ=202, 246 nm. 1H NMR: (CD3OD) δ 8.13 (s, 1H), 7.08 (s, 4H), 6.82 (m, 3H), 5.98 (s, 2H), 5.81 (s, 1H), 4.37 (s, 2H), 3.77 (m, 4H), 3.22 (m, 4H), 2.18 (s, 3H).

Example 255

(S)-6-(4-(4-acetylpiperazin-1-yl)phenylamino)-4-(2,3-dihydro-1H-inden-1-ylamino)nicotinamide

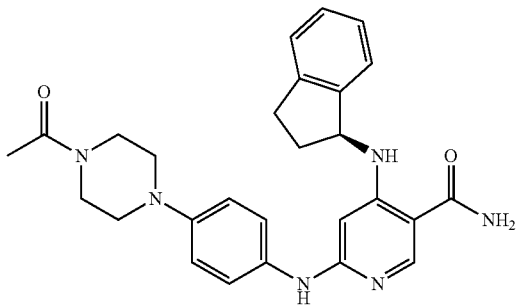 [SMILES: CC(=O)N1CCN(c2ccc(Nc3cc(N[C@H]4CCc5ccccc54)c(C(N)=O)cn3)cc2)CC1]

The title compound was synthesized using a procedure similar to that described in Example 36. MS found for C27H30N6O2 as (M+H)+ 471.2. UV: λ=205, 261 nm. 1H NMR: (CD3OD) δ 8.09 (s, 1H), 7.21-7.34 (m, 6H), 7.08 (d, 2H), 6.08 (s, 1H), 5.04 (m, 1H), 3.72 (m, 4H), 3.19 (m, 4H), 3.03 (m, 1H), 2.92 (m, 1H), 2.59 (m, 1H), 2.16 (s, 3H), 1.98 (m, 1H).

Example 256

Example S53 ( ) 6-(4-(4-acetylpiperazin-1-yl)phenylamino)-4-(2,3-difluorobenzylamino)nicotinamide

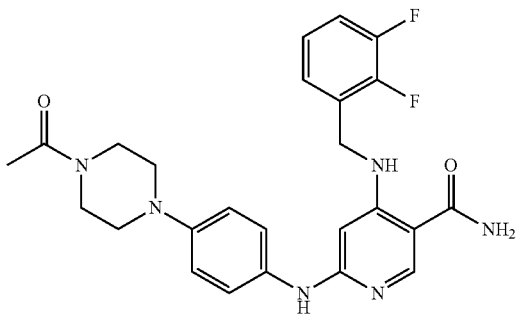 [SMILES: CC(=O)N1CCN(c2ccc(Nc3cc(NCc4cccc(F)c4F)c(C(N)=O)cn3)cc2)CC1]

The title compound was synthesized using a procedure similar to that described in Example 36. MS found for C25H26F2N6O2 as (M+H)+ 481.2. UV: λ=202, 246 nm. 1H NMR: (CD3OD) δ 8.09 (s, 1H), 7.23 (m, 1H), 7.15 (m, 1H), 7.07 (m, 5H), 5.72 (s, 1H), 4.54 (s, 2H), 3.73 (m, 4H), 3.23 (m, 4H), 2.17 (s, 3H).

Example 257

6-(4-(4-acetylpiperazin-1-yl)phenylamino)-4-(3-chlorobenzylamino)nicotinamide

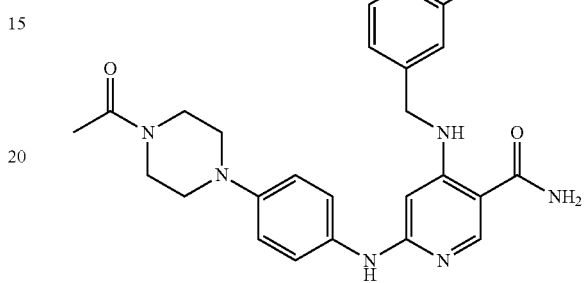

The title compound was synthesized using a procedure similar to that described in Example 36. MS found for C25H27ClN6O2 as (M+H)+ 479.2. 1H NMR: (CD3OD) δ 8.09 (s, 1H), 7.31 (m, 3H), 7.19 (d, 1H), 7.01 (s, 4H), 5.71 (s, 1H), 4.67 (s, 2H), 3.73 (m, 4H), 3.24 (m, 4H), 2.17 (s, 3H).

Example 258

6-(4-(4-acetylpiperazin-1-yl)phenylamino)-4-(2-fluorobenzylamino)nicotinamide

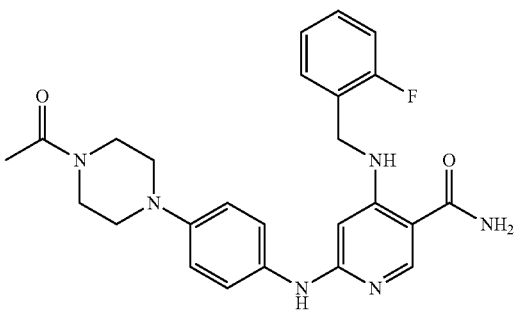 [SMILES: CC(=O)N1CCN(c2ccc(Nc3cc(NCc4ccccc4F)c(C(N)=O)cn3)cc2)CC1]

The title compound was synthesized using a procedure similar to that described in Example 36. MS found for C25H27FN6O2 as (M+H)+ 463.4. UV: λ=205, 249 nm. 1H NMR: (CD3OD) δ 8.13 (s, 1H), 7.40 (m, 1H), 7.31 (m, 1H), 7.18 (m, 2H), 7.08 (d (with shoulders), 4H), 5.82 (s, 1H), 4.54 (s, 2H), 3.76 (m, 4H), 3.26 (m, 4H), 2.18 (s, 3H).

Example 259

6-(4-(4-acetylpiperazin-1-yl)phenylamino)-4-(2,4-difluorobenzylamino)nicotinamide

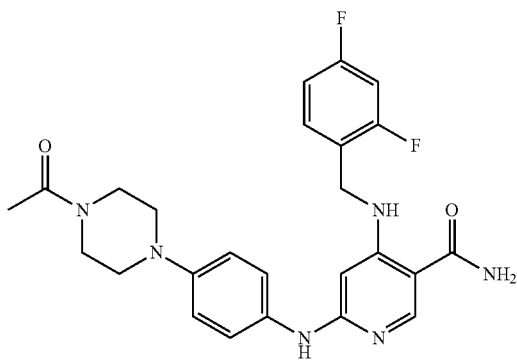 [SMILES: CC(=O)N1CCN(c2ccc(Nc3cc(NCc4ccc(F)cc4F)c(C(N)=O)cn3)cc2)CC1]

The title compound was synthesized using a procedure similar to that described in Example 36. MS found for C25H26F2N6O2 as (M+H)+ 481.4.

Example 260

(S)-4-(2-methoxy-1-phenylethylamino)-6-(4-methoxyphenylamino)nicotinamide

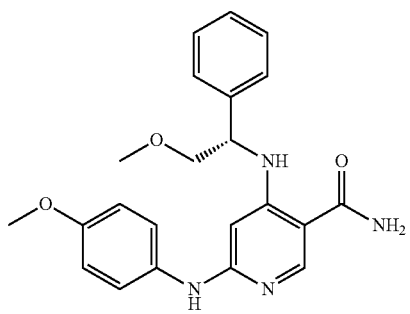 [SMILES: COC[C@@H](Nc1cc(Nc2ccc(OC)cc2)ncc1C(N)=O)c1ccccc1]

The title compound was synthesized using a procedure similar to that described in Example 36, using an amine prepared from (S)-alpha-methylbenzyl amine, iodomethane, and sodium hydride in dioxane. MS found for C22H24N4O3 as (M+H)+ 393.4. UV: λ=203, 259 nm. 1H NMR: (CD3OD) δ 8.11 (s, 1H), 7.36 (m, 3H), 7.23 (m, 2H), 6.91 (s, 4H), 5.56 (s, 1H), 4.58 (dd, 4 Hz, 7.6 Hz), 3.69 (dd, 1H, 4 Hz, 10 Hz), 3.60 (dd, 1H, 7.6 Hz, 10 Hz), 3.38 (s, 3H).

Example 261

(S)-4-(2-methoxy-1-phenylethylamino)-6-(3-morpholinophenylamino)nicotinamide

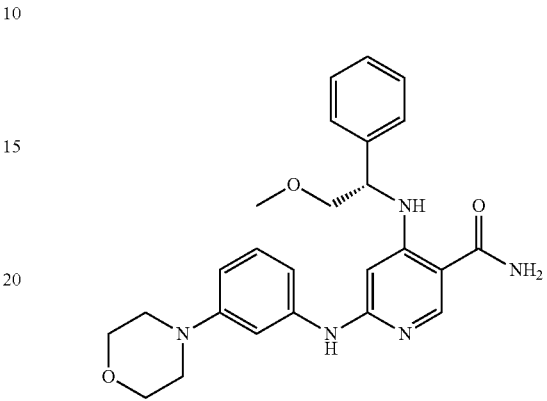

The title compound was synthesized using a procedure similar to that described in Example 36. MS found for C25H29N5O3 as (M+H)+ 448.5. UV: λ=205, 257 nm. 1H NMR: (CD3OD) δ 8.13 (s, 1H), 7.35 (m, 3H), 7.22 (m, 3H), 6.91 (d, 1H, 8.4 Hz), 6.56 (s, 1H), 6.40 (8.4 Hz), 5.72 (s, 1H), 4.62 (m, 1H), 3.82 (m, 4H), 3.70 (dd, 1H, 4 Hz, 8.8 Hz), 3.61 (dd, 1H, 7.6 Hz, 10 Hz) 3.37 (s, 3H), 3.12 (m, 4H).

Example 262

(S)-4-(2-methoxy-1-phenylethylamino)-6-(4-morpholinophenylamino)nicotinamide

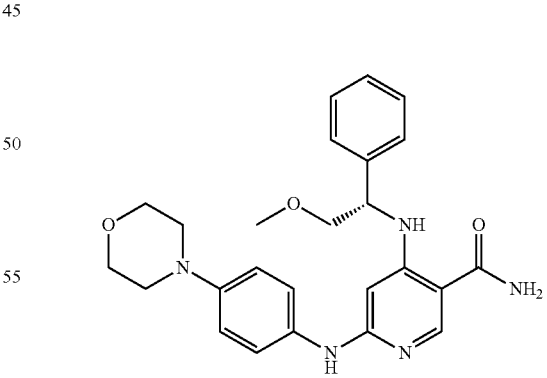

The title compound was synthesized using a procedure similar to that described in Example 36. MS found for C25H29N5O3 as (M+H)+ 448.5. UV: λ=202, 258 nm. 1H NMR: (CD3OD) δ 8.10 (s, 1H), 7.34 (m, 3H), 7.24 (d, 2H, 8

Hz), 6.34 (d, 2H, 8.8 Hz), 6.87 (d, 2H, 8.8 Hz), 5.58 (s, 1H), 4.59 (dd, 1H, 4 Hz, 10 Hz), 3.86 (m, 4H, 8.0 Hz, 10 Hz), 3.31 (s, 3H), 3.18 (m, 4H).

Example 263

(S)-6-(4-(dimethylcarbamoyl)phenylamino)-4-(2-methoxy-1-phenylethylamino)nicotinamide

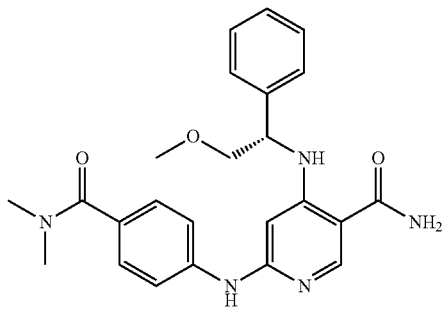 [SMILES: COC[C@@H](Nc1cc(Nc2ccc(C(=O)N(C)C)cc2)ncc1C(N)=O)c1ccccc1]

The title compound was synthesized using a procedure similar to that described in Example 36. MS found for C24H27N5O3 as (M+H)+ 434.4. UV: λ=202, 263 nm. ¹H NMR: (CD3OD) δ 8.22 (s, 1H), 7.38 (m, 5H), 7.29 (d, 2H, 7.6 Hz), 7.10 (d, 2H, 7.2 Hz), 5.84 (s, 1H), 4.69 (dd, 1H, 3.6 Hz, 6.8 Hz), 3.72 (dd, 1H, 4.4 Hz, 10.8 Hz), 3.63 (dd, 1H, 9.6 Hz, 10.2 Hz), 3.39 (s, 3H0, 3.13 (s, 3H0, 3.05 (s, 3H).

Example 264

(S)-6-(4-(azetidine-1-carbonyl)phenylamino)-4-(2-methoxy-1-phenylethylamino)nicotinamide

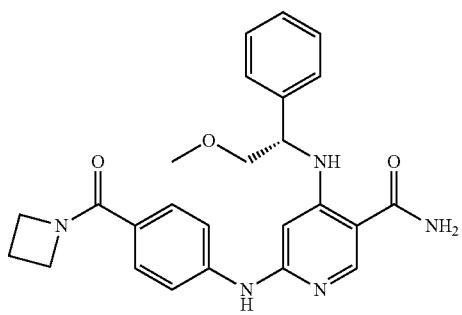 [SMILES: COC[C@@H](Nc1cc(Nc2ccc(C(=O)N3CCC3)cc2)ncc1C(N)=O)c1ccccc1]

The title compound was synthesized using a procedure similar to that described in Example 36. MS found for C25H27N5O3 as (M+H)+ 446.5. UV: =202, 261 nm. ¹H NMR: (CD3OD) δ 8.23 (s, 1H), 7.59 (dd, 2H, 1.2 Hz, 8 Hz), 7.39 (m, 3H), 7.30 (d, 2H, 7.6 Hz), 7.00 (dd, 2H, 1.6 Hz, 8.8 Hz).

Example 265

(R)-4-((1-acetylpiperidin-3-yl)methylamino)-6-(4-(pyrrolidine-1-carbonyl)phenylamino)nicotinamide

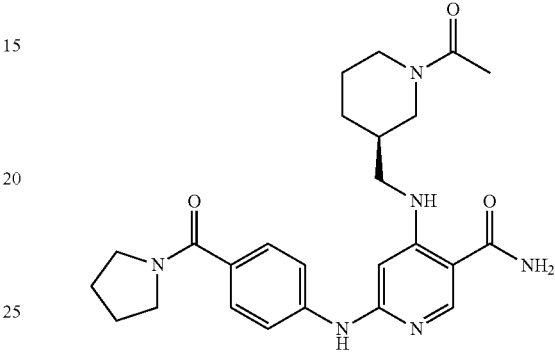

The title compound was synthesized using a procedure similar to that described in Example 36. MS found for C25H32N6O3 as (M+H)+ 465.5. UV: =203, 260 nm. ¹H NMR: (CD3OD) δ (mixture of rotamers) 8.18 (s, 0.5H), 8.16 (s, 0.5H), 7.65 (m, 2H), 7.39 (d, 1H, 4.8 Hz), 7.38 (d, 1H, 5.6 Hz), 6.12 (s, 0.5H), 6.11 (s, 0.5H), 4.26 (m, 1H), 3.86 (m, 0.5H), 3.77 (m, 0.5H), 3.61 (t, 2H, 7.2 Hz), 3.52 (t, 2H, 6.8 Hz), 3.18-3.26 (m, 4.5H), 3.01 (dd, 0.5H, 9.6 Hz, 13.2 Hz), 2.83 (m, 0.5H), 2.72 (dd, 0.5H, 9.6 Hz, 12.8 Hz), 2.10 (s, 1.5H), 2.04 (s, 1.5H), 2.00 (p, 2H, 6.4 Hz), 1.94 (p, 2H, 6.4 Hz), 1.82 (m, 1H), 1.53 (m, 1H), 1.40 (m, 1H).

Example 266

(R)-6-(4-(dimethylcarbamoyl)phenylamino)-4-((1-(2-methoxyacetyl)piperidin-3-yl)methylamino)nicotinamide

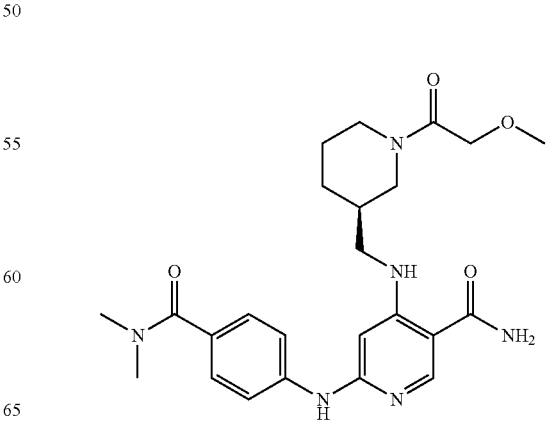

The title compound was synthesized using a procedure similar to that described in Example 36. MS found for C24H32N6O4 as (M+H)+ 469.4. UV: λ=202, 260 nm.

Example 267

(R)-4-((1-(2-methoxyacetyl)piperidin-3-yl)methylamino)-6-(4-(pyrrolidine-1-carbonyl)phenylamino)nicotinamide

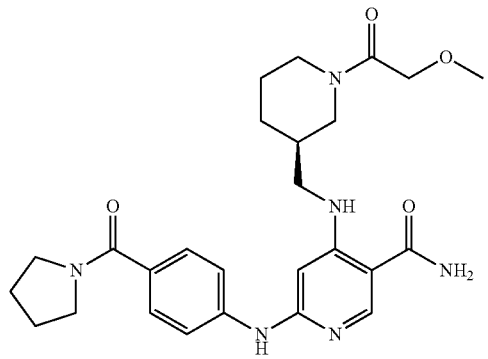 [SMILES: COCC(=O)N1CCC[C@H](CNc2cc(Nc3ccc(C(=O)N4CCCC4)cc3)ncc2C(N)=O)C1]

The title compound was synthesized using a procedure similar to that described in Example 36. MS found for C26H34N6O4 as (M+H)+ 495.5. UV: λ=201, 260 nm $^1$H NMR: (CD3OD) (mixture of rotamers) δ 8.17 (s, 0.3H), 8.16 (s, 0.7H) 7.64 (d, 2H, 8.4 Hz), 7.38 (d, 2H, 8.4 Hz), 6.11 (s, 1H), 4.24 (m, 1H), 4.13 (m, 2H), 3.61 (t, 2H, 6.8 Hz), 5.23 (t, 2H, 6.4 Hz), 3.38 (s, 3H), 3.24-3.03 (m, 3H), 2.66-2.98 (m, 3H), 2.01 (p, 2H, 6 Hz), 1.95 (p, 2H, 7.6 Hz), 1.77 (m, 1H), 1.53 (m, 1H), 1.77 (m, 1H0, 1.41 (m, 1H).

Example 268

4-(benzylamino)-6-(4-((N,N-dimethylsulfamoyl)(methyl)amino)phenylamino)nicotinamide

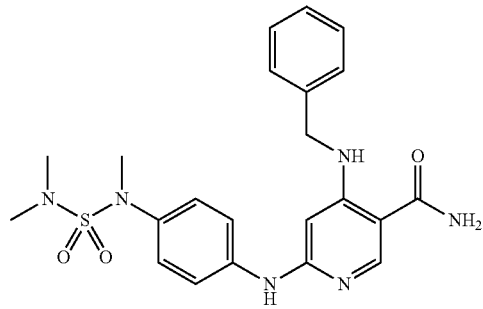 [SMILES: CN(C)S(=O)(=O)N(C)c1ccc(Nc2cc(NCc3ccccc3)c(C(N)=O)cn2)cc1]

The title compound was synthesized using a procedure similar to that described in Example 36. MS found for C22H26N6O3S as (M+H)+ 455.4. UV: λ=204, 261 nm. $^1$H NMR: (CD3OD) δ 8.16 (s, 1H), 7.44 (dt, 2H, 2 Hz, 4.4 Hz), 7.38 (t, 2H, 6.8 Hz), 7.32 (m, 1H), 7.27 (d, 2H, 6.8 Hz), 5.91 (s, 1H), 4.48 (s, 2H), 3.24 (s, 3H), 2.85 (s, 6H).

Example 269

(R)-4-((1-acetylpiperidin-3-yl)methylamino)-6-(4-(N,N-dimethylsulfamoylamino)phenylamino)nicotinamide

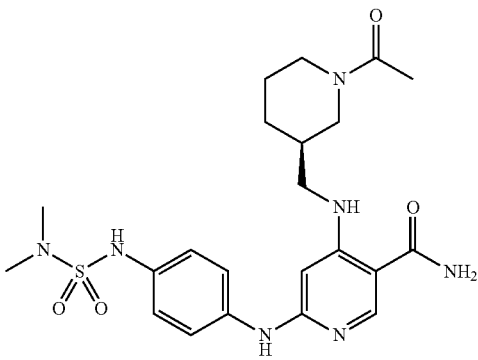 [SMILES: CC(=O)N1CCC[C@H](CNc2cc(Nc3ccc(NS(=O)(=O)N(C)C)cc3)ncc2C(N)=O)C1]

The title compound was synthesized using a procedure similar to that described in Example 36. MS found for C22H31N7O4S as (M+H)+ 490.5. UV: λ=202, 258 nm. $^1$H NMR: (CD3OD) (mixture of rotamers) δ 8.11 (s, 0.5H), 8.18 (s, 0.5H), 7.32 (d, 2H, 9.2 Hz), 7.25 (m, 2H), 5.92 (s, 1H), 4.27 (m, 1H), 3.84 (m, 0.5H), 3.77 (m, 0.5H), 3.03-3.28 (m, 3.5H), 3.98 (dd, 1H, 10 Hz, 13.6 Hz), 2.84 (s, 6H), 2.70 (dd, 2H, 10 Hz, 13.2 Hz), 2.10 (s, 1.8H), 2.07 (s, 1.2H), 1.90 (m, 1H), 1.77 (m, 1H), 1.49 (m, 1H), 1.38 (m, 1H).

Example 270

(S)-6-(4-methoxyphenylamino)-4-(piperidin-3-ylmethylamino)nicotinamide

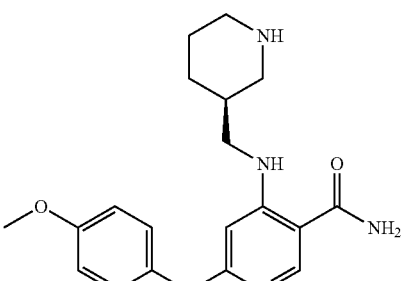

The title compound was synthesized using a procedure similar to that described in Example 36. MS found for C19H25N5O2 as (M+H)+ 356.3. UV: λ=201, 255 nm. $^1$H NMR: (CD3OD) δ 8.22 (s, 1H), 7.24 (d, 2H, 9.2 Hz), 7.05 (d, 2H, 8.8 Hz), 5.86 (s, 1H), 3.83 (s, 3H), 3.38 (m, 4H), 3.25 (m, 1H), 3.20 (d, 2H, 6.8 Hz), 2.90 (td, 1H, 2.4 Hz, 12.8 Hz), 2.78 (t, 1H, 12.4 Hz), 2.12 (m, 1H), 1.97 (m, 1H), 1.76 (m, 1H), 1.35 (m, 1H).

Example 271

(R)-6-(4-methoxyphenylamino)-4-((1-propionylpiperidin-3-yl)methylamino)nicotinamide

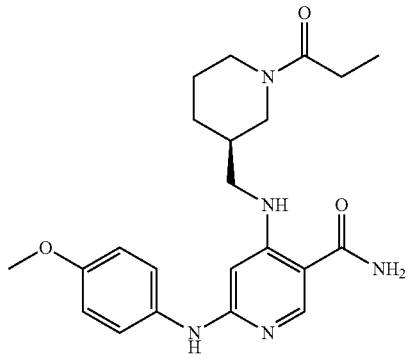

The title compound was synthesized using a procedure similar to that described in Example 36. MS found for C22H29N5O3 as (M+H)+ 412.4. UV: λ=203, 256 nm. ¹H NMR: (CD3OD) (mixture of rotamers) δ 8.08 (s, 0.4H), 8.05 (s, 0.6H), 7.25 (m, 2H), 7.06 (m, 2H), 5.86 (s, 0.6H), 5.84 (s, 0.4H), 4.29 (m, 1H), 3.84 (s, 3H), 3.80 m, 1H), 3.03-3.22 (m, 4H), 2.95 (dd, 0.5H, 10.4 Hz, 14 Hz), 2.79 (m, 0.5H), 2.69 (dd, 1H, 10.4 Hz, 13.6 Hz), 2.41 (q, 1.2H, 8 Hz), 2.36 (q, 0.8H, 7.2 Hz), 1.89 (m, 1H), 1.65-1.83 (m, 2H), 1.50 (m, 1H), 1.38 (m, 1H), 1.1 (t, 1.8H, 7.2 Hz), 1.08 (t, 1.2H, 8 Hz).

Example 272

4-(benzylamino)-6-(4-(dimethylcarbamoyl)-3-(trifluoromethyl)phenylamino)nicotinamide

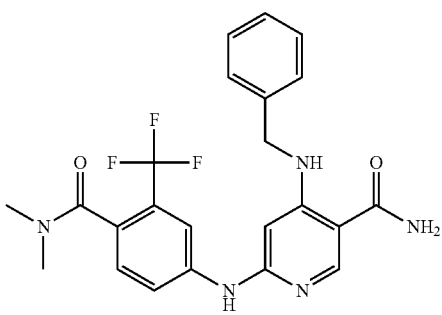 [SMILES: CN(C)C(=O)c1ccc(Nc2cc(NCc3ccccc3)c(C(N)=O)cn2)cc1C(F)(F)F]

The title compound was synthesized using a procedure similar to that described in Example 36. MS found for C23H22F3N5O2 as (M+H)+ 458.4. UV: λ=204, 265 nm. ¹H NMR: (CD3OD) δ 8.23 (s, 1H0, 7.63 (s, 1H), 7.39 (m, 4H), 7.30 (m, 3H), 6.04 (s, 1H), 4.83 (s, 2H), 3.13 (s, 3H), 2.87 (s, 3H).

Example 273

4-(benzylamino)-6-(4-(dimethylcarbamoyl)-3-fluorophenylamino)nicotinamide

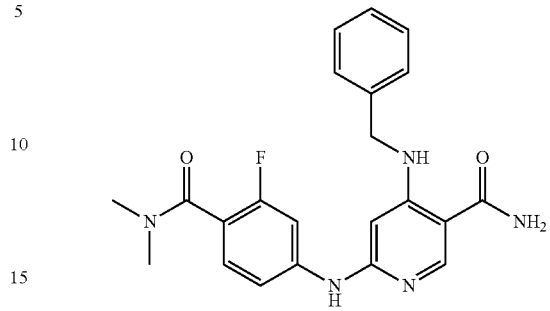

The title compound was synthesized using a procedure similar to that described in Example 36. MS found for C22H22FN5O2 as (M+H)+ 408.3. UV: λ=203, 264 nm. ¹H NMR: (CD3OD) δ 8.23 (s, 1H), 7.37 (m, 4H), 7.31 (d, 2H, 7.2H), 7.05 (dd, 1H, 10.8 Hz), 6.99 (dd, 1H, 2 Hz, 8.4 Hz), 6.06 (s, 1H), 4.54 (s, 2H), 3.13 (s, 3H), 2.99 (s, 3H).

Example 274

(R)-4-((1-acetylpiperidin-3-yl)methylamino)-6-(4-(dimethylcarbamoyl)-3-(trifluoromethyl)phenylamino)nicotinamide

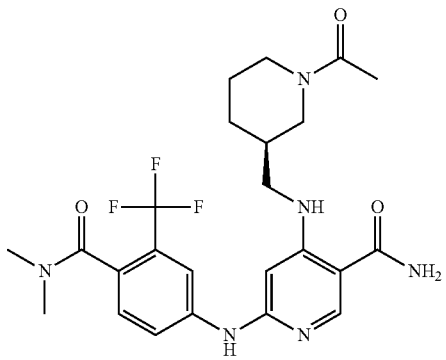 [SMILES: CC(=O)N1CCC[C@H](CNc2cc(Nc3ccc(C(=O)N(C)C)c(C(F)(F)F)c3)ncc2C(N)=O)C1]

The title compound was synthesized using a procedure similar to that described in Example 36. MS found for C24H29F3N6O3 as (M+H)+ 507.4. UV: λ=204, 273 nm.

Example 275

(R)-4-((1-acetylpiperidin-3-yl)methylamino)-6-(4-(dimethylcarbamoyl)-3-fluorophenylamino)nicotinamide

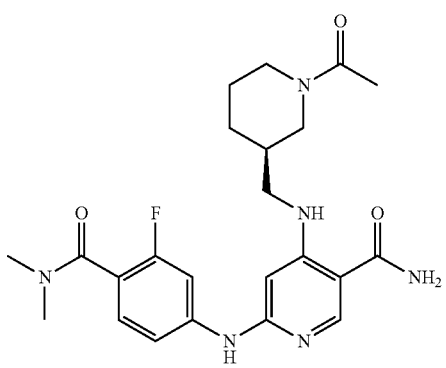 [SMILES: CC(=O)N1CCC[C@H](CNc2cc(Nc3ccc(C(=O)N(C)C)c(F)c3)ncc2C(N)=O)C1]

The title compound was synthesized using a procedure similar to that described in Example 36. MS found for C23H29FN6O3 as (M+H)+ 457.4. UV: λ=204, 263 nm. ¹H NMR: (CD3OD) δ 8.22 (s, 0.4H), 8.20 (s, 0.6H), 7.48 (t, 1H, 7.6 Hz), 7.22 (m, 2H), 6.19 (s, 0.4H), 6.18 (s, 0.6H), 4.28 (m, 1H), 3.87 (m, 1H), 3.78 (dt, 13.6 Hz), 3.16-3.27 (m, 4H), 3.13 (s, 3H), 3.00 (s, 3H), 2.99 (m, 0.5H), 2.67-2.85 (m, 2H), 2.10 (s, 1.8H), 2.08 (s, 1.2H), 1.93 (m, 1H), 1.70-1.89 (m, 2H), 1.54 (m, 1H), 1.41 (m, 1H).

Example 276

6-(4-(1H-imidazol-4-yl)phenylamino)-4-(benzylamino)nicotinamide

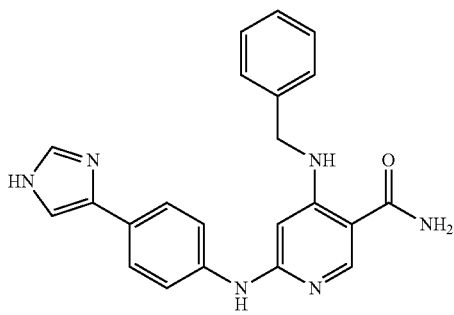 [SMILES: NC(=O)c1cnc(Nc2ccc(-c3c[nH]cn3)cc2)cc1NCc1ccccc1]

The title compound was synthesized using a procedure similar to that described in Example 36. MS found for C22H20N6O as (M+H)+ 385.3. UV: λ=109, 274 nm. ¹H NMR: (CD3OD) δ 9.34 (s, 1H), 8.23 (s, 1H), 8.02 (s, 1H), 7.73 (m, 3H), 7.35 (m, 6H), 6.03 (s, 1H), 4.51 (s, 2H).

Example 277

6-(4-(1H-pyrazol-1-yl)phenylamino)-4-(benzylamino)nicotinamide

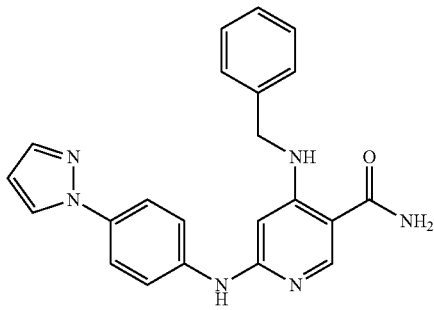 [SMILES: NC(=O)c1cnc(Nc2ccc(-n3cccn3)cc2)cc1NCc1ccccc1]

The title compound was synthesized using a procedure similar to that described in Example 36. MS found for C22H20N6O as (M+H)+ 385.3. UV: λ=206, 254, 274 nm. ¹H NMR: (CD3OD) δ 8.16 (d, 1H, 2 Hz), 8.07 (s, 1H), 7.68 (m, 3H), 7.13-7.26 (m, 7H), 6.48 (distorted t, 2 Hz), 5.83 (s, 1H), 4.40 (s, 2H).

Example 278

6-(6-(1H-pyrazol-1-yl)pyridin-3-ylamino)-4-(benzylamino)nicotinamide

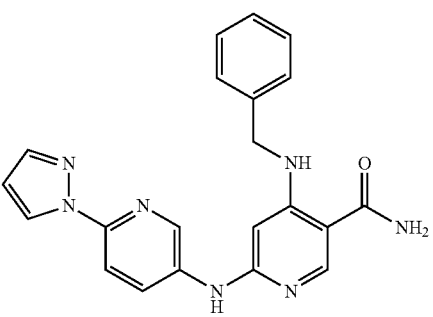 [SMILES: NC(=O)c1cnc(Nc2ccc(-n3cccn3)nc2)cc1NCc1ccccc1]

The title compound was synthesized using a procedure similar to that described in Example 36. MS found for C21H19N7O as (M+H)+ 386.3. UV: =204, 254 nm. ¹H NMR: (CD3OD) δ 8.60 (dd, 1H, 0.8 Hz, 2.4 Hz), 8.29 (d, 1H, 2.4 Hz), 8.19 (s, 1H), 7.95 (d, 1H, 9.2 Hz), 7.79 (d, 1H, 1.2 Hz), 7.68 (dd, 1H, 2.4 Hz, 8.4 Hz), 7.27-7.35 (m, 5H), 6.57 (dd, 1H, 1.6 Hz, 2.8 Hz), 5.90 (s, 1H), 4.51 (s, 2H).

Example 279

4-(benzylamino)-6-(4-methoxy-3-methylphenylamino)nicotinamide

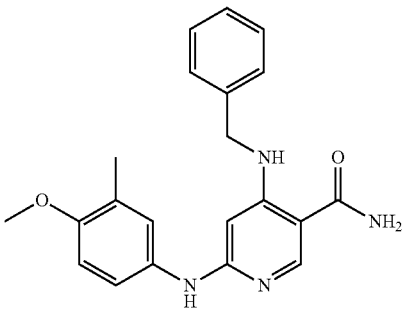 [SMILES: COc1ccc(Nc2cc(NCc3ccccc3)c(C(N)=O)cn2)cc1C]

The title compound was synthesized using a procedure similar to that described in Example 36. MS found for C21H22N4O2 as (M+H)+ 363.3. UV: λ=202, 257 nm. ¹H NMR: (CD3OD) δ 8.07 (s, 1H), 7.33 (m, 3H), 7.25 (dd, 2H, 1.6 Hz, 6.8 Hz), 6.94 (m, 3H), 5.76 (s, 1H), 4.44 (s, 2H), 3.87 (s, 3H), 2.18 (s, 3H).

Example 280

4-(benzylamino)-6-(3,4,5-trimethoxyphenylamino)nicotinamide

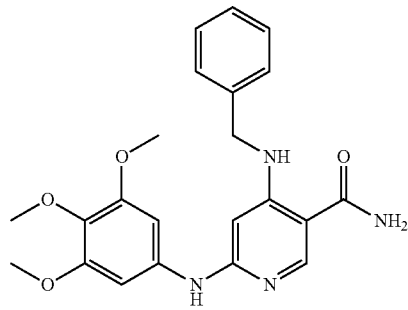 [SMILES: COc1cc(Nc2cc(NCc3ccccc3)c(C(N)=O)cn2)cc(OC)c1OC]

The title compound was synthesized using a procedure similar to that described in Example 36. MS found for C22H24N4O4 as (M+H)+ 409.3. UV: λ=209, 256 nm. $^1$H NMR: (CD3OD) δ 8.11 (s, 1H), 7.25-7.36 (m, 5H), 6.52 (s, 2H), 5.85 (s, 1H), 4.48 (s, 2H), 3.79 (s, 6H), 3.77 (s, 3H).

Example 281

6-(4-(1H-1,2,4-triazol-3-yl)phenylamino)-4-(benzylamino)nicotinamide

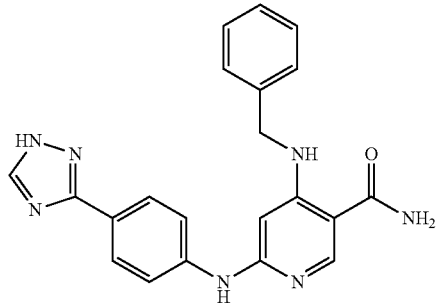 [SMILES: NC(=O)c1cnc(Nc2ccc(-c3nc[nH]n3)cc2)cc1NCc1ccccc1]

The title compound was synthesized using a procedure similar to that described in Example 36. MS found for C21H19N7O as (M+H)+ 386.3. UV: λ=203, 261 nm. $^1$H NMR: (CD3OD) δ 9.12 (s, 1H), 8.20 (d, 1H, 3.6 Hz), 7.85 (d, 2H, 8.8 Hz), 7.35 (m, 5H), 7.28 (d, 2H, 9.2 Hz), 5.96 (s, 1H), 4.51 (s, 2H).

Example 282

4-((1H-indol-7-yl)methylamino)-6-(4-methoxyphenylamino)nicotinamide

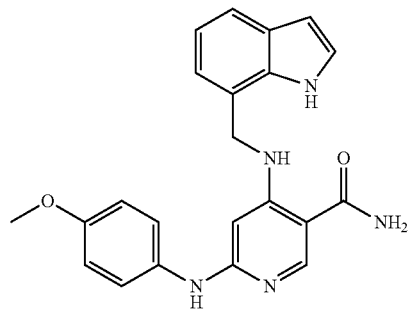 [SMILES: COc1ccc(Nc2cc(NCc3cccc4cc[nH]c34)c(C(N)=O)cn2)cc1]

The title compound was synthesized using a procedure similar to that described in Example 36. MS found for C22H21N5O2 as (M+H)+ 388.3. UV: λ=218, 257 nm. $^1$H NMR: (CD3OD) δ 8.08 (s, 1H), 7.53 (d, 1H, 12 Hz), 7.23 (m, 1H), 6.87-7.00 (m, 4H), 6.88 (d, 2H, 9.2 Hz), 6.50 (m, 1H), 5.84 (s, 1H), 4.68 (s, 2H), 3.82 (s, 3H).

Example 283

4-((1H-indol-7-yl)methylamino)-6-(4-(dimethylcarbamoyl)-3-methylphenylamino)nicotinamide

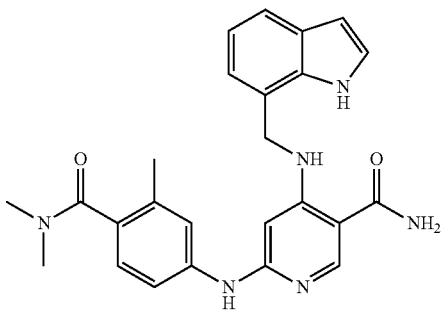 [SMILES: Cc1cc(Nc2cc(NCc3cccc4cc[nH]c34)c(C(N)=O)cn2)ccc1C(=O)N(C)C]

The title compound was synthesized using a procedure similar to that described in Example 36. MS found for C25H26N6O2 as (M+H)+ 443.3. UV: λ=216, 261 nm. $^1$H NMR: (CD3OD) δ 10.63 (s, 1H), 8.16 (s, 1H), 7.53 (dd, 1H, 1.2 Hz, 7.6 Hz), 7.26 (m, 1H), 7.09 (d, 8 Hz), 7.03 (m, 3H), 6.88 (dd, 1.6 Hz, 8 Hz), 6.50 (m, 1H), 6.05 (s, 1H), 4.74 (s, 2H), 3.13 (s, 3H), 2.84 (s, 3H), 2.18 (s, 3H).

Example 284

4-(benzo[b]thiophen-7-ylmethylamino)-6-(4-methoxyphenylamino)nicotinamide

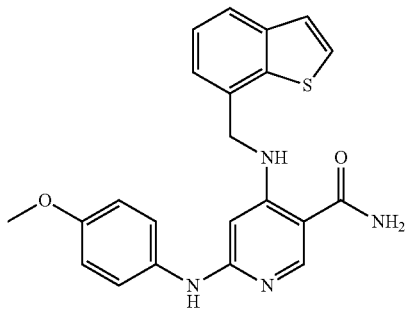 [SMILES: COc1ccc(Nc2cc(NCc3cccc4ccsc34)c(C(N)=O)cn2)cc1]

The title compound was synthesized using a procedure similar to that described in Example 36. MS found for C22H20N4O2S as (M+H)+ 405.2. UV: λ=202, 226, 257 nm. $^1$H NMR: (CD3OD) δ 8.11 (s, 1H), 7.83 (d, 1H, 8 Hz), 7.58 (d, 1H, 5.6 Hz), 7.45 (d, 1H, 5.6 Hz), 7.37 (t, 1H, 7.6 Hz), 7.21

(d, 1H, 7.6 Hz), 6.90 (d, 2H, 6.4 Hz), 6.84 (d, 2H, 6.4 Hz), 5.67 (s, 1H), 4.71 (s, 2H), 3.81 (s, 3H).

Example 285

4-(benzo[b]thiophen-7-ylmethylamino)-6-(4-(dimethylcarbamoyl)-3-methylphenylamino)nicotinamide

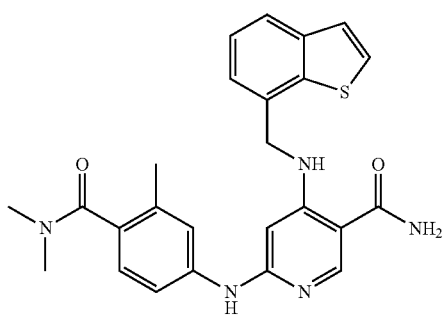 [SMILES: Cc1cc(Nc2cc(NCc3cccc4ccsc34)c(C(N)=O)cn2)ccc1C(=O)N(C)C]

The title compound was synthesized using a procedure similar to that described in Example 36. MS found for C25H25N5O2S as (M+H)+ 460.3. UV: λ=202, 226, 260 nm. ¹H NMR: (CD3OD) δ 8.18 (s, 1H), 7.84 (d, 1H, 7.6 Hz), 7.61 (d, 1H, 5.6 Hz), 7.45 (d, 1H, 5.6 Hz), 7.40 (t, 1H, 7.6 Hz), 7.26 (d, 1H, 7.2 Hz), 7.07 (8.4 Hz), 7.01 (d, 1H, 2.4 Hz), 6.84 (dd, 1H, 2 Hz, 8.4 Hz), 5.95 (s, 1H), 4.78 (s, 2H), 3.13 (s, 3H), 2.84 (s, 1H), 2.17 (s, 1H).

Example 286

6-(4-methoxyphenylamino)-4-(pyrimidin-5-ylmethylamino)nicotinamide

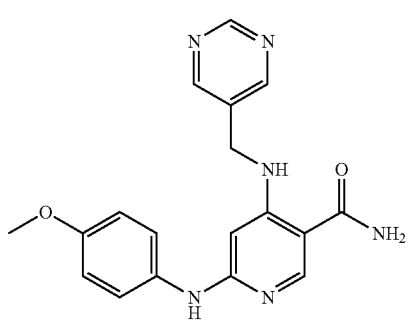 [SMILES: COc1ccc(Nc2cc(NCc3cncnc3)c(C(N)=O)cn2)cc1]

The title compound was synthesized using a procedure similar to that described in Example 36. MS found for C18H18N6O2 as (M+H)+ 351.2. UV: λ=200, 255 nm. ¹H NMR: (CD3OD) δ 9.13 (s, 1H), 8.70 (s, 2H), 8.08 (s, 1H), 7.09 (d, 2H), 6.98 (d, 2H), 5.74 (s, 1H), 4.57 (s, 2H), 3.83 (s, 3H).

Example 287

6-(4-(dimethylcarbamoyl)-3-methylphenylamino)-4-(pyrimidin-5-ylmethylamino)nicotinamide

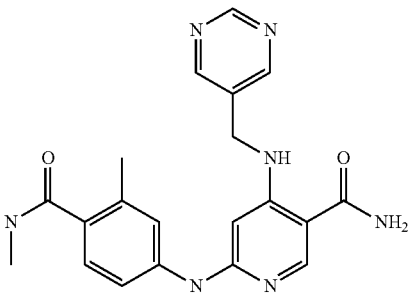

The title compound was synthesized using a procedure similar to that described in Example 36. MS found for C21H23N7O2 as (M+H)+ 406.3. UV: λ=202, 257 nm. ¹H NMR: (CD3OD) δ 9.13 (s, 1H), 8.75 (s, 2H), 8.18 (s, 1H), 7.25 (d, 1H, 8.4 Hz), 7.12 (d, 1H, 2 Hz), 7.04 (dd, 1H, 2 Hz, 8 Hz), 5.95 (s, 1H), 4.63 (s, 2H), 3.30 (s, 3H), 2.92 (s, 3H), 2.26 (s, 3H).

Example 288

4-((1H-indol-7-yl)methylamino)-6-(4-(dimethylcarbamoyl)phenylamino)nicotinamide

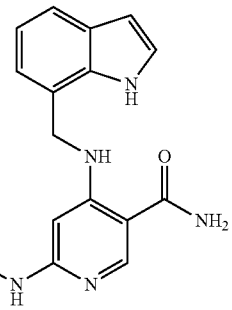

The title compound was synthesized using a procedure similar to that described in Example 36. MS found for C24H24N6O2 as (M+H)+ 429.3. UV: λ=216, 267 nm. ¹H NMR: (CD3OD) δ 8.18 (s, 1H), 7.55 (dd, 1H, 1.2 Hz, 7.2 Hz), 7.34 (d, 2H, 6.8 Hz), 7.25 (dd, 1H, 1.6 Hz, 3.2 Hz), 7.06 (d, 2H, 6.4 Hz), 7.02 (m, 2H), 6.51 (dd, 1H, 2 Hz, 3.2 Hz), 6.08 (s, 1H0, 4.76 (s, 2H), 3.13 (s, 3H), 3.00 (s, 3H).

Example 289

(R)-4-((1-(ethylsulfonyl)piperidin-3-yl)methylamino)-6-(4-methoxyphenylamino)nicotinamide

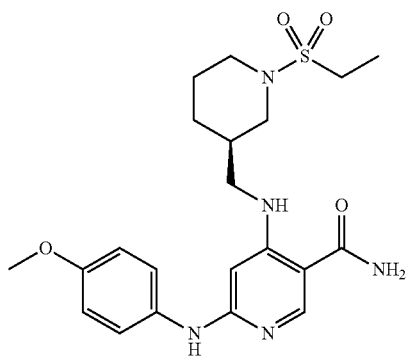 [SMILES: CCS(=O)(=O)N1CCC[C@H](CNc2cc(Nc3ccc(OC)cc3)ncc2C(N)=O)C1]

The title compound was synthesized using a procedure similar to that described in Example 36. MS found for C21H29N5O4S as (M+H)+ 448.3. UV: λ=202, 224, 256 nm. $^1$H NMR: (CD3OD) δ 8.07 (s, 1H), 7.25 (dt, 1H, 2.4 Hz, 9.2 Hz), 7.06 (dt, 2H, 2 Hz, 8.8 Hz), 5.87 (s, 1H), 3.84 (s, 3H), 3.59 (dd, 1H, 3.6 Hz, 12 Hz), 3.53 (m, 1H), 3.23 (dd, 1H, 7.6 Hz, 14 Hz), 3.14 (dd, 1H, 6.4 Hz, 13.6 Hz), 3.10 (q, 2H, 7.6 Hz), 2.98 (m, 1H), 2.79 (dd, 1H, 9.2 Hz, 12.4 Hz), 1.96 (m, 1H), 1.82 (m, 2H), 1.59 (m, 1H), 1.37 (dd, 1H, 3.6 Hz, 7.2 Hz), 1.30 (t, 3H, 7.2 Hz).

Example 290

(R)-6-(4-methoxyphenylamino)-4-((1-(pyrrolidine-1-carbonyl)piperidin-3-yl)methylamino)nicotinamide

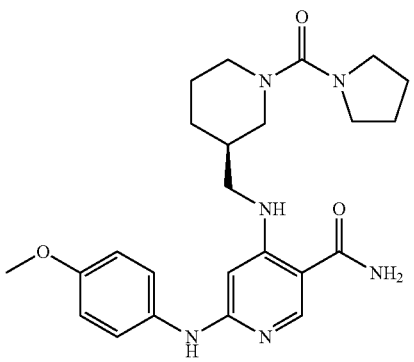 [SMILES: COc1ccc(Nc2cc(NC[C@H]3CCCN(C(=O)N4CCCC4)C3)c(C(N)=O)cn2)cc1]

The title compound was synthesized using a procedure similar to that described in Example 36. MS found for C24H32N6O3 as (M+H)+ 463.3. UV: λ=205, 256 nm. $^1$H NMR: (CD3OD) δ 8.06 (s, 1H), 7.24 (d, 2H, 9.2 Hz), 7.05 (d, 2H, 8.8 Hz), 5.86 (s, 1H), 3.84 (s, 3H), 3.68 (m, 1H), 3.62 (m, 1H), 3.13 (m, 2H), 2.87 (m, 2H), 2.65 (dd, 1H, 10 Hz, 13.2 Hz), 1.80-1.89 (m, 6H), 1.72 (m, 1H), 1.53 (m, 1H), 1.37 (dd, 1H, 3.6 Hz, 6.8 Hz), 1.29 (m, 1H).

Example 291

(R)-4-(1-(dimethylcarbamoyl)piperidin-3-yl)methylamino)-6-(4-methoxyphenylamino)nicotinamide

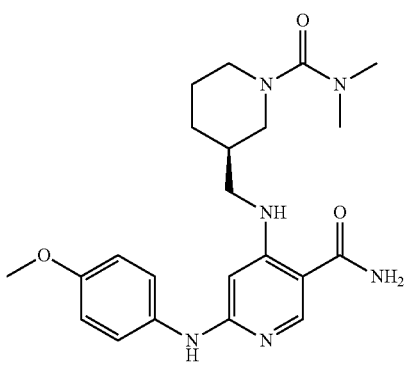

The title compound was synthesized using a procedure similar to that described in Example 36. MS found for C22H30N6O3 as (M+H)+ 427.3. UV: λ=205, 256 nm. $^1$H NMR: (CD3OD) δ 8.06 (s, 1H), 7.24 (d, 2H, 9.2 Hz), 7.05 (d, 2H, 8.4 Hz), 5.85 (s, 1H), 3.84 (s, 3H), 3.61 (m, 1H), 3.53 (m, 1H), 3.12 (dd, 2H, 5.7 Hz, 7.6 Hz), 2.94 (m, 1H), 2.82 (s, 6H), 2.63 (dd, 1H, 10 Hz, 13.2 Hz), 1.89 (m, 2H), 1.73 (dt, 1H, 3.6 Hz, 10 Hz), 1.55 (m, 1H), 1.32, (m, 1H).

Example 292

(R)-4-((1-(cyclopropylsulfonyl)piperidin-3-yl)methylamino)-6-(4-methoxyphenylamino)nicotinamide

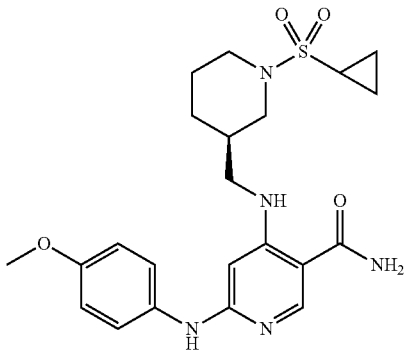 [SMILES: COc1ccc(Nc2cc(NC[C@H]3CCCN(S(=O)(=O)C4CC4)C3)c(C(N)=O)cn2)cc1]

The title compound was synthesized using a procedure similar to that described in Example 36. MS found for C22H29N5O4S as (M+H)+ 460.3. UV: λ=202, 256 nm. $^1$H NMR: (CD3OD) δ 8.07 (s, 1H), 7.24 (d, 2H, 9.2 Hz), 7.05 (d, 2H, 8.8 Hz), 5.88 (s, 1H), 3.84 (s, 3H), 3.60 (dd, 1H, 4 Hz, 11.6 Hz), 3.55 (m, 2H), 3.24 (dd, 1H, 7.2 Hz, 13.2 Hz), 3.15

(dd, 1H, 6.4 Hz, 13.6 Hz), 2.80 (dd, 1H, 9.2 Hz, 11.6 Hz), 2.45 (m, 1H), 1.99 (m, 1H), 1.82 (m, 1H), 1.61 (m, 1H), 1.30 (m, 1H), 1.02 (m, 4H).

Example 293

4-(benzylamino)-6-(3,4-dimethoxyphenylamino)nicotinamide

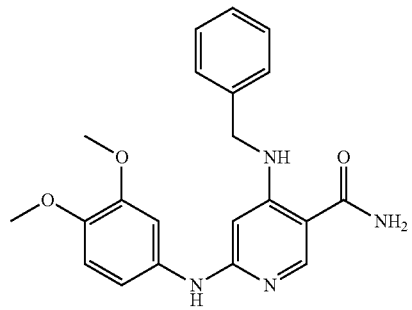 [SMILES: COc1ccc(Nc2cc(NCc3ccccc3)c(C(N)=O)cn2)cc1OC]

The title compound was synthesized using a procedure similar to that described in Example 36. MS found for C21H22N4O3 as (M+H)+ 379.3. UV: λ=204, 254 nm. ¹H NMR: (CD3OD) δ 8.08 (s, 1H), 7.24-7.36 (m, 5H), 6.98 (d, 1H, 8.4 Hz), 6.77 (d, 1H, 2 Hz), 6.71 (dd, 1H, 2.4 Hz, 8.4 Hz), 5.78 (s, 1H), 4.45 (s, 2H), 3.87 (s, 3H), 3.76 (s, 3H).

Example 294

4-((1H-indol-4-yl)methylamino)-6-(4-methoxyphenylamino)nicotinamide

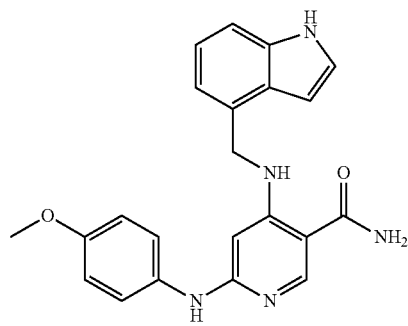 [SMILES: COc1ccc(Nc2cc(NCc3cccc4[nH]ccc34)c(C(N)=O)cn2)cc1]

The title compound was synthesized using a procedure similar to that described in Example 36. MS found for C22H21N5O2 as (M+H)+ 388.3. UV: λ=219, 258 nm. ¹H NMR: (CD3OD) δ 8.08 (s, 1H), 7.37 (d, 1H, 8.4 Hz), 7.25 (m, 1H), 7.07 (t, 1H, 7.2 Hz), 6.94 (d, 2H, 8.8 Hz), 6.86 (m, 3H), 6.48 (m, 1H), 5.81 (s, 1H), 4.69 (s, 2H), 3.82 (s, 3H).

Example 295

4-((1H-indol-4-yl)methylamino)-6-(4-(dimethylcarbamoyl)-3-methylphenylamino)nicotinamide

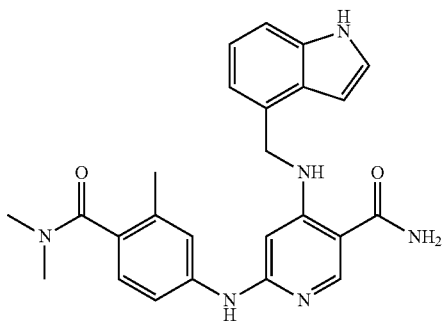 [SMILES: Cc1cc(Nc2cc(NCc3cccc4[nH]ccc34)c(C(N)=O)cn2)ccc1C(=O)N(C)C]

The title compound was synthesized using a procedure similar to that described in Example 36. MS found for C25H26N6O2 as (M+H)+ 443.3. UV: λ=216, 268 nm. ¹H NMR: (CD3OD) δ 8.16 (s, 1H), 7.37 (d, 1H, 8 Hz), 7.27 (d, 1H, 2.8 Hz), 7.09 (t, 1H, 7.2 Hz), 7.05 (d, 1H, 8 Hz), 7.01 (d, 1H, 2.4 Hz), 6.90 (d, 1H, 7.2 Hz), 6.90 (d, 1H, 7.2 Hz), 6.83 (dd, 1H, 2 Hz, 8 Hz), 6.51 (dd, 1H, 0.8 Hz, 3.2 Hz), 6.03 (s, 1H), 4.76 (s, 2H), 3.12 (s, 3H), 2.84 (s, 3H), 2.16 (s, 3H).

Example 296

4-((5-fluoropyridin-3-yl)methylamino)-6-(4-methoxyphenylamino)nicotinamide

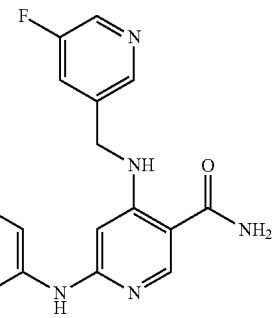

The title compound was synthesized using a procedure similar to that described in Example 36. MS found for C19H18FN5O2 as (M+H)+ 368.2. UV: λ=204, 224, 256 nm. ¹H NMR: (CD3OD) δ 8.22 (d, 1H, 2 Hz), 8.10 (s, 1H), 7.56

(m, 1H), 7.07 (d, 2H, 9.2 Hz), 6.98 (d, 2H, 8.8 Hz), 5.70 (s, 1H), 4.57 (s, 2H), 3.84 (s, 3H).

Example 297

6-(4-(dimethylcarbamoyl)-3-methylphenylamino)-4-((5-fluoropyridin-3-yl)methylamino)nicotinamide

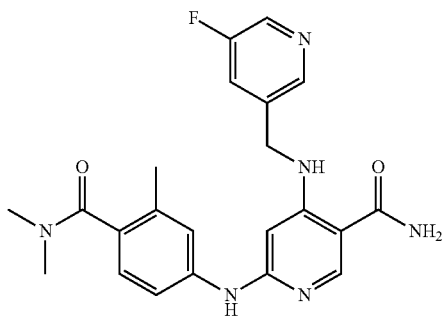 [SMILES: Cc1cc(Nc2cc(NCc3cncc(F)c3)c(C(N)=O)cn2)ccc1C(=O)N(C)C]

The title compound was synthesized using a procedure similar to that described in Example 36. MS found for C22H23FN6O2 as (M+H)+ 423.3. UV: λ=204, 261 nm. ¹H NMR: (CD3OD) δ 8.43 (d, 1H, 2.8 Hz), 8.38 (s, 1H), 7.61 (dt, 2 Hz, 9.2 Hz), 7.23 (d, 1H, 8 Hz), 7.11 (d, 1H), 7.03 (dd, 1H, 2 Hz, 8 Hz), 5.93 (s, 1H), 4.64 (s, 2H), 3.14 (s, 3H), 2.91 (s, 3H), 2.25 (s, 3H).

Example 298

6-(4-methoxyphenylamino)-4-(pyrimidin-4-ylmethylamino)nicotinamide

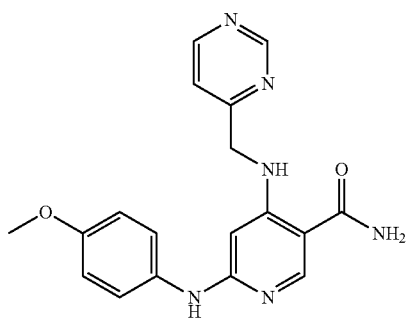 [SMILES: COc1ccc(Nc2cc(NCc3ccncn3)c(C(N)=O)cn2)cc1]

The title compound was synthesized using a procedure similar to that described in Example 36. MS found for C18H18N6O2 as (M+H)+ 351.3. UV: =202, 255 nm. ¹H NMR: (CD3OD) δ 9.11 (d, 1H, 1.2 Hz), 8.73 (d, 1H, 5.2 Hz), 7.48 (d, 1H, 3.6 Hz), 7.12 (d, 2H, 9.2 Hz), 6.98 (d, 2H, 9.2 Hz), 5.70 (s, 1H), 4.61 (s, 2H), 3.84 (s, 3H).

Example 299

6-(4-(dimethylcarbamoyl)phenylamino)-4-(pyrimidin-4-ylmethylamino)nicotinamide

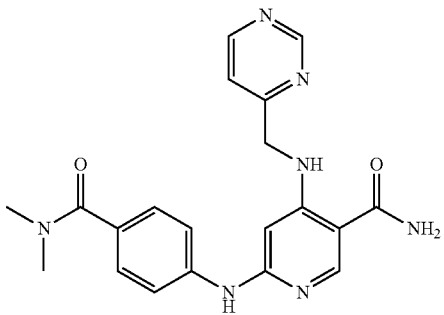 [SMILES: CN(C)C(=O)c1ccc(Nc2cc(NCc3ccncn3)c(C(N)=O)cn2)cc1]

The title compound was synthesized using a procedure similar to that described in Example 36. MS found for C20H21N7O2 as (M+H)+ 392.3. UV: λ=203, 257 nm. ¹H NMR: (CD3OD) δ 9.14 (d, 1H, 1.2 Hz), 8.75 (d, 1H, 5.6 Hz), 7.51 (s, 1H), 7.49 (d, 2H, 8.8 Hz), 7.28 (d, 2H, 8 Hz), 5.99 (s, 1H), 4.67 (s, 2H), 3.12 (s, 3H), 3.05 (s, 3H).

Example 300

6-(4-methoxyphenylamino)-4-(pyrimidin-2-ylmethylamino)nicotinamide

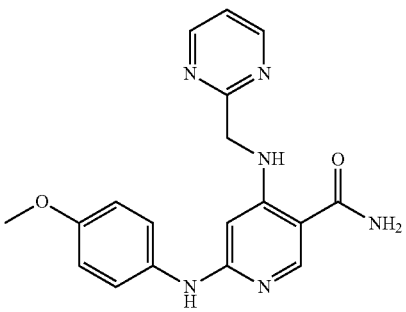

The title compound was synthesized using a procedure similar to that described in Example 36. MS found for C18H18N6O2 as (M+H)+ 351.2. UV: λ=205, 243 nm ¹H NMR: (CD3OD) δ 8.80 (d, 1H, 5.2 Hz), 8.09 (s, 1H), 7.43 (t, 1H, 4.4 Hz), 7.19 (d, 2H, 8.4 Hz), 7.03 (d, 2H, 9.6 Hz), 5.86 (s, 1H), 4.65 (s, 2H), 3.84 (s, 3H).

Example 301

6-(4-methoxyphenylamino)-4-(3-(methylsulfonyl)benzylamino)nicotinamide

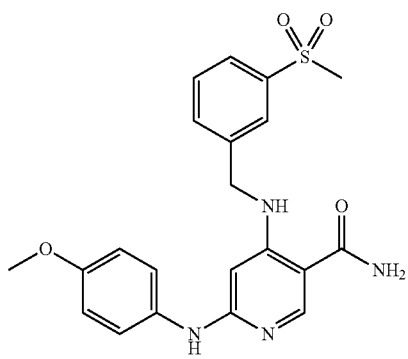 [SMILES: COc1ccc(Nc2cc(NCc3cccc(S(C)(=O)=O)c3)c(C(N)=O)cn2)cc1]

The title compound was synthesized using a procedure similar to that described in Example 36. MS found for C21H22N4O4S as (M+H)+ 427.2. UV: λ=218, 256 nm. ¹H NMR: (CD3OD) δ 8.16 (s, 1H), 7.93 (d, 1H, 7.2 Hz), 7.90 (s, 1H), 7.65 (t, 1H, 7.6 Hz), 7.64 (m, 1H), 7.08 (d, 2H, 9.2 Hz), 6.99 (d, 2H, 8.8 Hz), 5.73 (s, 1H), 4.63 (s, 2H), 3.85 (s, 3H), 3.15 (s, 3H).

Example 302

6-(4-(dimethylcarbamoyl)phenylamino)-4-(3-(methylsulfonyl)benzylamino)nicotinamide

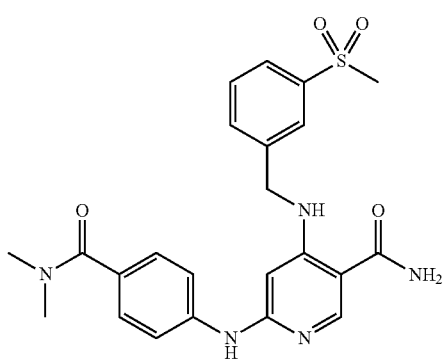 [SMILES: CN(C)C(=O)c1ccc(Nc2cc(NCc3cccc(S(C)(=O)=O)c3)c(C(N)=O)cn2)cc1]

The title compound was synthesized using a procedure similar to that described in Example 36. MS found for C23H25N5O4S as (M+H)+ 468.2. UV: λ=202, 261 nm. ¹H NMR: (CD3OD) δ 8.22 (s, 1H), 7.93 (m, 1H), 7.90 (s, 1H), 7.65 (m, 2H), 7.44 (d, 2H, 8.4 Hz), 7.19 (d, 2H, 8.4 Hz), 5.40 (s, 1H), 4.66 (s, 2H), 3.13 (s, 3H), 3.11 (s, 3H), 3.03 (s, 3H).

Example 303

6-(4-methoxyphenylamino)-4-((1-methyl-1H-indol-4-yl)methylamino)nicotinamide

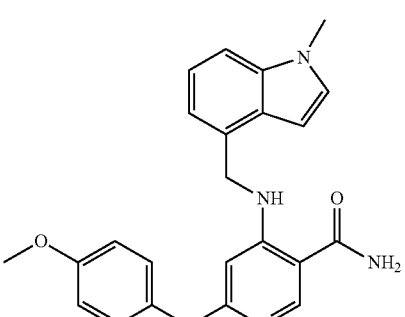

The title compound was synthesized using a procedure similar to that described in Example 36. MS found for C23H23N5O2 as (M+H)+ 402.3. UV: λ=223, 257 nm. ¹H NMR: (CD3OD) δ 8.07 (s, 1H), 7.35 (d, 1H, 8 Hz), 7.17 (d, 1H, 3.2 Hz), 7.14 (t, 1H, 8.4 Hz), 6.94 (d, 2H, 8.8 Hz), 6.90 (d, 1H, 6.8 Hz), 6.85 (d, 2H, 8.8 Hz), 6.45 (d, 1H, 2.8 Hz), 5.77 (s, 1H), 4.68 (s, 2H), 3.83 (s, 3H), 3.82 (s, 3H).

Example 304

6-(4-(dimethylcarbamoyl)phenylamino)-4-((1-methyl-1H-indol-4-yl)methylamino)nicotinamide

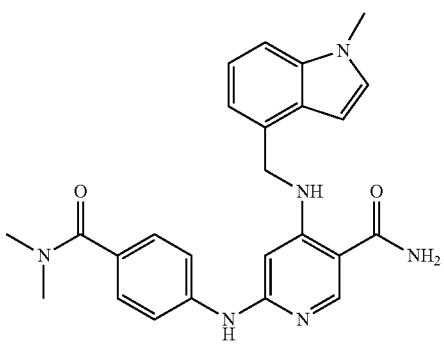 [SMILES: CN(C)C(=O)c1ccc(Nc2cc(NCc3cccc4c3ccn4C)c(C(N)=O)cn2)cc1]

The title compound was synthesized using a procedure similar to that described in Example 36. MS found for C25H26N6O2 as (M+H)+ 443.3. UV: λ=222, 276 nm. ¹H NMR: (CD3OD) δ 8.18 (s, 1H), 7.38 (d, 1H, 8 Hz), 7.29 (d, 2H, 9.2 Hz), 7.18 (m, 2H), 7.00 (d, 2H, 8.8 Hz), 6.96 (d, 1H, 7.6 Hz), 6.48 (dd, 1H, 0.4 Hz, 3.2 Hz), 6.03 (s, 1H), 4.76 (s, 2H), 3.13 (s, 3H), 3.01 (s, 3H).

Example 305

4-((5-fluoropyridin-3-yl)methylamino)-6-(4-(trifluoromethyl)phenylamino)nicotinamide

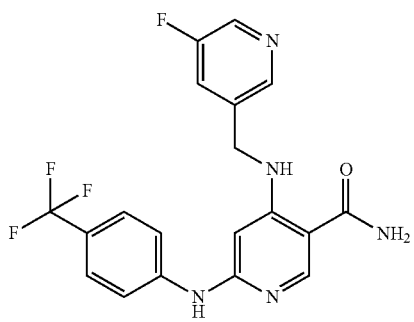 [SMILES: NC(=O)c1cnc(Nc2ccc(C(F)(F)F)cc2)cc1NCc1cncc(F)c1]

The title compound was synthesized using a procedure similar to that described in Example 36. MS found for C19H15F4N5O as (M+H)+ 406.2. UV: λ=205, 266 nm. ¹H NMR: (CD3OD) δ 8.46 (s, 1H), 8.39 (s, 1H), 8.23 (s, 1H), 7.71 (d, 2H, 8.4 Hz), 7.61 (d, 1H, 9.2 Hz), 7.30 (d, 2H, 8 Hz), 6.03 (s, 1H), 4.65 (s, 2H).

Example 306

6-(3-fluorophenylamino)-4-((5-fluoropyridin-3-yl)methylamino)nicotinamide

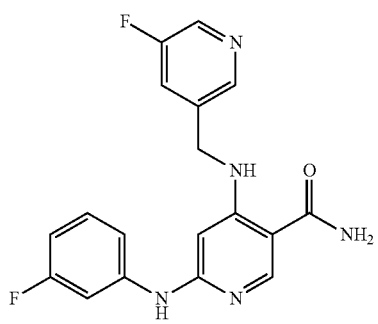 [SMILES: NC(=O)c1cnc(Nc2cccc(F)c2)cc1NCc1cncc(F)c1]

The title compound was synthesized using a procedure similar to that described in Example 36. MS found for C18H15F2N5O as (M+H)+ 356.2. UV: λ=205, 258 nm. ¹H NMR: (CD3OD) δ 8.44 (d, 1H, 2.8 Hz), 8.37 (s, 1H), 8.19 (s, 1H), 7.60 (d, 1H, 8.8 Hz), 7.43 (q, 1H, 8.4 Hz), 7.06 (td, 2.4 Hz, 7.6 Hz), 6.97 (m, 2H), 5.19 (s, 1H), 4.63 (s, 2H).

Example 307

6-(3-chlorophenylamino)-4-((5-fluoropyridin-3-yl)methylamino)nicotinamide

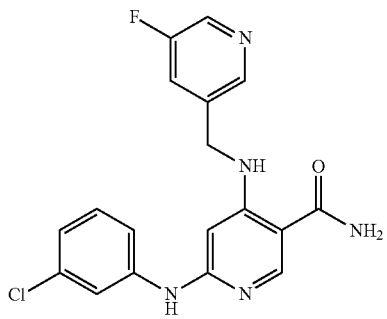 [SMILES: NC(=O)c1cnc(Nc2cccc(Cl)c2)cc1NCc1cncc(F)c1]

The title compound was synthesized using a procedure similar to that described in Example 36. MS found for C18H15ClFN5O as (M+H)+ 372.1. UV: λ=205, 258 nm. ¹H NMR: (CD3OD) δ 8.44 (d, 1H, 2.8 Hz), 8.18 (s, 1H), 7.61 (dt, 2.2 Hz, 9.2 Hz), 7.41 (t, 1H, 8.4 Hz), 7.33 (dt, 1.2 Hz, 7.2 Hz), 7.25 (t, 2 Hz), 7.07 (ddd, 0.8 Hz, 1.6 Hz, 7.6 Hz), 5.90 (s, 1H), 4.63 (s, 2H).

Example 308

6-(4-cyanophenylamino)-4-(5-fluoropyridin-3-yl)methylamino)nicotinamide

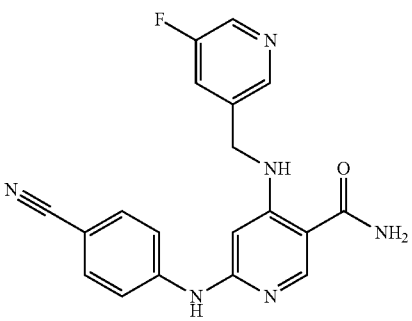 [SMILES: N#Cc1ccc(Nc2cc(NCc3cncc(F)c3)c(C(N)=O)cn2)cc1]

The title compound was synthesized using a procedure similar to that described in Example 36. MS found for C19H15FN6O as (M+H)+ 363.2. UV: λ=202, 268, 317 nm.

¹H NMR: (CD3OD) δ 8.47 (d, 1H, 2.4 Hz), 8.27 (s, 1H), 7.74 (d, 2H, 8.8 Hz), 7.64 (dt, 1H, 9.2 Hz), 7.27 (d, 2H, 8.8 Hz), 6.10 (s, 1H), 4.66 (s, 2H).

Example 309

6-(4-(difluoromethoxy)phenylamino)-4-((5-fluoropyridin-3-yl)methylamino)nicotinamide

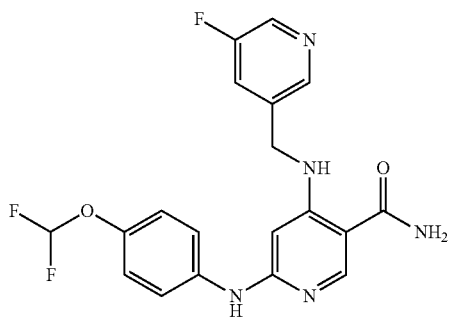 [SMILES: NC(=O)c1cnc(Nc2ccc(OC(F)F)cc2)cc1NCc1cncc(F)c1]

The title compound was synthesized using a procedure similar to that described in Example 36. MS found for C19H16F3N5O2 as (M+H)⁺ 404.2. UV: λ=205, 256 nm. ¹H NMR: (CD3OD) δ 8.44 (d, 1H, 2.8 Hz), 7.59 (dt, 1H, 9.6 Hz, 1.6 Hz), 7.10 (m, 4H), 6.89 (t, 1H, 33.6 Hz), 5.80 (s, 1H), 4.60 (s, 2H).

Example 310

4-((5-fluoropyridin-3-yl)methylamino)-6-(4-(trifluoromethoxy)phenylamino)nicotinamide

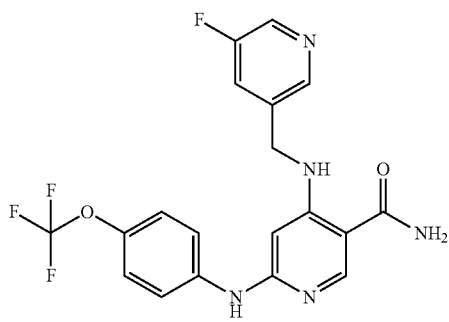 [SMILES: NC(=O)c1cnc(Nc2ccc(OC(F)(F)F)cc2)cc1NCc1cncc(F)c1]

The title compound was synthesized using a procedure similar to that described in Example 36. MS found for C19H15F4N5O2 as (M+H)⁺ 422.2. UV: λ=205, 258 nm. ¹H NMR: (CD3OD) δ 8.45 (d, 1H, 2.8 Hz), 8.17 (s, 1H), 7.59 (dt, 11.6 Hz, 2.4 Hz), 7.35 (d, 8 Hz), 7.26 (d, 2H, 9.2 Hz), 5.88 (s, 1H), 4.63 (s, 2H).

Example 311

4-((5-fluoropyridin-3-yl)methylamino)-6-(p-tolylamino)nicotinamide

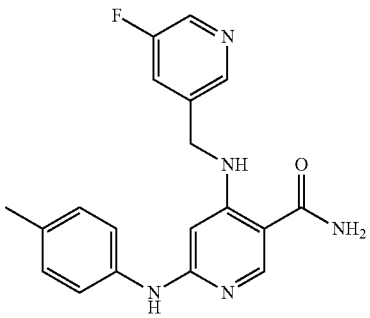 [SMILES: Cc1ccc(Nc2cc(NCc3cncc(F)c3)c(C(N)=O)cn2)cc1]

The title compound was synthesized using a procedure similar to that described in Example 36. MS found for C19H18FN5O as (M+H)⁺ 352.2. UV: λ=2.2, 256 nm. ¹H NMR: (CD3OD) δ 8.44 (s, 1H), 8.34 (s, 1H), 8.12 (s, 1H), 7.56 (d, 1H, 9.2 Hz), 7.25 (d, 2H, 8.4 Hz), 7.01 (d, 2H, 8.4 Hz), 5.76 (s, 1H), 4.58 (s, 2H), 2.38 (s, 3H).

Example 312

6-(4-(dimethylcarbamoyl)phenylamino)-4-((5-fluoropyridin-3-yl)methylamino)nicotinamide

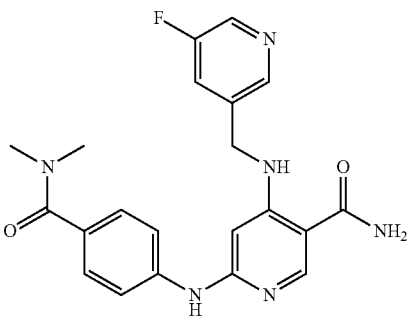 [SMILES: CN(C)C(=O)c1ccc(Nc2cc(NCc3cncc(F)c3)c(C(N)=O)cn2)cc1]

The title compound was synthesized using a procedure similar to that described in Example 36. MS found for C21H21FN6O2 as (M+H)⁺ 0.0. UV: =207, 264 nm. ¹H NMR: (CD3OD) δ 8.42 (s, 1H), 8.38 (s, 1H), 8.20 (d, 1H, 1.2 Hz), 7.62 (d, 1H, 9.2 Hz), 7.48 (d, 2H, 9.2 Hz), 7.20 (d, 2H, 8 Hz), 5.98 (s, 1H), 4.64 (s, 2H), 3.11 (s, 3H), 3.06 (s, 3H).

Example 313

4-((5-fluoropyridin-3-yl)methylamino)-6-(4-(2,2,2-trifluoroethylcarbamoyl)phenylamino)nicotinamide

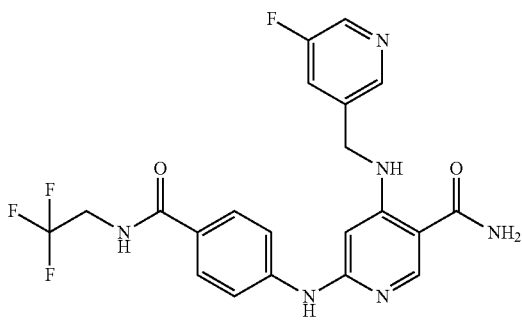 [SMILES: NC(=O)c1cnc(Nc2ccc(C(=O)NCC(F)(F)F)cc2)cc1NCc1cncc(F)c1]

The title compound was synthesized using a procedure similar to that described in Example 36, using an aniline prepared from 2,2,2-trifluoroethylamine and 4-nitrobenzoyl chloride. MS found for C21H18F4N6O2 as (M+H)+ 463.2. UV: λ=205, 268, 315 nm. $^1$H NMR: (CD3OD) δ 8.46 (d, 1H, 2.8 Hz), 8.23 (s, 1H), 7.91 (d, 2H, 8.8 Hz), 7.63 (dt, 1H, 7.2 Hz, 2.4 Hz), 7.22 (d, 2H, 8.4 Hz), 6.03 (s, 1H), 4.64 (s, 2H), 4.11 (q, 2H, 9.4 Hz).

Example 314

4-((5-fluoropyridin-3-yl)methylamino)-6-(4-(methyl(2,2,2-trifluoroethyl)carbamoyl)phenylamino)nicotinamide

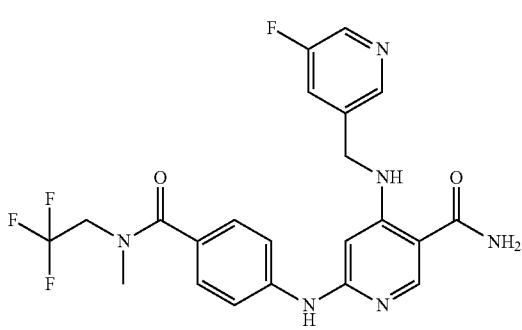 [SMILES: CN(CC(F)(F)F)C(=O)c1ccc(Nc2cc(NCc3cncc(F)c3)c(C(N)=O)cn2)cc1]

The title compound was synthesized using a procedure similar to that described in Example 36. MS found for C22H20F4N6O2 as (M+H)+ 477.2. UV: λ=205, 266 nm. $^1$H NMR: (CD3OD) δ 8.45 (d, 1H, 1.6 Hz), 8.39 (s, 1H), 8.21 (s, 1H), 7.62 (d, 1H, 9.6 Hz), 7.50 (d, 2H), 7.24 (d, 2H, 8.4 Hz), 6.00 (s, 1H), 4.65 (s, 2H), 4.33 (broad s, 2H), 3.17 (s, 3H).

Example 315

4-((6-fluoropyridin-2-yl)methylamino)-6-(4-methoxyphenylamino)nicotinamide

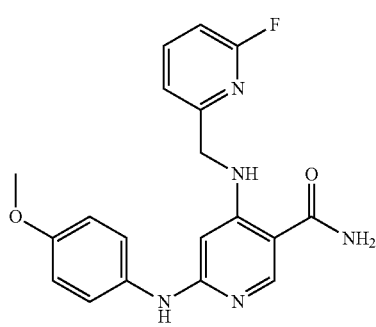 [SMILES: COc1ccc(Nc2cc(NCc3cccc(F)n3)c(C(N)=O)cn2)cc1]

The title compound was synthesized using a procedure similar to that described in Example 36. MS found for C19H18FN5O2 as (M+H)+ 368.2. UV: λ=205, 258 nm. $^1$H NMR: (CD3OD) δ 8.10 (s, 1H), 7.92 (q, 11-1, 8 Hz), 7.26 (d, 1H, 7.2 Hz), 7.11 (d, 2H, 8 Hz), 7.01 (s, 1H), 6.97 (d, 2H, 8.4 Hz), 5.75 (s, 1H), 4.50 (s, 2H), 8.83 (s, 3H).

Example 316

6-(4-(dimethylcarbamoyl)phenylamino)-4-((6-fluoropyridin-2-yl)methylamino)nicotinamide

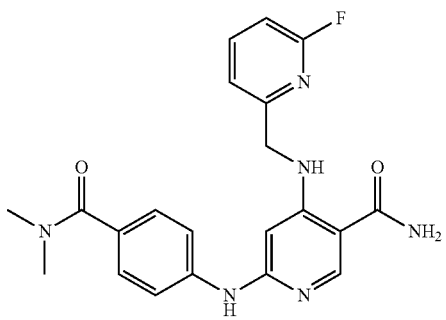 [SMILES: CN(C)C(=O)c1ccc(Nc2cc(NCc3cccc(F)n3)c(C(N)=O)cn2)cc1]

The title compound was synthesized using a procedure similar to that described in Example 36. MS found for C21H21FN6O2 as (M+H)+ 409.3. UV: λ=205, 263 nm. $^1$H NMR: (CD3OD) δ 8.19 (s, 1H), 7.94 (q, 1H, 8 Hz), 7.49 (d, 1H, 7.6 Hz), 7.31 (s, 1H), 7.27 (d, 2H, 7.2 Hz), 7.00 (d, 1H, 7.6 Hz), 6.07 (s, 1H), 4.58 (s, 2H), 3.12 (s, 3H), 3.05 (s, 3H).

Example 317

6-(4-methoxyphenylamino)-4-((1-methyl-1H-indol-7-yl)methylamino)nicotinamide

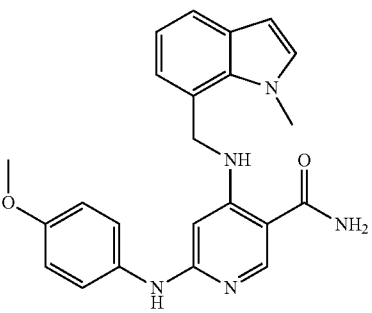 [SMILES: COc1ccc(Nc2cc(NCc3cccc4ccn(C)c34)c(C(N)=O)cn2)cc1]

The title compound was synthesized using a procedure similar to that described in Example 36. MS found for C23H23N5O2 as (M+H)+ 402.3. UV: λ=202, 258 nm ¹H NMR: (CD3OD) δ 8.11 (s, 1H), 7.52 (dd, 1H, 2 Hz, 9 Hz), 7.10 (m, 3H), 6.95 (m, 4H), 6.44 (d, 1H, 3.2 Hz), 5.95 (s, 1H), 4.88, (s, 2H), 3.98 (s, 3H), 3.81 (s, 3H).

Example 318

6-(4-(dimethylcarbamoyl)phenylamino)-4-(1-methyl-1H-indol-7-yl)methylamino)nicotinamide

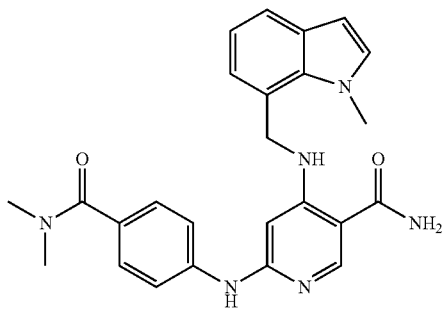 [SMILES: CN(C)C(=O)c1ccc(Nc2cc(NCc3cccc4ccn(C)c34)c(C(N)=O)cn2)cc1]

The title compound was synthesized using a procedure similar to that described in Example 36. MS found for C25H26N6O2 as (M+H)+ 443.3. UV: λ=224, 266 nm. ¹H NMR: (CD3OD) δ 8.22 (s, 1H), 7.53 (dd, 1H, 1.2 Hz, 7.6 Hz), 7.39 (d, 2H, 6.4 Hz), 7.21 (d, 2H, 8.8 Hz), 7.09 (d, 1H, 3.6

Hz), 7.01 (s, 1H), 7.00 (q, 1H, 7.6 Hz), 6.44 (d, 1H, 3.2 Hz), 4.97 (s, 2H), 4.00 (s, 3H), 3.12 (s, 3H), 3.00 (s, 3H).

Example 319

4-((1H-indol-4-yl)methylamino)-6-(4-fluorophenylamino)nicotinamide

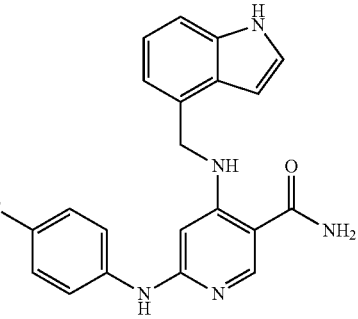

The title compound was synthesized using a procedure similar to that described in Example 36. MS found for C21H18FN5O as (M+H)+ 376.3. UV: λ=219, 258 nm. ¹H NMR: (CD3OD) δ 10.73 (broad s, 1H), 8.12 (s, 1H), 7.37 (d, 1H, 8.4 Hz), 7.25 (t, 1H, 2.8 Hz), 7.08 (t, 1H, 7.6 Hz), 7.01 (m, 4H), 6.87 (d, 1H, 7.2 Hz), 6.47 (m, 1H), 5.81 (s, 1H), 4.71 (s, 2H).

Example 320

4-((1H-indol-4-yl)methylamino)-6-(4-(methylsulfonyl)phenylamino)nicotinamide

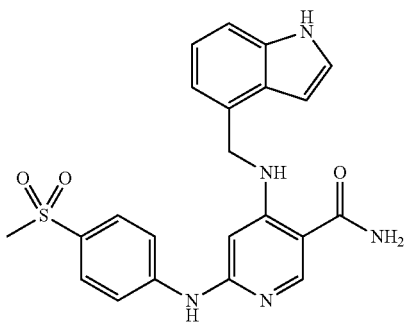 [SMILES: CS(=O)(=O)c1ccc(Nc2cc(NCc3cccc4[nH]ccc34)c(C(N)=O)cn2)cc1]

The title compound was synthesized using a procedure similar to that described in Example 36. MS found for C22H21N5O3S as (M+H)+ 436.2. UV: λ=219, 281 nm. ¹H NMR: (CD3OD) δ 10.78 (broad s, 1H), 8.27 (s, 1H), 7.67 (dd, 2H, 1.6 Hz, 6.4 Hz), 7.42 (d, 1H, 8.4 Hz), 7.27 (t, 1H, 2.4 Hz), 7.13 (t, 1H, 7.2 Hz), 7.01 (dd, 2H, 1.6 Hz, 7.2 Hz), 6.51 (m, 1H), 6.13 (s, 1H), 4.80 (s, 2H), 3.09 (s, 3H).

Example 321

4-((1H-indol-4-yl)methylamino)-6-(4-(difluoromethoxy)phenylamino)nicotinamide

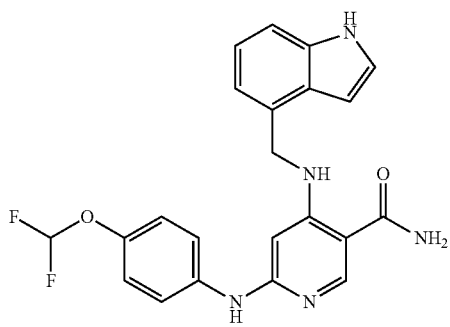 [SMILES: NC(=O)c1cnc(Nc2ccc(OC(F)F)cc2)cc1NCc1cccc2[nH]ccc12]

The title compound was synthesized using a procedure similar to that described in Example 36. MS found for C22H19F2N5O2 as (M+H)+ 424.3. UV: λ=216, 263 nm. ¹H NMR: (CD3OD) δ 10.74 (broad s, 1H), 8.13 (s, 1H), 7.37 (d, 1H, 8.4 Hz), 7.25 (t, 1H, 2.8 Hz), 7.09 (d, 1H, 7.6 Hz), 7.05 (d, 2H, 9.6 Hz), 7.01 (d, 2H, 8.8 Hz), 6.87 (d, 1H, 6.8 Hz), 6.81 (t, 1H, 74 Hz), 6.49 (m, 1H), 5.88 (s, 1H), 4.73 (s, 2H).

Example 322

4-((1H-indol-4-yl)methylamino)-6-(4-(trifluoromethoxy)phenylamino)nicotinamide

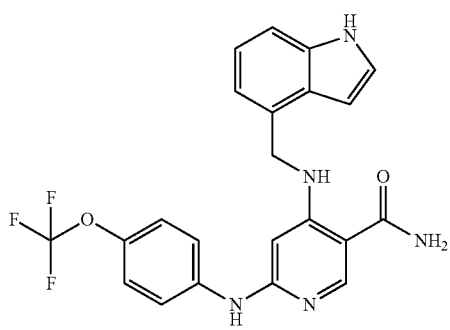 [SMILES: NC(=O)c1cnc(Nc2ccc(OC(F)(F)F)cc2)cc1NCc1cccc2[nH]ccc12]

The title compound was synthesized using a procedure similar to that described in Example 36. MS found for C22H18F3N5O2 as (M+H)+ 442.3. UV: λ=216, 266 nm. ¹H NMR: (CD3OD) δ 10.76 (broad s, 1H), 8.16 (s, 1H), 7.38 (d, 1H, 8.4 Hz), 7.26 (t, 1H, 2.8 Hz), 7.15 (d, 1H, 8 Hz), 7.08 (t, 1H, 7.6 Hz), 7.02 (m, 2H), 6.89 (dd, 1H, 0.8 Hz, 7.6 Hz), 6.49 (m, 1H), 5.94 (s, 1H), 4.75 (s, 2H).

Example 323

4-((1H-indol-4-yl)methylamino)-6-(3,5-difluorophenylamino)nicotinamide

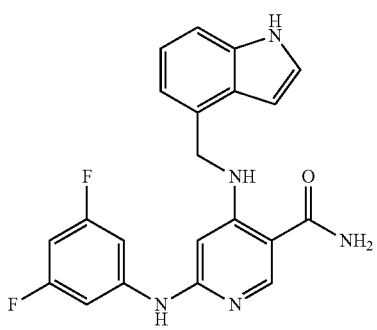 [SMILES: NC(=O)c1cnc(Nc2cc(F)cc(F)c2)cc1NCc1cccc2[nH]ccc12]

The title compound was synthesized using a procedure similar to that described in Example 36. MS found for C21H17F2N5O as (M+H)+ 394.3. UV: λ=219, 268 nm. ¹H NMR: (CD3OD) δ 10.69 (s, 1H), 8.19 (s, 1H), 7.34 (d, 1H, 8 Hz), 7.24 (dd, 1H, 1.6 Hz, 3.2 Hz), 7.07 (t, 1H, 7.6 Hz), 6.83 (tt, 1H, 2.4 Hz, 8.8 Hz), 6.73 (m, 2H), 6.52 (dd, 1H, 0.8 Hz, 3.2 Hz), 6.10 (s, 1H), 4.77 (s, 2H).

Example 324

6-(4-(1-acetylazetidin-3-yl)phenylamino)-4-(benzylamino)nicotinamide

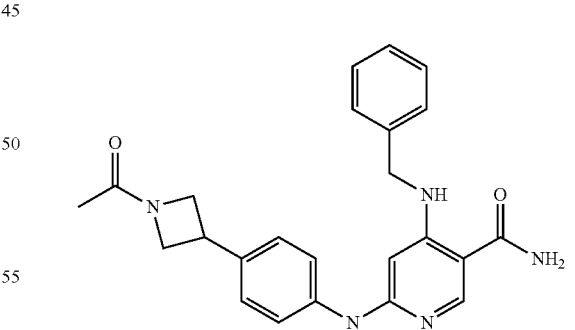

The title compound was synthesized using a procedure similar to that described in Example 36. MS found for C24H25N5O2 as (M+H)+ 416.3. UV: λ=205, 259 nm. ¹H NMR: (CD3OD) δ 8.14 (s, 1H), 7.40 (d, 2H, 8.8 Hz), 7.36 (m, 3H), 7.26 (d, 2H, 6.8 Hz), 7.12 (d, 2H, 8.8 Hz), 5.89 (s, 1H), 4.65 (t, 1H, 8.8 Hz), 4.48 (s, 2H), 4.26 (t, 1H), 4.24 (t, 1H), 3.94 (m, 2H), 1.94 (s, 3H).

Example 325

6-(4-(azetidin-3-yl)phenylamino)-4-(benzylamino)nicotinamide

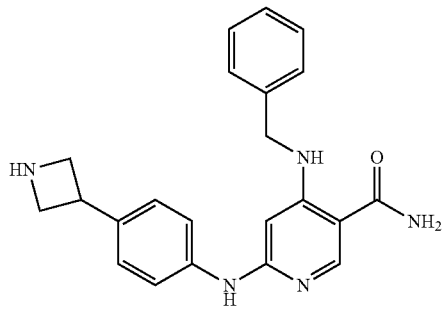 [SMILES: NC(=O)c1cnc(Nc2ccc(C3CNC3)cc2)cc1NCc1ccccc1]

The title compound was synthesized using a procedure similar to that described in Example 36. MS found for C22H23N5O as (M+H)⁺ 374.3. UV: λ=204, 259 nm. ¹H NMR: (CD3OD) δ 8.09 (s, 1H), 7.31 (d, 2H, 8 Hz), 7.26 (m, 3H), 7.18 (d, 2H, 8 Hz), 7.06 (dd, 1H, 2 Hz, 6.4 Hz), 5.19 (s, 1H), 4.37 (s, 2H), 4.30 (m, 2H), 4.16 (m, 3H).

Example 326

4-(benzylamino)-6-(4-(1-propionylazetidin-3-yl)phenylamino)nicotinamide

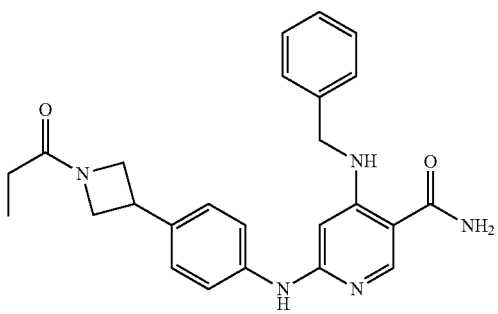 [SMILES: CCC(=O)N1CC(c2ccc(Nc3cc(NCc4ccccc4)c(C(N)=O)cn3)cc2)C1]

The title compound was synthesized using a procedure similar to that described in Example 36. MS found for C25H27N5O2 as (M+H)⁺ 430.3. UV: λ=207, 258 nm. ¹H NMR: (CD3OD) δ 8.14 (s, 1H), 7.39 (d, 2H, 8.4 Hz), 7.36 (d, 2H, 8 Hz), 7.33 (d, 1H, 6.8 Hz), 7.28 (d, 2H, 13.2 Hz), 7.11 (d, 2H, 8.8 Hz), 5.88 (s, 1H), 4.65 (t, 1H, 8.8 Hz), 4.45 (s, 2H), 4.24 (t, 1H, 9.2 Hz), 4.21 (m, 1H), 3.96 (m, 1H), 2.23 (q, 2H, 7.6 Hz), 1.34 (t, 3H, 7.6 Hz).

Example 327 methyl 3-(4-(4-(benzylamino)-5-carbamoylpyridin-2-ylamino)phenyl)azetidine-1-carboxylate

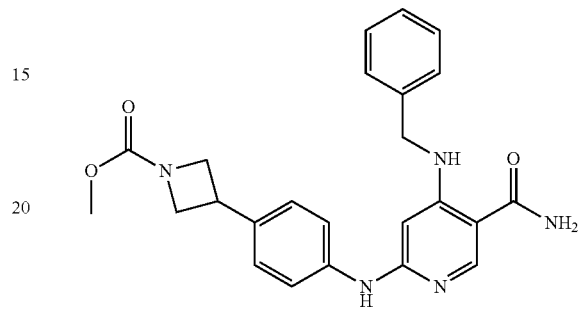

The title compound was synthesized using a procedure similar to that described in Example 36. MS found for C24H25N5O3 as (M+H)⁺ 432.3. UV: λ=204, 258 nm. ¹H NMR: (CD3OD) δ 8.07 (s, 1H), 7.13-7.35 (m, 7H), 7.00 (d, 2H, 8.4 Hz), 5.78 (s, 1H), 4.38 (s, 2H), 4.34 (t, 2H, 8.8 Hz), 3.90 (t, 2H, 6.4 Hz), 3.79 (m, 1H), 3.58 (s, 3H).

Example 328

4-(benzylamino)-6-(4-(2-(dimethylamino)-2-oxoethyl)phenylamino)nicotinamide

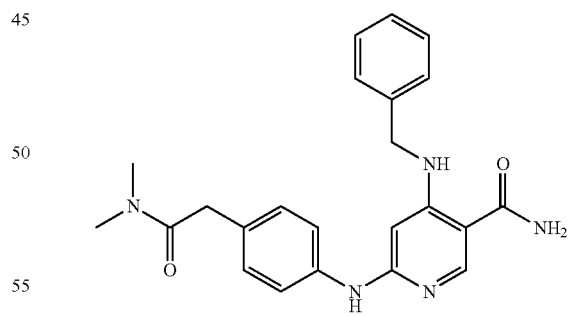

The title compound was synthesized using a procedure similar to that described in Example 36. MS found for C23H25N5O2 as (M+H)⁺ 404.3. UV: λ=207, 258 nm. ¹H NMR: (CD3OD) δ 8.11 (s, 1H), 7.08-7.39 (m, 9H), 7.07 (d, 2H, 8.4 Hz), 5.19 (s, 1H), 4.48 (s, 2H), 3.81 (s, 2H), 3.13 (s, 3H), 2.98 (s, 3H).

Example 329

4-(benzylamino)-6-(4-(2-oxo-2-(pyrrolidin-1-yl)ethyl)phenylamino)nicotinamide

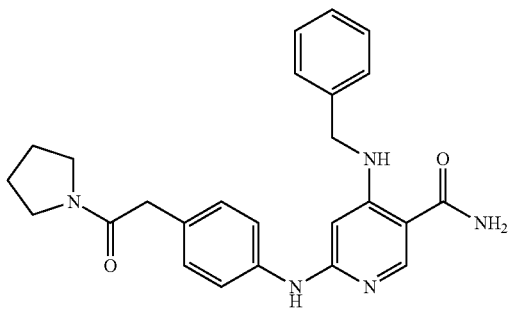 [SMILES: NC(=O)c1cnc(Nc2ccc(CC(=O)N3CCCC3)cc2)cc1NCc1ccccc1]

The title compound was synthesized using a procedure similar to that described in Example 36. MS found for C25H27N5O2 as (M+H)+ 430.4. UV: λ=207, 258 nm. ¹H NMR: (CD3OD) δ 8.11 (s, 1H), 7.27-7.37 (m, 7H), 7.07 (d, 2H, 8.8 Hz), 5.91 (s, 1H), 4.48 (s, 2H), 3.75 (s, 2H), 3.58 (t, 2H), 3.45 (t, 2H), 1.99 (p, 2H, 6.8 Hz), 1.90 (p, 2H, 7.2 Hz).

Example 330

4-(benzylamino)-6-(4-(2-morpholino-2-oxoethyl)phenylamino)nicotinamide

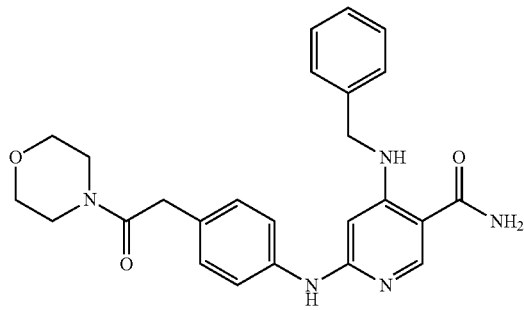 [SMILES: NC(=O)c1cnc(Nc2ccc(CC(=O)N3CCOCC3)cc2)cc1NCc1ccccc1]

The title compound was synthesized using a procedure similar to that described in Example 36. MS found for C25H27N5O3 as (M+H)+ 446.3. UV: λ=207, 258 nm. ¹H NMR: (CD3OD) δ 8.12 (s, 1H), 7.27-7.39 (m, 7H), 7.09 (d, 2H, 8.8 Hz), 5.92 (s, 1H), 4.48 (s, 2H), 3.83 (s, 2H), 3.60-3.66 (m, 8H).

Example 331

4-(benzylamino)-6-(4-(3-(dimethylcarbamoyl)azetidin-1-yl)phenylamino)nicotinamide

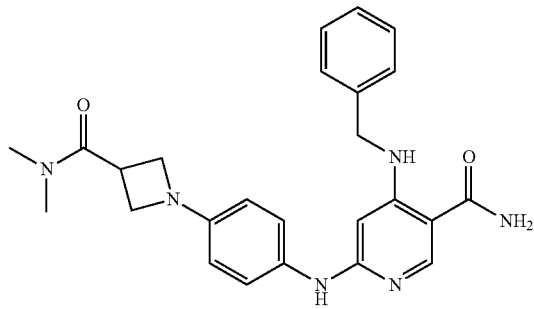 [SMILES: CN(C)C(=O)C1CN(c2ccc(Nc3cc(NCc4ccccc4)c(C(N)=O)cn3)cc2)C1]

The title compound was synthesized using a procedure similar to that described in Example 36. MS found for C25H28N6O2 as (M+H)+ 445.3. UV: λ=2.04, 246 nm. ¹H NMR: (CD3OD) δ 8.05 (s, 1H0, 7.26-7.37 (m, 5H), 6.97 (d, 2H, 8.8 Hz), 6.53 (d, 2H, 8.8 Hz), 5.74 (s, 1H), 4.43 (s, 2H), 4.15 (t, 2H, 8 Hz), 3.98 (t, 2H, 6.4 Hz), 3.94 (m, 1H), 3.03 (s, 3H), 2.97 (s, 3H).

Example 332

4-(benzylamino)-6-(3-chloro-4-methoxyphenylamino)nicotinamide

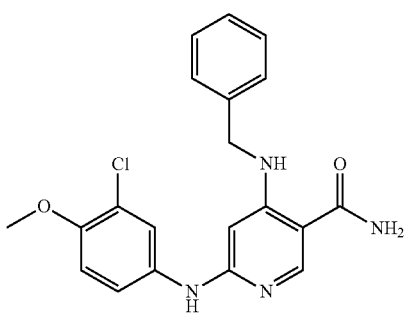 [SMILES: COc1ccc(Nc2cc(NCc3ccccc3)c(C(N)=O)cn2)cc1Cl]

The title compound was synthesized using a procedure similar to that described in Example 36. MS found for C20H19ClN4O2 as (M+H)+ 383.3, 385.3. UV: λ=207, 256 nm.

Example 333

6-(4-(1-acetylazetidin-3-yl)phenylamino)-4-(benzo[b]thiophen-7-ylmethylamino)nicotinamide

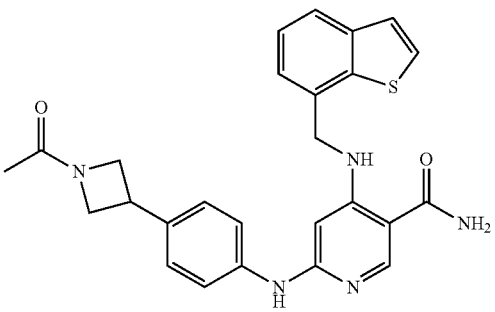 [SMILES: CC(=O)N1CC(c2ccc(Nc3cc(NCc4cccc5ccsc45)c(C(N)=O)cn3)cc2)C1]

The title compound was synthesized using a procedure similar to that described in Example 36. MS found for C26H25N5O2S as (M+H)+ 472.4. UV: λ=204, 259 nm. ¹H NMR: (CD3OD) δ 8.18 (s, 1H), 7.86 (d, 1H, 7.6 Hz), 7.60 (d, 1H, 5.2 Hz), 7.48 (d, 1H, 5.2 Hz), 7.39 (t, 1H, 7.2 Hz), 7.23 (d, 1H, 7.6 Hz), 7.22 (d, 2H, 8.8 Hz), 6.90 (d, 2H, 8.4 Hz), 5.78

(s, 1H), 6.74 (s, 2H), 4.63 (t, 1H, 8.8 Hz), 4.40 (t, 1H, 9.6 Hz), 4.18 (dd, 1H, 5.6 Hz, 8.0 Hz), 3.88 (m, 2H), 1.95 (s, 3H).

Example 334

6-(4-(1-acetylazetidin-3-yl)phenylamino)-4-((5-fluoropyridin-3-yl)methylamino)nicotinamide

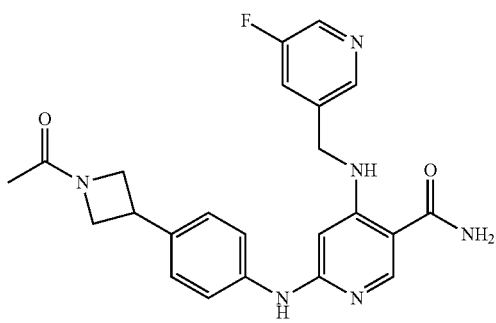 [SMILES: CC(=O)N1CC(c2ccc(Nc3cc(NCc4cncc(F)c4)c(C(N)=O)cn3)cc2)C1]

The title compound was synthesized using a procedure similar to that described in Example 36. MS found for C23H23FN6O2 as (M+H)+ 435.3. UV: λ=201, 259 nm. $^1$H NMR: (CD3OD) δ 8.45 (s, 1H), 8.33 (s, 1H), 7.57 (d, 1H, 9.6 Hz), 7.44 (d, 2H, 9.6 Hz), 7.13 (d, 2H, 8.4 Hz), 5.80 (s, 1H), 4.65 (t, 1H, 9.2 Hz), 4.59 (s, 2H), 4.42 (t, 1H, 8.8 Hz), 4.27 (t, 1H, 6.8 Hz), 3.99 (m, 2H), 1.93 (s, 3H).

Example 335

4-(benzylamino)-6-(4-(1-(methylsulfonyl)azetidin-3-yl)phenylamino)nicotinamide

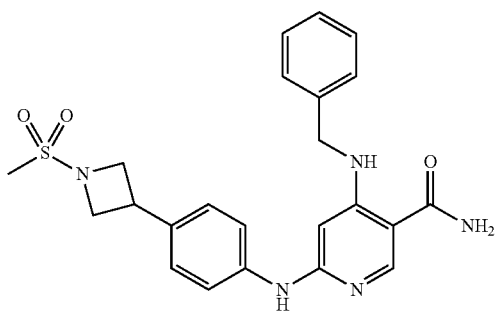 [SMILES: CS(=O)(=O)N1CC(c2ccc(Nc3cc(NCc4ccccc4)c(C(N)=O)cn3)cc2)C1]

The title compound was synthesized using a procedure similar to that described in Example 36. MS found for C23H25N5O3S as (M+H)+ 452.3. UV: λ=202, 259 nm. $^1$H NMR: (CD3OD) δ 8.15 (s, 1H), 7.43 (d, 2H, 8 Hz), 7.38 (m, 3H), 7.26 (d, 2H, 6.8 Hz), 7.11 (d, 2H, 6.4 Hz), 5.88 (s, 1H), 4.48 (s, 2H), 4.31 (t, 2H, 8 Hz), 4.00 (t, 2H, 6.4 Hz), 3.89 (p, 2H, 6.8 Hz), 3.01 (s, 3H).

Example 336

4-(benzylamino)-6-(4-(1-(2-methoxyacetyl)azetidin-3-yl)phenylamino)nicotinamide

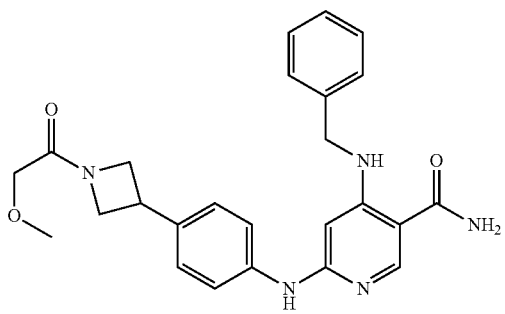

The title compound was synthesized using a procedure similar to that described in Example 36. MS found for C25H27N5O3 as (M+H)+ 446.3. UV: λ=204, 259 nm. $^1$H NMR: (CD3OD) δ 8.14 (s, 1H), 7.25-7.41 (m, 7H), 7.11 (d, 2H, 6.8 Hz), 5.88 (s, 1H), 3.73 (t, 1H, 8.4 Hz), 4.48 (s, 2H), 4.47 (m, 1H), 4.30 (m, 1H), 4.05 (s, 2H), 3.97 (m, 2H), 3.40 (s, 3H).

Example 337

4-(benzylamino)-6-(4-(1-(dimethylcarbamoyl)azetidin-3-yl)phenylamino)nicotinamide

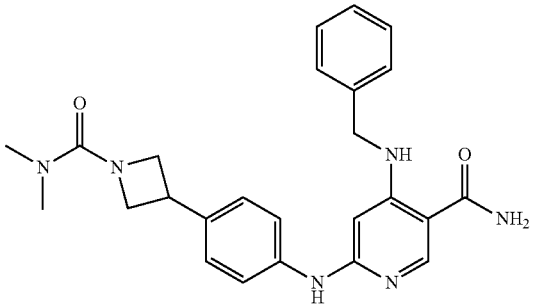

The title compound was synthesized using a procedure similar to that described in Example 36. MS found for C25H28N6O2 as (M+H)+ 445.2. UV: λ=202, 258 nm. $^1$H NMR: (CD3OD) δ 8.13 s, 1H), 7.39 (d, 2H, 8 Hz), 7.33 (m, 3H), 7.26 (d, 2H, 6.4 Hz), 7.09 (d, 2H, 8.4 Hz), 5.88 (s, 1H), 4.47 (s, 2H), 4.44 (t, 2H, 8.4 Hz), 4.01 (dd, 2H, 6 Hz, 8 Hz), 3.83 (1, 1H), 2.92 (s, 6H).

Example 338

4-(benzylamino)-6-(4-(1-(pyrrolidine-1-carbonyl)azetidin-3-yl)phenylamino)nicotinamide

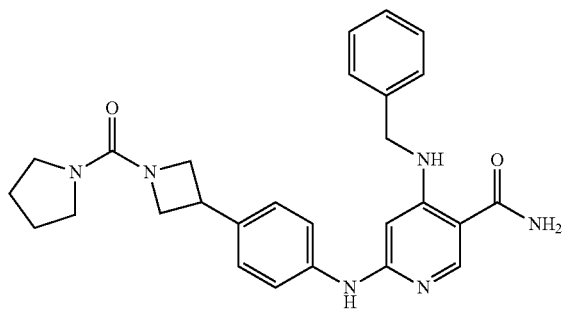 [SMILES: NC(=O)c1cnc(Nc2ccc(C3CN(C(=O)N4CCCC4)C3)cc2)cc1NCc1ccccc1]

The title compound was synthesized using a procedure similar to that described in Example 36. MS found for C27H30N6O2 as (M+H)+ 471.4. UV: λ=203, 259 nm. ¹H NMR: (CD3OD) δ 8.13 (s, 1H), 7.41 (d, 2H, 8.4 Hz), 7.34 (m, 3H), 7.26 (d, 6.4 Hz), 7.10 (d, 2H, 8.4 Hz), 5.88 (s, 1H), 4.48 (s, 2H), 4.45 (t, 2H, 8.8 Hz), 4.02 (dd, 2H, 5.6 Hz, 7.6 Hz), 3.85 (m, 1H), 3.36 (m, 4H), 1.89 (m, 4H).

Example 339

4-(benzylamino)-6-(4-(1-(N,N-dimethylsulfamoyl)azetidin-3-yl)phenylamino)nicotinamide

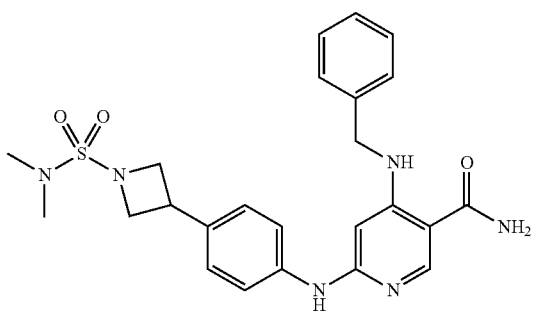 [SMILES: CN(C)S(=O)(=O)N1CC(c2ccc(Nc3cc(NCc4ccccc4)c(C(N)=O)cn3)cc2)C1]

The title compound was synthesized using a procedure similar to that described in Example 36. MS found for C24H28N6O3S as (M+H)+ 481.3. UV: λ=201, 259 nm. ¹H NMR: (CD3OD) δ 8.14 (s, 1H), 7.43 (d, 2H), 7.39 (m, 3H), 7.23 (d, 2H), 7.06 (d, 2H), 5.89 (s, 1H), 4.48 (s, 2H), 4.23 (t, 1H), 3.97 (t, 2H), 3.89 (m, 1H), 2.84 (s, 6H).

Example 340

4-(benzylamino)-6-(4-(2-(methylamino)-2-oxoethyl)phenylamino)nicotinamide

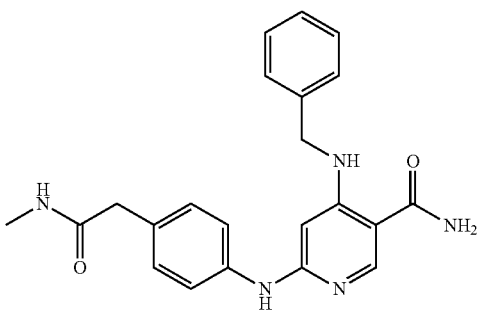 [SMILES: CNC(=O)Cc1ccc(Nc2cc(NCc3ccccc3)c(C(N)=O)cn2)cc1]

The title compound was synthesized using a procedure similar to that described in Example 36. MS found for C22H23N5O2 as (M+H)+ 390.3. UV: λ=203, 258 nm. ¹H NMR: (CD3OD) δ 8.12 (s, 1H), 7.31-7.36 (m, 5H), 7.28 (d, 2H, 8.4 Hz), 7.06 (d, 2H, 8.4 Hz), 5.89 (s, 1H), 4.46 (s, 2H), 3.52 (s, 2H), 2.74 (s, 3H).

Example 341

4-(benzylamino)-6-(4-(2-oxo-2-(2,2,2-trifluoroethylamino)ethyl)phenylamino)nicotinamide

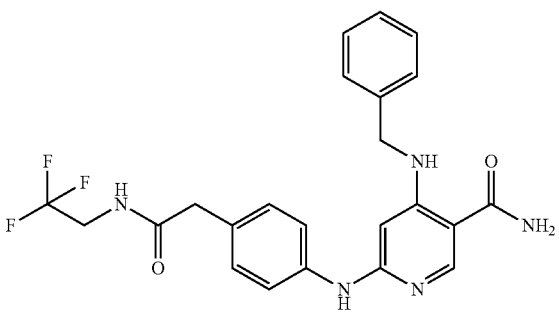 [SMILES: NC(=O)c1cnc(Nc2ccc(CC(=O)NCC(F)(F)F)cc2)cc1NCc1ccccc1]

The title compound was synthesized using a procedure similar to that described in Example 36. MS found for C23H22F3N5O2 as (M+H)+ 458.3. UV: λ=202, 258 nm. ¹H NMR: (CD3OD) δ 8.13 (s, 1H), 7.26-7.37 (m, 7H), 7.07 (d, 2H, 8.4 Hz), 5.90 (s, 1H), 4.46 (s, 2H), 3.93 (q, 2H, 9.2 Hz), 3.61 (s, 2H).

Example 342

4-(benzylamino)-6-(4-(3-(dimethylcarbamoyl)azetidin-1-yl)-3-fluorophenylamino)nicotinamide

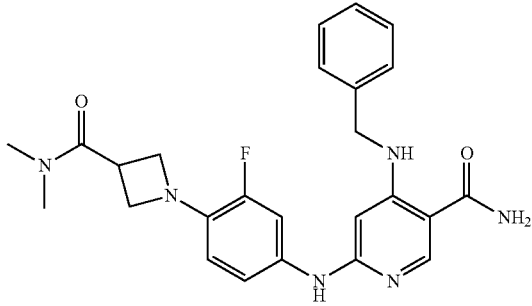

The title compound was synthesized using a procedure similar to that described in Example 36. MS found for C25H27FN6O2 as (M+H)+ 463.4. UV: λ=202, 243 nm. 1H NMR: (CD3OD) δ 8.08 (s, 1H), 7.26-7.38 (m, 5H), 6.86 (2H), 6.59 (td, 0.8 Hz, 8.4 Hz), 4.46 (s, 2H), 4.24 (td, 2H, 2.4 Hz, 8.4 Hz), 4.08 (td, 2H, 0.2 Hz, 7.2 Hz), 3.94 (m, 1H), 3.02 (s, 3H), 3.97 (s, 3H).

Example 343

4-(benzylamino)-6-(4-(4-(dimethylcarbamoyl)piperidin-1-yl)phenylamino)nicotinamide

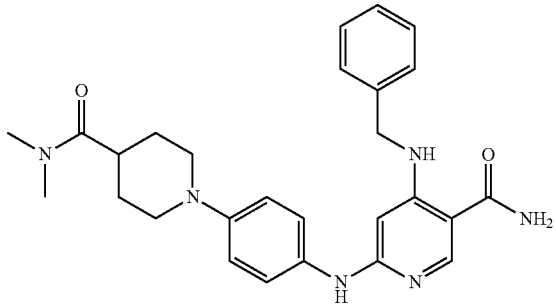 [SMILES: CN(C)C(=O)C1CCN(c2ccc(Nc3cc(NCc4ccccc4)c(C(N)=O)cn3)cc2)CC1]

The title compound was synthesized using a procedure similar to that described in Example 36. MS found for C27H32N6O2 as (M+H)+ 473.4. UV: λ=204, 264 nm. 1H NMR: (CD3OD) δ 8.09 (s, 1H), 7.23-7.49 (m, 5H), 7.04 (m, 4H), 5.79 (s, 1H), 4.45 (s, 2H), 3.72 (m, 2H), 3.15 (s, 3H), 2.93 (s, 3H), 2.92 (m, 4H), 1.87 (m, 4H).

Example 344

4-(benzo[b]thiophen-4-ylmethylamino)-6-(4-(4-(dimethylcarbamoyl)piperidin-1-yl)phenylamino)nicotinamide

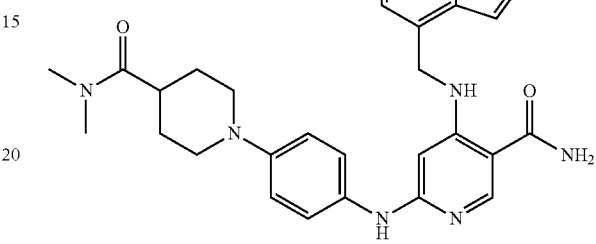

The title compound was synthesized using a procedure similar to that described in Example 36. MS found for C29H32N6O2S as (M+H)+ 529.5. UV: λ=205, 229, 268 nm. 1H NMR: (CD3OD) δ 8.12 (s, 1H), 7.92 (d, 1H, 8 Hz), 7.68 (d, 1H, 5.2 Hz), 7.38 (d, 1H, 5.2 Hz), 7.12 (t, 1H, 6.8 Hz), 7.22 (d, 1H, 6.8 Hz), 6.91 (s, 4H), 5.80 (s, 1H), 4.87 (s, 2H), 3.75 (m, 1H), 3.18 (s, 3H), 2.96 (s, 3H), 2.88 (m, 4H), 1.85 (m, 4H).

Example 345

4-((1H-indol-4-yl)methylamino)-6-(4-(4-(dimethylcarbamoyl)piperidin-1-yl)phenylamino)nicotinamide

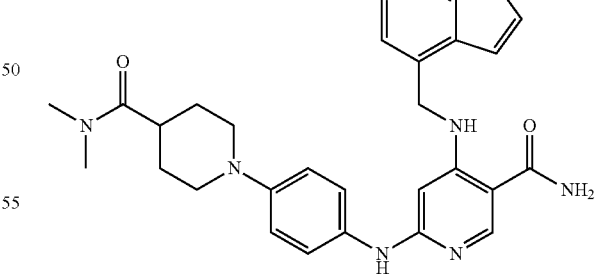

The title compound was synthesized using a procedure similar to that described in Example 36. MS found for C29H33N7O2 as (M+H)+ 512.4. UV: λ=212, 271 nm. 1H NMR: (CD3OD) δ 8.10 (s, 1H), 7.38 (d, 1H, 8.8 Hz), 7.26 (d, 1H, 3.2 Hz), 7.09 (t, 1H, 8 Hz), 6.98 (1, 1H), 6.92 (dd, 2H, 1.6 Hz, 6.8 Hz), 6.88 (d, 1H, 7.6 Hz), 6.50 (d, 1H, 3.2 Hz), 5.89 (s, 1H), 4.71 (s, 2H), 3.75 (m, 2H), 3.17 (s, 3H), 2.96 (s, 3H), 2.92 (m, 3H), 1.88 (m, 4H).

Example 346

4-(benzo[b]thiophen-7-ylmethylamino)-6-(4-(methylsulfonylmethyl)phenylamino)nicotinamide

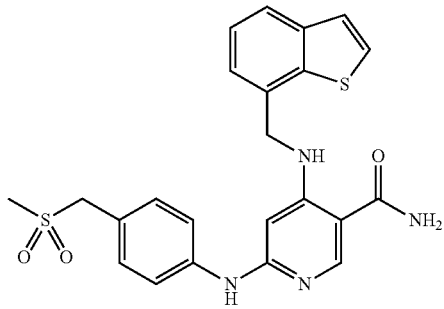 [SMILES: CS(=O)(=O)Cc1ccc(Nc2cc(NCc3cccc4ccsc34)c(C(N)=O)cn2)cc1]

The title compound was synthesized using a procedure similar to that described in Example 36. MS found for C23H22N4O3S2 as (M+H)+ 467.3. UV: λ=202, 227, 261 nm.

Example 347

4-(benzylamino)-6-(4-(methylsulfonylmethyl)phenylamino)nicotinamide

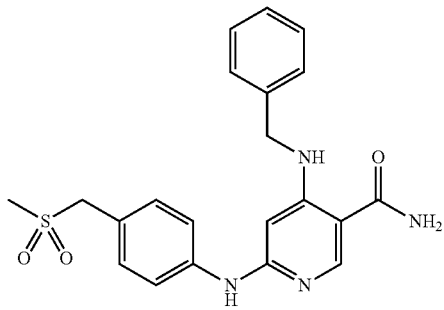 [SMILES: CS(=O)(=O)Cc1ccc(Nc2cc(NCc3ccccc3)c(C(N)=O)cn2)cc1]

The title compound was synthesized using a procedure similar to that described in Example 36. MS found for C21H22N4O3S as (M+H)+ 411.1. UV: λ=205, 261 nm. $^1$H NMR: (CD3OD) δ 8.07 (s, 1H), 7.37 (d, 2H, 8.8 Hz), 7.29 (t, 2H, 7.6 Hz), 7.21 (m, 1H), 7.19 (d, 2H, 8 Hz), 7.02 (d, 2H, 8.4 Hz), 5.86 (s, 1H), 4.39 (s, 2H), 4.38 (s, 2H), 2.86 (s, 3H).

Example 348

4-((1H-indol-4-yl)methylamino)-6-(4-(methylsulfonylmethyl)phenylamino)nicotinamide

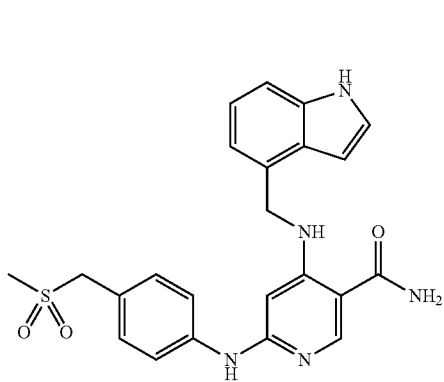 [SMILES: CS(=O)(=O)Cc1ccc(Nc2cc(NCc3cccc4[nH]ccc34)c(C(N)=O)cn2)cc1]

The title compound was synthesized using a procedure similar to that described in Example 36. MS found for C23H23N5O3S as (M+H)+ 450.3. UV: λ=217, 271 nm. $^1$H NMR: (CD3OD) δ 8.15 (s, 1H), 7.38 (t, 3H, 8 Hz). 7.26 (t, 1H, 2.8 Hz), 7.12 (t, 1H, 7.6 Hz), 7.01 (d, 2H, 8 Hz), 6.90 (d, 1H, 7.6 Hz), 6.50 (d, 1H, 2 Hz), 6.02 (s, 1H), 4.74 (s, 2H), 4.43 (s, 2H), 2.91 (s, 3H).

Example 349

4-(benzo[b]thiophen-7-ylmethylamino)-6-(4-(3-(dimethylcarbamoyl)azetidin-1-yl)-3-fluorophenylamino)nicotinamide

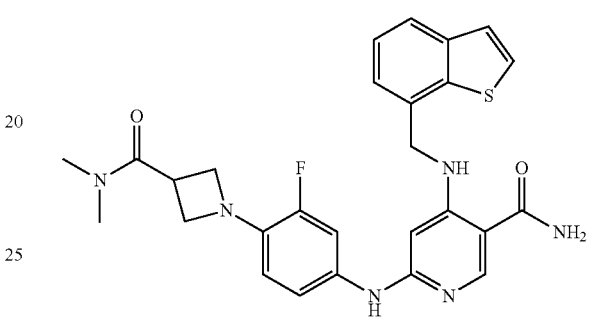

The title compound was synthesized using a procedure similar to that described in Example 36. MS found for C27H27FN6O2S as (M+H)+ 519.4. UV: λ=204, 229 nm. $^1$H NMR: (CD3OD) δ 8.16 (s, 1H), 7.87 (d, 1H, 8 Hz), 7.68 (d, 1H, 5.2 Hz), 7.50 (d, 1H, 5.6 Hz), 7.42 (t, 1H, 7.6 Hz), 7.26 (d, 1H, 6.8 Hz), 6.81 (dd, 1H, 2 Hz, 12.8 Hz), 6.67 (dd, 1H, 2 Hz, 9.6 Hz), 6.48 (t, 1H, 8.4 Hz), 5.72 (s, 1H), 4.74 (s, 2H), 2.36 (td, 2H, 2 Hz, 8.4 Hz), 4.10 (td, 1H, 1.2 Hz, 7.2 Hz), 3.97 (p, 1H, 7.2 Hz), 3.04 (s, 3H), 2.99 (s, 3H).

Example 350

4-(benzo[b]thiophen-7-ylmethylamino)-6-(4-(4-(dimethylcarbamoyl)piperidin-1-yl)phenylamino)nicotinamide

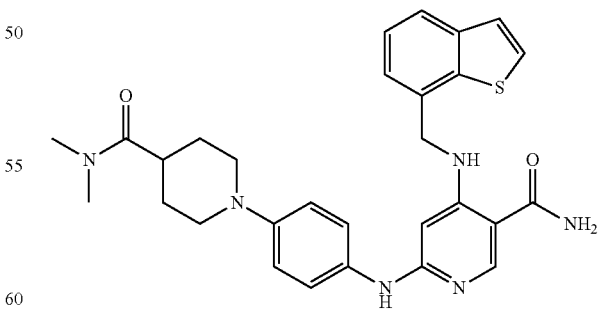

The title compound was synthesized using a procedure similar to that described in Example 36. MS found for C29H32N6O2S as (M+H)+ 529.4. UV: λ=205, 227, 261 nm. $^1$H NMR: (CD3OD) δ 8.11 (s, 1H), 7.84 (d, 1H, 7.6 Hz), 7.59 (d, 1H, 5.2 Hz), 7.46 (d, 1H, 5.6 Hz), 7.39 (t, 1H, 7.2 Hz), 6.92

(d, 2H, 9.6 Hz), 6.87 (d, 2H), 9.2 Hz), 5.75 (s, 1H), 4.73 (s, 2H), 3.75 (m, 2H), 3.17 (s, 3H), 2.96 (s, 3H), 2.91 (m, 3H), 1.85 (m, 4H).

Example 351

4-(benzo[b]thiophen-7-ylmethylamino)-6-(3-chloro-4-(4-(dimethylcarbamoyl)piperidin-1-yl)phenylamino)nicotinamide

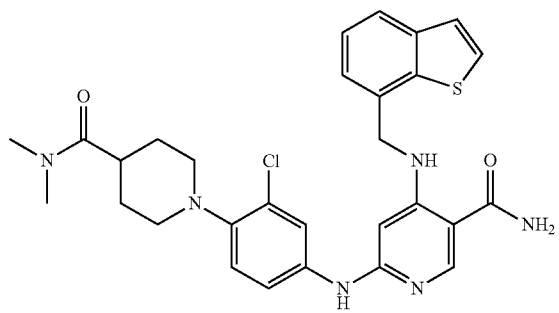 [SMILES: CN(C)C(=O)C1CCN(c2ccc(Nc3cc(NCc4cccc5ccsc45)c(C(N)=O)cn3)cc2Cl)CC1]

The title compound was synthesized using a procedure similar to that described in Example 36. MS found for C29H31ClN6O2S as (M+H)+ 563.4. UV: λ=207, 227, 251 nm. ¹H NMR: (CD3OD) δ 8.23 (s, 1H), 7.91 (d, 1H, 8 Hz), 7.71 (d, 1H, 5.6 Hz), 7.55 (d, 1H, 5.6 Hz), 7.45 (t, 1H, 5.6 Hz), 7.29 (d, 1H, 7.2 Hz), 7.26 (d, 1H, 2.8 Hz), 7.03 (d, 1H, 8.8 Hz), 6.90 (dd, 1H, 2.4 Hz, 8.4 Hz), 5.85 (s, 1H), 4.81 (s, 2H), 3.40 (m, 2H), 3.19 (s, 3H), 2.98 (s, 3H), 2.89 (m, 1H), 2.79 (td, 2H, 8.4 Hz, 2.8 Hz), 1.92 (m, 4H).

Example 352

6-(4-(acetamidomethyl)phenylamino)-4-(benzo[b]thiophen-7-ylmethylamino)nicotinamide

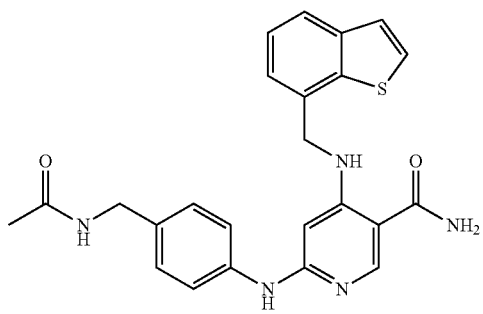 [SMILES: CC(=O)NCc1ccc(Nc2cc(NCc3cccc4ccsc34)c(C(N)=O)cn2)cc1]

The title compound was synthesized using a procedure similar to that described in Example 36. MS found for C24H23N5O2S as (M+H)+ 446.3. UV: λ=227, 258 nm. ¹H NMR: (CD3OD) δ 8.20 (s, 1H), 7.89 (d, 1H, 7.6 Hz), 7.67 (d, 1H, 5.6 Hz), 7.52 (d, 1H, 5.2 Hz), 7.44 (t, 1H, 6.8 Hz), 7.27 (d, 1H, 7.2 Hz), 7.23 (d, 2H, 7.6 Hz), 6.96 (d, 2H, 8.4 Hz), 5.86 (s, 1H), 4.77 (s, 2H), 4.36 (s, 2H), 2.02 (s, 3H).

Example 353

4-(benzo[b]thiophen-7-ylmethylamino)-6-(4-(methylsulfonamidomethyl)phenylamino)nicotinamide

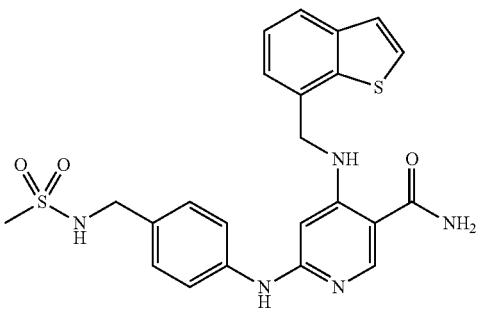 [SMILES: CS(=O)(=O)NCc1ccc(Nc2cc(NCc3cccc4ccsc34)c(C(N)=O)cn2)cc1]

The title compound was synthesized using a procedure similar to that described in Example 36. MS found for C23H23N5O3S2 as (M+H)+ 482.3. UV: λ=205, 227, 258 nm. ¹H NMR: (CD3OD) δ 8.18 (s, 1H), 7.85 (d, 1H, 7.6 Hz), 7.61 (d, 1H, 5.6 Hz), 7.48 (d, 1H, 5.2 Hz), 7.41 (t, 1H, 7.6 Hz), 7.25 (d, 2H, 7.6 Hz), 6.91 (d, 2H, 8.8 Hz), 5.82 (s, 1H), 4.72 (s, 2H), 4.22 (s, 2H), 2.91 (s, 3H).

Example 354

4-(benzo[b]thiophen-7-ylmethylamino)-6-(4-((3,3-dimethylureido)methyl)phenylamino)nicotinamide

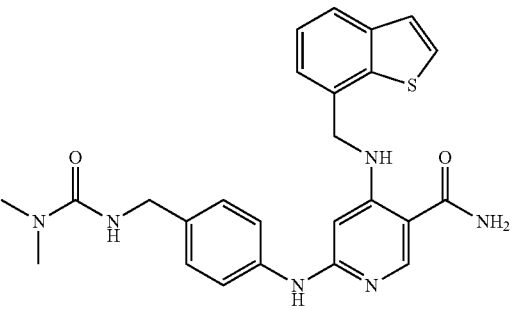 [SMILES: CN(C)C(=O)NCc1ccc(Nc2cc(NCc3cccc4ccsc34)c(C(N)=O)cn2)cc1]

The title compound was synthesized using a procedure similar to that described in Example 36. MS found for C25H26N6O2S as (M+H)+ 475.3. UV: λ=205, 227, 258 nm. ¹H NMR: (CD3OD) δ 8.13 (s, 1H), 7.84 (d, 1H, 7.6 Hz), 7.60

(d, 1H, 5.2 Hz), 7.46 (d, 1H, 5.6 Hz), 7.39 (t, 1H, 7.2 Hz), 7.23 (m, 3H), 6.91 (d, 2H, 8.4 Hz), 5.84 (s, 1H), 4.74 (s, 2H), 4.33 (s, 2H), 2.92 (s, 6H).

Example 355

4-(benzo[b]thiophen-7-ylmethylamino)-6-(4-((N,N-dimethylsulfamoylamino)methyl)phenylamino)nicotinamide

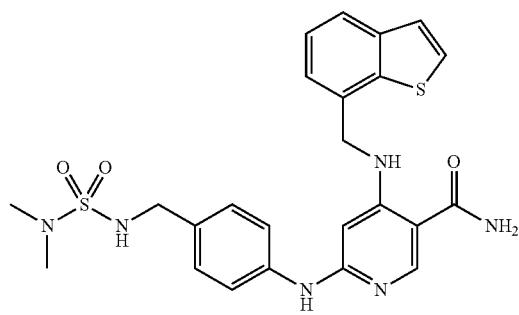 [SMILES: CN(C)S(=O)(=O)NCc1ccc(Nc2cc(NCc3cccc4ccsc34)c(C(N)=O)cn2)cc1]

The title compound was synthesized using a procedure similar to that described in Example 36. MS found for C24H26N6O3S2 as (M+H)+ 511.4. UV: =205, 227, 258 nm. $^1$H NMR: (CD3OD) δ 8.16 (s, 1H), 7.85 (d, 1H, 8.4 Hz), 7.61 (d, 1H, 5.2 Hz), 7.48 (d, 1H, 5.2 Hz), 7.42 (t, 1H, 7.6 Hz), 7.27 (d, 2H, 7.6 Hz), 6.90 (d, 2YH, 8.8 Hz), 5.19 (s, 1H), 4.74 (s, 2H), 4.17 (s, 2H), 2.76 (s, 6H).

Example 357

4-((1H-indol-5-yl)methylamino)-6-(4-(1-propionylpiperidin-4-yl)phenylamino)nicotinamide

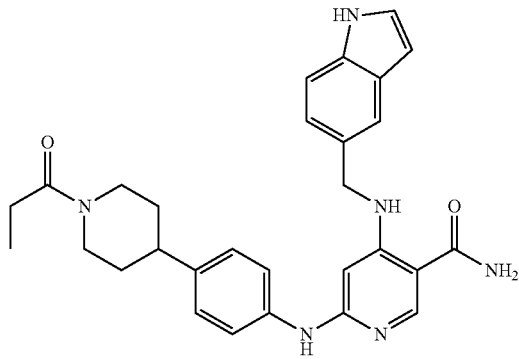 [SMILES: CCC(=O)N1CCC(c2ccc(Nc3cc(NCc4ccc5[nH]ccc5c4)c(C(N)=O)cn3)cc2)CC1]

The title compound was synthesized using a procedure similar to that described in Example 36. MS found for C29H32N6O2 as (M+H)+ 497.5. UV: λ=217, 263 nm. $^1$H NMR: (CD3OD) δ 8.13 (s, 1H), 7.45 (s, 1H), 7.40 (d, 1H, 8 Hz), 7.30 (t, 1H, 2.8 Hz), 7.16 (d, 2H, 8.8 Hz), 7.03 (dd, 1H, 1.6 Hz, 8.8 Hz), 6.98 (d, 2H, 8.4 Hz), 6.44 (s, 1H), 5.99 (s, 1H), 4.53 (s, 2H), 4.10 (m, 1H), 2.84 (m, 1H), 2.83 (m, 1H), 2.74 (m, 1H), 2.47 (q, 2H, 7.6 Hz), 1.86 (m, 2H), 1.58 (m, 2H), 1.16 (t, 3H, 7.2 Hz).

Example 359

4-((1H-indol-6-yl)methylamino)-6-(4-(1-propionylpiperidin-4-yl)phenylamino)nicotinamide

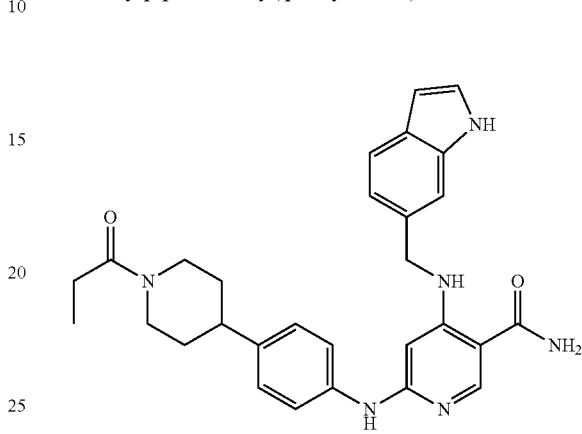

The title compound was synthesized using a procedure similar to that described in Example 36. MS found for C29H32N6O2 as (M+H)+ 497.4. UV: λ=217, 263 nm. $^1$H NMR: (CD3OD) δ 8.13 (s, 1H), 7.54 (d, 1H, 8.4 Hz), 7.29 (s, 1H), 7.25 (m, 1H), 7.00 (d, 1H, 8.8 Hz), 6.91 (dd, 1H, 1.6 Hz, 8.4 Hz), 6.86 (d, 2H, 8.8 Hz), 6.47 (m, 1H), 5.93 (s, 1H), 4.72 (m, 1H), 4.57 (s, 2H), 4.08 (m, 1H), 3.22 (m, 2H), 2.74 (m, 1H), 2.48 (q, 2H, 7.2 Hz), 1.86 (m, 2H), 1.56 (m, 2H), 1.17 (t, 3H, 7.6 Hz).

Example 361

6-(4-(N-methylacetamido)phenylamino)-4-(1-phenylcyclopropylamino)nicotinamide

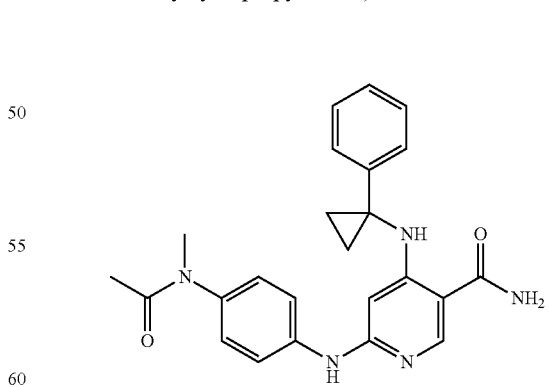

The title compound was synthesized using a procedure similar to that described in Example 124. MS found for C24H25N5O2 as (M+H)+ 416.5. UV: λ=258.2 nm. $^1$H NMR:

(CD3OD) δ 8.11 (s, 1H), 7.24 (m, 5H), 7.06 (d, J=8.4 Hz, 2H), 7.03 (d, J=7.8 Hz, 2H), 6.02 (s, 1H), 3.14 (s, 3H), 1.76 (s, 3H), 1.27 (m, 4H) ppm.

Example 362

4-(1-phenylcyclopropylamino)-6-(4-piperidin-1-yl)phenylamino) nicotinamide

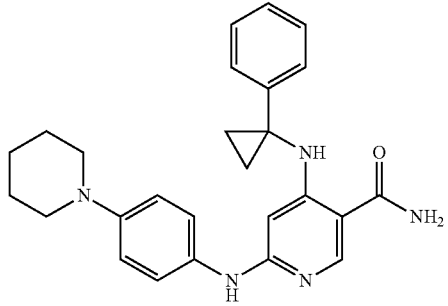 [SMILES: NC(=O)c1cnc(Nc2ccc(N3CCCCC3)cc2)cc1NC1(c2ccccc2)CC1]

The title compound was synthesized using a procedure similar to that described in Example 124. MS found for C26H29N5O as (M+H)+ 428.5. UV: λ=264.1 nm. ¹H NMR: (CD3OD) δ 8.16 (s, 1H), 7.31 (m, 2H), 7.22 (m, 3H), 7.32 (d, J=8.8 Hz, 2H), 7.08 (d, J=9.2 Hz, 2H), 6.06 (s, 1H), 3.35 (m, 4H), 1.86-1.70 (m, 6H), 1.34 (m, 4H) ppm.

Example 363

4-(1-phenylcyclopropylamino)-6-(3-(2-(pyrrolidin-1-yl)ethoxy)phenylamino)nicotinamide

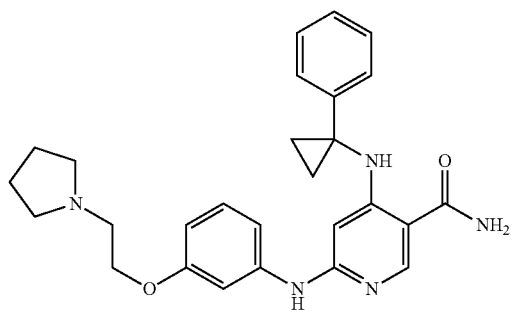 [SMILES: NC(=O)c1cnc(Nc2cccc(OCCN3CCCC3)c2)cc1NC1(c2ccccc2)CC1]

The title compound was synthesized using a procedure similar to that described in Example 124. MS found for C27H31N5O2 as (M+H)+ 458.6. UV: λ=259.4 nm. ¹H NMR: (CD3OD) δ 8.19 (s, 1H), 7.30 (m, 4H), 7.14 (m, 2H), 7.22 (dd, J=8.4, 2.4 Hz, 1H), 6.82 (t, J=2.4 Hz, 1H), 6.72 (dd, J=9.2, 2.0 Hz, 1H), 6.16 (s, 1H), 4.27 (t, J=4.4 Hz, 2H), 3.64 (t, J=4.8 Hz, 2H), 3.25 (m, 4H), 2.12 (m, 4H), 1.36 (m, 4H) ppm.

Example 364

6-(4-(4-(methylsulfonyl)piperazin-1-yl)phenylamino)-4-(1-phenylcyclopropylamino)nicotinamide

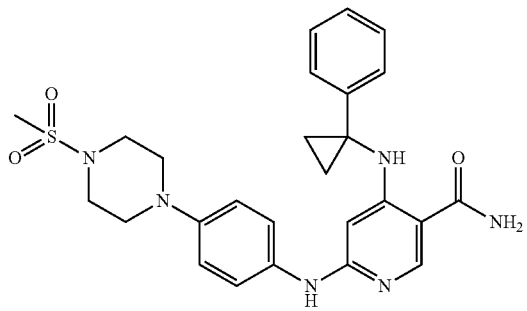 [SMILES: CS(=O)(=O)N1CCN(c2ccc(Nc3cc(NC4(c5ccccc5)CC4)c(C(N)=O)cn3)cc2)CC1]

The title compound was synthesized using a procedure similar to that described in Example 124. MS found for C26H30N6O3S as (M+H)+ 507.4. UV: λ=244.0 nm. ¹H NMR: (CD3OD) δ 8.01 (s, 1H), 7.24 (m, 1H), 7.23 (d, J=6.8 Hz, 2H), 7.14 (m, 1H), 7.03 (dd, J=8.4, 1.6 Hz, 2H), 6.90 (s, 3H), 5.90 (s, 1H), 3.28 (m, 4H), 3.23 (m, 4H), 2.80 (s, 3H), 1.23 (m, 4H) ppm.

Example 365

6-(3-(2-(dimethylamino)-2-oxoethoxy)phenylamino)-4-(1-phenylcyclopropylamino)nicotinamide

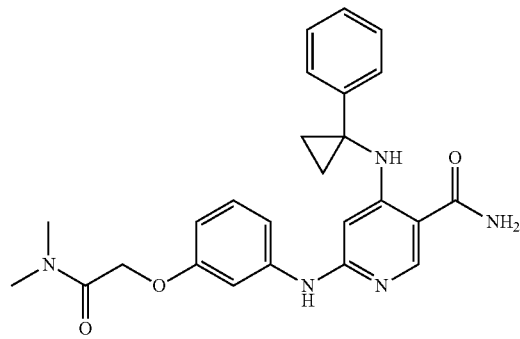 [SMILES: CN(C)C(=O)COc1cccc(Nc2cc(NC3(c4ccccc4)CC3)c(C(N)=O)cn2)c1]

The title compound was synthesized using a procedure similar to that described in Example 124. MS found for C25H27N5O3 as (M+H)+ 446.4. UV: λ=257.0 nm. ¹H NMR: (CD3OD) δ 8.14 (s, 1H), 7.33-7.14 (m, 6H), 7.14 (dd, J=8.4, 2.4 Hz, 1H), 6.78 (t, J=2.4 Hz, 1H), 6.75 (dd, J=8.0, 2.0 Hz, 1H), 6.15 (s, 1H), 4.90 (s, 2H), 3.30 (s, 3H), 2.97 (s, 3H), 1.38 (m, 4H) ppm.

Example 366

6-(4-(2-(dimethylamino)-2-oxoethoxy)phenylamino)-4-(1-phenylcyclopropylamino)nicotinamide

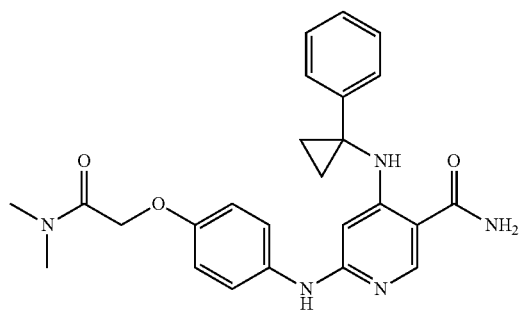 [SMILES: CN(C)C(=O)COc1ccc(Nc2cc(NC3(c4ccccc4)CC3)c(C(N)=O)cn2)cc1]

The title compound was synthesized using a procedure similar to that described in Example 124. MS found for C25H27N5O3 as (M+H)+ 446.4. UV: λ=257.0 nm. ¹H NMR: (CD3OD) δ 8.10 (s, 1H), 7.30 (m, 2H), 7.15 (m, 1H), 7.13 (d, J=8.4, 2H), 7.03 (m, 2H), 6.96 (m, 2H), 6.01 (s, 1H), 4.87 (s, 2H), 3.30 (s, 3H), 2.99 (s, 3H), 1.38 (m, 4H) ppm.

Example 367

4-(1-phenylcyclopropylamino)-6-(3-(piperazin-1-yl)phenylamino)nicotinamide

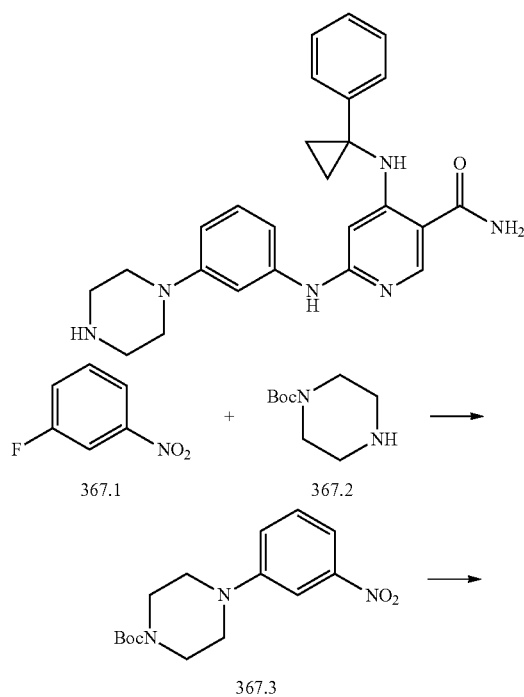

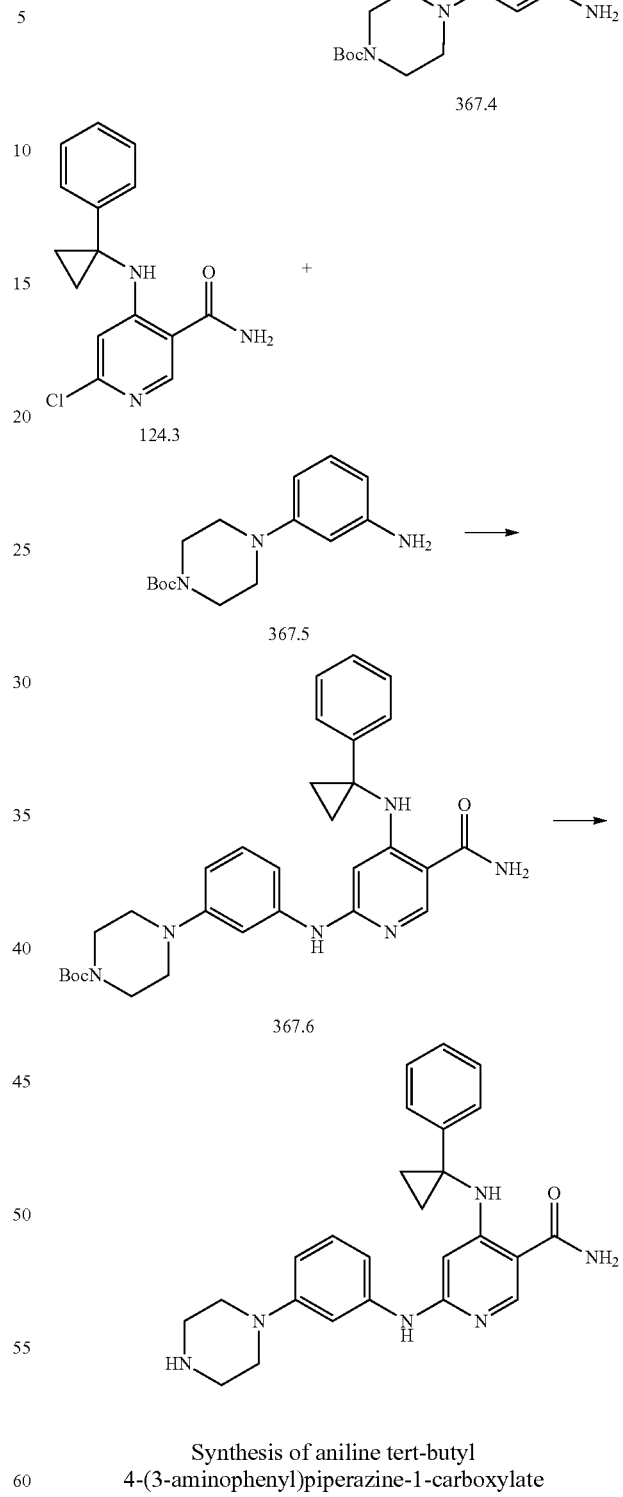

Synthesis of aniline tert-butyl 4-(3-aminophenyl)piperazine-1-carboxylate

Step 1: To a solution of 3-fluoronitrobenzene (2 mL, 18.8 mmol) in DMSO (20 mL) was added Boc-piperazine (10 g, 56.4 mmol), after stirring at 100° C. for 3 days, the mixture was poured to ice water, the resulting precipitate was collected by filtration to give tert-butyl 4-(3-nitrophenyl)piperazine-1-carboxylate (1.91 g).

Step 2: To a solution of tert-butyl 4-(3-nitrophenyl)piperazine-1-carboxylate in EtOH (20 mL) and THF (10 mL) was added Pd/C (500 mg), the mixture was charged with H₂ (1 atm) and stirred for 16 h. Pd/C was filtered off, the filtrate was concentrated to give tert-butyl 4-(3-aminophenyl)piperazine-1-carboxylate (1.71 g).

Synthesis of 4-(1-phenylcyclopropylamino)-6-(3-(piperazin-1-yl)phenylamino)nicotinamide To a mixture of 6-chloro-4-(1-phenylcyclopropylamino)nicotinamide (150 mg, 0.522 mmol) in p-Dioxane (4.5 mL) was added tert-butyl 4-(3-aminophenyl)piperazine-1-carboxylate (174 mg, 0.626 mmol), Pd(OAc)₂ (23 mg, 0.104 mmol), BINAP (65 mg, 0.104 mmol) and Cs₂CO₃ (510 mg, 1.566 mmol). After stirred at 80° C. for 15 h, it was concentrated to give crude residue, which was then treated with TFA in DCM, 30 min later, the solution was concentrated, the residue was purified by preparative HPLC to give 4-(1-phenylcyclopropylamino)-6-(3-(piperazin-1-yl)phenylamino)nicotinamide. MS found for C25H28N6O as (M+H)⁺ 429.4. UV: λ=254.6 nm. ¹H NMR: (CD3OD) δ 8.17 (s, 1H), 7.31-7.20 (m, 4H), 7.13 (m, 2H), 6.95 (dd, J=8.0, 2.0 Hz, 1H), 6.79 (t, J=2.0 Hz, 1H), 6.60 (dd, J=7.2, 2.0 Hz, 1H), 6.12 (s, 1H), 3.34 (m, 8H), 1.36 (m, 4H) ppm.

Example 371

6-(3-(4-acetylpiperazin-1-yl)phenylamino)-4-(1-phenylcyclopropylamino)nicotinamide

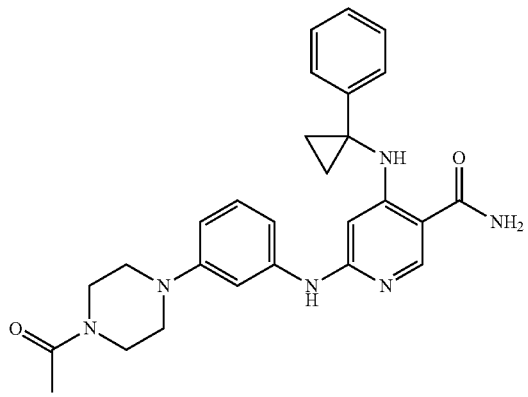 [SMILES: CC(=O)N1CCN(c2cccc(N(C(C)=O)c3cc(NC4(c5ccccc5)CC4)c(C(N)=O)cn3)c2)CC1]

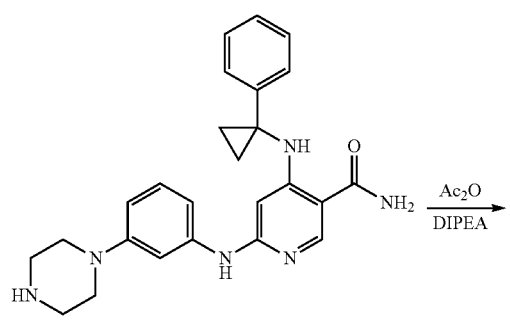

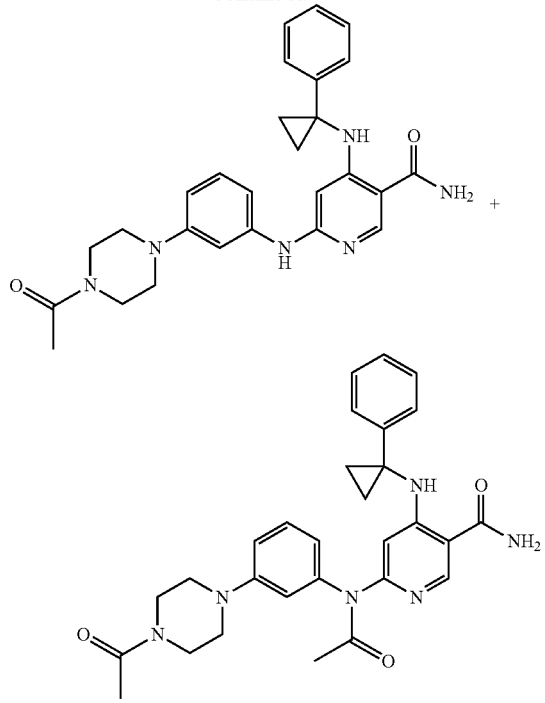

To a solution of 4-(1-phenylcyclopropylamino)-6-(3-(piperazin-1-yl)phenylamino)nicotinamide (30 mg, 0.07 mmol) in DCM was added Ac₂O (0.0066 mL, 0.07 mmol) and DIPEA (0.024 mL, 0.14 mmol), the mixture was concentrated and purified by preparative HPLC to give 6-(3-(4-acetylpiperazin-1-yl)phenylamino)-4-(1-phenylcyclopropylamino)nicotinamide. MS found for C27H30N6O2 as (M+H)⁺ 471.4. UV: λ=251.8 nm. ¹H NMR: (CD3OD) δ 8.14 (s, 1H), 7.27 (m, 4H), 7.12 (dd, J=8.8, 1.2 Hz, 2H), 6.93 (dd, J=8.4, 2.4 Hz, 1H), 6.72 (s, 1H), 6.56 (dd, J=7.6, 1.2 Hz, 1H), 6.11 (s, 1H), 3.68 (m, 4H), 3.17 (m, 2H), 3.09 (m, 2H), 2.15 (s, 3H), 1.38 (m, 4H) ppm.

Example 372

6-(N-(3-(4-acetylpiperazin-1-yl)phenyl)acetamino)-4-(1-phenylcyclopropylamino)nicotinamide

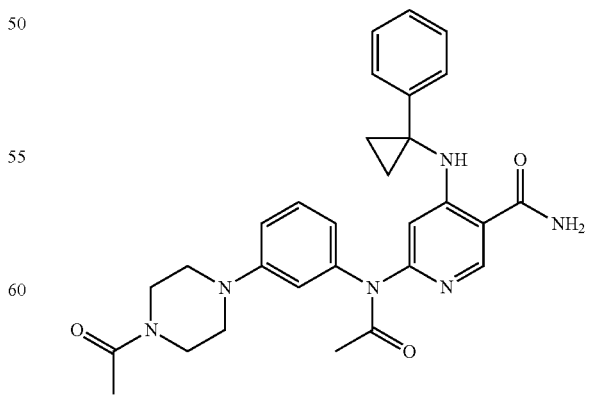

The title compound was synthesized using a procedure similar to that described in Example 36.71. MS found for C29H32N6O3 as (M+H)+ 513.4. UV: λ=254.6 nm. ¹H NMR: (CD3OD) δ 8.42 (s, 1H), 7.41 (t, J=8.4, 1.2 Hz, 1H), 7.18 (m, 4H), 6.86 (m, 3H), 6.74 (d, J=8.0 Hz, 1H), 5.86 (s, 1H), 3.70 (m, 4H), 3.19 (m, 2H), 3.69 (m, 2H), 2.18 (s, 3H), 2.07 (s, 3H), 1.17 (bs, 2H), 1.15 (bs, 2H) ppm.

Example 374

4-(1-(2,3-difluorophenyl)cyclopropylamino)-6-(4-(4-propionylpiperazin-1-yl)phenylamino)nicotinamide

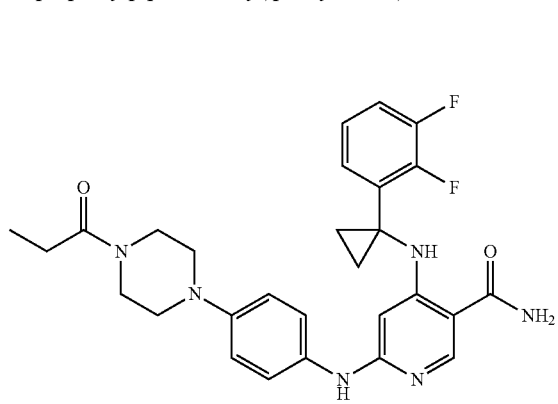

The title compound was synthesized using a procedure similar to that described in Example 124. MS found for C28H30F2N6O2 as (M+H)+ 521.4. UV: λ=246.3 nm. ¹H NMR: (CD3OD) δ 8.08 (d, J=3.2 Hz, 1H), 7.15 (m, 7H), 6.20 (d, J=3.2 Hz, 1H), 3.75 (m, 4H), 3.27 (m, 4H), 2.48 (dq, J=8.4, 3.2 Hz, 2H), 1.38 (bs, 2H), 1.27 (bs, 2H), 1.15 (dt, J=7.6, 3.2 Hz, 3H) ppm.

Example 375

4-(1-phenylcyclopropylamino)-6-(4-(1-propionylpiperidin-4-yl)phenylamino)nicotinamide

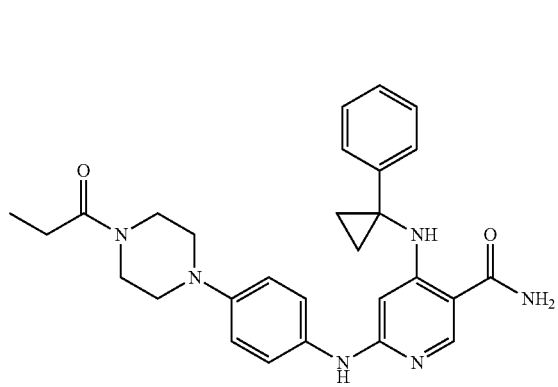 [SMILES: CCC(=O)N1CCN(c2ccc(Nc3cc(NC4(c5ccccc5)CC4)c(C(N)=O)cn3)cc2)CC1]

The title compound was synthesized using a procedure similar to that described in Example 124. MS found for C29H33N5O2 as (M+H)+ 484.3. UV: λ=258.2 nm. ¹H NMR: (CD3OD) δ 8.13 (d, J=2.4 Hz, 1H), 7.26 (m, 5H), 7.12 (d, J=8.0 Hz, 2H), 7.03 (dd, J=8.8, 2.4 Hz, 2H), 6.06 (d, J=2.8 Hz, 1H), 4.70 (m, 1H), 4.10 (m, 1H), 2.80 (m, 2H), 2.47 (q, J=7.6 Hz, 2H), 1.90 (m, 2H), 1.60 (m, 2H), 1.38 (bs, 2H), 1.32 (bs, 2H), 1.15 (dt, J=7.6, 2.8 Hz, 3H) ppm.

Example 376

6-(4-(4-acetylpiperazin-1-yl)phenylamino-5-chloro-4-(3-fluorobenzylamino)nicotinamide

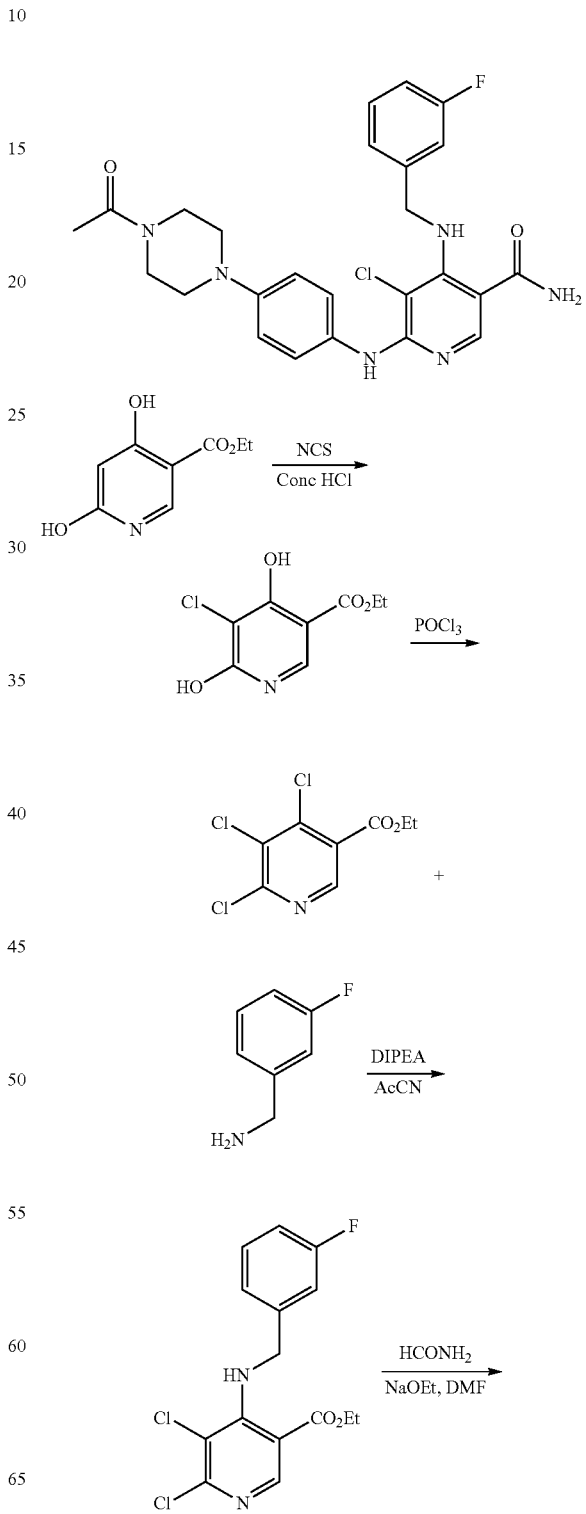

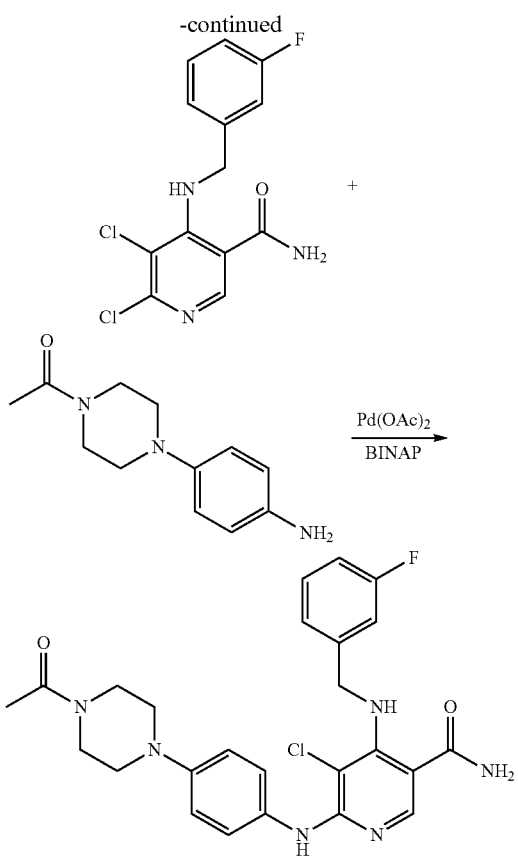

Step 1: To a solution of ethyl 4,6-dihydroxynicotinate (1.0 g, 5.43 mmol) in DMF (10 mL) was added NCS (797 mg, 5.96 mmol) and conc. HCl (0.05 mL). After stirring at room temperature for 2.5 h, it was added water and $Na_2S_2O_3$, the precipitate was collected by filtration, washed with 1N HCl and dried to give ethyl 5-chloro-4,6-dihydroxynicotinate (920 mg).

Step 2: A suspension of 5-chloro-4,6-dihydroxynicotinate (920 mg, 4.22 mmol) in POCl3 (10 mL) was heated at 100° C. for 4 h, then it was concentrated, quenched with ice water and NaHCO3, the resulting precipitate was collected by filtration to give ethyl 4,5,6-trichloronicotinate (700 mg).

Step 3: To a solution of ethyl 4,5,6-trichloronicotinate (200 mg, 0.78 mmol) in AcCN (1.5 mL) was added 3-fluorobenzylamine (0.108 mL, 0.94 mmol) and DIPEA (0.167 mL, 0.94 mmol). The mixture was stirred at room temperature for 5 h them at 50° C. until the reaction is over. The solution was cooled and concentrated, the resulting residue was diluted with water, the solid was then collected by filtration to give ethyl 5,6-dichloro-4-(3-fluorobenzylamino)nicotinate (260 mg).

Step 4: To a solution of ethyl 5,6-dichloro-4-(3-fluorobenzylamino)nicotinate (260 mg, 0.76 mmol) in DMF (1 mL) was added $HCONH_2$ (0.272 mL, 6.84 mmol) and NaOEt (21% in EtOH, 0.425 mL, 1.14 mmol). After stirring at room temperature for 30 min, the mixture was added water, and the precipitate was collected by filtration to give 5,6-dichloro-4-(3-fluorobenzylamino)nicotinamide (170 mg).

Step 5: To a mixture of 5,6-dichloro-4-(3-fluorobenzylamino)nicotinamide (31 mg, 0.1 mmol) in p-Dioxane (1.5 mL) was added 1-(4-(4-aminophenyl)piperazin-1-yl)ethanone (24 mg, 0.11 mmol), $Pd(OAc)_2$ (4 mg, 0.02 mmol), BINAP (12 mg, 0.02 mmol) and $Cs_2CO_3$ (100 mg, 0.3 mmol). After stirred at 80° C. for 15 h, it was concentrated and the residue was purified by preparative HPLC to give 6-(4-(4-acetylpiperazin-1-yl)phenylamino-5-chloro-4-(3-fluorobenzylamino)nicotinamide. MS found for C25H26ClFN6O2 as (M+H)+ 497.3. UV: λ=255.8, 303.3 nm. $^1$H NMR: (CD3OD) δ 7.67 (s, 1H), 7.27 (q, J=7.6 Hz, 1H), 7.16 (m, 3H), 7.13-6.93 (m, 4H), 4.87 (s, 2H), 3.64 (m, 4H), 3.20 (m, 4H), 2.06 (s, 3H) ppm.

Example 377

5-chloro-4-(3-fluorobenzylamino)-6-(4-morpholinophenylamino)nicotinamide

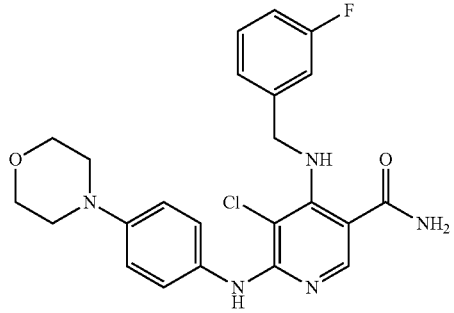 [SMILES: NC(=O)c1cnc(Nc2ccc(N3CCOCC3)cc2)c(Cl)c1NCc1cccc(F)c1]

The title compound was synthesized using a procedure similar to that described in Example 376. MS found for C23H23ClFN5O2 as (M+H)+ 456.2. UV: λ=258.0, 305.5 nm. $^1$H NMR: (CD3OD) δ 7.66 (s, 1H), 7.27 (q, J=7.6 Hz, 1H), 7.10 (m, 2H), 7.13-6.92 (m, 4H), 4.87 (s, 2H), 3.75 (t, J=4.8 Hz, 4H), 3.12 (t, J=4.8 Hz, 4H) ppm.

| Example | Structure | Formula | MS (M + H)+ | NB | Pg |
|---|---|---|---|---|---|
| 383 | 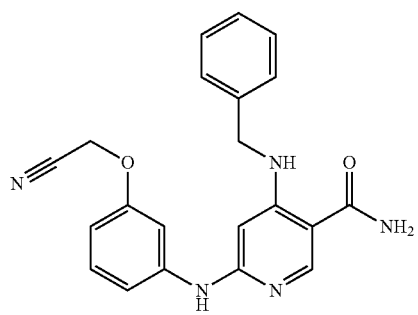 [SMILES: N#CCOc1cccc(Nc2cc(NCc3ccccc3)c(C(N)=O)cn2)c1] | C21H19N5O2 | MS: 374.3 | PN-00821 | 18 |

-continued

| Example | Structure | Formula | MS (M + H)+ | NB | Pg |
|---|---|---|---|---|---|
| 384 | 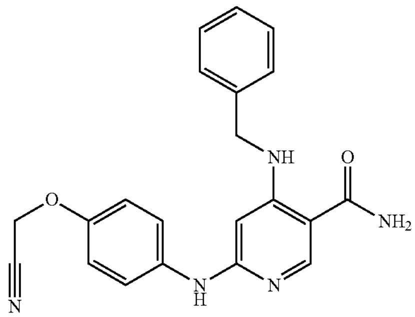 [SMILES: N#CCOc1ccc(Nc2cc(NCc3ccccc3)c(C(N)=O)cn2)cc1] | C21H19N5O2 | MS: 374.3 | PN-00821 | 22 |
| 385 | 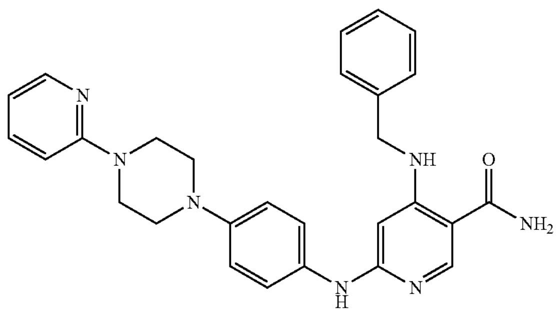 [SMILES: NC(=O)c1cnc(Nc2ccc(N3CCN(c4ccccn4)CC3)cc2)cc1NCc1ccccc1] | C28H29N7O | MS: 480.3 | PN-00821 | 28 |
| 386 | 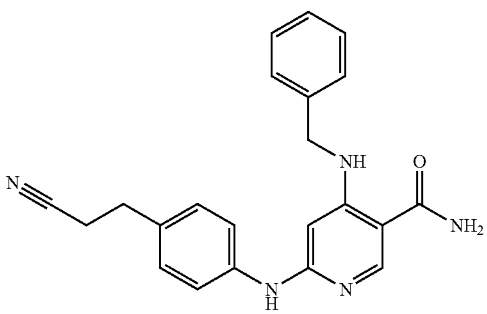 [SMILES: N#CCCc1ccc(Nc2cc(NCc3ccccc3)c(C(N)=O)cn2)cc1] | C22H21N5O | MS: 372.3 | PN-00821 | 29 |
| 387 | 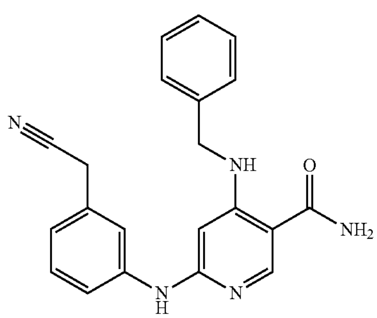 [SMILES: N#CCc1cccc(Nc2cc(NCc3ccccc3)c(C(N)=O)cn2)c1] | C21H19N5O | MS: 358.2 | PN-00821 | 30 |
| 388 | 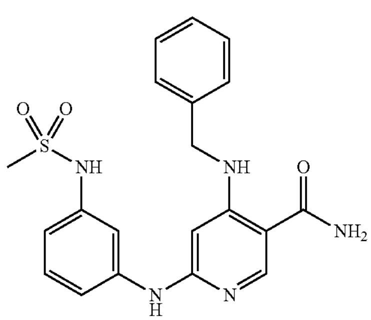 [SMILES: CS(=O)(=O)Nc1cccc(Nc2cc(NCc3ccccc3)c(C(N)=O)cn2)c1] | C20H21N5O3S | MS: 412.2 | PN-00821 | 47 |

-continued

| Example | Structure | Formula | MS (M + H)+ | NB | Pg |
|---|---|---|---|---|---|
| 389 | 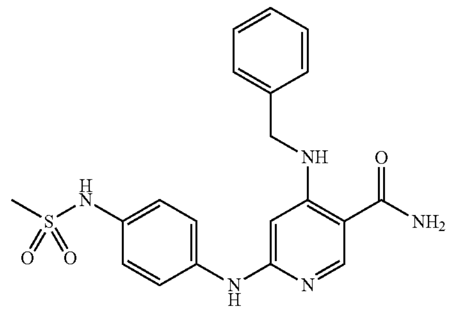 [SMILES: CS(=O)(=O)Nc1ccc(Nc2cc(NCc3ccccc3)c(C(N)=O)cn2)cc1] | C20H21N5O3S | MS: 412.2 | PN-00821 | 38 |
| 390 | 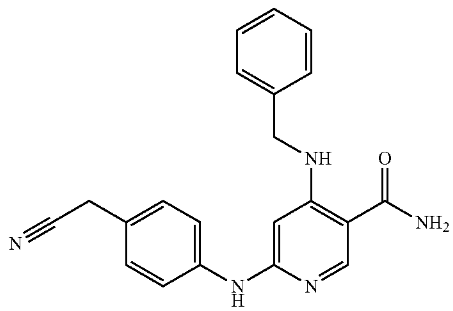 [SMILES: N#CCc1ccc(Nc2cc(NCc3ccccc3)c(C(N)=O)cn2)cc1] | C21H19N5O | MS: 358.3 | PN-00821 | 31 |
| 391 | 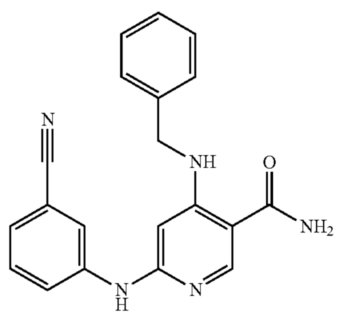 [SMILES: N#Cc1cccc(Nc2cc(NCc3ccccc3)c(C(N)=O)cn2)c1] | C20H17N5O | MS: 344.2 | PN-00821 | 32 |
| 392 | 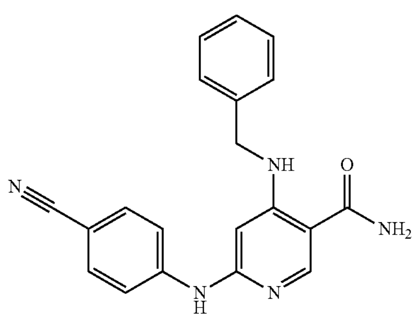 [SMILES: N#Cc1ccc(Nc2cc(NCc3ccccc3)c(C(N)=O)cn2)cc1] | C20H17N5O | MS: 344.3 | PN-00821 | 33 |
| 393 | 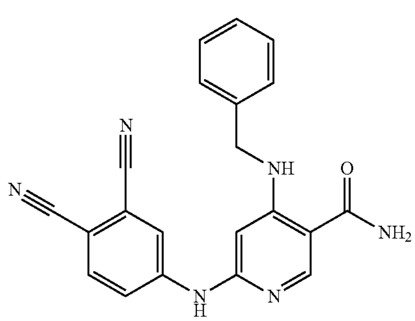 [SMILES: N#Cc1ccc(Nc2cc(NCc3ccccc3)c(C(N)=O)cn2)cc1C#N] | C21H16N6O | MS: 369.3 | PN-00821 | 52 |

| Example | Structure | Formula | MS (M + H)+ | NB | Pg |
|---|---|---|---|---|---|
| 402 | 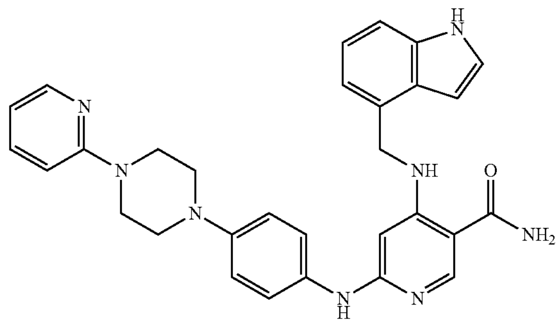 [SMILES: NC(=O)c1cnc(Nc2ccc(N3CCN(c4ccccn4)CC3)cc2)cc1NCc1cccc2[nH]ccc12] | C30H30N8O | MS: 519.4 | PN-00992 | 35 |

Example 412

6-(4-(dimethylcarbamoyl)phenylamino)-4-(3-(pyridine-4-yl)benzylamino)nicotinamide

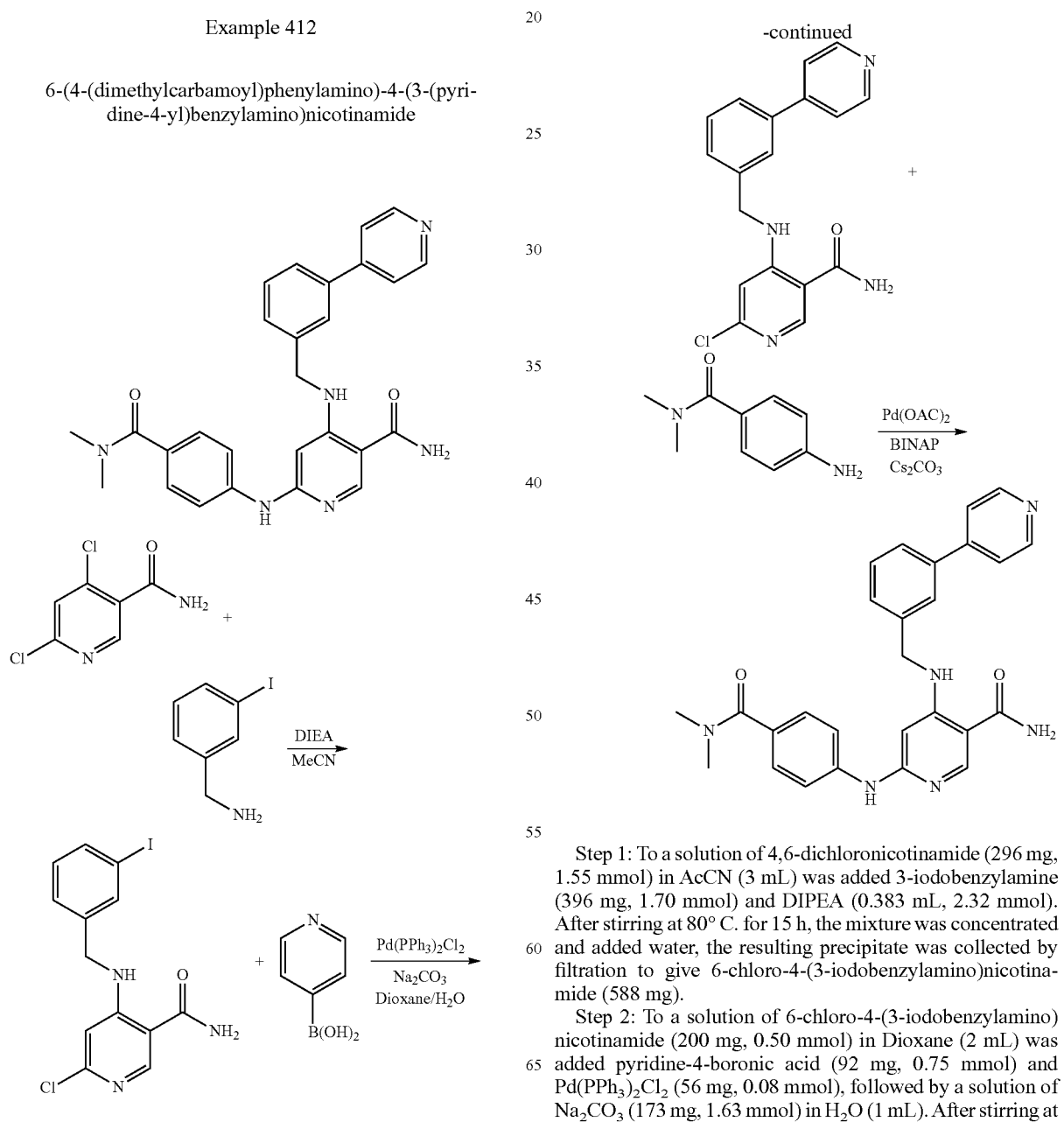

Step 1: To a solution of 4,6-dichloronicotinamide (296 mg, 1.55 mmol) in AcCN (3 mL) was added 3-iodobenzylamine (396 mg, 1.70 mmol) and DIPEA (0.383 mL, 2.32 mmol). After stirring at 80° C. for 15 h, the mixture was concentrated and added water, the resulting precipitate was collected by filtration to give 6-chloro-4-(3-iodobenzylamino)nicotinamide (588 mg).

Step 2: To a solution of 6-chloro-4-(3-iodobenzylamino)nicotinamide (200 mg, 0.50 mmol) in Dioxane (2 mL) was added pyridine-4-boronic acid (92 mg, 0.75 mmol) and Pd(PPh₃)₂Cl₂ (56 mg, 0.08 mmol), followed by a solution of Na₂CO₃ (173 mg, 1.63 mmol) in H₂O (1 mL). After stirring at 100° C. for 2 h, it was concentrated and purified by preparative HPLC to give 6-chloro-4-(3-(pyridine-4-yl)benzylamino)nicotinamide (56 mg).

Step 3: To a mixture of 6-chloro-4-(3-(pyridine-4-yl)benzylamino)nicotinamide (56 mg, 0.1 mmol) in p-Dioxane (2 mL) was added 4-amino-N,N-dimethylbenzamide (41 mg, 0.244 mmol), Pd(OAc)$_2$ (7.5 mg, 0.033 mmol), BINAP (21 mg, 0.033 mmol) and Cs$_2$CO$_3$ (162 mg, 0.498 mmol). After stirred at 80° C. for 15 h, it was concentrated and purified by preparative HPLC to give 6-(4-(dimethylcarbamoyl)phenylamino)-4-(3-(pyridine-4-yl)benzylamino)nicotinamide. MS found for C27H26N6O2 as (M+H)$^+$ 467.3. UV: λ=217.6, 272.7, 294.9 nm. $^1$H NMR: (CD3OD) δ 8.78 (dd, J=5.2, 1.2 Hz, 2H), 8.22 (s, 1H), 8.14 (dd, J=5.6, 1.2 Hz, 2H), 7.89 (bd, J=3.6 Hz, 1H), 7.85 (bs, 1H), 7.63 (t, J=3.6 Hz, 1H), 7.54 (d, J=7.2 Hz, 1H), 7.37 (d, J=9.2 Hz, 2H), 7.15 (d, J=8.4 Hz, 2H), 6.02 (s, 1H), 4.65 (s, 2H), 3.09 (s, 3H), 2.97 (s, 3H) ppm.

Example 413

6-(4-(methylsulfonyl)phenylamino)-4-(3-(pyridine-4-yl)benzylamino)nicotinamide

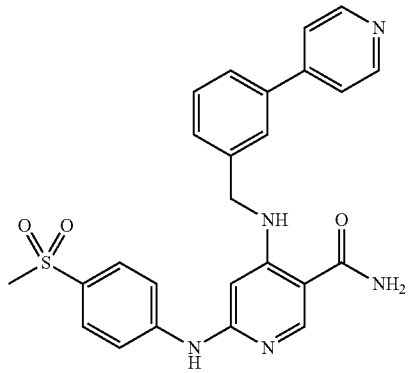

The title compound was synthesized using a procedure similar to that described in Example 412. MS found for C25H23N5O3S as (M+H)$^+$ 474.3. UV: λ=212.7, 274.5 nm. $^1$H NMR: (CD3OD) δ 8.80 (d, J=6.0 Hz, 2H), 8.32 (s, 1H), 8.21 (d, J=6.8 Hz, 2H), 7.94 (d, J=8.0 Hz, 1H), 7.89 (bs, 1H), 7.73 (d, J=8.0 Hz, 2H), 7.66 (t, J=8.0 Hz, 1H), 7.58 (d, J=8.0 Hz, 1H), 7.21 (d, J=8.8 Hz, 2H), 6.13 (s, 1H), 4.70 (s, 2H), 3.03 (s, 3H), 2.97 ppm.

Example 414

6-(4-(dimethylcarbamoyl)phenylamino)-4-(3-(pyridine-3-yl)benzylamino)nicotinamide

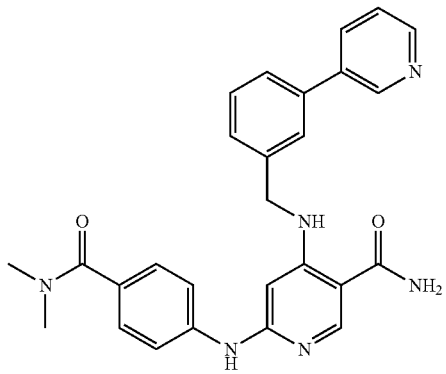 [SMILES: CN(C)C(=O)c1ccc(Nc2cc(NCc3cccc(-c4ccncc4)c3)c(C(N)=O)cn2)cc1]

The title compound was synthesized using a procedure similar to that described in Example 412. MS found for C27H26N6O2 as (M+H)$^+$ 467.3. UV: λ=214.0, 260.4 nm. $^1$H NMR: (CD3OD) δ 8.92 (d, J=2.4 Hz, 1H), 8.69 (dd, J=5.2, 1.2 Hz, 1H), 8.46 (dt, J=8.4, 1.6 Hz, 1H), 8.21 (s, 1H), 7.82 (dd, J=8.8, 5.2 Hz, 1H), 7.72 (d, J=8.0 Hz, 1H), 7.69 (s, 1H), 7.58 (t, J=8.0 Hz, 1H), 7.44 (d, J=7.2 Hz, 1H), 7.38 (d, J=6.8 Hz, 2H), 7.17 (d, J=6.8 Hz, 2H), 6.04 (s, 1H), 4.64 (s, 2H), 3.09 (s, 3H), 2.98 (s, 3H) ppm.

Example 415

6-(4-(1-propionylpiperidin-4-yl)phenylamino)-4-(3-(pyridine-3-yl)benzylamino)nicotinamide

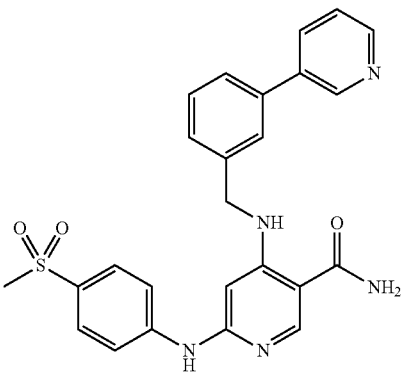 [SMILES: CS(=O)(=O)c1ccc(Nc2cc(NCc3cccc(-c4cccnc4)c3)c(C(N)=O)cn2)cc1]

The title compound was synthesized using a procedure similar to that described in Example 412. MS found for C25H23N5O3S as (M+H)$^+$ 474.3. UV: λ=214.0, 260.4 nm. $^1$H NMR: (CD3OD) δ 8.87 (m, 1H), 8.58 (m, 1H), 8.37 (m, 1H), 8.21 (s, 1H), 7.70-7.62 (m, 5H), 7.51 (t, J=7.2 Hz, 1H), 7.36 (d, J=8.0 Hz, 1H), 7.14 (d, J=8.4 Hz, 2H), 6.06 (s, 1H), 4.58 (s, 2H), 2.96 (s, 3H) ppm.

Example 416

6-(4-(1-propionylpiperidin-4-yl)phenylamino)-4-(3-(pyridine-3-yl)benzylamino)nicotinamide

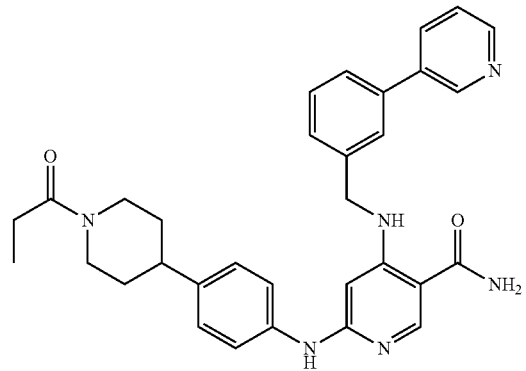 [SMILES: CCC(=O)N1CCC(c2ccc(Nc3cc(NCc4cccc(-c5cccnc5)c4)c(C(N)=O)cn3)cc2)CC1]

The title compound was synthesized using a procedure similar to that described in Example 412. MS found for C32H34N6O2 as (M+H)$^+$ 535.4. UV: λ=214.0, 259.2 nm. $^1$H NMR: (CD3OD) δ 8.87 (d, J=1.6 Hz, 1H), 8.58 (dd, J=5.2, 1.6 Hz, 1H), 8.35 (dt, J=8.0, 2.4 Hz, 1H), 8.05 (s, 1H), 7.70 (dd, J=7.6, 4.8 Hz, 1H), 7.63 (d, J=8.0 Hz, 1H), 7.59 (s, 1H), 7.47 (t, J=7.6 Hz, 1H), 7.31 (d, J=8.0 Hz, 1H), 7.11 (d, J=8.0 Hz, 2H), 6.94 (d, J=8.4 Hz, 2H), 5.80 (s, 1H), 4.50 (s, 2H), 3.91 (m, 1H), 3.04 (m, 2H), 2.69-2.56 (m, 2H), 2.36 (q, J=7.6 Hz, 2H), 1.71 (m, 2H), 1.50-1.34 (m, 2H), 1.05 (t, J=7.2 Hz, 3H) ppm.

Example 417

6-(4-((N,N-dimethylsulfamoyl)methyl)phenylamino)-4-(3-(pyridine-4-yl)benzylamino)nicotinamide

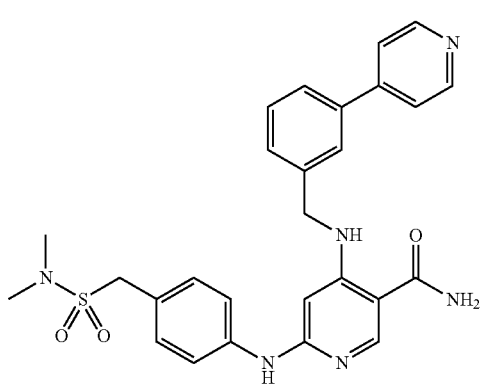 [SMILES: CN(C)S(=O)(=O)Cc1ccc(Nc2cc(NCc3cccc(-c4ccncc4)c3)c(C(N)=O)cn2)cc1]

The title compound was synthesized using a procedure similar to that described in Example 412. MS found for C27H28N6O3S as (M+H)+ 517.3. UV: λ=212.7, 272.7 nm. $^1$H NMR: (CD3OD) δ 8.74 (m, 2H), 8.19 (s, 1H), 8.06 (m, 2H), 7.83 (m, 2H), 7.63 (m, 1H), 7.47 (m, 1H), 7.39 (d, J=8.0 Hz, 2H), 7.10 (d, J=8.4 Hz, 2H), 5.96 (s, 1H), 4.61 (s, 2H), 4.24 (s, 2H), 2.84 (s, 6H) ppm.

Example 418

6-(4-(methylsulfonylmethyl)phenylamino)-4-(3-(pyridine-4-yl)benzylamino)nicotinamide

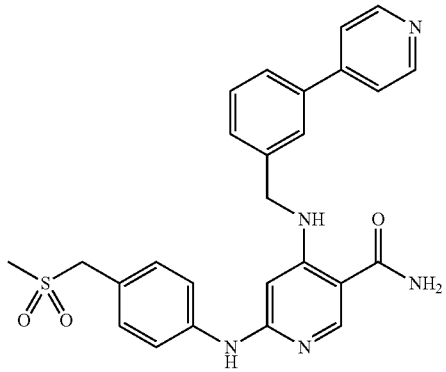 [SMILES: CS(=O)(=O)Cc1ccc(Nc2cc(NCc3cccc(-c4ccncc4)c3)c(C(N)=O)cn2)cc1]

The title compound was synthesized using a procedure similar to that described in Example 412. MS found for C26H25N5O3S as (M+H)+ 488.3. UV: λ=201.6, 272.4 nm. $^1$H NMR: (CD3OD) δ 8.70 (d, J=6.8 Hz, 2H), 8.11 (s, 1H), 8.08 (d, J=6.8 Hz, 2H), 7.78 (m, 2H), 7.56 (t, J=7.6 Hz, 1H), 7.42 (d, J=7.6 Hz, 1H), 7.30 (d, J=8.4 Hz, 2H), 7.02 (d, J=8.4 Hz, 2H), 5.90 (s, 1H), 4.54 (s, 2H), 4.30 (s, 2H), 2.84 (s, 3H) ppm.

Example 419

6-(4-(4-(dimethylcarbamoyl)piperidin-1-yl)phenylamino)-4-(3-(pyridine-4-yl)benzylamino)nicotinamide

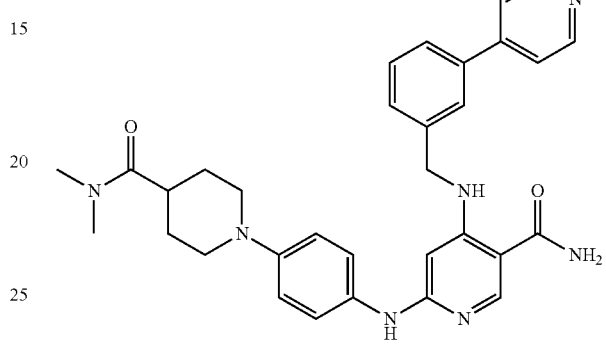

The title compound was synthesized using a procedure similar to that described in Example 412. MS found for C32H35N7O2 as (M+H)+ 550.4. UV: λ=202.8, 271.2 nm. $^1$H NMR: (CD3OD) δ 8.74 (d, J=7.6 Hz, 2H), 8.15 (d, J=6.4 Hz, 2H), 8.05 (s, 1H), 7.81 (m, 2H), 7.54 (t, J=8.0 Hz, 1H), 7.44 (d, J=8.8 Hz, 1H), 6.93 (bs, 4H), 5.75 (s, 1H), 4.51 (s, 2H), 3.59 (m, 2H), 3.06 (s, 3H) 3.03 (s, 3H), 2.82 (m, 3H), 1.73 (m, 4H) ppm.

Example 420

6-(4-(1-propionylpiperidin-4-yl)phenylamino)-4-(3-(pyridine-4-yl)benzylamino)nicotinamide

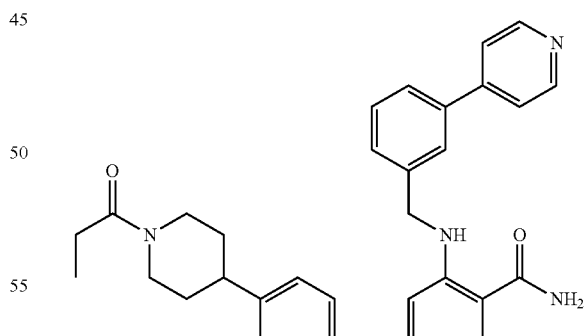

The title compound was synthesized using a procedure similar to that described in Example 412. MS found for C32H34N6O2 as (M+H)+ 535.4. UV: λ=206.7, 266.5 nm. $^1$H NMR: (CD3OD) δ 8.79 (d, J=6.8 Hz, 2H), 8.17 (d, J=6.8 Hz, 1H), 8.15 (s, 1H), 7.89 (d, J=8.4 Hz, 1H), 7.86 (s, 1H), 7.62 (t, J=7.6 Hz, 1H), 7.50 (d, J=8.0 Hz, 1H), 7.23 (d, J=8.4 Hz, 2H), 7.05 (d, J=8.8 Hz, 2H), 5.89 (s, 1H), 4.61 (s, 2H), 4.06 (m, 1H), 3.17 (m, 2H), 2.73 (m, 2H), 2.46 (q, J=7.2 Hz, 2H), 1.80 (m, 2H), 1.60-1.46 (m, 2H), 1.14 (t, J=7.6 Hz, 3H) ppm.

Example 421

6-(4-(dimethylcarbamoyl)phenylamino)-4-(3-(pyridine-2-yl)benzylamino)nicotinamide

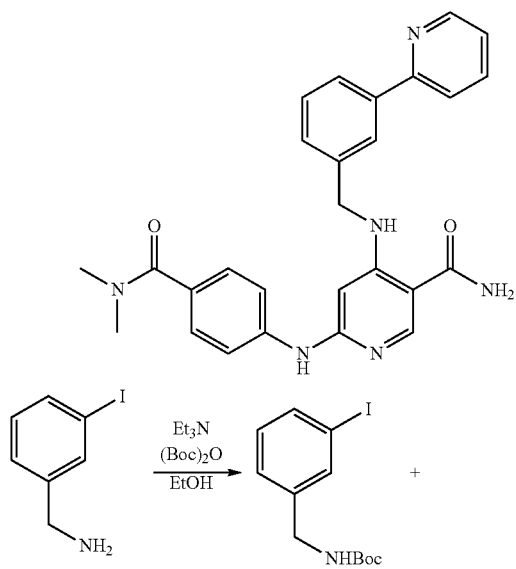

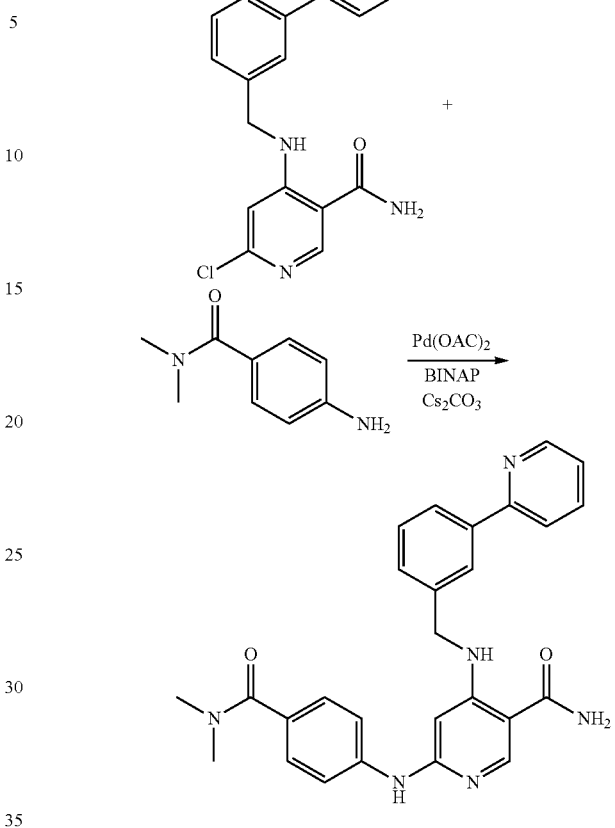

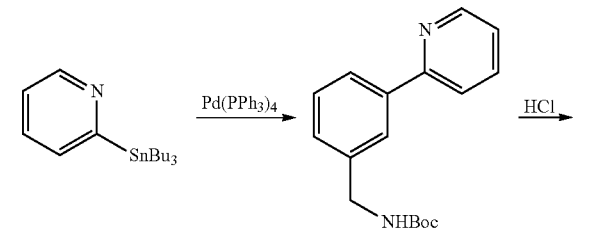

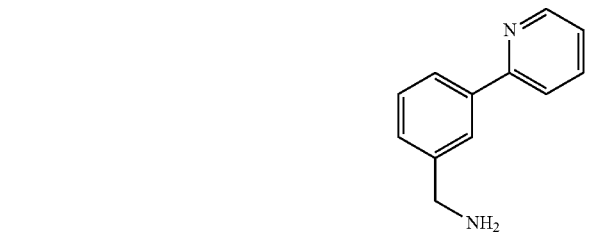

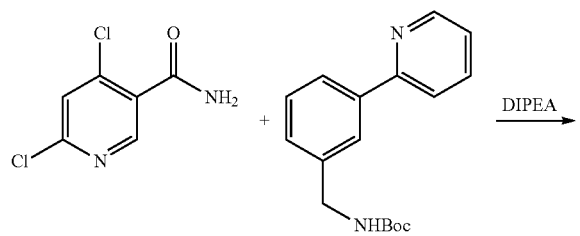

Step 1: To a solution of 3-iodobenzylamine HCl salt (2 g, 7.43 mmol) in EtOH (32 mL) was added Boc₂O (1.784 g, 8.17 mmol) and TEA (2.6 mL, 18.6 mmol). After stirring at room temperature for 15 h, it was concentrated and purified by column chromatography to give tert-butyl-3-iodobenzylcarbamate (2.97 g).

Step 2: To a solution of tert-butyl-3-iodobenzylcarbamate (166 mg, 0.50 mmol) in Dioxane (1.5 mL) was added Pd(PPh₃)₄ (58 mg, 0.05 mmol) and 2-(tributylstannyl)pyridine (275 mg, 0.75 mmol). After stirring at 100° C. for 2 h, it was concentrated and the residue was purified by column chromatography to give tert-butyl-3-(pyridin-2-yl)benzylcarbamate (111 mg).

Step 3: To a solid tert-butyl-3-(pyridin-2-yl)benzylcarbamate (111 mg, 0.39 mmol) was added HCl (4N in dioxane, 0.20 mL, 0.78 mmol), then it was concentrated to give (3-(pyridine-2-yl)phenyl)methanamine (77 mg).

Step 4: To a solution of 4,6-dichloronicotinamide (73 mg, 0.38 mmol) in NMP (0.75 mL) was added (3-(pyridine-2-yl)phenyl)methanamine (77 mg, 0.42 mmol) and DIPEA (0.22 mL, 1.33 mmol). After stirring at 80° C. for 15 h, the mixture was added water, the resulting precipitate was collected by filtration to give 6-chloro-4-(3-(pyridine-2-yl)benzylamino)nicotinamide (56 mg).

Step 3: To a mixture of 6-chloro-4-(3-(pyridine-2-yl)benzylamino)nicotinamide (82 mg, 0.24 mmol) in p-Dioxane (2.5 mL) was added 4-amino-N,N-dimethylbenzamide (51 mg, 0.31 mmol), Pd(OAc)₂ (11 mg, 0.05 mmol), BINAP (30 mg, 0.05 mmol) and Cs₂CO₃ (234 mg, 0.72 mmol). After stirred at 80° C. for 15 h, it was concentrated and purified by preparative HPLC to give 6-(4-(dimethylcarbamoyl)phenylamino)-4-(3-(pyridine-2-yl)benzylamino)nicotinamide. MS found for C27H26N6O2 as (M+H)+ 467.4. UV: λ=259.2, 301.6 nm. ¹H NMR: (CD3OD) δ 8.75 (dd, J=11.2, 5.2 Hz, 1H), 8.34 (m, 1H), 8.23 (d, J=5.6 Hz, 1H), 8.14 (m, 1H), 7.92 (m, 2H), 7.81-7.73 (m, 1H), 7.64 (m, 1H), 7.54 (m, 1H), 7.36 (dd, J=8.4, 2.8 Hz, 2H), 7.13 (dd, J=8.4, 2.8 Hz, 2H), 6.02 (d, J=1.6 Hz, 1H), 4.65 (d, J=2.0 Hz, 2H), 3.08 (s, 3H), 2.97 (s, 3H) ppm.

Example 422

4-(3-(1H-pyrazol-1-yl)benzylamino)-6-(4-(dimethylcarbamoyl)phenylamino)nicotinamide

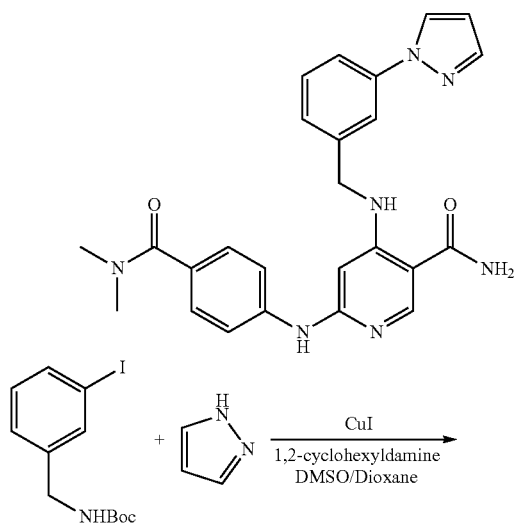

Synthesis of (3-(1H-pyrazol-1-yl)phenyl)methamine

Step 1: To a solution of tert-butyl-3-iodobenzylcarbamate (550 mg, 1.65 mmol) in Dioxane (1.2 mL) and DMSO (1.2 mL) was added CuI (16 mg, 0.083 mmol), (1S,2S)—N¹,N²-dimethylcyclohexane-1,2-diamine (0.052 ml, 0.33 mmol), pyrazole (135 mg, 1.98 mmol) and K₂CO₃ (479 mg, 3.47 mmol). After stirring at 120° C. for 3 h, it was concentrated and the residue was purified by column chromatography to give tert-butyl-3-(1H-pyrazol-1-yl)benzylcarbamate (317 mg).

Step 2: To a solid tert-butyl-3-(1H-pyrazol-1-yl)benzylcarbamate (317 mg, 1.16 mmol) was added HCl (4N in dioxane, 0.58 mL, 2.32 mmol), then it was concentrated to give (3-(1H-pyrazol-1-yl)phenyl)methamine (133 mg).

The title compound was synthesized using a procedure similar to that described in Example 421. MS found for C25H25N7O2 as (M+H)+ 456.4. UV: λ=215.2, 259.2 nm. ¹H NMR: (CD3OD) δ 8.24 (d, J=2.8 Hz, 1H), 8.20 (d, J=1.2 Hz, 1H), 7.34 (d, J=2.0 Hz, 1H), 7.71 (m, 2H), 7.51 (t, J=8.0 Hz, 1H), 7.32 (d, J=8.4 Hz, 2H), 7.29 (m, 1H), 7.09 (d, J=8.4 Hz, 2H), 6.54 (m, 1H), 6.00 (s, 1H), 4.62 (s, 2H), 3.09 (s, 3H), 2.96 (s, 3H) ppm.

Example 423

6-(4-(dimethylcarbamoyl)phenylamino)-4-(3-(pyrimidine-5-yl)benzylamino)nicotinamide

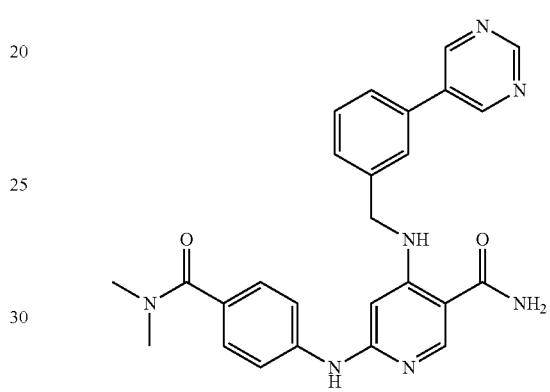

The title compound was synthesized using a procedure similar to that described in Example 412. MS found for C26H25N7O2 as (M+H)+ 468.3. UV: λ=207.3, 258.6 nm. ¹H NMR: (CD3OD) δ 9.16 (s, 1H), 9.06 (s, 2H), 8.19 (s, 1H), 7.72 (d, J=8.4 Hz, 1H), 7.69 (s, 1H), 7.58 (t, J=8.0 Hz, 1H), 7.44 (d, J=7.6 Hz, 1H), 7.39 (d, J=8.0 Hz, 2H), 7.16 (d, J=8.4 Hz, 2H), 6.02 (s, 1H), 4.63 (s, 2H), 3.09 (s, 3H), 3.00 (s, 3H) ppm.

Example 424

6-(4-(1-propionylpiperazin-4-yl)phenylamino)-4-(3-(pyridine-4-yl)benzylamino)nicotinamide

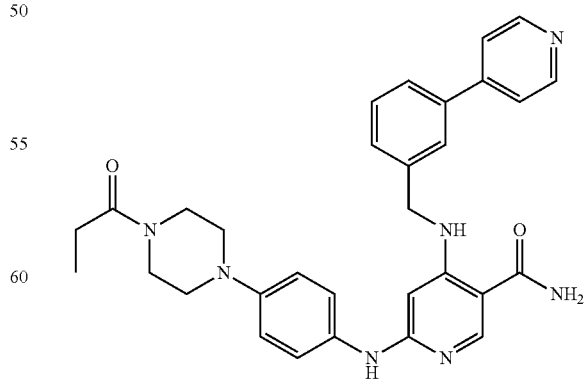

The title compound was synthesized using a procedure similar to that described in Example 412. MS found for C31H33N7O2 as (M+H)+ 536.4. UV: λ=201.6, 271.2 nm. ¹H NMR: (CD3OD) δ 8.81 (dd, J=4.4, 1.6 Hz, 2H), 8.17 (d, J=5.6 Hz, 2H), 8.11 (s, 1H), 7.90 (d, J=8.4 Hz, 1H), 7.87 (s, 1H), 7.62 (t, J=7.6 Hz, 1H), 7.52 (d, J=6.8 Hz, 1H), 7.03 (d, J=8.4 Hz, 2H), 6.96 (d, J=9.2 Hz, 2H), 5.82 (s, 1H), 4.60 (s, 2H), 3.69 (m, 4H), 3.13 (m, 4H), 2.46 (q, J=8.0 Hz, 2H), 1.14 (t, J=7.2 Hz, 3H) ppm.

Example 425

6-(4-(dimethylcarbamoyl)phenylamino)-4-(3-(thiazol-4-yl)benzylamino)nicotinamide

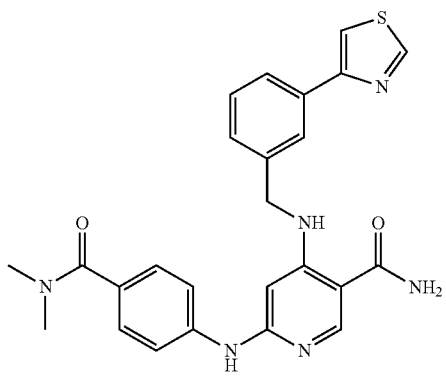 [SMILES: CN(C)C(=O)c1ccc(Nc2cc(NCc3cccc(-c4cscn4)c3)c(C(N)=O)cn2)cc1]

The title compound was synthesized using a procedure similar to that described in Example 421. MS found for C25H24N6O2S as (M+H)+ 473.3. UV: λ=204.2, 261.0 nm ¹H NMR: (CD3OD) δ 9.08 (d, J=2.0 Hz, 1H), 8.21 (s, 1H), 7.90 (m, 3H), 7.47 (t, J=8.0 Hz, 1H), 7.31 (d, J=8.4 Hz, 2H), 7.29 (m, 1H), 7.07 (d, J=8.4 Hz, 2H), 6.02 (s, 1H), 4.60 (s, 2H), 3.09 (s, 3H), 2.94 (s, 3H) ppm.

Example 426

6-(4-(dimethylcarbamoyl)phenylamino)-4-(3-(pyrazin-2-yl)benzylamino)nicotinamide

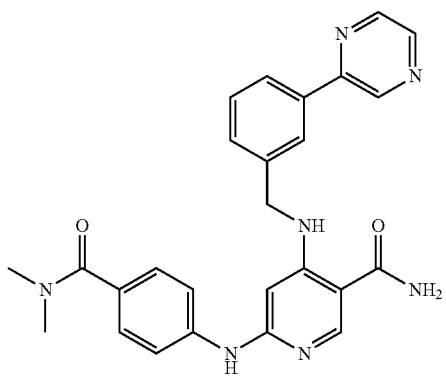 [SMILES: CN(C)C(=O)c1ccc(Nc2cc(NCc3cccc(-c4cnccn4)c3)c(C(N)=O)cn2)cc1]

The title compound was synthesized using a procedure similar to that described in Example 421. MS found for C26H25N7O2 as (M+H)+ 468.4. UV: λ=208.5, 256.7 nm. ¹H NMR: (CD3OD) δ 9.01 (d, J=1.6 Hz, 1H), 8.59 (dd, J=2.8, 1.6 Hz, 1H), 8.47 (d, J=2.4 Hz, 1H), 8.11 (s, 1H), 7.96 (m, 2H), 7.48 (t, J=7.6 Hz, 1H), 7.36 (d, J=7.6 Hz, 1H), 7.02 (d, J=8.4 Hz, 2H), 5.93 (s, 1H), 4.55 (s, 2H), 2.99 (s, 3H), 2.86 (s, 3H) ppm.

Example 427

6-(4-(morpholinomethyl)phenylamino)-4-(3-(pyridin-4-yl)benzylamino)nicotinamide

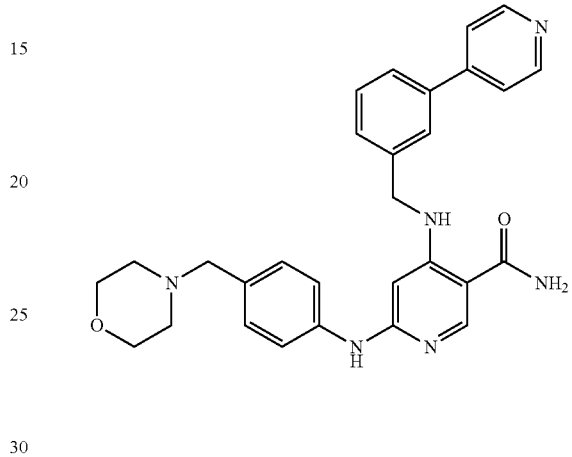

The title compound was synthesized using a procedure similar to that described in Example 412. MS found for C29H30N6O2 as (M+H)+ 495.4. UV: λ=203.0, 270.8 nm. ¹H NMR: (CD3OD) δ 8.81 (d, J=6.8 Hz, 2H), 8.34 (s, 1H), 8.25 (d, J=6.8 Hz, 2H), 7.90 (m, 2H), 7.65 (t, J=7.6 Hz, 1H), 7.57 (d, J=8.0 Hz, 1H), 7.52 (d, J=8.4 Hz, 2H), 7.27 (d, J=8.4 Hz, 2H), 6.10 (s, 1H), 4.64 (s, 2H), 4.32 (s, 2H), 4.01 (m, 2H), 3.77 (m, 2H), 3.25 (m, 4H) ppm.

Example 428

4-(benzylamino)-6-(4-(2-(pyrrolidin-1-yl)ethoxy)phenylamino)nicotinamide

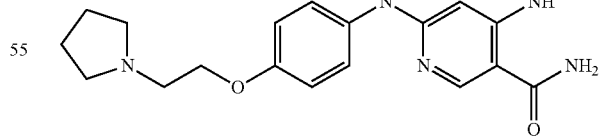

The title compound was synthesized using a procedure similar to that described in Example 36. MS found for C25H29N5O2 as (M+H)+ 432.3. UV: λ=208.5, 253.3, 299.6 nm. ¹H NMR: (DMSO-D6) δ 8.2 (s, 1H), 7.35 (m, 2H), 7.3 (d, 1H), 7.25 (d, 2H), 7.1 (m, 2H), 6.95 (d, 2H), 6.75 (s, 1H), 4.4 (d, 2H), 4.25 (d, 2H), 3.6 (m, 2H), 3.1 (t, 2H), 2.1 (m, 2H), 1.9 (m, 2H).

Example 429

4-(benzylamino)-6-(4-(2-morpholinoethoxy)phenylamino)nicotinamide

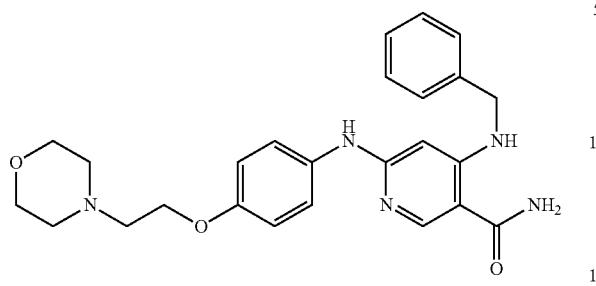

The title compound was synthesized using a procedure similar to that described in Example 36. MS found for C25H29N5O3 as (M+H)⁺ 446.5. UV: λ=203.8, 258.0 nm. ¹H NMR: (DMSO-D6) δ 8.25 (s, 1H), 7.35 (m, 2H), 7.3 (d, 1H), 7.25 (m, 2H), 7.1 (d, 2H), 7.0 (d, 2H), 5.65 (s, 1H), 4.25 (d, 2H), 4.35 (t, 2H), 3.85 (m, 2H), 3.65 (m, 2H), 3.5 (m, 4H), 3.2 (m, 2H).

Example 430

4-(benzylamino)-6-(3-(2-morpholino-2-oxoethoxy)phenylamino)nicotinamide

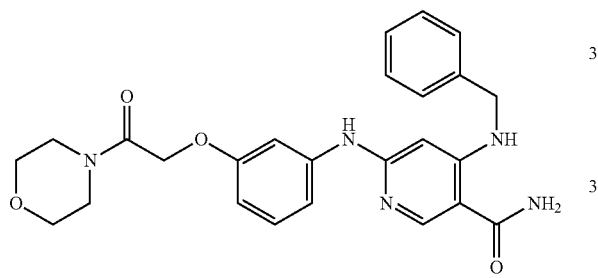

The title compound was synthesized using a procedure similar to that described in Example 36. MS found for C25H27N5O4 as (M+H)⁺ 462.2. UV: λ=202.2, 255.9 nm. ¹H NMR: (DMSO-D6) δ 8.25 (s, 1H), 7.45 (m, 2H), 7.35 (m, 2H), 7.15 (s, 3H), 6.9 (m, 2H), 5.7 (s, 1H), 4.8 (d, 2H), 4.6 (d, 2H), 3.6 (dd, 4H).

Example 431

4-(benzylamino)-6-(4-(morpholinomethyl)phenylamino)nicotinamide

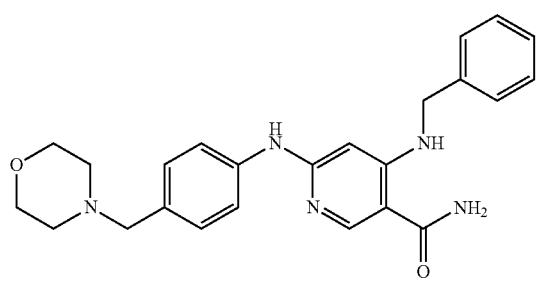 [SMILES: NC(=O)c1cnc(Nc2ccc(CN3CCOCC3)cc2)cc1NCc1ccccc1]

The title compound was synthesized using a procedure similar to that described in Example 36. MS found for C24H27N5O2 as (M+H)⁺ 448.2. UV: λ=207.1, 258.4 nm. ¹H NMR: (DMSO-6) δ 8.25 (s, 1H), 7.35 (m, 4H), 7.3 (s, 1H), 7.25 (m, 4H), 5.95 (s, 1H), 4.45 (d, 2H), 4.3 (d, 2H), 3.95 (m, 2H), 3.65 (m, 4H), 3.2 (m, 2H).

Example 432

4-(benzylamino)-6-(4-(2-methoxyethoxy)phenylamino)nicotinamide

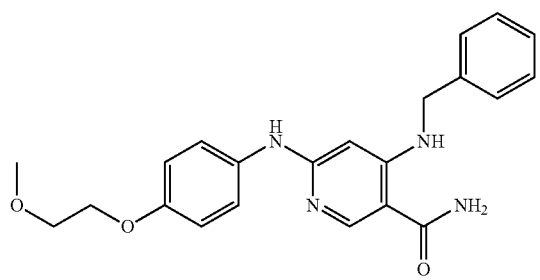 [SMILES: COCCOc1ccc(Nc2cc(NCc3ccccc3)c(C(N)=O)cn2)cc1]

The title compound was synthesized using a procedure similar to that described in Example 36. MS found for C22H24N4O3 as (M+H)⁺ 393.0. UV: λ=201.4, 258.0 nm.

Example 433

4-(benzylamino)-6-(3-(2-methoxyethoxyl)phenylamino)nicotinamide

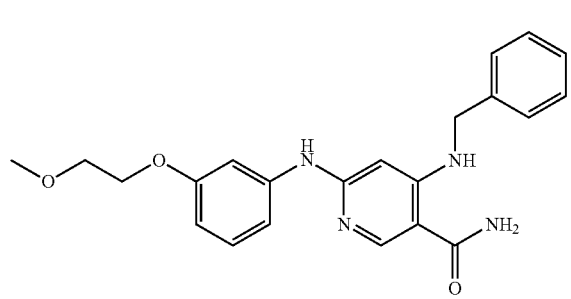 [SMILES: COCCOc1cccc(Nc2cc(NCc3ccccc3)c(C(N)=O)cn2)c1]

The title compound was synthesized using a procedure similar to that described in Example 36. MS found for C22H24N4O3 as (M+H)⁺ 393.3. UV: λ=258.0 nm. ¹H NMR: (DMSO-D6) δ 8.2 (s, 1H), 7.25 (d, 2H), 7.2 (d, 1H), 7.2 (d, 2H), 7.0 (d, 2H), 6.9 (d, 2H), 5.7 (s, 1H), 4.4 (d, 2H), 4.05 (d, 2H), 3.6 (d, 2H), 2.45 (s, 3H).

Example 434

2-(4-(azetidin-1-ylsulfonyl)phenylamino)-4-(benzylamino)pyrimidine-5-carboxamide

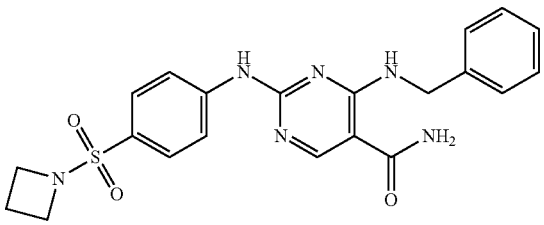 [SMILES: NC(=O)c1cnc(Nc2ccc(S(=O)(=O)N3CCC3)cc2)nc1NCc1ccccc1]

The title compound was synthesized using a procedure similar to that described in Example 36. MS found for C22H21F2N5O3S as (M+H)⁺ 474.4. UV: λ=200.4, 274.3, 313.1 nm.

Example 435

4-(2,3-difluorobenzylamino)-6-(4-(4-propionylpiperazin-1-yl)phenylamino)nicotinamide

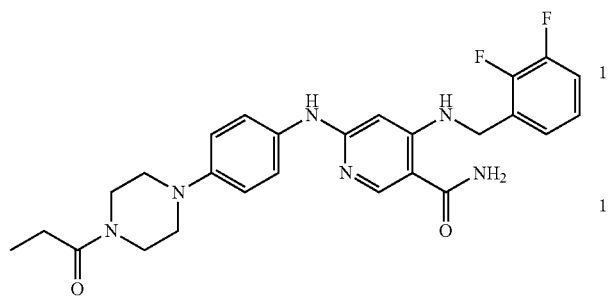

The title compound was synthesized using a procedure similar to that described in Example 36. MS found for C26H28F2N6O2 as (M+H)+ 495.3. UV: =203.5, 240.6, 306.9 nm. ¹H NMR: (CD3OD) δ 8.1 (s, 1H), 7.25 (d, 1H), 7.15 (d, 1H), 7.1 (d, 1H), 7.05 (m, 5H), 5.75 (s, 1H), 4.5 (s, 2H), 3.75 (dd, 2H), 3.3 (t, 2H), 3.25 (t, 2H), 2.5 (t, 2H), 1.1 (t, 3).

Example 436

4-(benzylamino)-6-(4-(dimethylcarbamoyl)-3-methoxyphenylamino)nicotinamide

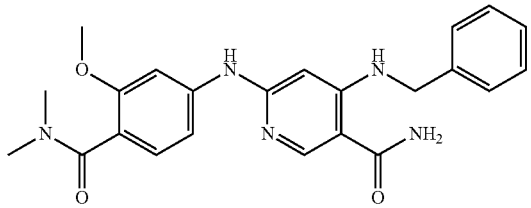 [SMILES: COc1cc(Nc2cc(NCc3ccccc3)c(C(N)=O)cn2)ccc1C(=O)N(C)C]

The title compound was synthesized using a procedure similar to that described in Example 36. MS found for C23H25N5O3 as (M+H)+ 420.3. UV: λ=205.9313.1 nm. ¹H NMR: (CD3OD) δ 8.1 (s, 1H), 7.3 (m, 3H), 7.2 (m, 2H), 7.15 (d, 1H), 6.8 (s, 1H), 6.5 (d, 1H), 5.9 (s, 1H), 4.4 (s, 2H), 3.7 (s, 3H), 3.0 (s, 3H), 2.8 (s, 3H).

Example 437

4-(benzylamino)-6-(3-chloro-4-(dimethylcarbamoyl)phenylamino)nicotinamide

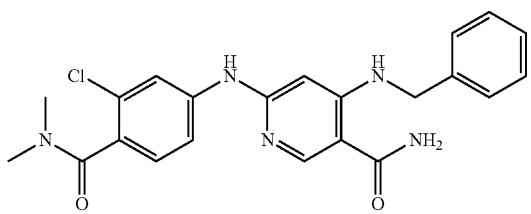 [SMILES: CN(C)C(=O)c1ccc(Nc2cc(NCc3ccccc3)c(C(N)=O)cn2)cc1Cl]

The title compound was synthesized using a procedure similar to that described in Example 36. MS found for C22H22ClN5O2 as (M+H)+ 424.3. UV: λ=208.9, 262.6 nm. ¹H NMR: (CD3OD) δ 8.1 (s, 1H), 7.3 (m, 4H), 7.2 (m, 4H), 5.9 (s, 1H), 4.4 (s, 2H), 3.1 (s, 3H), 2.9 (s, 3H).

Example 438

4-(benzylamino)-6-(4-(dimethylcarbamoyl)-3-methylphenylamino)nicotinamide

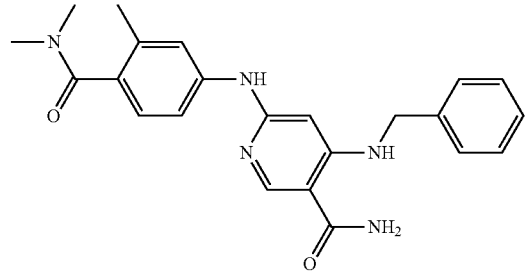 [SMILES: Cc1cc(Nc2cc(NCc3ccccc3)c(C(N)=O)cn2)ccc1C(=O)N(C)C]

The title compound was synthesized using a procedure similar to that described in Example 36. MS found for C23H25N5O2 as (M+H)+ 404.3. UV: λ=204.7, 252.8, 310.0 nm. ¹H NMR: (CD3OD) δ 8.1 (s, 1H), 7.3 (d, 2H), 7.25 (m, 2H), 7.15 (d, 1H), 7.0 (s, 1H), 6.9 (d, 2H), 5.9 (s, 1H), 4.4 (s, 2H), 3.0 (s, 3H), 2.8 (s, 3H), 2.1 (s, 3H).

Example 439

6-(3-(azetidine-1-carbonyl)-4-fluorophenylamino)-4-(benzylamino)nicotinamide

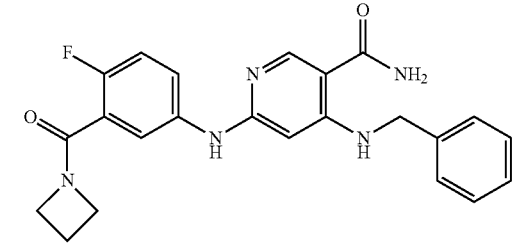 [SMILES: NC(=O)c1cnc(Nc2ccc(F)c(C(=O)N3CCC3)c2)cc1NCc1ccccc1]

The title compound was synthesized using a procedure similar to that described in Example 36. MS found for C23H22FN5O2 as (M+H)+ 420.3. UV: λ=204.0, 252.2, 294.0 nm. ¹H NMR: (CD3OD) δ 8.1 (s, 1H), 7.2 (m, 8H), 5.8 (s, 1H), 4.4 (s, 2H), 4.1 (dd, 4H), 2.3 (dd, 2H).

Example 440

4-(benzylamino)-6-(4-(dimethylamino)-3-(dimethylcarbamoyl)phenylamino)nicotinamide

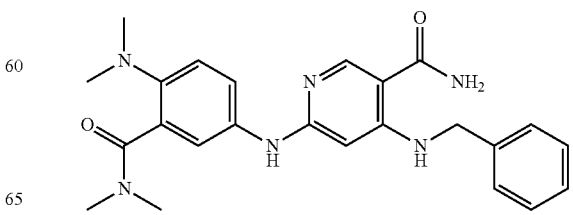

The title compound was synthesized using a procedure similar to that described in Example 36. MS found for C24H28N6O2 as (M+H)+ 433.2. UV: λ=204.0, 246.1, 304.1. nm. ¹H NMR: (CD3OD) δ 8.1 (s, 1H), 7.35 (m, 3H), 2.5 (m, 3H), 7.1 (d, 1H), 7.05 (d, 1H), 5.9 (s, 1H), 4.5 (s, 2H), 3.1 (s, 6H), 2.9 (s, 3H), 2.85 (s, 3H).

Example 441

(R)-4-((1-acetylpiperidin-3-yl)methylamino)-6-(4-(dimethylcarbamoyl)-3-methoxyphenylamino)nicotinamide

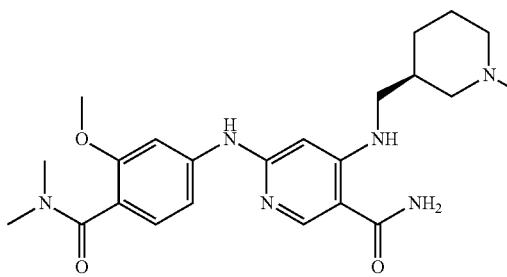

The title compound was synthesized using a procedure similar to that described in Example 36. MS found for C24H32N6O4 as (M+H)+ 469.5. UV: λ=201.6, 244.3, 33.7 nm. ¹H NMR: (CD3OD) δ 8.2 (d, 1H), 7.3 (s, 1H), 7.05 (d, 1H), 6.95 (m, 1H), 5.9 (d, 1H), 3.8 (s, 3H), 3.1 (m, 4H), 2.95 (s, 6H), 2.0 (d, 3H), 1.3 (m, 5H).

Example 442

(R)-4-((1-acetylpiperidin-3-yl)methylamino)-6-(3-chloro-4-(dimethylcarbamoyl)phenylamino)nicotinamide

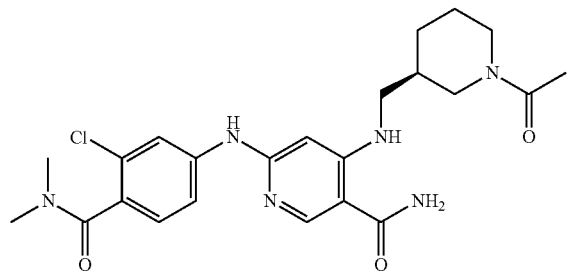 [SMILES: CC(=O)N1CCC[C@H](CNc2cc(Nc3ccc(C(=O)N(C)C)c(Cl)c3)ncc2C(N)=O)C1]

The title compound was synthesized using a procedure similar to that described in Example 36. MS found for C23H29ClN6O3 as (M+H)+ 473.4. UV: λ=202.9, 254.7, 310.6 nm. ¹H NMR: (CD3OD) δ 8.2 (d, 1H), 7.8 (s, 1H). 7.3 (d, 1H), 7.1 (d, 1H), 5.9 (d, 1H), 3.0 (m, 6H), 2.95 (s, 6H), 2.0 (d, 3H), 1.3 (m, 5H).

Example 443

(R)-4-((1-acetylpiperidin-3-yl)methylamino)-6-(4-(dimethylcarbamoyl)-3-methylphenylamino)nicotinamide

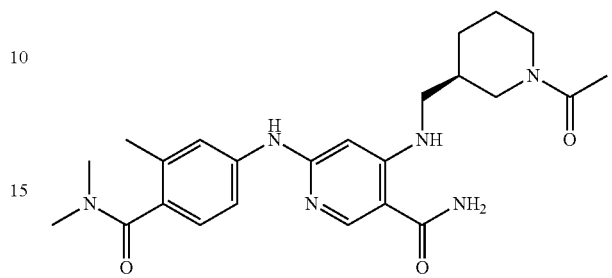

The title compound was synthesized using a procedure similar to that described in Example 36. MS found for C24H32N6O3 as (M+H)+ 453.5. UV: λ=203.5, 252.8, 309.4 nm. ¹H NMR: (CD3OD) δ 8.2 (d, 1H), 7.3 (d, 2H), 7.0 (d, 1H), 5.9 (s, 1H), 3.0 (m, 6H), 2.95 (s, 6H), 2.2 (s, 3H), 2.0 (d, 3H), 1.4 (m, 5H).

Example 444

(R)-4-((1-acetylpiperidin-3-yl)methylamino)-6-(3-(azetidine-1-carbonyl)-4-fluorophenylamino)nicotinamide

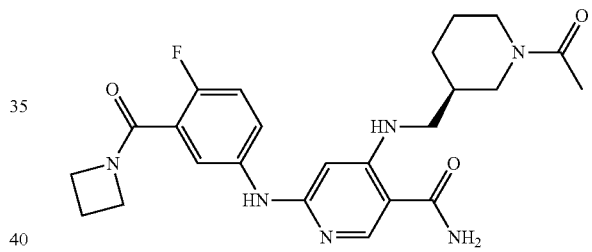

The title compound was synthesized using a procedure similar to that described in Example 36. MS found for C24H29FN6O3 as (M+H)+ 469.4. UV: λ=251.6, 297.9 nm. ¹H NMR: (CD3OD) δ 8.1 (d, 1H), 7.5 (m, 2H), 7.4 (t, 1H), 6.0 (s, 1H), 4.2 (m, 6H), 3.9 (d, 1H), 3.1 (m, 6H), 2.4 (t, 3H), 2.1 (d, 3H), 1.45 (m, 3H).

Example 445

(R)-4-((1-acetylpiperidin-3-yl)methylamino)-6-(3-(dimethylamino)-4-(dimethylcarbamoyl)phenylamino)nicotinamide

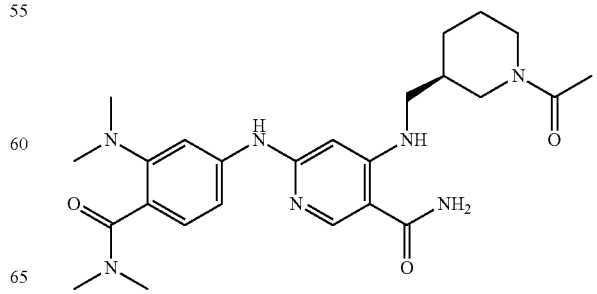

The title compound was synthesized using a procedure similar to that described in Example 36. MS found for C25H35N7O3 as (M+H)+ 482.4. UV: λ=202.2, 271.9 nm. ¹H NMR: (CD3OD) δ 8.1 (d, 1H), 7.3 (m, 1H), 7.1 (m, 2H), 5.9 (s, 1H), 3.1 (s, 6H), 2.9 (s, 3H), 2.85 (s, 3H), 2.1 (d, 3H), 1.9 (m, 3H), 1.4 (m, 6H).

Example 446

4-(benzylamino)-6-(3-methyl-4-(pyrrolidine-1-carbonyl)phenylamino)nicotinamide

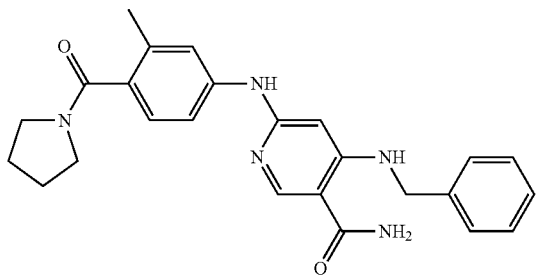 [SMILES: Cc1cc(Nc2cc(NCc3ccccc3)c(C(N)=O)cn2)ccc1C(=O)N1CCCC1]

The title compound was synthesized using a procedure similar to that described in Example 36. MS found for C25H27N5O2 as (M+H)+ 430.4. UV: λ=202.2, 252.8, 308.2 nm. ¹H NMR: (CD3OD) δ 8.1 (s, 1H), 7.3 (d, 2H), 7.2 (m, 4H), 7.0 (s, 1H), 6.9 (d, 1H), 5.9 (s, 1H), 4.4 (s, 2H), 3.5 (t, 2H), 3.1 (t, 2H), 2.2 (s, 3H), 1.9 (m, 2H), 1.85 (m, 2H).

Example 447

4-(benzylamino)-6-(3-methyl-4-(morpholine-4-carbonyl)phenylamino)nicotinamide

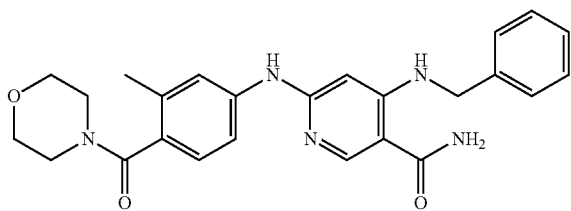 [SMILES: Cc1cc(Nc2cc(NCc3ccccc3)c(C(N)=O)cn2)ccc1C(=O)N1CCOCC1]

The title compound was synthesized using a procedure similar to that described in Example 36. MS found for C25H27N5O3 as (M+H)+ 446.3. UV: λ=252.2, 310.6 nm. ¹H NMR: (CD3OD) δ 8.1 (s, 1H), 7.5 (m, 2H), 7.21 (m, 3H), 7.18 (d, 2H), 7.0 (s, 1H), 5.9 (s, 1H), 4.4 (s, 2H), 3.7 (d, 4H), 3.55 (s, 4H), 2.2 (s, 3H).

Example 448

6-(4-(azetidine-1-carbonyl)-3-methylphenylamino)-4-(benzylamino)nicotinamide

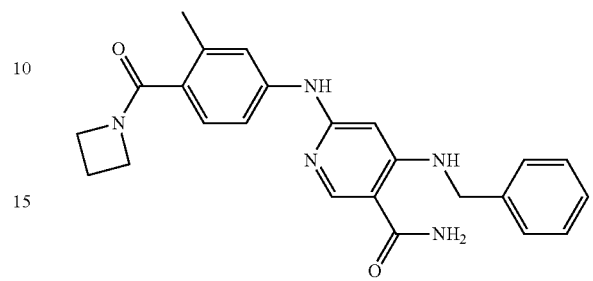

The title compound was synthesized using a procedure similar to that described in Example 36. MS found for C24H25N5O2 as (M+H)+ 416.3. UV: λ=212.0, 244.3, 311.3 nm. ¹H NMR: (CD3OD) δ 8.2 (s, 1H), 7.3 (m, 4H), 7.2 (m, 1H), 7.1 (s, 1H), 7.05 (m, 2H) 5.9 (s, 1H), 4.35 (s, 2H), 4.1 (t, 2H), 3.95 (t, 2H), 2.25 (m, 5H).

Example 449

4-(benzylamino)-6-(4-(2-hydroxyethylcarbamoyl)-3-methylphenylamino)nicotinamide

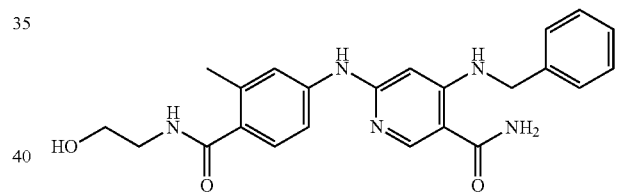

The title compound was synthesized using a procedure similar to that described in Example 36. MS found for C23H25N5O3 as (M+H)+ 420.0. UV: λ=246.1, 313.7 nm. ¹H NMR: (CD3OD) δ 8.1 (s, 1H), 7.3 (m, 3H), 7.05 (m, 3H), 6.95 (s, 1H), 6.9 (d, 1H), 5.9 (s, 1H), 4.4 (s, 2H), 3.6 (t, 2H), 3.4 (t, 2H), 2.3 (s, 3H).

Example 450

4-(benzylamino)-6-(4-(cyclopropyl(methyl)carbamoyl)-3-methylphenylamino)nicotinamide

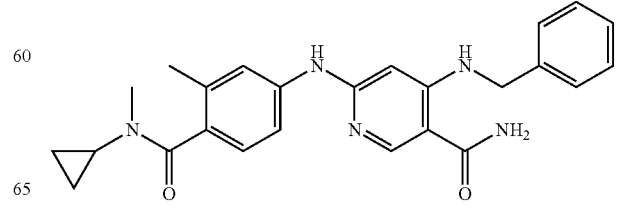

The title compound was synthesized using a procedure similar to that described in Example 36. MS found for C25H27N5O2 as (M+H)+ 430.4. UV: λ=204.1, 245.5, 313.1 nm. ¹H NMR: (CD3OD) δ 8.1 (s, 1H), 7.3 (m, 3H), 7.25 (m, 3H), 7.0 (s, 1H), 6.9 (d, 1H), 5.9 (s, 1H), 4.4 (s, 2H), 3.15 (m, 3H), 2.25 (s, 3H), 1.0 (t, 1H), 0.45 (d, 2H), 0.2 (d, 2H).

Example 451

4-(benzylamino)-6-(4-(2,5-dihydro-1H-pyrrole-1-carbonyl)-3-methylphenylamino)nicotinamide

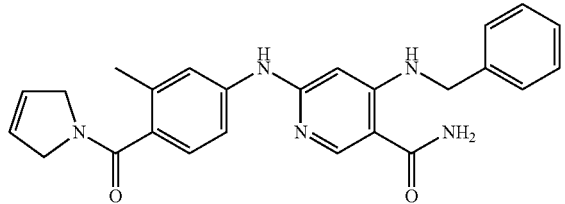 [SMILES: Cc1cc(Nc2cc(NCc3ccccc3)c(C(N)=O)cn2)ccc1C(=O)N1CC=CC1]

The title compound was synthesized using a procedure similar to that described in Example 36. MS found for C25H25N5O2 as (M+H)+ 428.3. UV: λ=205.3, 260.2 nm. ¹H NMR: (CD3OD) δ 8.1 (s, 1H), 7.25 (d, 2H), 7.2 (d, 4H), 7.1 (s, 1H), 6.9 (d, 1H), 6.9 (m, 2H), 5.75 (d, 1H), 4.4 (s, 2H), 4.35 (t, 2H), 3.9 (t, 2H), 2.2 (s, 3H).

Example 452

4-(benzylamino)-6-(4-((2-hydroxyethyl)(methyl)carbamoyl)-3-methylphenylamino)nicotinamide

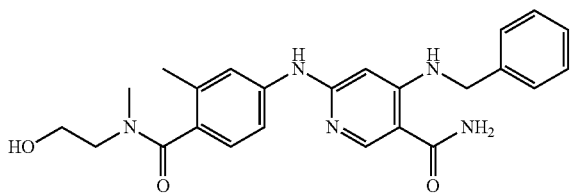 [SMILES: Cc1cc(Nc2cc(NCc3ccccc3)c(C(N)=O)cn2)ccc1C(=O)N(C)CCO]

The title compound was synthesized using a procedure similar to that described in Example 36. MS found for C24H27N5O3 as (M+H)+ 434.3. UV: λ=202.9, 253.5, 309.4 nm. ¹H NMR: (CD3OD) δ 8.2 (s, 1H), 7.4 (m, 2H), 7.35 (m, 3H), 7.25 (m, 1H), 7.1 (d, 1H), 7.0 (m, 1H), 5.95 (d, 1H), 4.5 (s, 2H), 3.85 (t, 1H), 3.7 (t, 1H), 3.6 (t, 1H), 3.15 (s, 2 h), 3.0 (s, 2H), 2.25 (d, 3H).

Example 453

PN-1010-20 4-(benzylamino)-6-(4-((2-methoxyethyl)(methyl)carbamoyl)-3-methylphenylamino)nicotinamide

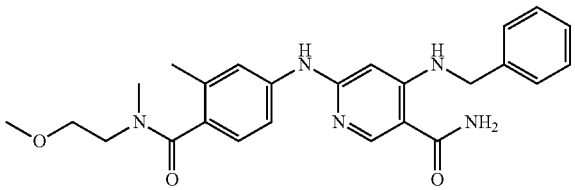 [SMILES: COCCN(C)C(=O)c1ccc(Nc2cc(NCc3ccccc3)c(C(N)=O)cn2)cc1C]

The title compound was synthesized using a procedure similar to that described in Example 36. MS found for C25H29N5O3 as (M+H)+ 448.4. UV: λ=209.5, 259.6 nm. ¹H NMR: (CD3OD) δ 8.3 (s, 1H), 7.35 (m, 4H), 7.3 (m, 1H), 7.2 (d, 1H), 7.15 (t, 1H), 7.05 (t, 1H), 5.95 (s, 1H), 4.4 (s, 2H), 3.75 (s, 1H), 3.7 (d, 1H), 3.45 (s, 3H), 3.3 (s, 3H), 2.9 (s, 2H), 2.2 (s, 3H).

Example 454

PN-1010-25 6-(4-(azetidine-1-carbonyl)-3-methylphenylamino)-4-(2,3-difluorobenzylamino)nicotinamide

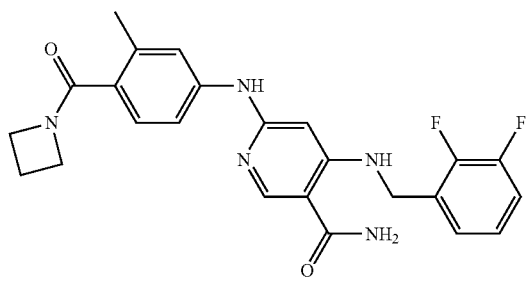 [SMILES: Cc1cc(Nc2cc(NCc3cccc(F)c3F)c(C(N)=O)cn2)ccc1C(=O)N1CCC1]

The title compound was synthesized using a procedure similar to that described in Example 36. MS found for C24H23F2N5O2 as (M+H)+ 452.3. UV: λ=201.0, 244.3, 313.1 nm. ¹H NMR: (CD3OD) δ 8.2 (s, 1H), 7.35 (d, 1H), 7.25 (d, 1H), 7.15 (m, 1H), 7.1 (m, 2H), 7.05 (d, 1H), 6.0 (s, 1H), 4.6 (s, 2H), 4.2 (t, 2H), 4.05 (t, 2H), 2.4 (m, 5H).

Example 455

4-(2,3-difluorobenzylamino)-6-(3-methyl-4-(morpholine-4-carbonyl)phenylamino)nicotinamide

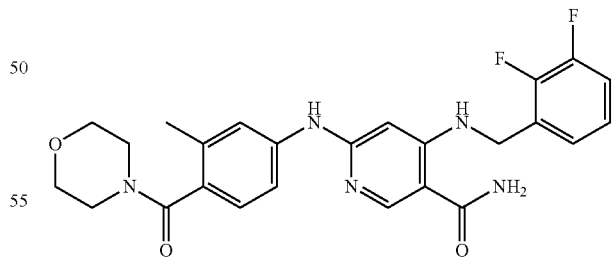

The title compound was synthesized using a procedure similar to that described in Example 36. MS found for C25H25F2N5O3 as (M+H)+ 466.4. UV: λ=202.2, 244.9, 311.9 nm. ¹H NMR: (CD3OD) δ 8.2 (s, 1H), 7.3 (m, 2H), 7.15 (m, 3H), 7.1 (d, 1H), 6.0 (s, 1H), 4.4 (s, 2H), 3.8 (d, 4H), 3.6 (s, 2H), 2.3 (s, 3H).

Example 456

4-(2,3-difluorobenzylamino)-6-(3-methyl-4-(pyrrolidine-1-carbonyl)phenylamino)nicotinamide

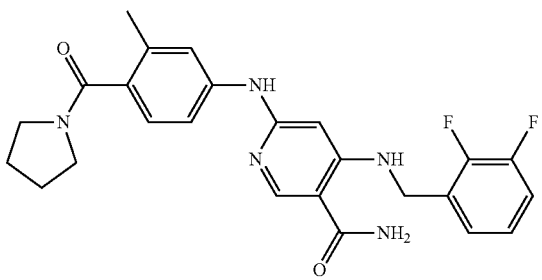 [SMILES: Cc1cc(Nc2cc(NCc3cccc(F)c3F)c(C(N)=O)cn2)ccc1C(=O)N1CCCC1]

The title compound was synthesized using a procedure similar to that described in Example 36. MS found for C25H25F2N5O2 as (M+H)+ 466.4. UV: λ=200.4, 243.7, 380.8 nm. ¹H NMR: (CD3OD) δ 8.1 (s, 1H), 7.2 (m, 3H), 7.1 (m, 2H), 6.95 (d, 1H), 5.9 (s, 1H), 4.5 (s, 2H), 3.5 (t, 2H), 3.1 (t, 2H), 2.2 (s, 3H), 1.95 (d, 2H), 1.85 (d, 2H).

Example 457

6-(4-(azetidine-1-carbonyl)-3-methylphenylamino)-4-(benzo[b]thiophen-7-ylmethylamino)nicotinamide

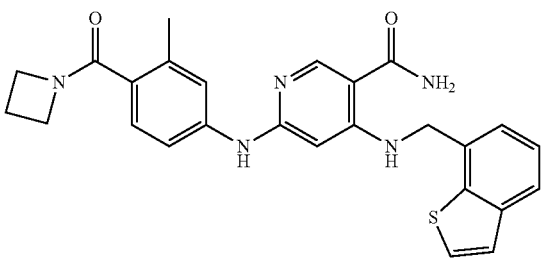 [SMILES: Cc1cc(Nc2cc(NCc3cccc4ccsc34)c(C(N)=O)cn2)ccc1C(=O)N1CCC1]

The title compound was synthesized using a procedure similar to that described in Example 36. MS found for C26H25N5O2S as (M+H)+ 472.3. UV: λ=226.0, 313.7 nm. ¹H NMR: (CD3OD) δ 8.1 (s, 1H), 7.75 (d, 1H), 5.5 (d, 1H), 7.4 (s, 2H), 7.35 (t, 1H), 7.2 (d, 1H), 7.1 (d, 1H), 6.9 (s, 1H), 6.7 (d, 1H), 5.9 (s, 1H), 4.65 (s, 2H), 4.1 (t, 2H), 3.8 (t, 2H), 2.25 (m, 2H), 2.2 (s, 3H).

Example 458

4-(benzo[b]thiophen-7-ylmethylamino)-6-(3-methyl-4-(pyrrolidine-1-carbonyl)phenylamino)nicotinamide

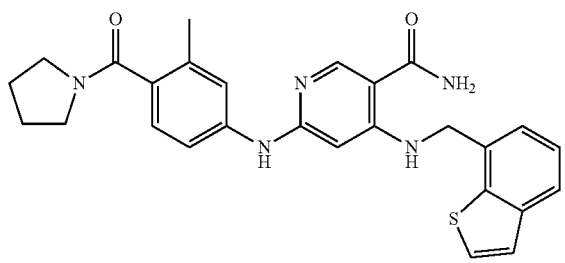 [SMILES: Cc1cc(Nc2cc(NCc3cccc4ccsc34)c(C(N)=O)cn2)ccc1C(=O)N1CCCC1]

The title compound was synthesized using a procedure similar to that described in Example 36. MS found for C27H27N5O2S as (M+H)+ 486.3. UV: λ=224.1, 311.3 nm. ¹H NMR: (CD3OD) δ 8.1 (s, 1H), 7.8 (d, 1H), 7.5 (d, 1H), 7.4 (d, 1H), 7.35 (t, 1H), 7.2 (d, 1H), 7.05 (d, 1H), 6.9 (s, 1H), 6.75 (d, 1H), 5.9 (s, 1H), 4.7 (s, 2H), 3.5 (t, 2H), 3.0 (t, 2H), 1.9 (d, 2H), 1.85 (d, 2H).

Example 459

4-(benzo[b]thiophen-7-ylmethylamino)-6-(3-methyl-4-(morpholine-4-carbonyl)phenylamino)nicotinamide

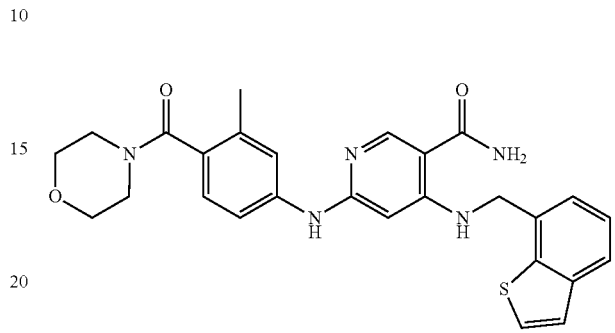

The title compound was synthesized using a procedure similar to that described in Example 36. MS found for C27H27N5O3S as (M+H)+ 502.3. UV: λ=200.4, 225.1, 311.3 nm. ¹H NMR: (CD3OD) δ 8.1 (s, 1H), 7.75 (d, 1H), 7.55 (d, 1H), 7.4 (d, 1H), 7.3 (t, 1H), 7.2 (d, 1H), 7.05 (d, 1H), 6.95 (s, 1H), 6.8 (d, 1H), 5.9 (s, 1H), 4.7 (s, 2H), 3.7 (s, 4H), 3.5 (s, 2H), 3.2 (s, 2H), 2.1 (s, 3H).

Example 460

4-((1H-indol-4-yl)methylamino)-6-(4-(azetidine-1-carbonyl)-3-methylphenylamino)nicotinamide

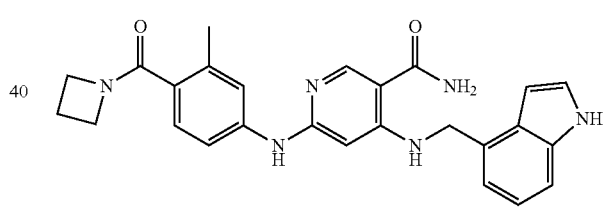

The title compound was synthesized using a procedure similar to that described in Example 36. MS found for C26H26N6O2 as (M+H)+ 455.3. UV: λ=216.8, 244.9, 313.1 nm. ¹H NMR: (CD3OD) δ 8.1 (s, 1H), 7.25 (d, 1H), 7.18 (s, 1H), 7.0 (m, 2H), 6.9 (d, 3H), 6.5 (s, 1H), 5.9 (s, 1H), 4.55 (s, 2H), 4.1 (t, 2H), 3.85 (t, 2H), 2.25 (t, 2H), 2.1 (s, 3H).

Example 461

4-((1H-indol-4-yl)methylamino)-6-(3-methyl-4-(pyrrolidine-1-carbonyl)phenylamino)nicotinamide

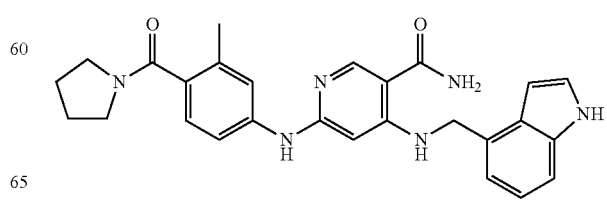

The title compound was synthesized using a procedure similar to that described in Example 36. MS found for C27H28N6O2 as (M+H)+ 469.4. UV: λ=223.5, 266.3 nm. ¹H NMR: (CD3OD) δ 8.2 (s, 1H), 7.35 (d, 1H), 7.3 (s, 1H), 7.1 (m, 4H), 6.9 (d, 1H), 6.85 (d, 1H), 6.5 (s, 1H), 6.05 (s, 1H), 4.75 (s, 2H), 3.6 (t, 2H), 3.1 (t, 2H), 2.2 (s, 3H), 2.0 (dd, 2H), 1.9 (dd, 2H).

Example 462

4-((1H-indol-4-yl)methylamino)-6-(3-methyl-4-(morpholine-4-carbonyl)phenylamino)nicotinamide

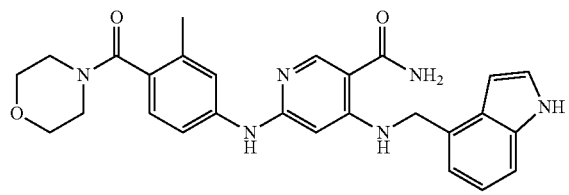 [SMILES: Cc1cc(Nc2cc(NCc3cccc4[nH]ccc34)c(C(N)=O)cn2)ccc1C(=O)N1CCOCC1]

The title compound was synthesized using a procedure similar to that described in Example 36. MS found for C27H28N6O3 as (M+H)+ 485.4. UV: λ=223.5, 266.3 nm. ¹H NMR: (CD3OD) δ 8.2 (s, 1H), 7.4 (d, 1H), 7.3 (s, 1H), 7.1 (m, 3H), 6.9 (d, 2H), 6.5 (s, 1H), 6.1 (s, 1H), 4.7 (s, 2H), 3.6 (bs, 2H), 3.3 (bs, 2H), 2.2 (s, 3H).

Example 463

4-((1H-indol-7-yl)methylamino)-6-(4-(azetidine-1-carbonyl)-3-methylphenylamino)nicotinamide

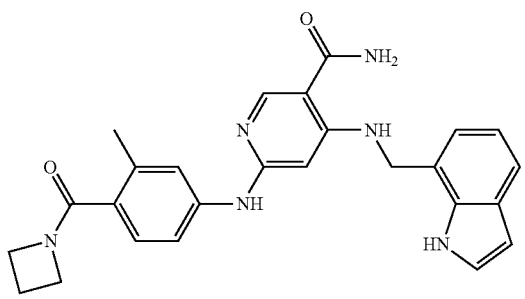 [SMILES: Cc1cc(Nc2cc(NCc3cccc4cc[nH]c34)c(C(N)=O)cn2)ccc1C(=O)N1CCC1]

The title compound was synthesized using a procedure similar to that described in Example 36. MS found for C26H26N6O2 as (M+H)+ 455.3. UV: λ=215.6, 312.5 nm. ¹H NMR: (CD3OD) δ 8.1 (s, 1H), 7.6 (d, 1H), 7.2 (s, 1H), 7.1 (d, 1H), 6.9 (m, 3H), 6.8 (d, 2H), 6.4 (s, 1H), 5.95 (s, 1H), 4.7 (s, 2H), 4.1 (t, 2H), 3.8 (t, 2H), 2.3 (t, 2H), 2.2 (s, 3H).

Example 464

4-((1H-indol-7-yl)methylamino)-6-(3-methyl-4-(pyrrolidine-1-carbonyl)phenylamino)nicotinamide

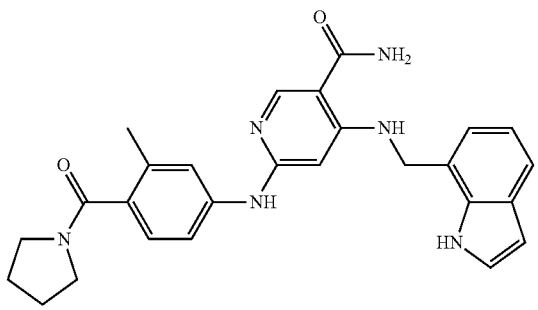 [SMILES: Cc1cc(Nc2cc(NCc3cccc4cc[nH]c34)c(C(N)=O)cn2)ccc1C(=O)N1CCCC1]

The title compound was synthesized using a procedure similar to that described in Example 36. MS found for C27H28N6O2 as (M+H)+ 469.3. UV: λ=216.8, 254.7, 310.6 nm. ¹H NMR: (CD3OD) δ 8.1 (s, 1H), 7.45 (d, 1H), 7.2 (s, 1H), 7.0 (d, 1H), 6.9 (m, 3H), 6.8 (d, 1H), 6.4 (s, 1H), 5.95 (s, 1H), 4.6 (s, 2H), 3.5 (t, 2H), 3.05 (t, 2H), 2.1 (s, 3H), 1.9 (dd, 2H), 1.8 (dd, 2H).

Example 465 methyl 4-(4-(benzo[b]thiophen-7-ylmethylamino)-5-carbamoylpyridin-2-ylamino)phenyl(methyl)carbamate

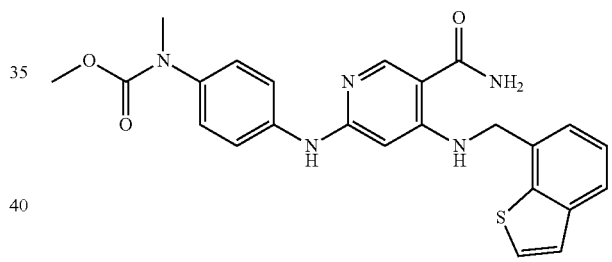

The title compound was synthesized using a procedure similar to that described in Example 36. MS found for C24H23N5O3S as (M+H)+ 462.3. UV: λ=229.0, 259.6 nm. ¹H NMR: (CD3OD) δ 8.2 (s, 1H), 7.7 (d, 1H), 7.5 (s, 1H), 7.35 (d, 1H), 7.25 (t, 1H), 7.2 (d, 1H), 6.9 (m, 4H), 5.8 (s, 1H), 4.75 (s, 2H), 3.6 (bs, 3H), 3.15 (s, 3H).

Example 466

4-(benzo[b]thiophen-7-ylmethylamino)-6-(4-(N-methylpropionamido)phenylamino)nicotinamide

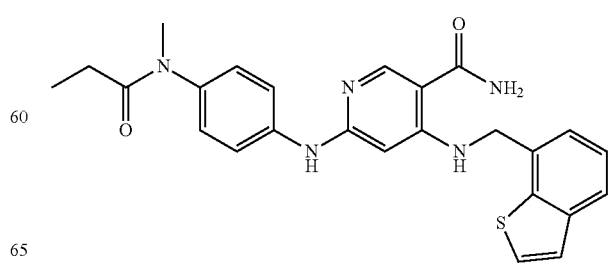

The title compound was synthesized using a procedure similar to that described in Example 36. MS found for C25H25N5O2S as (M+H)⁺ 460.2. UV: λ=227.2, 260.2 nm. ¹H NMR: (CD3OD) δ 8.15 (s, 1H), 7.95 (d, 1H), 7.8 (d, 1H), 7.5 (d, 1H), 7.35 (s, 1H), 7.3 (t, 1H), 7.2 (d, 1H), 7.05 (d, 1H), 6.9 (m, 1H), 6.5 (d, 1H), 5.8 (s, 1H), 4.7 (s, 2H), 3.1 (s, 3H), 2.8 (s, 1H), 2.0 (bd, 1H), 0.9 (bs, 3H).

Example 467

4-(benzo[b]thiophen-7-ylmethylamino)-6-(4-(N-methylcyclopropanecarboxamido)phenylamino)nicotinamide

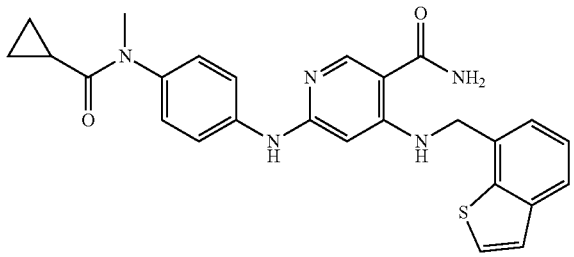 [SMILES: CN(C(=O)C1CC1)c1ccc(Nc2cc(NCc3cccc4ccsc34)c(C(N)=O)cn2)cc1]

The title compound was synthesized using a procedure similar to that described in Example 36. MS found for C26H25N5O2S as (M+H)⁺ 472.3. UV: λ=228.4, 260.8 nm. ¹H NMR: (CD3OD) δ 8.2 (s, 1H), 7.9 (d, 1H), 7.6 (d, 1H), 7.5 (d, 1H), 7.4 (t, 1H), 7.3 (d, 1H), 7.2 (d, 2H), 7.0 (d, 2H), 5.9 (s, 1H), 4.8 (s, 2H), 3.25 (s, 3H), 1.4 (bs, 1H), 1.0 (d, 2H), 0.7 (bs, 2H).

Example 468

4-(benzo[b]thiophen-7-ylmethylamino)-6-(4-(N-methylacetamido)phenylamino)nicotinamide

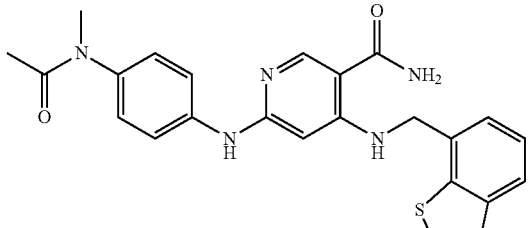

The title compound was synthesized using a procedure similar to that described in Example 36. MS found for C24H23N5O2S as (M+H)⁺ 446.3. UV: λ=227.2, 260.2 nm. ¹H NMR: (CD3OD) δ 8.1 (s, 1H), 7.8 (d, 1H), 7.45 (d, 1H), 7.4 (d, 1H), 7.35 (d, 1H), 7.4 (d, 1H), 7.1 (d, 2H), 6.9 (d, 2H), 5.8 (s, 1H), 4.7 (s, 2H), 3.1 (s, 3H), 1.8 (s, 3H).

Example 469

4-((1H-indol-4-yl)methylamino)-6-(4-(N-methylacetamido)phenylamino)nicotinamide

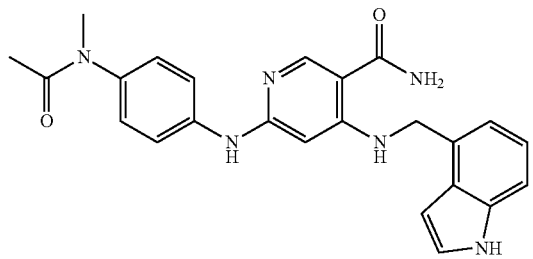 [SMILES: CC(=O)N(C)c1ccc(Nc2cc(NCc3cccc4[nH]ccc34)c(C(N)=O)cn2)cc1]

The title compound was synthesized using a procedure similar to that described in Example 36. MS found for C24H24N6O2 as (M+H)⁺ 429.4. UV: λ=217.4, 270.0 nm. ¹H NMR: (CD3OD) δ 8.2 (s, 1H), 7.3 (d, 1H), 7.15 (s, 1H), 7.0 (t, 1H), 6.9 (m, 3H), 6.85 (d, 2H), 6.4 (d, 1H), 5.9 (s, 1H), 4.7 (s, 2H), 3.1 (s, 3H), 1.7 (s, 3H).

Example 470

4-((1H-indol-7-yl)methylamino)-6-(4-(N-methylacetamido)phenylamino)nicotinamide

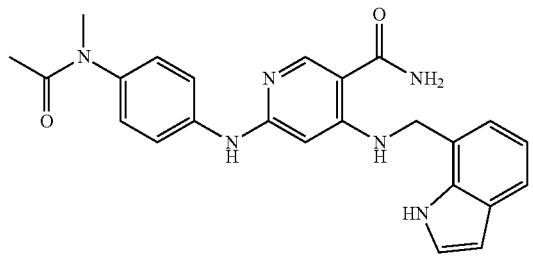 [SMILES: CC(=O)N(C)c1ccc(Nc2cc(NCc3cccc4cc[nH]c34)c(C(N)=O)cn2)cc1]

The title compound was synthesized using a procedure similar to that described in Example 36. MS found for C24H24N6O2 as (M+H)⁺ 429.4. UV: λ=216.3, 306.9 nm. ¹H NMR: (CD3OD) δ 8.1 (s, 1H), 7.5 (bs, 1H), 7.2 (m, 2H), 7.1 (d, 1H), 6.9 (m, 4H), 6.4 (s, 1H), 5.9 (s, 1H), 4.7 (s, 2H), 3.3 (s, 3H), 1.8 (s, 3H).

Example 471

6-(4-acetamidophenylamino)-4-(benzo[b]thiophen-7-ylmethylamino)nicotinamide

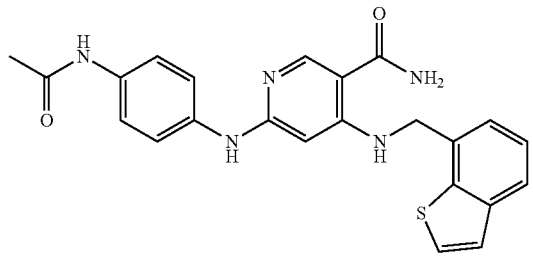 [SMILES: CC(=O)Nc1ccc(Nc2cc(NCc3cccc4ccsc34)c(C(N)=O)cn2)cc1]

The title compound was synthesized using a procedure similar to that described in Example 36. MS found for C23H21N5O2S as (M+H)+ 432.4. UV: λ=205.9, 227.2, 259.0 nm. $^1$H NMR: (CD3OD) δ 8.1 (s, 1H), 7.8 (d, 1H), 7.45 (d, 1H), 7.4 (d, 3H), 7.3 (t, 1H), 7.15 (d, 1H), 6.8 (d, 2H), 5.7 (s, 1H), 4.65 (s, 2H), 2.1 (s, 3H).

Example 472

4-((1H-indol-4-yl)methylamino)-6-(4-acetamidophenylamino)nicotinamide

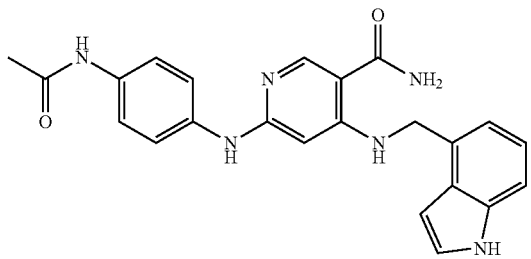

The title compound was synthesized using a procedure similar to that described in Example 36. MS found for C23H22N6O2 as (M+H)+ 415.3. UV: λ=218.7, 247.3, 279.2, 310.0 nm. $^1$H NMR: (CD3OD) δ 8.0 (s, 1H), 7.45 (d, 1H), 7.3 (d, 1H), 7.2 (d, 1H), 7.0 (t, 1H), 6.9 (s, 4H), 6.8 (s, 1H), 5.9 (s, 1H), 4.6 (s, 2H), 2.1 (s, 3H).

Example 473

4-((1H-indol-7-yl)methylamino)-6-(4-acetamidophenylamino)nicotinamide

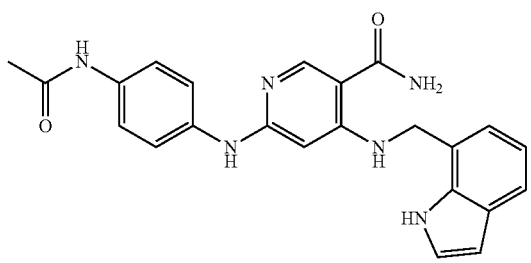

The title compound was synthesized using a procedure similar to that described in Example 36. MS found for C23H22N6O2 as (M+H)+ 415.4. UV: λ=217.4, 261.4 nm. $^1$H NMR: (CD3OD) δ 8.0 (s, 1H), 7.45 (m, 3H), 7.15 (s, 1H), 6.9 (m, 5H), 6.4 (s, 1H), 5.8 (s, 1H), 4.6 (s, 3H), 2.1 (s, 3H).

Example 474 methyl 4-(4-((1H-indol-4-yl)methylamino)-5-carbamoylpyridin-2-ylamino)phenyl(methyl)carbamate

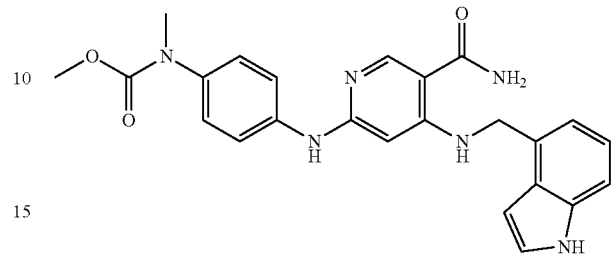

The title compound was synthesized using a procedure similar to that described in Example 36. MS found for C24H24N6O3 as (M+H)+ 445.4. UV: λ=218.0, 306.9 nm. $^1$H NMR: (CD3OD) δ 8.1 (s, 1H), 7.3 (d, 1H), 7.15 (d, 1H), 7.1 (d, 2H), 7.0 (t, 1H), 6.9 (d, 2H), 6.8 (d, 1H), 6.4 (s, 1H), 5.9 (s, 1H), 4.65 (s, 2H), 3.6 (s, 3H), 3.2 (s, 3H).

Example 475

4-((1H-indol-4-yl)methylamino)-6-(4-(N-methylpropionamido)phenylamino)nicotinamide

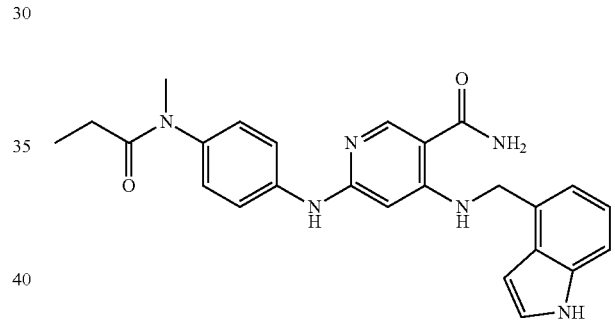

The title compound was synthesized using a procedure similar to that described in Example 36. MS found for C25H26N6O2 as (M+H)+ 443.4. UV: λ=217.4, 306.9 nm. $^1$H NMR: (CD3OD) δ 8.1 (s, 1H), 7.3 (d, 1H), 7.2 (s, 1H), 7.0 (m, 4H), 6.9 (d, 2H), 6.4 (s, 1H), 5.9 (s, 1H), Example 476

4-((1H-indol-4-yl)methylamino)-6-(4-(N-methylcyclopropanecarboxamido)phenylamino)nicotinamide

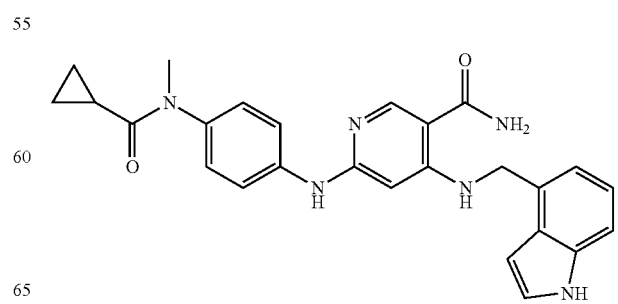

The title compound was synthesized using a procedure similar to that described in Example 36. MS found for C26H26N6O2 as (M+H)+ 455.4. UV: λ=217.4, 307.6 nm. ¹H NMR: (CD3OD) δ 8.2 (s, 1H), 7.35 (d, 1H), 7.3 (s, 1H), 7.15 (d, 2H), 7.1 (t, 1H), 7.0 (d, 2H), 6.9 (d, 1H), 6.5 (s, 1H), 6.0 (s, 1H), 4.9 (s, 2H), 1.4 (m, 1H), 0.95 (m, 2H). 0.08 (m, 2H).

Example 477

4-((1H-indol-7-yl)methylamino)-6-(4-(N-methylpropionamido)phenylamino)nicotinamide

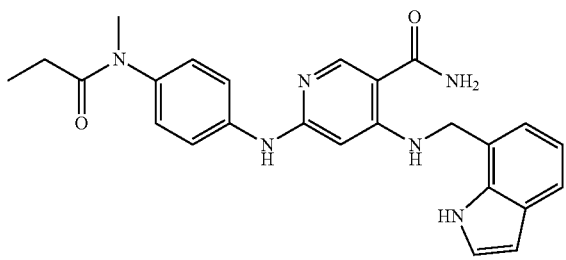 [SMILES: CCC(=O)N(C)c1ccc(Nc2cc(NCc3cccc4cc[nH]c34)c(C(N)=O)cn2)cc1]

The title compound was synthesized using a procedure similar to that described in Example 36. MS found for C25H26N6O2 as (M+H)+ 443.4. UV: λ=222.9, 308.2 nm. ¹H NMR: (CD3OD) δ 8.1 (s, 1H), 7.5 (d, 1H), 7.2 (s, 1H), 7.1 (d, 2H), 6.9 (m, 4H), 6.45 (s, 1H), 5.9 (s, 1H), Example 478

4-((1H-indol-7-yl)methylamino)-6-(4-(N-methylcyclopropanecarboxamido)phenylamino)nicotinamide

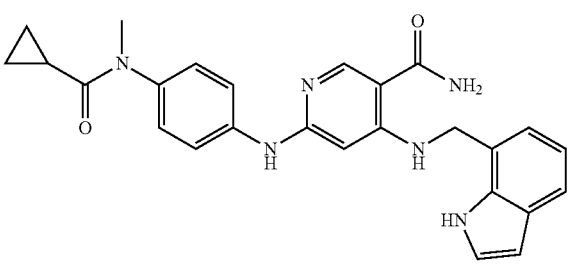 [SMILES: CN(C(=O)C1CC1)c1ccc(Nc2cc(NCc3cccc4cc[nH]c34)c(C(N)=O)cn2)cc1]

The title compound was synthesized using a procedure similar to that described in Example 36. MS found for C26H26N6O2 as (M+H)+ 455.4. UV: λ=218.0, 255.9, 307.6 nm. ¹H NMR: (CD3OD) δ 8.1 (s, 1H), 7.5 (d, 1H), 7.1 (m, 3H), 6.9 (m, 4H), 6.45 (s, 1H), 5.9 (s, 1H), 4.6 (s, 2H), 3.1 (s, 3H), 1.3 (bs, 1H), 0.9 (m, 2H), 0.7 (m, 2H).

Example 479 methyl 4-(5-carbamoyl-4-((5-fluoropyridin-3-yl)methylamino)pyridin-2-ylamino)phenyl(methyl)carbamate

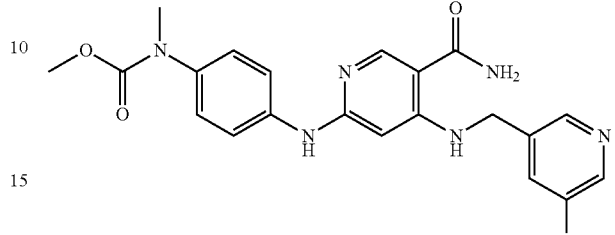

The title compound was synthesized using a procedure similar to that described in Example 36. MS found for C21H21FN6O3 as (M+H)+ 425.4. UV: λ=306.4 nm. ¹H NMR: (CD3OD) δ 8.35 (s, 1H), 8.3 (s, 1H), 8.1 (s, 1H), 7.5 (d, 1H), 7.25 (d, 2H), 7.05 (d, 2H), 5.8 (s, 1H), 4.7 (s, 2H), 4.55 (s, 3H), 3.6 (s, 3H).

Example 480

4-((5-fluoropyridin-3-yl)methylamino)-6-(4-(N-methylpropionamido)phenylamino)nicotinamide

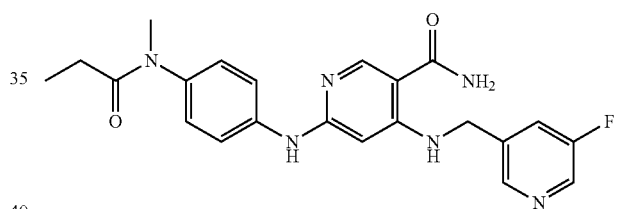

The title compound was synthesized using a procedure similar to that described in Example 36. MS found for C22H23FN6O2 as (M+H)+ 423.4. UV: λ=307.1 nm. ¹H NMR: (CD3OD) δ 8.3 (bd, 2H), 8.1 (s, 1H), 7.5 (d, 1H), 7.25 (d, 2H), 7.1 (d, 2H), 5.8 (s, 1H), 4.45 (s, 2H), 2.1 (bs, 2H), 0.95 (bs, 3H).

Example 481

4-((5-fluoropyridin-3-yl)methylamino)-6-(4-(N-methylcyclopropanecarboxamido)phenylamino)nicotinamide

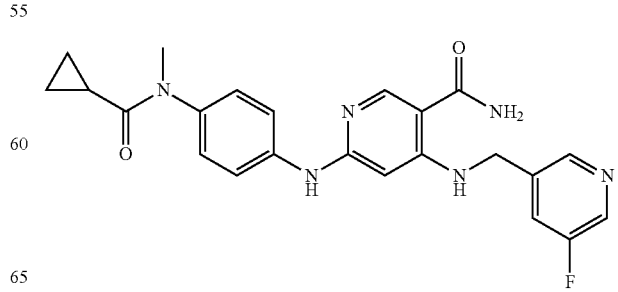

The title compound was synthesized using a procedure similar to that described in Example 36. MS found for C23H23FN6O2 as (M+H)+ 435.4. UV: λ=251.7, 307.1 nm. ¹H NMR: (CD3OD) δ 8.35 (s, 1H), 8.25 (s, 1H), 8.1 (s, 1H), 7.5 (d, 1H), 7.35 (d, 2H), 7.15 (d, 2H), 5.8 (s, 1H), 4.7 (s, 2H), 1.2 (s, 1H), 0.85 (m, 2H), 0.65 (m, 2H).

Example 482 methyl 4-(4-(OH-indol-7-yl)methylamino)-5-carbamoylpyridin-2-ylamino)phenyl(methyl)carbamate

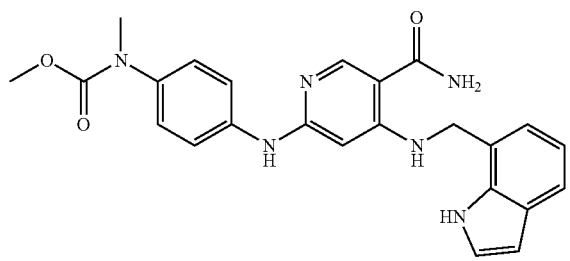 [SMILES: COC(=O)N(C)c1ccc(Nc2cc(NCc3cccc4cc[nH]c34)c(C(N)=O)cn2)cc1]

The title compound was synthesized using a procedure similar to that described in Example 36. MS found for C24H24N6O3 as (M+H)+ 445.4. UV: λ=216.9, 255.4, 306.4 nm. ¹H NMR: (CD3OD) δ 8.15 (s, 1H), 7.55 (d, 1H), 7.25 (s, 1H), 7.2 (d, 2H), 7.0 (m, 4H), 6.5 (s, 1H), 6.0 (s, 1H), 4.75 (s, 2H), 3.75 (s, 3H).

Example 483

4-((5-fluoropyridin-3-yl)methylamino)-6-(4-(N-methylacetamido)phenylamino)nicotinamide

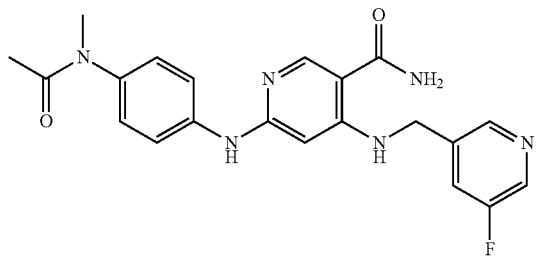 [SMILES: CC(=O)N(C)c1ccc(Nc2cc(NCc3cncc(F)c3)c(C(N)=O)cn2)cc1]

The title compound was synthesized using a procedure similar to that described in Example 36. MS found for C21H21FN6O2 as (M+H)+ 409.4. UV: λ=203.6, 252.3, 307.7 nm. ¹H NMR: (CD3OD) δ 8.45 (d, 1H), 8.35 (s, 1H), 8.2 (s, 1H), 7.6 (d, 1H), 7.35 (d, 2H), 7.25 (d, 2H), 5.9 (s, 1H), 4.65 (s, 2H), 3.25 (s, 3H), 1.9 (s, 3H).

Example 484

6-(4-acetamidophenylamino)-4-((5-fluoropyridin-3-yl)methylamino)nicotinamide

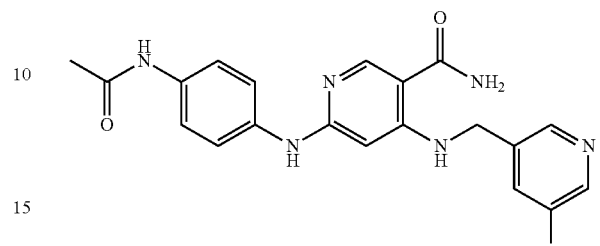

The title compound was synthesized using a procedure similar to that described in Example 36. MS found for C20H19FN6O2 as (M+H)+ 395.3. UV: λ=245.6, 308.9 nm.

Example 485

4-((6-fluoropyridin-2-yl)methylamino)-6-(4-(N-methylacetamido)phenylamino)nicotinamide

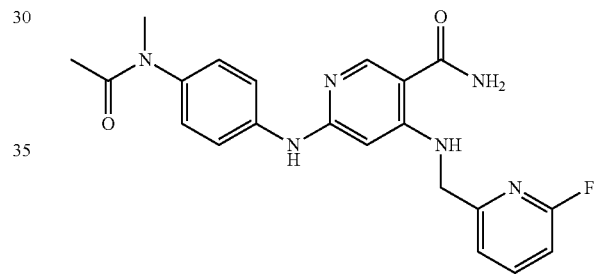

The title compound was synthesized using a procedure similar to that described in Example 36. MS found for C21H21FN6O2 as (M+H)+ 409.3. UV: λ=201.1, 305.2 nm. ¹H NMR: (CD3OD) δ 8.1 (s, 1H), 7.9 (q, 1H), 7.25 (m, 2H), 7.2 (m, 3H), 6.95 (d, 1H), 5.9 (s, 1H), 4.5 (s, 2H), 3.15 (s, 3H), 1.85 (s, 3H).

Example 486

6-(4-acetamidophenylamino)-4-((6-fluoropyridin-2-yl)methylamino)nicotinamide

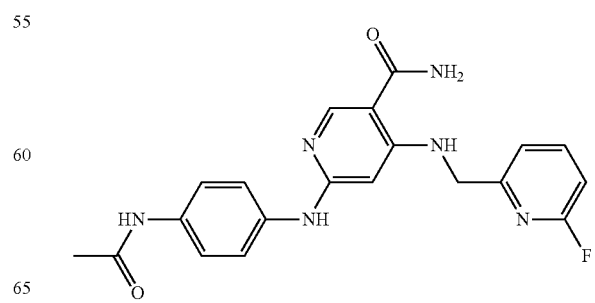

The title compound was synthesized using a procedure similar to that described in Example 36. MS found for C20H19FN6O2 as (M+H)+ 395.3. UV: λ=259.7, 308.9 nm. ¹H NMR: (CD3OD) δ 8.05 (s, 1H), 7.85 (q, 1H), 7.55 (d, 1H), 7.2 (d, 1H), 7.1 (d, 3H), 6.9 (d, 1H), 5.8 (s, 1H), 4.5 (s, 2H), 2.1 (s, 3H).

Example 487 methyl 4-(5-carbamoyl-4-((6-fluoropyridin-2-yl)methylamino)pyridin-2-ylamino)phenyl(methyl)carbamate

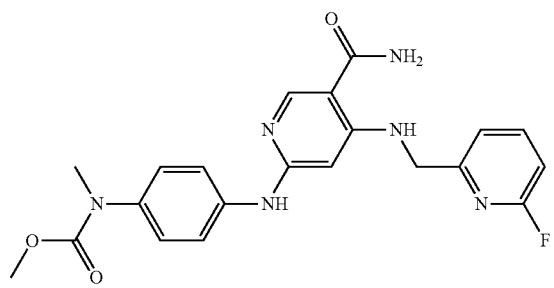 [SMILES: COC(=O)N(C)c1ccc(Nc2cc(NCc3cccc(F)n3)c(C(N)=O)cn2)cc1]

The title compound was synthesized using a procedure similar to that described in Example 36. MS found for C21H21FN6O3 as (M+H)+ 425.3. UV: λ=200.6, 262.1, 306.1 nm. ¹H NMR: (CD3OD) δ 8.1 (s, 1H), 7.85 (q, 1H), 7.23 (m, 2H), 7.2 (d, 1H), 7.1 (m, 2H), 6.9 (d, 1H), 5.95 (s, 1H), 4.5 (s, 2H), 3.6 (s, 3H).

Example 488

4-((6-fluoropyridin-2-yl)methylamino)-6-(4-(N-methylpropionamido)phenylamino)nicotinamide

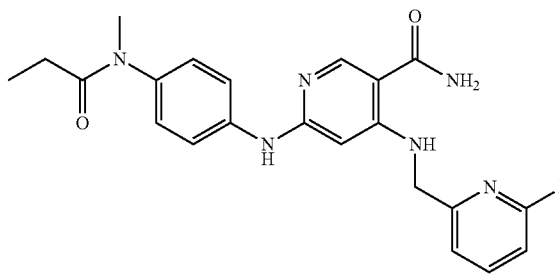

The title compound was synthesized using a procedure similar to that described in Example 36. MS found for C22H23FN6O2 as (M+H)+ 423.3. UV: λ=262.1, 307.7 nm. ¹H NMR: (CD3OD) δ 8.1 (s, 1H), 7.85 (q, 1H), 7.2 (m, 5H), 6.9 (d, 1H), 5.9 (s, 1H), 4.45 (s, 2H), 3.15 (s, 3H), 2.05 (bs, 2H), 1.0 (bs, 3H).

Example 489

4-((6-fluoropyridin-2-yl)methylamino)-6-(4-(N-methylcyclopropanecarboxamido)phenylamino)nicotinamide

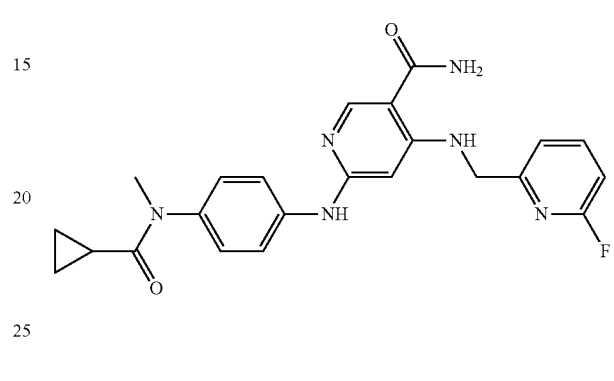

The title compound was synthesized using a procedure similar to that described in Example 36. MS found for C23H23FN6O2 as (M+H)+ 435.4. UV: λ=262.1, 307.7 nm. ¹H NMR: (CD3OD) δ 8.1 (s, 1H), 7.85 (q, 1H), 7.35 (m, 2H), 7.2 (m, 3H), 6.9 (d, 1H), 5.9 (s, 1H), 4.5 (s, 2H), 1.4 (bs, 1H), 0.9 (m, 2H), 0.7 (bs, 2H).

Example 490

4-((6-fluoropyridin-2-yl)methylamino)-6-(4-(1-propionylazetidin-3-yl)phenylamino)nicotinamide

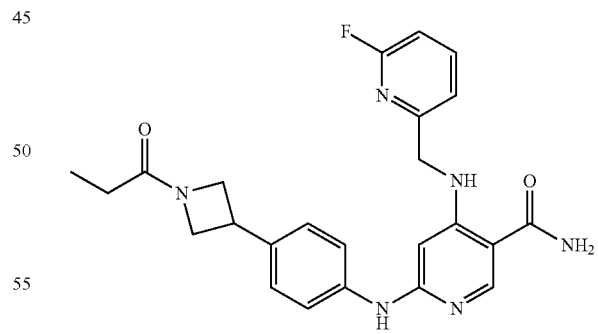

The title compound was synthesized using a procedure similar to that described in Example 36. MS found for C24H25FN6O2 as (M+H)+ 449.4. UV: λ=262.8, 305.2 nm. ¹H NMR: (CD3OD) δ 8.1 (s, 1H), 7.85 (q, 1H), 7.35 (d, 2H), 7.2 (d, 1H), 7.1 (d, 2H). 6.9 (d, 1H), 5.8 (s, 1H), 4.55 (t, 1H), 4.45 (s, 2H), 4.3 (t, 1H), 4.2 (m, 1H), 3.9 (m, 3H), 2.1 (q, 2H), 1.1 (t, 3H).

Example 491

4-(benzo[b]thiophen-7-ylmethylamino)-6-(4-(1-propionylazetidin-3-yl)phenylamino)nicotinamide

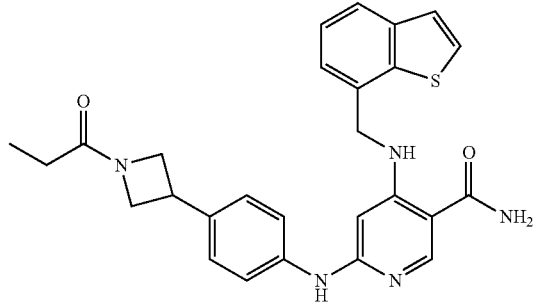 [SMILES: CCC(=O)N1CC(c2ccc(Nc3cc(NCc4cccc5ccsc45)c(C(N)=O)cn3)cc2)C1]

The title compound was synthesized using a procedure similar to that described in Example 36. MS found for C27H27N5O2S as (M+H)+ 486.4. UV: λ=204.2, 255.4, 300.3 nm. ¹H NMR: (CD3OD) δ 8.1 (s, 1H), 7.8 (d, 1H), 7.5 (d, 1H), 7.4 (d, 1H), 7.3 (t, 1H), 7.1 (m, 3H), 6.8 (d, 2H), 5.7 (s, 1H), 4.45 (t, 1H), 4.3 (t, 1H), 4.1 (t, 1H), 3.8 (m, 2H), 2.1 (q, 2H), 1.1 (t, 3H).

Example 492

4-((1H-indol-4-yl)methylamino)-6-(4-(1-propionylazetidin-3-yl)phenylamino)nicotinamide

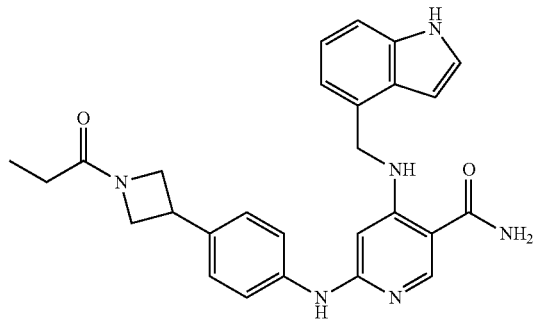 [SMILES: CCC(=O)N1CC(c2ccc(Nc3cc(NCc4cccc5[nH]ccc45)c(C(N)=O)cn3)cc2)C1]

The title compound was synthesized using a procedure similar to that described in Example 36. MS found for C27H28N6O2 as (M+H)+ 469.4. UV: λ=219.4, 266.4 nm. ¹H NMR: (CD3OD) δ 8.2 8.2 (s, 1H), 7.25 (d, 1H), 7.15 (s, 1H), 7.0 (t, 1H), 6.9 (m, 5H), 6.4 (s, 1H), 5.8 (s, 1H), 4.5 (s, 2H), 4.45 (t, 1H), 4.3 (t, 1H), 4.05 (t, 1H), 3.8 (t, 1H), 3.7 (m, 1H), 2.1 (q, 2H), 1.1 (s, 3H).

Example 493

4-((6-fluoropyridin-2-yl)methylamino)-6-(4-(1-(2-methoxyacetyl)azetidin-3-yl)phenylamino)nicotinamide

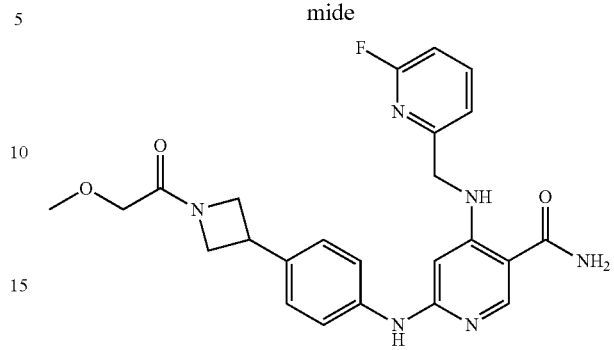

The title compound was synthesized using a procedure similar to that described in Example 36. MS found for C24H25FN6O3 as (M+H)+ 465.4. UV: λ=305.2 nm. ¹H NMR: (CD3OD) δ 8.1 (s, 1H), 7.85 (q, 1H), 7.35 (d, 2H), 7.2 (d, 1H), 7.1 (d, 2H), 6.9 (d, 1H), 5.8 (s, 1H), 4.8 (s, 2H), 4.4 (m, 4H), 4.2 (m, 1H), 3.95 (m, 2H), 3.3 (s, 3H).

Example 494

4-((1H-indol-4-yl)methylamino)-6-(4-(1-(2-methoxyacetyl)azetidin-3-yl)phenylamino)nicotinamide

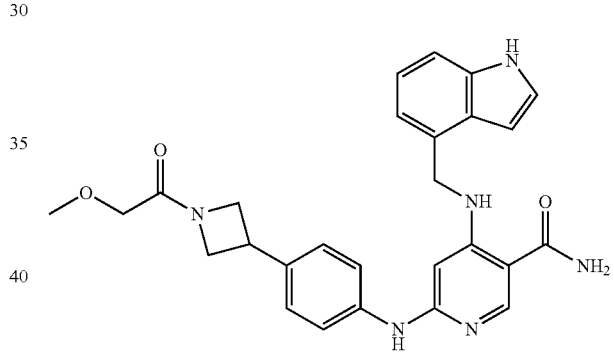

The title compound was synthesized using a procedure similar to that described in Example 36. MS found for C27H28N6O3 as (M+H)+ 485.5. UV: λ=216.3, 272.0, 289.8, 305.8 nm.

Example 495

4-(benzo[b]thiophen-7-ylmethylamino)-6-(4-(1-(2-methoxyacetyl)azetidin-3-yl)phenylamino)nicotinamide

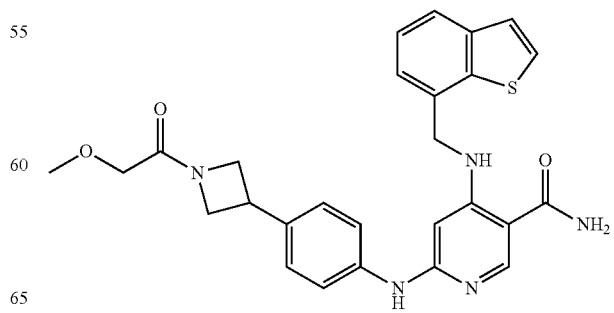

The title compound was synthesized using a procedure similar to that described in Example 36. MS found for C27H27N5O3S as (M+H)+ 502.4. UV: λ=201.7, 225.4, 254.8, 300.3 nm. ¹H NMR: (CD3OD) δ 8.1 (s, 1H), 7.8 (d, 1H), 7.5 (d, 1H), 7.4 (d, 1H), 7.3 (t, 1H), 7.1 (m, 3H), 6.8 (d, 2H), 5.7 (s, 1H), 4.4 (m, 2H), 4.35 (t, 1H), 4.15 (t, 1H), 4.0 (s, 3H), 3.85 (m, 2H), 3.35 (s, 3H).

Example 499

Preparation of 4-(2,3-difluorobenzylamino)-6-(4-(1-formylpiperidin-4-yl)phenylamino)nicotinamide

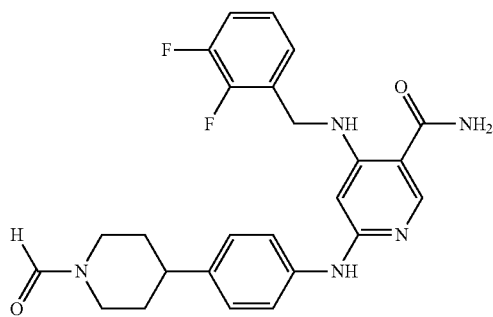 [SMILES: NC(=O)c1cnc(Nc2ccc(C3CCN(C=O)CC3)cc2)cc1NCc1cccc(F)c1F]

Compound 4-(2,3-difluorobenzylamino)-6-(4-(piperidin-4-yl)phenylamino)nicotinamide (Example 209) (70 mg, 0.15 mmol) was stirred in 4 mL DMF with DIEA (300 μL) at 120° C. in a sealed tube for two days. The mixture was acidified with 0.5 mL TFA and subjected to reverse phase preparative HPLC to isolate the title compound (41 mg). MS found for C25H25F2N5O2 as (M+H)+ 466.4. UV: λ=259 nm. ¹H NMR: (CD3OD) δ 8.15 (1H, s), 8.06 (1H, s), 7.33 (2H, dt, J=8.8; 2.0 Hz), 7.28 (1H, m), 7.16 (1H, m), 7.13-7.07 (3H, m), 5.80 (1H, s), 4.56 (2H, s), 4.48 (1H, m), 3.86 (1H, m), 3.27 (1H, m), 2.93 (1H, m), 2.82 (1H, m), 1.94 (2H, m), 1.64 (2H, m) ppm.

Example 500

Preparation of 4-(2,5-difluorobenzylamino)-6-(4-(1-formylpiperidin-4-yl)phenylamino)nicotinamide

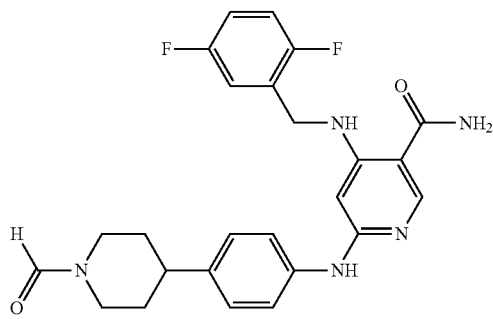 [SMILES: NC(=O)c1cnc(Nc2ccc(C3CCN(C=O)CC3)cc2)cc1NCc1cc(F)ccc1F]

Compound 4-(2,5-difluorobenzylamino)-6-(4-(piperidin-4-yl)phenylamino)nicotinamide (Example 214) (70 mg, 0.15 mmol) was stirred in 4 mL DMF with DIEA (300 μL) at 120° C. in a sealed tube for two days. The mixture was acidified with 0.5 mL TFA and subjected to reverse phase preparative HPLC to isolate the title compound (46 mg). MS found for C25H25F2N5O2 as (M+H)+ 466.4. UV: λ=259 nm. ¹H NMR: (CD3OD) δ 8.05 (1H, s), 7.97 (1H, s), 7.25 (2H, dt, J=8.8; 2.0 Hz), 7.08-6.98 (4H, m), 6.94 (1H, m), 5.74 (1H, s), 4.41 (2H, s), 4.38 (1H, m), 3.77 (1H, m), 3.17 (1H, m), 2.83 (1H, m), 2.72 (1H, m), 1.85 (2H, m), 1.53 (2H, m) ppm.

Example 501

Preparation of 4-((1H-indol-4-yl)methylamino)-6-(4-(1-formylpiperidin-4-yl)phenylamino)nicotinamide

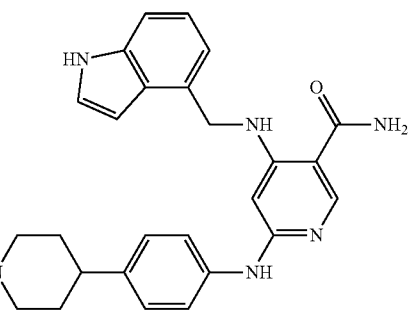

The title compound was synthesized using a procedure similar to that described in Example 499. MS found for C27H28N6O2 as (M+H)+ 469.4. UV: λ=258 nm.

Example 502

Preparation of 4-(2,3-difluorobenzylamino)-6-(4-(1-formylazetidin-3-yl)phenylamino)nicotinamide

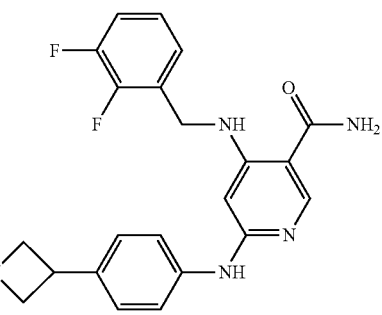

Compound 6-(4-(azetidin-3-yl)phenylamino)-4-(2,3-difluorobenzylamino)nicotinamide (Example 212) (35 mg, 0.08 mmol) was stirred in 4 mL DMF with DIEA (300 μL) at 120° C. in a sealed tube for three days. The mixture was acidified with 0.5 mL TFA and subjected to reverse phase preparative HPLC to isolate the title compound (11 mg). MS found for C23H21F2N5O2 as (M+H)+ 438.4. UV: λ=259 nm. ¹H NMR: (CD3OD) δ 8.17 (1H, s), 8.02 (1H, s), 7.44 (2H, dt, J=8.0; 1.6 Hz), 7.24 (1H, m), 7.17 (2H, dt, J=8.4; 1.6 Hz), 7.14 (1H, m), 7.11 (1H, m), 5.82 (1H, s), 4.68 (1H, t, J=8.0 Hz), 4.56 (2H, s), 4.46 (1H, m), 4.27 (1H, m), 4.05 (2H, m) ppm.

Example 503

Preparation of 4-(2,5-difluorobenzylamino)-6-(4-(1-formylazetidin-3-yl)phenylamino)nicotinamide

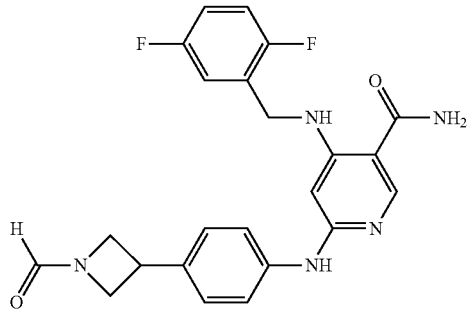 [SMILES: NC(=O)c1cnc(Nc2ccc(C3CN(C=O)C3)cc2)cc1NCc1cc(F)ccc1F]

Compound 6-(4-(azetidin-3-yl)phenylamino)-4-(2,5-difluorobenzylamino)nicotinamide (Example 213) (35 mg, 0.08 mmol) was stirred in 4 mL DMF with DMA (300 µL) at 120° C. in a sealed tube for three days. The mixture was acidified with 0.5 mL TFA and subjected to reverse phase preparative HPLC to isolate the title compound (15 mg). MS found for C23H21F2N5O2 as (M+H)+ 438.4. UV: λ=259 nm. $^1$H NMR: (CD3OD) δ 8.17 (1H, s), 8.02 (1H, s), 7.44 (2H, dt, J=8.0; 1.6 Hz), 7.21 (1H, m), 7.15-7.04 (3H, m), 5.85 (1H, s), 4.67 (1H, m), 4.51 (2H, s), 4.46 (1H, m), 4.27 (1H, m), 4.04 (2H, m) ppm.

Example 507

Preparation of 4-(2,3-difluorobenzylamino)-6-(4-(1-(2-fluoroethyl)azetidin-3-yl)phenylamino)nicotinamide

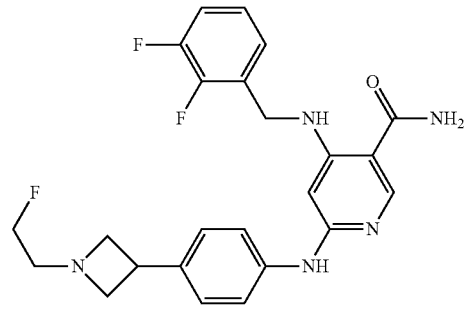 [SMILES: NC(=O)c1cnc(Nc2ccc(C3CN(CCF)C3)cc2)cc1NCc1cccc(F)c1F]

The title compound was synthesized using a procedure similar to that described in Example 217. MS found for C24H24F3N5O as (M+H)+ 456.4. UV: λ=259 nm. $^1$H NMR: (CD3OD) δ 8.22 (1H, s), 7.51 (2H d, J=8.0 Hz), 7.29-7.22 (3H, m), 7.17 (1H, m), 7.13 (1H, m), 5.85 (1H, s), 4.86 (1H, m), 4.71 (1H, m), 4.63 (2H, m), 4.56 (2H, s), 4.34 (3H, m), 3.72 (2H, m) ppm.

Example 517

Preparation of 4-(2,3-difluorobenzylamino)-6-(4-(1-(1,3-difluoropropan-2-yl)piperidin-4-yl)phenylamino)nicotinamide

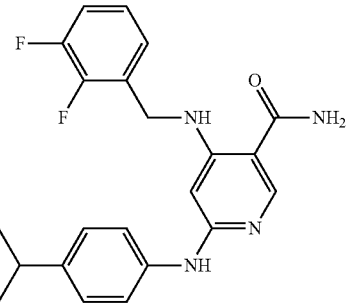

Compound 4-(2,3-difluorobenzylamino)-6-(4-(piperidin-4-yl)phenylamino)nicotinamide (Example 209) (100 mg, 0.21 mmol) was stirred in 5 mL 1,2-dichloroethane and 5 mL dioxane as a slurry. To it were added DIEA (150 µL, 0.84 mmol) and then 1,3-difluoroacetone (100 mg, 1.05 mmol). The mixture was stirred at RT for 2 h. To the mixture were then added HOAc (200 µL) and NaBH(OAc)$_3$ (222 mg, 1.05 mmol). The mixture was stirred at RT for overnight (incomplete reaction). To it was added water, and the mixture was concentrated in vacuo and subjected to reverse phase preparative HPLC to isolate the desired product (10 mg) and remaining starting compound. MS found for C27H29F4N5O as (M+H)+ 516.4. UV: λ=259 nm. $^1$H NMR: (CD3OD) δ 8.18 (1H, s), 7.38 (2H, d, J=8.0 Hz), 7.25 (1H, m), 7.19-7.09 (4H, m), 5.82 (1H, s), 5.15-4.90 (5H, m), 4.55 (2H, s), 3.77 (2H, m), 3.48 (2H, m), 3.03 (1H, m), 2.18 (4H, m) ppm.

Example 521

Preparation of 4-(2,3-difluorobenzylamino)-6-(4-(1-(2-(dimethylamino)acetyl)piperidin-4-yl)phenylamino)nicotinamide

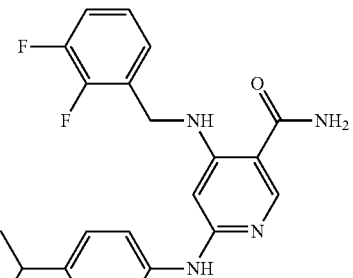

The mixture of compound 4-(2,3-difluorobenzylamino)-6-(4-(piperidin-4-yl)phenylamino)nicotinamide (Example 209) (50 mg, 0.11 mmol), N,N-dimethylglycine hydrochloride (31 mg, 0.22 mmol), DIEA (180 µL, 1.1 mmol) in 4 mL NMP was stirred at RT. To it was added BOP (210 mg, 0.55 mmol). The mixture was stirred for overnight, quenched with TFA, and subjected to reverse phase preparative HPLC to isolate the title compound (44 mg). MS found for C28H32F2N6O2 as (M+H)⁺ 523.5. UV: λ=259 nm. ¹H NMR: (CD3OD) δ 8.17 (1H, s), 7.33 (2H, d, J=8.8 Hz), 7.26 (1H, m), 7.17 (1H, m), 7.14-7.07 (3H, m), 5.80 (1H, s), 4.68 (1H, m), 4.55 (2H, s), 4.37 (1H, d, J=16.0 Hz), 4.27 (1H, d, J=16.0 Hz), 3.81 (1H, m), 3.27 (1H, m), 2.97 (6H, s), 2.92-2.83 (2H, m), 1.95 (2H, m), 1.71 (2H, m) ppm.

Example 522

Preparation of (S)-4-(2,3-difluorobenzylamino)-6-(4-(1-(1-methylpyrrolidine-2-carbonyl)piperidin-4-yl)phenylamino)nicotinamide

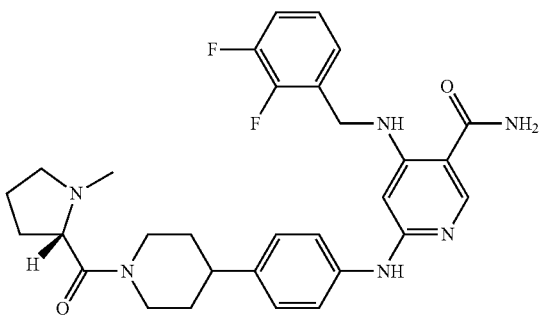 [SMILES: CN1CCC[C@H]1C(=O)N1CCC(c2ccc(Nc3cc(NCc4cccc(F)c4F)c(C(N)=O)cn3)cc2)CC1]

The mixture of compound 4-(2,3-difluorobenzylamino)-6-(4-(piperidin-4-yl)phenylamino)nicotinamide (Example 209) (50 mg, 0.11 mmol), N-methyl-L-proline monohydrate (33 mg, 0.22 mmol), DIEA (180 µL, 1.1 mmol) in 4 mL NMP was stirred at RT. To it was added BOP (210 mg, 0.55 mmol). The mixture was stirred for overnight, quenched with TFA, and subjected to reverse phase preparative HPLC to isolate the title compound (39 mg). MS found for C30H34F2N6O2 as (M+H)⁺ 549.5. UV: λ=259 nm. ¹H NMR (a pair of rotomers): (CD3OD) δ 8.18 (1H, s), 7.32 (with 7.33, 2H, d, J=8.4 Hz), 7.25 (1H, m), 7.17 (1H, m), 7.13-7.07 (3H, m), 5.77 (with 5.79, 1H, s), 4.68 (2H, m), 4.57 (1H, m), 4.54 (2H, s), 3.90 (1H, m), 3.74 (1H, m), 3.27 (1H, m), 2.93 (with 2.97, 3H, s), 2.90 (2H, m), 2.68 (1H, m), 2.25 (1H, m), 2.11-1.95 (4H, m), 1.82-1.63 (2H, m) ppm.

Example 523

Preparation of (S)-6-(4-(1-(1-acetylpyrrolidine-2-carbonyl)piperidin-4-yl)phenylamino)-4-(2,3-difluorobenzylamino)nicotinamide

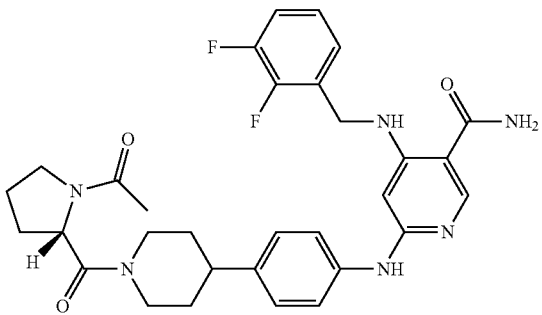 [SMILES: CC(=O)N1CCC[C@H]1C(=O)N1CCC(c2ccc(Nc3cc(NCc4cccc(F)c4F)c(C(N)=O)cn3)cc2)CC1]

The mixture of compound 4-(2,3-difluorobenzylamino)-6-(4-(piperidin-4-yl)phenylamino)nicotinamide (Example 209) (50 mg, 0.11 mmol), (S)-acetyl-pyrrolidine-2-carboxylic acid (35 mg, 0.22 mmol), DIEA (180 µL, 1.1 mmol) in 4 mL NMP was stirred at RT. To it was added BOP (210 mg, 0.55 mmol). The mixture was stirred for overnight, quenched with TFA, and subjected to reverse phase preparative HPLC to isolate the title compound (64 mg). MS found for C31H34F2N6O3 as (M+H)⁺ 577.5. UV: λ=259 nm. ¹H NMR (a pair of rotomers): (CD3OD) δ 8.13 (with 8.15, 1H, s), 7.36 (with 7.32, 2H, d, J=8.8 Hz), 7.25 (1H, m), 7.16 (1H, m), 7.13-7.07 (3H, m), 5.83 (with 5.79, 1H, s), 4.95 (1H, m), 4.65 (1H, m), 4.56 (with 4.55, 2H, s), 4.20 (1H, m), 3.66 (2H, m), 3.30 (1H, m), 2.92 (1H, m), 2.79 (1H, m), 2.27 (1H, m), 2.12 (with 2.10, 3H, s), 2.07-1.85 (5H, m), 1.68 (2H, m) ppm.

Example 524

Preparation of (R)-4-(2,3-difluorobenzylamino)-6-(4-(1-(1-methylpyrrolidine-2-carbonyl)piperidin-4-yl)phenylamino)nicotinamide

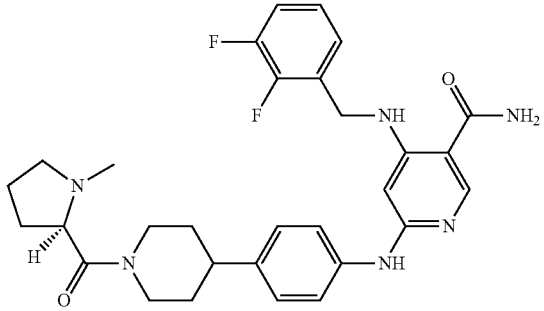 [SMILES: CN1CCC[C@@H]1C(=O)N1CCC(c2ccc(Nc3cc(NCc4cccc(F)c4F)c(C(N)=O)cn3)cc2)CC1]

The mixture of compound 4-(2,3-difluorobenzylamino)-6-(4-(piperidin-4-yl)phenylamino)nicotinamide (Example 209) (50 mg, 0.11 mmol), N-methyl-D-proline monohydrate (33 mg, 0.22 mmol), DIEA (180 µL, 1.1 mmol) in 4 mL NMP was stirred at RT. To it was added BOP (210 mg, 0.55 mmol). The mixture was stirred for overnight, quenched with TFA, and subjected to reverse phase preparative HPLC to isolate the title compound (32 mg). MS found for C30H34F2N6O2 as (M+H)⁺ 549.5. UV: =259 nm. ¹H NMR (a pair of rotomers): (CD3OD) δ 8.18 (1H, s), 7.32 (with 7.33, 2H, d, J=8.4 Hz), 7.25 (1H, m), 7.17 (1H, m), 7.13-7.07 (3H, m), 5.77 (with 5.79, 1H, s), 4.68 (2H, m), 4.57 (1H, m), 4.54 (2H, s), 3.90 (1H, m), 3.74 (1H, m), 3.27 (1H, m), 2.93 (with 2.97, 3H, s), 2.90 (2H, m), 2.68 (1H, m), 2.25 (1H, m), 2.11-1.95 (4H, m), 1.82-1.63 (2H, m) ppm.

Example 525

Preparation of (R)-6-(4-(1-(1-acetylpyrrolidine-2-carbonyl)piperidin-4-yl)phenylamino)-4-(2,3-difluorobenzylamino)nicotinamide

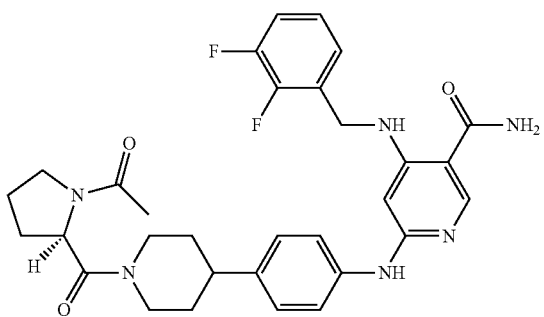 [SMILES: CC(=O)N1CCC[C@@H]1C(=O)N1CCC(c2ccc(Nc3cc(NCc4cccc(F)c4F)c(C(N)=O)cn3)cc2)CC1]

The mixture of compound 4-(2,3-difluorobenzylamino)-6-(4-(piperidin-4-yl)phenylamino)nicotinamide (Example 209) (50 mg, 0.11 mmol), (R)-acetyl-pyrrolidine-2-carboxylic acid (35 mg, 0.22 mmol), DIEA (180 μL, 1.1 mmol) in 4 mL NMP was stirred at RT. To it was added BOP (210 mg, 0.55 mmol). The mixture was stirred for overnight, quenched with TFA, and subjected to reverse phase preparative HPLC to isolate the title compound (65 mg). MS found for C31H34F2N6O3 as (M+H)+ 577.5. UV: λ=259 nm. 1H NMR (a pair of rotomers): (CD3OD) δ 8.13 (with 8.15, 1H, s), 7.36 (with 7.32, 2H, d, J=8.8 Hz), 7.25 (1H, m), 7.16 (1H, m), 7.13-7.07 (3H, m), 5.83 (with 5.79, 1H, s), 4.95 (1H, m), 4.65 (1H, m), 4.56 (with 4.55, 2H, s), 4.20 (1H, m), 3.66 (2H, m), 3.30 (1H, m), 2.92 (1H, m), 2.79 (1H, m), 2.27 (1H, m), 2.12 (with 2.10, 3H, s), 2.07-1.85 (5H, m), 1.68 (2H, m) ppm.

Example 526

Preparation of 4-(2,3-difluorobenzylamino)-6-(4-(1-(pyridin-2-yl)azetidin-3-yl)phenylamino)nicotinamide

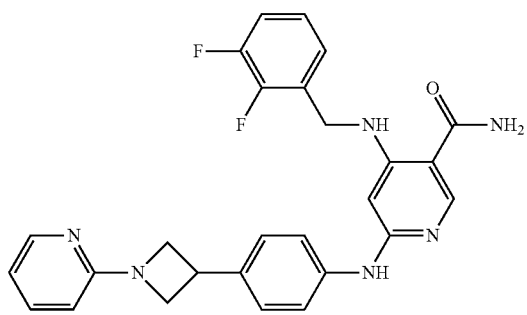 [SMILES: NC(=O)c1cnc(Nc2ccc(C3CN(c4ccccn4)C3)cc2)cc1NCc1cccc(F)c1F]

The title compound was synthesized using a procedure similar to that described in Example 527. MS found for C27H24F2N6O as (M+H)+ 487.4. UV: λ=249, 306 nm. 1H NMR: (CD3OD) δ 8.21 (1H, s), 8.01 (1H, m), 7.93 (1H, m), 7.53 (2H, dt, J=8.4; 2.0 Hz), 7.25-7.10 (5H, m), 6.98-6.95 (2H, m), 5.81 (1H, s), 4.78 (2H, t, J=8.0 Hz), 4.55 (2H, s), 4.39 (2H, m), 4.26 (1H, m) ppm.

Example 527

Preparation of 4-(2,3-difluorobenzylamino)-6-(4-(1-(pyridin-2-yl)piperidin-4-yl)phenylamino)nicotinamide

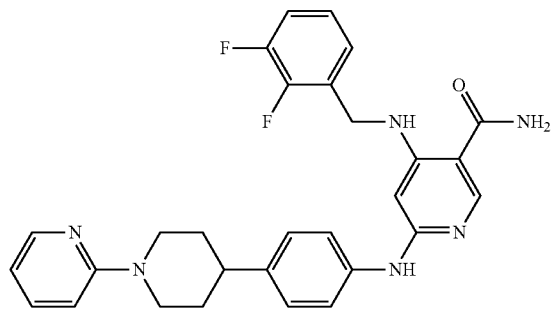 [SMILES: NC(=O)c1cnc(Nc2ccc(C3CCN(c4ccccn4)CC3)cc2)cc1NCc1cccc(F)c1F]

The mixture of 4-(2,3-difluorobenzylamino)-6-(4-(piperidin-4-yl)phenylamino)nicotinamide (Example 209) (55 mg, 0.11 mmol), DIEA (0.1 mL, 0.55 mmol), 2-fluoropyridine (110 mg, 1.10 mmol) in 3 mL NMP was stirred in a sealed tube at 125° C. for 1 day. It was acidified with TFA and subjected to reverse phase preparative HPLC to isolate the title compound. MS found for C29H28F2N6O as (M+H)+ 515.4. UV: λ=249, 306 nm. 1H NMR: (CD3OD) δ 8.17 (1H, s), 8.00-7.94 (2H, m), 7.39 (1H, d, J=9.2 Hz), 7.36 (2H, dt, J=8.0; 2.0 Hz), 7.25 (1H, m), 7.18 (1H, m), 7.14-7.07 (3H, m), 6.94 (1H, t, J=7.2 Hz), 5.79 (1H, s), 4.55 (2H, s), 4.36 (2H, m), 3.38 (2H, m), 3.03 (1H, m), 2.08 (2H, m), 1.87 (2H, m) ppm.

Example 528

Preparation of 4-((1H-indol-4-yl)methylamino)-6-(4-(1-(pyridin-2-yl)piperidin-4-yl)phenylamino)nicotinamide

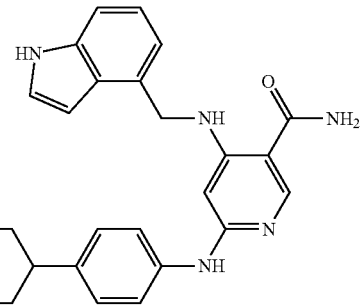

The title compound was synthesized using a procedure similar to that described in Example 527. MS found for C31H31N7O as (M+H)+ 518.5. UV: λ=254 nm. 1H NMR: (CD3OD) δ 10.64 (1H, s), 8.04 (1H, s), 7.89 (1H, d, J=5.6 Hz), 7.83 (1H, m), 7.29 (1H, d, J=8.4 Hz), 7.23 (1H, m), 7.15 (1H, m), 7.10 (2H, d, J=8.0 Hz), 6.99 (1H, t, J=8.0 Hz), 6.85 (2H, d, J=8.4 Hz), 6.81 (1H, m), 6.77 (1H, d, J=7.6 Hz), 6.41 (1H, m), 5.84 (1H, s), 4.62 (2H, s), 4.26 (2H, m), 3.34 (2H, m), 2.85 (1H, m), 1.93 (2H, m), 1.71 (2H, m) ppm.

Example 529

Preparation of 4-(2,3-difluorobenzylamino)-6-(4-(1-(pyridin-3-yl)piperidin-4-yl)phenylamino)nicotinamide

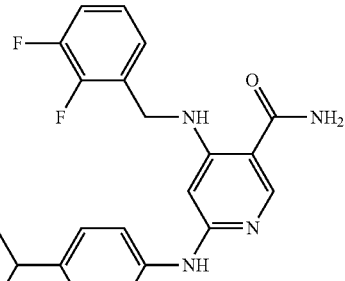

The mixture of 4-(2,3-difluorobenzylamino)-6-(4-(piperidin-4-yl)phenylamino)nicotinamide (Example 209) (100 mg, 0.21 mmol), 3-pyridineboronic acid (265 mg, 2.10 mmol), Cu(OAc)$_2$ powder (190 mg, 1.05 mmol) in 5 mL DCM and 1 mL pyridine was stirred at RT for 2 days. It was diluted with methanol and filtered through celite. The filtrate was treated with TFA and concentrated in vacuo. The residue was subjected to reverse phase HPLC to isolate the title compound. MS found for C29H28F2N6O as (M+H)$^+$ 515.5. UV: λ=268 nm. $^1$H NMR: (CD3OD) δ 8.41 (1H, m), 8.16 (1H, s), 8.09 (1H, s), 8.06 (1H, s), 7.81 (1H, m), 7.35 (2H, dt, J=8.4; 2.0 Hz), 7.24 (1H, m), 7.16 (1H, m), 7.12-7.07 (3H, m), 5.79 (1H, s), 4.55 (2H, s), 4.12 (2H, m), 3.13 (2H, m), 2.91 (1H, m), 2.04 (2H, m), 1.87 (2H, m) ppm.

Example 530

Preparation of 4-(2,3-difluorobenzylamino)-6-(4-(1-phenylpiperidin-4-yl)phenylamino)nicotinamide

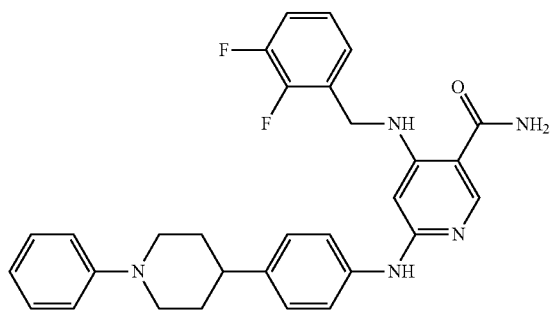 [SMILES: NC(=O)c1cnc(Nc2ccc(C3CCN(c4ccccc4)CC3)cc2)cc1NCc1cccc(F)c1F]

The title compound was synthesized using a procedure similar to that described in Example 529. MS found for C30H29F2N5O as (M+H)$^+$ 514.5. UV: λ=259 nm. $^1$H NMR: (CD3OD) δ 8.05 (1H, s), 7.36 (1H, m), 7.29-7.00 (10H, m), 6.84 (1H, m), 5.73 (1H, s), 4.47 (2H, s), 3.71 (2H, m), 3.03 (2H, m), 2.85 (1H, m), 2.06-1.89 (4H, m) ppm.

Example 531

Preparation of 6-(4-(1-(2-cyanoacetyl)piperidin-4-yl)phenylamino)-4-(2,3-difluorobenzylamino)nicotinamide

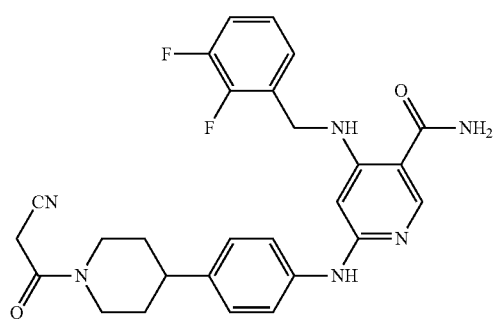 [SMILES: N#CCC(=O)N1CCC(c2ccc(Nc3cc(NCc4cccc(F)c4F)c(C(N)=O)cn3)cc2)CC1]

The mixture of 4-(2,3-difluorobenzylamino)-6-(4-(piperidin-4-yl)phenylamino)nicotinamide (Example 209) (90 mg, 0.19 mmol), cyanoacetic acid (81 mg, 0.95 mmol), DIEA (330 µL, 1.9 mmol) in 4 mL NMP was stirred at RT. To it was added BOP (360 mg, 0.95 mmol). The mixture was stirred at RT for overnight. To it was added TFA (0.5 mL). The mixture was subjected to reverse phase preparative HPLC to isolate the title compound (81 mg). MS found for C27H26F2N6O2 as (M+H)$^+$ 505.4. UV: λ=259 nm. $^1$H NMR: (CD3OD) δ 8.05 (1H, s), 7.24 (2H, d, J=8.4 Hz), 7.15 (1H, m), 7.06 (1H, m), 7.04-6.97 (3H, m), 5.71 (1H, s), 4.56 (1H, m), 4.46 (2H, s), 3.91-3.77 (3H, m), 3.16 (1H, m), 2.83-2.69 (2H, m), 1.84 (2H, m), 1.60 (2H, m) ppm.

Example 532

Preparation of 4-(2,3-difluorobenzylamino)-6-(4-(1-(2-morpholinoacetyl)piperidin-4-yl)phenylamino)nicotinamide

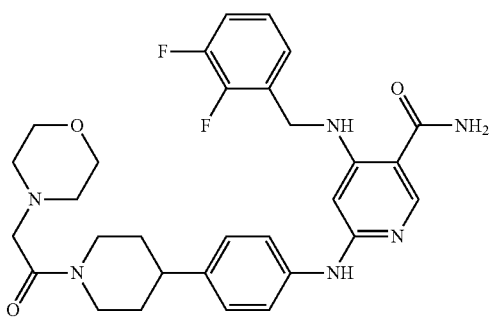 [SMILES: NC(=O)c1cnc(Nc2ccc(C3CCN(C(=O)CN4CCOCC4)CC3)cc2)cc1NCc1cccc(F)c1F]

The mixture of 4-(2,3-difluorobenzylamino)-6-(4-(piperidin-4-yl)phenylamino)nicotinamide (Example 209) (80 mg, 0.17 mmol), 4-morphonlineacetic acid (100 mg, 0.68 mmol), DIEA (240 µL, 1.36 mmol) in 4 mL NMP was stirred at RT. To it was added BOP (260 mg, 0.68 mmol). The mixture was stirred at RT for overnight. To it was added TFA (0.5 mL). The mixture was subjected to reverse phase preparative HPLC to isolate the title compound (59 mg). MS found for C30H34F2N6O3 as (M+H)$^+$ 565.5. UV: λ=259 nm. $^1$H NMR: (CD3OD) δ 8.17 (1H, s), 7.33 (2H, d, J=8.0 Hz), 7.26 (1H, m), 7.16 (1H, m), 7.13-7.07 (3H, m), 5.79 (1H, s), 4.68 (2H, m), 4.55 (2H, s), 4.41-4.27 (2H, m), 3.96 (4H, m), 3.84 (2H, m), 2.95-2.82 (3H, m), 1.96 (2H, m), 1.70 (2H, m) ppm.

Example 533

Preparation of 4-(2,3-difluorobenzylamino)-6-(4-(1-(2-(piperidin-1-yl)acetyl)piperidin-4-yl)phenylamino)nicotinamide

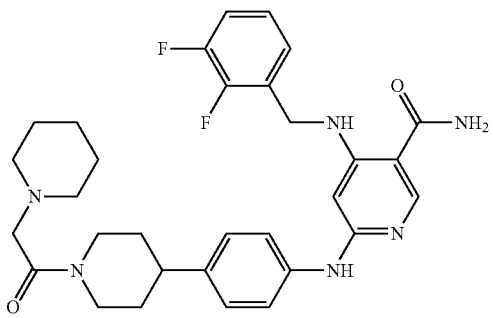 [SMILES: NC(=O)c1cnc(Nc2ccc(C3CCN(C(=O)CN4CCCCC4)CC3)cc2)cc1NCc1cccc(F)c1F]

The mixture of 4-(2,3-difluorobenzylamino)-6-(4-(piperidin-4-yl)phenylamino)nicotinamide (Example 209) (80 mg, 0.17 mmol), 4-morphonlineacetic acid (100 mg, 0.68 mmol), DIEA (240 µL, 1.36 mmol) in 4 mL NMP was stirred at RT. To it was added BOP (260 mg, 0.68 mmol). The mixture was stirred at RT for overnight. To it was added TFA (0.5 mL). The mixture was subjected to reverse phase preparative HPLC to isolate the title compound (70 mg). MS found for C31H36F2N6O2 as (M+H)$^+$ 563.5. UV: $\lambda$=259 nm. $^1$H NMR: (CD3OD) $\delta$ 8.18 (1H, s), 7.34-7.11 (7H, m), 5.80 (1H, s), 4.55 (2H, s), 4.35-4.26 (4H, m), 3.83 (2H, m), 3.60 (2H, m), 3.05 (2H, m), 2.89 (1H, m), 1.95-1.57 (10H, m) ppm.

Example 534

This example illustrates methods for evaluating the compounds of the invention, along with results obtained for such assays. The in vitro and in vivo human Syk activities of the inventive compounds can be determined by various procedures known in the art, such as a test for their ability to inhibit the activity of human plasma Syk. The potent affinities for human Syk inhibition exhibited by the inventive compounds can be measured by an $IC_{50}$ value (in nM). The $IC_{50}$ value is the concentration (in nM) of the compound required to provide 50% inhibition of human Syk proteolytic activity. The smaller the $IC_{50}$ value, the more active (potent) is a compound for inhibiting Syk activity.

An in vitro assay for detecting and measuring inhibition activity against Syk is as follows:

Inhibition of Syk Tyrosine Phosphorylation Activity

Potency of candidate molecules for inhibiting Syk tyrosine phosphorylation activity is assessed by measuring the ability of a test compound to inhibit Syk-mediated tyrosine phosphorylation of a Syk-specific substrate.

SYK tyrosine phosphorylation activity is measured using the LANCE™ Technology developed by Perkin Elmer Life and Analytical Sciences (Boston, Mass.). LANCE™ refers to homogeneous time resolved fluorometry applications using techniques such as time-resolved fluorescence resonance energy transfer assay (TR-FRET) (see generally for procedures in Perkin Elmer Application Note—How to Optimize a Tyrosine Kinase Assay Using Time Resolved Fluorescence-Based LANCE Detection, wwww.perkinelmer.com/lifesciences). The assay principle involves detection of a phosphorylated substrate using energy transfer from a phosphospecific europium-labeled antibody to streptavidin-allophycocyanin as an acceptor.

To test the ability of candidate molecules to inhibit SYK tyrosine phosphorylation activity, molecules are reconstituted in 30% DMSO and serially diluted 1:3 with the final dilution containing DMSO in the absence of the candidate molecule. The final DMSO concentration in the assay is 3%. Kinase assays are performed as a two part reaction. The first reaction is a kinase reaction and which comprises of a candidate molecule, full length active recombinant SYK enzyme (Millipore, Calif.) and biotin-labeled SYK-specific substrate biotin-DEEDYESP-OH. The second reaction involves termination of the kinase reaction and the simultaneous addition of the detection reagents-europium-labeled anti-phosphotyrosine reagent (Eu-W1024-PY100, Perkin Elmer, Boston, Mass.) and Streptavidin-Allophycocyanin detection reagent (SA-APC, Prozyme, Calif.). The kinase reaction is performed in a black U-bottom 96-well microtitre plate. The final reaction volume is 50 µL and contains a final concentration of 1 nM active SYK enzyme, 550 nM SYK-substrate, and 100 µM ATP diluted in a buffer containing 50 mM Tris pH 7.5, 5 mM $MgCl_2$, and 1 mM DTT. The reaction is allowed to proceed for 1 hour at room temperature. The quench buffer contains 100 mM Tris pH 7.5, 300 mM $NaCl_2$, 20 mM EDTA, 0.02% Brij35, and 0.5% BSA. The detection reagents are added to the reaction mixture at the following dilutions-1:500 for Eu-W1024-PY100 and 1:250 for SA-APC. The kinase reaction is terminated by the addition of 50 µL quench buffer containing the detection reagents. The detection is allowed to proceed for 1 hr at room temperature. Detection of the phosphorylated substrate in the absence and presence of inhibitors is measured in the TR-FRET instrument, Analyst HT (Molecular Probes, Sunnyvale, Calif.) and the condition for measurements are set up using CriterionHost Release 2.0 (Molecular Probes, Sunnyvale, Calif.). The settings used are a follows: excitation 360 nm, emission 665-7.5 nm, beam splitter 350 nm 50/50, flash 100 pulses, delay 60 us, integration 400 us, z-height 2 mm. Inhibition of SYK-tyrosine kinase activity is calculated as the maximum response observed in the presence of inhibitor, compared to that in the absence of inhibitor. $IC_{50}$s were derived by non-linear regression analysis.

Intracellular phospho-flow cytometry was used to test compound inhibition of Syk activity in intact non-Hodgkin's lymphoma cell lines Ramos. $10 \times 10^6$ cells in log phase growth were aliquoted; Syk kinase is activated by incubating cells for 10 minutes with 3 µg/ml antibody specific to the B cell receptor. Directly following, cells are fixed in 1% paraformaldehyde for 5 minutes at room temperature, washed in phosphate buffered saline, and then permeabalized by incubation for 2 hours in ice cold methanol. Cells are again washed in phosphate buffered saline, then incubated for 30 minutes with antibody specific for phosphorylated Erk (Y204) which are indicators of Syk kinase activity. All antibodies used are purchased from BD Pharmingen (San Jose, Calif.). After incubation with antibodies, cells are again washed and subjected to flow cytometry.

The anti-proliferative effects of compounds on non-Hodgkin's lymphoma B cell lines SUDHL-4, SUDHL-6, and Toledo was also assessed. SUDHL-4 and SUDHL-6 require B cell receptor signaling for growth and survival, while the Toledo cell line (serving here as a negative control) does not. Cells were aliquoted into each well of a 96-well plate and incubated with increasing concentrations of compound for 72 hours, after which cell survival and proliferation was determined using the MTT assay (Chemicon International, Inc., Temecula, Calif.) following protocols supplied by the manufacturer. Data are detailed in the Tables and Figures herein as $IC_{50}$ values plus or minus standard deviations from 5 or 6 independent experiments.

Induction of apoptosis in non-Hodgkin's lymphoma B cell lines SUDHL-4, SUDHL-6, and Toledo was assessed by measuring the apoptosis marker Caspase 3. Cells were incubated with 1, 3, or 10 µM compound for 24, 48, and 72 hours. At the conclusion of each time point, cells were processed for flow cytometry analysis using the Monoclonal Rabbit Anti-Active Caspase-3 Antibody Kit and related protocols (BD Pharmingen). Data from two independent experiments are presented in Table 1, representing the percent of total cells undergoing apoptosis following incubation with compounds under the indicated conditions.

Syk activity is not only required for B cell signaling, proliferation, and survival, as shown, but is also critical for cellular activation upon cross-linking of the B cell receptor. B cell activation leads to increased cell surface expression of several proteins involved in cell signaling, antigen presentation, and adhesion. Among these, CD80, CD86, and CD69 are commonly measured to determine B cell activation status. Therefore, primary mouse B cells isolated from spleen were aliquoted and incubated with increasing concentrations of compound (0.05 to 2 µM) in the presence of goat anti-mouse IgD (eBiosciences, Inc., San Diego, Calif.) for 20 hours to cross-link the B cell receptor. Following, cells were washed and incubated for 30 minutes on ice with antibodies specific for the CD80, CD86, and CD69 B cell activation markers. B cells were identified from the pooled population by staining with the B cell marker CD45RO. All antibodies were purchased from BD Pharmingen. Table 1 depicts the $IC_{50}$ range in which these compounds inhibited B cell receptor induced activation of mouse primary B cells In the table below, activity in the Syk assays is provided as follows: +++++=$IC_{50}$<0.0010 µM; ++++=0.0010 µM<$IC_{50}$<0.010 µM, +++=0.010 µM<$IC_{50}$<0.10 µM, ++=0.10 µM<$IC_{50}$<1 µM, +=$IC_{50}$>1 µM.

Example 535

Kinase Assay Protocols

JAK and TYK2 tyrosine phosphorylation activity is measured using the Z'-LYTE™ Technology developed by Invitrogen Corporation (Carlsbad, Calif.). For JAK1, JAK2 and JAK3 the Z'-LYTE™ Kinase Assay Kit-Tyr6 Peptide (part number PV4122) was used. For TYK2 the Z'-LYTE™ Kinase Assay Kit-Tyr6 Peptide (part number PV3192) was used. The Z'-LYTE™ biochemical assay employs a fluorescence resonance energy transfer (FRET) coupled-enzyme format and is based on the differential sensitivity of phosphorylated and non-phosphorylated peptides to proteolitic cleavage. The assay uses a synthetic peptide substrate that is labelled with a donor fluorophore (coumarin) and an acceptor fluorophore (fluorescein) that make up a FRET pair. In the primary reaction (the Kinase Reaction), the kinase transfers the γ-phosphate of ATP to a single tyrosine residue on the substrate, while the presence of a kinase inhibitor in the primary reaction suppresses phosphorylation. In the secondary reaction (the Development Reaction), a site-specific protease (the Development Reagent) is added. The development buffer quenches the Kinase Reaction, while the protease recognizes and cleaves non-phosphorylated Z'-LYTE™ peptide substrate. Cleavage disrupts FRET between the donor and acceptor fluorophores on the non-phosphorylated substrate, while uncleaved, phosphorylated substrate maintains FRET.

To test the ability of candidate molecules to inhibit JAK tyrosine phosphorylation activity, molecules are reconstituted in 100% DMSO and serially diluted 1:10 in polypropylene v-bottom microtiter plates. The candidate molecules are then diluted 1:25 into kinase buffer and 2.5 µl transferred into duplicate wells of a 384 well low volume black microtiter assay plate (Corning, USA). The final DMSO concentration in the assay is 1%. The kinase reaction contains 2.5 µl of a candidate molecule, 5 µl of catalytic domain recombinant Kinase enzyme+Tyr peptide substrate (Invitrogen, CA) and 2.5 µl ATP (Invitrogen, CA). The kinase reaction is allowed to proceed for 1 hour at room temperature. The protease reaction is initiated by the addition of 5 µl Development Reagent (Invitrogen, CA). After 1 hour incubation at room temperature the fluorescence is measured using a FlexStation plate reader (Molecular Devices, Sunnyvale, Calif.). The reader settings used are as follows: Fluorescence mode, endpoint, top read, excitation 400 nm, emission 445 nm and 520 nm, Auto Cutoff 435 nm and 515 nm, PMT sensitivity high, 6 reads per well. Inhibition of JAK kinase activity is calculated as the percent phosphorylation of substrate in the presence of inhibitor compared to the percent phosphorylation of substrate in the absence of inhibitor. IC50's were derived using Xlfit 4.3 (IDBS, UK), 4 parameter logistic model 205: Y=(A+((B−A)/(1+((C/x)^D)))).

Inhibition of IL4-induced phospho STAT6 formation was measured by pre-incubating 0.5 million Ramos B lymphocytes (ATCC) with 5 µl compound or DMSO vehicle for 1 hour at 37° C./5% $CO_2$. Cells were activated by addition of 1 ng/ml [f] IL4 (R & D Research Systems) for 10 min at 37° C./5% $CO_2$ and then fixed by addition of 1.6% [f] PFA (Electron Microscopy Services). Following a PBS wash step and permeabilization with 100% methanol, cells were incubated with ALEXA-conjugated anti-phosphoSTAT6 (Y641) antibody (BD 612600). The extent of cell associated-fluorescence was determined by flow cytometry and data expressed as mean fluorescent intensity. The extent of inhibition of the IL4-induced signal was then calculated.

In the table below, activity in the assays is provided as follows: +++++=$IC_{50}$<0.0010 µM; ++++=0.0010 µM<$IC_{50}$<0.010 µM, +++=0.010 µM<$IC_{50}$<0.10 µM, ++=0.10 µM<$IC_{50}$<1 µM, +=$IC_{50}$>1 µM, −−=Not given.

TABLE 1

Select data for Examples.

| Example | Syk | JAK1 | JAK2 | JAK3 | Tyk2 |
|---|---|---|---|---|---|
| 1 | + | ++ | ++ | ++ | -- |
| 2 | + | ++ | ++ | +++ | ++ |
| 3 | -- | ++ | +++ | +++ | ++ |
| 4 | -- | ++ | ++ | ++++ | ++ |
| 5 | -- | ++ | ++ | ++++ | ++ |
| 6 | -- | ++ | ++ | ++++ | ++ |
| 7 | -- | ++ | ++ | ++++ | + |
| 8 | -- | ++ | ++ | ++++ | + |
| 9 | -- | + | + | +++ | + |
| 10 | -- | + | + | ++ | + |
| 11 | -- | + | + | +++ | + |
| 12 | -- | + | ++ | +++ | + |
| 13 | -- | + | + | ++ | + |
| 14 | -- | + | ++ | ++ | ++ |
| 15 | -- | -- | -- | -- | -- |
| 16 | -- | + | + | +++ | + |
| 17 | -- | + | + | ++ | + |
| 18 | -- | + | + | + | ++ |
| 19 | -- | + | + | + | + |
| 20 | -- | + | + | + | + |
| 22 | -- | + | + | ++ | + |
| 25 | -- | + | + | + | + |
| 26 | -- | + | + | + | + |
| 27 | -- | + | + | + | + |
| 21 | -- | + | + | + | + |
| 24 | -- | + | + | + | + |
| 23 | -- | + | + | + | + |
| 28 | -- | + | + | +++ | -- |
| 29 | -- | + | ++ | +++ | ++ |
| 30 | -- | + | + | + | -- |
| 31 | -- | ++ | ++ | ++++ | ++ |
| 32 | -- | + | + | ++ | -- |
| 33 | -- | + | + | + | -- |
| 34 | -- | + | + | + | -- |
| 35 | -- | + | + | + | -- |
| 36 | -- | + | + | + | -- |
| 37 | -- | + | + | + | -- |
| 38 | -- | + | + | ++ | -- |
| 39 | -- | ++ | ++ | ++++ | ++ |
| 40 | -- | ++ | ++ | ++++ | ++ |
| 41 | -- | ++ | ++ | +++ | +++ |
| 42 | -- | ++ | ++ | +++ | -- |
| 43 | -- | + | + | ++ | -- |
| 44 | -- | + | + | + | -- |
| 45 | -- | ++ | ++ | +++ | + |
| 46 | -- | ++ | ++ | ++++ | ++ |
| 47 | -- | + | + | ++ | -- |
| 48 | -- | ++ | ++ | +++ | -- |
| 49 | -- | + | + | ++ | -- |
| 50 | -- | + | + | + | -- |
| 51 | -- | + | + | ++ | -- |
| 52 | -- | + | + | ++ | -- |
| 53 | -- | + | + | ++ | -- |

TABLE 1-continued

Select data for Examples.

| Example | Syk | JAK1 | JAK2 | JAK3 | Tyk2 |
|---|---|---|---|---|---|
| 54 | -- | + | ++ | +++ | -- |
| 55 | -- | + | + | +++ | -- |
| 56 | -- | + | + | ++ | -- |
| 57 | -- | + | ++ | +++ | -- |
| 58 | -- | ++ | +++ | ++++ | + |
| 59 | -- | + | ++ | ++++ | + |
| 60 | -- | ++ | ++ | ++++ | + |
| 61 | -- | ++ | +++ | ++++ | ++ |
| 62 | -- | ++ | ++ | +++ | + |
| 63 | -- | ++ | ++ | ++++ | + |
| 64 | -- | ++ | +++ | ++++ | ++ |
| 65 | -- | ++ | +++ | ++++ | + |
| 66 | -- | ++ | ++ | ++++ | ++ |
| 67 | -- | ++ | +++ | ++++ | ++ |
| 68 | -- | + | ++ | +++ | -- |
| 69 | -- | + | ++ | +++ | -- |
| 70 | -- | ++ | +++ | ++++ | ++ |
| 71 | -- | ++ | ++ | ++++ | ++ |
| 72 | -- | ++ | ++ | ++++ | ++ |
| 73 | -- | ++ | +++ | ++++ | ++ |
| 74 | -- | + | ++ | +++ | ++ |
| 75 | -- | + | + | +++ | + |
| 76 | -- | + | + | +++ | -- |
| 77 | -- | + | + | ++ | + |
| 78 | -- | ++ | +++ | ++++ | ++ |
| 79 | -- | ++ | ++ | +++ | ++ |
| 80 | -- | + | ++ | +++ | + |
| 81 | -- | + | ++ | +++ | + |
| 82 | -- | ++ | ++ | +++ | -- |
| 83 | -- | ++ | ++ | +++ | -- |
| 84 | -- | + | ++ | +++ | -- |
| 85 | -- | + | + | +++ | -- |
| 86 | -- | + | + | +++ | -- |
| 87 | -- | + | + | ++ | -- |
| 88 | -- | + | + | +++ | -- |
| 89 | -- | + | + | ++ | -- |
| 90 | -- | + | + | +++ | -- |
| 91 | -- | + | ++ | +++ | -- |
| 92 | -- | ++ | +++ | ++++ | ++ |
| 93 | -- | +++ | +++ | ++++ | -- |
| 94 | -- | ++ | +++ | ++++ | ++ |
| 95 | -- | ++ | ++ | +++ | -- |
| 96 | -- | ++ | ++ | +++ | -- |
| 97 | -- | + | + | ++ | -- |
| 98 | -- | + | ++ | +++ | -- |
| 99 | -- | ++ | ++ | ++++ | -- |
| 101 | -- | + | + | +++ | -- |
| 102 | -- | ++ | +++ | ++++ | +++ |
| 103 | -- | -- | -- | -- | -- |
| 104 | -- | -- | -- | -- | -- |
| 105 | -- | +++ | +++ | ++++ | +++ |
| 106 | -- | ++ | ++ | ++++ | ++ |
| 107 | -- | ++ | ++ | ++++ | ++ |
| 108 | -- | ++ | +++ | ++++ | -- |
| 109 | -- | ++ | ++ | ++++ | ++ |
| 110 | -- | ++ | +++ | ++++ | -- |
| 111 | -- | + | + | +++ | -- |
| 112 | -- | + | + | +++ | -- |
| 113 | -- | + | + | +++ | -- |
| 114 | -- | + | ++ | +++ | -- |
| 115 | -- | ++ | ++ | +++ | ++ |
| 116 | -- | ++ | +++ | ++++ | ++ |
| 117 | -- | ++ | ++ | ++++ | ++ |
| 118 | -- | + | + | +++ | -- |
| 119 | -- | ++ | +++ | ++++ | ++ |
| 120 | -- | ++ | +++ | ++++ | -- |
| 121 | -- | ++ | ++ | +++ | -- |
| 122 | -- | ++ | ++ | ++++ | +++ |
| 123 | -- | ++ | ++ | +++ | -- |
| 124 | -- | + | ++ | +++ | -- |
| 125 | -- | + | ++ | +++ | -- |
| 126 | -- | + | ++ | ++++ | + |
| 127 | -- | + | ++ | +++ | -- |
| 128 | -- | + | + | +++ | -- |
| 129 | -- | + | ++ | +++ | -- |
| 130 | -- | ++ | +++ | ++++ | ++ |
| 131 | -- | + | + | ++ | -- |
| 132 | -- | + | ++ | +++ | -- |
| 133 | -- | + | ++ | +++ | -- |
| 134 | -- | + | + | +++ | -- |
| 135 | -- | + | + | ++ | -- |
| 136 | -- | + | + | +++ | -- |
| 139 | -- | + | + | ++ | -- |
| 140 | -- | + | ++ | ++ | -- |
| 141 | -- | + | ++ | +++ | -- |
| 142 | -- | + | ++ | +++ | -- |
| 143 | -- | + | + | +++ | + |
| 144 | -- | + | ++ | +++ | -- |
| 145 | -- | + | +++ | ++++ | -- |
| 146 | -- | + | ++ | ++ | -- |
| 147 | -- | ++ | ++ | +++ | -- |
| 148 | -- | + | ++ | ++ | -- |
| 149 | -- | ++ | +++ | ++++ | ++ |
| 150 | -- | ++ | ++ | ++ | -- |
| 151 | -- | ++ | ++ | ++ | -- |
| 152 | -- | ++ | +++ | ++++ | -- |
| 153 | -- | + | ++ | ++ | -- |
| 154 | -- | + | ++ | +++ | -- |
| 155 | -- | ++ | ++ | ++ | -- |
| 156 | -- | ++ | ++ | ++ | -- |
| 157 | -- | + | + | ++ | -- |
| 158 | -- | + | + | +++ | -- |
| 159 | -- | + | + | ++ | -- |
| 160 | -- | + | + | + | -- |
| 161 | -- | + | + | + | -- |
| 162 | -- | + | + | ++ | -- |
| 163 | -- | + | + | ++ | -- |
| 164 | -- | + | + | + | -- |
| 165 | -- | ++ | + | ++ | -- |
| 166 | -- | + | ++ | ++ | -- |
| 167 | -- | + | + | ++ | -- |
| 168 | -- | ++ | +++ | +++ | -- |
| 171 | -- | + | + | ++ | -- |
| 172 | -- | ++ | ++ | +++ | -- |
| 173 | -- | + | + | ++ | -- |
| 174 | -- | + | ++ | +++ | -- |
| 175 | -- | + | + | ++ | -- |
| 176 | -- | ++ | ++ | +++ | -- |
| 177 | -- | ++ | ++ | +++ | -- |
| 178 | -- | + | + | ++ | -- |
| 179 | -- | + | ++ | +++ | -- |
| 180 | -- | + | + | ++ | -- |
| 181 | -- | + | + | + | -- |
| 182 | -- | + | + | + | -- |
| 183 | -- | ++ | ++ | +++ | -- |
| 184 | -- | + | + | ++ | -- |
| 185 | -- | ++ | ++ | +++ | -- |
| 186 | -- | ++ | ++ | +++ | -- |
| 187 | -- | ++ | ++ | +++ | ++ |
| 188 | -- | ++ | +++ | ++++ | ++ |
| 189 | -- | +++ | +++ | ++++ | -- |
| 190 | -- | +++ | +++ | ++++ | -- |
| 191 | -- | + | + | ++ | -- |
| 192 | -- | + | ++ | +++ | -- |
| 193 | -- | + | ++ | +++ | ++ |
| 194 | -- | + | + | ++ | -- |
| 195 | -- | + | +++ | ++++ | + |
| 196 | -- | ++ | +++ | ++++ | ++ |
| 197 | -- | ++ | ++ | ++++ | ++ |
| 198 | -- | + | ++ | ++++ | ++ |
| 199 | -- | + | ++ | +++ | + |
| 200 | -- | +++ | +++ | ++++ | +++ |
| 201 | -- | + | + | + | -- |
| 202 | -- | ++ | ++ | +++ | -- |
| 203 | -- | ++ | +++ | ++++ | -- |
| 204 | -- | ++ | +++ | ++++ | -- |
| 205 | -- | ++ | +++ | ++++ | -- |
| 206 | -- | ++ | +++ | ++++ | -- |
| 207 | -- | ++ | +++ | ++++ | -- |
| 208 | -- | ++ | +++ | ++++ | -- |
| 209 | -- | ++ | +++ | ++++ | ++ |
| 210 | -- | +++ | +++ | ++++ | -- |

TABLE 1-continued

Select data for Examples.

| Example | Syk | JAK1 | JAK2 | JAK3 | Tyk2 |
|---|---|---|---|---|---|
| 211 | -- | + | ++ | ++++ | -- |
| 212 | -- | ++ | +++ | ++++ | -- |
| 213 | -- | ++ | +++ | ++++ | -- |
| 214 | -- | +++ | +++ | ++++ | -- |
| 215 | -- | + | ++ | +++ | -- |
| 216 | -- | + | + | +++ | -- |
| 217 | -- | ++ | +++ | ++++ | -- |
| 218 | -- | ++ | +++ | ++++ | -- |
| 219 | -- | -- | -- | -- | -- |
| 220 | -- | -- | -- | -- | -- |
| 221 | -- | -- | -- | -- | -- |
| 222 | -- | ++ | ++ | ++++ | +++ |
| 224 | -- | ++ | ++ | ++++ | -- |
| 228 | -- | ++ | ++ | ++++ | + |
| 229 | + | ++ | +++ | ++++ | ++ |
| 230 | + | + | ++ | ++++ | -- |
| 231 | + | + | ++ | ++++ | -- |
| 232 | -- | + | ++ | +++ | -- |
| 233 | -- | ++ | ++ | ++++ | ++ |
| 234 | -- | + | + | ++ | ++ |
| 235 | -- | ++ | ++ | +++ | +++ |
| 238 | -- | + | ++ | ++ | ++ |
| 239 | -- | ++ | ++ | +++ | +++ |
| 240 | -- | + | ++ | +++ | ++ |
| 241 | -- | + | ++ | +++ | + |
| 242 | -- | + | + | ++ | ++ |
| 243 | -- | ++ | ++ | +++ | +++ |
| 245 | -- | ++ | +++ | ++++ | +++ |
| 246 | -- | ++ | ++ | +++ | + |
| 247 | -- | ++ | ++ | +++ | ++ |
| 248 | -- | ++ | ++ | ++++ | ++ |
| 249 | -- | ++ | ++ | +++ | + |
| 250 | -- | + | ++ | ++++ | + |
| 251 | -- | + | ++ | +++ | + |
| 252 | -- | + | ++ | +++ | + |
| 253 | -- | + | ++ | ++ | ++ |
| 254 | -- | + | ++ | +++ | + |
| 255 | -- | + | ++ | +++ | ++ |
| 256 | -- | ++ | +++ | ++++ | ++ |
| 257 | -- | ++ | +++ | ++++ | ++ |
| 258 | -- | ++ | +++ | ++++ | ++ |
| 259 | -- | + | ++ | +++ | -- |
| 260 | -- | + | + | +++ | -- |
| 261 | -- | + | ++ | +++ | -- |
| 262 | -- | + | ++ | +++ | -- |
| 263 | -- | + | ++ | +++ | -- |
| 264 | -- | ++ | ++ | +++ | -- |
| 265 | -- | + | ++ | +++ | ++ |
| 266 | -- | + | + | +++ | -- |
| 267 | -- | + | ++ | +++ | -- |
| 268 | -- | ++ | ++ | +++ | -- |
| 269 | -- | ++ | ++ | +++ | -- |
| 270 | -- | ++ | + | ++ | -- |
| 271 | -- | + | + | +++ | -- |
| 272 | -- | + | + | +++ | -- |
| 273 | -- | + | ++ | +++ | -- |
| 274 | -- | + | + | ++ | -- |
| 275 | -- | + | + | ++ | -- |
| 276 | -- | ++ | ++ | +++ | -- |
| 277 | -- | + | + | +++ | -- |
| 278 | -- | + | + | ++ | -- |
| 279 | -- | + | + | +++ | -- |
| 280 | -- | + | ++ | +++ | -- |
| 281 | -- | ++ | ++ | +++ | -- |
| 282 | -- | + | + | +++ | -- |
| 283 | -- | + | +++ | ++++ | + |
| 284 | -- | ++ | ++ | +++ | + |
| 285 | -- | +++ | +++ | +++++ | ++ |
| 286 | -- | + | + | ++ | -- |
| 287 | -- | + | + | ++ | -- |
| 288 | -- | + | +++ | ++++ | -- |
| 289 | -- | + | ++ | +++ | -- |
| 290 | -- | + | + | ++ | -- |
| 291 | -- | + | + | ++ | -- |
| 292 | -- | + | + | ++ | -- |
| 293 | -- | ++ | ++ | +++ | -- |
| 294 | -- | +++ | +++ | ++++ | ++ |
| 295 | -- | ++++ | ++++ | +++++ | -- |
| 296 | -- | ++ | ++ | +++ | -- |
| 297 | -- | ++ | +++ | ++++ | ++ |
| 298 | -- | + | + | ++ | -- |
| 299 | -- | + | + | + | -- |
| 300 | -- | + | + | ++ | -- |
| 301 | -- | + | + | +++ | -- |
| 302 | -- | + | ++ | +++ | -- |
| 303 | -- | + | + | +++ | -- |
| 304 | -- | ++ | ++ | ++++ | -- |
| 305 | -- | + | + | ++ | -- |
| 306 | -- | ++ | ++ | +++ | -- |
| 307 | -- | + | ++ | +++ | -- |
| 308 | -- | + | + | +++ | -- |
| 309 | -- | + | ++ | +++ | -- |
| 310 | -- | + | + | ++ | -- |
| 311 | -- | ++ | ++ | +++ | -- |
| 312 | -- | ++ | ++ | ++++ | -- |
| 313 | -- | ++ | ++ | +++ | -- |
| 314 | -- | + | ++ | +++ | -- |
| 315 | -- | ++ | ++ | +++ | -- |
| 316 | -- | ++ | ++ | ++++ | -- |
| 317 | -- | + | + | ++ | -- |
| 318 | -- | + | ++ | +++ | -- |
| 319 | -- | ++ | ++ | ++++ | ++ |
| 320 | -- | +++ | +++ | ++++ | +++ |
| 321 | -- | ++ | ++ | +++ | + |
| 322 | -- | + | + | ++ | + |
| 323 | -- | + | + | ++ | -- |
| 324 | -- | ++ | ++ | ++++ | -- |
| 325 | -- | + | ++ | ++++ | -- |
| 326 | -- | ++ | ++ | ++++ | -- |
| 327 | -- | + | ++ | +++ | -- |
| 328 | -- | ++ | ++ | ++++ | -- |
| 329 | -- | ++ | ++ | ++++ | -- |
| 330 | -- | ++ | ++ | ++++ | -- |
| 331 | -- | ++ | ++ | ++++ | -- |
| 332 | -- | + | + | +++ | -- |
| 333 | -- | ++ | +++ | ++++ | -- |
| 334 | -- | ++ | ++ | +++ | -- |
| 335 | -- | ++ | ++ | +++ | -- |
| 336 | -- | ++ | ++ | ++++ | -- |
| 337 | -- | ++ | ++ | ++++ | -- |
| 338 | -- | ++ | ++ | ++++ | -- |
| 339 | -- | + | + | +++ | -- |
| 340 | -- | ++ | ++ | +++ | -- |
| 341 | -- | ++ | ++ | ++++ | -- |
| 342 | -- | ++ | ++ | ++++ | -- |
| 343 | -- | ++ | +++ | ++++ | -- |
| 344 | -- | ++ | +++ | ++++ | -- |
| 345 | -- | ++++ | ++++ | +++++ | -- |
| 346 | -- | +++ | +++ | +++++ | -- |
| 347 | -- | ++ | ++ | ++++ | -- |
| 348 | -- | ++++ | ++++ | +++++ | -- |
| 349 | -- | ++ | +++ | ++++ | -- |
| 350 | -- | +++ | +++ | +++++ | -- |
| 351 | -- | ++ | ++ | ++++ | -- |
| 352 | -- | +++ | +++ | ++++ | -- |
| 353 | -- | ++ | +++ | ++++ | -- |
| 354 | -- | ++ | +++ | ++++ | -- |
| 355 | -- | ++ | ++ | ++++ | -- |
| 357 | -- | -- | -- | -- | -- |
| 359 | -- | -- | -- | -- | -- |
| 361 | -- | + | + | ++ | -- |
| 362 | -- | + | + | +++ | -- |
| 363 | -- | + | ++ | +++ | + |
| 364 | -- | + | ++ | +++ | + |
| 365 | -- | + | + | +++ | + |
| 366 | -- | + | ++ | +++ | + |
| 367 | -- | + | ++ | +++ | + |
| 371 | -- | + | ++ | +++ | -- |
| 372 | -- | + | + | + | -- |
| 374 | -- | ++ | +++ | ++++ | -- |
| 375 | -- | + | + | +++ | -- |
| 376 | -- | + | + | ++ | -- |

TABLE 1-continued

Select data for Examples.

| Example | Syk | JAK1 | JAK2 | JAK3 | Tyk2 |
|---|---|---|---|---|---|
| 377 | -- | + | + | ++ | + |
| 378 | -- | + | + | + | -- |
| 379 | -- | + | + | +++ | -- |
| 380 | -- | + | ++ | +++ | -- |
| 381 | -- | + | + | + | -- |
| 383 | -- | ++ | ++ | +++ | -- |
| 384 | -- | ++ | ++ | ++++ | + |
| 385 | -- | + | + | +++ | -- |
| 386 | -- | ++ | ++ | ++++ | ++ |
| 387 | -- | ++ | ++ | ++++ | -- |
| 388 | -- | ++ | ++ | ++++ | ++ |
| 389 | -- | ++ | ++ | ++++ | ++ |
| 390 | -- | ++ | ++ | +++ | -- |
| 391 | -- | + | + | +++ | -- |
| 392 | -- | + | + | ++ | -- |
| 393 | -- | + | + | + | -- |
| 402 | -- | +++ | +++ | ++++ | -- |
| 412 | -- | ++ | ++ | ++++ | -- |
| 413 | -- | + | + | +++ | -- |
| 414 | -- | ++ | ++ | ++++ | -- |
| 415 | -- | + | + | +++ | -- |
| 416 | -- | + | + | ++++ | -- |
| 417 | -- | ++ | ++ | ++++ | -- |
| 418 | -- | ++ | ++ | ++++ | -- |
| 419 | -- | + | ++ | ++++ | -- |
| 420 | -- | + | + | ++++ | -- |
| 421 | -- | + | ++ | +++ | -- |
| 422 | -- | + | ++ | +++ | -- |
| 423 | -- | -- | -- | -- | -- |
| 424 | -- | -- | -- | -- | -- |
| 425 | -- | -- | -- | -- | -- |
| 426 | -- | -- | -- | -- | -- |
| 427 | -- | -- | -- | -- | -- |
| 428 | -- | + | ++ | ++++ | + |
| 429 | -- | ++ | ++ | ++++ | + |
| 430 | -- | ++ | ++ | ++++ | ++ |
| 431 | -- | + | ++ | ++++ | + |
| 432 | -- | + | ++ | +++ | + |
| 433 | -- | ++ | ++ | +++ | + |
| 434 | -- | + | ++ | +++ | -- |
| 435 | -- | ++ | +++ | ++++ | ++ |
| 436 | -- | + | ++ | ++++ | ++ |
| 437 | -- | + | ++ | ++++ | ++ |
| 438 | -- | ++ | +++ | ++++ | ++ |
| 439 | -- | ++ | ++ | +++ | -- |
| 440 | -- | ++ | ++ | +++ | -- |
| 441 | -- | + | ++ | +++ | -- |
| 442 | -- | + | ++ | +++ | -- |
| 443 | -- | + | ++ | ++++ | ++ |
| 444 | -- | + | + | ++ | -- |
| 445 | -- | + | ++ | ++ | -- |
| 446 | -- | ++ | +++ | ++++ | ++ |
| 447 | -- | ++ | +++ | ++++ | ++ |
| 448 | -- | ++ | +++ | ++++ | +++ |
| 449 | -- | ++ | ++ | ++++ | ++ |
| 450 | -- | ++ | ++ | ++++ | +++ |
| 451 | -- | ++ | +++ | ++++ | ++ |
| 452 | -- | ++ | +++ | ++++ | ++ |
| 453 | -- | ++ | +++ | ++++ | ++ |
| 454 | -- | ++ | +++ | +++++ | -- |
| 455 | -- | ++ | +++ | ++++ | -- |
| 456 | -- | ++ | +++ | +++++ | -- |
| 457 | -- | ++ | +++ | +++++ | ++ |
| 458 | -- | ++ | +++ | ++++ | +++ |
| 459 | -- | ++ | +++ | ++++ | -- |
| 460 | -- | ++++ | ++++ | +++++ | -- |
| 461 | -- | ++++ | +++++ | +++++ | ++++ |
| 462 | -- | ++++ | ++++ | +++++ | -- |
| 463 | -- | + | +++ | ++++ | -- |
| 464 | -- | + | +++ | ++++ | + |
| 465 | -- | + | ++ | ++++ | -- |
| 466 | -- | ++ | ++ | ++++ | -- |
| 467 | -- | ++ | ++ | +++ | -- |
| 468 | -- | ++ | +++ | ++++ | -- |
| 469 | -- | +++ | +++ | ++++ | -- |
| 470 | -- | + | ++ | +++ | -- |
| 471 | -- | +++ | +++ | ++++ | -- |
| 472 | -- | ++++ | +++ | +++++ | -- |
| 473 | -- | ++ | ++ | +++ | -- |
| 474 | -- | +++ | +++ | ++++ | -- |
| 475 | -- | +++ | +++ | ++++ | -- |
| 476 | -- | +++ | +++ | ++++ | -- |
| 477 | -- | + | ++ | +++ | -- |
| 478 | -- | + | ++ | ++ | -- |
| 479 | -- | ++ | ++ | +++ | -- |
| 480 | -- | + | ++ | +++ | -- |
| 481 | -- | ++ | ++ | +++ | -- |
| 482 | -- | + | + | +++ | -- |
| 483 | -- | + | ++ | +++ | -- |
| 484 | -- | ++ | ++ | ++++ | -- |
| 485 | -- | + | ++ | +++ | -- |
| 486 | -- | ++ | ++ | +++ | -- |
| 487 | -- | ++ | ++ | +++ | -- |
| 488 | -- | ++ | ++ | +++ | -- |
| 489 | -- | ++ | ++ | +++ | -- |
| 490 | -- | ++ | ++ | +++ | -- |
| 491 | -- | ++ | +++ | ++++ | -- |
| 492 | -- | +++ | ++++ | ++++ | -- |
| 493 | -- | ++ | ++ | +++ | -- |
| 494 | -- | ++++ | ++++ | +++++ | -- |
| 495 | -- | ++ | +++ | ++++ | -- |

Example 536

Cellular Assay Protocols

IL4 Stimulation of JAK1/3 Signaling to STAT6 in Ramos B Cells:

As an alternative strategy to measure effect of JAK3 inhibitors on JAK1/3 dependent cytokine signaling pathways, IL4 stimulation of the Ramos Burkett's B cell line is used. IL4 engages a receptor consisting of the IL4 receptor alpha chain and the common gamma chain. This initiates the activation of JAK 1 and JAK3 and leads to the phosphorylation of STAT6 at tyrosine position 641. Ramos B cells are suspended in tissue culture media containing 10% fetal calf serum at 10×10^6 cells/ml. 100 µl aliquots are pre-treated for 1 hour with various concentrations of compound, and then stimulated for 15 minutes with 15 ng IL4. The signaling reaction is terminated by fixing in 2% paraformaldehyde for 10 minutes at room temperature. Fixed cells are then washed and permeabalized by suspension in 100% methanol at −80° C. Following overnight incubation at 4° C., cells are washed and resuspended in PBS containing 0.5% bovine serum albumin containing pSTAT6 Y641-PE conjugated antibody. After 1 hour incubation, cells are washed and the extent of STAT6 phosphorylation in Ramos cells is measured by FACS analysis.

| Example | IL-4/STAT6 in Ramos Percent Inhibition at 0.2 uM | IL-4/STAT6 in Ramos Percent Inhibition at 1.0 uM |
|---|---|---|
| 2 | 29 | 77 |
| 3 | 22 | 43 |
| 4 | 32 | 68 |
| 5 | 37 | 61 |
| 6 | 39 | 65 |
| 7 | 10 | 40 |
| 8 | 8 | 30 |
| 9 | 3 | 12 |
| 10 | 6 | 20 |

| Example | IL-4/STAT6 in Ramos Percent Inhibition at 0.2 uM | IL-4/STAT6 in Ramos Percent Inhibition at 1.0 uM |
| --- | --- | --- |
| 11 | 11 | 15 |
| 12 | 15 | 11 |
| 16 | 17 | 46 |
| 31 | 27 | 50 |
| 39 | 47 | 52 |
| 40 | 46 | 69 |
| 41 | 31 | 59 |
| 46 | 54 | 80 |
| 58 | 33 | 60 |
| 59 | 11 | 27 |
| 60 | 22 | 40 |
| 61 | 40 | 60 |
| 62 | 29 | 42 |
| 63 | 32 | 46 |
| 64 | 32 | 50 |
| 65 | 28 | 49 |
| 66 | 21 | 35 |
| 67 | 48 | 69 |
| 68 |  | 7 |
| 69 | 16 | 40 |
| 70 | 23 | 45 |
| 71 | 22 | 37 |
| 72 | 27 | 54 |
| 73 | 23 | 53 |
| 74 | 21 | 43 |
| 75 | 11 | 26 |
| 76 | 8 | 20 |
| 78 |  | 14 |
| 79 | 20 | 43 |
| 80 | 23 | 43 |
| 81 | 29 | 48 |
| 82 | 7 | 34 |
| 83 | 10 | 23 |
| 84 | 3 | 8 |
| 91 | 6 | 16 |
| 92 | 41 | 67 |
| 93 | 43 | 76 |
| 94 | 35 | 62 |
| 105 | 53 | 88 |
| 106 | 28 | 49 |
| 107 | 43 | 73 |
| 108 | 14 | 37 |
| 109 | 23 | 60 |
| 110 | 24 | 68 |
| 111 | 22 | 46 |
| 112 | 8 | 42 |
| 114 | 14 | 51 |
| 115 | 31 | 64 |
| 116 | 25 | 43 |
| 117 | 43 | 67 |
| 119 | 17 | 47 |
| 122 | 34 | 57 |
| 228 | 24 | 48 |
| 229 | 38 | 67 |
| 230 | 21 | 36 |
| 231 | 13 | 16 |
| 232 | 4 | 5 |
| 233 | 17 | 33 |
| 240 |  | 8 |
| 241 |  | 2 |
| 245 | 14 | 38 |
| 246 | 6 | 11 |
| 247 | 6 | 24 |
| 248 | 24 | 50 |
| 249 | 23 | 32 |
| 250 | 11 | 26 |
| 251 | 17 | 51 |
| 255 | 11 | 18 |
| 256 | 37 | 64 |
| 257 | 34 | 65 |
| 258 | 39 | 63 |
| 428 | 33 | 46 |
| 429 | 19 | 33 |
| 430 | 15 | 36 |
| 431 | 7 | 24 |
| 432 | 16 | 17 |
| 433 | 18 | 27 |

IL2 Stimulation of JAK1/3 Signaling to STAT5 in Primary T Cells:

The effect of JAK inhibitors on cytokine signaling pathways utilizing JAK3 was determined using an IL2 stimulation assay. IL2 engages a receptor complex that contains the IL2 receptor alpha and beta subunits, and the common gamma chain, to initiate activation of JAK1 and JAK3 leading to phosphorylation of STAT5 at tyrosine position 694. Lymphocytes are isolated from heparinized whole blood over a ficoll gradient, then resuspended in tissue culture media containing 10% fetal calf serum at 10×10^6 cells/ml. 100 μl aliquots are pre-treated for 1 hour with various concentrations of compound, and then stimulated for 12 minutes with 100 U/ml IL2. The signaling reaction is terminated by fixing in 2% paraformaldehyde for 10 minutes at room temperature. Fixed cells are then washed and permeabalized by suspension in 50% methanol (in PBS) at −80° C. Following overnight incubation at 4° C., cells are washed and resuspended in PBS containing 0.5% bovine serum albumin containing CD3-APC and pSTAT5 Y694-PE conjugated antibodies. After 1 hour incubation, cells are washed and the extent of STAT5 phosphorylation in T cells is measured by FACS analysis.

| Example | IL-2/STAT5 Percent Inhibition at 0.2 uM | IL-2/STAT5 Percent Inhibition at 1.0 μM |
| --- | --- | --- |
| 7 | 29 | 74 |
| 39 | 37 | 65 |
| 45 | 22 | 25 |
| 59 | 12 | 50 |
| 61 | 39 | 67 |
| 67 | 61 | 89 |
| 79 | 53 | 73 |
| 105 | 72 | 99 |
| 107 | 58 | 82 |
| 119 | 54 | 83 |
| 200 | 77 | 103 |
| 209 | 70 | 99 |
| 249 | 12 | 29 |
| 250 | 18 | 50 |
| 256 | 69 | 100 |
| 283 | 42 | 65 |
| 284 | 39 | 75 |
| 285 | 58 | 96 |
| 294 | 75 | 102 |
| 319 | 81 | 103 |
| 320 | 90 | 108 |
| 321 | 42 | 94 |
| 322 | 27 | 70 |
| 333 | 35 | 84 |
| 385 | 37 | 62 |
| 388 | 18 | 55 |
| 389 | 56 | 88 |
| 412 | 25 | 59 |
| 428 | 56 | 84 |
| 429 | 60 | 77 |
| 435 | 63 | 102 |
| 457 | 56 | 100 |
| 458 | 49 | 104 |
| 461 | 94 | 101 |
| 464 | 22 | 55 |

The present invention provides a number of embodiments. It is apparent that the examples may be altered to provide other embodiments of this invention. Therefore, it will be appreciated that the scope of this invention is to be defined by the appended claims rather than by the specific embodiments, which have been represented by way of example.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety. From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the formula:

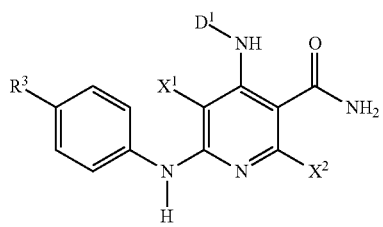

or a tautomer thereof or a pharmaceutically acceptable salt or hydrate thereof
wherein:
each $X^1$ or $X^2$ is independently H or halogen;
$D^1$ is selected from the group consisting of:
-$L^1$-phenyl, wherein the phenyl is further optionally substituted with from 1 to 3 substituents, $R^1$, independently selected from the group consisting of $C_{1-8}$alkyl, $C_{1-8}$alkoxy, halo, hydroxy, $C_{1-8}$alkylsulfonyl, $C_{3-8}$cycloalkylsulfonyl, $C_{1-8}$dialkylaminoaminocarbonyl, $C_{1-8}$alkylcarbonyl, $C_{1-8}$alkoxyC$_{1-8}$alkylcarbonyl, $C_{1-8}$alkoxycarbonyl, heterocyclyl, heterocyclyl$C_{1-8}$alkyl, heterocyclylcarbonyl, aryl and heteroaryl, wherein the aryl is further optionally substituted with halo;
$L^1$ is selected from the group consisting of a bond, —C(R)$_2$—, and CH$_2$CH$_2$;
each R is independently selected from the group consisting of hydrogen, $C_{1-8}$ alkyl, and alkoxyC$_{1-8}$ alkyl;
and wherein the moiety:

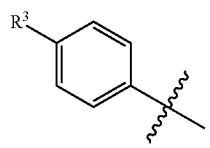

is selected from the group consisting of:

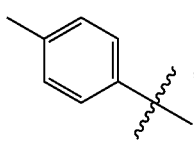 , 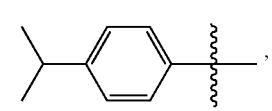 ,

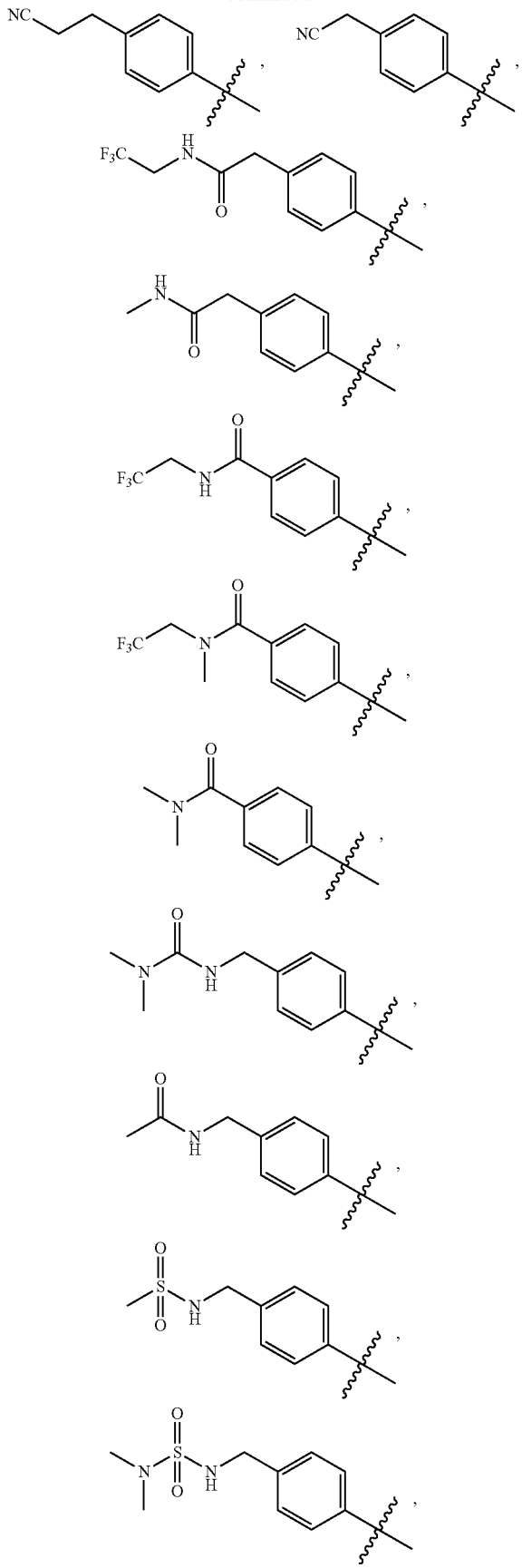

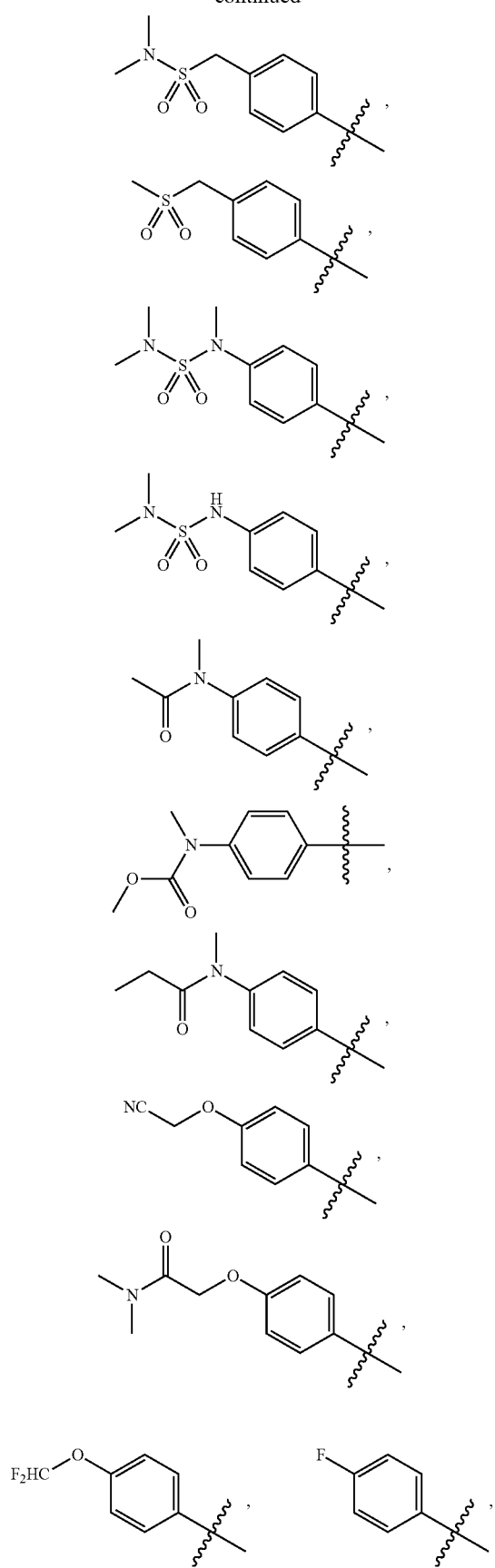
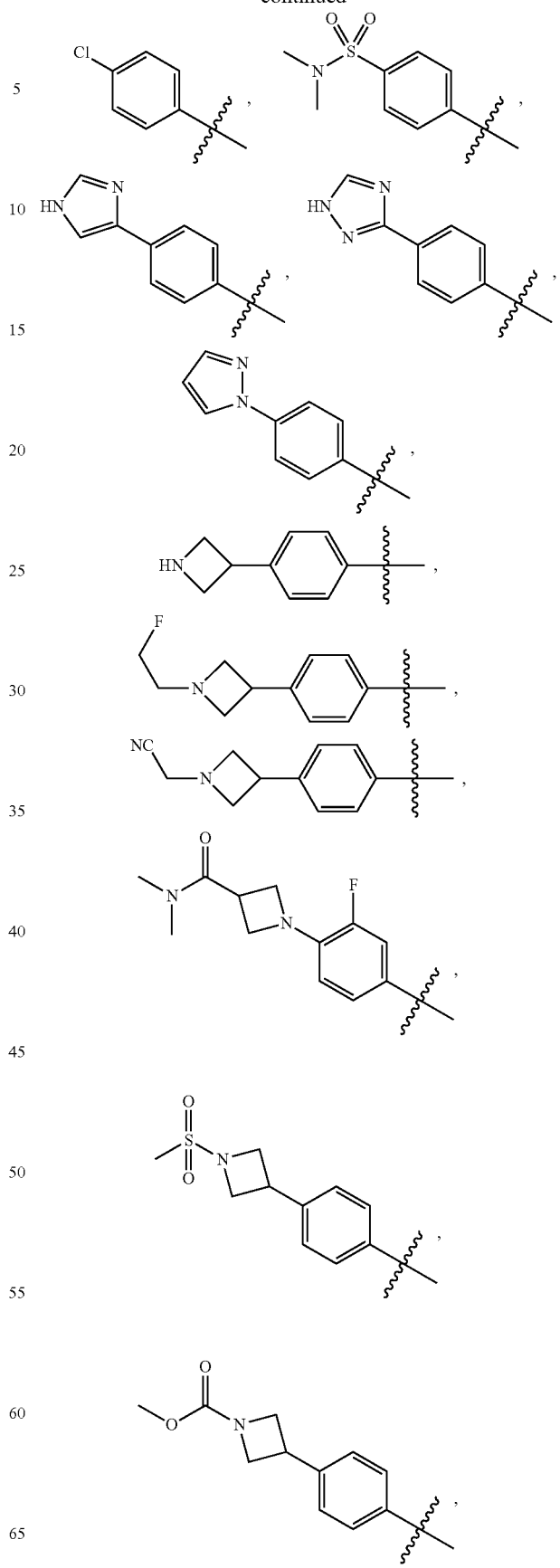

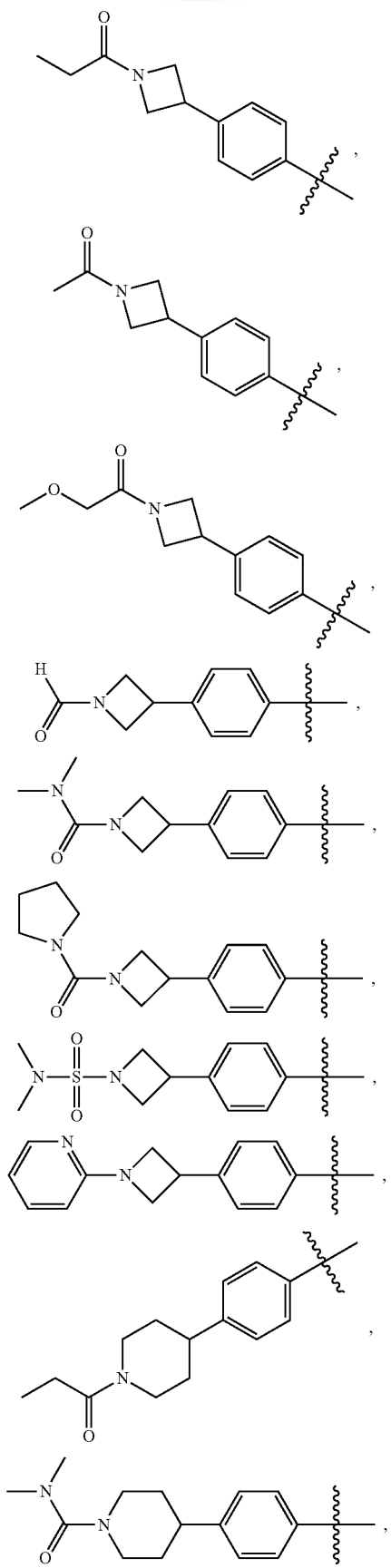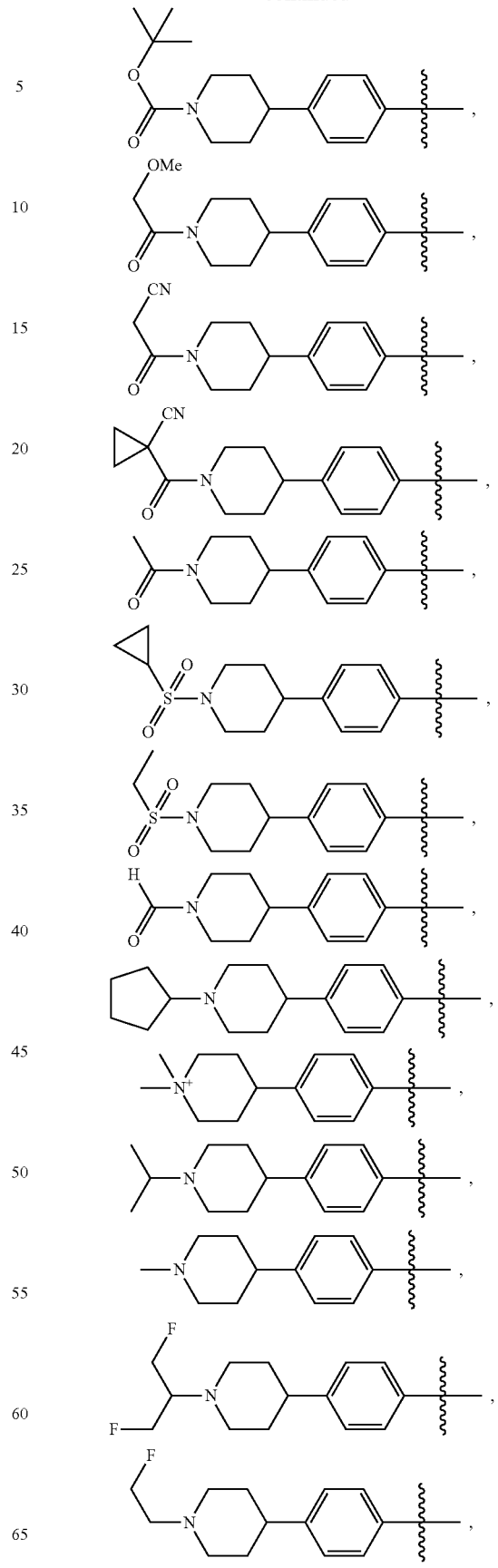

-continued
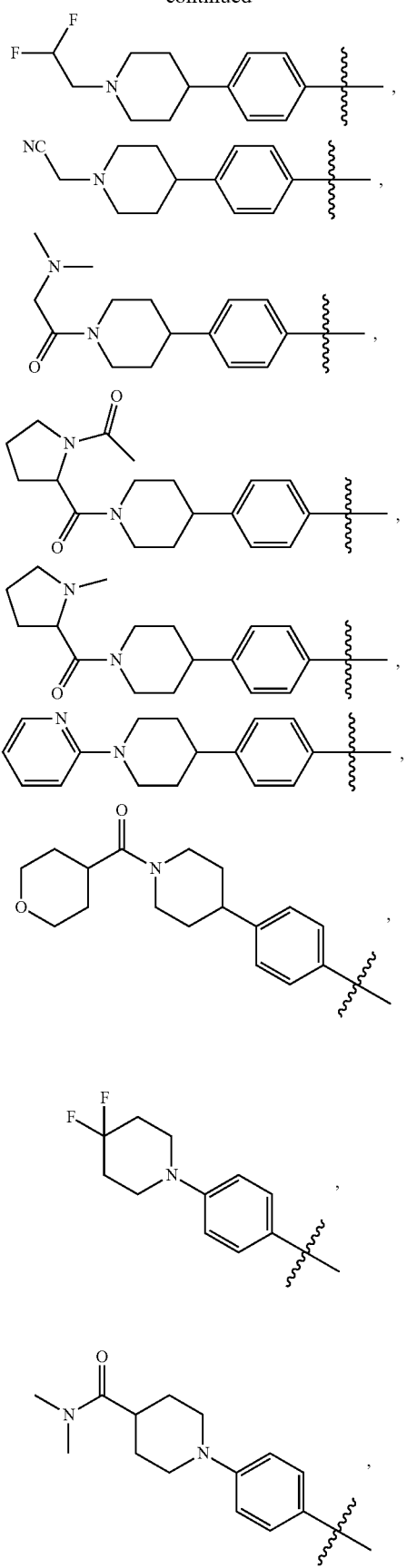
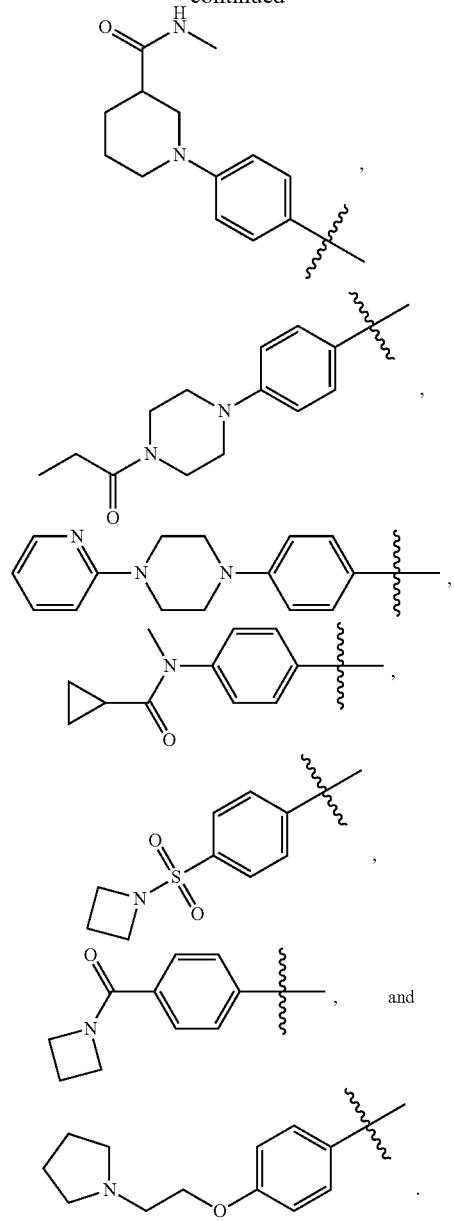
and the wavy line indicates the point of attachment to the rest of the molecule;
provided that when D¹ is 2,6-difluorobenzyl, then R³ is not 2-(pyrrolidin-1-yl)ethanoxy.
2. The compound of claim 1, wherein D¹ is selected from the group consisting of:
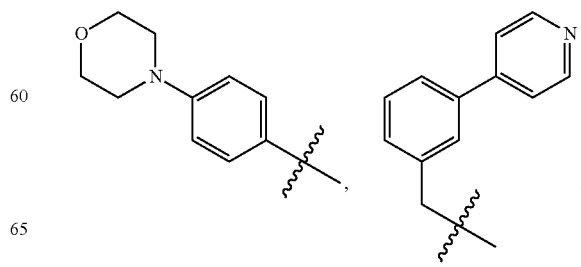

-continued

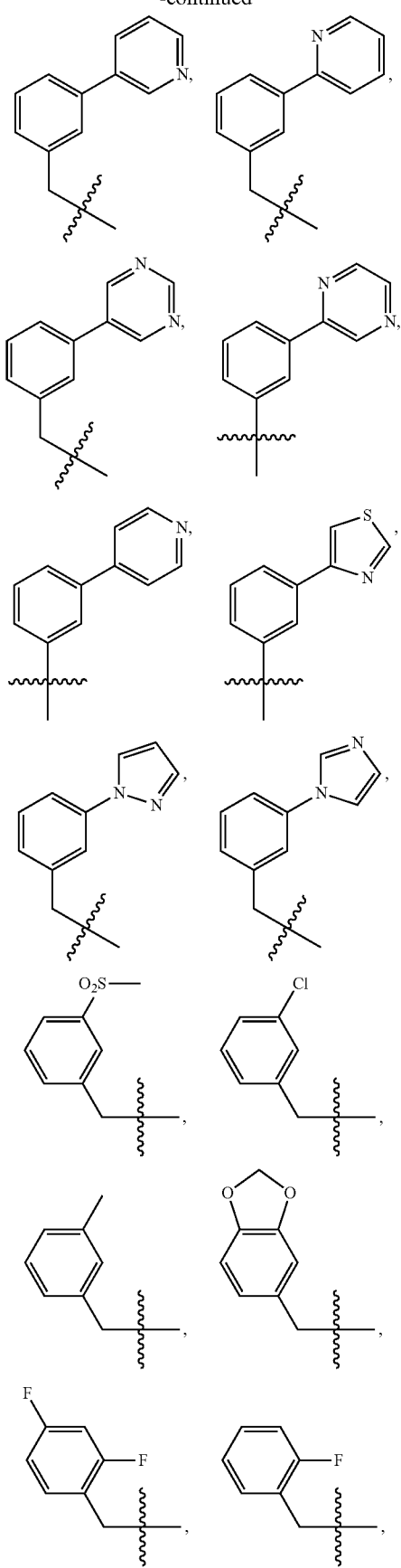

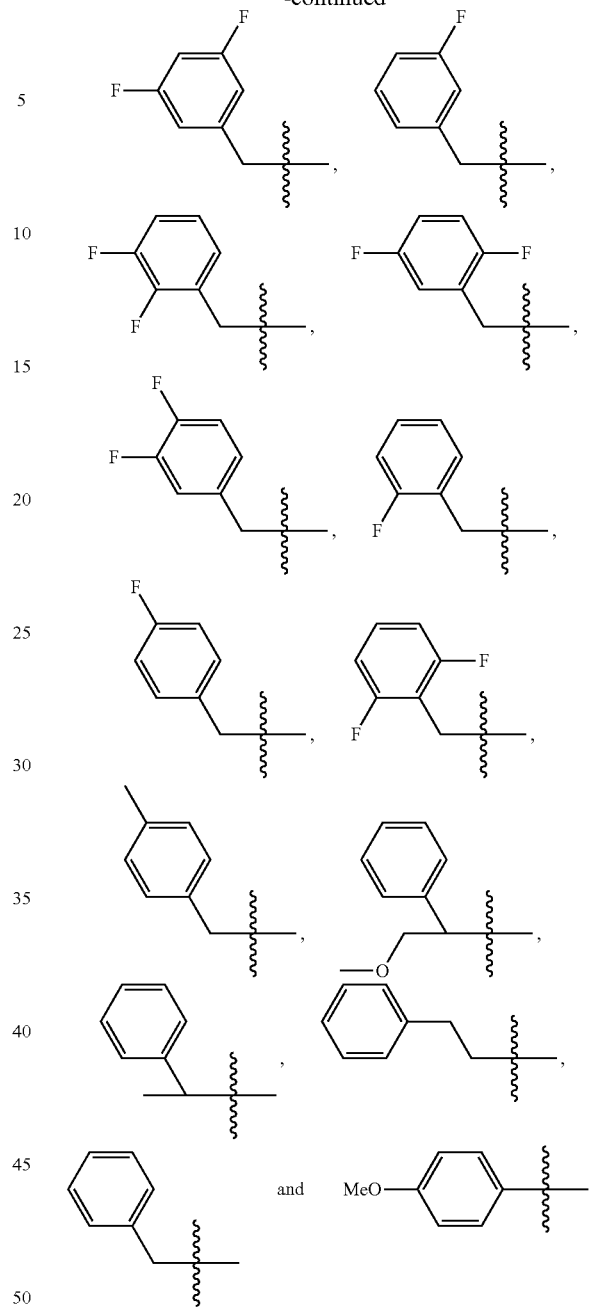

and the wavy line indicates the point of attachment to the rest of the molecule.

3. A compound of claim 1 selected from the group consisting of:

(S)-4-(benzylamino)-6-(4-(3-(methylcarbamoyl)piperidin-1-yl)phenylamino)nicotinamide; (R)-4-(benzylamino)-6-(4-(3-(methylcarbamoyl)piperidin-1-yl)phenylamino)nicotinamide; 4-(benzylamino)-6-(4-(dimethylcarbamoyl)phenylamino)-N,N-dimethylnicotinamide; 6-(4-(azetidine-1-carbonyl)phenylamino)-4-(benzylamino)nicotinamide; 6-(4-(azetidin-1-ylsulfonyl)phenylamino)-4-(benzylamino) nicotinamide; tert-butyl 4-(4-(5-carbamoyl-4-(3-fluorobenzylamino)pyridin-2-ylamino)phenyl)piperidine-1-carboxylate; 4-(4-(5-carbamoyl-4-(3- fluorobenzylamino)pyridin-2-ylamino)phenyl)-1,1-dimethylpiperidinium formate; 4-(2,5-difluorobenzylamino)-6-(4-(dimethylcarbamoyl)phenylamino)nicotinamide; 6-(4-(azetidine-1-carbonyl)phenylamino)-4-(2,5-difluorobenzylamino)nicotinamide; 4-(2,5-difluorobenzylamino)-6-(4-(N,N-dimethylsulfamoyl)phenylamino)nicotinamide; 4-(2,6-difluorobenzylamino)-6-(4-(dimethylcarbamoyl)phenylamino)nicotinamide; 4-(2,6-difluorobenzylamino)-6-(4-(N,N-dimethylsulfamoyl)phenylamino)nicotinamide; 6-(4-(azetidine-1-carbonyl)phenylamino)-4-(2,6-difluorobenzylamino)nicotinamide; 4-(2-fluorobenzylamino)-6-(4-(1-methylpiperidin-4-yl)phenylamino)nicotinamide; 4-(2-fluorobenzylamino)-6-(4-(1-isopropylpiperidin-4-yl)phenylamino)nicotinamide; 6-(4-(1-cyclopentylpiperidin-4-yl)phenylamino)-4-(2-fluorobenzylamino)nicotinamide; 6-(4-(1-(ethylsulfonyl)piperidin-4-yl)phenylamino)-4-(2-fluorobenzylamino)nicotinamide; 6-(4-(1-(cyclopropylsulfonyl)piperidin-4-yl)phenylamino)-4-(2-fluorobenzylamino)nicotinamide; 6-(4-(1-(dimethylcarbamoyl)piperidin-4-yl)phenylamino)-4-(2-fluorobenzylamino)nicotinamide; 6-(4-(1-acetylpiperidin-4-yl)phenylamino)-4-(2-fluorobenzylamino)nicotinamide; 4-(2-fluorobenzylamino)-6-(4-(1-(2-methoxyacetyl)piperidin-4-yl)phenylamino)nicotinamide; 6-(4-(1-(2-cyanoacetyl)piperidin-4-yl)phenylamino)-4-(2-fluorobenzylamino)nicotinamide; 6-(4-(1-(1-cyanocyclopropanecarbonyl)piperidin-4-yl)phenylamino)-4-(2-fluorobenzylamino)nicotinamide; 4-(2-fluorobenzylamino)-6-(4-(1-(tetrahydro-2H-pyran-4-carbonyl)piperidin-4-yl)phenylamino)nicotinamide.

4. A compound of claim 1 selected from the group consisting of: 4-(3-fluorobenzylamino)-6-(4-(1-propionylpiperidin-4-yl)phenylamino)nicotinamide; 4-(3,4-difluorobenzylamino)-6-(4-(1-propionylpiperidin-4-yl)phenylamino)nicotinamide; 4-(2,5-difluorobenzylamino)-6-(4-(1-propionylpiperidin-4-yl)phenylamino)nicotinamide; 4-(2 fluorobenzylamino)-6-(4-isopropylphenylamino)nicotinamide; 4-(3,5-difluorobenzylamino)-6-(4-(1-propionylpiperidin-4-yl)phenylamino)nicotinamide; 4-(2,3-difluorobenzylamino)-6-(4-(1-propionylpiperidin-4-yl)phenylamino)nicotinamide; 4-(benzylamino)-6-(4-(1-propionylpiperidin-4-yl)phenylamino)nicotinamide; (R)-4-(1-phenylethylamino)-6-(4-(1-propionylpiperidin-4-yl)phenylamino)nicotinamide; 4-(2,6-difluorobenzylamino)-6-(4-(1-propionylpiperidin-4-yl)phenylamino)nicotinamide; 6-(4-(azetidin-3-yl)phenylamino)-4-(2,3-difluorobenzylamino)nicotinamide; 6-(4-(azetidin-3-yl)phenylamino)-4-(2,5-difluorobenzylamino)nicotinamide; 6-(4-(1-(cyanomethyl)piperidin-4-yl)phenylamino)-4-(2,3-difluorobenzylamino)nicotinamide; 4-(2,3-difluorobenzylamino)-6-(4-(1-(2,2-difluoroethyl)piperidin-4-yl)phenylamino)nicotinamide; 4-(2,3-difluorobenzylamino)-6-(4-(1-(2-fluoroethyl)piperidin-4-yl)phenylamino)nicotinamide; 6-(4-(1-(cyanomethyl)piperidin-4-yl)phenylamino)-4-(2,5-difluorobenzylamino)nicotinamide; 6-(4-(1-(cyanomethyl)azetidin-3-yl)phenylamino)-4-(2,3-difluorobenzylamino)nicotinamide; 6-(4-(1-(cyanomethyl)azetidin-3-yl)phenylamino)-4-(2,5-difluorobenzylamino)nicotinamide; 4-(3-(1H-imidazol-1-yl)benzylamino)-6-(4-(dimethylcarbamoyl)phenylamino)nicotinamide; 4-(benzylamino)-6-(4-(dimethylcarbamoyl)phenylamino)nicotinamide; (S)-6-(4-(dimethylcarbamoyl)phenylamino)-4-(2-methoxy-1-phenylethylamino)nicotinamide; (S)-6-(4-(azetidine-1-carbonyl)phenylamino)-4-(2-methoxy-1-phenylethylamino)nicotinamide; 6-(4-(1H-imidazol-4-yl)phenylamino)-4-(benzylamino)nicotinamide; 6-(4-(1H-pyrazol-1-yl)phenylamino)-4-(benzylamino)nicotinamide; 6-(4-(1,2,4-triazol-3-yl)phenylamino)-4-(benzylamino)nicotinamide; 6-(4-(1 acetylazetidin-3-yl)phenylamino)-4-(benzylamino)nicotinamide; 6-(4-(azetidin-3-yl)phenylamino)-4-(benzylamino)nicotinamide; 4-(benzylamino)-6-(4-(1-propionylazetidin-3-yl)phenylamino)nicotinamide; methyl 3-(4-(4-(benzylamino)-5-carbamoylpyridin-2-ylamino)phenyl)azetidine-1-carboxylate; 4-(benzylamino)-6-(4-(1-(methylsulfonyl)azetidin-3-yl)phenylamino)nicotinamide; 4-(benzylamino)-6-(4-(1-(2-methoxyacetyl)azetidin-3-yl)phenylamino)nicotinamide; 4-(benzylamino)-6-(4-(1-(dimethylcarbamoyl)azetidin-3-yl)phenylamino)nicotinamide; 4-(benzylamino)-6-(4-(1-(pyrrolidine-1-carbonyl)azetidin-3-yl)phenylamino)nicotinamide; 4-(benzylamino)-6-(4-(1-(N,N-dimethylsulfamoyl)azetidin-3-yl)phenylamino)nicotinamide; 4-(benzylamino)-6-(4-(2-(methylamino)-2-oxoethyl)phenylamino)nicotinamide; 4-(benzylamino)-6-(4-(2-oxo-2-(2,2,2-trifluoroethylamino)ethyl)phenylamino)nicotinamide; 4-(benzylamino)-6-(4-(3-(dimethylcarbamoyl)azetidin-1-yl)-3-fluorophenylamino)nicotinamide; 4-(benzylamino)-6-(4-(4-(dimethylcarbamoyl)piperidin-1-yl)phenylamino)nicotinamide; 4-(benzylamino)-6-(4-(methylsulfonylmethyl)phenylamino)nicotinamide; 6-(4-(dimethylcarbamoyl)phenylamino)-4-(3-(pyridine-4-yl)benzylamino)nicotinamide; 6-(4-(dimethylcarbamoyl)phenylamino)-4-(3-(pyridine-3-yl)benzylamino)nicotinamide; 6-(4-(1-propionylpiperidin-4-yl)phenylamino)-4-(3-(pyridine-3-yl)benzylamino)nicotinamide; 6-(4-((N,N-dimethylsulfamoyl)methyl)phenylamino)-4-(3-(pyridine-4-yl)benzylamino)nicotinamide 6-(4-(methylsulfonylmethyl)phenylamino)-4-(3-(pyridine-4-yl)benzylamino)nicotinamide; 6-(4-(4-(dimethylcarbamoyl)piperidin-1-yl)phenylamino)-4-(3-(pyridine-4-yl)benzylamino)nicotinamide; 6-(4-(1-propionylpiperidin-4-yl)phenylamino)-4-(3-(pyridine-4-yl)benzylamino)nicotinamide; 6-(4-(dimethylcarbamoyl)phenylamino)-4-(3-(pyridine-2-yl)benzylamino)nicotinamide; 4-(3-(1H-pyrazol-1-yl)benzylamino)-6-(4-(dimethylcarbamoyl)phenylamino)nicotinamide; 6-(4-(dimethylcarbamoyl)phenylamino)-4-(3-(pyrimidine-5-yl)benzylamino)nicotinamide; 6-(4-(1-propionylpiperazin-4-yl)phenylamino)-4-(3-(pyridine-4-yl)benzylamino)nicotinamide; 6-(4-(dimethylcarbamoyl)phenylamino)-4-(3-(thiazol-4-yl)benzylamino)nicotinamide; 6-(4-(dimethylcarbamoyl)phenylamino)-4-(3-(pyrazin-2-yl)benzylamino)nicotinamide; 4-(benzylamino)-6-(4-(2-(pyrrolidin-1-yl)ethoxy)phenylamino)nicotinamide; 4-(2,3-difluorobenzylamino)-6-(4-(4-propionylpiperazin-1-yl)phenylamino)nicotinamide; 4-(2,3-difluorobenzylamino)-6-(4-(1-(1,3-difluoropropan-2-yl)piperidin-4-yl)phenylamino)nicotinamide; 4-(2,3-difluorobenzylamino)-6-(4-(1-(2-(dimethylamino)acetyl)piperidin-4-yl)phenylamino)nicotinamide; (R)-4-(2,3-difluorobenzylamino)-6-(4-(1-(1-methylpyrrolidine-2-carbonyl)piperidin-4-yl)phenylamino)nicotinamide; (S)-4-(2,3-difluorobenzylamino)-6-(4-(1-(1-methylpyrrolidine-2-carbonyl)piperidin-4-yl)phenylamino)nicotinamide; (R)-6-(4-(1-(1-acetylpyrrolidine-2-carbonyl)piperidin-4-yl)phenylamino)-4-(2,3-difluorobenzylamino)nicotinamide; (S)-6-(4-(1-(1-acetylpyrrolidine-2-carbonyl)piperidin-4-yl)phenylamino)-4-(2,3-difluorobenzylamino)nicotinamide; 4-(2,5-difluorobenzylamino)-6-(4-(1-formylpiperidin-4-yl)phenylamino)nicotinamide; 4-(2,3- difluorobenzylamino)-6-(4-(1-formylazetidin-3-yl) phenylamino)nicotinamide; 4-(2,5-difluorobenzylamino)-6-(4-(1-formylazetidin-3-yl)phenylamino)nicotinamide; 4-(2,3-difluorobenzylamino)-6-(4-(1-(2-fluoroethyl)azetidin-3-yl)phenylamino)nicotinamide; 4-(2,3-difluorobenzylamino)-6-(4-(1-(pyridin-2-yl)piperidin-4-yl)phenylamino)nicotinamide; and 4-(2,3-difluorobenzylamino)-6-(4-(1-pyridin-2-yl)azetidin-3-yl)phenylamino)nicotinamide.

5. A composition comprising a compound of claim 1, in combination with a pharmaceutically acceptable carrier or diluent.

6. A kit comprising a composition of claim 5, packaging and instructions for use.

7. The compound of claim 1, wherein the moiety:

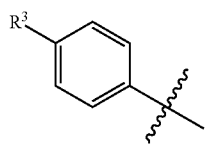

is selected from the group consisting of:

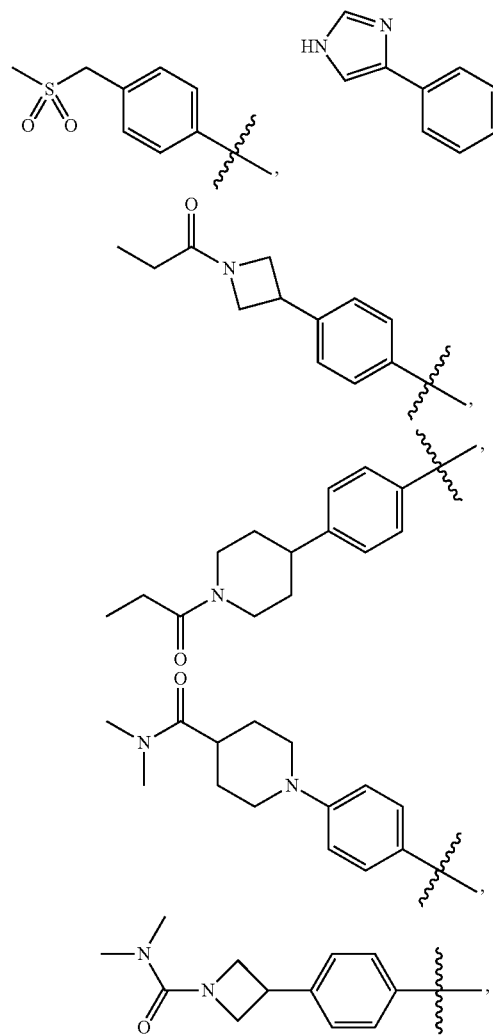

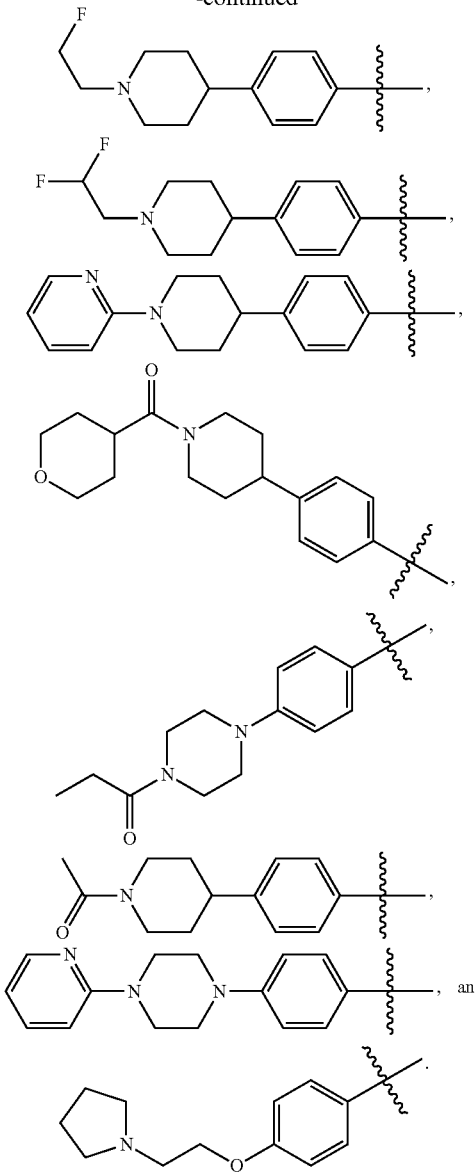

8. A compound of claim 1 selected from the group consisting of:
4-(benzylamino)-6-((4-(2-(pyrrolidin-1-yl)ethoxy)phenyl)amino)nicotinamide; 4-((2-fluorobenzyl)amino)-6-((4-(1-propionylpiperidin-4-yl)phenyl)amino)nicotinamide; 4-((2,3-difluorobenzyl)amino)-6-((4-(4-propionylpiperazin-1-yl)phenyl)amino)nicotinamide; 4-(benzylamino)-6-((4-(4-(pyridin-2-yl)piperazin-1-yl)phenyl)amino)nicotinamide; 6-((4-(1H-imidazol-4-yl)phenyl)amino)-4-(benzylamino)nicotinamide; 4-((3,5-difluorobenzyl)amino)-6-((4-(1-propionylpiperidin-4-yl)phenyl)amino)nicotinamide; 4-(benzylamino)-6-((4-(1-propionylazetidin-3-yl)phenyl)amino)nicotinamide; 4-((2,3-difluorobenzyl)amino)-6-((4-(1-(2,2-difluoroethyl)piperidin-4-yl)phenyl)amino)nicotinamide; and 4-((2,3-difluorobenzyl)amino)-6-((4-(1-(2-fluoroethyl)piperidin-4-yl)phenyl)amino)nicotinamide.

9. A method for inhibiting JAK kinase or a signal transduction pathway mediated at least in part by JAK kinase activity comprising the step of contacting a cell with a compound of claim 1.

10. A method for treating a condition or disorder mediated at least in part by JAK kinase activity in a subject comprising the step of administering to a subject in need of such treatment a therapeutically effective amount of a composition of claim 5.

* * * * *